US012698530B2

(12) United States Patent
Lotta et al.

(10) Patent No.: US 12,698,530 B2
(45) Date of Patent: *Aug. 4, 2026

(54) TREATMENT OF OBESITY WITH G-PROTEIN COUPLED RECEPTOR 75 (GPR75) INHIBITORS

(71) Applicant: Regeneron Pharmaceuticals, Inc., Tarrytown, NY (US)

(72) Inventors: Luca Andrea Lotta, Tarrytown, NY (US); Manuel Allen Revez Ferreira, Tarrytown, NY (US); Aris Baras, Tarrytown, NY (US); Parsa Akbari, Tarrytown, NY (US); Olukayode Sosina, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 495 days.

This patent is subject to a terminal disclaimer.

(21) Appl. No.: 17/748,110

(22) Filed: May 19, 2022

(65) Prior Publication Data

US 2022/0411870 A1     Dec. 29, 2022

Related U.S. Application Data

(63) Continuation of application No. 17/353,313, filed on Jun. 21, 2021, now Pat. No. 11,359,246.

(60) Provisional application No. 63/042,327, filed on Jun. 22, 2020, provisional application No. 63/066,185, filed on Aug. 15, 2020, provisional application No. 63/075,858, filed on Sep. 9, 2020, provisional application No. 63/089,625, filed on Oct. 9, 2020, provisional application No. 63/104,613, filed on Oct. 23, 2020, provisional application No. 63/142,632, filed on Jan. 28, 2021, provisional application No. 63/159,017, filed on Mar. 10, 2021, provisional application No. 63/210,287, filed on Jun. 14, 2021, provisional application No. 63/211,061, filed on Jun. 16, 2021.

(51) Int. Cl.
| | |
|---|---|
| *C12Q 1/6883* | (2018.01) |
| *A61K 31/7105* | (2006.01) |
| *A61K 38/46* | (2006.01) |
| *A61P 3/04* | (2006.01) |
| *C12N 15/113* | (2010.01) |

(52) U.S. Cl.
CPC ........ *C12Q 1/6883* (2013.01); *A61K 31/7105* (2013.01); *A61K 38/465* (2013.01); *A61P 3/04* (2018.01); *C12N 15/1138* (2013.01); *C12N 2310/11* (2013.01); *C12N 2310/14* (2013.01); *C12Q 2600/106* (2013.01); *C12Q 2600/156* (2013.01)

(58) Field of Classification Search
CPC .......... C12Q 1/6883; A61P 3/04; A71K 38/46
See application file for complete search history.

(56) References Cited

U.S. PATENT DOCUMENTS

| | | | | |
|---|---|---|---|---|
| 8,185,323 | B1 | 5/2012 | Zhou | |
| 10,446,261 | B1 | 10/2019 | Zhou | |
| 11,359,246 | B2 * | 6/2022 | Lotta .................. | C12N 15/1138 |
| 2008/0108080 | A1 * | 5/2008 | Chissoe .............. | C12Q 1/6883 |
| | | | | 435/6.11 |
| 2008/0108145 | A1 | 5/2008 | Chissoe | |
| 2010/0113297 | A1 | 5/2010 | Lidereau et al. | |
| 2011/0177964 | A1 | 7/2011 | Broach et al. | |
| 2014/0377278 | A1 * | 12/2014 | Elinav .................. | A61K 35/747 |
| | | | | 435/6.12 |
| 2016/0169918 | A1 | 6/2016 | Murray et al. | |
| 2018/0100201 | A1 | 4/2018 | Garraway et al. | |
| 2019/0117689 | A1 | 4/2019 | Balin et al. | |
| 2019/0241633 | A1 | 8/2019 | Fotin-Mleczek et al. | |
| 2020/0030291 | A1 * | 1/2020 | Falck .................... | C07C 233/47 |
| 2020/0113950 | A1 | 4/2020 | Cohen et al. | |
| 2020/0207836 | A1 | 7/2020 | Pfleger et al. | |
| 2021/0002296 | A1 | 1/2021 | Mainolfi et al. | |
| 2021/0283262 | A1 | 9/2021 | Dominy et al. | |

FOREIGN PATENT DOCUMENTS

| | | |
|---|---|---|
| WO | 2005040790 | 5/2005 |
| WO | 2013036290 | 3/2013 |
| WO | 2017132291 | 8/2017 |
| WO | 2017156164 | 9/2017 |
| WO | 2020118363 | 6/2020 |
| WO | 2020247220 | 12/2020 |

OTHER PUBLICATIONS

Taylor. Jul. 27, 2021; Regeneron AZ team up on drugs for obesity "superpower" gene. On the web at pharmaphorum.com/news/regeneron-az-team-up-on-drugs-for-obesity-superpower-gene. pp. 1-2.*
LOVD3. 2020; Whole genome datasets GPR75 (G protein-coupled receptor 75) on the web at databases.lovd.nl/whole genome/view/GPR75, pp. 1-3.*
Akbari et al. Jul. 7, 2021; Sequencing of 640,000 exomes identifies GPR75 variants associated with protection from obesity. Science. 373, eabf8683, pp. 1-11.*
Prasad-Reddy et al. 2015; A clinical review of GLP-1 receptor agonists: efficacy and safely in diabetes and beyond. Drugs in Context 4: 212283, pp. 1-19.*
Tan et al. 2017; Efficacy and safety of once weekly semaglutide for the treatment of type 2 diabetes. Expert Opinion on Investigational Drugs. 26(9): 1083-1089.*

(Continued)

*Primary Examiner* — Suzanne M Noakes
(74) *Attorney, Agent, or Firm* — Armstrong Teasdale LLP

(57) ABSTRACT

The present disclosure provides methods of treating subjects having obesity, methods of identifying subjects having an increased risk of developing obesity, methods of detecting human G-protein coupled receptor 75 variant nucleic acid molecules and variant polypeptides, and GPR75 variant nucleic acid molecules and variant polypeptides.

23 Claims, 47 Drawing Sheets
(4 of 47 Drawing Sheet(s) Filed in Color)
Specification includes a Sequence Listing.

(56)        References Cited

OTHER PUBLICATIONS

Sauer et al., "Evaluation of the G Protein Coupled Receptor-75 (GPR75) in Age Related Macular Degeneration", British Journal of Opthalmology, 2001, 85(8), pp. 969-975.

Dedoni et al., "The orphan G-protein-coupled receptor 75 signaling is activated by the chemokine CCL5", Journal of Neurochemistry, 2018, 146(5), pp. 526-539.

Liu et al., "The novel chemokine receptor, G-protein-coupled receptor 75, is expressed by islets and is coupled to stimulation of insulin secretion and improved glucose homeostasis", Diabetologia, 2013, 56(11), pp. 2467-2476.

Taneera et al., "Orphan G-Protein coupled receptor 183 (GPR183) potentiates insulin secretion and prevents glucotoxicity-induced [beta]-cell dysfunction", Molecular and Cellular Endocrinology, 2020, 499, pp. 1-9.

Dewey et al., "Distribution and clinical impact of functional variants in 50,726 whole-exome sequences from the DiscovEHR Study", Science, 2016, 354(6319), pp. aaf6814.

Garcia et al., "20-HETE Signals Through G-Protein-Coupled Receptor GPR75 (Gq) to Affect Vascular Function and Trigger Hypertension", Circ Res, 2017, 120, pp. 1776-1788.

Pappalardo et al., "A Whole-Genome RNA Interference Screen Reveals a Role for Spry2 in Insulin Transcription and the Unfolded Protein Response", Diabetes, 2017, 66, pp. 1703-1712.

Lovd3, Whole genome datasets GPR75 (G-protein-coupled receptor 75) on the web at databases.lovd.nl/whole_genome/viewGPR75, 2020, pp. 1-3.

Taylor, "Regeneron AZ team up on drugs for obesity superpower gene", on the web at pharmaphorum.com/news/regeneron-az-team-up-on-drugs-for-obesity-superpower-gene, 2021, pp. 1-2.

Akbari et al., "Sequencing of 640,000 exomes identifies GPR75 variants associated with protection from obesity", Science, 2021, 373, eabf8683, pp. 1-11.

* cited by examiner

| Variable | UKB study (N=428,719) | GHS study (N=121,061) | MCPS study (N=95,846) |
|---|---|---|---|
| Age, mean (SD) in years | 57 (8) | 53 (17) | 52 (13) |
| Women, N (%) | 232,553 (54) | 73,769 (61) | 65,330 (68) |
| Body mass index, mean (SD) in kg/m² | 27.4 (4.8) | 31.1 (7.3) | 29.1 (5.1) |
| Body weight, mean (SD) in kg | 78 (16) | 88 (23) | 70 (14) |
| Body mass index WHO categories, N (%) | | | |
| Underweight (< 18.5 kg/m²) | 2,089 (0.49) | 994 (0.82) | 499 (0.52) |
| Healthy weight (18.5 to < 25 kg/m²) | 140,175 (32.70) | 23,784 (19.65) | 18,599 (19.41) |
| Overweight (25 to < 30 kg/m²) | 182,564 (42.58) | 35,787 (29.56) | 40,672 (42.43) |
| Obesity, non-severe (30 to < 40 kg/m²) | 95,928 (22.37) | 46,067 (38.05) | 33,203 (34.64) |
| Severe obesity (≤ 40 kg/m²) | 7,963 (1.86) | 14,429 (11.92) | 2,873 (3.00) |
| Blood pressure, mean (SD) in mmHg | | | |
| Systolic | 138 (19) | 124 (11) | 127 (17) |
| Diastolic | 82 (11) | 74 (7) | 83 (10) |
| Low-density lipoprotein cholesterol, mean (SD) in mg/dL | 138 (34) | 107 (29) | Not measured |
| Triglycerides, median (IQR) in mg/dL | 132 (93, 191) | 124 (90, 172) | Not measured |

Figure 1

| Gene | Genetic exposure, variant type; allele frequency cut-off in % | Study | Beta (95% CI) per allele in SD units of BMI | p | AAF, fraction of 1 | Genotype counts, RR\|RA\|AA genotypes |
|------|------|------|------|------|------|------|
| GPR75 | pLOF; AAF < 1% | UKB | -0.34 (-0.49, -0.19) | 6.6E-06 | 0.0002 | 428,572\|147\|0 |
| GPR75 | pLOF; AAF < 1% | MCPS | -0.48 (-0.82, -0.13) | 7.1E-03 | 0.0002 | 95,816\|30\|0 |
| GPR75 | pLOF; AAF < 1% | GHS | -0.27 (-0.52, -0.02) | 3.6E-02 | 0.0002 | 121,010\|51\|0 |

Figure 2

| Gene | Genomic Coordinates | Genetic exposure, variant type; frequency cut-off in % | Beta (95% CI) per allele in SD units of BMI | p |
|---|---|---|---|---|
| GPR75 | 2: 53853133 | pLOF; AAF < 1% | -0.34 (-0.46, -0.22) | $2.6 \times 10^{-08}$ |

| Gene | AAF, fraction of 1 | Genotype counts, RR\|RA\|AA genotypes | Beta (95% CI) per allele in kg/m² units of BMI | Beta (95% CI) per allele in kgs of body weight | Beta (95% CI) per allele in lbs of body weight |
|---|---|---|---|---|---|
| GPR75 | 0.0002 | 645,398\|228\|0 | -1.8 (-2.5, -1.2) | -5.3 (-7.1, -3.4) | -11.6 (-15.7, -7.5) |

Figure 3

| Genetic exposure, variant type, frequency cutoff in % | Group | Beta (95% CI) per allele in SD units of BMI | Beta (95% CI) per allele in kg/m² units of BMI | p | AAF, fraction of 1 | Genotype counts, RR\|RA\|AA genotypes | p-value for heterogeneity in effect estimates between groups |
|---|---|---|---|---|---|---|---|
| GPR75 pLOF; AAF < 1% | Age ≤ median value in cohort | -0.33 (-0.50, -0.17) | -1.80 (-2.70, -0.89) | 1.0E-04 | 0.0002 | 331,175\|117\|0 | 0.93 |
| GPR75 pLOF; AAF < 1% | Age > median value in cohort | -0.35 (-0.52, -0.18) | -1.90 (-2.80, -0.95) | 7.8E-05 | 0.0002 | 314,223\|111\|0 | |
| GPR75 pLOF; AAF < 1% | Men | -0.35 (-0.55, -0.16) | -1.90 (-3.00, -0.86) | 3.5E-04 | 0.0002 | 273,885\|89\|0 | 0.91 |
| GPR75 pLOF; AAF < 1% | Women | -0.33 (-0.49, -0.18) | -1.80 (-2.60, -0.97) | 2.4E-05 | 0.0002 | 371,513\|139\|0 | |

Figure 5

| Gene | Genetic exposure, variant type; allele frequency cut-off in % | Per-allele OR (95% CI) for obesity | p | AAF, fraction of 1 | Genotype counts (cases), RR\|RA\|AA genotypes | Genotype counts (controls), RR\|RA\|AA genotypes |
|---|---|---|---|---|---|---|
| GPR75 | pLOF; AAF < 1% | 0.46 (0.31, 0.67) | 6.9E-05 | 0.0002 | 200,613\|45\|0 | 186,335\|94\|0 |

Figure 6

| Genetic exposure; variant type; frequency cutoff in % | Outcome | AAF, fraction of 1 | OR (95% CI) per allele | p | Genotype counts (cases), RR\|RA\|AA genotypes | Genotype counts (controls), RR\|RA\|AA genotypes |
|---|---|---|---|---|---|---|
| GPR75 pLOF; AAF < 1% | Responded "Thinner" to multiple choice question: "When you were 10 years old, compared to average would you describe yourself as: thinner, plumper, about average, do not know, prefer not to answer?" | 1.7E-04 | 1.66 (1.18, 2.34) | 3.9E-03 | 141,442\|62\|0 | 282,026\|82\|0 |

Figure 8

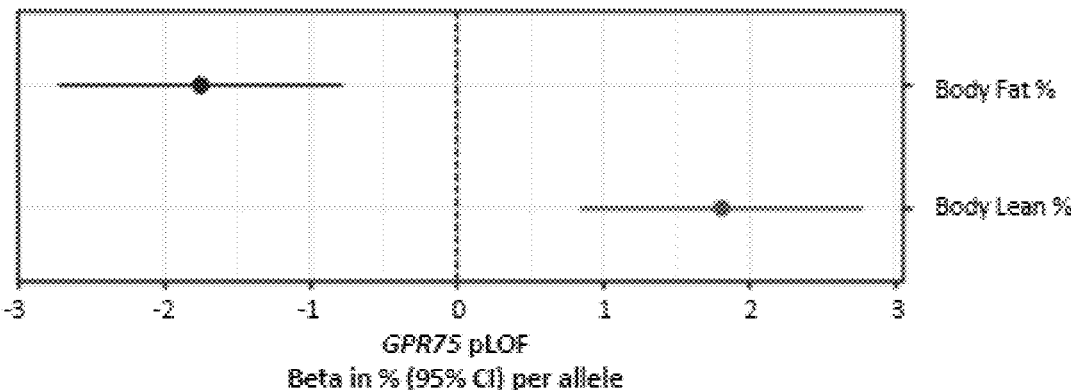
*GPR75* pLOF
Beta in % (95% CI) per allele
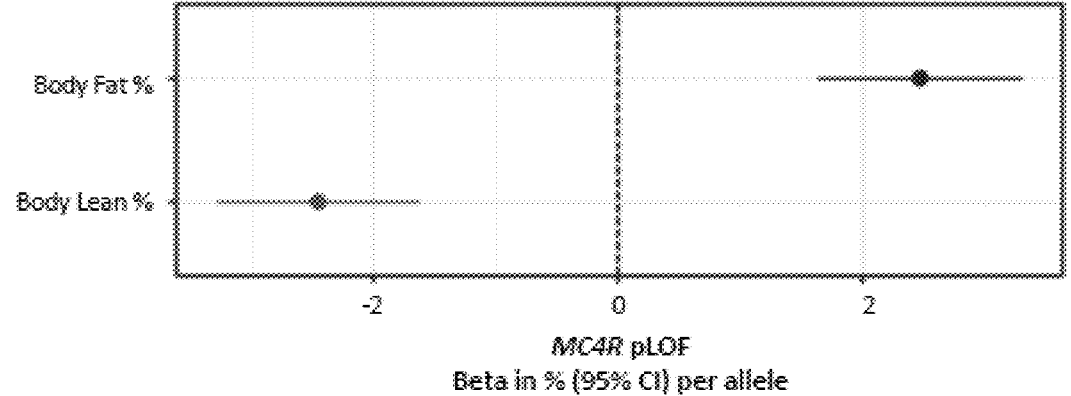
*MC4R* pLOF
Beta in % (95% CI) per allele
——◆—— Fat-mass related traits
——◆—— Lean-mass related traits
Figure 9 (cont.)

| Exposure | Outcome, clinical unit | Beta in SDs or odds ratio (95% CI) per allele | p | Allele counts participants (or disease cases for binary traits), RR\|RA\|AA | Allele counts controls, RR\|RA\|AA | Beta in clinical units (95% CI) per allele |
|---|---|---|---|---|---|---|
| GPR75 pLOF genetic variants, AAF < 1% | Glucose[a], mg/dL | -0.04 | 5.8E-01 | 461,056\|162\|0 | - | -0.9 |
| | | (-0.19, 0.11) | | | | (-4.1, 2.3) |
| | HbA1c, % | -0.06 | 3.5E-01 | 574,999\|191\|0 | - | -0.06 |
| | | (-0.19, 0.07) | | | | (-0.17, 0.06) |
| | AST[a], U/L | -0.01 | 9.0E-01 | 515,532\|182\|0 | - | -0.1 |
| | | (-0.15, 0.13) | | | | (-1.4, 1.3) |
| | ALT[a], U/L | -0.11 | 1.2E-01 | 518,135\|182\|0 | - | -1.5 |
| | | (-0.25, 0.03) | | | | (-3.4, 0.4) |
| | Triglycerides[a], mg/dL | -0.05 | 4.4E-01 | 501,508\|178\|0 | - | -4.8 |
| | | (-0.19, 0.08) | | | | (-16.7, 7.2) |
| | HDL-C[a], mg/dL | 0.19 | 6.3E-03 | 467,058\|167\|0 | - | 2.9 |
| | | (0.05, 0.33) | | | | (0.8, 4.9) |
| | LDL-C[a], mg/dL | -0.02 | 7.9E-01 | 500,249\|177\|0 | - | -0.6 |
| | | (-0.15, 0.12) | | | | (-5.2, 3.9) |
| | Systolic blood pressure, mmHg | -0.03 | 5.8E-01 | 622,080\|222\|0 | - | -0.6 |
| | | (-0.15, 0.08) | | | | (-2.7, 1.5) |
| | Diastolic blood pressure, mmHg | -0.03 | 6.5E-01 | 618,264\|222\|0 | - | -0.3 |
| | | (-0.15, 0.1) | | | | (-1.6, 1) |
| | Waist-to-hip ratio, ratio units | -0.13 | 8.0E-02 | 525,809\|177\|0 | - | -0.011 |
| | | (-0.27, 0.01) | | | | (-0.024, 0.001) |
| | Type 2 diabetes | 0.92 | 7.3E-01 | 63,468\|24\|0 | 549,770\|191\|0 | - |
| | | (0.59, 1.45)[b] | | | | |

Figure 10

| Variant (CPRA) | AAF | cDNA change HGVS | Protein change HGVS | Affected exon | In genotyping array | In raw imputed data | Imputation quality INFO score, fraction of 1[a] |
|---|---|---|---|---|---|---|---|
| 2:53853134:T:G | 2.3E-06 | c.1623A>C | p.Ter541Tyrext*? | Exon 2 | No | No | - |
| 2:53853135:T:G | 1.2E-06 | c.1622A>C | p.Ter541Serext*? | Exon 2 | No | No | - |
| 2:53853136:A:C | 2.3E-06 | c.1621T>G | p.Ter541Gluext*? | Exon 2 | No | No | - |
| 2:53853200:GGT:G | 7.6E-06 | c.1555_1556delAC | p.Thr519fs | Exon 2 | No | No | - |
| 2:53853245:GT:G | 1.2E-06 | c.1511delA | p.Asn504fs | Exon 2 | No | No | - |
| 2:53853256:G:A | 1.2E-06 | c.1501C>T | p.Gln501* | Exon 2 | No | No | - |
| 2:53853352:G:A | 1.3E-05 | c.1405C>T | p.Gln469* | Exon 2 | No | No | - |
| 2:53853354:CCA:C | 5.4E-05 | c.1401_1402delTG | p.Cys467fs | Exon 2 | No | No | - |
| 2:53853382:TG:T | 1.8E-05 | c.1374delC | p.Lys459fs | Exon 2 | No | No | - |
| 2:53853502:T:A | 5.8E-06 | c.1255A>T | p.Arg419* | Exon 2 | No | No | - |
| 2:53853535:G:A | 1.4E-05 | c.1222C>T | p.Arg408* | Exon 2 | No | No | - |
| 2:53853547:T:A | 1.0E-05 | c.1210A>T | p.Lys404* | Exon 2 | No | No | - |
| 2:53853560:G:GA | 1.2E-06 | c.1196dupT | p.Cys400fs | Exon 2 | No | No | - |
| 2:53853641:GTT:G | 9.0E-06 | c.1114_1115delAA | p.Asn372fs | Exon 2 | No | No | - |
| 2:53853680:CAATTCAAACTGGT:C | 1.2E-06 | c.1064_1076delACCAGTTTGAATT | p.Tyr355fs | Exon 2 | No | No | - |
| 2:53853692:G:T | 1.2E-06 | c.1065C>A | p.Tyr355* | Exon 2 | No | No | - |

Figure 12

| Variant (CPRA) | AAF | cDNA change HGVS | Protein change HGVS | Affected exon | In genotyping array | In raw imputed data | Imputation quality INFO score, fraction of 1[a] |
|---|---|---|---|---|---|---|---|
| 2:53853 730:G:A | 3.5E-06 | c.1027C>T | p.Gln343* | Exon 2 | No | No | - |
| 2:53853 771:G:C | 2.1E-05 | c.986C>G | p.Ser329* | Exon 2 | No | No | - |
| 2:53853 853:G:A | 5.1E-06 | c.904C>T | p.Arg302* | Exon 2 | No | No | - |
| 2:53853 877:G:A | 7.3E-05 | c.880C>T | p.Gln294* | Exon 2 | No | No | - |
| 2:53853 926:G:T | 1.8E-05 | c.831C>A | p.Tyr277* | Exon 2 | No | No | - |
| 2:53853 927:T:T A | 1.2E-06 | c.829dupT | p.Tyr277fs | Exon 2 | No | No | - |
| 2:53853 946:G:G T | 2.3E-06 | c.810_811ins A | p.Leu271fs | Exon 2 | No | No | - |
| 2:53853 967:TGG :T | 4.7E-06 | c.788_789del CC | p.Pro263fs | Exon 2 | No | No | - |
| 2:53854 009:G:A | 1.2E-06 | c.748C>T | p.Gln250* | Exon 2 | No | No | - |
| 2:53854 037:A:A G | 4.7E-06 | c.719dupC | p.Val241fs | Exon 2 | No | No | - |
| 2:53854 045:ACT TT:A | 1.7E-05 | c.708_711del AAAG | p.Arg236fs | Exon 2 | No | No | - |
| 2:53854 051:T:A | 9.3E-06 | c.706A>T | p.Arg236* | Exon 2 | No | No | - |
| 2:53854 057:G:A | 2.9E-05 | c.700C>T | p.Gln234* | Exon 2 | No | Yes, but excluded after QC due to very low imputation quality | 0.007 |
| 2:53854 078:G:A | 5.2E-06 | c.679C>T | p.Gln227* | Exon 2 | No | No | - |
| 2:53854 099:CAG :C | 3.5E-06 | c.656_657del CT | p.Ser219fs | Exon 2 | No | No | - |

Figure 12 (cont.)

| Variant (CPRA) | AAF | cDNA change HGVS | Protein change HGVS | Affected exon | In genotyping array | In raw imputed data | Imputation quality INFO score, fraction of 1[a] |
|---|---|---|---|---|---|---|---|
| 2:53854135:CAT:C | 1.2E-06 | c.620_621delAT | p.Tyr207fs | Exon 2 | No | No | - |
| 2:53854137:TAGAG:T | 1.7E-05 | c.616_619delCTCT | p.Leu206fs | Exon 2 | No | No | - |
| 2:53854306:G:A | 1.2E-05 | c.451C>T | p.Gln151* | Exon 2 | No | No | - |
| 2:53854380:G:C | 2.1E-06 | c.377C>G | p.Ser126* | Exon 2 | No | No | - |
| 2:53854409:A:AG | 7.6E-06 | c.347dupC | p.Cys118fs | Exon 2 | No | No | - |
| 2:53854421:ACTACTGG:A | 1.2E-05 | c.329_335delCCAGTAG | p.Ala110fs | Exon 2 | No | No | - |
| 2:53854474:C:A | 1.2E-05 | c.283G>T | p.Gly95* | Exon 2 | No | No | - |
| 2:53854476:C:CA | 1.2E-06 | c.280dupT | p.Cys94fs | Exon 2 | No | No | - |
| 2:53854485:AG:A | 1.2E-06 | c.271delC | p.Leu91fs | Exon 2 | No | No | - |
| 2:53854644:TG:T | 4.2E-05 | c.112delC | p.His38fs | Exon 2 | No | No | - |
| 2:53854685:TC:T | 5.2E-06 | c.71delG | p.Gly24fs | Exon 2 | No | No | - |
| 2:53854695:G:T | 1.2E-06 | c.62C>A | p.Ser21* | Exon 2 | No | No | - |
| 2:53854740:TG:T | 1.2E-06 | c.16delC | p.His6fs | Exon 2 | No | No | - |
| 2:53854755:A:G | 9.0E-06 | c.2T>C | p.Met1? | Exon 2 | No | No | - |
| 2:53859827:C:T | 1.2E-06 | c.-110+1G>A | - | Exon 1 | No | No | - |

Figure 12 (cont.)

| Gene | Genetic exposure, variant type; frequency cutoff in % | AAF, fraction of 1 | Beta (95% CI) per allele in SD units of BMI | Beta (95% CI) per allele in kg/m2 units of BMI | p | Genotype counts, RR\|RA\|AA genotypes |
|---|---|---|---|---|---|---|
| ASB3 | pLOF; AAF < 1% | 0.00015 | -0.037 (-0.17, 0.091) | -0.2 (-0.9, 0.49) | 0.57 | 645,432\|194\|0 |
| ASB3 | pLOF plus any missense; AAF < 0.1% | 0.00467 | -0.0081 (-0.031, 0.015) | -0.044 (-0.17, 0.082) | 0.50 | 639,601\|6,023\|2 |
| ASB3 | pLOF plus any missense; AAF < 1% | 0.01375 | -0.0069 (-0.021, 0.0068) | -0.037 (-0.11, 0.037) | 0.33 | 627,913\|17,677\|36 |
| ASB3 | pLOF plus deleterious missense (5/5); AAF < 0.1% | 0.00015 | -0.037 (-0.17, 0.091) | -0.2 (-0.9, 0.49) | 0.57 | 645,432\|194\|0 |
| ASB3 | pLOF plus deleterious missense (5/5); AAF < 1% | 0.00015 | -0.037 (-0.17, 0.091) | -0.2 (-0.9, 0.49) | 0.57 | 645,432\|194\|0 |
| ASB3 | pLOF plus deleterious missense (1/5); AAF < 0.1% | 0.00355 | -0.019 (-0.045, 0.0079) | -0.1 (-0.25, 0.042) | 0.17 | 641,041\|4,583\|2 |
| ASB3 | pLOF plus deleterious missense (1/5); AAF < 1% | 0.01150 | -0.011 (-0.026, 0.0039) | -0.059 (-0.14, 0.021) | 0.15 | 630,803\|14,798\|25 |

Figure 13

| Gene | Genetic exposure, variant type; frequency cutoff in % | AAF, fraction of 1 | Beta (95% CI) per allele in SD units of BMI | Beta (95% CI) per allele in kg/m2 units of BMI | p | Genotype counts, RR\|RA\|AA genotypes |
|---|---|---|---|---|---|---|
| GPR75-ASB3 | pLOF; AAF < 1% | 0.00015 | -0.039 (-0.17, 0.088) | -0.21 (-0.89, 0.47) | 0.55 | 645,426\|200\|0 |
| GPR75-ASB3 | pLOF plus any missense; AAF < 0.1% | 0.00497 | -0.0096 (-0.032, 0.013) | -0.052 (-0.17, 0.071) | 0.41 | 639,208\|6,416\|2 |
| GPR75-ASB3 | pLOF plus any missense; AAF < 1% | 0.01565 | -0.0012 (-0.014, 0.012) | -0.0065 (-0.076, 0.063) | 0.85 | 625,469\|20,110\|47 |
| GPR75-ASB3 | pLOF plus deleterious missense (5/5); AAF < 0.1% | 0.00015 | -0.039 (-0.17, 0.088) | -0.21 (-0.89, 0.47) | 0.55 | 645,426\|200\|0 |
| GPR75-ASB3 | pLOF plus deleterious missense (5/5); AAF < 1% | 0.00015 | -0.039 (-0.17, 0.088) | -0.21 (-0.89, 0.47) | 0.55 | 645,426\|200\|0 |
| GPR75-ASB3 | pLOF plus deleterious missense (1/5); AAF < 0.1% | 0.00385 | -0.02 (-0.046, 0.0056) | -0.11 (-0.25, 0.03) | 0.13 | 640,655\|4,969\|2 |
| GPR75-ASB3 | pLOF plus deleterious missense (1/5); AAF < 1% | 0.01319 | -0.0045 (-0.019, 0.0096) | -0.024 (-0.1, 0.052) | 0.53 | 628,634\|16,956\|36 |

Figure 13 (cont.)

| Genetic exposure, variant type; frequency cutoff in % | Additional covariates adjusted for in the analysis in addition to standard covariates* | Beta (95% CI) per allele in SD units of BMI | Beta (95% CI) per allele in kg/m² units of BMI | p | AAF, fraction of 1 | Genotype counts, RR\|RA\|AA genotypes |
|---|---|---|---|---|---|---|
| GPR75 pLOF; AAF < 1% | ASB3 pLOF (AAF < 1%); ASB3 pLOF plus any missense (AAF < 0.1%); ASB3 pLOF plus any missense (AAF < 1%); ASB3 pLOF plus deleterious missense (5/5) (AAF < 0.1%); ASB3 pLOF plus deleterious missense (5/5) (AAF < 1%); ASB3 pLOF plus deleterious missense (1/5) (AAF < 0.1%); ASB3 pLOF plus deleterious missense (1/5) (AAF < 1%); GPR75-ASB3 pLOF (AAF < 1%); GPR75-ASB3 pLOF plus any missense (AAF < 0.1%); GPR75-ASB3 pLOF plus any missense (AAF < 1%); GPR75-ASB3 pLOF plus deleterious missense (5/5) (AAF < 0.1%); GPR75-ASB3 pLOF plus deleterious missense (5/5) (AAF < 1%); GPR75-ASB3 pLOF plus deleterious missense (1/5) (AAF < 0.1%); GPR75-ASB3 pLOF plus deleterious missense (1/5) (AAF < 1%) | -0.34 (-0.46, -0.22) | -1.85 (-2.50, -1.19) | 3.1E-08 | 0.00018 | 645,398\|228\|0 |
| GPR75 pLOF; AAF < 1% | 26 common variants associated with BMI at the locus in Europeans (listed in Table S9) | -0.34 (-0.46, -0.22) | -1.85 (-2.50, -1.19) | 3.1E-08 | 0.00018 | 645,398\|228\|0 |

Figure 14

| Variant (CPRA) | dbSNP rsID | AAF | PPA | Sentinel variant in credible set | Nearest gene |
|---|---|---|---|---|---|
| 2:53634252:A:G | rs59428052 | 0.147 | 0.304 | Yes | ASB3,GPR75-ASB3 |
| 2:53899622:C:A | rs805422 | 0.431 | 0.063 | No | PSME4 |
| 2:53966056:T:C | rs805343 | 0.524 | 0.047 | No | PSME4 |
| 2:53965962:A:G | rs805342 | 0.523 | 0.046 | No | PSME4 |
| 2:53893683:G:A | rs805412 | 0.415 | 0.045 | No | PSME4 |
| 2:53812428:C:G | rs2287347 | 0.092 | 0.039 | No | ERLEC1,GPR75-ASB3 |
| 2:53813267:A:G | rs6545368 | 0.092 | 0.026 | No | ERLEC1,GPR75-ASB3 |
| 2:53965020:G:A | rs805341 | 0.522 | 0.024 | No | PSME4 |
| 2:53921194:C:A | rs805330 | 0.431 | 0.022 | No | PSME4 |
| 2:53807744:G:T | rs6724214 | 0.092 | 0.021 | No | ERLEC1,GPR75-ASB3 |
| 2:53938709:G:T | rs805361 | 0.438 | 0.02 | No | PSME4 |
| 2:53934885:C:T | rs805358 | 0.439 | 0.015 | No | PSME4 |
| 2:53907915:C:T | rs805318 | 0.44 | 0.01 | No | PSME4 |
| 2:54051530:T:C | rs7590846 | 0.374 | 0.007 | No | ACYP2 |
| 2:54051448:C:G | rs1559037 | 0.373 | 0.006 | No | ACYP2 |
| 2:54052186:A:G | rs1833497 | 0.375 | 0.005 | No | ACYP2 |
| 2:54052992:A:C | rs1862122 | 0.375 | 0.005 | No | ACYP2 |
| 2:53899904:C:T | rs805423 | 0.482 | 0.005 | No | PSME4 |
| 2:53995028:C:A | rs7591431 | 0.361 | 0.004 | No | ACYP2 |
| 2:53958004:A:G | rs805335 | 0.49 | 0.004 | No | PSME4 |
| 2:54053847:A:G | rs7558126 | 0.374 | 0.004 | No | ACYP2 |
| 2:53733092:C:T | rs114272138 | 0.022 | 0.003 | No | ASB3,GPR75-ASB3 |
| 2:53822332:G:A | rs3095756 | 0.412 | 0.002 | No | GPR75-ASB3 |
| 2:53720820:C:A | rs77601694 | 0.022 | 0.002 | No | ASB3,GPR75-ASB3 |
| 2:53822111:G:A | rs2542577 | 0.412 | 0.002 | No | GPR75-ASB3 |
| 2:53821221:G:A | rs2542575 | 0.412 | 0.002 | No | GPR75-ASB3 |

Figure 15

| Variant (CPRA) | Annotation | Nonsynonymous variants in LD (R^2 > 0.8) | R^2 with nonsynonymous variant |
|---|---|---|---|
| 2:53634252:A:G | intergenic | None | |
| 2:53899622:C:A | intronic | None | |
| 2:53966056:T:C | intronic | None | |
| 2:53965962:A:G | intronic | None | |
| 2:53893683:G:A | synonymous | None | |
| 2:53812428:C:G | intronic;intronic | None | |
| 2:53813267:A:G | intronic;intronic | None | |
| 2:53965020:G:A | intronic | None | |
| 2:53921194:C:A | intronic | None | |
| 2:53807744:G:T | intronic | None | |
| 2:53938709:G:T | intronic | None | |
| 2:53934885:C:T | intronic | None | |
| 2:53907915:C:T | intronic | None | |
| 2:54051530:T:C | intronic | None | |
| 2:54051448:C:G | intronic | None | |
| 2:54052186:A:G | intronic | None | |
| 2:54052992:A:C | intronic | None | |
| 2:53899904:C:T | synonymous | None | |
| 2:53995028:C:A | intronic | None | |
| 2:53958004:A:G | intronic | None | |
| 2:54053847:A:G | intronic | None | |
| 2:53733092:C:T | intronic | 2:53765485:G:C,2:53765485:G:C | 0.83,0.83 |
| 2:53822332:G:A | intergenic | None | |
| 2:53720820:C:A | intronic;intronic | 2:53765485:G:C,2:53765485:G:C | 0.83,0.83 |
| 2:53822111:G:A | intergenic | None | |
| 2:53821221:G:A | intergenic | None | |

Figure 15 (cont.)

| Variant (CPRA) | Nonsynonymous variant effect | Gene for nonsynonymous change | Sentinel eQTL in LD (R^2 > 0.8) |
|---|---|---|---|
| 2:53634252:A:G | | | None |
| 2:53899622:C:A | | | None |
| 2:53966056:T:C | | | None |
| 2:53965962:A:G | | | None |
| 2:53893683:G:A | | | None |
| 2:53812428:C:G | | | None |
| 2:53813267:A:G | | | None |
| 2:53965020:G:A | | | None |
| 2:53921194:C:A | | | None |
| 2:53807744:G:T | | | None |
| 2:53938709:G:T | | | None |
| 2:53934885:C:T | | | None |
| 2:53907915:C:T | | | None |
| 2:54051530:T:C | | | None |
| 2:54051448:C:G | | | None |
| 2:54052186:A:G | | | None |
| 2:54052992:A:C | | | None |
| 2:53899904:C:T | | | None |
| 2:53995028:C:A | | | None |
| 2:53958004:A:G | | | None |
| 2:54053847:A:G | | | None |
| 2:53733092:C:T | missense,missense | ASB3,GPR75-ASB3 | None |
| 2:53822332:G:A | | | None |
| 2:53720820:C:A | missense,missense | ASB3,GPR75-ASB3 | None |
| 2:53822111:G:A | | | None |
| 2:53821221:G:A | | | None |

Figure 15 (cont.)

| Exposure | Excluded genetic variants | Number of genetic variants left in the analysis | Beta (95% CI) per allele in SD units of BMI | p |
|---|---|---|---|---|
| GPR75 pLOF genetic variants with AAF < 1% | None (main analysis as reported in Table 1) | 46 | -0.34 (-0.46, -0.22) | 2.6E-08 |
| | 2:53853134:T:G | 45 | -0.34 (-0.46, -0.22) | 2.5E-08 |
| | 2:53853135:T:G | 45 | -0.33 (-0.45, -0.22) | 3.9E-08 |
| | 2:53853136:A:C | 45 | -0.34 (-0.45, -0.22) | 3.9E-08 |
| | 2:53853200:GGT:G | 45 | -0.34 (-0.46, -0.22) | 3.0E-08 |
| | 2:53853245:GT:G | 45 | -0.34 (-0.46, -0.22) | 2.7E-08 |
| | 2:53853256:G:A | 45 | -0.33 (-0.45, -0.22) | 3.9E-08 |
| | 2:53853352:G:A | 45 | -0.36 (-0.49, -0.24) | 4.9E-09 |
| | 2:53853354:CCA:C | 45 | -0.36 (-0.48, -0.24) | 8.1E-09 |
| | 2:53853382:TG:T | 45 | -0.35 (-0.48, -0.23) | 3.6E-08 |
| | 2:53853502:T:A | 45 | -0.33 (-0.45, -0.21) | 7.0E-08 |
| | 2:53853535:G:A | 45 | -0.34 (-0.47, -0.22) | 5.5E-08 |
| | 2:53853547:T:A | 45 | -0.33 (-0.45, -0.21) | 8.4E-08 |
| | 2:53853560:G:GA | 45 | -0.33 (-0.45, -0.21) | 6.2E-08 |

Figure 17

| Exposure | Excluded genetic variants | Number of genetic variants left in the analysis | Beta (95% CI) per allele in SD units of BMI | p |
|---|---|---|---|---|
| GPR75 pLOF genetic variants with AAF < 1% | 2:53853641:GTT:G | 45 | -0.34 (-0.46, -0.22) | 2.8E-08 |
| | 2:53853680:CAATTCAAAC TGGT:C | 45 | -0.34 (-0.46, -0.22) | 2.4E-08 |
| | 2:53853692:G:T | 45 | -0.34 (-0.46, -0.22) | 1.9E-08 |
| | 2:53853730:G:A | 45 | -0.34 (-0.46, -0.22) | 2.3E-08 |
| | 2:53853771:G:C | 45 | -0.34 (-0.46, -0.22) | 2.2E-08 |
| | 2:53853853:G:A | 45 | -0.34 (-0.46, -0.22) | 2.2E-08 |
| | 2:53853877:G:A | 45 | -0.33 (-0.45, -0.21) | 1.2E-07 |
| | 2:53853926:G:T | 45 | -0.33 (-0.45, -0.21) | 5.9E-08 |
| | 2:53853927:T:TA | 45 | -0.34 (-0.46, -0.22) | 3.0E-08 |
| | 2:53853946:G:GT | 45 | -0.33 (-0.45, -0.21) | 5.4E-08 |
| | 2:53853967:TGG:T | 45 | -0.34 (-0.46, -0.22) | 1.9E-08 |
| | 2:53854009:G:A | 45 | -0.34 (-0.46, -0.22) | 2.1E-08 |
| | 2:53854037:A:AG | 45 | -0.33 (-0.45, -0.21) | 4.6E-08 |
| | 2:53854045:ACTTT:A | 45 | -0.34 (-0.46, -0.21) | 1.0E-07 |

Figure 17 (cont.)

| Exposure | Excluded genetic variants | Number of genetic variants left in the analysis | Beta (95% CI) per allele in SD units of BMI | p |
|---|---|---|---|---|
| *GPR75* pLOF genetic variants with AAF < 1% | 2:53854051:T:A | 45 | -0.33 (-0.45, -0.21) | 8.5E-08 |
| | 2:53854057:G:A | 45 | -0.34 (-0.47, -0.2) | 4.7E-07 |
| | 2:53854078:G:A | 45 | -0.34 (-0.46, -0.22) | 1.7E-08 |
| | 2:53854099:CAG:C | 45 | -0.33 (-0.45, -0.21) | 8.9E-08 |
| | 2:53854135:CAT:C | 45 | -0.34 (-0.46, -0.22) | 3.0E-08 |
| | 2:53854137:TAGAG:T | 45 | -0.34 (-0.46, -0.22) | 3.3E-08 |
| | 2:53854306:G:A | 45 | -0.34 (-0.46, -0.22) | 3.1E-08 |
| | 2:53854380:G:C | 45 | -0.34 (-0.46, -0.22) | 2.3E-08 |
| | 2:53854409:A:AG | 45 | -0.34 (-0.46, -0.22) | 2.7E-08 |
| | 2:53854421:ACTACTGG:A | 45 | -0.31 (-0.43, -0.19) | 7.2E-07 |
| | 2:53854474:C:A | 45 | -0.34 (-0.46, -0.22) | 1.8E-08 |
| | 2:53854476:C:CA | 45 | -0.34 (-0.46, -0.23) | 1.4E-08 |
| | 2:53854485:AG:A | 45 | -0.34 (-0.46, -0.22) | 2.3E-08 |
| | 2:53854644:TG:T | 45 | -0.34 (-0.46, -0.21) | 5.6E-08 |
| | 2:53854685:TC:T | 45 | -0.34 (-0.45, -0.22) | 3.5E-08 |

Figure 17 (cont.)

| Exposure | Excluded genetic variants | Number of genetic variants left in the analysis | Beta (95% CI) per allele in SD units of BMI | p |
|---|---|---|---|---|
| GPR75 pLOF genetic variants with AAF < 1% | 2:53854695:G:T | 45 | -0.34 (-0.46, -0.22) | 2.3E-08 |
| | 2:53854740:TG:T | 45 | -0.34 (-0.46, -0.22) | 2.6E-08 |
| | 2:53854755:A:G | 45 | -0.34 (-0.46, -0.22) | 2.1E-08 |
| | 2:53859827:C:T | 45 | -0.33 (-0.45, -0.21) | 4.9E-08 |
| | 5 variants associated with body mass index (Ala110fs, Ser219fs, Gln234*, Cys400fs, Lys404*) | 41 | -0.26 (-0.39, -0.12) | 2.2E-04 |

Figure 17 (cont.)

| Gene | Genetic exposure, variant type | Description | AAF, fraction of 1 | Beta (95% CI) per allele in SD units of BMI | p |
|---|---|---|---|---|---|
| 2:53853547:T:A; GPR75 Lys404* | 404* allele | Single variant exome analysis (AAF<1%) | 1.0E-05 | -1.77 (-3.12, -0.43) | 9.5E-03 |
| 2:53853560:G:GA; GPR75 Cys400fs | 400fs allele | Single variant exome analysis (AAF<1%) | 1.2E-06 | -2.25 (-4.04, -0.47) | 1.3E-02 |
| 2:53854057:G:A; GPR75 Gln234* | 234* allele | Single variant exome analysis (AAF<1%) | 2.9E-05 | -0.35 (-0.64, -0.06) | 1.8E-02 |
| 2:53854099:CAG:C; GPR75 Ser219fs | 219fs allele | Single variant exome analysis (AAF<1%) | 3.5E-06 | -1.16 (-2.19, -0.13) | 2.8E-02 |
| 2:53854421:ACTACTGG:A; GPR75 Ala110fs | 110fs allele | Single variant exome analysis (AAF<1%) | 1.2E-05 | -0.99 (-1.55, -0.42) | 6.2E-04 |

Figure 18

A)
B)
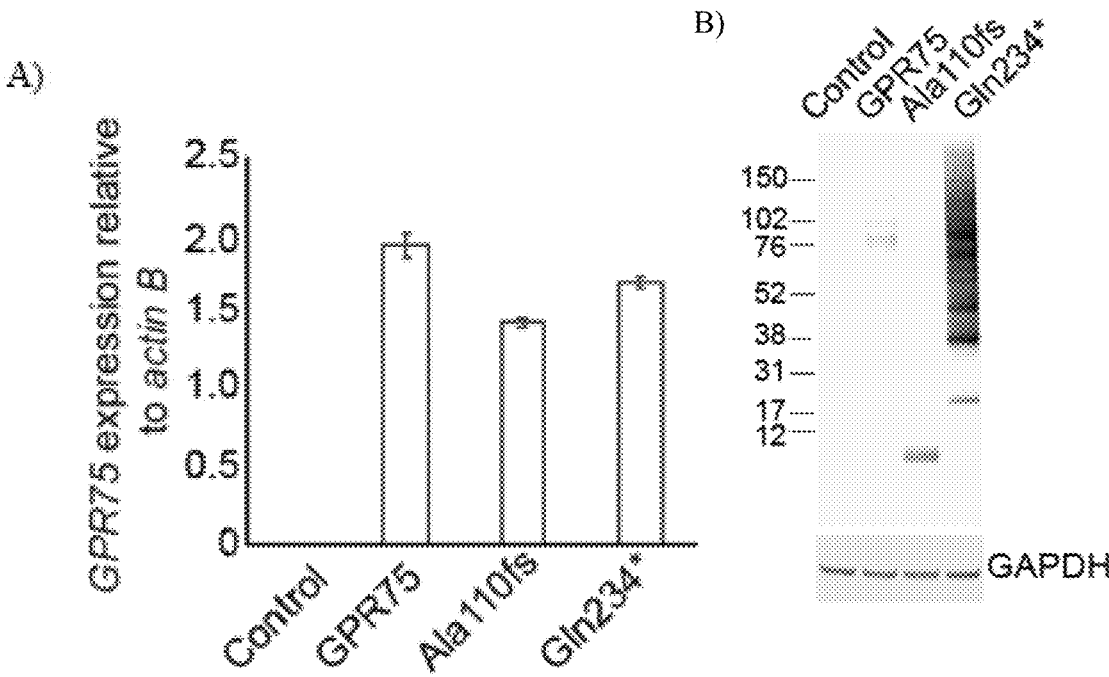
C)
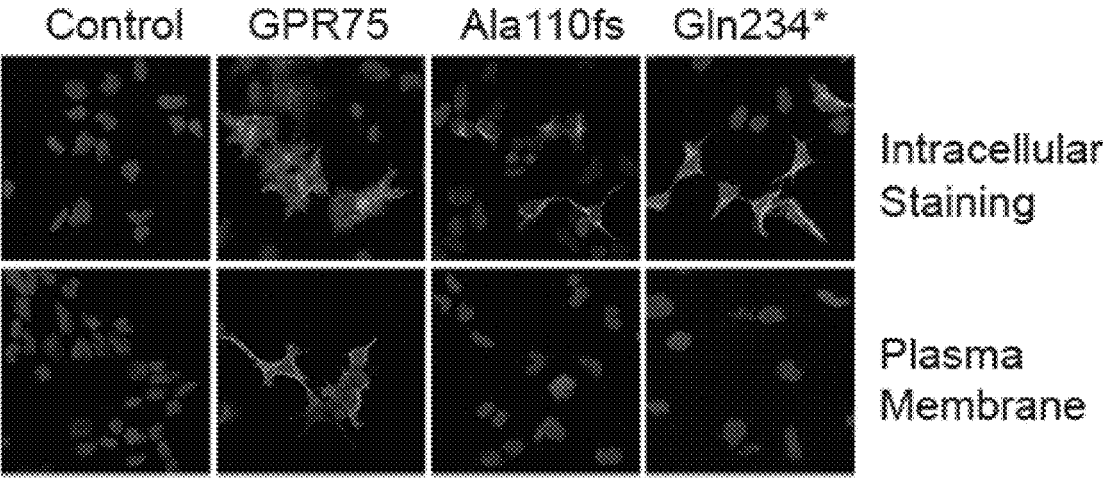
Figure 19

D)
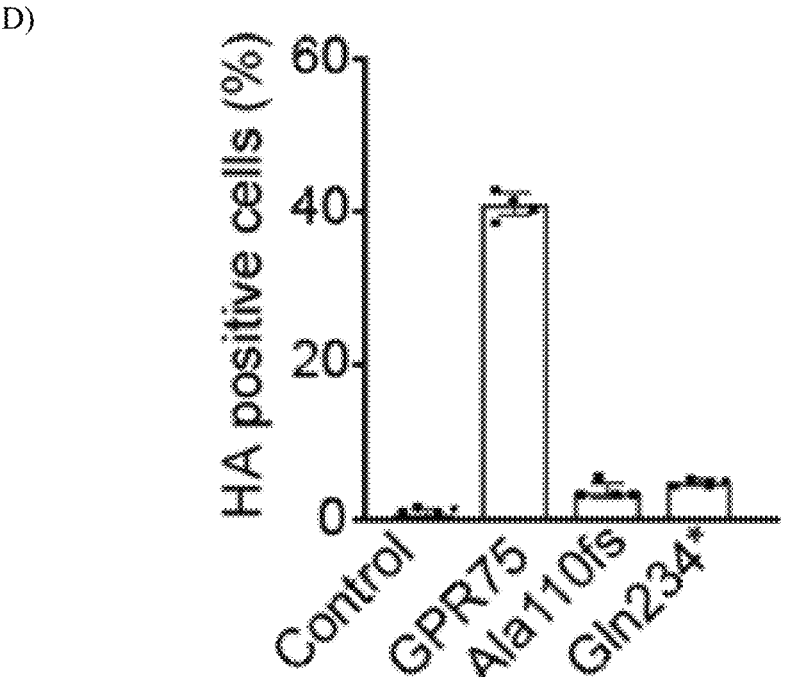
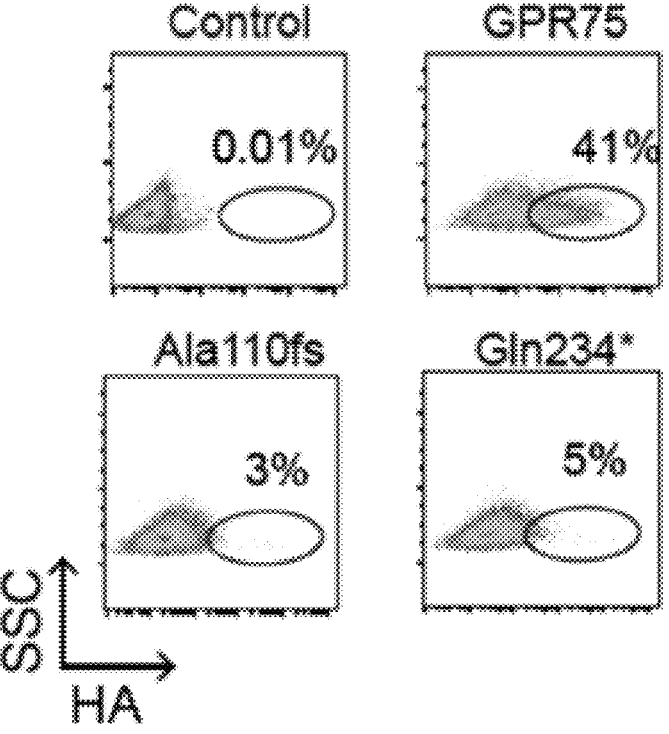
Figure 19 (cont.)

| Exposure | Number of variant sites | Beta (95% CI) per allele in SD units of BMI | p | AAF, fraction of 1 | Genotype counts, RR\|RA\|AA genotypes | Beta (95% CI) per allele in kg/m² units of BMI |
|---|---|---|---|---|---|---|
| N-terminal variants – truncation *before* last intracellular domain | 32 | -0.38 (-0.53, -0.23) | 4.1E-07 | 0.00012 | 645,477\|149\|0 | -2.1 (-2.9, -1.3) |
| C-terminal variants – truncation *within* last intracellular domain | 14 | -0.26 (-0.46, -0.06) | 0.012 | 0.00006 | 645,547\|79\|0 | -1.4 (-2.5, -0.3) |
| N-terminal variants – truncation *before* last 100 amino acids | 37 | -0.4 (0.54, -0.26) | 6.4E-09 | 0.00014 | 645,450\|176\|0 | -2.2 (-2.9, -1.4) |
| C-terminal variants – truncation *within* last 100 amino acids | 9 | -0.13 (-0.38, 0.12) | 0.32 | 0.00004 | 645,574\|52\|0 | -0.7 (-2.1, 0.7) |

Figure 20

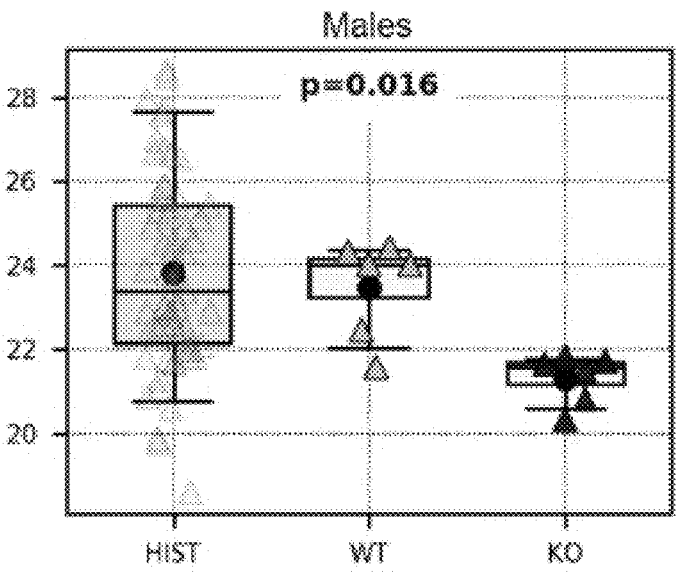
| p-value | EXP/WT ratio | effect-size (95% CI) |
|---------|--------------|----------------------|
| 0.016 | 0.909 | -2.33 (-4.07-0.582) |
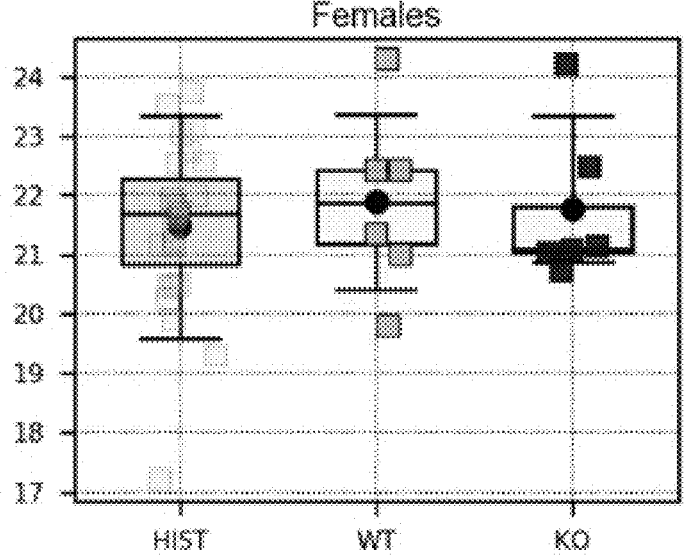
| p-value | EXP/WT ratio | effect-size (95% CI) |
|---------|--------------|----------------------|
| 0.873 | 0.995 | -0.072 (-1.37-1.22) |
Figure 21

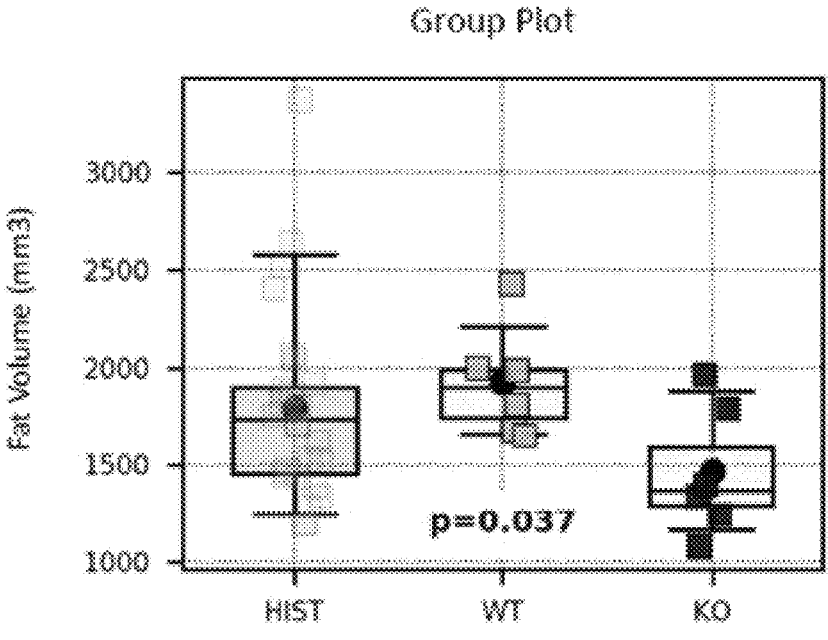
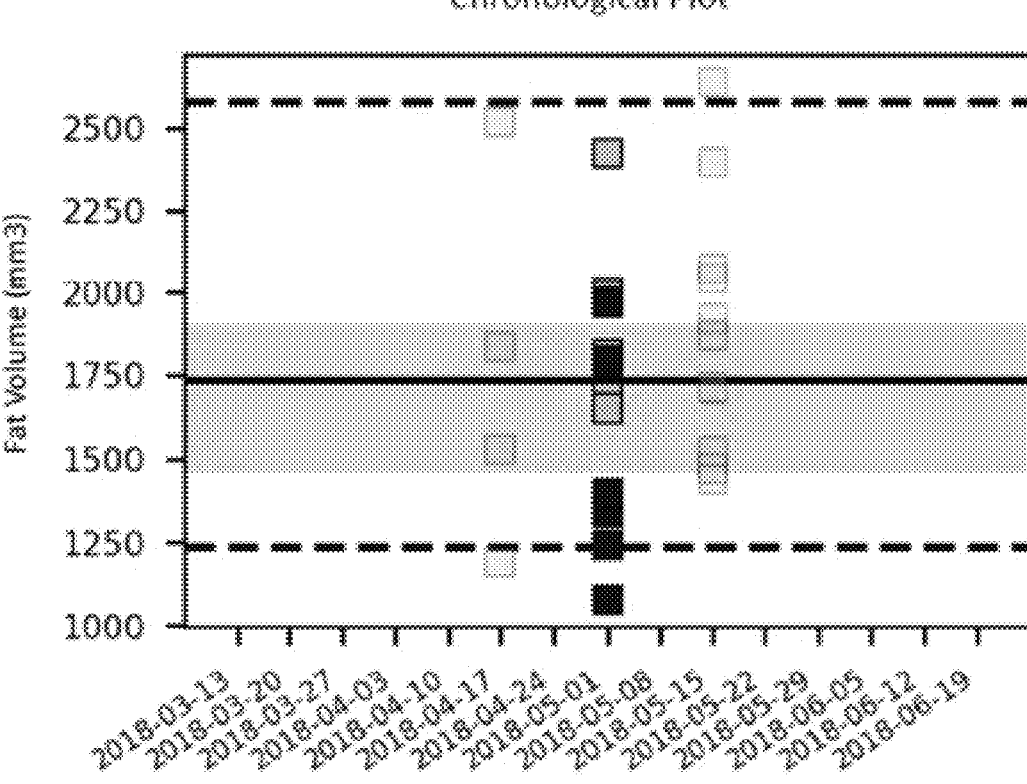
Figure 23

Fat Volume (mm3)

| group | n | mean | std | p05 | med. | p95 |
|-------|----|------|-----|------|------|------|
| WT | 6 | 1926 | 285 | 1666 | 1900 | 2212 |
| KO | 6 | 1469 | 340 | 1160 | 1368 | 1879 |
| HIST | 26 | 1799 | 496 | 1239 | 1736 | 2578 |

| p-value | EXP/WT ratio | effect-size (95% CI) |
|---------|--------------|----------------------|
| 0.037 | 0.763 | -1.45 (-2.94-0.032) |

| group | n | mean | std | p05 | med. | p95 |
|-------|---|------|-----|-----|------|-----|
| WT | 6 | 10.9 | 1.78 | 8.85 | 11.5 | 12.5 |
| KO | 6 | 8.32 | 1.36 | 6.98 | 8.06 | 9.91 |
| HIST | 26 | 10.3 | 2.41 | 7.41 | 9.79 | 14.0 |

| p-value | EXP/WT ratio | effect-size (95% CI) |
|---------|--------------|----------------------|
| 0.025 | 0.760 | -1.66 (-3.20~-0.118) |

A)
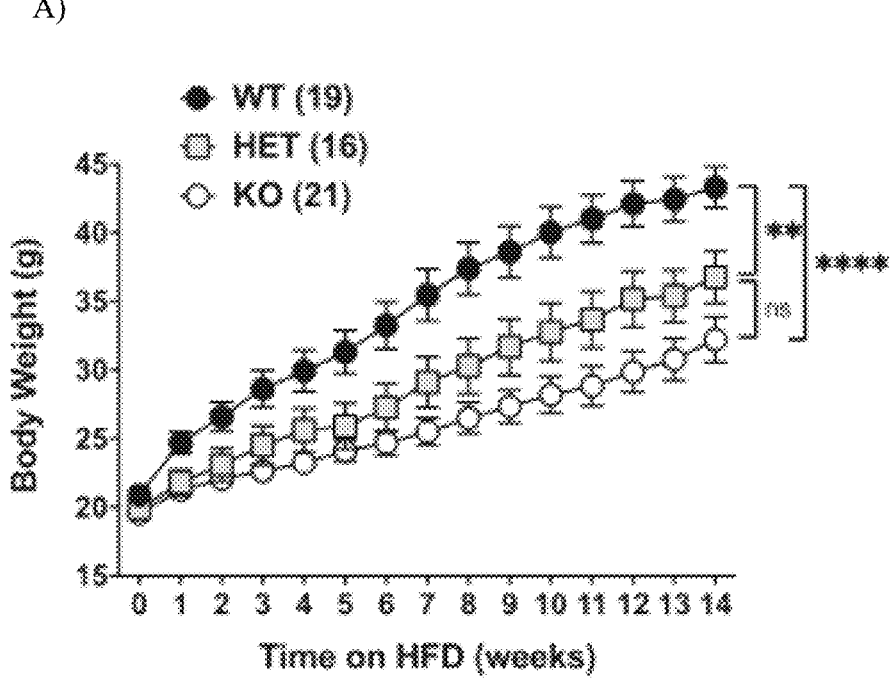
B)
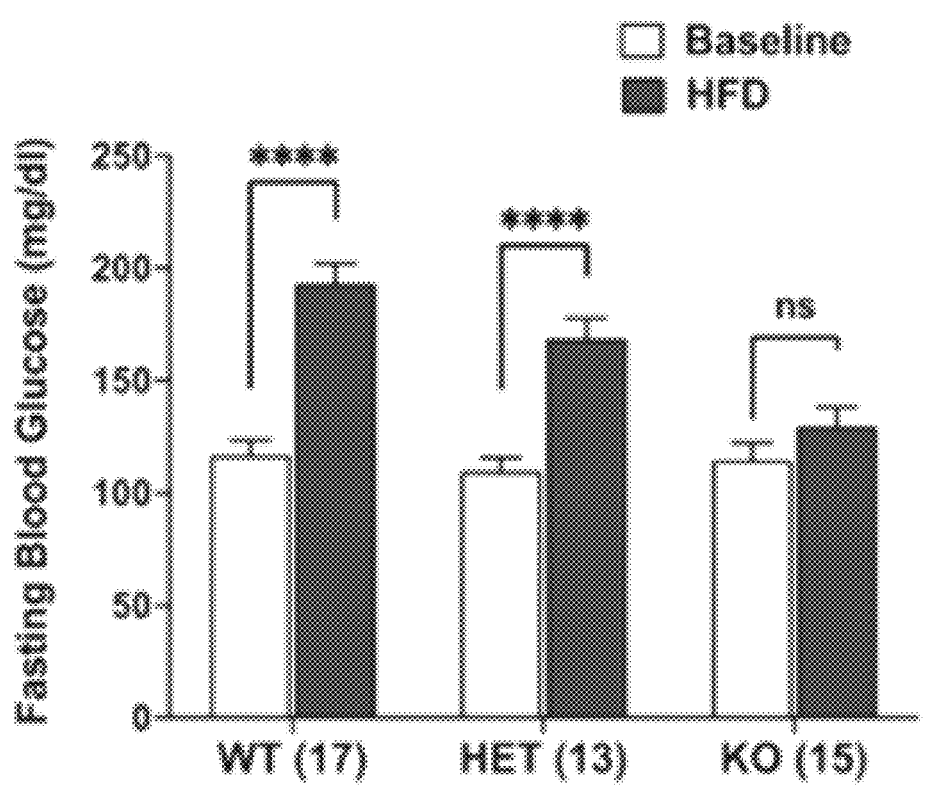
Figure 24

C)
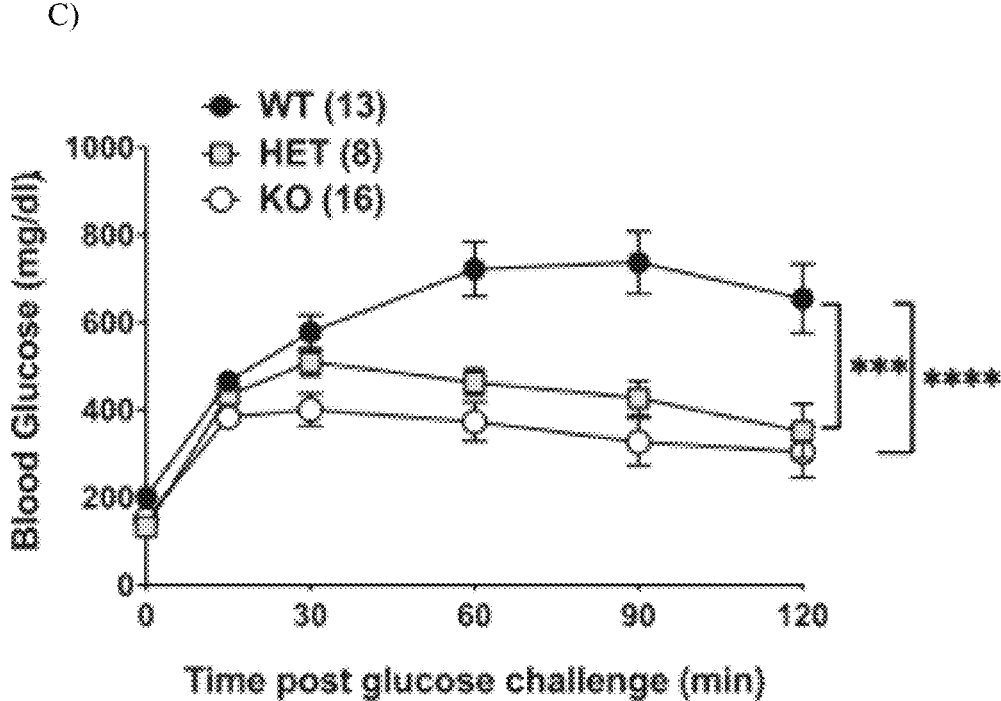
D)
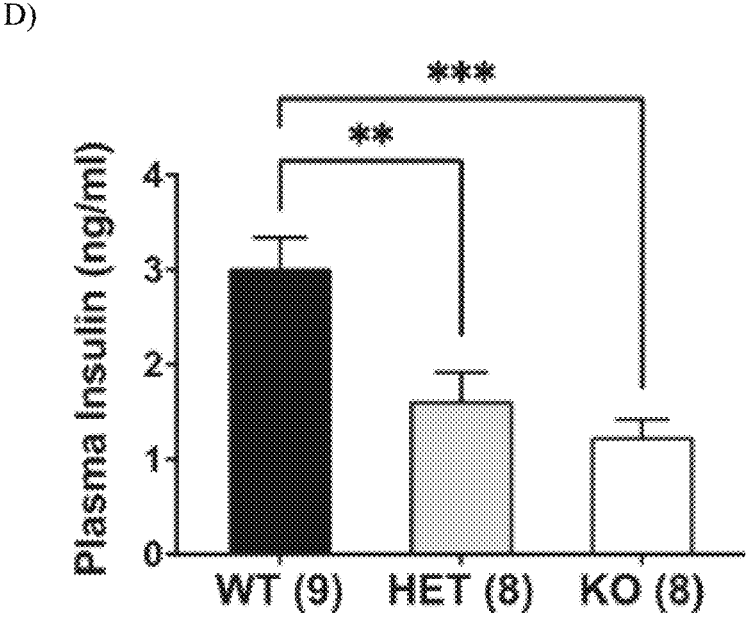
Figure 24 (cont.)

A)
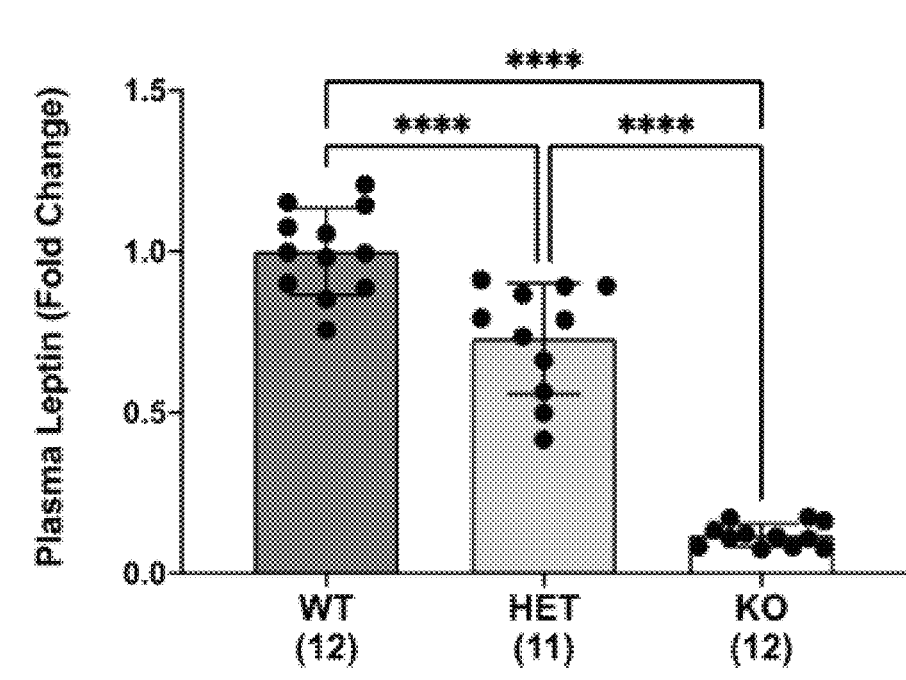
B)
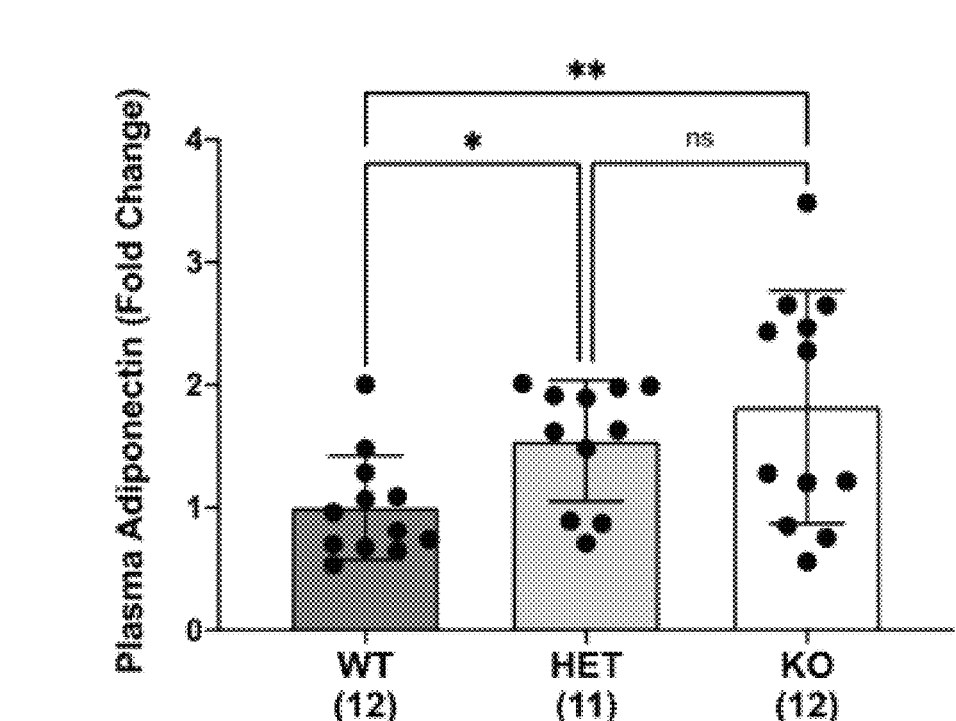
Figure 25

C)

A)

B)

B)

B)

C)

SEQUENCE LISTING

<160> NUMBER OF SEQ ID NOS: 1461

<210> SEQ ID NO 1
<211> LENGTH: 7056
<212> TYPE: DNA
<213> ORGANISM: homo sapien

<400> SEQUENCE: 1

```
gtcttgccgc ggctcccggg atgcgcggag gcggtggcga tggcgatgat gcctctagtc      60
ctgcatcatc cagagcggca ggcggagctg gggtccggac tgcgagatgg aggaggggcg     120
gcgctgcggc cacccggcag gtgagaggcc gcgggcccct ggaggaggac aaccccacga     180
tgccggagac ggctcccgga ggctggcggg atagcgagga gcgcggctgc gctgggccag     240
gcccggctcc gcgtacctgt cttcctggtg cggcctgcag ggtagccttc tcgcccgtcc     300
ctgccggttc ccaggctctg ctcggccgtg gaaccccccc cacccaccca cccaccgccc     360
ctaccctggc tgagccctcc taacccacca cccctctgcg gcattctttt gcaagcttac     420
ctggcccggc ctaggccctc cttaccgtca cctcaccctt ctccgggaag cccctaccca     480
ccgccagccc ctcacggggg ggtcgacctt ccctgcccgc agtttcccac tctgtcctca     540 ggctggggc tccctggcct cttcatccct cccatcaaat gactcaggtc ttcccatccc     600
attagctgct ccgggttcaa tgtagttcta ctggatagaa agagcaaggg ctttgaaatc     660
agataatgac cttggggaag ttatctaacc tccctgaggt tttcctgatc gatagaaata     720
caatgggaat cacaataata cagaaccttg ctctctgtga ggattaggct ttgaaaatgc     780
taacctaaga cattttgggg cgcgcgggga atggggttgg aagaattcag gtcgtgagtt     840
gatttatgaa agcccctata gcatgtttta atgttcacta aaaatttaaa acagcacact     900
agatatatca gaggctgttc acatatctta atgaaaaatc attgccactc aaattataca     960
ataaattttc atccatattc tttgcttgct agttacttca ggatgtctca tttgtaagaa    1020
tatgcatgtg aattcattct tactgcagct aatatgcatg cttaagactg gtgttccagc    1080
ttaaaatctt tctgattttg tgactttaat cacatcttct ataacctatt ctccgtccca    1140
gagatgaaga gtagcttgta tgtttgcatt gcaaataaca tgggtaatct ttattgaata    1200
tttatgagta gcaaagcagt attaatttat tccccttcca aaaccacttt tattttctgc    1260
cgtcatcatg tcattccaaa ttatggtcac agcctccttt ttcttaaagt ctcaggagtt    1320
actactaaga cctgagttta ctttccctcc attttcttga tttctgttat actaaagttt    1380
ttctgcaaac cttttcgtct tttctgtcct ctgctttttc tccctttct cttcccagcc    1440 catgattcct ttttttctaa ttatctcaat aggagtgatt tatgattact ttatatgtga    1500
actacagtta gatacataga agaatgtgtg tgtgtgtgtg tgtgtgtgtg tgtgtgtgtg    1560
tgtgtctatc tgtatctaca tagatgtaga tatagctata taggtgtatc agaatttcgg    1620
attccagaaa gtttcagtgg ggaagggatt gcaataccta ttcataggat tattgtgaga    1680
atgaaataaa gcttgataat ttatgtaaag cctctagaat aggtgcctgg tgtgtaataa    1740
ccacttaata cttctgacct ggggatgcct cccaaaaagg ttttttttgtt gttcgggtta    1800 gcatggtggt gaagagtgtg gaagagcaac tgcttagatt caaatccatg ttccaccact    1860
ttagataacc tctctttgac ttggtttcct catctgcaaa atggagatgt tatatcaagt    1920
atttcagggt tgttatgagg actcaataag ctaatagtgt ggaacattga gaaaagtacc    1980
tggcacatca taagcacttg ataaaattaa tatactaata atgatgctga taattatact    2040
gccattgtta tttcctgacc tggaattctt attttttttta atttactgaa ggctgggtac    2100
```

-continued

```
agtggctcac acctgtaatc tcagcacttt gggaggccaa agcaggcaga ttgcttgagc   2160
ccagaagttg gagaccagtg agggcaacat agtgagactc catctctatt aaaaatatat   2220
atattgaaaa atttaaaatt tgttgaaaaa atgtaactgt acaaaacgtg aaagttgcct   2280
ctcctctacc ccaaatcacc ttttttcctc ctgcctccta ttcttgacta atgttagtgc   2340
ttcatcatct cattttctc ctaatccctt tttccaaata tctcttagcc tgaggtcttc    2400
ataacttcca tcatcccgct tcattattac ctagttactt ttcatttgtc ttagcatcct   2460
aattccagac tcctcattct tctaatttcc ccaggccaaa ttcctgcatc cctcttcacc   2520
cctcttcatc tctctacctc caaagaggaa acccttggag ataaggggt tagagacacc    2580 agtatcacct ccctgctctt cctgcctcct caaattgttt tctcttctac ttcccttttc   2640
ataaattagc tgtaatactc ctgttagcaa ctttttaaaaa cagtaaaaaa ttgtctttct   2700
cggccgggcg cggtggctca cgcctgtaat cccagcactt tgggaggccg aggcgggtgg   2760
atcatgaggt caggagatcg agaccatcct ggctaacaag gtgaaacccc gtctctacta   2820
aaaatacaaa aaaaaatta gccgggcacg gtggcgggcg cctgtagtcc cagctactcg   2880
ggaggctgag gcaggagaat ggcgtgaacc cgggaagcgg agcttgcagt gagccgagat   2940
tgcgccactg cagtccgcag tcccgcctgg gcgacagagc gagactccgt ctcaaaaaaa   3000
aaaaaaaaaa aaaaaaaaaa attgtctttc tcattatata ggtatcaaaa gtgttcagaa   3060
acaaatatac agcctttaag tggaaataga gctatctggt actattttta aaaaattcta   3120
accatcaaga aacaaaagtt caggattttc ttctcttatg gaacttttat ttgaaaggaa   3180
agtatagaaa agttggtctc actttccagt ggacaaattc accatatcgt cctgatctgt   3240
accatatgaa tgttaagaat atagattaag ttatctttt ccttgattaa ggacaccagt    3300
caattatatg gatttcccag gactggtata tgtctgatag tcactggcat ggctgtatct   3360
gttgttaaat gtggagagac ttctgtattg ggtagtccat agctgctaat tggagcccca   3420
ggtaatccct gactgacctg gttcattccg ctgtaccccc ttgatctggc aactaaaggg   3480
ttaacagctg gaggcttctg ggatccagct tgagctggtg gttaagtaca ctgaacatca   3540
gccctggacc tctgcagtgc cacttattgt tcctaaaatt ctagattaag gcaaaccctt   3600
tttggttgtc aagaacatag tgctgtctcc aaggaacagc ttagtcggtc ccaccagaag   3660
catctgttgg gagcaggttg ggcaccaacc cttgcaggac tttgggattt gggacaatgt   3720
agatttgtgt gagtgcacat taagtctcat tgcaaaatag aaaaaaaaaa gttaggaaaa   3780
aggagcaaga agttattctt ttaaagtaga gactgcctta ctcatcgtag cacctagcac   3840
ctggcgtaat gctggcatat ggtatgcaca taattaatat aaattgagcg aacgaatgca   3900
ggaatgggtg catgcctcct gcttcaccat caggatattc ttgttgggat aatggtaact   3960
cacatttata tagcagttta gactttacaa tgtggtgctt tgcaccttgt aaatttctaa   4020
tataattcca acatccttgg ttacttccag ttttccgtct cacatgtagt cctacacaag   4080
gtttttttcc aaaggagaat atgtagttaa ttggccaaga aattgcaagc tggggggaaaa   4140 attataaata ctgggaaata aaggattctt cataggggaac gaaacagggt ttgttaatga   4200
tttatgggaa ttatgtgaag ggccacatta tgcatcaaca atacccctcca gcctatattt   4260 caagcacatg cagttttttg ccgcagtgct tctgctgcaa agacctaccc ccacttctct   4320
tagcctgtct gtccccactc catacccccg acctttcatc cagctggcct gtgcttgcta   4380 aagctcccctt tatcctttcc cagctcccctt tccatgttgg agtaggttcc cccccttccat  4440
```

```
gctctcatag caccctgcaa ccttattagg ctgtaattat tacatagtta gattgatctc    4500
caactagatt gtcatctctt tggtggagag attacgttct tgtgtatctt cagtgcctga    4560
cacagaagtg tttctaaaag taacatctgc acacccctca aacagaatca caaggggcga    4620
ggccaagaaa tctgctctcc aagtgataac ttaaactttt taacatgctc ttcaggtgac    4680
acttaaactt gtttgaaaac ctctgtgtca taaaactaaa tattagctgg atgaatgtat    4740
ttgtatcttt ttctgtgttg gcctttgtga ggagaaatgc tgtctatgca ccaaatcaga    4800
gctgaaaaat tctagtgttt tgttaaaaaa aaaaagaga gagagagagc tgggtttggt    4860
ggtgcatgcc tgtagtccca gctacttggg aagctaagcc aggaggactg cttgagcaca    4920
ggagttcaag tccagcctgg gcaacatggt aagaccccat tgctaataaa tgaataaatt    4980
tttctctcaa ggtgagagat actagtacta atactactac taataatgag atcactgtat    5040
gaattccttt ctgtttctac attaatccct ttctgtttct gggtgtgcat ttttgtgtgt    5100
aggcttatct gtcttgggcc tcttttgtca catattgctc atctgtgagc tgaggccctg    5160
actcactgag tatttttggg gagcagaaga aggagacatt tctctccgaa aatgaactca    5220
acaggccacc ttcaggatgc ccccaatgcc acctcgctcc atgtgcctca ctcacaggaa    5280
ggaaacagca cctctctcca ggagggtctt caggatctca tccacacagc caccttggtg    5340
acctgtactt ttctactggc ggtcatcttc tgcctgggtt cctatggcaa cttcattgtc    5400
ttcttgtcct tcttcgatcc agccttcagg aaattcagaa ccaactttga tttcatgatc    5460
ctgaacctgt ccttctgtga cctcttcatt tgtggagtga cagcccccat gttccacttt    5520
gtgttattct tcagctcagc cagtagtatc ccggatgctt tctgcttcac tttccatctc    5580
accagttcag gcttcatcat catgtctctg aagacagtgg cagtgatcgc cctgcaccgg    5640
ctccggatgg tgttggggaa acagcctaat cgcacggcct cctttccctg caccgtactc    5700
ctcaccctgc ttctctgggc caccagtttc accccttgcca ccttggctac cttgaaaacc    5760
agcaagtccc acctctgtct tcccatgtcc agtctgattg ctggaaaagg gaaagccatt    5820
ttgtctctct atgtggtcga cttcaccttc tgtgttgctg tggtctctgt ctcttacatc    5880
atgattgctc agaccctgcg gaagaacgct caagtcagaa agtgcccccc tgtaatcaca    5940
gtcgatgctt ccagaccaca gcctttcatg ggggtccctg tgcagggagg tggagatccc    6000
atccagtgtg ccatgccggc tctgtatagg aaccagaatt acaacaaact gcagcacgtt    6060
cagacccgtg gatataccaa gagtcccaac caactggtca cccctgcagc aagccgactc    6120
cagctcgtat cagccatcaa cctctccact gccaaggatt ccaaagccgt ggtcacctgt    6180
gtgatcattg tgctgtcagt cctggtgtgc tgtcttccac tggggatttc cttggtacag    6240
gtggttctct ccagcaatgg gagcttcatt ctttaccagt ttgaattgtt tggatttact    6300
cttatatttt tcaagtcagg attaaaccct tttatatatt ctcggaacag tgcagggctg    6360
agaaggaaag tgctctggtg cctccaatac ataggcctgg gttttttctg ctgcaaacaa    6420
aagactcgac ttcgagccat gggaaaaggg aacctcgaag tcaacagaaa caaatcctcc    6480
catcatgaaa caaactctgc ctacatgtta tctccaaagc cacagaagaa atttgtggac    6540
caggcttgtg gccaagtca ttcaaaagaa agtatggtga gtcccaagat ctctgctgga    6600
catcaacact gtggtcagag cagctcgacc cccatcaaca ctcggattga accttactac    6660
agcatctata acagcagccc ttcccaggag gagagcagcc catgtaactt acagccagta    6720
aactcttttg gatttgccaa ttcatatatt gccatgcatt atcacaccac taatgactta    6780
gtgcaggaat atgacagcac ttcagccaag cagattccag tcccctccgt ttaaagtcat    6840
```

```
ggaggctata ggatcttatg taaacagttt ttgtttctga tagtaatgga ctttattcta    6900
acttgagatc agtggcggat caaaacctac aagattcaac tgaaaagttg gcagttatgg    6960
ttttctttca tctgatgtgt cagtatctgt tgatttgctt tgtagtttgt tgacatctta    7020
agatttgatg tgaaagtttt agatttttta ccctgc                             7056

<210> SEQ ID NO 2
<211> LENGTH: 7049
<212> TYPE: DNA
<213> ORGANISM: homo sapien

<400> SEQUENCE: 2
gtcttgccgc ggctcccggg atgcgcggag gcggtggcga tggcgatgat gcctctagtc      60
ctgcatcatc cagagcggca ggcggagctg gggtccggac tgcgagatgg aggaggggcg     120
gcgctgcggc cacccggcag gtgagaggcc gcgggcccct ggaggaggac aaccccacga     180
tgccggagac ggctcccgga ggctggcggg atagcgagga gcgcggctgc gctgggccag     240
gcccggctcc gcgtacctgt cttcctggtg cggcctgcag ggtagccttc tcgcccgtcc     300
ctgccggttc ccaggctctg ctcggccgtg gaacccccc cacccaccca cccaccgccc      360
ctaccctggc tgagccctcc taacccacca cccctctgcg gcattctttt gcaagcttac     420
ctggcccggc ctaggccctc cttaccgtca cctcaccctt ctccgggaag ccctacccca    480
ccgccagccc ctcacggggg ggtcgacctt ccctgcccgc agtttcccac tctgtcctca    540
ggctgggggc tccctggcct cttcatccct cccatcaaat gactcaggtc ttcccatccc    600
attagctgct ccgggttcaa tgtagttcta ctggatagaa agagcaaggg ctttgaaatc     660
agataatgac cttggggaag ttatctaacc tccctgaggt tttcctgatc gatagaaata     720
caatgggaat cacaataata cagaaccttg ctctctgtga ggattaggct ttgaaaatgc     780
taacctaaga cattttgggg cgcgcgggga atggggttgg aagaattcag gtcgtgagtt     840
gatttatgaa agcccctata gcatgtttta atgttcacta aaaatttaaa acagcacact     900
agatatatca gaggctgttc acatatctta atgaaaaatc attgccactc aaattataca     960
ataaattttc atccatattc tttgcttgct agttacttca ggatgtctca tttgtaagaa    1020
tatgcatgtg aattcattct tactgcagct aatatgcatg cttaagactg gtgttccagc    1080
ttaaaatctt tctgattttg tgactttaat cacatcttct ataacctatt ctccgtccca    1140
gagatgaaga gtagcttgta tgtttgcatt gcaaataaca tgggtaatct ttattgaata    1200
tttatgagta gcaaagcagt attaatttat tccccttcca aaaccacttt tattttctgc    1260
cgtcatcatg tcattccaaa ttatggtcac agcctccttt ttcttaaagt ctcaggagtt    1320
actactaaga cctgagttta ctttccctcc attttcttga tttctgttat actaaagttt    1380
ttctgcaaac cttttcgtct tttctgtcct ctgctttttc tccttttct cttcccagcc     1440 catgattcct tttttctaa ttatctcaat aggagtgatt tatgattact ttatatgtga     1500
actacagtta gatacataga agaatgtgtg tgtgtgtgtg tgtgtgtgtg tgtgtgtgtg    1560
tgtgtctatc tgtatctaca tagatgtaga tatagctata taggtgtatc agaatttcgg    1620
attccagaaa gtttcagtgg ggaagggatt gcaataccta ttcataggat tattgtgaga    1680
atgaaataaa gcttgataat ttatgtaaag cctctagaat aggtgcctgg tgtgtaataa    1740
ccacttaata cttctgacct ggggatgcct cccaaaaagg ttttttttgtt gttcgggtta    1800 gcatggtggt gaagagtgtg gaagagcaac tgcttagatt caaatccatg ttccaccact    1860
```

-continued

```
ttagataacc tctctttgac ttggtttcct catctgcaaa atggagatgt tatatcaagt    1920
atttcagggt tgttatgagg actcaataag ctaatagtgt ggaacattga gaaaagtacc    1980
tggcacatca taagcacttg ataaaattaa tatactaata atgatgctga taattatact    2040
gccattgtta tttcctgacc tggaattctt attttttttta atttactgaa ggctgggtac    2100
agtggctcac acctgtaatc tcagcacttt gggaggccaa agcaggcaga ttgcttgagc    2160
ccagaagttg gagaccagtg agggcaacat agtgagactc catctctatt aaaaatatat    2220
atattgaaaa atttaaaatt tgttgaaaaa atgtaactgt acaaacgtg aaagttgcct     2280 ctcctctacc ccaaatcacc ttttttcctc ctgcctccta ttcttgacta atgttagtgc    2340
ttcatcatct cattttctc ctaatccctt tttccaaata tctcttagcc tgaggtcttc     2400
ataacttcca tcatcccgct tcattattac ctagttactt ttcatttgtc ttagcatcct    2460
aattccagac tcctcattct tctaatttcc ccaggccaaa ttcctgcatc cctcttcacc    2520
cctcttcatc tctctacctc caaagaggaa acccttggag ataagggggt tagagacacc    2580
agtatcacct ccctgctctt cctgcctcct caaattgttt tctcttctac ttcccttttc    2640
ataaattagc tgtaatactc ctgttagcaa cttttaaaaa cagtaaaaaa ttgtctttct    2700
cggccgggcg cggtggctca cgcctgtaat cccagcactt tgggaggccg aggcgggtgg    2760
atcatgaggt caggagatcg agaccatcct ggctaacaag gtgaaacccc gtctctacta    2820
aaaatacaaa aaaaaaatta gccgggcacg gtggcgggcg cctgtagtcc cagctactcg    2880
ggaggctgag gcaggagaat ggcgtgaacc cgggaagcgg agcttgcagt gagccgagat    2940
tgcgccactg cagtccgcag tcccgcctgg gcgacagagc gagactccgt ctcaaaaaaa    3000
aaaaaaaaaa aaaaaaaaaa attgtctttc tcattatata ggtatcaaaa gtgttcagaa    3060
acaaatatac agcctttaag tggaaataga gctatctggt actattttta aaaaattcta    3120
accatcaaga aacaaaagtt caggattttc ttctcttatg gaacttttat ttgaaaggaa    3180
agtatagaaa agttggtctc actttccagt ggacaaattc accatatcgt cctgatctgt    3240
accatatgaa tgttaagaat atagattaag ttatcttttt ccttgattaa ggacaccagt    3300
caattatatg gatttcccag gactggtata tgtctgatag tcactggcat ggctgtatct    3360
gttgttaaat gtggagagac ttctgtattg ggtagtccat agctgctaat tggagcccca    3420
ggtaatccct gactgacctg gttcattccg ctgtaccccc ttgatctggc aactaaaggg    3480
ttaacagctg gaggcttctg ggatccagct tgagctggtg gttaagtaca ctgaacatca    3540
gccctggacc tctgcagtgc cacttattgt tcctaaaatt ctagattaag gcaaacccctt   3600 tttggttgtc aagaacatag tgctgtctcc aaggaacagc ttagtcggtc ccaccagaag    3660
catctgttgg gagcaggttg ggcaccaacc cttgcaggac tttgggattt gggacaatgt    3720
agatttgtgt gagtgcacat taagtctcat tgcaaaatag aaaaaaaaaa gttaggaaaa    3780
aggagcaaga agttattctt ttaaagtaga gactgcctta ctcatcgtag cacctagcac    3840
ctggcgtaat gctggcatat ggtatgcaca taattaatat aaattgagcg aacgaatgca    3900
ggaatgggtg catgcctcct gcttcaccat caggatattc ttgttgggat aatggtaact    3960
cacatttata tagcagttta gactttacaa tgtggtgctt tgcaccttgt aaatttctaa    4020
tataattcca acatccttgg ttacttccag ttttccgtct cacatgtagt cctacacaag    4080
gtttttttcc aaaggagaat atgtagttaa ttggccaaga aattgcaagc tggggggaaaa   4140 attataaata ctgggaaata aaggattctt cataggggaac gaaacagggt ttgttaatga    4200
tttatgggaa ttatgtgaag ggccacatta tgcatcaaca atacccctcca gcctatattt    4260
```

-continued

```
caagcacatg cagttttttg ccgcagtgct tctgctgcaa agacctaccc ccacttctct   4320
tagcctgtct gtccccactc catacccccg acctttcatc cagctggcct gtgcttgcta   4380
aagctccctt tatcctttcc cagctccctt tccatgttgg agtaggttcc cccccttccat   4440 gctctcatag caccctgcaa ccttattagg ctgtaattat tacatagtta gattgatctc   4500
caactagatt gtcatctctt tggtggagag attacgttct tgtgtatctt cagtgcctga   4560
cacagaagtg tttctaaaag taacatctgc acacccctca aacagaatca caaggggcga   4620
ggccaagaaa tctgctctcc aagtgataac ttaaactttt taacatgctc ttcaggtgac   4680
acttaaactt gtttgaaaac ctctgtgtca taaaactaaa tattagctgg atgaatgtat   4740
ttgtatcttt ttctgtgttg gcctttgtga ggagaaatgc tgtctatgca ccaaatcaga   4800
gctgaaaaat tctagtgttt tgttaaaaaa aaaaagaga gagagagagc tgggtttggt   4860
ggtgcatgcc tgtagtccca gctacttggg aagctaagcc aggaggactg cttgagcaca   4920
ggagttcaag tccagcctgg gcaacatggt aagaccccat tgctaataaa tgaataaatt   4980
tttctctcaa ggtgagagat actagtacta atactactac taataatgag atcactgtat   5040
gaattccttt ctgtttctac attaatccct ttctgtttct gggtgtgcat ttttgtgtgt   5100
aggcttatct gtcttgggcc tcttttgtca catattgctc atctgtgagc tgaggccctg   5160
actcactgag tattttgggg gagcagaaga aggagacatt tctctccgaa aatgaactca   5220
acaggccacc ttcaggatgc ccccaatgcc acctcgctcc atgtgcctca ctcacaggaa   5280
ggaaacagca cctctctcca ggagggtctt caggatctca tccacacagc caccttggtg   5340
acctgtactt ttctactggc ggtcatcttc tgcctgggtt cctatggcaa cttcattgtc   5400
ttcttgtcct tcttcgatcc agccttcagg aaattcagaa ccaactttga tttcatgatc   5460
ctgaacctgt ccttctgtga cctcttcatt tgtggagtga cagcccccat gttcacctttt   5520 gtgttattct tcagctcagt atcccggatg ctttctgctt cactttccat ctcaccagtt   5580
caggcttcat catcatgtct ctgaagacag tggcagtgat cgccctgcac cggctccgga   5640
tggtgttggg gaaacagcct aatcgcacgg cctcctttcc ctgcaccgta ctcctcaccc   5700
tgcttctctg ggccaccagt ttcacccttg ccaccttggc taccttgaaa accagcaagt   5760
cccacctctg tcttcccatg tccagtctga ttgctggaaa agggaaagcc attttgtctc   5820 tctatggt cgacttcacc ttctgtgttg ctgtggtctc tgtctcttac atcatgattg   5880
ctcagaccct gcggaagaac gctcaagtca gaaagtgccc ccctgtaatc acagtcgatg   5940
cttccagacc acagcctttc atggggggtcc ctgtgcaggg aggtggagat cccatccagt   6000
gtgccatgcc ggctctgtat aggaaccaga attacaacaa actgcagcac gttcagaccc   6060
gtggatatac caagagtccc aaccaactgg tcacccctgc agcaagccga ctccagctcg   6120
tatcagccat caacctctcc actgccaagg attccaaagc cgtggtcacc tgtgtgatca   6180
ttgtgctgtc agtcctggtg tgctgtcttc cactgggat ttccttggta caggtggttc   6240
tctccagcaa tgggagcttc attctttacc agtttgaatt gtttggattt actcttatat   6300
ttttcaagtc aggattaaac cctttttatat attctcggaa cagtgcaggg ctgagaagga   6360
aagtgctctg gtgcctccaa tacataggcc tgggtttttt ctgctgcaaa caaaagactc   6420
gacttcgagc catgggaaaa gggaacctcg aagtcaacag aaacaaatcc tcccatcatg   6480
aaacaaactc tgcctacatg ttatctccaa agccacagaa gaaatttgtg gaccaggctt   6540
gtggcccaag tcattcaaaa gaaagtatgg tgagtcccaa gatctctgct ggacatcaac   6600
```

-continued

```
actgtggtca gagcagctcg acccccatca acactcggat tgaaccttac tacagcatct      6660
ataacagcag cccttcccag gaggagagca gcccatgtaa cttacagcca gtaaactctt      6720
ttggatttgc caattcatat attgccatgc attatcacac cactaatgac ttagtgcagg      6780
aatatgacag cacttcagcc aagcagattc cagtcccctc cgtttaaagt catggaggct      6840
ataggatctt atgtaaacag ttttttgtttc tgatagtaat ggactttatt ctaacttgag      6900
atcagtggcg gatcaaaacc tacaagattc aactgaaaag ttggcagtta tggttttctt      6960
tcatctgatg tgtcagtatc tgttgatttg ctttgtagtt tgttgacatc ttaagatttg      7020
atgtgaaagt tttagatttt ttaccctgc                                      7049
```

<210> SEQ ID NO 3
<211> LENGTH: 7056
<212> TYPE: DNA
<213> ORGANISM: homo sapien

<400> SEQUENCE: 3

```
gtcttgccgc ggctcccggg atgcgcggag gcggtggcga tggcgatgat gcctctagtc        60
ctgcatcatc cagagcggca ggcggagctg gggtccggac tgcgagatgg aggaggggcg       120
gcgctgcggc cacccggcag gtgagaggcc gcgggcccct ggaggaggac aaccccacga       180
tgccggagac ggctcccgga ggctggcggg atagcgagga gcgcggctgc gctgggccag       240
gcccggctcc gcgtacctgt cttcctggtg cggcctgcag ggtagccttc tcgcccgtcc       300
ctgccggttc ccaggctctg ctcggccgtg gaacccccccc cacccaccca cccaccgccc       360
ctaccctggc tgagccctcc taacccacca cccctctgcg gcattctttt gcaagcttac       420
ctggcccggc ctaggccctc cttaccgtca cctcacccctt ctccgggaag ccctaccca       480 ccgccagccc ctcacggggg ggtcgacctt ccctgcccgc agtttcccac tctgtcctca       540
ggctgggggc tccctggcct cttcatccct cccatcaaat gactcaggtc ttcccatccc       600
attagctgct ccgggttcaa tgtagttcta ctggatagaa agagcaaggg ctttgaaatc       660
agataatgac cttggggaag ttatctaacc tccctgaggt tttcctgatc gatagaaata       720
caatgggaat cacaataata cagaaccttg ctctctgtga ggattaggct ttgaaaatgc       780
taacctaaga cattttgggg cgcgcgggga atggggttgg aagaattcag gtcgtgagtt       840
gatttatgaa agccctata gcatgtttta atgttcacta aaaatttaaa acagcacact       900
agatatatca gaggctgttc acatatctta atgaaaaatc attgccactc aaattataca       960
ataaattttc atccatattc tttgcttgct agttacttca ggatgtctca tttgtaagaa      1020
tatgcatgtg aattcattct tactgcagct aatatgcatg cttaagactg gtgttccagc      1080
ttaaaatctt tctgattttg tgactttaat cacatcttct ataacctatt ctccgtccca      1140
gagatgaaga gtagcttgta tgtttgcatt gcaaataaca tgggtaatct ttattgaata      1200
tttatgagta gcaaagcagt attaatttat tcccctccca aaaccacttt tattttctgc      1260
cgtcatcatg tcattccaaa ttatggtcac agcctccttt ttcttaaagt ctcaggagtt      1320
actactaaga cctgagttta ctttccctcc attttcttga tttctgttat actaaagttt      1380
ttctgcaaac cttttcgtct tttctgtcct ctgctttttc tcccttttct cttcccagcc      1440
catgattcct tttttctaa ttatctcaat aggagtgatt tatgattact ttatatgtga      1500
actacagtta gatacataga agaatgtgtg tgtgtgtgtg tgtgtgtgtg tgtgtgtgtg      1560
tgtgtctatc tgtatctaca tagatgtaga tatagctata taggtgtatc agaatttcgg      1620
attccagaaa gtttcagtgg ggaagggatt gcaataccta ttcataggat tattgtgaga      1680
```

-continued

```
atgaaataaa gcttgataat ttatgtaaag cctctagaat aggtgcctgg tgtgtaataa    1740
ccacttaata cttctgacct ggggatgcct cccaaaaagg tttttttgtt gttcgggtta    1800
gcatggtggt gaagagtgtg gaagagcaac tgcttagatt caaatccatg ttccaccact    1860
ttagataacc tctctttgac ttggtttcct catctgcaaa atggagatgt tatatcaagt    1920
atttcagggt tgttatgagg actcaataag ctaatagtgt ggaacattga gaaaagtacc    1980
tggcacatca taagcacttg ataaaattaa tatactaata atgatgctga taattatact    2040
gccattgtta tttcctgacc tggaattctt attttttta atttactgaa ggctgggtac    2100
agtggctcac acctgtaatc tcagcacttt gggaggccaa agcaggcaga ttgcttgagc    2160
ccagaagttg gagaccagtg agggcaacat agtgagactc catctctatt aaaaatatat    2220
atattgaaaa atttaaaatt tgttgaaaaa atgtaactgt acaaaacgtg aaagttgcct    2280
ctcctctacc ccaaatcacc ttttttcctc ctgcctccta ttcttgacta atgttagtgc    2340
ttcatcatct cattttctc ctaatccctt tttccaaata tctcttagcc tgaggtcttc     2400
ataacttcca tcatcccgct tcattattac ctagttactt ttcatttgtc ttagcatcct    2460
aattccagac tcctcattct tctaatttcc ccaggccaaa ttcctgcatc cctcttcacc    2520
cctcttcatc tctctacctc caaagaggaa acccttggag ataaggggt tagagacacc     2580 agtatcacct ccctgctctt cctgcctcct caaattgttt tctcttctac ttcccttttc    2640
ataaattagc tgtaatactc ctgttagcaa cttttaaaaa cagtaaaaaa ttgtctttct    2700
cggccgggcg cggtggctca cgcctgtaat cccagcactt tgggaggccg aggcgggtgg    2760
atcatgaggt caggagatcg agaccatcct ggctaacaag gtgaaacccc gtctctacta    2820
aaaatacaaa aaaaaaatta gccgggcacg gtggcgggcg cctgtagtcc cagctactcg    2880
ggaggctgag gcaggagaat ggcgtgaacc cgggaagcgg agcttgcagt gagccgagat    2940
tgcgccactg cagtccgcag tcccgcctgg gcgacagagc gagactccgt ctcaaaaaaa    3000
aaaaaaaaaa aaaaaaaaa attgtctttc tcattatata ggtatcaaaa gtgttcagaa     3060
acaaatatac agcctttaag tggaaataga gctatctggt actattttta aaaaattcta    3120
accatcaaga aacaaaagtt caggattttc ttctcttatg gaactttat ttgaaaggaa     3180 agtatagaaa agttggtctc actttccagt ggacaaattc accatatcgt cctgatctgt    3240
accatatgaa tgttaagaat atagattaag ttatcttttt ccttgattaa ggacaccagt    3300
caattatatg gatttcccag gactggtata tgtctgatag tcactggcat ggctgtatct    3360
gttgttaaat gtggagagac ttctgtattg ggtagtccat agctgctaat tggagcccca    3420
ggtaatccct gactgacctg gttcattccg ctgtaccccc ttgatctggc aactaaaggg    3480
ttaacagctg gaggcttctg ggatccagct tgagctggtg gttaagtaca ctgaacatca    3540
gccctggacc tctgcagtgc cacttattgt tcctaaaatt ctagattaag gcaaaccctt    3600
tttggttgtc aagaacatag tgctgtctcc aaggaacagc ttagtcggtc ccaccagaag    3660
catctgttgg gagcaggttg ggcaccaacc cttgcaggac tttgggattt gggacaatgt    3720
agatttgtgt gagtgcacat taagtctcat tgcaaaatag aaaaaaaaaa gttaggaaaa    3780
aggagcaaga agttattctt ttaaagtaga gactgcctta ctcatcgtag cacctagcac    3840
ctggcgtaat gctggcatat ggtatgcaca taattaatat aaattgagcg aacgaatgca    3900
ggaatgggtg catgcctcct gcttcaccat caggatattc ttgttgggat aatggtaact    3960
cacatttata tagcagttta gactttacaa tgtggtgctt tgcaccttgt aaatttctaa    4020
```

-continued

```
tataattcca acatccttgg ttacttccag ttttccgtct cacatgtagt cctacacaag    4080
gtttttttcc aaaggagaat atgtagttaa ttggccaaga aattgcaagc tggggggaaaa    4140 attataaata ctgggaaata aaggattctt catagggaac gaaacagggt ttgttaatga    4200
tttatgggaa ttatgtgaag ggccacatta tgcatcaaca ataccctcca gcctatattt    4260
caagcacatg cagttttttg ccgcagtgct tctgctgcaa agacctaccc ccacttctct    4320
tagcctgtct gtccccactc catcccccg acctttcatc cagctggcct gtgcttgcta    4380
aagctccctt tatcctttcc cagctccctt tccatgttgg agtaggttcc cccttccat    4440 gctctcatag caccctgcaa ccttattagg ctgtaattat tacatagtta gattgatctc    4500
caactagatt gtcatctctt tggtggagag attacgttct tgtgtatctt cagtgcctga    4560
cacagaagtg tttctaaaag taacatctgc acacccctca aacagaatca caaggggcga    4620
ggccaagaaa tctgctctcc aagtgataac ttaaactttt taacatgctc ttcaggtgac    4680
acttaaactt gtttgaaaac ctctgtgtca taaaactaaa tattagctgg atgaatgtat    4740
ttgtatcttt ttctgtgttg gcctttgtga ggagaaatgc tgtctatgca ccaaatcaga    4800
gctgaaaaat tctagtgttt tgttaaaaaa aaaaagaga gagagagagc tgggtttggt    4860
ggtgcatgcc tgtagtccca gctacttggg aagctaagcc aggaggactg cttgagcaca    4920
ggagttcaag tccagcctgg gcaacatggt aagaccccat tgctaataaa tgaataaatt    4980
tttctctcaa ggtgagagat actagtacta atactactac taataatgag atcactgtat    5040
gaattccttt ctgtttctac attaatccct ttctgtttct gggtgtgcat ttttgtgtgt    5100
aggcttatct gtcttgggcc tcttttgtca catattgctc atctgtgagc tgaggccctg    5160
actcactgag tatttttggg gagcagaaga aggagacatt tctctccgaa aatgaactca    5220
acaggccacc ttcaggatgc ccccaatgcc acctcgctcc atgtgcctca ctcacaggaa    5280
ggaaacagca cctctctcca ggagggtctt caggatctca tccacacagc caccttggtg    5340
acctgtactt ttctactggc ggtcatcttc tgcctgggtt cctatggcaa cttcattgtc    5400
ttcttgtcct tcttcgatcc agccttcagg aaattcagaa ccaactttga tttcatgatc    5460
ctgaacctgt ccttctgtga cctcttcatt tgtggagtga cagcccccat gttcaccttt    5520
gtgttattct tcagctcagc cagtagtatc ccggatactt tctgcttcac tttccatctc    5580
accagttcag gcttcatcat catgtctctg aagacagtgg cagtgatcgc cctgcaccgg    5640
ctccggatgg tgttggggaa acagcctaat cgcacggcct cctttccctg caccgtactc    5700
ctcaccctgc ttctctgggc caccagtttc acccttgcca ccttggctac cttgaaaacc    5760
agcaagtccc acctctgtct tcccatgtcc agtctgattg ctggaaaagg gaaagccatt    5820
ttgtctctct atgtggtcga cttcaccttc tgtgttgctg tggtctctgt ctcttacatc    5880
atgattgctc agaccctgcg gaagaacgct caagtcagaa agtgcccccc tgtaatcaca    5940
gtcgatgctt ccagaccaca gcctttcatg ggggtccctg tgcagggagg tggagatccc    6000
atccagtgtg ccatgccggc tctgtatagg aaccagaatt acaacaaact gcagcacgtt    6060
cagacccgtg gatataccaa gagtcccaac caactggtca ccctgcagc aagccgactc    6120 cagctcgtat cagccatcaa cctctccact gccaaggatt ccaaagccgt ggtcacctgt    6180
gtgatcattg tgctgtcagt cctggtgtgc tgtcttccac tgggggattc cttggtacag    6240
gtggttctct ccagcaatgg gagcttcatt ctttaccagt ttgaattgtt tggatttact    6300
cttatatttt tcaagtcagg attaaaccct tttatatatt ctcggaacag tgcagggctg    6360
agaaggaaag tgctctggtg cctccaatac ataggcctgg gttttttctg ctgcaaacaa    6420
```

-continued

```
aagactcgac ttcgagccat gggaaaaggg aacctcgaag tcaacagaaa caaatcctcc      6480
catcatgaaa caaactctgc ctacatgtta tctccaaagc cacagaagaa atttgtggac      6540
caggcttgtg gcccaagtca ttcaaaagaa agtatggtga gtcccaagat ctctgctgga      6600
catcaacact gtggtcagag cagctcgacc cccatcaaca ctcggattga accttactac      6660
agcatctata acagcagccc ttcccaggag gagagcagcc catgtaactt acagccagta      6720
aactcttttg gatttgccaa ttcatatatt gccatgcatt atcacaccac taatgactta      6780
gtgcaggaat atgacagcac ttcagccaag cagattccag tcccctccgt ttaaagtcat      6840
ggaggctata ggatcttatg taaacagttt ttgtttctga tagtaatgga ctttattcta      6900
acttgagatc agtggcggat caaaacctac aagattcaac tgaaaagttg gcagttatgg      6960
ttttctttca tctgatgtgt cagtatctgt tgatttgctt tgtagtttgt tgacatctta      7020
agatttgatg tgaaagtttt agattttta ccctgc                                7056
```

<210> SEQ ID NO 4
<211> LENGTH: 7056
<212> TYPE: DNA
<213> ORGANISM: homo sapien

<400> SEQUENCE: 4

```
gtcttgccgc ggctcccggg atgcgcggag gcggtggcga tggcgatgat gcctctagtc        60
ctgcatcatc cagagcggca ggcggagctg gggtccggac tgcgagatgg aggagggggcg       120 gcgctgcggc cacccggcag gtgagaggcc gcgggcccct ggaggaggac aaccccacga       180
tgccggagac ggctcccgga ggctggcggg atagcgagga gcgcggctgc gctgggccag       240
gcccggctcc gcgtacctgt cttcctggtg cggcctgcag ggtagccttc tcgcccgtcc       300
ctgccggttc ccaggctctg ctcggccgtg gaaccccccc cacccaccca cccaccgccc       360
ctaccctggc tgagccctcc taacccacca cccctctgcg gcattctttt gcaagcttac       420
ctggcccggc ctaggccctc cttaccgtca cctcaccctt ctccgggaag ccctacccca       480
ccgccagccc ctcacggggg ggtcgacctt ccctgcccgc agtttcccac tctgtcctca       540 ggctggggggc tccctggcct cttcatccct cccatcaaat gactcaggtc ttcccatccc       600
attagctgct ccgggttcaa tgtagttcta ctggatagaa agagcaaggg ctttgaaatc       660
agataatgac cttggggaag ttatctaacc tccctgaggt tttcctgatc gatagaaata       720
caatgggaat cacaataata cagaaccttg ctctctgtga ggattaggct ttgaaaatgc       780
taacctaaga cattttgggg cgcgcgggga atggggttgg aagaattcag gtcgtgagtt       840
gatttatgaa agcccctata gcatgtttta atgttcacta aaaatttaaa acagcacact       900
agatatatca gaggctgttc acatatctta atgaaaaatc attgccactc aaattataca       960
ataaattttc atccatattc tttgcttgct agttacttca ggatgtctca tttgtaagaa      1020
tatgcatgtg aattcattct tactgcagct aaatatgcatg cttaagactg gtgttccagc      1080
ttaaaatctt tctgattttg tgactttaat cacatcttct ataacctatt ctccgtccca      1140
gagatgaaga gtagcttgta tgtttgcatt gcaaataaca tgggtaatct ttattgaata      1200
tttatgagta gcaaagcagt attaatttat tccccttcca aaaccacttt tattttctgc      1260
cgtcatcatg tcattccaaa ttatggtcac agcctccttt ttcttaaagt ctcaggagtt      1320
actactaaga cctgagttta ctttccctcc attttcttga tttctgttat actaaagttt      1380
ttctgcaaac ctttcgtct tttctgtcct ctgcttttc tcccttttct cttcccagcc        1440
```

```
catgattcct tttttttctaa ttatctcaat aggagtgatt tatgattact ttatatgtga      1500
actacagtta gatacataga agaatgtgtg tgtgtgtgtg tgtgtgtgtg tgtgtgtgtg      1560
tgtgtctatc tgtatctaca tagatgtaga tatagctata taggtgtatc agaatttcgg      1620
attccagaaa gtttcagtgg ggaagggatt gcaataccta ttcataggat tattgtgaga      1680
atgaaataaa gcttgataat ttatgtaaag cctctagaat aggtgcctgg tgtgtaataa      1740
ccacttaata cttctgacct ggggatgcct cccaaaaagg ttttttttgtt gttcgggtta      1800 gcatggtggt gaagagtgtg gaagagcaac tgcttagatt caaatccatg ttccaccact      1860
ttagataacc tctctttgac ttggtttcct catctgcaaa atggagatgt tatatcaagt      1920
atttcagggt tgttatgagg actcaataag ctaatagtgt ggaacattga gaaaagtacc      1980
tggcacatca taagcacttg ataaaattaa tatactaata atgatgctga taattatact      2040
gccattgtta tttcctgacc tggaattctt atttttttta atttactgaa ggctgggtac      2100
agtggctcac acctgtaatc tcagcacttt gggaggccaa agcaggcaga ttgcttgagc      2160
ccagaagttg gagaccagtg agggcaacat agtgagactc catctctatt aaaaatatat      2220
atattgaaaa atttaaaatt tgttgaaaaa atgtaactgt acaaacgtg aaagttgcct      2280 ctcctctacc ccaaatcacc ttttttcctc ctgcctccta ttcttgacta atgttagtgc      2340
ttcatcatct cattttctc ctaatcccctt tttccaaata tctcttagcc tgaggtcttc      2400
ataacttcca tcatcccgct tcattattac ctagttactt ttcatttgtc ttagcatcct      2460
aattccagac tcctcattct tctaatttcc ccaggccaaa ttcctgcatc cctcttcacc      2520
cctcttcatc tctctacctc caaagaggaa acccttggag ataagggggt tagagacacc      2580
agtatcacct ccctgctctt cctgcctcct caaattgttt tctcttctac ttcccttttc      2640
ataaattagc tgtaatactc ctgttagcaa ctttttaaaaa cagtaaaaaa ttgtctttct      2700
cggccgggcg cggtggctca cgcctgtaat cccagcactt tgggaggccg aggcgggtgg      2760
atcatgaggt caggagatcg agaccatcct ggctaacaag gtgaaacccc gtctctacta      2820
aaaatacaaa aaaaaaatta gccgggcacg gtggcgggcg cctgtagtcc cagctactcg      2880
ggaggctgag gcaggagaat ggcgtgaacc cgggaagcgg agcttgcagt gagccgagat      2940
tgcgccactg cagtccgcag tcccgcctgg gcgacagagc gagactccgt ctcaaaaaaa      3000
aaaaaaaaaa aaaaaaaaaa attgtctttc tcattatata ggtatcaaaa gtgttcagaa      3060
acaaatatac agcctttaag tggaaataga gctatctggt actattttta aaaaattcta      3120
accatcaaga aacaaaagtt caggatttttc ttctcttatg gaactttttat ttgaaaggaa      3180 agtatagaaa agttggtctc actttccagt ggacaaattc accatatcgt cctgatctgt      3240
accatatgaa tgttaagaat atagattaag ttatcttttt ccttgattaa ggacaccagt      3300
caattatatg gatttcccag gactggtata tgtctgatag tcactggcat ggctgtatct      3360
gttgttaaat gtggagagac ttctgtattg ggtagtccat agctgctaat tggagcccca      3420
ggtaatccct gactgacctg gttcattccg ctgtaccccc ttgatctggc aactaaaggg      3480
ttaacagctg gaggcttctg ggatccagct tgagctggtg gttaagtaca ctgaacatca      3540
gccctggacc tctgcagtgc cacttattgt tcctaaaatt ctagattaag gcaaacccctt      3600 tttggttgtc aagaacatag tgctgtctcc aaggaacagc ttagtcggtc ccaccagaag      3660
catctgttgg gagcaggttg ggcaccaacc cttgcaggac tttgggattt gggacaatgt      3720
agatttgtgt gagtgcacat taagtctcat tgcaaaatag aaaaaaaaaa gttaggaaaa      3780
aggagcaaga agttattctt ttaaagtaga gactgcctta ctcatcgtag cacctagcac      3840
```

```
ctggcgtaat gctggcatat ggtatgcaca taattaatat aaaattgagcg aacgaatgca      3900 ggaatgggtg catgcctcct gcttcaccat caggatattc ttgttgggat aatggtaact      3960
cacatttata tagcagttta gactttacaa tgtggtgctt tgcaccttgt aaatttctaa      4020
tataattcca acatccttgg ttacttccag ttttccgtct cacatgtagt cctacacaag      4080
gtttttttcc aaaggagaat atgtagttaa ttggccaaga aattgcaagc tggggggaaaa    4140 attataaata ctgggaaata aaggattctt cataggggaac gaaacagggt ttgttaatga      4200
tttatgggaa ttatgtgaag ggccacatta tgcatcaaca atacccctcca gcctatattt      4260 caagcacatg cagttttttg ccgcagtgct tctgctgcaa agacctaccc ccacttctct      4320
tagcctgtct gtccccactc catacccccg acctttcatc cagctggcct gtgcttgcta      4380
aagctccctt tatcctttcc cagctccctt tccatgttgg agtaggttcc cccccttccat    4440 gctctcatag caccctgcaa ccttattagg ctgtaattat tacatagtta gattgatctc      4500
caactagatt gtcatctctt tggtggagag attacgttct tgtgtatctt cagtgcctga      4560
cacagaagtg tttctaaaag taacatctgc acacccctca aacagaatca caaggggcga      4620
ggccaagaaa tctgctctcc aagtgataac ttaaactttt taacatgctc ttcaggtgac      4680
acttaaactt gtttgaaaac ctctgtgtca taaaactaaa tattagctgg atgaatgtat      4740
ttgtatcttt ttctgtgttg gcctttgtga ggagaaatgc tgtctatgca ccaaatcaga      4800
gctgaaaaat tctagtgttt tgttaaaaaa aaaaaagaga gagagagagc tgggtttggt      4860
ggtgcatgcc tgtagtccca gctacttggg aagctaagcc aggaggactg cttgagcaca      4920
ggagttcaag tccagcctgg gcaacatggt aagaccccat tgctaataaa tgaataaatt      4980
tttctctcaa ggtgagagat actagtacta atactactac taataatgag atcactgtat      5040
gaattccttt ctgtttctac attaatccct ttctgtttct gggtgtgcat ttttgtgtgt      5100
aggcttatct gtcttgggcc tcttttgtca catattgctc atctgtgagc tgaggccctg      5160
actcactgag tattttgggg gagcagaaga aggagacatt tctctccgaa aatgaactca      5220
acaggccacc ttcaggatgc ccccaatgcc acctcgctcc atgtgcctca ctcacaggaa      5280
ggaaacagca cctctctcca ggagggtctt caggatctca tccacacagc caccttggtg      5340
acctgtactt ttctactggc ggtcatcttc tgcctgggtt cctatggcaa cttcattgtc      5400
ttcttgtcct tcttcgatcc agccttcagg aaattcagaa ccaactttga tttcatgatc      5460
ctgaacctgt ccttctgtga cctcttcatt tgtggagtga cagcccccat gttcaccttt      5520
gtgttattct tcagctcagc cagtagtatc ccggatgctt tctgcttcac tttccatctc      5580
accagttcag gcttcatcat catgtctctg aagacagtgg cagtgatcgc cctgcaccgg      5640
ctccggatgt gtgtggggaa acagcctaat cgcacggcct cctttccctg caccgtactc      5700
ctcaccctgc ttctctgggc caccagtttc acccttgcca ccttggctac cttgaaaacc      5760
agcaagtccc acctctgtct tcccatgtcc agtctgattg ctggaaaagg gaaagccatt      5820
ttgtctctct atgtggtcga cttcaccttc tgtgttgctg tggtctctgt ctcttacatc      5880
atgattgctc agaccctgcg gaagaacgct taagtcagaa agtgcccccc tgtaatcaca      5940
gtcgatgctt ccagaccaca gcctttcatg ggggtccctg tgcagggagg tggagatccc      6000
atccagtgtg ccatgccggc tctgtatagg aaccagaatt acaacaaact gcagcacgtt      6060
cagacccgtg gatataccaa gagtcccaac caactggtca cccctgcagc aagccgactc      6120
cagctcgtat cagccatcaa cctctccact gccaaggatt ccaaagccgt ggtcacctgt      6180
```

-continued

```
gtgatcattg tgctgtcagt cctggtgtgc tgtcttccac tggggatttc cttggtacag    6240
gtggttctct ccagcaatgg gagcttcatt ctttaccagt ttgaattgtt tggatttact    6300
cttatatttt tcaagtcagg attaaaccct tttatatatt ctcggaacag tgcagggctg    6360
agaaggaaag tgctctggtg cctccaatac ataggcctgg gttttttctg ctgcaaacaa    6420
aagactcgac ttcgagccat gggaaaaggg aacctcgaag tcaacagaaa caaatcctcc    6480
catcatgaaa caaactctgc ctacatgtta tctccaaagc cacagaagaa atttgtggac    6540
caggcttgtg gcccaagtca ttcaaaagaa agtatggtga gtcccaagat ctctgctgga    6600
catcaacact gtggtcagag cagctcgacc cccatcaaca ctcggattga accttactac    6660
agcatctata acagcagccc ttcccaggag gagagcagcc catgtaactt acagccagta    6720
aactcttttg gatttgccaa ttcatatatt gccatgcatt atcacaccac taatgactta    6780
gtgcaggaat atgacagcac ttcagccaag cagattccag tcccctccgt ttaaagtcat    6840
ggaggctata ggatcttatg taaacagttt ttgtttctga tagtaatgga ctttattcta    6900
acttgagatc agtggcggat caaaacctac aagattcaac tgaaaagttg gcagttatgg    6960
ttttctttca tctgatgtgt cagtatctgt tgatttgctt tgtagtttgt tgacatctta    7020
agatttgatg tgaaagtttt agatttttta ccctgc                             7056
```

<210> SEQ ID NO 5
<211> LENGTH: 7052
<212> TYPE: DNA
<213> ORGANISM: homo sapien

<400> SEQUENCE: 5

```
gtcttgccgc ggctcccggg atgcgcggag gcggtggcga tggcgatgat gcctctagtc      60
ctgcatcatc cagagcggca ggcggagctg gggtccggac tgcgagatgg aggaggggcg     120
gcgctgcggc cacccggcag gtgagaggcc gcgggcccct ggaggaggac aaccccacga     180
tgccggagac ggctcccgga ggctggcggg atagcgagga gcgcggctgc gctgggccag     240
gcccggctcc gcgtacctgt cttcctggtg cggcctgcag ggtagccttc tcgcccgtcc     300
ctgccggttc ccaggctctg ctcggccgtg gaaccccccc cacccaccca cccaccgccc     360
ctaccctggc tgagccctcc taacccacca ccctctgcg gcattctttt gcaagcttac      420
ctggcccggc ctaggccctc cttaccgtca cctcaccctt ctccgggaag cccctaccca     480
ccgccagccc ctcacggggg ggtcgacctt ccctgcccgc agtttcccac tctgtcctca     540 ggctggggc tccctggcct cttcatccct cccatcaaat gactcaggtc ttcccatccc     600
attagctgct ccgggttcaa tgtagttcta ctggatagaa agagcaaggg ctttgaaatc     660
agataatgac cttggggaag ttatctaacc tccctgaggt tttcctgatc gatagaaata     720
caatgggaat cacaataata cagaaccttg ctctctgtga ggattaggct ttgaaaatgc     780
taacctaaga cattttgggg cgcgcgggga atggggttgg aagaattcag gtcgtgagtt     840
gatttatgaa agcccctata gcatgtttta atgttcacta aaaatttaaa acagcacact     900
agatatatca gaggctgttc acatatctta atgaaaaatc attgccactc aaattataca     960
ataaattttc atccatattc tttgcttgct agttacttca ggatgtctca tttgtaagaa    1020
tatgcatgtg aattcattct tactgcagct aatatgcatg cttaagactg gtgttccagc    1080
ttaaaatctt tctgattttg tgactttaat cacatcttct ataacctatt ctccgtccca    1140
gagatgaaga gtagcttgta tgtttgcatt gcaaataaca tgggtaatct ttattgaata    1200
tttatgagta gcaaagcagt attaattat tccccttcca aaaccacttt tattttctgc     1260
```

```
cgtcatcatg tcattccaaa ttatggtcac agcctccttt ttcttaaagt ctcaggagtt      1320
actactaaga cctgagttta ctttccctcc attttcttga tttctgttat actaaagttt      1380
ttctgcaaac cttttcgtct tttctgtcct ctgctttttc tcccttttct cttcccagcc      1440
catgattcct tttttttctaa ttatctcaat aggagtgatt tatgattact ttatatgtga      1500
actacagtta gatacataga agaatgtgtg tgtgtgtgtg tgtgtgtgtg tgtgtgtgtg      1560
tgtgtctatc tgtatctaca tagatgtaga tatagctata taggtgtatc agaatttcgg      1620
attccagaaa gtttcagtgg ggaagggatt gcaataccta ttcataggat tattgtgaga      1680
atgaaataaa gcttgataat ttatgtaaag cctctagaat aggtgcctgg tgtgtaataa      1740
ccacttaata cttctgacct ggggatgcct cccaaaaagg ttttttttgtt gttcgggtta      1800 gcatggtggt gaagagtgtg gaagagcaac tgcttagatt caaatccatg ttccaccact      1860
ttagataacc tctctttgac ttggtttcct catctgcaaa atggagatgt tatatcaagt      1920
atttcagggt tgttatgagg actcaataag ctaatagtgt ggaacattga gaaaagtacc      1980
tggcacatca taagcacttg ataaaattaa tatactaata atgatgctga taattatact      2040
gccattgtta tttcctgacc tggaattctt atttttttta atttactgaa ggctgggtac      2100
agtggctcac acctgtaatc tcagcacttt gggaggccaa agcaggcaga ttgcttgagc      2160
ccagaagttg gagaccagtg agggcaacat agtgagactc catctctatt aaaaatatat      2220
atattgaaaa atttaaaatt tgttgaaaaa atgtaactgt acaaacgtg aaagttgcct      2280 ctcctctacc ccaaatcacc tttttttcctc ctgcctccta ttcttgacta atgttagtgc      2340
ttcatcatct catttttctc ctaatccctt tttccaaata tctcttagcc tgaggtcttc      2400
ataacttcca tcatcccgct tcattattac ctagttactt ttcatttgtc ttagcatcct      2460
aattccagac tcctcattct tctaatttcc ccaggccaaa ttcctgcatc cctcttcacc      2520
cctcttcatc tctctacctc caaagaggaa acccttggag ataagggggt tagagacacc      2580
agtatcacct ccctgctctt cctgcctcct caaattgttt tctcttctac ttcccttttc      2640
ataaattagc tgtaatactc ctgttagcaa cttttaaaaa cagtaaaaaa ttgtctttct      2700
cggccgggcg cggtggctca cgcctgtaat cccagcactt tgggaggccg aggcgggtgg      2760
atcatgaggt caggagatcg agaccatcct ggctaacaag gtgaaacccc gtctctacta      2820
aaaatacaaa aaaaaaatta gccgggcacg gtggcgggcg cctgtagtcc cagctactcg      2880
ggaggctgag gcaggagaat ggcgtgaacc cgggaagcgg agcttgcagt gagccgagat      2940
tgcgccactg cagtccgcag tcccgcctgg gcgacagagc gagactccgt ctcaaaaaaa      3000
aaaaaaaaaa aaaaaaaaaa attgtctttc tcattatata ggtatcaaaa gtgttcagaa      3060
acaaatatac agcctttaag tggaaataga gctatctggt actattttta aaaaattcta      3120
accatcaaga aacaaaagtt caggattttc ttctcttatg gaacttttat ttgaaaggaa      3180
agtatagaaa agttggtctc actttccagt ggacaaattc accatatcgt cctgatctgt      3240
accatatgaa tgttaagaat atagattaag ttatcttttt ccttgattaa ggacaccagt      3300
caattatatg gatttcccag gactggtata tgtctgatag tcactggcat ggctgtatct      3360
gttgttaaat gtggagagac ttctgtattg ggtagtccat agctgctaat tggagcccca      3420
ggtaatccct gactgacctg gttcattccg ctgtaccccc ttgatctggc aactaaaggg      3480
ttaacagctg gaggcttctg ggatccagct tgagctggtg gttaagtaca ctgaacatca      3540
gccctggacc tctgcagtgc cacttattgt tcctaaaatt ctagattaag gcaaaccctt      3600
```

-continued

```
tttggttgtc aagaacatag tgctgtctcc aaggaacagc ttagtcggtc ccaccagaag      3660
catctgttgg gagcaggttg ggcaccaacc cttgcaggac tttgggattt gggacaatgt      3720
agatttgtgt gagtgcacat taagtctcat tgcaaaatag aaaaaaaaaa gttaggaaaa      3780
aggagcaaga agttattctt ttaaagtaga gactgcctta ctcatcgtag cacctagcac      3840
ctggcgtaat gctggcatat ggtatgcaca taattaatat aaattgagcg aacgaatgca      3900
ggaatgggtg catgcctcct gcttcaccat caggatattc ttgttgggat aatggtaact      3960
cacatttata tagcagttta gactttacaa tgtggtgctt tgcaccttgt aaatttctaa      4020
tataattcca acatccttgg ttacttccag ttttccgtct cacatgtagt cctacacaag      4080 gttttttttcc aaaggagaat atgtagttaa ttggccaaga aattgcaagc tgggggaaaa      4140
attataaata ctgggaaata aaggattctt cataggggaac gaaacagggt ttgttaatga      4200
tttatgggaa ttatgtgaag ggccacatta tgcatcaaca ataccctcca gcctatattt      4260
caagcacatg cagttttttg ccgcagtgct tctgctgcaa agacctaccc ccacttctct      4320
tagcctgtct gtccccactc catacccccg acctttcatc cagctggcct gtgcttgcta      4380
aagctccctt tatcctttcc cagctccctt tccatgttgg agtaggttcc cccttccat      4440 gctctcatag caccctgcaa ccttattagg ctgtaattat tacatagtta gattgatctc      4500
caactagatt gtcatctctt tggtggagag attacgttct tgtgtatctt cagtgcctga      4560
cacagaagtg tttctaaaag taacatctgc acacccctca aacagaatca caaggggcga      4620
ggccaagaaa tctgctctcc aagtgataac ttaaactttt taacatgctc ttcaggtgac      4680
acttaaactt gtttgaaaac ctctgtgtca taaaactaaa tattagctgg atgaatgtat      4740
ttgtatcttt ttctgtgttg gcctttgtga ggagaaatgc tgtctatgca ccaaatcaga      4800
gctgaaaaat tctagtgttt tgttaaaaaa aaaaagaga gagagagagc tgggtttggt      4860
ggtgcatgcc tgtagtccca gctacttggg aagctaagcc aggaggactg cttgagcaca      4920
ggagttcaag tccagcctgg gcaacatggt aagaccccat tgctaataaa tgaataaatt      4980
tttctctcaa ggtgagagat actagtacta atactactac taataatgag atcactgtat      5040
gaattccttt ctgtttctac attaatccct ttctgtttct gggtgtgcat ttttgtgtgt      5100
aggcttatct gtcttgggcc tcttttgtca catattgctc atctgtgagc tgaggccctg      5160
actcactgag tattttttggg gagcagaaga aggagacatt tctctccgaa aatgaactca      5220
acaggccacc ttcaggatgc ccccaatgcc acctcgctcc atgtgcctca ctcacaggaa      5280
ggaaacagca cctctctcca ggagggtctt caggatctca tccacacagc caccttggtg      5340
acctgtactt ttctactggc ggtcatcttc tgcctgggtt cctatggcaa cttcattgtc      5400
ttcttgtcct tcttcgatcc agccttcagg aaattcagaa ccaactttga tttcatgatc      5460
ctgaacctgt ccttctgtga cctcttcatt tgtggagtga cagcccccat gttcaccttt      5520
gtgttattct tcagctcagc cagtagtatc ccggatgctt tctgcttcac tttccatctc      5580
accagttcag gcttcatcat catgtctctg aagacagtgg cagtgatcgc cctgcaccgg      5640
ctccggatgg tgttggggaa acagcctaat cgcacggcct cctttccctg caccgtactc      5700 ctcacctgc ttctctgggc caccagtttc acccttgcca ccttggctac cttgaaaacc      5760
agcaagtccc acctctgtct tcccatgtcc agtctgattg ctggaaaagg gaaagccatt      5820
ttgtctctct atgtggtcga cttcacctttg tgtgttgctg tggtctctgt ctcttacatc      5880
atgattgctc agaccctgcg gaagaacgct caagtcagtg ccccccctgta atcacagtcg      5940 atgcttccag accacagcct ttcatggggg tccctgtgca gggaggtgga gatcccatcc      6000
```

-continued

```
agtgtgccat gccggctctg tataggaacc agaattacaa caaactgcag cacgttcaga   6060
cccgtggata taccaagagt cccaaccaac tggtcacccc tgcagcaagc cgactccagc   6120
tcgtatcagc catcaacctc tccactgcca aggattccaa agccgtggtc acctgtgtga   6180
tcattgtgct gtcagtcctg gtgtgctgtc ttccactggg gatttccttg gtacaggtgg   6240
ttctctccag caatgggagc ttcattcttt accagtttga attgtttgga tttactctta   6300 tattttcaa gtcaggatta aacccttta tatattctcg gaacagtgca gggctgagaa    6360
ggaaagtgct ctggtgcctc caatacatag gcctgggttt tttctgctgc aaacaaaga   6420 ctcgacttcg agccatggga aaagggaacc tcgaagtcaa cagaaacaaa tcctcccatc   6480
atgaaacaaa ctctgcctac atgttatctc caaagccaca gaagaaattt gtggaccagg   6540
cttgtggccc aagtcattca aaagaaagta tggtgagtcc caagatctct gctggacatc   6600
aacactgtgg tcagagcagc tcgacccCa tcaacactcg gattgaacct tactacagca   6660
tctataacag cagcccttcc caggaggaga gcagcccatg taacttacag ccagtaaact   6720
cttttggatt tgccaattca tatattgcca tgcattatca caccactaat gacttagtgc   6780
aggaatatga cagcacttca gccaagcaga ttccagtccc ctccgtttaa agtcatggag   6840
gctataggat cttatgtaaa cagttttgt ttctgatagt aatggacttt attctaactt    6900
gagatcagtg gcggatcaaa acctacaaga ttcaactgaa aagttggcag ttatggtttt   6960
ctttcatctg atgtgtcagt atctgttgat ttgctttgta gtttgttgac atcttaagat   7020
ttgatgtgaa agttttagat tttttaccct gc                                7052
```

```
<210> SEQ ID NO 6
<211> LENGTH: 7057
<212> TYPE: DNA
<213> ORGANISM: homo sapien

<400> SEQUENCE: 6
```

```
gtcttgccgc ggctcccggg atgcgcggag gcggtggcga tggcgatgat gcctctagtc    60
ctgcatcatc cagagcggca ggcggagctg gggtccggac tgcgagatgg aggaggggcg   120
gcgctgcggc cacccggcag gtgagaggcc gcgggccccct ggaggaggac aaccccacga   180
tgccggagac ggctcccgga ggctggcggg atagcgagga gcgcggctgc gctgggccag   240
gcccggctcc gcgtacctgt cttcctggtg cggcctgcag ggtagccttc tcgcccgtcc   300
ctgccggttc ccaggctctg ctcggccgtg gaacccccCc cacccaccca cccaccgccc   360
ctaccctggc tgagccctcc taacccacca ccCctctgcg gcattctttt gcaagcttac   420
ctggcccggc ctaggccctc cttaccgtca cctcaccctt ctccgggaag ccCctaccca   480
ccgccagccc ctcacggggg ggtcgacctt ccctgcccgc agtttccCac tctgtcctca   540
ggctgggggc tccctggcct cttcatccct cccatcaaat gactcaggtc ttcccatccc    600
attagctgct ccgggttcaa tgtagttcta ctggatagaa agagcaaggg ctttgaaatc   660
agataatgac cttggggaag ttatctaacc tccctgaggt tttcctgatc gatagaaata   720
caatgggaat cacaataata cagaaccttg ctctctgtga ggattaggct ttgaaaatgc   780
taacctaaga cattttgggg cgcgcgggga atggggttgg aagaattcag gtcgtgagtt   840
gatttatgaa agcccctata gcatgtttta atgttcacta aaaatttaaa acagcacact   900
agatatatca gaggctgttc acatatctta atgaaaaatc attgccactc aaattataca   960
ataaattttc atccatattc tttgcttgct agttacttca ggatgtctca tttgtaagaa   1020
```

```
tatgcatgtg aattcattct tactgcagct aatatgcatg cttaagactg gtgttccagc     1080
ttaaaatctt tctgattttg tgactttaat cacatcttct ataacctatt ctccgtccca     1140
gagatgaaga gtagcttgta tgtttgcatt gcaaataaca tgggtaatct ttattgaata     1200
tttatgagta gcaaagcagt attaatttat tcccctcca aaaccactt tattttctgc       1260 cgtcatcatg tcattccaaa ttatggtcac agcctccttt ttcttaaagt ctcaggagtt     1320
actactaaga cctgagttta ctttccctcc attttcttga tttctgttat actaaagttt     1380
ttctgcaaac cttttcgtct tttctgtcct ctgctttttc tcccttttct cttcccagcc     1440
catgattcct tttttctaa ttatctcaat aggagtgatt tatgattact ttatatgtga      1500
actacagtta gatacataga agaatgtgtg tgtgtgtgtg tgtgtgtgtg tgtgtgtgtg     1560
tgtgtctatc tgtatctaca tagatgtaga tatagctata taggtgtatc agaatttcgg     1620
attccagaaa gtttcagtgg ggaagggatt gcaataccta ttcataggat tattgtgaga     1680
atgaaataaa gcttgataat ttatgtaaag cctctagaat aggtgcctgg tgtgtaataa     1740
ccacttaata cttctgacct ggggatgcct cccaaaaagg tttttttgtt gttcgggtta     1800
gcatggtggt gaagagtgtg gaagagcaac tgcttagatt caaatccatg ttccaccact     1860
ttagataacc tctctttgac ttggtttcct catctgcaaa atggagatgt tatatcaagt     1920
atttcagggt tgttatgagg actcaataag ctaatagtgt ggaacattga gaaaagtacc     1980
tggcacatca taagcacttg ataaaattaa tatactaata atgatgctga taattatact     2040
gccattgtta tttcctgacc tggaattctt atttttttta atttactgaa ggctgggtac     2100
agtggctcac acctgtaatc tcagcacttt gggaggccaa agcaggcaga ttgcttgagc     2160
ccagaagttg gagaccagtg agggcaacat agtgagactc catctctatt aaaaatatat     2220
atattgaaaa atttaaaatt tgttgaaaaa atgtaactgt acaaacgtg aaagttgcct       2280 ctcctctacc ccaaatcacc ttttttcctc ctgcctccta ttcttgacta atgttagtgc     2340
ttcatcatct cattttctc ctaatccctt tttccaaata tctcttagcc tgaggtcttc        2400
ataacttcca tcatcccgct tcattattac ctagttactt ttcatttgtc ttagcatcct     2460
aattccagac tcctcattct tctaatttcc ccaggccaaa ttcctgcatc cctcttcacc     2520
cctcttcatc tctctacctc caaagaggaa acccttggag ataaggggt tagagacacc       2580 agtatcacct ccctgctctt cctgcctcct caaattgttt tctcttctac ttcccttttc     2640
ataaattagc tgtaatactc ctgttagcaa cttttaaaaa cagtaaaaaa ttgtctttct     2700
cggccgggcg cggtggctca cgcctgtaat cccagcactt tgggaggccg aggcgggtgg     2760
atcatgaggt caggagatcg agaccatcct ggctaacaag gtgaaacccc gtctctacta     2820
aaaatacaaa aaaaaaatta gccgggcacg gtggcgggcg cctgtagtcc cagctactcg     2880
ggaggctgag gcaggagaat ggcgtgaacc cgggaagcgg agcttgcagt gagccgagat     2940
tgcgccactg cagtccgcag tcccgcctgg gcgacagagc gagactccgt ctcaaaaaaa     3000
aaaaaaaaaa aaaaaaaaaa attgtctttc tcattatata ggtatcaaaa gtgttcagaa     3060
acaaatatac agcctttaag tggaaataga gctatctggt actatttta aaaaattcta       3120 accatcaaga aacaaaagtt caggattttc ttctcttatg gaactttat ttgaaaggaa       3180 agtatagaaa agttggtctc actttccagt ggacaaattc accatatcgt cctgatctgt     3240
accatatgaa tgttaagaat atagattaag ttatcttttt ccttgattaa ggacaccagt     3300
caattatatg gatttcccag gactggtata tgtctgatag tcactggcat ggctgtatct     3360
gttgttaaat gtggagagac ttctgtattg ggtagtccat agctgctaat tggagcccca     3420
```

-continued

```
ggtaatccct gactgacctg gttcattccg ctgtaccccc ttgatctggc aactaaaggg    3480
ttaacagctg gaggcttctg ggatccagct tgagctggtg gttaagtaca ctgaacatca    3540
gccctggacc tctgcagtgc cacttattgt tcctaaaatt ctagattaag gcaaaccctt    3600
tttggttgtc aagaacatag tgctgtctcc aaggaacagc ttagtcggtc ccaccagaag    3660
catctgttgg gagcaggttg ggcaccaacc cttgcaggac tttgggattt gggacaatgt    3720
agatttgtgt gagtgcacat taagtctcat tgcaaaatag aaaaaaaaaa gttaggaaaa    3780
aggagcaaga agttattctt ttaaagtaga gactgcctta ctcatcgtag cacctagcac    3840
ctggcgtaat gctggcatat ggtatgcaca taattaatat aaattgagcg aacgaatgca    3900
ggaatgggtg catgcctcct gcttcaccat caggatattc ttgttgggat aatggtaact    3960
cacatttata tagcagttta gactttacaa tgtggtgctt tgcaccttgt aaatttctaa    4020
tataattcca acatccttgg ttacttccag tttttcgtct cacatgtagt cctacacaag    4080
gtttttttcc aaaggagaat atgtagttaa ttggccaaga aattgcaagc tgggggaaaa    4140
attataaata ctgggaaata aaggattctt catagggaac gaaacagggt ttgttaatga    4200
tttatgggaa ttatgtgaag ggccacatta tgcatcaaca ataccctcca gcctatattt    4260
caagcacatg cagtttttttg ccgcagtgct tctgctgcaa agacctaccc ccacttctct    4320
tagcctgtct gtccccactc catacccccg acctttcatc cagctggcct gtgcttgcta    4380
aagctccctt tatcctttcc cagctccctt tccatgttgg agtaggttcc ccccttccat    4440
gctctcatag caccctgcaa ccttattagg ctgtaattat tacatagtta gattgatctc    4500
caactagatt gtcatctctt tggtggagag attacgttct tgtgtatctt cagtgcctga    4560
cacagaagtg tttctaaaag taacatctgc acacccctca aacagaatca caaggggcga    4620
ggccaagaaa tctgctctcc aagtgataac ttaaactttt taacatgctc ttcaggtgac    4680
acttaaactt gtttgaaaac ctctgtgtca taaaactaaa tattagctgg atgaatgtat    4740
ttgtatcttt ttctgtgttg gcctttgtga ggagaaatgc tgtctatgca ccaaatcaga    4800
gctgaaaaat tctagtgttt tgttaaaaaa aaaaagaga gagagagagc tgggtttggt    4860
ggtgcatgcc tgtagtccca gctacttggg aagctaagcc aggaggactg cttgagcaca    4920
ggagttcaag tccagcctgg gcaacatggt aagaccccat tgctaataaa tgaataaatt    4980
tttctctcaa ggtgagagat actagtacta atactactac taataatgag atcactgtat    5040
gaattccttt ctgtttctac attaatccct ttctgtttct gggtgtgcat ttttgtgtgt    5100
aggcttatct gtcttgggcc tcttttgtca catattgctc atctgtgagc tgaggccctg    5160
actcactgag tatttttggg gagcagaaga aggagacatt tctctccgaa aatgaactca    5220
acaggccacc ttcaggatgc ccccaatgcc acctcgctcc atgtgcctca ctcacaggaa    5280
ggaaacagca cctctctcca ggagggtctt caggatctca tccacacagc caccttggtg    5340
acctgtactt ttctactggc ggtcatcttc tgcctgggtt cctatggcaa cttcattgtc    5400
ttcttgtcct tcttcgatcc agccttcagg aaaattcagaa ccaactttga tttcatgatc    5460
ctgaacctgt ccttctgtga cctcttcatt tgtggagtga cagcccccat gttcaccttt    5520
gtgttattct tcagctcagc cagtagtatc ccggatgctt tctgcttcac tttccatctc    5580
accagttcag gcttcatcat catgtctctg aagacagtgg cagtgatcgc cctgcaccgg    5640
ctccggatgg tgttggggaa acagcctaat cgcacggcct cctttccctg caccgtactc    5700 ctcacccgc ttctctgggc caccagtttc acccttgcca ccttggctac cttgaaaacc    5760
```

-continued

```
agcaagtccc acctctgtct tcccatgtcc agtctgattg ctggaaaagg gaaagccatt    5820
ttgtctctct atgtggtcga cttcaccttc tgtgttgctg tggtctctgt ctcttacatc    5880
atgattgctc agaccctgcg gaagaacgct caagtcagaa agtgccccc tgtaatcaca     5940 gtcgatgctt ccagaccaca gcctttcatg ggggtccctg tgcagggagg tggagatccc    6000
atccagtgtg ccatgccggc tctgtatagg aaccagaatt acaacaaact gcagcacgtt    6060
cagacccgtg gatataccaa gagtcccaac caactggtca cccctgcagc aagccgactc    6120
cagctcgtat cagccatcaa cctctccact gccaaggatt ccaaagccgt ggtcacctgt    6180
gtgatcattg tgctgtcagt cctggtgtgc tgtcttccac tggggatttc cttggtacag    6240
gtggttctct ccagcaatgg gagcttcatt cttacagt ttgaattgtt tggatttact     6300
cttatatttt tcaagtcagg attaaaccct tttatatatt ctcggaacag tgcagggctg    6360
agaaggaaag tgctctggtg cctccaatac ataggcctgg gttttttctg tctgcaaaca    6420
aaagactcga cttcgagcca tgggaaaagg gaacctcgaa gtcaacagaa acaaatcctc    6480
ccatcatgaa acaaactctg cctacatgtt atctccaaag ccacagaaga aatttgtgga    6540
ccaggcttgt ggcccaagtc attcaaaaga aagtatggtg agtcccaaga tctctgctgg    6600
acatcaacac tgtggtcaga gcagctcgac ccccatcaac actcggattg aaccttacta    6660
cagcatctat aacagcagcc cttcccagga ggagagcagc ccatgtaact tacagccagt    6720
aaactctttt ggatttgcca attcatatat tgccatgcat tatcacacca ctaatgactt    6780
agtgcaggaa tatgacagca cttcagccaa gcagattcca gtcccctccg tttaaagtca    6840
tggaggctat aggatcttat gtaaacagtt tttgtttctg atagtaatgg actttattct    6900
aacttgagat cagtggcgga tcaaaaccta caagattcaa ctgaaaagtt ggcagttatg    6960
gttttctttc atctgatgtg tcagtatctg ttgatttgct ttgtagtttg ttgacatctt    7020
aagatttgat gtgaaagttt tagattttt accctgc                             7057
```

<210> SEQ ID NO 7
<211> LENGTH: 2054
<212> TYPE: RNA
<213> ORGANISM: homo sapien

<400> SEQUENCE: 7

```
gcgauggcga ugaugccucu aguccugcau cauccagagc ggcaggcgag cugggguccg     60
gacugcgaga uggaggaggg gcgcgcugcg gcacccggca ggcuuaucug ucuugggccu    120
cuuuugucac auauugcuca ucugugagcu gaggcccuga cucacugagu auuuuugggg    180
agcagaagaa ggagacauuu cucuccgaaa augaacucaa caggccaccu ucaggaugcc    240
cccaaugcca ccucgcucca ugugccucac ucacaggaag gaaacagcac cucucuccag    300
gagggucuuc aggaucucau ccacacagcc accuuggug a ccuguacuuu ucuacuggcg    360
gucaucuucu gccuggguuc cuauggcaac uucauugucu ucuugucccuu cuucgaucca    420 gccuucagga aauucagaac caacuuugau ucaugaucc ugaaccuguc cuucugugac      480
cucuucauuu guggagugac agcccccaug uucaccuuug uguuauucuu cagcucagcc     540
aguaguaucc cggaugcuuu cugcuucacu uuccaucuca ccaguucagg cuucaucauc     600
augucucuga agacaguggc agugaucgcc cugcaccggc uccggauggu guuggggaaa     660
cagccuaauc gcacggccuc cuuucccugc accguacucc ucacccugcu ucucugggcc     720
accaguuuca cccuugccac cuuggcuacc uugaaaacca gcaaguccca ccucugucuu     780
cccaugucca gucugauugc uggaaaaggg aaagccauuu ugucucucua uguggucgac     840
```

```
uucaccuucu guguugcugu ggucucuguc ucuuacauca ugauugcuca gacccugcgg        900
aagaacgcuc aagucagaaa gugcccccu guaaucacag ucgaugcuuc cagaccacag        960
ccuuucaugg gggucccugu gcagggaggu ggagauccca uccagugugc caugccggcu       1020
cuguauagga accagaauua caacaaacug cagcacguuc agacccgugg auauaccaag       1080
agucccaacc aacuggucac cccugcagca agccgacucc agcucguauc agccaucaac       1140
cucuccacug ccaaggauuc caaagccgug gucaccugug ugaucauugu gcugucaguc       1200
cuggugugcu gucuuccacu ggggauuucc uugguacagg ugguucucuc cagcaauggg       1260
agcuucauuc uuuaccaguu ugaauugumu ggauuuacuc uuauauuuuu caagucagga       1320
uuaaacccuu uuauauauuc ucggaacagu gcagggcuga gaaggaaagu gcucuggugc       1380
cuccaauaca uaggccuggg uuuuuucugc ugcaaacaaa agacucgacu ucgagccaug       1440
ggaaaaggga accucgaagu caacagaaac aaauccuccc aucaugaaac aaacucugcc       1500
uacauguuau cuccaaagcc acagaagaaa uuuguggacc aggcuugugg cccaagucau       1560
ucaaaagaaa guaggugag ucccaagauc ucugcuggac aucaacacug uggucagagc        1620
agcucgaccc ccaucaacac ucggauugaa ccuuacuaca gcaucuauaa cagcagcccu       1680
ucccaggagg agagcagccc auguaacuua cagccaguaa acucuuuugg auuugccaau       1740
ucauauauug ccaugcauua ucacaccacu aaugacuuag ugcaggaaua ugacagcacu       1800
ucagccaagc agauuccagu ccccuccguu uaaagucaug gaggcuauag gaucuuaugu       1860
aaacaguuuu uguuucugau aguaauggac uuuauucuaa cuugagauca guggcggauc       1920
aaaaccuaca agauucaacu gaaaaguugg caguuauggu uuucuuucau cugaugugu        1980 aguaucuguu gauuugcuuu guaguuuguu gacaucuuaa gauuugaugu gaaaguuuua       2040
gauuuuuuac ccug                                                         2054
```

```
<210> SEQ ID NO 8
<211> LENGTH: 1913
<212> TYPE: RNA
<213> ORGANISM: homo sapien

<400> SEQUENCE: 8
```

```
caggcuuacu gucuugggcc ucuuuuguca cauauugcuc aucgugagc ugaggcccug          60 acucacugag uauuuuuggg gagcagaaga aggagacauu ucucuccgaa aaugaacuca        120
acaggccacc uucaggaugc ccccaaugcc accucgcucc augugccuca cucacaggaa        180
ggaaacagca ccucucucca ggagggucuu caggaucuca uccacacagc caccuugguu        240
accuguacuu uucuacuggc ggucaucuuc ugccugggpu ccuauggcaa cuucauuguc        300
uucuuguccu ucuucgaucc agccuucagg aaauucagaa ccaacuuuga uuucaugauc        360
cugaaccugu ccuucuguga cccuuucauu uguggaguga cagcccccau guucaccuuu        420
guguuauucu ucagcucagc caguaguauc ccggaugcuu ucugcuucac uuuccaucuc       480
accaguucag gcuucaucau caugucucug aagacagugg cagugaucgc ccugcaccgg        540
cuccggaugg uguggggaa acagccuaau cgcacggccu ccuuucccug caccguacuc        600
cucacccugc uucucugggc caccaguuuc accccugcca ccuuggcuac cuugaaaaacc       660 agcaagtucc accucugucu ucccaugucc agucugauug cuggaaaagg gaaagccauu        720
uugucucucu auguggucga cuucaccuuc ugcguugcg uggucucugu cucuuacauc        780
augauugcuc agacccugcg gaagaacgcu caagucagaa agugcccccc uguaaucaca        840
```

-continued

```
gucgaugcuu ccagaccaca gccuuucaug ggggucccug ugcagggagg uggagauccc      900
auccagugug ccaugccggc ucuguauagg aaccagaauu acgacaaacu gcagcacguu      960
cagacccgug gauauaccaa gagucccaac caacugguca ccccugcagc aagccgacuc     1020
cagcucguau cagccaucaa ccucuccacu gccaaggauu ccaaagccgu ggucaccugu     1080
gugaucauug ugcugucagu ccuggugugc ugucuuccac uggggauuuc cuugguacag     1140
gugguucucu ccagcaaugg gagcuucauu cuuuaccagu uugaauuguu uggauuuacu     1200
cuuauauuuu ucaagucagg auuaaacccu uuuauauauu cucggaacag ugcagggcug     1260
agaaggaaag ugcucuggug ccuccaauac auaggccugg guuuuuucug cugcaaacaa     1320
aagacucgac uucgagccau gggaaaaggg aaccucgaag ucaacagaaa caaauccucc     1380
caucaugaaa caaacucugc cuacauguua ucuccaaagc cacagaagaa auuuguggac     1440
caggcuugug gcccaaguca uucaaaagaa aguaugguga gucccaagau cucugcugga     1500
caucaacacu guggucagag cagcucgacc cccaucaaca cucggauuga accuuacuac     1560
agcaucuaua acagcagccc uucccaggag gagagcagcc cauguaacuu acagccagua     1620
aacucuuuug gauuugccaa uucauauauu gccaugcauu aucacaccac uaaugacuua     1680
gugcaggaau augacagcac uucagccaag cagauuccag uccccuccgu uuaaagucau     1740
ggaggcuaua ggaucuuaug uaaacaguuu uuguuucuga uaguaauggg cuuuauucua     1800
acuugagauc aguggcggau caaaaccuac aagauucaac ugaaaaguug gcaguuaugg     1860
uuuucuuuca ucugaugugu caguaucugu ugauuugcuu uguaguuugu uga           1913
```

<210> SEQ ID NO 9
<211> LENGTH: 1741
<212> TYPE: RNA
<213> ORGANISM: homo sapien

<400> SEQUENCE: 9

```
ggagcagaag aaggagacau uucucuccga aaaugaacuc aacaggccac cuucaggaug       60
cccccaaugc caccucgcuc caugugccuc acucacagga aggaaacagc accucucucc      120
aggagggucu ucaggaucuc auccacacag ccaccuuggu gaccuguacu uuucuacugg      180
cggucaucuu cugccugggu uccuauggca acuucauugu cuucuugucc uucuucgauc      240
cagccuucag gaaauucaga accaacuuug auuucaugau ccugaaccug ccuucucugg      300
accucuucau uuguggagug acagccccca uguucacccu ugugguuauuc uucagcucag      360 ccaguaguau cccggaugcu uucugcuuca cuuuccaucu caccaguuca ggcuucauca      420
ucaugucucu gaagacagug gcagugaucg cccugcaccg gcuccggaug guguugggga      480
aacagccuaa ucgcacggcc uccuuucccu gcaccguacu ccucacccug cuucucuggg      540
ccaccaguuu caccccuugcc accuuggcua ccuugaaaac cagcaagucc caccucuguc      600
uucccauguc cagucugauu gcuggaaaag ggaaagccau uuugucucuc uaugugguucg      660 acuucaccuu cuguguugcu guggcucug ucucuuacau caugauugcu cagacccugc      720
ggaagaacgc ucaagucaga aagugccccc cuguaaucac agucgaugcu uccagaccac      780
agccuuucau gggggu25cccu gugcaggag guggagaucc cauccagugu gccaugccgg      840
cucuguauag gaaccagaau uacaacaaac ugcagcacgu ucagacccgu ggauauacca      900
agagucccaa ccaacugguc accccugcag caagccgacu ccagcucgua ucagccauca      960
accucuccac ugccaaggau uccaaagccg uggucaccug ugugaucauu gugcugucag     1020
uccuggugug cugucuucca cuggggauuu ccuugguaca gguggguucuc uccagcaaug     1080
```

-continued

```
ggagcuucau ucuuuaccag uuugaauugu uuggauuuac ucuuauauuu uucaagucag     1140
gauuaaaccc uuuuauauau ucucggaaca gugcaggggcu gagaaggaaa gugcucuggu     1200
gccuccaaua cauaggccug gguuuuuucu gcugcaaaca aaagacucga cuucgagcca     1260
ugggaaaagg gaaccucgaa gucaacagaa acaaauccuc ccaucaugaa acaaacucug     1320
ccuacauguu aucuccaaag ccacagaaga aauuugugga ccaggcuugu ggcccaaguc     1380
auucaaaaga aaguauggug agucccaaga ucucugcugg acaucaacac uguggucaga     1440
gcagcucgac ccccaucaac acucggauug aaccuuacua cagcaucuau aacagcagcc     1500
cuucccagga ggagagcagc ccauguaacu uacagccagu aaaacucuuu ggauuugcca     1560
auucauauau ugccaugcau uaucacacca cuaaugacuu agugcaggaa uaugacagca     1620
cuucagccaa gcagauucca gucccccuccg uuuaaaaguca uggaggcuau aggaucuuau     1680
guaaacaguu uuuguuucug auaguaaugg acuuuauucu aacuugagau aguggcggau     1740
c                                                                      1741
```

<210> SEQ ID NO 10
<211> LENGTH: 1894
<212> TYPE: RNA
<213> ORGANISM: homo sapien

<400> SEQUENCE: 10

```
gugacugcgc cucugcgccc gcgucuugcc gcggcucccg ggaugcgcgg aggcgguggc       60
gauggcgaug augccucuag uccugcauca uccagagcgg caggcggagc uggggguccgg      120 acugcgagau ggaggagggg cggcgcugcg gccacccggc aggcuuaucu gucucugggc      180 ucuuuugguca cauauugcuc aucgugagc ugaggcccug acucacugag uauuuuugggg      240 gagcagaaga aggagacauu ucucuccgaa aaugaacuca acaggccacc uucaggaugc       300
ccccaaugcc accucgcucc augugccuca cucacaggaa ggaaacagca ccucucucca       360
ggagggucuu caggaucuca uccacacagc caccuuggug accuguacuu uucuacuggc       420
ggucaucuuc ugccuggguu ccuauggcaa cuucauugc uucuugccu ucuucgaucc        480 agccuucagg aaauucagaa ccaacuuuga uuucaugauc cugaaccugu ccuucuguga      540 ccucuuucauu uguggagauga cagcccccau guucacuuu guguuauucu ucagcucagc      600
caguaguauc ccggaugcuu ucugcuucac uuuccaucuc accaguucag gcuucaucau       660
caugucucug aagacagugg caguga ucgc ccugcaccgg cuccggauggg uguuggggaa      720 acagccuaau cgcacggccu ccuuucccug caccguacuc cucacccugc uucucugggc       780
caccaguuuc acccuugcca ccuuggcuac cuugaaaacc agcaagucc accucugucu       840 ucccaugucc agucugauug cuggaaaagg gaaagccauu uugucucucu auguggucga      900
cuucaccuuc uguguugcug uggucucugu cucuuacauc augauugcuc agacccugcg      960
gaagaacgcu caagucagaa agugccccccc uguaaucaca gucgaugcuu ccagaccaca      1020
gccuuucaug ggggucccug ugcagggagg uggagauccc auccagugug ccaugccggc     1080
ucuguauagg aaccagaauu acaacaaacu gcagcacguu cagacccgug gauauaccaa      1140
gagucccaac caacugguca ccccugcagc aagccgacuc cagcucguau cagccaucaa      1200
ccucuccacu gccaaggauu ccaaagccgu ggucaccugu gugaucauug ugcugucagu      1260
ccuggugugc ugucuuccac ugggggauuuc cuugguacag guggguucucu ccagcaaugg     1320 gagcuucauu cuuuaccagu uugaauuguu uggauuuacu cuuauauuuu ucaagucagg      1380
```

```
auuaaacccu uuuauauauu cucggaacag ugcagggcug agaaggaaag ugcucuggug     1440
ccuccaauac auaggccugg guuuuuucug cugcaaacaa aagacucgac uucgagccau     1500
gggaaaaggg aaccucgaag ucaacagaaa caaauccucc caucaugaaa caaacucugc     1560
cuacauguua ucuccaaagc cacagaagaa auuuguggac caggcuugug gcccaaguca     1620
uucaaaagaa aguaugguga gucccaagau cucugcugga caucaacacu guggucagag     1680
cagcucgacc cccaucaaca cucggauuga accuuacuac agcaucuaua acagcagccc     1740
uucccaggag gagagcagcc cauguaacuu acagccagua aacucuuuug gauuugccaa     1800
uucauauauu gccaugcauu aucacaccac uaaugacuua gugcaggaau augacagcac     1860
uucagccaag cagauuccag uccccuccgu uuaa                                1894
```

```
<210> SEQ ID NO 11
<211> LENGTH: 2047
<212> TYPE: RNA
<213> ORGANISM: homo sapien

<400> SEQUENCE: 11
gcgauggcga ugaugccucu aguccugcau cauccagagc ggcaggcgag cuggggguccg      60 gacugcgaga uggaggaggg gcgcgcugcg gcacccggca ggcuuaucug ucuuggggccu     120 cuuuugucac auauugcuca ucugugagcu gaggcccuga cucacugagu auuuuuggggg     180 agcagaagaa ggagacauuu cucuccgaaa augaacucaa caggccaccu ucaggaugcc     240
cccaaugcca ccucgcucca ugugccucac ucacaggaag gaaacagcac cucucuccag     300
gagggucuuc aggaucucau ccacacagcc accuugguga ccaguacuuu ucuacggcg      360 gucaucuucu gccugggu uc cuauggcaac uucauugucu ucuugucccuu cuucgaucca     420 gccuucagga aauucagaac caacuuugau uucaugaucc ugaaccuguc cuucugugac     480
cucuucauuu guggagugac agcccccaug uucaccuuug uguuauucuu cagcucagua     540
ucccggaugc uuucugcuuc acuuuccauc ucaccaguuc aggcuucauc aucaugucuc     600
ugaagacagu ggcagugauc gcccugcacc ggcuccggau gguguugggg aaacagccua     660
aucgcacggc cuccuuuccc ugcaccguac uccucacccu gcuucucugg gccaccaguu     720
ucacccuugc caccuuggcu accuugaaaa ccagcaaguc ccaccucugu cuucccaugu     780
ccagucugau ugcuggaaaa gggaaagcca uuuugucucu cuaugugguc gacuucaccu     840
ucuguguugc uguggucucu gucucuuaca ucaugauugc ucagacccug cggaagaacg     900
cucaagucag aaagugcccc ccuguaauca cagucgaugc uuccagacca cagccuuuca     960
uggggguccc ugugcaggga gguggagauc ccauccagug ugccaugccg gcucuguaua    1020
ggaaccagaa uuacaacaaa cugcagcacg uucagacccg uggauauacc aagagucccaa   1080 accaacuggu caccccugca gcaagccgac uccagcucgu aucagccauc aaccucucca    1140
cugccaagga uucaaagcc guggucaccu guguaucau ugcgcuguca guccuggugu     1200
gcugucuucc acuggggauu uccuugguac aggugguucu cuccagcaau gggagcuuca    1260
uucuuuacca guuugaauug uuuggauuua cucuuauauu uucaaguca ggauuaaacc      1320 cuuuuauaua uucucggaac agugcagggc ugagaaggaa agugcucugg ugccuccaau     1380
acauaggccu ggguuuuuuc ugcugcaaac aaaagacucg acuucgagcc augggaaaag     1440
ggaaccucga agucaacaga aacaaauccu cccaucauga aacaaacucu gccuacaugu     1500
uaucuccaaa gccacagaag aaauuugugg accaggcuug uggcccaagu cauucaaaag     1560
aaaguauggu gagucccaag aucucugcug gacaucaaca cuguggucag agcagcucga    1620
```

-continued

```
cccccaucaa cacucggauu gaaccuuacu acagcaucua uaacagcagc ccuucccagg    1680
aggagagcag cccauguaac uuacagccag uaaacucuuu uggauuugcc aauucauaua    1740
uugccaugca uuaucacacc acuaaugacu uagugcagga auaugacagc acuucagcca    1800
agcagauucc aguccccucc guuuaaaguc auggaggcua uaggaucuua uguaaacagu    1860
uuuuguuucu gauaguaaug gacuuuauuc uaacuugaga ucaguggcgg aucaaaaccu    1920
acaagauuca acugaaaagu uggcaguuau gguuuucuuu caucugaugu gucaguaucu    1980
guugauuugc uuuguaguuu guugacaucu uaagauuuga ugugaaaguu uuagauuuuu    2040
uacccug                                                              2047

<210> SEQ ID NO 12
<211> LENGTH: 2054
<212> TYPE: RNA
<213> ORGANISM: homo sapien

<400> SEQUENCE: 12
gcgauggcga ugaugccucu aguccugcau cauccagagc ggcaggcgag cugggguccg      60
gacugcgaga uggaggaggg gcgcgcugcg gcacccggca ggcuuaucug ucuugggccu     120
cuuuugucac auauugcuca ucugugagcu gaggcccuga cucacugagu auuuuugggg     180
agcagaagaa ggagacauuu cucuccgaaa augaacucaa caggccaccu ucaggaugcc     240
cccaaugcca ccucgcucca ugugccucac ucacaggaag gaaacagcac cucucuccag     300
gagggucuuc aggaucucau ccacacagcc accuugguga ccguacuuu ucuacuggcg      360 gucaucuucu gccuggguuc cuauggcaac uucauugucu ucuugccuu cuucgaucca     420 gccuucagga aauucagaac caacuuugau uucaugaucc ugaaccuguc cuucugugac     480
cucuucauuu guggagugac agcccccaug uucacccuug uguuauucuu cagcucagcc     540
aguaguaucc cggauacuuu cugcuucacu uuccaucuca ccaguucagg cuucaucauc     600
augucucuga agacaguggc agugaucgcc cugcaccggc uccggauggu guuggggaaa     660
cagccuaauc gcacggccuc cuuucccugc accguacucc ucacccugcu ucucugggcc     720
accaguuuca cccuugccac cuuggcuacc uugaaaacca gcaaguccca ccucugucuu     780
cccaugucca gucugauugc uggaaaaggg aaagccauuu ugucucucua uguggucgac     840
uucaccuucu guguugcugu ggucucuguc ucuuacauca ugauugcuca gacccugcgg     900
aagaacgcuc aagucagaaa gugcccccu guaaucacag ucgaugcuuc cagaccacag     960
ccuuucaugg gggucccugu gcagggaggu ggagaucca uccagugugc caugccggcu    1020
cuguauagga accagaauua caacaaacug cagcacguuc agacccgugg auauaccaag    1080
agucccaacc aacuggucac cccugcagca agccgacucc agcucguauc agccaucaac    1140
cucuccacug ccaaggauuc caaagccgug gucaccugug ugaucauugu gcugucaguc    1200
cuggugugcu gucuuccacu ggggauuucc uugguacagg ugguucucuc cagcaauggg    1260
agcuucauuc uuuaccaguu ugaauuguuu ggauuuacuc uuauauuuuu caagucagga    1320
uuaaacccuu uuauauauuc ucggaacagu gcagggcuga gaaggaaagu gcucuggugc    1380
cuccaauaca uaggccuggg uuuuuucgc ugcaaacaaa agacucgacu ucgagccaug    1440
ggaaaaggga accucgaagu caacagaaac aaauccuccc aucaugaaac aaacucugcc    1500
uacauguuau cuccaaagcc acagaagaaa uuuguggacc aggcuugugg cccaagucau    1560
ucaaaagaaa guauggugag ucccaagauc ucugcuggac aucaacacug uggucagagc    1620
```

-continued agcucgaccc ccaucaacac ucggauugaa ccuuacuaca gcaucuauaa cagcagcccu      1680
ucccaggagg agagcagccc auguaacuua cagccaguaa acucuuuugg auuugccaau      1740
ucauauauug ccaugcauua ucacaccacu aaugacuuag ugcaggaaua ugacagcacu      1800
ucagccaagc agauuccagu ccccuccguu uaaagucaug gaggcuauag gaucuuuaugu     1860 aaacaguuuu uguuucugau aguaauggac uuuauucuaa cuugagauca guggcggauc      1920
aaaaccuaca agauucaacu gaaaaguugg caguuauggu uuucuuucau cugauguguc      1980
aguaucuguu gauuugcuuu guaguuuguu gacaucuuaa gauuugaugu gaaaguuuua      2040
gauuuuuuac ccug                                                       2054

<210> SEQ ID NO 13
<211> LENGTH: 2054
<212> TYPE: RNA
<213> ORGANISM: homo sapien

<400> SEQUENCE: 13
gcgauggcga ugaugccucu aguccugcau cauccagagc ggcaggcgag cuggggguccg      60 gacugcgaga uggaggaggg gcgcgcugcg gcacccggca ggcuuaucug ucuugggccu      120
cuuuugucac auauugcuca ucugugagcu gaggcccuga cucacugagu auuuuugggg      180
agcagaagaa ggagacauuu cucuccgaaa augaacucaa caggccaccu ucaggaugcc      240
cccaaugcca ccucgcucca ugugccucac ucacaggaag gaaacagcac cucucuccag      300
gagggucuuc aggaucucau ccacacagcc accuugguga ccuguacuuu ucuacuggcg      360
gucaucuucu gccuggguuc cuauggcaac uucauugucu ucuugucucuu cuucgaucca      420 gccuucagga aauucagaac caacuuugau uucaugaucc ugaaccuguc cuucugugac      480
cucuucauuu guggagugac agcccccaug uucaccuuug uguuauucuu cagcucagcc      540
aguaguaucc cggaugcuuu cugcuucacu uuccaucuca ccaguucagg cuucaucauc      600
augucucuga agacaguggc agugaucgcc cugcaccggc uccggauggu guuggggaaa      660
cagccuaauc gcacggccuc cuuucccugc accguacucc ucacccugcu ucucugggcc      720
accaguuuca cccuugccac cuuggcuacc uugaaaacca gcaaguccca ccucugucuu      780
cccaugucca gucugauugc uggaaaaggg aaagccauuu ugucucucua uguggucgac      840
uucaccuucu guguugcugu ggcucucguc ucuuacauca ugauugcuca gacccugcgg      900
aagaacgcuu aagucagaaa gugcccccu guaaucacag ucgaugcuuc cagaccacag      960
ccuuucaugg gggucccugu gcagggaggu ggagauccca uccagugugc caugccggcu     1020
cuguauagga accagaauua caacaaacug cagcacguuc agacccgugg auauaccaag     1080
agucccaacc aacuggucac cccugcagca agccgacucc agcucguauc agccaucaac     1140
cucuccacug ccaaggauuc caaagccgug gucaccgugu ugaucauugu gcugucaguc     1200
cuggugugcu gucuuuccacu ggggauuuuucc uugguacagg ugguucucuc cagcaauggg     1260
agcuucauuc uuuaccaguu ugaauuguuu ggauuuacuc uuauauuuuu caagucagga     1320
uuaaacccuu uuauauauuc ucggaacagu gcagggcuga gaaggaaagu gcucuggugc     1380
cuccaauaca uaggccuggg uuuuuuucgc ugcaaacaaa agacucgacu ucagccaug     1440 ggaaaaggga accucgaagu caacagaaac aaauccuccc aucaugaaac aaacucugcc     1500
uacauguuau cuccaaagcc acagaagaaa uuuguggacc aggcuugugg cccaagucau     1560
ucaaaagaaa guaggugag ucccaagauc ucugcuggac aucaacacug uggucagagc     1620
agcucgaccc ccaucaacac ucggauugaa ccuuacuaca gcaucuauaa cagcagcccu     1680

```
ucccaggagg agagcagccc auguaacuua cagccaguaa acucuuuugg auuugccaau     1740
ucauauauug ccaugcauua ucacaccacu aaugacuuag ugcaggaaua ugacagcacu     1800
ucagccaagc agauuccagu cccccuccguu uaaagucaug gaggcuauag gaucuuaugu    1860
aaacaguuuu uguuucugau aguaauggac uuuauucuaa cuugagauca guggcggauc     1920
aaaaccuaca agauucaacu gaaaaguugg caguuauggu uuucuuucau cugauguguc     1980
aguaucuguu gauuugcuuu guaguuuguu gacaucuuaa gauuugaugu gaaaguuuua     2040
gauuuuuuac ccug                                                      2054

<210> SEQ ID NO 14
<211> LENGTH: 2050
<212> TYPE: RNA
<213> ORGANISM: homo sapien

<400> SEQUENCE: 14
gcgauggcga ugaugccucu aguccugcau cauccagagc ggcaggcgag cuggggguccg      60 gacugcgaga uggaggaggg gcgcgcugcg gcacccggca ggcuuaucug ucuugggccu     120
cuuuugucac auauugcuca ucugugagcu gaggcccuga cucacugagu auuuuugggg     180
agcagaagaa ggagacauuu cucuccgaaa augaacucaa caggccaccu ucaggaugcc     240
cccaaugcca ccucgcucca ugugccucac ucacaggaag gaaacagcac cucucuccag     300
gagggucuuc aggaucucau ccacacagcc accuugguga ccguacuuu ucuacuggcg      360 gucaucuucu gccuggguuc cuauggcaac uucauugucu ucuugucccuu cuucgaucca     420 gccuucagga aauucagaac caacuuugau uucaugaucc ugaaccuguc cuucugugac     480
cucuucauuu guggagugac agcccccaug uucaccuuug uguuauucuu cagcucagcc     540
aguaguaucc cggaugcuuu cugcuucacu uuccaucuca ccaguucagg cuucaucauc     600
augucucuga agacaguggc agugaucgcc cugcaccggc uccggauggu guugggggaaa     660 cagccuaauc gcacggccuc cuuucccugc accguacucc ucacccugcu ucucugggcc     720
accaguuuca cccuugccac cuuggcuacc uugaaaacca gcaaguccca ccucugucuu     780
cccaugucca gucugauugc uggaaaaggg aaagccauuu ugucucucua uguggucgac     840
uucaccuucu guguugcgu ggcucucguc ucuuacauca ugauugcuca gacccugcgg     900
aagaacgcuc aagucagugc cccccuguaa ucacagucga ugcuuccaga ccacagccuu     960 ucauggggguu cccugugcag ggagguggag aucccaucca gugugccaug ccggcucugu    1020
auaggaacca gaauuacaac aaacugcagc acguucagac ccguggauau accaagaguc    1080
ccaaccaacu ggucacccccu gcagcaagcc gacuccagcu cguaucagcc aucaaccucu    1140
ccacugccaa ggauuccaaa gccgguguca ccugugugau cauugugcug ucaguccugg    1200
ugugcugucu uccacugggg auuuccuugg uacagugggu ucucuccagc aaugggagcu    1260
ucauucuuua ccaguuugaa uuguuuggau uuacucuuau auuuucaag ucaggauuaa     1320 acccuuuuau auauucucgg aacagugcag ggcugagaag gaaagugcuc uggugccucc    1380
aauacauagg ccugggguuuu uucugcugca aacaaaagac ucgacuucga gccaugggaa    1440
aagggaaccu cgaagucaac agaaacaaau ccucccauca ugaaacaaac ucugccuaca    1500
uguuaucucc aaagccacag aagaaauuug uggaccaggc uuguggccca agucauucaa    1560
aagaaaguau ggugagucccc aagaucucug cuggacauca acacuguggu cagagcagcu    1620 cgaccccccau caacacucgg auugaaccuu acuacagcau cuauaacagc agcccuuccc    1680
```

-continued

```
aggaggagag cagcccaugu aacuuacagc caguaaacuc uuuuggauuu gccaauucau   1740
auauugccau gcauuaucac accacuaaug acuuagugca ggaauaugac agcacuucag   1800
ccaagcagau uccagucccc uccguuuaaa gucauggagg cuauaggauc uuauguaaac   1860
aguuuuuguu ucugauagua auggacuuua uucuaacuug agaucagugg cggaucaaaa   1920
ccuacaagau ucaacugaaa aguuggcagu uauggguuuc uuucaucuga ugugucagua   1980
ucuguugauu ugcuuuguag uuuguugaca ucuuaagauu ugaugugaaa guuuuagauu   2040
uuuuacccug                                                          2050

<210> SEQ ID NO 15
<211> LENGTH: 2055
<212> TYPE: RNA
<213> ORGANISM: homo sapien

<400> SEQUENCE: 15
gcgauggcga ugaugccucu aguccugcau cauccagagc ggcaggcgag cuggggguccg     60 gacugcgaga uggaggaggg gcgcgcugcg gcacccggca ggcuuaucug ucuugggccu    120
cuuuugucac auauugcuca ucugugagcu gaggcccuga cucacugagu auuuuugggg    180
agcagaagaa ggagacauuu cucuccgaaa augaacucaa caggccaccu ucaggaugcc    240
cccaaugcca ccucgcucca ugugccucac ucacaggaag gaaacagcac cucucuccag    300
gagggucuuc aggaucucau ccacacagcc accuugguga ccguacuuu ucuacuggcg    360 gucaucuucu gccuggguuc cuauggcaac uucauugucu ucuugccuu cuucgaucca    420 gccuucagga aauucagaac caacuuugau uucaugaucc ugaaccuguc cuucugugac    480
cucuucauuu guggagugac agcccccaug uucaccuuug uguuauucuu cagcucagcc    540
aguaguaucc cggaugcuuu cugcuucacu uuccaucuca ccaguucagg cuucaucauc    600
augucucuga agacaguggc agugaucgcc cugcaccggc uccggauggu guuggggaaa    660
cagccuaauc gcacgccuc cuuucccugc accguacucc ucacccugcu ucucugggcc    720
accaguuuca cccuugccac cuuggcuacc uugaaaacca gcaaguccca ccucugucuu    780
cccaugucca gucugauugc uggaaaaggg aaagccauuu ugucucucua uguggucgac    840
uucaccuucu guguugcugu ggcucucguc ucuuacauca ugauugcuca gacccugcgg    900
aagaacgcuc aagucagaaa gugccccccu guaaucacag ucgaugcuuc cagaccacag    960
ccuuucaugg gggucccugu gcagggaggu ggagaucccâ uccagugugc caugccggcu   1020
cuguauagga accagaauua caacaaacug cagcacguuc agacccgugg auauaccaag   1080
agucccaacc aacuggucac cccugcagca agccgacucc agcucguauc agccaucaac   1140
cucuccacug ccaaggauuc caaagccgug gucaccugug ugaucauugu gcugucaguc   1200
cuggugugcu gucuuccacu ggggauuucc uugguacagg ugguucucuc cagcaauggg   1260
agcuucauuc uuuaccaguu ugaauuguuu ggauuuacuc uuauauuuuu caagucagga   1320
uuaaacccuu uuauauauuc ucggaacagu gcagggcuga gaaggaaagu gcucuggugc   1380
cuccaauaca uaggccuggg uuuuuucugu cugcaaacaa aagacucgac uucgagccau   1440
gggaaaaggg aaccucgaag ucaacagaaa caaauccucc caucaugaaa caaacucugc   1500
cuacauguua ucuccaaagc cacagaagaa auuuguggac caggcuugug gcccaaguca   1560
uucaaaagaa aguaugguga gucccaagau cucugcugga caucaacacu gugguucagag   1620 cagcucgacc cccaucaaca cucggauuga accuuacuac agcaucuaua acagcagccc   1680
uucccaggag gagagcagcc caguguaacu uacagccagua aacucuuuug gauuugccaa   1740
```

-continued

```
uucauauauu gccaugcauu aucacaccac uaaugacuua gugcaggaau augacagcac     1800
uucagccaag cagauuccag uccccuccgu uuaaagucau ggaggcuaua ggaucuuaug     1860
uaaacaguuu uuguuucuga uaguaaugga cuuuauucua acuugagauc aguggcggau     1920
caaaaccuac aagauucaac ugaaaaguug gcaguuaugg uuuucuuuca ucugaugugu     1980
caguaucugu ugauuugcuu uguaguuugu ugacaucuua agauuugaug ugaaaguuuu     2040
agauuuuuua cccug                                                     2055

<210> SEQ ID NO 16
<211> LENGTH: 1906
<212> TYPE: RNA
<213> ORGANISM: homo sapien

<400> SEQUENCE: 16
caggcuuacu gucuugggcc ucuuuuguca cauauugcuc aucugugagc ugaggcccug       60
acucacugag uauuuuuggg gagcagaaga aggagacauu ucucuccgaa aaugaacuca      120
acaggccacc uucaggaugc ccccaaugcc accucgcucc augugccuca cucacaggaa      180
ggaaacagca ccucucucca ggagggucuu caggaucuca uccacacagc caccuugguu      240 accguacuu uucuacuggc ggucaucuuc ugccuggguu ccuauggcaa cuucauuguc      300
uucuuguccu ucuucgaucc agccuucagg aaauucagaa ccaacuuuga uuucaugauc      360
cugaaccugu ccuucuguga ccucuucauu uguggaguga cagcccccau guucaccuuu      420
guguuauucu ucagcucagu aucccggaug cuuucugcuu cacuuuccau cucaccaguu      480
caggcuucau caucaugucu cugaagacag uggcagugau cgcccugcac cggcuccgga      540
uggugugggg aaacagccu aaucgcacgg ccuccuuucc cugcaccgua cuccucaccc      600
ugcuucucug ggccaccagu uucaccccug ccaccuuggc uaccuugaaa accagcaagu      660
cccaccucug ucuucccaug uccagucuga uugcuggaaa agggaaagcc auuuugucuc      720
ucuauguggu cgacuucacc uucuguguug cuguggcucuc ugucucuuac aucaugauug      780
cucagacccu gcggaagaac gcucaaguca gaaagugccc cccguaaauc acagucgaug      840
cuuccagacc acagccuuuc auggggguccc cugugcaggg aggugagau cccauccagu      900 gugccaugcc ggcucuguau aggaaccaga auuacgacaa acugcagcac guucagaccc      960
guggauauac caagaguccc aaccaacugg ucaccccugc agcaagccga cuccagcucg     1020
uaucagccau caaccucucc acugccaagg auuccaaagc cguggucacc ugugugauca     1080
uugugcuguc aguccuggug ugcugucuuc cacuggggau uuccuuggua caggugguuc     1140
ucuccagcaa ugggagcuuc auucuuuacc aguuugaauu guuuggauuu acucuuauau     1200 uuucaaguc aggauuaaac ccuuuuauau auucucggaa caguguugggg cugagaagga     1260 aagugcucug gugccuccaa uacauaggcc uggguuuuu cugcugcaaa caaaagacuc     1320
gacuucgagc cauggggaaaa gggaaccucg aagucaacag aaacaaaucc ucccaucaug     1380
aaacaaacuc ugccuacaug uuaucuccaa agccacagaa gaaauuugug gaccaggcuu     1440
guggcccaag ucauucaaaa gaaaguaugg ugagucccaa gaucucugcu ggacaucaac     1500 acuggguca gagcagcucg accccaauca acacucggau ugaaccuuac uacagcaucu     1560
auaacagcag cccuucccag gaggagagca gcccauguaa cuuacagcca guaaacucuu     1620
uuggauuugc caauucauau auuggccaugc auuaucacac cacuaaugac uuagugcagg     1680
aauaugacag cacuucagcc aagcagauuc cagucccccuc cguuuaaagu cauggaggcu     1740
```

-continued

```
auaggaucuu auguaaacag uuuuuguuuc ugauaguaau gggcuuuauu cuaacuugag      1800
aucaguggcg gaucaaaacc uacaagauuc aacugaaaag uuggcaguua ugguuuucuu      1860
ucaucugaug ugucaguauc uguugauuug cuuuguaguu uguuga                     1906

<210> SEQ ID NO 17
<211> LENGTH: 1913
<212> TYPE: RNA
<213> ORGANISM: homo sapien

<400> SEQUENCE: 17
caggcuuacu gucuugggcc ucuuuuguca cauauugcuc aucugugagc ugaggcccug        60
acucacugag uauuuuuggg gagcagaaga aggagacauu ucucuccgaa aaugaacuca       120
acaggccacc uucaggaugc ccccaaugcc accucgcucc augugccuca cucacaggaa       180
ggaaacagca ccucucucca ggagggucuu caggaucuca uccacacagc caccuugguug      240 accuguacuu uucuacuggc ggucaucuuc ugccuggguu ccuauggcaa cuucauuguc       300 uucuugucu ucuucgaucc agccuucagg aaauucagaa ccaacuuuga uuucaugauc        360
cugaaccugu ccuucuguga ccucuucauu uguggaguga cagcccccau guucaccuuu       420
guguuauucu ucagcucagc caguaguauc ccggauacuu ucugcuucac uuuccaucuc       480
accaguucag gcuucaucau caugucucug aagacagugg caguaucgc ccugcaccgg        540 cuccggaugg uguggggggaa acagccuaau cgcacggccu ccuuucccug caccguacuc      600
cucacccugc uucucugggc caccaguuuc accccugcca ccuuggcuac cuugaaaacc       660
agcaaguccc accucugucu ucccaugucc agucugauug cuggaaaagg gaaagccauu       720
uugucucucu auggggucga cuucaccuuc ugguugcug uggucucugu cucuuacauc        780
augauugcuc agaccccggcg gaagaacgcu caagucagaa agugcccccc uguaaucaca      840
gucgaugcuu ccagaccaca gccuuucaug gggguccccug ugcagggagg uggagauccc     900
auccagugug ccaugccggc ucuguauagg aaccagaauu acgacaaacu gcagcacguu       960
cagacccgug gauauaccaa gagucccaac caacugguca ccccugcagc aagccgacuc      1020
cagcucguau cagccaucaa ccucuccacu gccaaggauu ccaaagccgu ggucaccugu      1080
gugaucauug ugcugucagu ccuggugugc ugucuuccac ugggggauuuc cuugguacag     1140 gugguucucu ccagcaaugg gagcuucauu cuuuaccagu uugaauuguu uggauuuacu      1200
cuuauauuuu ucaagucagg auuaaacccu uuuauauauu cucggaacag ugcagggcug      1260
agaaggaaag ugcucuggug ccuccaauac auaggccugg guuuuuucug cugcaaacaa      1320
aagacucgac uucgagccau gggaaaaggg aaccucgaag ucaacagaaa caaauccucc      1380
caucaugaaa caaacucugc cuacauguua ucuccaaagc cacagaagaa auuuguggac      1440
caggcuugug gcccaaguca uucaaaagaa aguauggguga gucccaagau cucugcugga     1500
caucaacacu gguggcagag cagcucgacc cccaucaaca cucggauuga accuuacuac      1560
agcaucuaua acagcagccc uucccaggag gagagcagcc cauguaacuu acagccagua      1620
aacucuuuug gauuugccaa uucauauauu gccaugcauu aucacaccac uaaugacuua      1680
gugcaggaau augacagcac uucagccaag cagauuccag uccccuccgu uuaaaagucau     1740 ggaggcuaua ggaucuuaug uaaacaguuu uuguuucuga uaguaauggg cuuuauucua      1800
acuugagauc aguggcggau caaaaccuac aagauucaac ugaaaaguug gcaguuaugg      1860
uuuucuuuca ucugaugugu caguaucugu ugauuugcuu uguaguuugu uga            1913
```

-continued

<210> SEQ ID NO 18
<211> LENGTH: 1913
<212> TYPE: RNA
<213> ORGANISM: homo sapien

<400> SEQUENCE: 18

```
caggcuuacu gucuugggcc ucuuuuguca cauauugcuc aucgugagc ugaggcccug        60 acucacugag uauuuuuggg gagcagaaga aggagacauu ucucuccgaa aaugaacuca       120
acaggccacc uucaggaugc ccccaaugcc accucgcucc augugccuca cucacaggaa       180
ggaaacagca ccucucucca ggagggucuu caggaucuca uccacacagc caccuuggug       240
accuguacuu uucuacuggc ggucaucuuc ugccugggu ucuauggcaa cuucauugc         300 uucuuguccu ucuucgaucc agccuucagg aaauucagaa ccaacuuuga uuucaugauc        360
cugaaccugu ccuucuguga ccucuucauu uguggaguga cagcccccau guucaccuuu       420
guguuauucu ucagcucagc caguaguauc ccggaugcuu ucugcuucac uuuccaucuc       480
accaguucag gcuucaucau caugucucug aagacagugg cagugaucgc ccugcaccgg       540
cuccggaugg uguuggggaa acagccuaau cgcacggccu ccuuucccug caccguacuc       600
cucacccugc uucucugggc caccaguuuc accccugcca ccuuggcuac cuugaaaacc       660 agcaagucc accucugucu ucccaugucc agucugauug cuggaaaagg gaaagccauu        720
uugucucucu augugguga cuucaccuuc uguguugcg uggucucugu cucuuacauc         780
augauugcuc agacccugcg gaagaacgcu uaagucagaa agugccccc uguaaucaca        840 gucgaugcuu ccagaccaca gccuuucaug ggggucccug ugcagggagg uggagauccc       900
auccagugug ccaugccggc ucuguauagg aaccagaauu acgacaaacu gcagcacguu       960
cagacccgug gauauaccaa gagucccaac caacugguca ccccugcagc aagccgacuc      1020
cagcucguau cagccaucaa ccucuccacu gccaaggauu ccaaagccgu ggucaccgu       1080 gugaucauug ugcugucagu ccuggugugc ugucuuccac uggggauuuc cuugguacag      1140
gugguucucu ccagcaaugg gagcuucauu cuuuaccagu uugaauuguu uggauuuacu      1200
cuuauauuuu ucaagucagg auuaaacccu uuuauauauu cucggaacag ugcagggcug      1260
agaaggaaag ugcucuggug ccuccaauac auaggccugg guuuuuucug cugcaaacaa      1320
aagacucgac uucgagccau gggaaaaggg aaccucgaag ucaacagaaa caaauccucc      1380
caucaugaaa caaacucugc cuacauguua ucuccaaagc cacagaagaa auuuguggac      1440
caggcuugug gcccaaguca uucaaaagaa aguauggug ucccaagau cucugcugga        1500 caucaacacu guggucagag cagcucgacc cccaucaaca cucggauuga accuuacuac      1560
agcaucuaua acagcagccc uucccaggag gagagcagcc cauguaacuu acagccagua      1620
aacucuuuug gauuugccaa uucauauau gccaugcauu aucacaccac uaaugacuua       1680
gugcaggaau augacagcac uucagccaag cagauccag uccccuccgu uuaaagucau        1740
ggaggcuaua ggaucuuaug uaaacaguuu uuguuucuga uaguaauggg cuuuauucua      1800
acuugagauc aguggcggau caaaaccuac aagauucaac ugaaaaguug gcaguuaugg      1860
uuuucuuuca ucugaugugu caguaucugu ugauuugcuu uguaguuugu uga            1913
```

<210> SEQ ID NO 19
<211> LENGTH: 1909
<212> TYPE: RNA
<213> ORGANISM: homo sapien

<400> SEQUENCE: 19

-continued

```
caggcuuacu gucuugggcc ucuuuuguca cauauugcuc aucgugagc ugaggcccug       60 acucacugag uauuuuuggg gagcagaaga aggagacauu ucucuccgaa aaugaacuca      120
acaggccacc uucaggaugc ccccaaugcc accucgcucc augugccuca cucacaggaa     180
ggaaacagca ccucucucca ggagggucuu caggaucuca uccacacagc caccuugguug    240 accguacuu uucuacuggc ggucaucuuc ugccugggu ccuauggcaa cuucauuguc       300 uucuugccu ucuucgaucc agccuucagg aaauucagaa ccaacuuuga uuucaugauc      360
cugaaccugu ccuucuguga ccccuucauu uguggaguga cagcccccau guucaccuuu     420
guguuauucu ucagcucagc caguaguauc ccggaugcuu ucugcuucac uuuccaucuc     480
accaguucag gcuucaucau caugucucug aagacagugg cagugaucgc ccugcaccgg     540
cuccggaugg uguuggggaa acagccuaau cgcacggccu ccuuucccug caccguacuc     600
cucacccugc uucucugggc caccaguuuc accccugcca ccuuggcuac cuugaaaacc     660 agcaagucc accucugucu ucccaugucc agucugauug cuggaaaagg gaaagccauu      720
uugucucucu auguggucga cuucaccuuc uguguugcug uggucucugu ucuuacauc      780 augauugcuc agaccugcg gaagaacgcu caagucagug cccccugua aucacagucg       840 augcuuccag accacagccu uucauggggg ucccugugca gggaggugga gaucccaucc     900
agugugccau gccggcucug uauaggaacc agaauuacga caaacugcag cacguucaga     960 cccgguggaua uaccaagagu cccaaccaac uggucacccc ugcagcaagc cgacuccagc   1020
ucguaucagc caucaaccuc uccacugcca aggauuccaa agccgugguc accuguguga   1080
ucauugugcu gucaguccug gugugucuguc uuccacuggg gauuuccuug guacaggugg   1140
uucucuccag caaugggagc uucauucuuu accaguuuga auuguuugga uuuacucuua   1200 uauuuucaa gucaggauua aacccuuuua uauauucucg gaacagugca gggcugagaa    1260
ggaaagugcu cuggugccuc caauacauag gccugggutu uuucugcugc aaacaaaaga   1320
cucgacuucg agccauggga aaagggaacc ucgaagucaa cagaaacaaa uccucccauc   1380
augaaacaaa cucugccuac auguuaucuc caaagccaca gaagaaauuu guggaccagg   1440
cuuguggccc aagucauuca aaagaaagua uggugaguccc caagaucucu gcuggacauc   1500
aacacugugg ucagagcagc ucgacccca ucaacacucg gauugaaccu uacuacagca     1560
ucuauaacag cagcccuucc caggaggaga gcagcccaug uaacuuacag ccaguaaacu    1620
cuuuuggauu ugccaauuca uauauugcca ugcauuauca caccacuaau gacuuagugc    1680
aggaauauga cagcacuuca gccaagcaga uuccaguccc cuccguuuaa agucauggag    1740
gcuauaggau cuuauguaaa caguuuuugu uucugauagu aaugggcuuu auucuaacuu    1800
gagaucagug gcggaucaaa accuacaaga uucaacugaa aaguuggcag uuaugguuuu    1860
cuuucaucug augugucagu aucguugau uugcuuugua guuuguuga              1909
```

<210> SEQ ID NO 20
<211> LENGTH: 1914
<212> TYPE: RNA
<213> ORGANISM: homo sapien

<400> SEQUENCE: 20

```
caggcuuacu gucuugggcc ucuuuuguca cauauugcuc aucgugagc ugaggcccug       60 acucacugag uauuuuuggg gagcagaaga aggagacauu ucucuccgaa aaugaacuca      120
acaggccacc uucaggaugc ccccaaugcc accucgcucc augugccuca cucacaggaa     180
ggaaacagca ccucucucca ggagggucuu caggaucuca uccacacagc caccuugguug    240
```

-continued

```
accuguacuu uucuacuggc ggucaucuuc ugccuggguu ccuauggcaa cuucauuguc      300
uucuuguccu ucuucgaucc agccuucagg aaauucagaa ccaacuuuga uuucaugauc      360
cugaaccugu ccuucuguga ccucuuucauu uguggaguga cagcccccau guucaccuuu      420
guguuauucu ucagcucagc caguaguauc ccggaugcuu ucugcuucac uuuccaucuc      480
accaguucag gcuucaucau caugucucug aagacagugg cagugaucgc ccugcaccgg      540
cuccggaugg uguuggggaa acagccuaau cgcacggccu ccuuucccug caccguacuc      600
cucacccugc uucucugggc caccaguuuc accccugcca ccuuggcuac cuugaaaacc      660
agcaaguccc accucugucu ucccaugucc agucugauug cuggaaaagg gaaagccauu      720
uugucucucu auguggucga cuucaccuuc uguguugcug uggucucugu cucuuacauc      780
augauugcuc agacccugcg gaagaacgcu caagucagaa agugcccccc uguaaucaca      840
gucgaugcuu ccagaccaca gccuuucaug ggggucccug ugcagggagg uggagauccc      900
auccagugug ccaugccggc ucuguauagg aaccagaauu acgacaaacu gcagcacguu      960
cagacccgug gauauaccaa gagucccaac caacugguca ccccugcagc aagccgacuc      1020
cagcucguau cagccaucaa ccucuccacu gccaaggauu ccaaagccgu ggucaccugu      1080
gugaucauug ugcugucagu ccuggugugc ugucuuccac uggggauuuc cuugguacag      1140
gugguucucu ccagcaaugg gagcuucauu cuuuaccagu uugaauuguu uggauuuacu      1200
cuuauauuuu ucaagucagg auuaaacccu uuuauauauu cucggaacag ugcagggcug      1260
agaaggaaag ugcucuggug ccuccaauac auaggccugg guuuuuucug ucugcaaaca      1320
aaagacucga cuucgagcca ugggaaaagg gaaccucgaa gucaacagaa acaaauccuc      1380
ccaucaugaa acaaacucug ccuacauguu aucuccaaag ccacagaaga aauuugugga      1440
ccaggcuugu ggcccaaguc auucaaaaga aaguauggug agucccaaga ucucugcugg      1500
acaucaacac ugugggucaga gcagcucgac ccccaucaac acucggauug aaccuuacua      1560
cagcaucuau aacagcagcc cuucccagga ggagagcagc ccauguaacu uacagccagu      1620
aaacucuuuu ggauuugcca auucauauau ugccaugcau uaucacacca cuaaugacuu      1680
agugcaggaa uaugacagca cuucagccaa gcagauucca gucccuccg uuuaaaguca      1740 uggaggcuau aggaucuuau guaaacaguu uuuguuucug auaguaaugg gcuuuauucu      1800
aacuugagau caguggcgga ucaaaaccua caagaucaa cugaaaaguu ggcaguuaug      1860
guuuucuuuc aucugaugug ucaguaucug uugauuugcu uuguaguuug uuga            1914
```

<210> SEQ ID NO 21
<211> LENGTH: 1734
<212> TYPE: RNA
<213> ORGANISM: homo sapien

<400> SEQUENCE: 21

```
ggagcagaag aaggagacau uucucuccga aaaugaacuc aacaggccac cuucaggaug       60
cccccaaugc caccucgcuc caugugccuc acucacagga aggaaacagc accucucucc      120 aggaggggucu ucaggaucuc auccacacag ccaccuuggu gaccuguacu uuucuacugg      180
cggucaucuu cugccugggu uccuauggca acuucauugu cuucuugucc uucuucgauc      240
cagccuucag gaaauucaga accaacuuug auuucaugau ccugaaccug ccuucugug       300 accucuucau uuguggagug acagcccca uguucaccuu uguguuauuc uucagcucag       360
uaucccggau gcuuucugcu ucacuuucca ucucaccagu ucaggcuuca ucaucauguc      420
```

-continued

```
ucugaagaca guggcaguga ucgcccugca ccggcuccgg auggguguugg ggaaacagcc      480 uaaucgcacg gccuccuuuc ccugcaccgu acuccucacc cugcuucucu gggccaccag      540
uuucacccuu gccaccuugg cuaccuugaa aaccagcaag ucccaccucu gucuucccau      600
guccagucug auugcuggaa aagggaaagc cauuuugucu cucuaugugg ucgacuucac      660
cuucuguguu gcuguggucu cugucucuua caucaugauu gcucagaccc ugcggaagaa      720
cgcucaaguc agaaagugcc ccccuguaau cacagucgau gcuuccagac cacagccuuu      780
cauggggguc ccugugcagg gaggguggaga ucccauccag uguggccaugc cggcucugua     840 uaggaaccag aauuacaaca aacugcagca cguucagacc cguggauaua ccaagagucc      900
caaccaacug gucacccccug cagcaagccg acuccagcuc guaucagcca ucaaccucuc      960
cacugccaag gauccaaag ccguggucac cugugugauc auugugcugu cagucuggu       1020 gugcugucuu ccacugggga uuuccuuggu acaguggguu cucuccagca augggagcuu     1080
cauucuuuac caguuugaau uguugggauu uacucuuaua uuuuucaagu caggauuaaa     1140
cccuuuuaua uauuucucgga acagugcagg gcugagaagg aaagugcucu ggugccucca     1200
auacauaggc cugggguuuu ucugcugcaa acaaaagacu cgacuucgag ccaugggaaa     1260
agggaaccuc gaagucaaca gaaacaaauc cucccaucau gaaacaaacu cugccuacau     1320
guuaucucca aagccacaga agaaauuugu ggaccaggcu uguggcccaa gucauucaaa     1380
agaaaguaug gugagucccca agaucucugc uggacaucaa cacugugguc agagcagcuc     1440 gaccccauc aacacucgga uugaaccuuua cuacagcauc uauaacagca gcccuuccca     1500
ggaggagagc agcccaugua acuuacagcc aguaaacucu uuuggauuug ccaauucaua     1560
uauugccaug cauuaucaca ccacuaauga cuuagugcag gaauaugaca gcacuucagc     1620
caagcagauu ccagucccecu ccguuuaaag ucauggaggc uauaggaucu uauguaaaca     1680
guuuuuguuu cugauaguaa uggacuuuau ucuaacuuga gauaguggcg gauc          1734
```

<210> SEQ ID NO 22
<211> LENGTH: 1741
<212> TYPE: RNA
<213> ORGANISM: homo sapien

<400> SEQUENCE: 22

```
ggagcagaag aaggagacau uucucuccga aaaugaacuc aacaggccac cuucaggaug       60
cccccaaugc caccucgcuc caugugccuc acucacagga aggaaacagc accucucucc      120 aggaggguu ucaggaucuc auccacacag ccaccuuggu gaccuguacu uuucuacugg       180
cggucaucuu cugccugggu uccuauggca acuucauugu cuucuugucc uucucgauc       240 cagccuucag gaaauucaga accaacuuug auuucaugau ccugaaccug ccuucugug       300 accucuucau uuguggagug acagccccca uguucaccuu uguguuauuc uucagcucag      360
ccaguaguau cccggauacu uucugcuuca cuuccaucu caccaguuca ggcuucauca      420
ucaugucucu gaagacagug gcagugaucg cccugcaccg gccuccggaug uguuggggga     480 aacagccuaa ucgcacggcc uccuucccu gcaccguacu ccucacccug cuucucuggg      540
ccaccaguuu caccccuugcc accuggcua ccuugaaaac cagcaagucc caccucuguc      600 uucccaugue cagucugauu gcuggaaaag ggaaagccau uuugucucuc uauguggucg      660
acuucaccuu cugucuugcu guggucucug ucucuuacau caugauugcu cagacccugc      720
ggaagaacgc ucaagucaga aagugccccc cuguaaucac agucgaugcu uccagaccac      780
agccuuucau gggggucccu gugcagggag guggagaucc cauccagugu gccaugccgg      840
```

-continued

```
cucuguauag gaaccagaau uacaacaaac ugcagcacgu ucagacccgu ggauauacca      900
agagucccaa ccaacugguc accccugcag caagccgacu ccagcucgua ucagccauca      960
accucuccac ugccaaggau uccaaagccg uggucaccug ugugaucauu gugcugucag      1020
uccuggugug cugucuucca cuggggauuu ccuugguaca ggugguucuc uccagcaaug      1080
ggagcuucau ucuuuaccag uuugaauugu uuggauuuac ucuuauauuu uucaagucag      1140
gauuaaaccc uuuuauauau ucucggaaca gugcagggcu gagaaggaaa gugcucuggu      1200
gccuccaaua cauaggccug gguuuuuucu gcugcaaaca aaagacucga cuucgagcca      1260
ugggaaaagg gaaccucgaa gucaacagaa acaaauccuc ccaucaugaa acaaacucug      1320
ccuacauguu aucuccaaag ccacagaaga aauuugugga ccaggcuugu ggcccaaguc      1380
auucaaaaga aaguauggug agucccaaga ucucugcugg acaucaacac uguggucaga      1440
gcagcucgac ccccaucaac acucggauug aaccuuacua cagcaucuau aacagcagcc      1500
cuucccagga ggagagcagc ccauguaacu uacagccagu aaacucuuuu ggauuugcca      1560
auucauauau ugccaugcau uaucacacca cuaaugacuu agugcaggaa uaugacagca      1620
cuucagccaa gcagauucca guccc@uccg uuuaaaaguca uggaggcuau aggaucuuau      1680
guaaacaguu uuuguuucug auaguaaugg acuuuauucu aacuugagau aguggcggau      1740
c                                                                     1741

<210> SEQ ID NO 23
<211> LENGTH: 1741
<212> TYPE: RNA
<213> ORGANISM: homo sapien

<400> SEQUENCE: 23
ggagcagaag aaggagacau uucucuccga aaaugaacuc aacaggccac cuucaggaug       60
cccccaaugc caccucgcuc caugugccuc acucacagga aggaaacagc accucucucc      120
aggagggucu ucaggaucuc auccacacag ccaccuuggu gaccuguacu uuucuacugg      180
cggucaucuu cugccggggu uccuauggca acuucauugu cuucuugucc uucuucgauc      240
cagccuucag gaaauucaga accaacuuug auuucaugau ccugaaccug uccuucugug      300
accucuucau uuguggagug acagcccccca uguucaccuu uguguuauuc uucagcucag      360
ccaguaguau cccggaugcu uucugcuuca cuuuccaucu caccaguuca ggcuucauca      420
ucaugucucu gaagacagug gcagugaucg cccugcaccg gcuccggaug ugguuggga      480 aacagccuaa ucgcacggcc uccuuucccu gcaccguacu ccucacccug cuucucuggg      540
ccaccaguuu caccccuugcc accuuggcua ccuugaaaac cagcaagucc caccucuguc      600
uucccauguc cagucugauu gcuggaaaag ggaaagccau uuugucucuc uauguggucg      660
acuucaccuu cuguguugcu guggucucug ucucuuacau caugauugcu cagacccugc      720
ggaagaacgc uuaagucaga aagugcccccc cuguaaucac agucgaugcu uccagaccac      780
agccuuucau ggggguccccu gugcagggag guggagaucc cauccagugu gccaugccgg      840
cucuguauag gaaccagaau uacaacaaac ugcagcacgu ucagacccgu ggauauacca      900
agagucccaa ccaacugguc accccugcag caagccgacu ccagcucgua ucagccauca      960
accucuccac ugccaaggau uccaaagccg uggucaccug ugugaucauu gugcugucag      1020
uccuggugug cugucuucca cuggggauuu ccuugguaca ggugguucuc uccagcaaug      1080
ggagcuucau ucuuuaccag uuugaauugu uuggauuuac ucuuauauuu uucaagucag      1140
```

-continued

```
gauuaaacccc uuuuauauau ucucggaaca gugcagggcu gagaaggaaa gugcucuggu    1200
gccuccaaua cauaggccug gguuuuuucu gcugcaaaca aaagacucga cuucgagcca    1260
ugggaaaagg gaaccucgaa gucaacagaa acaaauccuc ccaucaugaa acaaacucug    1320
ccuacauguu aucuccaaag ccacagaaga aauuugugga ccaggcuugu ggcccaaguc    1380
auucaaaaga aaguauggug agcccaaga ucucugcugg acaucaacac uguggucaga     1440
gcagcucgac ccccaucaac acucggauug aaccuuacua cagcaucuau aacagcagcc    1500
cuucccagga ggagagcagc ccauguaacu uacagccagu aaacucuuuu ggauuugcca    1560
auucauauau ugccaugcau uaucacacca cuaaugacuu agugcaggaa uaugacagca    1620
cuucagccaa gcagauucca gucccccuccg uuuaaaguca uggaggcuau aggaucuuau    1680
guaaacaguu uuuguuucug auaguaaugg acuuuauucu aacuugagau aguggcggau    1740
c                                                                     1741

<210> SEQ ID NO 24
<211> LENGTH: 1737
<212> TYPE: RNA
<213> ORGANISM: homo sapien

<400> SEQUENCE: 24
ggagcagaag aaggagacau uucucuccga aaaugaacuc aacaggccac cuucaggaug      60
cccccaaugc caccucgcuc caugugccuc acucacagga aggaaacagc accucucucc     120
aggagggucu ucaggaucuc auccacacag ccaccuuggu gaccuguacu uuucuacugg     180
cggucaucuu cugccugggu uccuauggca acuucauugu cuucuugucc uucuucgauc     240
cagccuucag gaaauucaga accaacuuug auuucaugau ccugaaccug uccuucugug     300
accucuucau uuguggagug acagcccca uguucacc uuguguuauc uucagcucag          360
ccaguaguau cccggaugcu uucugcuuca cuuccaucu caccaguuca ggcuucauca     420
ucaugucucu gaagacagug gcagugaucg cccugcaccg gcuccggaug uguguggggga    480 aacagccuaa ucgcacggcc uccuuucccu gcaccguacu ccucacccug cuucucuggg      540
ccaccaguuu caccccuugcc accuuggcua ccuugaaaac cagcaagucc caccucuguc    600 uucccaugu cagucugauu gcuggaaaag ggaaagccau uuugucucuc uaugugggucg      660 acuucaccuu cugugugcu guggcucug ucucuuacau caugauugcu cagacccuugc        720 ggaagaacgc ucaagucagu gccccccugu aaucacaguc gaugcuucca gaccacagcc      780 uuucauggg gucccugugc agggaggugg agaucccauc cagugugcca ugccggcucu        840
guauaggaac cagaauuaca acaaacugca gcacguucag acccguggau auaccaagag      900
ucccaaccaa cuggucaccc cugcagcaag ccgacuccag cucguaucag ccaucaaccu      960
cuccacugcc aaggauucca aagccguggu caccugugug aucauugugc ugucaguccu    1020
ggugugcugu cuuccacugg ggauuuccuu gguacaggug uucucucca gcaaugggag      1080 cuucauucuu uaccaguuug aauuguuugg auuuacucuu auauuuuuca agucaggauu      1140
aaacccuuuu auauauucuc ggaacagugc agggcugaga aggaaagugc ucuggugccu    1200
ccaauacaua ggccuggguu uuuucugcug caaacaaaag acucgacuuc gagccauggg    1260
aaaagggaac cucgaaguca acagaaacaa auccucccau caugaaacaa acucugccua    1320
cauguuaucu ccaaagccac agaagaaauu uguggaccag gcuuguggcc caagucauuc    1380
aaaagaaagu augguggagc ccaagaucuc ugcuggacau caacacugug gucagagcag    1440
cucgaccccc aucaacacuc ggauugaacc uuacuacagc aucuauaaca gcagcccuuc    1500
```

```
ccaggaggag agcagcccau guaacuuaca gccaguaaac ucuuuuggau uugccaauuc    1560
auauauugcc augcauuauc acaccacuaa ugacuuagug caggaauaug acagcacuuc    1620
agccaagcag auuccagucc ccuccguuua aagucaugga ggcuauagga ucuuauguaa    1680
acaguuuuug uuucugauag uaauggacuu uauucuaacu ugagauagug gcggauc      1737

<210> SEQ ID NO 25
<211> LENGTH: 1742
<212> TYPE: RNA
<213> ORGANISM: homo sapien

<400> SEQUENCE: 25
ggagcagaag aaggagacau uucucuccga aaaugaacuc aacaggccac cuucaggaug      60
cccccaaugc caccucgcuc caugugccuc acucacagga aggaaacagc accucucucc     120
aggagggucu ucaggaucuc auccacacag ccaccuuggu gaccuguacu uuucuacugg     180
cggucaucuu cugccugggu uccuauggca acuucauugu cuucuugucc uucuucgauc     240
cagccuucag gaaauucaga accaacuuug auuucaugau ccugaaccug uccuucugug     300
accucuucau uuguggagug acagccccca uguucacccu uguguuauuc uucagcucag     360
ccaguaguau cccggaugcu uucugcuuca cuuuccaucu caccaguuca ggcuucauca     420
ucaugucucu gaagacagug gcagugaucg cccugcaccg gcuccggaug uguuggggga     480
aacagccuaa ucgcacggcc uccuuucccu gcaccguacu ccucacccug cuucucuggg     540
ccaccaguuu caccccuugcc accuuggcua ccuugaaaac cagcaagucc caccucuguc     600
uucccauguc cagucugauu gcuggaaaag ggaaagccau uuugucucuc uaugugggucg     660 acuucacccu ucuguuugcu guggucucug ucucuuacau caugauugcu cagacccugc     720
ggaagaacgc ucaagucaga aagugccccc cguuaaucac agucgaugcu uccagaccac     780
agccuuucau gggggucccu ugcagggag guggagaucc cauccagugu gccaugccgg     840
cucuguauag gaaccagaau uacaacaaac ugcagcacgu ucagacccgu ggauauacca     900 agaguucccaa ccaacggguc accccugcag caagccgacu ccagcucgua ucagccauca     960
accucuccac ugccaaggau uccaaagccg uggucaccug ugugaucauu gugcugucag   1020
uccuggugug cugucuucca cuggggauuu ccuugguaca ggugguucuc uccagcaaug   1080
ggagcuucau ucuuuaccag uuugaauugu uggauuuuac ucuuauauuu uucaagucag   1140
gauuaaaccc uuuuauauau ucucggaaca gugcagggcu gagaaggaaa gugcucuggu   1200
gccuccaaua cauaggccug gguuuuuucu gucugcaaac aaaagacucg acuucgagcc   1260
augggaaaag ggaaccucga agucaacaga aacaaaucu cccaucauga aacaaacucu   1320
gccuacaugu uaucuccaaa gccacagaag aaauuugugg accaggcuug uggcccaagu   1380
cauucaaaag aaaguauggu gagucccaag aucucugcug gacaucaaca cuguggucag   1440
agcagcucga ccccccaucaa cacucggauu gaaccuuacu acagcaucua uaacagcagc   1500
ccuucccagg aggagagcag cccauguaac uuacagccag uaaacucuuu uggauuugcc   1560
aauucauaua uugccaugca uuaucacacc acuaaugacu uagugcagga auaugacagc   1620
acuucagcca agcagauucc aguccccucc guuuaaaguc auggaggcua uaggaucuua   1680
uguaaacagu uuuuguuucu gauaguaaug gacuuuauuc uaacuugaga uaguggcgga   1740
uc                                                                  1742

<210> SEQ ID NO 26
```

```
<211> LENGTH: 1887
<212> TYPE: RNA
<213> ORGANISM: homo sapien

<400> SEQUENCE: 26
gugacugcgc cucugcgccc gcgucuugcc gcggcucccg ggaugcgcgg aggcgguggc      60
gauggcgaug augccucuag uccugcauca uccagagcgg caggcggagc uggggguccgg     120 acugcgagau ggaggagggg cggcgcgucg gccacccggc aggcuuaucu gucuugggcc     180
ucuuuuguca cauauugcuc aucugugagc ugaggcccug acucacugag uauuuuuggg     240
gagcagaaga aggagacauu ucucuccgaa aaugaacuca acaggccacc uucaggaugc     300
ccccaaugcc accucgcucc augugccuca cucacaggaa ggaaacagca ccucucucca     360
ggagggucuu caggaucuca uccacacagc caccuuggug accuacuacu uucuacuggc     420
ggucaucuuc ugccuggguu ccuauggcaa cuucauuguc uucuuguccu ucuucgaucc     480
agccuucagg aaauucagaa ccaacuuuga uuucaugauc cugaaccugu ccuucuguga     540
ccucuucauu uguggaguga cagcccccau guucaccuuu guguuauucu ucagcucagu     600
aucccggaug cuuucugcuu cacuuuccau cucaccaguu caggcuucau caucaugucu     660
cugaagacag uggcagugau cgcccugcac cggcuccgga ugguguuggg gaaacagccu     720
aaucgcacgg ccuccuuucc cugcaccgua cuccucaccc ugcuucucug ggccaccagu     780
uucacccuug ccaccuuggc uaccuugaaa accagcaagu cccacccucg ucuucccaug     840
uccagucuga uugcuggaaa agggaaagcc auuuugucuc ucuauguggu cgacuucacc     900
uucuguguug cuguggucuc ugucucuuac aucaugauug cucagacccu gcggaagaac     960
gcucaaguca gaaagugccc cccuguaauc acagucgaug cuuccagacc acagccuuuc    1020
augggggucc cugugcaggg agguggagau cccauccagu gugccaugcc ggcucuguau    1080
aggaaccaga auuacaacaa acugcagcac guucagaccc guggauauac caagaguccc    1140
aaccaacugu ucacccccugc agcaagccga cuccagcucg uaucagccau caaccucucc    1200
acugccaagg auuccaaagc cguggucacc ugugugauca uugugcuguc aguccuggug    1260 ugcugcuuc cacuggggau uuccuuggua caggugguuc ucuccagcaa ugggagcuuc    1320
auucuuuacc aguuugaauu guuuggauuu acucuuauau uuuucaaguc aggauuaaac    1380
ccuuuuauau auuucucggaa cagugcaggg cugagaagga aagugcucug gugccuccaa    1440
uacauaggcc uggguuuuuu cugcugcaaa caaaagacuc gacuucgagc caugggaaaa    1500
gggaaccucg aagucaacag aaacaaaucc ucccaucaug aaacaaacuc ugccuacaug    1560
uuaucuccaa agccacagaa gaaauuugug gaccaggcuu guggcccaag ucauucaaaa    1620
gaaaguaugg ugagucccaa gaucucugcu ggacaucaac acugugguca gagcagcucg    1680 accccccauca acacucggau ugaaccuuac uacagcaucu auaacagcag cccuucccag    1740
gaggagagca gcccauguaa cuuacagcca guaaacucuu uuggauuugc caauucauau    1800
auugccaugc auuaucacac cacuaaugac uuagugcagg aauaugacag cacuucagcc    1860
aagcagauuc cagucccuc cguuuaa                                        1887

<210> SEQ ID NO 27
<211> LENGTH: 1894
<212> TYPE: RNA
<213> ORGANISM: homo sapien

<400> SEQUENCE: 27
gugacugcgc cucugcgccc gcgucuugcc gcggcucccg ggaugcgcgg aggcgguggc      60
```

```
gauggcgaug augccucuag uccugcauca uccagagcgg caggcggagc ugggguccgg      120
acugcgagau ggaggagggg cggcgcugcg gccacccggc aggcuuaucu gucuugggcc      180
ucuuuuguca cauauugcuc aucugugagc ugaggcccug acucacugag uauuuuuggg      240
gagcagaaga aggagacauu ucucuccgaa aaugaacuca acaggccacc uucaggaugc      300
ccccaaugcc accucgcucc augugccuca cucacaggaa ggaaacagca ccucucucca      360
ggagggucuu caggaucuca uccacacagc caccuuggug accuguacuu uucuacuggc      420
ggucaucuuc ugccuggguu ccuauggcaa cuucauuguc uucuuguccu ucuucgaucc      480
agccuucagg aaauucagaa ccaacuuuga uuucaugauc cugaaccugu ccuucuguga      540
ccucuucauu uguggaguga cagcccccau guucaccuuu guguuauucu ucagcucagc      600
caguaguauc ccggauacuu ucugcuucac uuuccaucuc accaguucag gcuucaucau      660
caugucucug aagacagugg cagugaucgc ccugcaccgg cuccggaugg uguuggggaa      720
acagccuaau cgcacggccu ccuuucccug caccguacuc cucacccugc uucucugggc      780
caccaguuuc acccuugcca ccuuggcuac cuugaaaacc agcaaguccc accucugucu      840
ucccaugucc agucugauug cuggaaaagg gaaagccauu uugucucucu auguggucga      900
cuucaccuuc ugguugcug uggucucugu cucuuacauc augauugcuc agacccugcg      960
gaagaacgcu caagucagaa agugcccccc uguaaucaca gucgaugcuu ccagaccaca      1020
gccuuucaug ggggucccug ugcagggagg uggagauccc auccagugug ccaugccggc      1080
ucuguauagg aaccagaauu acaacaaacu gcagcacguu cagacccgug gauauaccaa      1140
gagucccaac caacugguca ccccugcagc aagccgacuc cagcucguau cagccaucaa      1200
ccucuccacu gccaaggauu ccaaagccgu ggucaccugu gugaucauug ugcugucagu      1260
ccuggugugc ugucuuccac uggggauuuc cuugguacag gugguucucu ccagcaaugg      1320
gagcuucauu cuuuaccagu uugaauuguu uggauuuacu cuuauauuuu ucaagucagg      1380
auuaaacccu uuuauauauu cucggaacag ugcagggcug agaaggaaag ugcucugggu      1440
ccuccaauac auaggccugg guuuuuucug cugcaaacaa aagacucgac uucgagccau      1500
gggaaaaggg aaccucgaag ucaacagaaa caaauccucc caucaugaaa caaacucugc      1560
cuacauguua ucuccaaagc cacagaagaa auuuguggac caggcuugug gcccaaguca      1620
uucaaaagaa aguaugguga gucccaagau cucugcugga caucaacacu gugguucagag     1680 cagcucgacc cccaucaaca cucggauuga accuuacuac agcaucuaua acagcagccc      1740
uucccaggag gagagcagcc cauguaacuu acagccagua aacucuuuug gauuugccaa      1800
uucauauauu gccaugcauu aucacaccac uaaugacuua gugcaggaau augacagcac      1860
uucagccaag cagauuccag uccccuccgu uuaa                                 1894
```

```
<210> SEQ ID NO 28
<211> LENGTH: 1894
<212> TYPE: RNA
<213> ORGANISM: homo sapien

<400> SEQUENCE: 28
gugacugcgc cucugcgccc gcgucuugcc gcggcucccg ggaugcgcgg aggcgguggc       60
gauggcgaug augccucuag uccugcauca uccagagcgg caggcggagc ugggguccgg      120
acugcgagau ggaggagggg cggcgcugcg gccacccggc aggcuuaucu gucuugggcc      180
ucuuuuguca cauauugcuc aucugugagc ugaggcccug acucacugag uauuuuuggg      240
```

-continued

```
gagcagaaga aggagacauu ucucuccgaa aaugaacuca acaggccacc uucaggaugc    300
ccccaaugcc accucgcucc augugccuca cucacaggaa ggaaacagca ccucucucca    360
ggaggguuuu caggaucuca uccacacagc caccuuggug accuguacuu uucuacuggc    420
ggucaucuuc ugccugggu ccuauggcaa cuucauugu uuccugucc uuucgaucc       480 agccuucagg aaauucagaa ccaacuuuga uuucaugauc cugaaccugu ccuucuguga    540
ccucuucauu uguggaguga cagcccccau guucaccuuu guguuauucu ucagcucagc    600
caguaguauc ccggaugcuu ucugcuucac uuuccaucuc accaguucag gcuucaucau    660 cauguucucug aagacagugg cagugaucgc ccugcaccgg cuccggaugg uguugggaa    720 acagccuaau cgcacggccu ccuuucccug caccguacuc cucacccugc uucucugggc    780
caccaguuuc accccuugcca ccuuggcuac cuugaaaacc agcaagcccc accucugucu    840
ucccaugucc agucugauug cuggaaaagg gaaagccauu uugucucucu auguggucga    900
cuucaccuuc uguguugcug uggucucugu cucuuacauc augauugcuc agacccugcg    960
gaagaacgcu uaagucagaa agugccccccu uguaaucaca gucgaugcuu ccagaccaca   1020
gccuuucaug gggucccug ugcagggagg uggagauccc auccaguug ccaugccggc     1080 ucuguauagg aaccagaauu acaacaaacu gcagcacguu cagacccgug gauauaccaa    1140
gagucccaac caacugguca ccccugcagc aagccgacuc cagcucguau cagccaucaa    1200
ccucuccacu gccaaggauu ccaaagccgu ggucaccgu gugaucauug ugcugucagu    1260
ccuggugugc ugucuuccac uggggauuuc cuugguacag gugguucucu ccagcaaugg    1320
gagcuucauu cuuuaccagu uugaauuguu uggauuuacu cuuauauuuu ucaagucagg    1380
auuaaacccu uuuauauauu cucggaacag ugcagggcug agaaggaaag ugcucuggug    1440
ccuccaauac auaggccugg guuuuuucug cugcaaacaa aagacucgac uucgagccau    1500
gggaaaaggg aaccucgaag ucaacagaaa caaauccucc caucaugaaa caaacucugc    1560
cuacauguua ucuccaaagc cacagaagaa auuuguggac caggcuugug gcccaaguca    1620
uucaaaagaa aguaugguga gucccaagau cucugcugga caucaacacu guggucagag    1680
cagcucgacc cccaucaaca cucggauuga accuuacuac agcaucuaua acagcagccc    1740
uucccaggag gagagcagcc cauguaacuu acagccagua aacucuuuug gauuugccaa    1800
uucauauauu gccaugcauu aucacaccac uaaugacuua gugcaggaau augacagcac    1860
uucagccaag cagauuccag uccccuccgu uuaa                                1894
```

```
<210> SEQ ID NO 29
<211> LENGTH: 1890
<212> TYPE: RNA
<213> ORGANISM: homo sapien

<400> SEQUENCE: 29
gugacugcgc cucugcgccc gcgucuugcc gcggcucccg ggaugcgcgg aggcgguggc     60
gauggcgaug augccucuag uccugcauca uccagagcgg caggcggagc uggggucuccg   120 acugcgagau ggaggagggg cggcgcugcg gccacccggc aggcuuaucu gucuugggcc    180 ucuuuugcu cauauugcuc aucugugagc ugaggcccug acucacugag uauuuuuggg     240
gagcagaaga aggagacauu ucucuccgaa aaugaacuca acaggccacc uucaggaugc   300
ccccaaugcc accucgcucc augugccuca cucacaggaa ggaaacagca ccucucucca   360
ggaggguuuu caggaucuca uccacacagc caccuuggug accuguacuu uucuacuggc   420
ggucaucuuc ugccugggu ccuauggcaa cuucauugu uucuugucc uuucgaucc      480
```

```
agccuucagg aaauucagaa ccaacuuuga uuucaugauc cugaaccugu ccuucuguga      540
ccucuucauu uguggaguga cagcccccau guucacccuuu guguuuauucu ucagcucagc     600 caguaguauc ccggaugcuu ucugcuucac uuuccaucuc accaguucag gcuucaucau      660
caugucucug aagacagugg cagugaucgc ccugcaccgg cuccggaugg uguugggggaa     720 acagccuaau cgcacggccu ccuuucccug caccguacuc cucacccugc uucucugggc      780
caccaguuuc acccuugcca ccuuggcuac cuugaaaacc agcaagucccc accucugucu     840 ucccaugucc agucugauug cuggaaaagg gaaagccauu uugucucucu auguggucga     900
cuucaccuuc uguguugcug uggucucugu cucuuacauc augauugcuc agacccugcg      960
gaagaacgcu caagucagug ccccccugua aucacagucg augcuuccag accacagccu     1020
uucauggggg ucccugugca gggaggugga gaucccaucc agugugccau gccggcucug    1080
uauaggaacc agaauuacaa caaacugcag cacguucaga cccguggaua uaccaagagu    1140
cccaaccaac uggucaccccc ugcagcaagc cgacuccagc ucguaucagc caucaaccuc    1200
uccacugcca aggauuccaa agccgugguc accguguga ucaugugcu gucaguccug      1260 gugugcuguc uuccacuggg gauuuccuug guacaggugg uucucuccag caaugggagc    1320
uucauucuuu accaguuuga auuguuugga uuuacucuua uauuuuucaa gucaggauua     1380
aacccuuuua uauauucucg gaacagugca gggcugagaa ggaaagugcu cuggugccuc    1440
caauacauag gccugggguu uuucugcugc aaacaaaaga cucgacuucg agccauggga    1500
aaagggaacc ucgaagucaa cagaaacaaa uccucccauc augaaacaaa cucugccuac    1560
auguuaucuc caaagccaca gaagaaauuu guggaccagg cuuguggccc aagucauuca    1620
aaagaaagua uggugagucc caagaucucu gcuggacauc aacacugugg ucagagcagc    1680 ucgacccccca ucaacacucg gauugaaccu uacuacagca ucuauaacag cagcccuucc    1740
caggaggaga gcagcccaug uaacuuacag ccaguaaacu cuuuuggauu ugccaauuca    1800
uauauugcca ugcauuauca caccacuaau gacuuagugc aggaauauga cagcacuuca    1860
gccaagcaga uuccaguccc cuccguuuaa                                      1890
```

<210> SEQ ID NO 30  
<211> LENGTH: 1895  
<212> TYPE: RNA  
<213> ORGANISM: homo sapien

<400> SEQUENCE: 30

```
gugacugcgc cucugcgccc gcgucuugcc gcggcucccg ggaugcgcgg aggcgguggc        60
gauggcgaug augccucuag uccugcauca uccagagcgg caggcggagc uggggguccgg       120 acugcgagau ggaggagggg cggcgcugcg gccacccggc aggcuuaucu gucuuggggcc      180 ucuuuuguca cauauugcuc aucugugagc ugaggcccug acucacugag uauuuuuggg       240
gagcagaaga aggagacauu ucucuccgaa aaugaacuca acaggccacc uucaggaugc       300
ccccaaugcc accucgcucc augugccuca cucacaggaa ggaaacagca ccucucucca      360
ggagggucuu caggaucuca uccacacagc caccuugguig accuguacuu uucuacuggc      420
ggucaucuuc ugccuggguu ccuauggcaa cuucauugac uucuugucccu ucuucgaucc     480 agccuucagg aaauucagaa ccaacuuuga uuucaugauc cugaaccugu ccuucuguga     540
ccucuucauu uguggaguga cagcccccau guucacccuuu guguuuauucu ucagcucagc    600 caguaguauc ccggaugcuu ucugcuucac uuuccaucuc accaguucag gcuucaucau     660
```

```
caugucucug aagacagugg cagugaucgc ccugcaccgg cuccggaugg uguuggggaa        720
acagccuaau cgcacggccu ccuuucccug caccguacuc cucacccugc uucucugggc        780
caccaguuuc acccuugcca ccuuggcuac cuugaaaacc agcaagucec accucugucu        840 ucccaugucc agucugauug cuggaaaagg gaaagccauu uugucucucu auguggucga        900
cuucaccuuc ugguugcug uggucucugu cucuuacauc augauugcuc agacccugcg        960
gaagaacgcu caagucagaa agugcccccc uguaaucaca gucgaugcuu ccagaccaca       1020
gccuuucaug ggggucccug ugcagggagg uggagauccc auccagugug ccaugccggc       1080
ucuguauagg aaccagaauu acaacaaacu gcagcacguu cagacccgug gauauaccaa       1140
gagucccaac caacugguca ccccugcagc aagccgacuc cagcucguau cagccaucaa       1200
ccucuccacu gccaaggauu ccaaagccgu ggucaccugu gugaucauug ugcugucagu       1260
ccuggugugc ugucuuccac uggggauuuc cuugguacag gugguucucu ccagcaaugg       1320
gagcuucauu cuuuaccagu uugaauuguu uggauuuacu cuuauauuuu ucaagucagg       1380
auuaaacccu uuuauauauu cucggaacag ugcagggcug agaaggaaag ugcucuggug       1440
ccuccaauac auaggccugg guuuuuucug ucugcaaaca aaagacucga cuucgagcca       1500
ugggaaaagg gaaccucgaa gucaacagaa acaaauccuc ccaucaugaa acaaacucug       1560
ccuacauguu aucuccaaag ccacagaaga aauuugugga ccaggcuugu ggcccaaguc       1620
auucaaaaga aaguauggug agucccaaga ucucugcugg acaucaacac uguggucaga       1680
gcagcucgac ccccaucaac acucggauug aaccuuacua cagcaucuau aacagcagcc       1740
cuucccagga ggagagcagc ccauguaacu uacagccagu aaacucuuuu ggauuugcca       1800
auucauauau ugccaugcau uaucacacca cuaaugacuu agugcaggaa uaugacagca       1860
cuucagccaa gcagauucca gucccecuccg uuuaa                                1895
```

<210> SEQ ID NO 31
<211> LENGTH: 2054
<212> TYPE: DNA
<213> ORGANISM: homo sapien

<400> SEQUENCE: 31

```
gcgatggcga tgatgcctct agtcctgcat catccagagc ggcaggcgag ctggggtccg         60
gactgcgaga tggaggaggg gcgcgctgcg gcacccggca ggcttatctg tcttgggcct        120
cttttgtcac atattgctca tctgtgagct gaggccctga ctcactgagt attttttgggg        180 agcagaagaa ggagacattt ctctccgaaa atgaactcaa caggccacct tcaggatgcc        240
cccaatgcca cctcgctcca tgtgcctcac tcacaggaag gaaacagcac ctctctccag        300
gagggtcttc aggatctcat ccacacagcc accttggtga cctgtacttt tctactggcg        360
gtcatcttct gcctgggttc ctatggcaac ttcattgtct tcttgtcctt cttcgatcca        420
gccttcagga aattcagaac caactttgat ttcatgatcc tgaacctgtc cttctgtgac        480
ctcttcattt gtggagtgac agcccccatg ttcacctttg tgttattctt cagctcagcc        540
agtagtatcc cggatgcttt ctgcttcact ttccatctca ccagttcagg cttcatcatc        600
atgtctctga agacagtggc agtgatcgcc ctgcaccggc tccggatggt gttggggaaa        660
cagcctaatc gcacggcctc ctttccctgc accgtactcc tcaccctgct tctctgggcc        720
accagtttca cccttgccac cttggctacc ttgaaaacca gcaagtccca cctctgtctt        780
cccatgtcca gtctgattgc tggaaaaggg aaagccattt gtctctctta tgtggtcgac        840
ttcaccttct gtgttgctgt ggtctctgtc tcttacatca tgattgctca gaccctgcgg        900
```

-continued

```
aagaacgctc aagtcagaaa gtgccccct gtaatcacag tcgatgcttc cagaccacag       960
cctttcatgg gggtccctgt gcagggaggt ggagatccca tccagtgtgc catgccggct      1020
ctgtatagga accagaatta caacaaactg cagcacgttc agacccgtgg atataccaag      1080
agtcccaacc aactggtcac ccctgcagca agccgactcc agctcgtatc agccatcaac      1140
ctctccactg ccaaggattc caaagccgtg gtcacctgtg tgatcattgt gctgtcagtc      1200
ctggtgtgct gtcttccact ggggatttcc ttggtacagg tggttctctc cagcaatggg      1260
agcttcattc tttaccagtt tgaattgttt ggatttactc ttatatttt caagtcagga       1320 ttaaacccctt ttatatattc tcggaacagt gcagggctga gaaggaaagt gctctggtgc     1380
ctccaataca taggcctggg ttttttctgc tgcaaacaaa agactcgact tcgagccatg      1440
ggaaaaggga acctcgaagt caacagaaac aaatcctccc atcatgaaac aaactctgcc      1500
tacatgttat ctccaaagcc acagaagaaa tttgtggacc aggcttgtgg cccaagtcat      1560
tcaaaagaaa gtatggtgag tcccaagatc tctgctggac atcaacactg tggtcagagc      1620
agctcgaccc ccatcaacac tcggattgaa ccttactaca gcatctataa cagcagccct      1680
tcccaggagg agagcagccc atgtaactta cagccagtaa actcttttgg atttgccaat      1740
tcatatattg ccatgcatta tcacaccact aatgacttag tgcaggaata tgacagcact      1800
tcagccaagc agattccagt cccctccgtt taaagtcatg gaggctatag gatcttatgt      1860
aaacagtttt tgtttctgat agtaatggac tttattctaa cttgagatca gtggcggatc      1920
aaaacctaca agattcaact gaaaagttgg cagttatggt tttctttcat ctgatgtgtc      1980
agtatctgtt gatttgcttt gtagtttgtt gacatcttaa gatttgatgt gaaagtttta      2040
gattttttac cctg                                                        2054
```

```
<210> SEQ ID NO 32
<211> LENGTH: 1913
<212> TYPE: DNA
<213> ORGANISM: homo sapien

<400> SEQUENCE: 32
```

```
caggcttact gtcttgggcc tcttttgtca catattgctc atctgtgagc tgaggccctg        60
actcactgag tatttttggg gagcagaaga aggagacatt tctctccgaa aatgaactca       120
acaggccacc ttcaggatgc ccccaatgcc acctcgctcc atgtgcctca ctcacaggaa       180
ggaaacagca cctctctcca ggagggtctt caggatctca tccacacagc caccttggtg       240
acctgtactt ttctactggc ggtcatcttc tgcctgggtt cctatggcaa cttcattgtc       300
ttcttgtcct tcttcgatcc agccttcagg aaattcagaa ccaactttga tttcatgatc       360
ctgaacctgt ccttctgtga cctcttcatt tgtggagtga cagcccccat gttcacctttt      420 gtgttattct tcagctcagc cagtagtatc ccggatgctt tctgcttcac tttccatctc       480
accagttcag gcttcatcat catgtctctg aagacagtgg cagtgatcgc cctgcaccgg       540
ctccggatgg tgttggggaa acagcctaat cgcacggcct cctttccctg caccgtactc       600
ctcaccctgc ttctctgggc caccagtttc acccctgcca ccttggctac cttgaaaacc       660
agcaagtccc acctctgtct tcccatgtcc agtctgattg ctggaaaagg gaaagccatt       720
ttgtctctct atgtggtcga cttcaccttc tgtgttgctg tggtctctgt ctcttacatc       780
atgattgctc agaccctgcg gaagaacgct caagtcagaa agtgcccccc tgtaatcaca       840
gtcgatgctt ccagaccaca gcctttcatg ggggtccctg tgcagggagg tggagatccc       900
```

-continued

```
atccagtgtg ccatgccggc tctgtatagg aaccagaatt acgacaaact gcagcacgtt    960
cagacccgtg gatataccaa gagtcccaac caactggtca cccctgcagc aagccgactc   1020
cagctcgtat cagccatcaa cctctccact gccaaggatt ccaaagccgt ggtcacctgt   1080
gtgatcattg tgctgtcagt cctggtgtgc tgtcttccac tggggatttc cttggtacag   1140
gtggttctct ccagcaatgg gagcttcatt ctttaccagt ttgaattgtt tggatttact   1200
cttatatttt tcaagtcagg attaaaccct tttatatatt ctcggaacag tgcagggctg   1260
agaaggaaag tgctctggtg cctccaatac ataggcctgg gttttttctg ctgcaaacaa   1320
aagactcgac ttcgagccat gggaaaaggg aacctcgaag tcaacagaaa caaatcctcc   1380
catcatgaaa caaactctgc ctacatgtta tctccaaagc cacagaagaa atttgtggac   1440
caggcttgtg gcccaagtca ttcaaaagaa agtatggtga gtcccaagat ctctgctgga   1500
catcaacact gtggtcagag cagctcgacc cccatcaaca ctcggattga accttactac   1560
agcatctata acagcagccc ttcccaggag gagagcagcc catgtaactt acagccagta   1620
aactcttttg gatttgccaa ttcatatatt gccatgcatt atcacaccac taatgactta   1680
gtgcaggaat atgacagcac ttcagccaag cagattccag tccctccgt ttaaagtcat   1740 ggaggctata ggatcttatg taaacagttt ttgtttctga tagtaatggg ctttattcta   1800
acttgagatc agtggcggat caaaacctac aagattcaac tgaaaagttg gcagttatgg   1860
ttttctttca tctgatgtgt cagtatctgt tgatttgctt tgtagtttgt tga         1913
```

```
<210> SEQ ID NO 33
<211> LENGTH: 1741
<212> TYPE: DNA
<213> ORGANISM: homo sapien

<400> SEQUENCE: 33
ggagcagaag aaggagacat ttctctccga aaatgaactc aacaggccac cttcaggatg     60
cccccaatgc cacctcgctc catgtgcctc actcacagga aggaaacagc acctctctcc    120
aggagggtct tcaggatctc atccacacag ccaccttggt gacctgtact tttctactgg    180
cggtcatctt ctgcctgggt tcctatggca acttcattgt cttcttgtcc ttcttcgatc    240
cagccttcag gaaattcaga accaactttg atttcatgat cctgaacctg tccttctgtg    300
acctcttcat ttgtggagtg acagccccca tgttcacctt tgtgttattc ttcagctcag    360
ccagtagtat cccggatgct ttctgcttca ctttccatct caccagttca ggcttcatca    420
tcatgtctct gaagacagtg gcagtgatcg ccctgcaccg gctccggatg gtgttgggga    480
aacagcctaa tcgcacggcc tcctttccct gcaccgtact cctcaccctg cttctctggg    540
ccaccagttt caccccttgcc accttggcta ccttgaaaac cagcaagtcc cacctctgtc    600
ttcccatgtc cagtctgatt gctggaaaag ggaaagccat tttgtctctc tatgtggtcg    660
acttcacctt ctgtgttgct gtggtctctg tctcttacat catgattgct cagaccctgc    720
ggaagaacgc tcaagtcaga aagtgccccc ctgtaatcac agtcgatgct tccagaccac    780
agcctttcat gggggtccct gtgcagggag gtggagatcc catccagtgt gccatgccgg    840
ctctgtatag gaaccagaat tacaacaaac tgcagcacgt tcagacccgt ggatatacca    900
agagtcccaa ccaactggtc accctgcag caagccgact ccagctcgta tcagccatca    960
acctctccac tgccaaggat tccaaagccg tggtcacctg tgtgatcatt gtgctgtcag   1020
tcctggtgtg ctgtcttcca ctggggattt ccttggtaca ggtggttctc tccagcaatg   1080
ggagcttcat tctttaccag tttgaattgt ttggatttac tcttatattt ttcaagtcag   1140
```

-continued

```
gattaaaccc ttttatatat tctcggaaca gtgcagggct gagaaggaaa gtgctctggt    1200
gcctccaata cataggcctg ggttttttct gctgcaaaca aaagactcga cttcgagcca    1260
tgggaaaagg gaacctcgaa gtcaacagaa acaaatcctc ccatcatgaa acaaactctg    1320
cctacatgtt atctccaaag ccacagaaga aatttgtgga ccaggcttgt ggcccaagtc    1380
attcaaaaga aagtatggtg agtcccaaga tctctgctgg acatcaacac tgtggtcaga    1440
gcagctcgac ccccatcaac actcggattg aaccttacta cagcatctat aacagcagcc    1500
cttcccagga ggagagcagc ccatgtaact tacagccagt aaactctttt ggatttgcca    1560
attcatatat tgccatgcat tatcacacca ctaatgactt agtgcaggaa tatgacagca    1620
cttcagccaa gcagattcca gtcccctccg tttaaagtca tggaggctat aggatcttat    1680
gtaaacagtt tttgtttctg atagtaatgg actttattct aacttgagat agtggcggat    1740
c                                                                   1741

<210> SEQ ID NO 34
<211> LENGTH: 1894
<212> TYPE: DNA
<213> ORGANISM: homo sapien

<400> SEQUENCE: 34
gtgactgcgc ctctgcgccc gcgtcttgcc gcggctcccg ggatgcgcgg aggcggtggc      60
gatggcgatg atgcctctag tcctgcatca tccagagcgg caggcggagc tggggtccgg     120
actgcgagat ggaggagggg cggcgctgcg gccacccggc aggcttatct gtcttgggcc     180
tcttttgtca catattgctc atctgtgagc tgaggccctg actcactgag tatttttggg     240
gagcagaaga aggagacatt tctctccgaa aatgaactca acaggccacc ttcaggatgc     300
ccccaatgcc acctcgctcc atgtgcctca ctcacaggaa ggaaacagca cctctctcca     360
ggagggtctt caggatctca tccacacagc caccttggtg acctgtactt ttctactggc     420
ggtcatcttc tgcctgggtt cctatggcaa cttcattgtc ttcttgtcct tcttcgatcc     480
agccttcagg aaattcagaa ccaactttga tttcatgatc ctgaacctgt ccttctgtga     540
cctcttcatt tgtggagtga cagcccccat gttcacctttt gtgttattct tcagctcagc     600
cagtagtatc ccggatgctt tctgcttcac tttccatctc accagttcag gcttcatcat     660
catgtctctg aagacagtgg cagtgatcgc cctgcaccgg ctccggatgg tgttggggaa     720
acagcctaat cgcacggcct cctttccctg caccgtactc ctcaccctgc ttctctgggc     780
caccagtttc accctttgcca ccttggctac cttgaaaacc agcaagtccc acctctgtct     840
tcccatgtcc agtctgattg ctggaaaagg gaaagccatt ttgtctctct atgtggtcga     900
cttcaccttc tgtgttgctg tggtctctgt ctcttacatc atgattgctc agaccctgcg     960
gaagaacgct caagtcagaa agtgcccccc tgtaatcaca gtcgatgctt ccagaccaca    1020
gcctttcatg ggggtccctg tgcagggagg tggagatccc atccagtgtg ccatgccggc    1080
tctgtatagg aaccagaatt acaacaaact gcagcacgtt cagacccgtg gatataccaa    1140
gagtcccaac caactggtca cccctgcagc aagccgactc cagctcgtat cagccatcaa    1200
cctctccact gccaaggatt ccaaagccgt ggtcacctgt gtgatcattg tgctgtcagt    1260
cctggtgtgc tgtcttccac tggggatttc cttggtacag gtggttctct ccagcaatgg    1320
gagcttcatt ctttaccagt ttgaattgtt tggatttact cttatatttt tcaagtcagg    1380
attaaaccct tttatatatt ctcggaacag tgcagggctg agaaggaaag tgctctggtg    1440
```

-continued

```
cctccaatac ataggcctgg gttttttctg ctgcaaacaa aagactcgac ttcgagccat    1500
gggaaaaggg aacctcgaag tcaacagaaa caaatcctcc catcatgaaa caaactctgc    1560
ctacatgtta tctccaaagc cacagaagaa atttgtggac caggcttgtg gcccaagtca    1620
ttcaaaagaa agtatggtga gtcccaagat ctctgctgga catcaacact gtggtcagag    1680
cagctcgacc cccatcaaca ctcggattga accttactac agcatctata acagcagccc    1740
ttcccaggag gagagcagcc catgtaactt acagccagta aactcttttg gatttgccaa    1800
ttcatatatt gccatgcatt atcacaccac taatgactta gtgcaggaat atgacagcac    1860
ttcagccaag cagattccag tcccctccgt ttaa                                1894

<210> SEQ ID NO 35
<211> LENGTH: 2047
<212> TYPE: DNA
<213> ORGANISM: homo sapien

<400> SEQUENCE: 35
gcgatggcga tgatgcctct agtcctgcat catccagagc ggcaggcgag ctggggtccg      60
gactgcgaga tggaggaggg gcgcgctgcg gcacccggca ggcttatctg tcttgggcct     120
cttttgtcac atattgctca tctgtgagct gaggccctga ctcactgagt atttttgggg     180
agcagaagaa ggagacattt ctctccgaaa atgaactcaa caggccacct tcaggatgcc     240
cccaatgcca cctcgctcca tgtgcctcac tcacaggaag gaaacagcac ctctctccag     300
gagggtcttc aggatctcat ccacacagcc accttggtga cctgtacttt tctactggcg     360
gtcatcttct gcctgggttc ctatggcaac ttcattgtct tcttgtcctt cttcgatcca     420
gccttcagga aattcagaac caactttgat ttcatgatcc tgaacctgtc cttctgtgac     480
ctcttcattt gtggagtgac agcccccatg ttcacctttg tgttattctt cagctcagta     540
tcccggatgc tttctgcttc actttccatc tcaccagttc aggcttcatc atcatgtctc     600
tgaagacagt ggcagtgatc gccctgcacc ggctccggat ggtgttgggg aaacagccta     660
atcgcacggc ctcctttccc tgcaccgtac tcctcaccct gcttctctgg gccaccagtt     720
tcacccttgc caccttggct accttgaaaa ccagcaagtc ccacctctgt cttcccatgt     780
ccagtctgat tgctggaaaa gggaaagcca ttttgtctct ctatgtggtc gacttcacct     840
tctgtgttgc tgtggtctct gtctcttaca tcatgattgc tcagaccctg cggaagaacg     900
ctcaagtcag aaagtgcccc cctgtaatca cagtcgatgc ttccagacca cagcctttca     960 tggggtgtccc tgtgcaggga ggtggagatc ccatccagtg tgccatgccg gctctgtata    1020
ggaaccagaa ttacaacaaa ctgcagcacg ttcagacccg tggatatacc aagagtccca    1080
accaactggt caccctgca gcaagccgac tccagctcgt atcagccatc aacctctcca    1140
ctgccaagga ttccaaagcc gtggtcacct gtgtgatcat tgtgctgtca gtcctggtgt    1200
gctgtcttcc actggggatt tccttggtac aggtggttct ctccagcaat gggagcttca    1260
ttctttacca gtttgaattg tttggatta ctcttatatt tttcaagtca ggattaaacc    1320
cttttatata ttctcggaac agtgcagggc tgagaaggaa agtgctctgg tgcctccaat    1380
acataggcct gggttttttc tgctgcaaac aaaagactcg acttcgagcc atgggaaaag    1440
ggaacctcga agtcaacaga aacaaatcct cccatcatga aacaaactct gcctacatgt    1500
tatctccaaa gccacagaag aaatttgtgg accaggcttg tggcccaagt cattcaaaag    1560
aaagtatggt gagtcccaag atctctgctg gacatcaaca ctgtggtcag agcagctcga    1620
cccccatcaa cactcggatt gaaccttact acagcatcta taacagcagc ccttcccagg    1680
```

-continued

```
aggagagcag cccatgtaac ttacagccag taaactcttt tggatttgcc aattcatata      1740
ttgccatgca ttatcacacc actaatgact tagtgcagga atatgacagc acttcagcca      1800
agcagattcc agtccctcc  gtttaaagtc atggaggcta taggatctta tgtaaacagt      1860
ttttgtttct gatagtaatg gactttattc taacttgaga tcagtggcgg atcaaaacct      1920
acaagattca actgaaaagt tggcagttat ggttttcttt catctgatgt gtcagtatct      1980
gttgatttgc tttgtagttt gttgacatct taagatttga tgtgaaagtt ttagattttt      2040
taccctg                                                                2047
```

```
<210> SEQ ID NO 36
<211> LENGTH: 2054
<212> TYPE: DNA
<213> ORGANISM: homo sapien

<400> SEQUENCE: 36
```

```
gcgatggcga tgatgcctct agtcctgcat catccagagc ggcaggcgag ctggggtccg        60
gactgcgaga tggaggaggg gcgcgctgcg gcacccggca ggcttatctg tcttgggcct       120
cttttgtcac atattgctca tctgtgagct gaggccctga ctcactgagt atttttgggg       180
agcagaagaa ggagacattt ctctccgaaa atgaactcaa caggccacct tcaggatgcc       240
cccaatgcca cctcgctcca tgtgcctcac tcacaggaag gaaacagcac ctctctccag       300
gagggtcttc aggatctcat ccacacagcc accttggtga cctgtacttt tctactggcg       360
gtcatcttct gcctgggttc ctatggcaac ttcattgtct tcttgtcctt cttcgatcca       420
gccttcagga aattcagaac caactttgat ttcatgatcc tgaacctgtc cttctgtgac       480
ctcttcattt gtggagtgac agcccccatg ttcacctttg tgttattctt cagctcagcc       540
agtagtatcc cggatacttt ctgcttcact ttccatctca ccagttcagg cttcatcatc       600
atgtctctga agacagtggc agtgatcgcc ctgcaccggc tccggatggt gttggggaaa       660
cagcctaatc gcacggcctc ctttccctgc accgtactcc tcaccctgct tctctgggcc       720
accagtttca cccttgccac cttggctacc ttgaaaacca gcaagtccca cctctgtctt       780
cccatgtcca gtctgattgc tggaaaaggg aaagccattt tgtctctcta tgtggtcgac       840
ttcaccttct gtgttgctgt ggtctctgtc tcttacatca tgattgctca gaccctgcgg       900
aagaacgctc aagtcagaaa gtgcccccct gtaatcacag tcgatgcttc cagaccacag       960
cctttcatgg gggtccctgt gcagggaggt ggagatccca tccagtgtgc catgccggct      1020
ctgtatagga accagaatta caacaaactg cagcacgttc agacccgtgg atataccaag      1080
agtcccaacc aactggtcac ccctgcagca agccgactcc agctcgtatc agccatcaac      1140
ctctccactg ccaaggattc caaagccgtg gtcacctgtg tgatcattgt gctgtcagtc      1200
ctggtgtgct gtcttccact ggggatttcc ttggtacagg tggttctctc cagcaatggg      1260
agcttcattc tttaccagtt tgaattgttt ggatttactc ttatattttt caagtcagga      1320
ttaaaccctt ttatatattc tcggaacagt gcagggctga aaggaaagt gctctggtgc      1380 ctccaataca taggcctggg ttttttctgc tgcaaacaaa agactcgact tcgagccatg      1440
ggaaaaggga acctcgaagt caacagaaac aaatcctccc atcatgaaac aaactctgcc      1500
tacatgttat ctccaaagcc acagaagaaa tttgtggacc aggcttgtgg cccaagtcat      1560
tcaaaagaaa gtatggtgag tcccaagatc tctgctggac atcaacactg tggtcagagc      1620
agctcgaccc ccatcaacac tcggattgaa ccttactaca gcatctataa cagcagccct      1680
```

-continued

| | | | | | |
|---|---|---|---|---|---|
| tcccaggagg | agagcagccc | atgtaactta | cagccagtaa | actcttttgg | atttgccaat | 1740 |
| tcatatattg | ccatgcatta | tcacaccact | aatgacttag | tgcaggaata | tgacagcact | 1800 |
| tcagccaagc | agattccagt | cccctccgtt | taaagtcatg | gaggctatag | gatcttatgt | 1860 |
| aaacagtttt | tgtttctgat | agtaatggac | tttattctaa | cttgagatca | gtggcggatc | 1920 |
| aaaacctaca | agattcaact | gaaaagttgg | cagttatggt | tttctttcat | ctgatgtgtc | 1980 |
| agtatctgtt | gatttgcttt | gtagtttgtt | gacatcttaa | gatttgatgt | gaaagtttta | 2040 |
| gattttttac | cctg | | | | | 2054 |

```
<210> SEQ ID NO 37
<211> LENGTH: 2054
<212> TYPE: DNA
<213> ORGANISM: homo sapien

<400> SEQUENCE: 37
```

| | | | | | |
|---|---|---|---|---|---|
| gcgatggcga | tgatgcctct | agtcctgcat | catccagagc | ggcaggcgag | ctggggtccg | 60 |
| gactgcgaga | tggaggaggg | gcgcgctgcg | gcacccggca | ggcttatctg | tcttgggcct | 120 |
| cttttgtcac | atattgctca | tctgtgagct | gaggccctga | ctcactgagt | attttgtgggg | 180 |
| agcagaagaa | ggagacattt | ctctccgaaa | atgaactcaa | caggccacct | tcaggatgcc | 240 |
| cccaatgcca | cctcgctcca | tgtgcctcac | tcacaggaag | gaaacagcac | ctctctccag | 300 |
| gagggtcttc | aggatctcat | ccacacagcc | accttggtga | cctgtacttt | tctactggcg | 360 |
| gtcatcttct | gcctgggttc | ctatggcaac | ttcattgtct | tcttgtcctt | cttcgatcca | 420 |
| gccttcagga | aattcagaac | caactttgat | ttcatgatcc | tgaacctgtc | cttctgtgac | 480 |
| ctcttcattt | gtggagtgac | agcccccatg | ttcacctttg | tgttattctt | cagctcagcc | 540 |
| agtagtatcc | cggatgcttt | ctgcttcact | ttccatctca | ccagttcagg | cttcatcatc | 600 |
| atgtctctga | agacagtggc | agtgatcgcc | ctgcaccggc | tccggatggt | gttggggaaa | 660 |
| cagcctaatc | gcacggcctc | ctttccctgc | accgtactcc | tcaccctgct | tctctgggcc | 720 |
| accagtttca | cccttgccac | cttggctacc | ttgaaaacca | gcaagtccca | cctctgtctt | 780 |
| cccatgtcca | gtctgattgc | tggaaaaggg | aaagccattt | tgtctctcta | tgtggtcgac | 840 |
| ttcaccttct | gtgttgctgt | ggtctctgtc | tcttacatca | tgattgctca | gaccctgcgg | 900 |
| aagaacgctt | aagtcagaaa | gtgccccccct | gtaatcacag | tcgatgcttc | cagaccacag | 960 |
| cctttcatgg | gggtccctgt | gcagggaggt | ggagatccca | tccagtgtgc | catgccggct | 1020 |
| ctgtatagga | accagaatta | caacaaactg | cagcacgttc | agacccgtgg | atataccaag | 1080 |
| agtcccaacc | aactggtcac | ccctgcagca | agccgactcc | agctcgtatc | agccatcaac | 1140 |
| ctctccactg | ccaaggattc | caaagccgtg | gtcacctgtg | tgatcattgt | gctgtcagtc | 1200 |
| ctggtgtgct | gtcttccact | ggggatttcc | ttggtacagg | tggttctctc | cagcaatggg | 1260 |
| agcttcattc | tttaccagtt | tgaattgttt | ggatttactc | ttatattttt | caagtcagga | 1320 |
| ttaaacccctt | ttatatattc | tcggaacagt | gcagggctga | gaaggaaagt | gctctggtgc | 1380 |
| ctccaataca | taggcctggg | ttttttctgc | tgcaaacaaa | agactcgact | tcgagccatg | 1440 |
| ggaaaaggga | acctcgaagt | caacagaaac | aaatcctccc | atcatgaaac | aaactctgcc | 1500 |
| tacatgttat | ctccaaagcc | acagaagaaa | tttgtggacc | aggcttgtgg | cccaagtcat | 1560 |
| tcaaaagaaa | gtatggtgag | tcccaagatc | tctgctggac | atcaacactg | tggtcagagc | 1620 |
| agctcgaccc | ccatcaacac | tcggattgaa | ccttactaca | gcatctataa | cagcagccct | 1680 |
| tcccaggagg | agagcagccc | atgtaactta | cagccagtaa | actcttttgg | atttgccaat | 1740 |

-continued

```
tcatatattg ccatgcatta tcacaccact aatgacttag tgcaggaata tgacagcact    1800
tcagccaagc agattccagt cccctccgtt taaagtcatg gaggctatag gatcttatgt    1860
aaacagtttt tgtttctgat agtaatggac tttattctaa cttgagatca gtggcggatc    1920
aaaacctaca agattcaact gaaaagttgg cagttatggt tttctttcat ctgatgtgtc    1980
agtatctgtt gatttgcttt gtagtttgtt gacatcttaa gatttgatgt gaaagtttta    2040
gattttttac cctg                                                      2054
```

```
<210> SEQ ID NO 38
<211> LENGTH: 2050
<212> TYPE: DNA
<213> ORGANISM: homo sapien

<400> SEQUENCE: 38
```

```
gcgatggcga tgatgcctct agtcctgcat catccagagc ggcaggcgag ctggggtccg      60
gactgcgaga tggaggaggg gcgcgctgcg gcacccggca ggcttatctg tcttgggcct     120
cttttgtcac atattgctca tctgtgagct gaggccctga ctcactgagt attttggggg     180
agcagaagaa ggagacattt ctctccgaaa atgaactcaa caggccacct tcaggatgcc     240
cccaatgcca cctcgctcca tgtgcctcac tcacaggaag gaaacagcac ctctctccag     300
gagggtcttc aggatctcat ccacacagcc accttggtga cctgtacttt tctactggcg     360
gtcatcttct gcctgggttc ctatggcaac ttcattgtct tcttgtcctt cttcgatcca     420
gccttcagga aattcagaac caactttgat ttcatgatcc tgaacctgtc cttctgtgac     480
ctcttcattt gtggagtgac agcccccatg ttcacctttg tgttattctt cagctcagcc     540
agtagtatcc cggatgcttt ctgcttcact ttccatctca ccagttcagg cttcatcatc     600
atgtctctga agacagtggc agtgatcgcc ctgcaccggc tccggatggt gttggggaaa     660
cagcctaatc gcacggcctc ctttccctgc accgtactcc tcaccctgct tctctgggcc     720
accagtttca cccttgccac cttggctacc ttgaaaacca gcaagtccca cctctgtctt     780
cccatgtcca gtctgattgc tggaaaaggg aaagccattt tgtctctcta tgtggtcgac     840
ttcaccttct gtgttgctgt ggtctctgtc tcttacatca tgattgctca gaccctgcgg     900
aagaacgctc aagtcagtgc ccccctgtaa tcacagtcga tgcttccaga ccacagcctt     960
tcatgggggt ccctgtgcag ggaggtggag atcccatcca gtgtgccatg ccggctctgt    1020
ataggaacca gaattacaac aaactgcagc acgttcagac ccgtggatat accaagagtc    1080
ccaaccaact ggtcacccct gcagcaagcc gactccagct cgtatcagcc atcaacctct    1140
ccactgccaa ggattccaaa gccgtggtca cctgtgtgat cattgtgctg tcagtcctgg    1200
tgtgctgtct tccactgggg atttccttgg tacaggtggt tctctccagc aatgggagct    1260
tcattcttta ccagtttgaa ttgtttggat ttactcttat attttttcaag tcaggattaa    1320 accctttttat atattctcgg aacagtgcag ggctgagaag gaaagtgctc tggtgcctcc    1380
aatacatagg cctgggtttt ttctgctgca aacaaaagac tcgacttcga gccatgggaa    1440
aagggaacct cgaagtcaac agaaacaaat cctcccatca tgaaacaaac tctgcctaca    1500
tgttatctcc aaagccacag aagaaatttg tggaccaggc ttgtggccca agtcattcaa    1560
aagaaagtat ggtgagtccc aagatctctg ctggacatca acactgtggt cagagcagct    1620
cgacccccat caacactcgg attgaacctt actacagcat ctataacagc agcccttccc    1680
aggaggagag cagcccatgt aacttacagc cagtaaactc ttttggattt gccaattcat    1740
```

```
atattgccat gcattatcac accactaatg acttagtgca ggaatatgac agcacttcag    1800
ccaagcagat tccagtcccc tccgtttaaa gtcatggagg ctataggatc ttatgtaaac    1860 agttttttgtt tctgatagta atggacttta ttctaacttg agatcagtgg cggatcaaaa    1920
cctacaagat tcaactgaaa agttggcagt tatggttttc tttcatctga tgtgtcagta    1980
tctgttgatt tgctttgtag tttgttgaca tcttaagatt tgatgtgaaa gttttagatt    2040
ttttaccctg                                                           2050

<210> SEQ ID NO 39
<211> LENGTH: 2055
<212> TYPE: DNA
<213> ORGANISM: homo sapien

<400> SEQUENCE: 39
gcgatggcga tgatgcctct agtcctgcat catccagagc ggcaggcgag ctggggtccg      60
gactgcgaga tggaggaggg gcgcgctgcg gcacccggca ggcttatctg tcttgggcct     120
cttttgtcac atattgctca tctgtgagct gaggccctga ctcactgagt attttttgggg     180 agcagaagaa ggagacattt ctctccgaaa atgaactcaa caggccacct tcaggatgcc     240
cccaatgcca cctcgctcca tgtgcctcac tcacaggaag gaaacagcac ctctctccag     300
gagggtcttc aggatctcat ccacacagcc accttggtga cctgtacttt tctactggcg     360
gtcatcttct gcctgggttc ctatggcaac ttcattgtct tcttgtcctt cttcgatcca     420
gccttcagga aattcagaac caactttgat ttcatgatcc tgaacctgtc cttctgtgac     480
ctcttcattt gtggagtgac agcccccatg ttcacctttg tgttattctt cagctcagcc     540
agtagtatcc cggatgcttt ctgcttcact ttccatctca ccagttcagg cttcatcatc     600
atgtctctga agacagtggc agtgatcgcc ctgcaccggc tccggatggt gttggggaaa     660
cagcctaatc gcacggcctc ctttccctgc accgtactcc tcaccctgct tctctgggcc     720
accagtttca cccttgccac cttggctacc ttgaaaacca gcaagtccca cctctgtctt     780
cccatgtcca gtctgattgc tggaaaaggg aaagccattt tgtctctcta tgtggtcgac     840
ttcaccttct gtgttgctgt ggtctctgtc tcttacatca tgattgctca gaccctgcgg     900
aagaacgctc aagtcagaaa gtgcccccct gtaatcacag tcgatgcttc cagaccacag     960
cctttcatgg gggtccctgt gcagggaggt ggagatccca tccagtgtgc catgccggct    1020
ctgtatagga accagaatta caacaaactg cagcacgttc agacccgtgg atataccaag    1080
agtcccaacc aactggtcac ccctgcagca agccgactcc agctcgtatc agccatcaac    1140
ctctccactg ccaaggattc caaagccgtg gtcacctgtg tgatcattgt gctgtcagtc    1200
ctggtgtgct gtcttccact ggggatttcc ttggtacagg tggttctctc cagcaatggg    1260
agcttcattc tttaccagtt tgaattgttt ggatttactc ttatatttt caagtcagga    1320 ttaaacccct ttatatattc tcggaacagt gcagggctga aaggaaagt gctctggtgc    1380 ctccaataca taggcctggg ttttttctgt ctgcaaacaa aagactcgac ttcgagccat    1440
gggaaaaggg aacctcgaag tcaacagaaa caaatcctcc catcatgaaa caaactctgc    1500
ctacatgtta tctccaaagc cacagaagaa atttgtggac caggcttgtg gcccaagtca    1560
ttcaaaagaa agtatggtga gtcccaagat ctctgctgga catcaacact gtggtcagag    1620
cagctcgacc cccatcaaca ctcggattga accttactac agcatctata acagcagccc    1680
ttcccaggag gagagcagcc catgtaactt acagccagta aactcttttg gatttgccaa    1740
ttcatatatt gccatgcatt atcacaccac taatgactta gtgcaggaat atgacagcac    1800
```

-continued

```
ttcagccaag cagattccag tcccctccgt ttaaagtcat ggaggctata ggatcttatg   1860
taaacagttt ttgtttctga tagtaatgga ctttattcta acttgagatc agtggcggat   1920
caaaacctac aagattcaac tgaaaagttg gcagttatgg ttttctttca tctgatgtgt   1980
cagtatctgt tgatttgctt tgtagtttgt tgacatctta agatttgatg tgaaagtttt   2040 agattttta ccctg                                                     2055

<210> SEQ ID NO 40
<211> LENGTH: 1906
<212> TYPE: DNA
<213> ORGANISM: homo sapien

<400> SEQUENCE: 40
caggcttact gtcttgggcc tcttttgtca catattgctc atctgtgagc tgaggccctg     60
actcactgag tattttgggg gagcagaaga aggagacatt tctctccgaa aatgaactca    120
acaggccacc ttcaggatgc ccccaatgcc acctcgctcc atgtgcctca ctcacaggaa    180
ggaaacagca cctctctcca ggagggtctt caggatctca tccacacagc caccttggtg    240
acctgtactt ttctactggc ggtcatcttc tgcctgggtt cctatggcaa cttcattgtc    300
ttcttgtcct tcttcgatcc agccttcagg aaattcagaa ccaactttga tttcatgatc    360
ctgaacctgt ccttctgtga cctcttcatt tgtggagtga cagcccccat gttcaccttt    420
gtgttattct tcagctcagt atcccggatg ctttctgctt cactttccat ctcaccagtt    480
caggcttcat catcatgtct ctgaagacag tggcagtgat cgccctgcac cggctccgga    540
tggtgttggg gaaacagcct aatcgcacgg cctcctttcc ctgcaccgta ctcctcaccc    600
tgcttctctg ggccaccagt ttcacccctg ccaccttggc taccttgaaa accagcaagt    660
cccacctctg tcttcccatg tccagtctga ttgctggaaa agggaaagcc attttgtctc    720
tctatgtggt cgacttcacc ttctgtgttg ctgtggtctc tgtctcttac atcatgattg    780
ctcagaccct gcggaagaac gctcaagtca gaaagtgccc ccctgtaatc acagtcgatg    840
cttccagacc acagcctttc atgggggtcc ctgtgcaggg aggtggagat cccatccagt    900
gtgccatgcc ggctctgtat aggaaccaga attacgacaa actgcagcac gttcagaccc    960
gtggatatac caagagtccc aaccaactgg tcaccccctgc agcaagccga ctccagctcg   1020
tatcagccat caacctctcc actgccaagg attccaaagc cgtggtcacc tgtgtgatca   1080
ttgtgctgtc agtcctggtg tgctgtcttc cactggggat ttccttggta caggtggttc   1140
tctccagcaa tgggagcttc attctttacc agtttgaatt gtttggattt actcttatat   1200
ttttcaagtc aggattaaac cctttttatat attctcggaa cagtgcaggg ctgagaagga   1260
aagtgctctg gtgcctccaa tacataggcc tgggttttt ctgctgcaaa caaaagactc   1320
gacttcgagc catgggaaaa gggaacctcg aagtcaacag aaacaaatcc tcccatcatg   1380
aaacaaactc tgcctacatg ttatctccaa agccacagaa gaaatttgtg gaccaggctt   1440
gtggcccaag tcattcaaaa gaaagtatgg tgagtcccaa gatctctgct ggacatcaac   1500
actgtggtca gagcagctcg accccccatca acactcggat tgaaccttac tacagcatct   1560
ataacagcag cccttcccag gaggagagca gcccatgtaa cttacagcca gtaaactctt   1620
ttggatttgc caattcatat attgccatgc attatcacac cactaatgac ttagtgcagg   1680
aatatgacag cacttcagcc aagcagattc cagtcccctc cgtttaaagt catgtgaggct   1740 ataggatctt atgtaaacag tttttgtttc tgatagtaat gggctttatt ctaacttgag   1800
```

-continued

```
atcagtggcg gatcaaaacc tacaagattc aactgaaaag ttggcagtta tggtttctt     1860 tcatctgatg tgtcagtatc tgttgatttg ctttgtagtt tgttga               1906

<210> SEQ ID NO 41
<211> LENGTH: 1913
<212> TYPE: DNA
<213> ORGANISM: homo sapien

<400> SEQUENCE: 41
caggcttact gtcttgggcc tcttttgtca catattgctc atctgtgagc tgaggccctg       60
actcactgag tatttttggg gagcagaaga aggagacatt tctctccgaa aatgaactca      120
acaggccacc ttcaggatgc ccccaatgcc acctcgctcc atgtgcctca ctcacaggaa      180
ggaaacagca cctctctcca ggagggtctt caggatctca tccacacagc caccttggtg      240
acctgtactt ttctactggc ggtcatcttc tgcctgggtt cctatggcaa cttcattgtc      300
ttcttgtcct tcttcgatcc agccttcagg aaattcagaa ccaactttga tttcatgatc      360
ctgaacctgt ccttctgtga cctcttcatt tgtggagtga cagcccccat gttcacctt       420 gtgttattct tcagctcagc cagtagtatc ccggatactt tctgcttcac tttccatctc      480
accagttcag gcttcatcat catgtctctg aagacagtgg cagtgatcgc cctgcaccgg      540
ctccggatgg tgttggggaa acagcctaat cgcacggcct cctttccctg caccgtactc      600
ctcaccctgc ttctctgggc caccagtttc acccctgcca ccttggctac cttgaaaacc      660
agcaagtccc acctctgtct tcccatgtcc agtctgattg ctggaaaagg gaaagccatt      720
ttgtctctct atgtggtcga cttcaccttc tgtgttgctg tggtctctgt ctcttacatc      780
atgattgctc agaccctgcg gaagaacgct caagtcagaa agtgccccc tgtaatcaca      840 gtcgatgctt ccagaccaca gccttt catg ggggtccctg tgcagggagg tggagatccc      900
atccagtgtg ccatgccggc tctgtatagg aaccagaatt acgacaaact gcagcacgtt      960
cagacccgtg gatataccaa gagtcccaac caactggtca cccctgcagc aagccgactc     1020
cagctcgtat cagccatcaa cctctccact gccaaggatt ccaaagccgt ggtcacctgt     1080
gtgatcattg tgctgtcagt cctggtgtgc tgtcttccac tggggatttc cttggtacag     1140
gtggttctct ccagcaatgg gagcttcatt ctttaccagt ttgaattgtt tggatttact     1200
cttatatttt tcaagtcagg attaaaccct tttatatatt ctcggaacag tgcagggctg     1260
agaaggaaag tgctctggtg cctccaatac ataggcctgg gttttttctg ctgcaaacaa     1320
aagactcgac ttcgagccat gggaaaaggg aacctcgaag tcaacagaaa caaatcctcc     1380
catcatgaaa caaactctgc ctacatgtta tctccaaagc cacagaagaa atttgtggac     1440
caggcttgtg gcccaagtca ttcaaaagaa agtatggtga gtcccaagat ctctgctgga     1500
catcaacact gtggtcagag cagctcgacc cccatcaaca ctcggattga accttactac     1560
agcatctata acagcagccc ttcccaggag gagagcagcc catgtaactt acagccagta     1620
aactcttttg gatttgccaa ttcatatatt gccatgcatt atcacaccac taatgactta     1680
gtgcaggaat atgacagcac ttcagccaag cagattccag tcccctccgt ttaaagtcat     1740
ggaggctata ggatcttatg taaacagttt ttgtttctga tagtaatggg ctttattcta     1800
acttgagatc agtggcggat caaaacctac aagattcaac tgaaaagttg gcagttatgg     1860
ttttctttca tctgatgtgt cagtatctgt tgatttgctt tgtagtttgt tga           1913

<210> SEQ ID NO 42
<211> LENGTH: 1913
```

-continued

```
<212> TYPE: DNA
<213> ORGANISM: homo sapien

<400> SEQUENCE: 42
caggcttact gtcttgggcc tcttttgtca catattgctc atctgtgagc tgaggccctg      60
actcactgag tatttttggg gagcagaaga aggagacatt tctctccgaa aatgaactca     120
acaggccacc ttcaggatgc ccccaatgcc acctcgctcc atgtgcctca ctcacaggaa     180
ggaaacagca cctctctcca ggagggtctt caggatctca tccacacagc caccttggtg     240
acctgtactt ttctactggc ggtcatcttc tgcctgggtt cctatggcaa cttcattgtc     300
ttcttgtcct tcttcgatcc agccttcagg aaattcagaa ccaactttga tttcatgatc     360
ctgaacctgt ccttctgtga cctcttcatt tgtggagtga cagcccccat gttcaccttt     420
gtgttattct tcagctcagc cagtagtatc ccggatgctt tctgcttcac tttccatctc     480
accagttcag gcttcatcat catgtctctg aagacagtgg cagtgatcgc cctgcaccgg     540
ctccggatgg tgttggggaa acagcctaat cgcacggcct cctttccctg caccgtactc     600
ctcaccctgc ttctctgggc caccagtttc accccctgcca ccttggctac cttgaaaacc     660
agcaagtccc acctctgtct tcccatgtcc agtctgattg ctggaaaagg gaaagccatt     720
ttgtctctct atgtggtcga cttcaccttc tgtgttgctg tggtctctgt ctcttacatc     780
atgattgctc agaccctgcg gaagaacgct taagtcagaa agtgccccc tgtaatcaca     840 gtcgatgctt ccagaccaca gcctttcatg ggggtccctg tgcagggagg tggagatccc     900
atccagtgtg ccatgccggc tctgtatagg aaccagaatt acgacaaact gcagcacgtt     960
cagacccgtg gatataccaa gagtcccaac caactggtca ccctgcagc aagccgactc    1020 cagctcgtat cagccatcaa cctctccact gccaaggatt ccaaagccgt ggtcacctgt    1080
gtgatcattg tgctgtcagt cctggtgtgc tgtcttccac tggggatttc cttggtacag    1140
gtggttctct ccagcaatgg gagcttcatt ctttaccagt ttgaattgtt tggatttact    1200
cttatatttt tcaagtcagg attaaaccct tttatatatt ctcggaacag tgcagggctg    1260
agaaggaaag tgctctggtg cctccaatac ataggcctgg gttttttctg ctgcaaacaa    1320
aagactcgac ttcgagccat gggaaaaggg aacctcgaag tcaacagaaa caaatcctcc    1380
catcatgaaa caaactctgc ctacatgtta tctccaaagc cacagaagaa atttgtggac    1440
caggcttgtg gcccaagtca ttcaaaagaa agtatggtga gtcccaagat ctctgctgga    1500
catcaacact gtggtcagag cagctcgacc cccatcaaca ctcggattga accttactac    1560
agcatctata acagcagccc ttcccaggag gagagcagcc catgtaactt acagccagta    1620
aactcttttg gatttgccaa ttcatatatt gccatgcatt atcacaccac taatgactta    1680
gtgcaggaat atgacagcac ttcagccaag cagattccag tcccctccgt ttaaagtcat    1740
ggaggctata ggatcttatg taaacagttt ttgtttctga tagtaatggg ctttattcta    1800
acttgagatc agtggcggat caaaacctac aagattcaac tgaaaagttg gcagttatgg    1860
ttttctttca tctgatgtgt cagtatctgt tgatttgctt tgtagtttgt tga          1913
```

```
<210> SEQ ID NO 43
<211> LENGTH: 1909
<212> TYPE: DNA
<213> ORGANISM: homo sapien

<400> SEQUENCE: 43
caggcttact gtcttgggcc tcttttgtca catattgctc atctgtgagc tgaggccctg      60
```

```
actcactgag tattttttggg gagcagaaga aggagacatt tctctccgaa aatgaactca      120
acaggccacc ttcaggatgc ccccaatgcc acctcgctcc atgtgcctca ctcacaggaa      180
ggaaacagca cctctctcca ggagggtctt caggatctca tccacacagc caccttggtg      240
acctgtactt ttctactggc ggtcatcttc tgcctgggtt cctatggcaa cttcattgtc      300
ttcttgtcct tcttcgatcc agccttcagg aaattcagaa ccaactttga tttcatgatc      360
ctgaacctgt ccttctgtga cctcttcatt tgtggagtga cagcccccat gttcacctt      420 gtgttattct tcagctcagc cagtagtatc ccggatgctt tctgcttcac tttccatctc      480
accagttcag gcttcatcat catgtctctg aagacagtgg cagtgatcgc cctgcaccgg      540
ctccggatgg tgttggggaa acagcctaat cgcacggcct cctttccctg caccgtactc      600
ctcaccctgc ttctctgggc caccagtttc acccctgcca ccttggctac cttgaaaacc      660
agcaagtccc acctctgtct tcccatgtcc agtctgattg ctggaaaagg gaaagccatt      720
ttgtctctct atgtggtcga cttcacctt tgtgttgctg tggtctctgt ctcttacatc      780
atgattgctc agaccctgcg gaagaacgct caagtcagtg ccccctgta atcacagtcg      840 atgcttccag accacagcct ttcatggggg tccctgtgca gggaggtgga gatcccatcc      900
agtgtgccat gccggctctg tataggaacc agaattacga caaactgcag cacgttcaga      960
cccgtggata taccaagagt cccaaccaac tggtcacccc tgcagcaagc cgactccagc     1020
tcgtatcagc catcaacctc tccactgcca aggattccaa agccgtggtc acctgtgtga     1080
tcattgtgct gtcagtcctg gtgtgctgtc ttccactggg gatttccttg gtacaggtgg     1140
ttctctccag caatgggagc ttcattcttt accagtttga attgtttgga tttactctta     1200 tattttcaa gtcaggatta aacccttta tatattctcg gaacagtgca gggctgagaa     1260
ggaaagtgct ctggtgcctc caatacatag gcctgggttt tttctgctgc aaacaaaaga     1320
ctcgacttcg agccatggga aaagggaacc tcgaagtcaa cagaaacaaa tcctcccatc     1380
atgaaacaaa ctctgcctac atgttatctc caaagccaca gaagaaattt gtggaccagg     1440
cttgtggccc aagtcattca aaagaaagta tggtgagtcc caagatctct gctggacatc     1500
aacactgtgg tcagagcagc tcgacccca tcaacactcg gattgaacct tactacagca     1560
tctataacag cagcccttcc caggaggaga gcagcccatg taacttacag ccagtaaact     1620
cttttggatt tgccaattca tatattgcca tgcattatca caccactaat gacttagtgc     1680
aggaatatga cagcacttca gccaagcaga ttccagtccc ctccgtttaa agtcatggag     1740
gctataggat cttatgtaaa cagttttgt ttctgatagt aatgggcttt attctaactt     1800
gagatcagtg gcggatcaaa acctacaaga ttcaactgaa aagttggcag ttatggtttt     1860
ctttcatctg atgtgtcagt atctgttgat ttgctttgta gtttgttga                1909
```

```
<210> SEQ ID NO 44
<211> LENGTH: 1914
<212> TYPE: DNA
<213> ORGANISM: homo sapien

<400> SEQUENCE: 44
caggcttact gtcttgggcc tcttttgtca catattgctc atctgtgagc tgaggccctg       60
actcactgag tattttttggg gagcagaaga aggagacatt tctctccgaa aatgaactca      120
acaggccacc ttcaggatgc ccccaatgcc acctcgctcc atgtgcctca ctcacaggaa      180
ggaaacagca cctctctcca ggagggtctt caggatctca tccacacagc caccttggtg      240
acctgtactt ttctactggc ggtcatcttc tgcctgggtt cctatggcaa cttcattgtc      300
```

-continued

```
ttcttgtcct tcttcgatcc agccttcagg aaattcagaa ccaactttga tttcatgatc    360
ctgaacctgt ccttctgtga cctcttcatt tgtggagtga cagcccccat gttcacctttt   420 gtgttattct tcagctcagc cagtagtatc ccggatgctt tctgcttcac tttccatctc    480
accagttcag gcttcatcat catgtctctg aagacagtgg cagtgatcgc cctgcaccgg    540
ctccggatgg tgttgggggaa acagcctaat cgcacggcct cctttccctg caccgtactc   600
ctcaccctgc ttctctgggc caccagtttc accccctgcca ccttggctac cttgaaaacc    660
agcaagtccc acctctgtct tcccatgtcc agtctgattg ctggaaaagg gaaagccatt     720
ttgtctctct atgtggtcga cttcaccttc tgtgttgctg tggtctctgt ctcttacatc    780
atgattgctc agaccctgcg gaagaacgct caagtcagaa agtgcccccc tgtaatcaca     840
gtcgatgctt ccagaccaca gcctttcatg ggggtccctg tgcagggagg tggagatccc    900
atccagtgtg ccatgccggc tctgtatagg aaccagaatt acgacaaact gcagcacgtt    960
cagacccgtg gatataccaa gagtcccaac caactggtca ccctgcagc aagccgactc     1020 cagctcgtat cagccatcaa cctctccact gccaaggatt ccaaagccgt ggtcacctgt    1080
gtgatcattg tgctgtcagt cctggtgtgc tgtcttccac tggggatttc cttggtacag    1140
gtggttctct ccagcaatgg gagcttcatt ctttaccagt ttgaattgtt tggatttact    1200
cttatatttt tcaagtcagg attaaaccct tttatatatt ctcggaacag tgcagggctg    1260
agaaggaaag tgctctggtg cctccaatac ataggcctgg gtttttttctg tctgcaaaca    1320 aaagactcga cttcgagcca tgggaaaagg gaacctcgaa gtcaacagaa acaaatcctc    1380
ccatcatgaa acaaactctg cctacatgtt atctccaaag ccacagaaga aatttgtgga    1440
ccaggcttgt ggcccaagtc attcaaaaga aagtatggtg agtcccaaga tctctgctgg    1500
acatcaacac tgtggtcaga gcagctcgac ccccatcaac actcggattg aaccttacta    1560
cagcatctat aacagcagcc cttcccagga ggagagcagc ccatgtaact tacagccagt    1620
aaactctttt ggatttgcca attcatatat tgccatgcat tatcacacca ctaatgactt    1680
agtgcaggaa tatgacagca cttcagccaa gcagattcca gtcccctccg tttaaagtca    1740
tggaggctat aggatcttat gtaaacagtt tttgtttctg atagtaatgg gctttattct    1800
aacttgagat cagtggcgga tcaaaaccta caagattcaa ctgaaaagtt ggcagttatg    1860 gttttcttttc atctgatgtg tcagtatctg ttgatttgct ttgtagtttg ttga         1914
```

```
<210> SEQ ID NO 45
<211> LENGTH: 1734
<212> TYPE: DNA
<213> ORGANISM: homo sapien

<400> SEQUENCE: 45
```

```
ggagcagaag aaggagacat ttctctccga aaatgaactc aacaggccac cttcaggatg     60
cccccaatgc cacctcgctc catgtgcctc actcacagga aggaaacagc acctctctcc    120
aggagggtct tcaggatctc atccacacag ccaccttggt gacctgtact tttctactgg    180
cggtcatctt ctgcctgggt tcctatggca acttcattgt cttcttgtcc ttcttcgatc    240
cagccttcag gaaattcaga accaactttg atttcatgat cctgaacctg tccttctgtg    300
acctcttcat ttgtggagtg acagccccca tgttcacctt tgtgttattc ttcagctcag    360
tatcccggat gctttctgct tcactttcca tctcaccagt tcaggcttca tcatcatgtc    420
tctgaagaca gtggcagtga tcgccctgca ccggctccgg atggtgttgg ggaaacagcc    480
```

-continued

```
taatcgcacg gcctcctttc cctgcaccgt actcctcacc ctgcttctct gggccaccag      540
tttcaccctt gccaccttgg ctaccttgaa aaccagcaag tcccacctct gtcttcccat      600
gtccagtctg attgctggaa aagggaaagc cattttgtct ctctatgtgg tcgacttcac      660
cttctgtgtt gctgtggtct ctgtctctta catcatgatt gctcagaccc tgcggaagaa      720
cgctcaagtc agaaagtgcc ccctgtaat cacagtcgat gcttccagac cacagccttt      780
catgggggtc cctgtgcagg gaggtggaga tcccatccag tgtgccatgc cggctctgta      840
taggaaccag aattacaaca aactgcagca cgttcagacc cgtggatata ccaagagtcc      900
caaccaactg gtcacccctg cagcaagccg actccagctc gtatcagcca tcaacctctc      960
cactgccaag gattccaaag ccgtggtcac ctgtgtgatc attgtgctgt cagtcctggt     1020
gtgctgtctt ccactgggga tttccttggt acaggtggtt ctctccagca atgggagctt     1080
cattctttac cagtttgaat tgtttggatt tactcttata ttttttcaagt caggattaaa     1140 ccctttata tattctcgga acagtgcagg gctgagaagg aaagtgctct ggtgcctcca      1200
atacataggc ctgggtttttt tctgctgcaa acaaaagact cgacttcgag ccatgggaaa     1260
agggaacctc gaagtcaaca gaaacaaatc ctcccatcat gaaacaaact ctgcctacat      1320
gttatctcca aagccacaga agaaatttgt ggaccaggct tgtggcccaa gtcattcaaa      1380
agaaagtatg gtgagtccca agatctctgc tggacatcaa cactgtggtc agagcagctc      1440 gaccccatc aacactcgga ttgaacctta ctacagcatc tataacagca gcccttccca      1500
ggaggagagc agcccatgta acttacagcc agtaaactct tttggatttg ccaattcata      1560
tattgccatg cattatcaca ccactaatga cttagtgcag gaatatgaca gcacttcagc      1620
caagcagatt ccagtcccct ccgtttaaag tcatggaggc tataggatct tatgtaaaca      1680 gttttttgttt ctgatagtaa tggactttat tctaacttga gatagtggcg gatc          1734
```

<210> SEQ ID NO 46
<211> LENGTH: 1741
<212> TYPE: DNA
<213> ORGANISM: homo sapien

<400> SEQUENCE: 46

```
ggagcagaag aaggagacat ttctctccga aaatgaactc aacaggccac cttcaggatg      60
cccccaatgc cacctcgctc catgtgcctc actcacagga aggaaacagc acctctctcc      120
aggagggtct tcaggatctc atccacacag ccaccttggt gacctgtact tttctactgg      180
cggtcatctt ctgcctgggt tcctatggca acttcattgt cttcttgtcc ttcttcgatc      240
cagccttcag gaaattcaga accaactttg atttcatgat cctgaacctg tccttctgtg      300
acctcttcat ttgtggagtg acagcccca tgttcacctt tgtgttattc ttcagctcag      360
ccagtagtat cccggatact ttctgcttca cttttccatct caccagttca ggcttcatca      420
tcatgtctct gaagacagtg gcagtgatcg ccctgcaccg gctccggatg gtgttgggga      480
aacagcctaa tcgcacggcc tcctttccct gcaccgtact cctcaccctg cttctctggg      540
ccaccagttt caccctttgcc accttggcta ccttgaaaac cagcaagtcc cacctctgtc      600
ttcccatgtc cagtctgatt gctggaaaag ggaaagccat tttgtctctc tatgtggtcg      660
acttcacctt ctgtgttgct gtggtctctg tctcttacat catgattgct cagaccctgc      720
ggaagaacgc tcaagtcaga aagtgccccc ctgtaatcac agtcgatgct tccagaccac      780
agcctttcat ggggggtccct gtgcaggag gtggagatcc catccagtgt gccatgccgg      840
ctctgtatag gaaccagaat tacaacaaac tgcagcacgt tcagacccgt ggatatacca      900
```

-continued

```
agagtcccaa ccaactggtc acccctgcag caagccgact ccagctcgta tcagccatca      960
acctctccac tgccaaggat tccaaagccg tggtcacctg tgtgatcatt gtgctgtcag     1020
tcctggtgtg ctgtcttcca ctggggattt ccttggtaca ggtggttctc tccagcaatg     1080
ggagcttcat tctttaccag tttgaattgt ttggatttac tcttatattt ttcaagtcag     1140
gattaaaccc ttttatatat tctcggaaca gtgcagggct gagaaggaaa gtgctctggt     1200
gcctccaata cataggcctg ggttttttct gctgcaaaca aaagactcga cttcgagcca     1260
tgggaaaagg gaacctcgaa gtcaacagaa acaaatcctc ccatcatgaa acaaactctg     1320
cctacatgtt atctccaaag ccacagaaga aatttgtgga ccaggcttgt ggcccaagtc     1380
attcaaaaga aagtatggtg agtcccaaga tctctgctgg acatcaacac tgtggtcaga     1440
gcagctcgac ccccatcaac actcggattg aaccttacta cagcatctat aacagcagcc     1500
cttcccagga ggagagcagc ccatgtaact tacagccagt aaaactcttt ggatttgcca     1560
attcatatat tgccatgcat tatcacacca ctaatgactt agtgcaggaa tatgacagca     1620
cttcagccaa gcagattcca gtcccctccg tttaaagtca tggaggctat aggatcttat     1680
gtaaacagtt tttgtttctg atagtaatgg actttattct aacttgagat agtggcggat     1740
c                                                                      1741
```

```
<210> SEQ ID NO 47
<211> LENGTH: 1741
<212> TYPE: DNA
<213> ORGANISM: homo sapien

<400> SEQUENCE: 47
```

```
ggagcagaag aaggagacat ttctctccga aaatgaactc aacaggccac cttcaggatg       60
cccccaatgc cacctcgctc catgtgcctc actcacagga aggaaacagc acctctctcc      120
aggagggtct tcaggatctc atccacacag ccaccttggt gacctgtact tttctactgg      180
cggtcatctt ctgcctgggt tcctatggca acttcattgt cttcttgtcc ttcttcgatc      240
cagccttcag gaaattcaga accaactttg atttcatgat cctgaacctg tccttctgtg      300
acctcttcat ttgtggagtg acagcccca tgttcacctt tgtgttattc ttcagctcag      360
ccagtagtat cccggatgct ttctgcttca ctttccatct caccagttca ggcttcatca      420
tcatgtctct gaagacagtg gcagtgatcg ccctgcaccg gctccggatg gtgttgggga      480
aacagcctaa tcgcacggcc tcctttccct gcaccgtact cctcaccctg cttctctggg      540
ccaccagttt caccccttgcc accttggcta ccttgaaaac cagcaagtcc cacctctgtc      600
ttcccatgtc cagtctgatt gctggaaaag gaaagccat tttgtctctc tatgtggtcg      660
acttcacctt ctgtgttgct gtggtctctg tctcttacat catgattgct cagaccctgc      720
ggaagaacgc ttaagtcaga aagtgccccc ctgtaatcac agtcgatgct tccagaccac      780
agcctttcat gggggtccct gtgcaggag gtggagatcc catccagtgt gccatgccgg      840
ctctgtatag gaaccagaat tacaacaaac tgcagcacgt tcagacccgt ggatatacca      900
agagtcccaa ccaactggtc acccctgcag caagccgact ccagctcgta tcagccatca      960
acctctccac tgccaaggat tccaaagccg tggtcacctg tgtgatcatt gtgctgtcag     1020
tcctggtgtg ctgtcttcca ctggggattt ccttggtaca ggtggttctc tccagcaatg     1080
ggagcttcat tctttaccag tttgaattgt ttggatttac tcttatattt ttcaagtcag     1140
gattaaaccc ttttatatat tctcggaaca gtgcagggct gagaaggaaa gtgctctggt     1200
```

-continued

```
gcctccaata cataggcctg ggttttttct gctgcaaaca aaagactcga cttcgagcca    1260
tgggaaaagg gaacctcgaa gtcaacagaa acaaatcctc ccatcatgaa acaaactctg    1320
cctacatgtt atctccaaag ccacagaaga aatttgtgga ccaggcttgt ggcccaagtc    1380
attcaaaaga aagtatggtg agtcccaaga tctctgctgg acatcaacac tgtggtcaga    1440
gcagctcgac ccccatcaac actcggattg aaccttacta cagcatctat aacagcagcc    1500
cttcccagga ggagagcagc ccatgtaact tacagccagt aaactctttt ggatttgcca    1560
attcatatat tgccatgcat tatcacacca ctaatgactt agtgcaggaa tatgacagca    1620
cttcagccaa gcagattcca gtcccctccg tttaaagtca tggaggctat aggatcttat    1680
gtaaacagtt tttgtttctg atagtaatgg actttattct aacttgagat agtggcggat    1740
c                                                                    1741

<210> SEQ ID NO 48
<211> LENGTH: 1737
<212> TYPE: DNA
<213> ORGANISM: homo sapien

<400> SEQUENCE: 48
ggagcagaag aaggagacat ttctctccga aaatgaactc aacaggccac cttcaggatg      60
cccccaatgc cacctcgctc catgtgcctc actcacagga aggaaacagc acctctctcc     120
aggagggtct tcaggatctc atccacacag ccaccttggt gacctgtact tttctactgg     180
cggtcatctt ctgcctgggt tcctatggca acttcattgt cttcttgtcc ttcttcgatc     240
cagccttcag gaaattcaga accaactttg atttcatgat cctgaacctg tccttctgtg     300
acctcttcat ttgtggagtg acagccccca tgttcacctt tgtgttattc ttcagctcag     360
ccagtagtat cccggatgct ttctgcttca ctttccatct caccagttca ggcttcatca     420
tcatgtctct gaagacagtg gcagtgatcg ccctgcaccg gctccggatg gtgttgggga     480
aacagcctaa tcgcacggcc tcctttccct gcaccgtact cctcaccctg cttctctggg     540
ccaccagttt caccccttgcc accttggcta ccttgaaaac cagcaagtcc cacctctgtc     600
ttcccatgtc cagtctgatt gctggaaaag ggaaagccat tttgtctctc tatgtggtcg     660
acttcacctt ctgtgttgct gtggtctctg tctcttacat catgattgct cagaccctgc     720
ggaagaacgc tcaagtcagt gccccctgt aatcacagtc gatgcttcca gaccacagcc     780
tttcatgggg gtccctgtgc agggaggtgg agatcccatc cagtgtgcca tgccggctct     840
gtataggaac cagaattaca acaaactgca gcacgttcag acccgtggat ataccaagag     900
tcccaaccaa ctggtcaccc ctgcagcaag ccgactccag ctcgtatcag ccatcaacct     960
ctccactgcc aaggattcca aagccgtggt cacctgtgtg atcattgtgc tgtcagtcct    1020
ggtgtgctgt cttccactgg ggatttcctt ggtacaggtg gttctctcca gcaatgggag    1080
cttcattctt taccagtttg aattgtttgg atttactctt atattttca agtcaggatt    1140 aaacccttt atatattctc ggaacagtgc agggctgaga aggaaagtgc tctggtgcct    1200
ccaatacata ggcctgggtt ttttctgctg caaacaaaag actcgacttc gagccatggg    1260
aaaaggggac ctcgaagtca acagaaacaa atcctcccat catgaaacaa actctgccta    1320
catgttatct ccaaagccac agaagaaatt tgtggaccag gcttgtggcc caagtcattc    1380
aaaagaaagt atggtgagtc ccaagatctc tgctggacat caacactgtg gtcagagcag    1440
ctcgaccccc atcaacactc ggattgaacc ttactacagc atctataaca gcagcccttc    1500
ccaggaggag agcagcccat gtaacttaca gccagtaaac tcttttggat ttgccaattc    1560
```

-continued

```
atatattgcc atgcattatc acaccactaa tgacttagtg caggaatatg acagcacttc    1620
agccaagcag attccagtcc cctccgttta aagtcatgga ggctatagga tcttatgtaa    1680
acagtttttg tttctgatag taatggactt tattctaact tgagatagtg gcggatc       1737

<210> SEQ ID NO 49
<211> LENGTH: 1742
<212> TYPE: DNA
<213> ORGANISM: homo sapien

<400> SEQUENCE: 49
ggagcagaag aaggagacat ttctctccga aaatgaactc aacaggccac cttcaggatg     60
cccccaatgc cacctcgctc catgtgcctc actcacagga aggaaacagc acctctctcc    120
aggagggtct tcaggatctc atccacacag ccaccttggt gacctgtact tttctactgg    180
cggtcatctt ctgcctgggt tcctatggca acttcattgt cttcttgtcc ttcttcgatc    240
cagccttcag gaaattcaga accaactttg atttcatgat cctgaacctg tccttctgtg    300
acctcttcat ttgtggagtg acagccccca tgttcacctt tgtgttattc ttcagctcag    360
ccagtagtat cccggatgct ttctgcttca ctttccatct caccagttca ggcttcatca    420
tcatgtctct gaagacagtg gcagtgatcg ccctgcaccg gctccggatg gtgttgggga    480
aacagcctaa tcgcacggcc tcctttccct gcaccgtact cctcaccctg cttctctggg    540
ccaccagttt caccccttgcc accttggcta ccttgaaaac cagcaagtcc cacctctgtc    600
ttcccatgtc cagtctgatt gctggaaaag ggaaagccat tttgtctctc tatgtggtcg    660
acttcacctt ctgtgttgct gtggtctctg tctcttacat catgattgct cagaccctgc    720
ggaagaacgc tcaagtcaga aagtgccccc ctgtaatcac agtcgatgct tccagaccac    780
agcctttcat gggggtccct gtgcagggag gtggagatcc catccagtgt gccatgccgg    840
ctctgtatag gaaccagaat tacaacaaac tgcagcacgt tcagacccgt ggatatacca    900
agagtcccaa ccaactggtc accctgcag caagccgact ccagctcgta tcagccatca    960
acctctccac tgccaaggat tccaaagccg tggtcacctg tgtgatcatt gtgctgtcag   1020
tcctggtgtg ctgtcttcca ctggggattt ccttggtaca ggtggttctc tccagcaatg   1080
ggagcttcat tctttaccag tttgaattgt ttggatttac tcttatattt ttcaagtcag   1140
gattaaaccc ttttatatat tctcggaaca gtgcagggct gagaaggaaa gtgctctggt   1200
gcctccaata cataggcctg ggtttttttct gtctgcaaac aaaagactcg acttcgagcc   1260
atgggaaaag ggaacctcga agtcaacaga aacaaatcct cccatcatga aacaaactct   1320
gcctacatgt tatctccaaa gccacagaag aaatttgtgg accaggcttg tggcccaagt   1380
cattcaaaag aaagtatggt gagtcccaag atctctgctg gacatcaaca ctgtggtcag   1440
agcagctcga cccccatcaa cactcggatt gaaccttact acagcatcta taacagcagc   1500
ccttcccagg aggagagcag cccatgtaac ttacagccag taaactcttt tggatttgcc   1560
aattcatata ttgccatgca ttatcacacc actaatgact tagtgcagga atatgacagc   1620
acttcagcca agcagattcc agtccctcc gtttaaagtc atggaggcta taggatctta   1680
tgtaaacagt ttttgtttct gatagtaatg gactttattc taacttgaga tagtggcgga   1740
tc                                                                   1742

<210> SEQ ID NO 50
<211> LENGTH: 1887
<212> TYPE: DNA
```

```
<213> ORGANISM: homo sapien

<400> SEQUENCE: 50
gtgactgcgc ctctgcgccc gcgtcttgcc gcggctcccg ggatgcgcgg aggcggtggc      60
gatggcgatg atgcctctag tcctgcatca tccagagcgg caggcggagc tggggtccgg     120
actgcgagat ggaggagggg cggcgctgcg gccacccggc aggcttatct gtcttgggcc     180
tcttttgtca catattgctc atctgtgagc tgaggccctg actcactgag tattttgggg     240
gagcagaaga aggagacatt tctctccgaa aatgaactca acaggccacc ttcaggatgc     300
ccccaatgcc acctcgctcc atgtgcctca ctcacaggaa ggaaacagca cctctctcca     360
ggagggtctt caggatctca tccacacagc caccttggtg acctgtactt ttctactggc     420
ggtcatcttc tgcctgggtt cctatggcaa cttcattgtc ttcttgtcct tcttcgatcc     480
agccttcagg aaaattcagaa ccaactttga tttcatgatc ctgaacctgt ccttctgtga     540
cctcttcatt tgtggagtga cagcccccat gttcaccttt gtgttattct tcagctcagt     600
atcccggatg ctttctgctt cactttccat ctcaccagtt caggcttcat catcatgtct     660
ctgaagacag tggcagtgat cgccctgcac cggctccgga tggtgttggg gaaacagcct     720
aatcgcacgg cctcctttcc ctgcaccgta ctcctcaccc tgcttctctg ggccaccagt     780 ttcaccccttg ccaccttggc taccttgaaa accagcaagt cccacctctg tcttcccatg     840
tccagtctga ttgctggaaa agggaaagcc attttgtctc tctatgtggt cgacttcacc     900
ttctgtgttg ctgtggtctc tgtctcttac atcatgattg ctcagaccct gcggaagaac     960
gctcaagtca gaaagtgccc ccctgtaatc acagtcgatg cttccagacc acagcctttc    1020
atgggggtcc ctgtgcaggg aggtggagat cccatccagt gtgccatgcc ggctctgtat    1080
aggaaccaga attacaacaa actgcagcac gttcagaccc gtggatatac caagagtccc    1140
aaccaactgg tcacccctgc agcaagccga ctccagctcg tatcagccat caacctctcc    1200
actgccaagg attccaaagc cgtggtcacc tgtgtgatca ttgtgctgtc agtcctggtg    1260
tgctgtcttc cactggggat ttccttggta caggtggttc tctccagcaa tgggagcttc    1320
attctttacc agtttgaatt gtttggattt actcttatat ttttcaagtc aggattaaac    1380
ccttttatat attctcggaa cagtgcaggg ctgagaagga aagtgctctg gtgcctccaa    1440
tacataggcc tgggtttttt ctgctgcaaa caaaagactc gacttcgagc catgggaaaa    1500
gggaacctcg aagtcaacag aaacaaatcc tcccatcatg aaacaaactc tgcctacatg    1560
ttatctccaa agccacagaa gaaatttgtg gaccaggctt gtggcccaag tcattcaaaa    1620
gaaagtatgg tgagtcccaa gatctctgct ggacatcaac actgtggtca gagcagctcg    1680
acccccatca acactcggat tgaaccttac tacagcatct ataacagcag cccttcccag    1740
gaggagagca gcccatgtaa cttacagcca gtaaactctt ttggatttgc caattcatat    1800
attgccatgc attatcacac cactaatgac ttagtgcagg aatatgacag cacttcagcc    1860
aagcagattc cagtcccctc cgtttaa                                        1887
```

```
<210> SEQ ID NO 51
<211> LENGTH: 1894
<212> TYPE: DNA
<213> ORGANISM: homo sapien

<400> SEQUENCE: 51
gtgactgcgc ctctgcgccc gcgtcttgcc gcggctcccg ggatgcgcgg aggcggtggc      60
gatggcgatg atgcctctag tcctgcatca tccagagcgg caggcggagc tggggtccgg     120
```

```
actgcgagat ggaggagggg cggcgctgcg gccacccggc aggcttatct gtcttgggcc        180
tcttttgtca catattgctc atctgtgagc tgaggccctg actcactgag tatttttggg        240
gagcagaaga aggagacatt tctctccgaa aatgaactca acaggccacc ttcaggatgc        300
ccccaatgcc acctcgctcc atgtgcctca ctcacaggaa ggaaacagca cctctctcca        360
ggagggtctt caggatctca tccacacagc caccttggtg acctgtactt ttctactggc        420
ggtcatcttc tgcctgggtt cctatggcaa cttcattgtc ttcttgtcct cttcgatcc         480 agccttcagg aaattcagaa ccaactttga tttcatgatc ctgaacctgt ccttctgtga        540
cctcttcatt tgtggagtga cagcccccat gttcaccttt gtgttattct tcagctcagc        600
cagtagtatc ccggatactt tctgcttcac tttccatctc accagttcag gcttcatcat        660
catgtctctg aagacagtgg cagtgatcgc cctgcaccgg ctccggatgg tgttggggaa        720
acagcctaat cgcacggcct cctttccctg caccgtactc ctcaccctgc ttctctgggc        780
caccagtttc acccttgcca ccttggctac cttgaaaacc agcaagtccc acctctgtct        840
tcccatgtcc agtctgattg ctggaaaagg gaaagccatt ttgtctctct atgtggtcga        900
cttcaccttc tgtgttgctg tggtctctgt ctcttacatc atgattgctc agaccctgcg        960
gaagaacgct caagtcagaa agtgcccccc tgtaatcaca gtcgatgctt ccagaccaca       1020
gcctttcatg ggggtccctg tgcagggagg tggagatccc atccagtgtg ccatgccggc       1080
tctgtatagg aaccagaatt acaacaaact gcagcacgtt cagacccgtg gatataccaa       1140
gagtcccaac caactggtca cccctgcagc aagccgactc cagctcgtat cagccatcaa       1200
cctctccact gccaaggatt ccaaagccgt ggtcacctgt gtgatcattg tgctgtcagt       1260
cctggtgtgc tgtcttccac tggggatttc cttggtacag gtggttctct ccagcaatgg       1320
gagcttcatt ctttaccagt ttgaattgtt tggatttact cttatatttt tcaagtcagg       1380
attaaaccct tttatatatt ctcggaacag tgcagggctg agaaggaaag tgctctggtg       1440
cctccaatac ataggcctgg gttttttctg ctgcaaacaa aagactcgac ttcgagccat       1500
gggaaaaggg aacctcgaag tcaacagaaa caaatcctcc catcatgaaa caaactctgc       1560
ctacatgtta tctccaaagc cacagaagaa atttgtggac caggcttgtg gcccaagtca       1620
ttcaaaagaa agtatggtga gtcccaagat ctctgctgga catcaacact gtggtcagag       1680
cagctcgacc cccatcaaca ctcggattga accttactac agcatctata acagcagccc       1740
ttcccaggag gagagcagcc catgtaactt acagccagta aactcttttg gatttgccaa       1800
ttcatatatt gccatgcatt atcacaccac taatgactta gtgcaggaat atgacagcac       1860
ttcagccaag cagattccag tcccctccgt ttaa                                   1894
```

<210> SEQ ID NO 52
<211> LENGTH: 1894
<212> TYPE: DNA
<213> ORGANISM: homo sapien

<400> SEQUENCE: 52

```
gtgactgcgc ctctgcgccc gcgtcttgcc gcggctcccg ggatgcgcgg aggcggtggc         60
gatggcgatg atgcctctag tcctgcatca tccagagcgg caggcggagc tggggtccgg        120
actgcgagat ggaggagggg cggcgctgcg gccacccggc aggcttatct gtcttgggcc        180
tcttttgtca catattgctc atctgtgagc tgaggccctg actcactgag tatttttggg        240
gagcagaaga aggagacatt tctctccgaa aatgaactca acaggccacc ttcaggatgc        300
```

-continued

```
ccccaatgcc acctcgctcc atgtgcctca ctcacaggaa ggaaacagca cctctctcca      360
ggagggtctt caggatctca tccacacagc caccttggtg acctgtactt ttctactggc      420
ggtcatcttc tgcctgggtt cctatggcaa cttcattgtc ttcttgtcct tcttcgatcc      480
agccttcagg aaaattcagaa ccaactttga tttcatgatc ctgaacctgt ccttctgtga      540
cctcttcatt tgtggagtga cagcccccat gttcaccttt gtgttattct tcagctcagc      600
cagtagtatc ccggatgctt tctgcttcac tttccatctc accagttcag gcttcatcat      660
catgtctctg aagacagtgg cagtgatcgc cctgcaccgg ctccggatgg tgttggggaa      720
acagcctaat cgcacggcct cctttccctg caccgtactc ctcaccctgc ttctctgggc      780
caccagtttc accccttgcca ccttggctac cttgaaaacc agcaagtccc acctctgtct      840
tcccatgtcc agtctgattg ctggaaaagg gaaagccatt ttgtctctct atgtggtcga      900
cttcaccttc tgtgttgctg tggtctctgt ctcttacatc atgattgctc agaccctgcg      960
gaagaacgct taagtcagaa agtgcccccc tgtaatcaca gtcgatgctt ccagaccaca     1020
gcctttcatg ggggtccctg tgcagggagg tggagatccc atccagtgtg ccatgccggc     1080
tctgtatagg aaccagaatt acaacaaact gcagcacgtt cagacccgtg gatataccaa     1140
gagtcccaac caactggtca cccctgcagc aagccgactc cagctcgtat cagccatcaa     1200
cctctccact gccaaggatt ccaaagccgt ggtcacctgt gtgatcattg tgctgtcagt     1260
cctggtgtgc tgtcttccac tggggatttc cttggtacag gtggtctctct ccagcaatgg     1320 gagcttcatt ctttaccagt ttgaattgtt tggatttact cttatatttt tcaagtcagg     1380
attaaaccct tttatatatt ctcggaacag tgcaggactg agaaggaaag tgctctggtg     1440
cctccaatac ataggcctgg gttttttctg ctgcaaacaa aagactcgac ttcgagccat     1500
gggaaaaggg aacctcgaag tcaacagaaa caaatcctcc catcatgaaa caaactctgc     1560
ctacatgtta tctccaaagc cacagaagaa atttgtggac caggcttgtg gcccaagtca     1620
ttcaaaagaa agtatggtga gtcccaagat ctctgctgga catcaacact gtggtcagag     1680
cagctcgacc cccatcaaca ctcggattga accttactac agcatctata acagcagccc     1740
ttcccaggag gagagcagcc catgtaactt acagccagta aactcttttg gatttgccaa     1800
ttcatatatt gccatgcatt atcacaccac taatgactta gtgcaggaat atgacagcac     1860
ttcagccaag cagattccag tcccctccgt ttaa                                 1894
```

<210> SEQ ID NO 53
<211> LENGTH: 1890
<212> TYPE: DNA
<213> ORGANISM: homo sapien

<400> SEQUENCE: 53

```
gtgactgcgc ctctgcgccc gcgtcttgcc gcggctcccg ggatgcgcgg aggcggtggc       60
gatggcgatg atgcctctag tcctgcatca tccagagcgg caggcggagc tggggtccgg      120
actgcgagat ggaggagggg cggcgctgcg gccacccggc aggcttatct gtcttgggcc      180
tcttttgtca catattgctc atctgtgagc tgaggccctg actcactgag tattttttggg      240 gagcagaaga aggagacatt tctctccgaa aatgaactca acaggccacc ttcaggatgc      300
ccccaatgcc acctcgctcc atgtgcctca ctcacaggaa ggaaacagca cctctctcca      360
ggagggtctt caggatctca tccacacagc caccttggtg acctgtactt ttctactggc      420
ggtcatcttc tgcctgggtt cctatggcaa cttcattgtc ttcttgtcct tcttcgatcc      480
agccttcagg aaaattcagaa ccaactttga tttcatgatc ctgaacctgt ccttctgtga      540
```

-continued

```
cctcttcatt tgtggagtga cagcccccat gttcaccttt gtgttattct tcagctcagc    600
cagtagtatc ccggatgctt tctgcttcac tttccatctc accagttcag gcttcatcat    660
catgtctctg aagacagtgg cagtgatcgc cctgcaccgg ctccggatgg tgttgggggaa   720 acagcctaat cgcacggcct cctttccctg caccgtactc ctcaccctgc ttctctgggc    780
caccagtttc acccttgcca ccttggctac cttgaaaacc agcaagtccc acctctgtct    840
tcccatgtcc agtctgattg ctggaaaagg gaaagccatt ttgtctctct atgtggtcga    900
cttcaccttc tgtgttgctg tggtctctgt ctcttacatc atgattgctc agaccctgcg    960
gaagaacgct caagtcagtg ccccctgta atcacagtcg atgcttccag accacagcct    1020
ttcatggggg tccctgtgca gggaggtgga gatcccatcc agtgtgccat gccggctctg   1080
tataggaacc agaattacaa caaactgcag cacgttcaga cccgtggata taccaagagt   1140
cccaaccaac tggtcacccc tgcagcaagc cgactccagc tcgtatcagc catcaacctc   1200
tccactgcca aggattccaa agccgtggtc acctgtgtga tcattgtgct gtcagtcctg   1260
gtgtgctgtc ttccactggg gatttccttg gtacaggtgg ttctctccag caatgggagc   1320
ttcattcttt accagtttga attgtttgga tttactctta tatttttcaa gtcaggatta   1380 aacccttta tatattctcg gaacagtgca gggctgagaa ggaaagtgct ctggtgcctc     1440
caatacatag gcctgggttt tttctgctgc aaacaaaaga ctcgacttcg agccatggga   1500
aaagggaacc tcgaagtcaa cagaaacaaa tcctcccatc atgaaacaaa ctctgcctac   1560
atgttatctc caaagccaca gaagaaattt gtggaccagg cttgtggccc aagtcattca   1620
aaagaaagta tggtgagtcc caagatctct gctggacatc aacactgtgg tcagagcagc   1680
tcgaccccca tcaacactcg gattgaacct tactacagca tctataacag cagcccttcc   1740
caggaggaga gcagcccatg taacttacag ccagtaaact cttttggatt tgccaattca   1800
tatattgcca tgcattatca caccactaat gacttagtgc aggaatatga cagcacttca   1860
gccaagcaga ttccagtccc ctccgtttaa                                    1890
```

<210> SEQ ID NO 54
<211> LENGTH: 1895
<212> TYPE: DNA
<213> ORGANISM: homo sapien

<400> SEQUENCE: 54

```
gtgactgcgc ctctgcgccc gcgtcttgcc gcggctcccg ggatgcgcgg aggcggtggc     60
gatggcgatg atgcctctag tcctgcatca tccagagcgg caggcggagc tggggtccgg    120
actgcgagat ggaggagggg cggcgctgcg gccacccggc aggcttatct gtcttgggcc    180
tcttttgtca catattgctc atctgtgagc tgaggccctg actcactgag tattttttggg   240 gagcagaaga aggagacatt tctctccgaa aatgaactca acaggccacc ttcaggatgc    300
ccccaatgcc acctcgctcc atgtgcctca ctcacaggaa ggaaacagca cctctctcca   360
ggagggtctt caggatctca tccacacagc caccttggtg acctgtactt ttctactggc    420
ggtcatcttc tgcctgggtt cctatggcaa cttcattgtc ttcttgtcct tcttcgatcc    480
agccttcagg aaaattcagaa ccaactttga tttcatgatc ctgaacctgt ccttctgtga   540
cctcttcatt tgtggagtga cagcccccat gttcaccttt gtgttattct tcagctcagc    600
cagtagtatc ccggatgctt tctgcttcac tttccatctc accagttcag gcttcatcat    660
catgtctctg aagacagtgg cagtgatcgc cctgcaccgg ctccggatgg tgttgggggaa   720
```

-continued

```
acagcctaat cgcacggcct cctttccctg caccgtactc ctcaccctgc ttctctgggc      780
caccagtttc acccttgcca ccttggctac cttgaaaacc agcaagtccc acctctgtct      840
tcccatgtcc agtctgattg ctggaaaagg gaaagccatt ttgtctctct atgtggtcga      900
cttcaccttc tgtgttgctg tggtctctgt ctcttacatc atgattgctc agaccctgcg      960
gaagaacgct caagtcagaa agtgcccccc tgtaatcaca gtcgatgctt ccagaccaca     1020
gcctttcatg ggggtccctg tgcagggagg tggagatccc atccagtgtg ccatgccggc     1080
tctgtatagg aaccagaatt acaacaaact gcagcacgtt cagacccgtg gatataccaa     1140
gagtcccaac caactggtca cccctgcagc aagccgactc cagctcgtat cagccatcaa     1200
cctctccact gccaaggatt ccaaagccgt ggtcacctgt gtgatcattg tgctgtcagt     1260
cctggtgtgc tgtcttccac tggggatttc cttggtacag gtggttctct ccagcaatgg     1320
gagcttcatt ctttaccagt ttgaattgtt tggatttact cttatatttt tcaagtcagg     1380
attaaaccct tttatatatt ctcggaacag tgcagggctg agaaggaaag tgctctggtg     1440
cctccaatac ataggcctgg gttttttctg tctgcaaaca aaagactcga cttcgagcca     1500
tgggaaaagg gaacctcgaa gtcaacagaa acaaatcctc ccatcatgaa acaaactctg     1560
cctacatgtt atctccaaag ccacagaaga aatttgtgga ccaggcttgt ggcccaagtc     1620
attcaaaaga aagtatggtg agtcccaaga tctctgctgg acatcaacac tgtggtcaga     1680
gcagctcgac ccccatcaac actcggattg aaccttacta cagcatctat aacagcagcc     1740
cttcccagga ggagagcagc ccatgtaact tacagccagt aaactctttt ggatttgcca     1800
attcatatat tgccatgcat tatcacacca ctaatgactt agtgcaggaa tatgacagca     1860
cttcagccaa gcagattcca gtcccctccg tttaa                                1895
```

```
<210> SEQ ID NO 55
<211> LENGTH: 540
<212> TYPE: PRT
<213> ORGANISM: homo sapien

<400> SEQUENCE: 55

Met Asn Ser Thr Gly His Leu Gln Asp Ala Pro Asn Ala Thr Ser Leu
1               5                   10                  15

His Val Pro His Ser Gln Glu Gly Asn Ser Thr Ser Leu Gln Glu Gly
            20                  25                  30

Leu Gln Asp Leu Ile His Thr Ala Thr Leu Val Thr Cys Thr Phe Leu
        35                  40                  45

Leu Ala Val Ile Phe Cys Leu Gly Ser Tyr Gly Asn Phe Ile Val Phe
    50                  55                  60

Leu Ser Phe Phe Asp Pro Ala Phe Arg Lys Phe Arg Thr Asn Phe Asp
65                  70                  75                  80

Phe Met Ile Leu Asn Leu Ser Phe Cys Asp Leu Phe Ile Cys Gly Val
                85                  90                  95

Thr Ala Pro Met Phe Thr Phe Val Leu Phe Phe Ser Ser Ala Ser Ser
            100                 105                 110

Ile Pro Asp Ala Phe Cys Phe Thr Phe His Leu Thr Ser Ser Gly Phe
        115                 120                 125

Ile Ile Met Ser Leu Lys Thr Val Ala Val Ile Ala Leu His Arg Leu
    130                 135                 140

Arg Met Val Leu Gly Lys Gln Pro Asn Arg Thr Ala Ser Phe Pro Cys
145                 150                 155                 160

Thr Val Leu Leu Thr Leu Leu Leu Trp Ala Thr Ser Phe Thr Leu Ala
```

-continued

```
           165              170              175

Thr Leu Ala Thr Leu Lys Thr Ser Lys Ser His Leu Cys Leu Pro Met
           180              185              190

Ser Ser Leu Ile Ala Gly Lys Gly Lys Ala Ile Leu Ser Leu Tyr Val
           195              200              205

Val Asp Phe Thr Phe Cys Val Ala Val Val Ser Val Ser Tyr Ile Met
       210              215              220

Ile Ala Gln Thr Leu Arg Lys Asn Ala Gln Val Arg Lys Cys Pro Pro
   225              230              235              240

Val Ile Thr Val Asp Ala Ser Arg Pro Gln Pro Phe Met Gly Val Pro
               245              250              255

Val Gln Gly Gly Gly Asp Pro Ile Gln Cys Ala Met Pro Ala Leu Tyr
               260              265              270

Arg Asn Gln Asn Tyr Asn Lys Leu Gln His Val Gln Thr Arg Gly Tyr
               275              280              285

Thr Lys Ser Pro Asn Gln Leu Val Thr Pro Ala Ala Ser Arg Leu Gln
       290              295              300

Leu Val Ser Ala Ile Asn Leu Ser Thr Ala Lys Asp Ser Lys Ala Val
   305              310              315              320

Val Thr Cys Val Ile Ile Val Leu Ser Val Leu Val Cys Cys Leu Pro
               325              330              335

Leu Gly Ile Ser Leu Val Gln Val Val Leu Ser Ser Asn Gly Ser Phe
               340              345              350

Ile Leu Tyr Gln Phe Glu Leu Phe Gly Phe Thr Leu Ile Phe Phe Lys
               355              360              365

Ser Gly Leu Asn Pro Phe Ile Tyr Ser Arg Asn Ser Ala Gly Leu Arg
       370              375              380

Arg Lys Val Leu Trp Cys Leu Gln Tyr Ile Gly Leu Gly Phe Phe Cys
   385              390              395              400

Cys Lys Gln Lys Thr Arg Leu Arg Ala Met Gly Lys Gly Asn Leu Glu
               405              410              415

Val Asn Arg Asn Lys Ser Ser His His Glu Thr Asn Ser Ala Tyr Met
               420              425              430

Leu Ser Pro Lys Pro Gln Lys Lys Phe Val Asp Gln Ala Cys Gly Pro
       435              440              445

Ser His Ser Lys Glu Ser Met Val Ser Pro Lys Ile Ser Ala Gly His
       450              455              460

Gln His Cys Gly Gln Ser Ser Ser Thr Pro Ile Asn Thr Arg Ile Glu
   465              470              475              480

Pro Tyr Tyr Ser Ile Tyr Asn Ser Ser Pro Ser Gln Glu Glu Ser Ser
               485              490              495

Pro Cys Asn Leu Gln Pro Val Asn Ser Phe Gly Phe Ala Asn Ser Tyr
               500              505              510

Ile Ala Met His Tyr His Thr Thr Asn Asp Leu Val Gln Glu Tyr Asp
               515              520              525

Ser Thr Ser Ala Lys Gln Ile Pro Val Pro Ser Val
       530              535              540
```

<210> SEQ ID NO 56
<211> LENGTH: 130
<212> TYPE: PRT
<213> ORGANISM: homo sapien

<400> SEQUENCE: 56

-continued

```
Met Asn Ser Thr Gly His Leu Gln Asp Ala Pro Asn Ala Thr Ser Leu
1               5                   10                  15

His Val Pro His Ser Gln Glu Gly Asn Ser Thr Ser Leu Gln Glu Gly
            20                  25                  30

Leu Gln Asp Leu Ile His Thr Ala Thr Leu Val Thr Cys Thr Phe Leu
        35                  40                  45

Leu Ala Val Ile Phe Cys Leu Gly Ser Tyr Gly Asn Phe Ile Val Phe
    50                  55                  60

Leu Ser Phe Phe Asp Pro Ala Phe Arg Lys Phe Arg Thr Asn Phe Asp
65                  70                  75                  80

Phe Met Ile Leu Asn Leu Ser Phe Cys Asp Leu Phe Ile Cys Gly Val
                85                  90                  95

Thr Ala Pro Met Phe Thr Phe Val Leu Phe Phe Ser Ser Val Ser Arg
            100                 105                 110

Met Leu Ser Ala Ser Leu Ser Ile Ser Pro Val Gln Ala Ser Ser Ser
        115                 120                 125

Cys Leu
    130
```

```
<210> SEQ ID NO 57
<211> LENGTH: 540
<212> TYPE: PRT
<213> ORGANISM: homo sapien

<400> SEQUENCE: 57
```

```
Met Asn Ser Thr Gly His Leu Gln Asp Ala Pro Asn Ala Thr Ser Leu
1               5                   10                  15

His Val Pro His Ser Gln Glu Gly Asn Ser Thr Ser Leu Gln Glu Gly
            20                  25                  30

Leu Gln Asp Leu Ile His Thr Ala Thr Leu Val Thr Cys Thr Phe Leu
        35                  40                  45

Leu Ala Val Ile Phe Cys Leu Gly Ser Tyr Gly Asn Phe Ile Val Phe
    50                  55                  60

Leu Ser Phe Phe Asp Pro Ala Phe Arg Lys Phe Arg Thr Asn Phe Asp
65                  70                  75                  80

Phe Met Ile Leu Asn Leu Ser Phe Cys Asp Leu Phe Ile Cys Gly Val
                85                  90                  95

Thr Ala Pro Met Phe Thr Phe Val Leu Phe Phe Ser Ser Ala Ser Ser
            100                 105                 110

Ile Pro Asp Thr Phe Cys Phe Thr Phe His Leu Thr Ser Ser Gly Phe
        115                 120                 125

Ile Ile Met Ser Leu Lys Thr Val Ala Val Ile Ala Leu His Arg Leu
    130                 135                 140

Arg Met Val Leu Gly Lys Gln Pro Asn Arg Thr Ala Ser Phe Pro Cys
145                 150                 155                 160

Thr Val Leu Leu Thr Leu Leu Leu Trp Ala Thr Ser Phe Thr Leu Ala
                165                 170                 175

Thr Leu Ala Thr Leu Lys Thr Ser Lys Ser His Leu Cys Leu Pro Met
            180                 185                 190

Ser Ser Leu Ile Ala Gly Lys Gly Lys Ala Ile Leu Ser Leu Tyr Val
        195                 200                 205

Val Asp Phe Thr Phe Cys Val Ala Val Val Ser Val Ser Tyr Ile Met
    210                 215                 220

Ile Ala Gln Thr Leu Arg Lys Asn Ala Gln Val Arg Lys Cys Pro Pro
225                 230                 235                 240
```

-continued

```
Val Ile Thr Val Asp Ala Ser Arg Pro Gln Pro Phe Met Gly Val Pro
             245                 250                 255

Val Gln Gly Gly Gly Asp Pro Ile Gln Cys Ala Met Pro Ala Leu Tyr
             260                 265                 270

Arg Asn Gln Asn Tyr Asn Lys Leu Gln His Val Gln Thr Arg Gly Tyr
             275                 280                 285

Thr Lys Ser Pro Asn Gln Leu Val Thr Pro Ala Ala Ser Arg Leu Gln
             290                 295                 300

Leu Val Ser Ala Ile Asn Leu Ser Thr Ala Lys Asp Ser Lys Ala Val
305                 310                 315                 320

Val Thr Cys Val Ile Ile Val Leu Ser Val Leu Val Cys Cys Leu Pro
             325                 330                 335

Leu Gly Ile Ser Leu Val Gln Val Val Leu Ser Ser Asn Gly Ser Phe
             340                 345                 350

Ile Leu Tyr Gln Phe Glu Leu Phe Gly Phe Thr Leu Ile Phe Phe Lys
             355                 360                 365

Ser Gly Leu Asn Pro Phe Ile Tyr Ser Arg Asn Ser Ala Gly Leu Arg
             370                 375                 380

Arg Lys Val Leu Trp Cys Leu Gln Tyr Ile Gly Leu Gly Phe Phe Cys
385                 390                 395                 400

Cys Lys Gln Lys Thr Arg Leu Arg Ala Met Gly Lys Gly Asn Leu Glu
             405                 410                 415

Val Asn Arg Asn Lys Ser Ser His His Glu Thr Asn Ser Ala Tyr Met
             420                 425                 430

Leu Ser Pro Lys Pro Gln Lys Lys Phe Val Asp Gln Ala Cys Gly Pro
             435                 440                 445

Ser His Ser Lys Glu Ser Met Val Ser Pro Lys Ile Ser Ala Gly His
             450                 455                 460

Gln His Cys Gly Gln Ser Ser Ser Thr Pro Ile Asn Thr Arg Ile Glu
465                 470                 475                 480

Pro Tyr Tyr Ser Ile Tyr Asn Ser Ser Pro Ser Gln Glu Glu Ser Ser
             485                 490                 495

Pro Cys Asn Leu Gln Pro Val Asn Ser Phe Gly Phe Ala Asn Ser Tyr
             500                 505                 510

Ile Ala Met His Tyr His Thr Thr Asn Asp Leu Val Gln Glu Tyr Asp
             515                 520                 525

Ser Thr Ser Ala Lys Gln Ile Pro Val Pro Ser Val
             530                 535                 540
```

```
<210> SEQ ID NO 58
<211> LENGTH: 233
<212> TYPE: PRT
<213> ORGANISM: homo sapien

<400> SEQUENCE: 58
```

```
Met Asn Ser Thr Gly His Leu Gln Asp Ala Pro Asn Ala Thr Ser Leu
1                 5                 10                  15

His Val Pro His Ser Gln Glu Gly Asn Ser Thr Ser Leu Gln Glu Gly
             20                  25                  30

Leu Gln Asp Leu Ile His Thr Ala Thr Leu Val Thr Cys Thr Phe Leu
             35                  40                  45

Leu Ala Val Ile Phe Cys Leu Gly Ser Tyr Gly Asn Phe Ile Val Phe
             50                  55                  60

Leu Ser Phe Phe Asp Pro Ala Phe Arg Lys Phe Arg Thr Asn Phe Asp
```

-continued

```
65                    70                   75                   80

Phe Met Ile Leu Asn Leu Ser Phe Cys Asp Leu Phe Ile Cys Gly Val
                85                   90                   95

Thr Ala Pro Met Phe Thr Phe Val Leu Phe Phe Ser Ser Ala Ser Ser
            100                 105                 110

Ile Pro Asp Ala Phe Cys Phe Thr Phe His Leu Thr Ser Ser Gly Phe
            115                 120                 125

Ile Ile Met Ser Leu Lys Thr Val Ala Val Ile Ala Leu His Arg Leu
        130                 135                 140

Arg Met Val Leu Gly Lys Gln Pro Asn Arg Thr Ala Ser Phe Pro Cys
145                 150                 155                 160

Thr Val Leu Leu Thr Leu Leu Leu Trp Ala Thr Ser Phe Thr Leu Ala
                165                 170                 175

Thr Leu Ala Thr Leu Lys Thr Ser Lys Ser His Leu Cys Leu Pro Met
            180                 185                 190

Ser Ser Leu Ile Ala Gly Lys Gly Lys Ala Ile Leu Ser Leu Tyr Val
            195                 200                 205

Val Asp Phe Thr Phe Cys Val Ala Val Val Ser Val Ser Tyr Ile Met
        210                 215                 220

Ile Ala Gln Thr Leu Arg Lys Asn Ala
225                 230

<210> SEQ ID NO 59
<211> LENGTH: 239
<212> TYPE: PRT
<213> ORGANISM: homo sapien

<400> SEQUENCE: 59

Met Asn Ser Thr Gly His Leu Gln Asp Ala Pro Asn Ala Thr Ser Leu
1               5                   10                  15

His Val Pro His Ser Gln Glu Gly Asn Ser Thr Ser Leu Gln Glu Gly
            20                  25                  30

Leu Gln Asp Leu Ile His Thr Ala Thr Leu Val Thr Cys Thr Phe Leu
        35                  40                  45

Leu Ala Val Ile Phe Cys Leu Gly Ser Tyr Gly Asn Phe Ile Val Phe
    50                  55                  60

Leu Ser Phe Phe Asp Pro Ala Phe Arg Lys Phe Arg Thr Asn Phe Asp
65                  70                  75                  80

Phe Met Ile Leu Asn Leu Ser Phe Cys Asp Leu Phe Ile Cys Gly Val
                85                   90                   95

Thr Ala Pro Met Phe Thr Phe Val Leu Phe Phe Ser Ser Ala Ser Ser
            100                 105                 110

Ile Pro Asp Ala Phe Cys Phe Thr Phe His Leu Thr Ser Ser Gly Phe
            115                 120                 125

Ile Ile Met Ser Leu Lys Thr Val Ala Val Ile Ala Leu His Arg Leu
        130                 135                 140

Arg Met Val Leu Gly Lys Gln Pro Asn Arg Thr Ala Ser Phe Pro Cys
145                 150                 155                 160

Thr Val Leu Leu Thr Leu Leu Leu Trp Ala Thr Ser Phe Thr Leu Ala
                165                 170                 175

Thr Leu Ala Thr Leu Lys Thr Ser Lys Ser His Leu Cys Leu Pro Met
            180                 185                 190

Ser Ser Leu Ile Ala Gly Lys Gly Lys Ala Ile Leu Ser Leu Tyr Val
            195                 200                 205
```

-continued

```
Val Asp Phe Thr Phe Cys Val Ala Val Val Ser Val Ser Tyr Ile Met
    210                 215                 220

Ile Ala Gln Thr Leu Arg Lys Asn Ala Gln Val Ser Ala Pro Leu
225                 230                 235

<210> SEQ ID NO 60
<211> LENGTH: 425
<212> TYPE: PRT
<213> ORGANISM: homo sapien

<400> SEQUENCE: 60

Met Asn Ser Thr Gly His Leu Gln Asp Ala Pro Asn Ala Thr Ser Leu
1               5                   10                  15

His Val Pro His Ser Gln Glu Gly Asn Ser Thr Ser Leu Gln Glu Gly
                20                  25                  30

Leu Gln Asp Leu Ile His Thr Ala Thr Leu Val Thr Cys Thr Phe Leu
            35                  40                  45

Leu Ala Val Ile Phe Cys Leu Gly Ser Tyr Gly Asn Phe Ile Val Phe
        50                  55                  60

Leu Ser Phe Phe Asp Pro Ala Phe Arg Lys Phe Arg Thr Asn Phe Asp
65                  70                  75                  80

Phe Met Ile Leu Asn Leu Ser Phe Cys Asp Leu Phe Ile Cys Gly Val
                85                  90                  95

Thr Ala Pro Met Phe Thr Phe Val Leu Phe Phe Ser Ser Ala Ser Ser
                100                 105                 110

Ile Pro Asp Ala Phe Cys Phe Thr Phe His Leu Thr Ser Ser Gly Phe
            115                 120                 125

Ile Ile Met Ser Leu Lys Thr Val Ala Val Ile Ala Leu His Arg Leu
    130                 135                 140

Arg Met Val Leu Gly Lys Gln Pro Asn Arg Thr Ala Ser Phe Pro Cys
145                 150                 155                 160

Thr Val Leu Leu Thr Leu Leu Leu Trp Ala Thr Ser Phe Thr Leu Ala
                165                 170                 175

Thr Leu Ala Thr Leu Lys Thr Ser Lys Ser His Leu Cys Leu Pro Met
            180                 185                 190

Ser Ser Leu Ile Ala Gly Lys Gly Lys Ala Ile Leu Ser Leu Tyr Val
        195                 200                 205

Val Asp Phe Thr Phe Cys Val Ala Val Val Ser Val Ser Tyr Ile Met
    210                 215                 220

Ile Ala Gln Thr Leu Arg Lys Asn Ala Gln Val Arg Lys Cys Pro Pro
225                 230                 235                 240

Val Ile Thr Val Asp Ala Ser Arg Pro Gln Pro Phe Met Gly Val Pro
                245                 250                 255

Val Gln Gly Gly Gly Asp Pro Ile Gln Cys Ala Met Pro Ala Leu Tyr
                260                 265                 270

Arg Asn Gln Asn Tyr Asn Lys Leu Gln His Val Gln Thr Arg Gly Tyr
                275                 280                 285

Thr Lys Ser Pro Asn Gln Leu Val Thr Pro Ala Ala Ser Arg Leu Gln
    290                 295                 300

Leu Val Ser Ala Ile Asn Leu Ser Thr Ala Lys Asp Ser Lys Ala Val
305                 310                 315                 320

Val Thr Cys Val Ile Ile Val Leu Ser Val Leu Val Cys Cys Leu Pro
                325                 330                 335

Leu Gly Ile Ser Leu Val Gln Val Val Leu Ser Ser Asn Gly Ser Phe
            340                 345                 350
```

-continued

```
Ile Leu Tyr Gln Phe Glu Leu Phe Gly Phe Thr Leu Ile Phe Phe Lys
        355                 360                 365

Ser Gly Leu Asn Pro Phe Ile Tyr Ser Arg Asn Ser Ala Gly Leu Arg
    370                 375                 380

Arg Lys Val Leu Trp Cys Leu Gln Tyr Ile Gly Leu Gly Phe Phe Cys
385                 390                 395                 400

Leu Gln Thr Lys Asp Ser Thr Ser Ser His Gly Lys Arg Glu Pro Arg
                405                 410                 415

Ser Gln Gln Lys Gln Ile Leu Pro Ser
            420                 425
```

<210> SEQ ID NO 61
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 61
acaccatccg gagccggtgc agg                                                                23

<210> SEQ ID NO 62
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 62
gaaagcatcc gggatactac tgg                                                                23

<210> SEQ ID NO 63
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 63
tgatcgccct gcaccggctc cgg                                                                23

<210> SEQ ID NO 64
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 64
gcaccggctc cggatggtgt tgg                                                                23

<210> SEQ ID NO 65
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 65
accggctccg gatggtgttg ggg                                                                23

<210> SEQ ID NO 66
<211> LENGTH: 23

-continued

<212> TYPE: DNA
<213> ORGANISM: artificial sequence
<220> FEATURE:
<223> OTHER INFORMATION: gRNA Recognition Sequence

<400> SEQUENCE: 66
caccggctcc ggatggtgtt ggg                                                    23

<210> SEQ ID NO 67
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 67
ggaaaggagg ccgtgcgatt agg                                                    23

<210> SEQ ID NO 68
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 68
ggggaaacag cctaatcgca cgg                                                    23

<210> SEQ ID NO 69
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 69
caccatccgg agccggtgca ggg                                                    23

<210> SEQ ID NO 70
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 70
tggcagtgat cgccctgcac cgg                                                    23

<210> SEQ ID NO 71
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 71
catgatgatg aagcctgaac tgg                                                    23

<210> SEQ ID NO 72
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 72

-continued cgccctgcac cggctccgga tgg                                                            23

<210> SEQ ID NO 73
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 73
tccccaacac catccggagc cgg                                                            23

<210> SEQ ID NO 74
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 74
ctgtcactcc acaaatgaag agg                                                            23

<210> SEQ ID NO 75
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 75
gacttgagcg ttcttccgca ggg                                                            23

<210> SEQ ID NO 76
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 76
gcatcgactg tgattacagg ggg                                                            23

<210> SEQ ID NO 77
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 77
gccggcatgg cacactggat ggg                                                            23

<210> SEQ ID NO 78
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 78
gaagcatcga ctgtgattac agg                                                            23

<210> SEQ ID NO 79
<211> LENGTH: 23
<212> TYPE: DNA
<213> ORGANISM: artificial sequence -continued

```
<220> FEATURE:
<223> OTHER INFORMATION: gRNA Recognition Sequence

<400> SEQUENCE: 79
agcatcgact gtgattacag ggg                                              23

<210> SEQ ID NO 80
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 80
tgacttgagc gttcttccgc agg                                              23

<210> SEQ ID NO 81
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 81
tcatgattgc tcagaccctg cgg                                              23

<210> SEQ ID NO 82
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 82
catcgactgt gattacaggg ggg                                              23

<210> SEQ ID NO 83
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 83
aagcatcgac tgtgattaca ggg                                              23

<210> SEQ ID NO 84
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 84
tccagaccac agcctttcat ggg                                              23

<210> SEQ ID NO 85
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 85
cccatgtcca gtctgattgc tgg                                              23
```

-continued

```
<210> SEQ ID NO 86
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 86
acagagccgg catggcacac tgg                                                 23

<210> SEQ ID NO 87
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 87
cagaccacag cctttcatgg ggg                                                 23

<210> SEQ ID NO 88
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 88
ttcatggggg tccctgtgca ggg                                                 23

<210> SEQ ID NO 89
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 89
aagactcgac ttcgagccat ggg                                                 23

<210> SEQ ID NO 90
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 90
aaagactcga cttcgagcca tgg                                                 23

<210> SEQ ID NO 91
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 91
cgacttcgag ccatgggaaa agg                                                 23

<210> SEQ ID NO 92
<211> LENGTH: 23
<212> TYPE: DNA
<213> ORGANISM: artificial sequence
<220> FEATURE:
<223> OTHER INFORMATION: gRNA Recognition Sequence
```

-continued

<400> SEQUENCE: 92
tatattctcg gaacagtgca ggg                                                23

<210> SEQ ID NO 93
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 93
ctctggtgcc tccaatacat agg                                                23

<210> SEQ ID NO 94
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 94
atatattctc ggaacagtgc agg                                                23

<210> SEQ ID NO 95
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 95
tgcctccaat acataggcct ggg                                                23

<210> SEQ ID NO 96
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 96
aacccaggcc tatgtattgg agg                                                23

<210> SEQ ID NO 97
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 97
aaaaacccag gcctatgtat tgg                                                23

<210> SEQ ID NO 98
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 98
ttcgaggttc ccttttccca tgg                                                23

<210> SEQ ID NO 99

```
<211> LENGTH: 7056
<212> TYPE: DNA
<213> ORGANISM: homo sapien

<400> SEQUENCE: 99
gtcttgccgc ggctcccggg atgcgcggag gcggtggcga tggcgatgat gcctctagtc      60
ctgcatcatc cagagcggca ggcggagctg gggtccggac tgcgagatgg aggaggggcg     120
gcgctgcggc cacccggcag gtgagaggcc gcgggcccct ggaggaggac aaccccacga     180
tgccggagac ggctcccgga ggctggcggg atagcgagga gcgcggctgc gctgggccag     240
gcccggctcc gcgtacctgt cttcctggtg cggcctgcag ggtagccttc tcgcccgtcc     300
ctgccggttc ccaggctctg ctcggccgtg gaacccccc cacccaccca cccaccgccc     360
ctaccctggc tgagccctcc taacccacca ccctctgcg gcattctttt gcaagcttac     420
ctggcccggc ctaggccctc cttaccgtca cctcacccctt ctccgggaag ccctaccca     480 ccgccagccc ctcacggggg ggtcgacctt ccctgcccgc agtttcccac tctgtcctca     540
ggctgggggc tccctggcct cttcatccct cccatcaaat gactcaggtc ttcccatccc     600
attagctgct ccgggttcaa tgtagttcta ctggatagaa agagcaaggg ctttgaaatc     660
agataatgac cttggggaag ttatctaacc tccctgaggt tttcctgatc gatagaaata     720
caatgggaat cacaataata cagaaccttg ctctctgtga ggattaggct ttgaaaatgc     780
taacctaaga cattttgggg cgcgcgggga atggggttgg aagaattcag gtcgtgagtt     840
gatttatgaa agccctata gcatgtttta atgttcacta aaaatttaaa acagcacact     900
agatatatca gaggctgttc acatatctta atgaaaaatc attgccactc aaattataca     960
ataaattttc atccatattc tttgcttgct agttacttca ggatgtctca tttgtaagaa    1020
tatgcatgtg aattcattct tactgcagct aatatgcatg cttaagactg gtgttccagc    1080
ttaaaatctt tctgattttg tgactttaat cacatcttct ataacctatt ctccgtccca    1140
gagatgaaga gtagcttgta tgtttgcatt gcaaataaca tgggtaatct ttattgaata    1200
tttatgagta gcaaagcagt attaatttat tccccttcca aaaccacttt tattttctgc    1260
cgtcatcatg tcattccaaa ttatggtcac agcctccttt ttcttaaagt ctcaggagtt    1320
actactaaga cctgagttta ctttccctcc attttcttga tttctgttat actaaagttt    1380
ttctgcaaac ctttttcgtct tttctgtcct ctgcttttc tcccttttct cttcccagcc    1440
catgattcct tttttttctaa ttatctcaat aggagtgatt tatgattact ttatatgtga    1500
actacagtta gatacataga agaatgtgtg tgtgtgtgtg tgtgtgtgtg tgtgtgtgtg    1560
tgtgtctatc tgtatctaca tagatgtaga tatagctata taggtgtatc agaatttcgg    1620
attccagaaa gtttcagtgg ggaagggatt gcaataccta ttcataggat tattgtgaga    1680
atgaaataaa gcttgataat ttatgtaaag cctctagaat aggtgcctgg tgtgtaataa    1740
ccacttaata cttctgacct ggggatgcct cccaaaaagg ttttttttgtt gttcgggtta    1800 gcatggtggt gaagagtgtg gaagagcaac tgcttagatt caaatccatg ttccaccact    1860
ttagataacc tctctttgac ttggtttcct catctgcaaa atggagatgt tatatcaagt    1920
atttcagggt tgttatgagg actcaataag ctaatagtgt ggaacattga gaaaagtacc    1980
tggcacatca taagcacttg ataaaattaa tatactaata atgatgctga taattatact    2040
gccattgtta tttcctgacc tggaattctt attttttta atttactgaa ggctgggtac    2100
agtggctcac acctgtaatc tcagcacttt gggaggccaa agcaggcaga ttgcttgagc    2160
ccagaagttg gagaccagtg agggcaacat agtgagactc catctctatt aaaaatatat    2220
```

-continued

```
atattgaaaa atttaaaatt tgttgaaaaa atgtaactgt acaaaacgtg aaagttgcct    2280
ctcctctacc ccaaatcacc tttttttcctc ctgcctccta ttcttgacta atgttagtgc    2340
ttcatcatct cattttttctc ctaatccctt tttccaaata tctcttagcc tgaggtcttc    2400
ataacttcca tcatcccgct tcattattac ctagttactt ttcatttgtc ttagcatcct    2460
aattccagac tcctcattct tctaatttcc ccaggccaaa ttcctgcatc cctcttcacc    2520
cctcttcatc tctctacctc caaagaggaa acccttggag ataaggggggt tagagacacc    2580 agtatcacct ccctgctctt cctgcctcct caaattgttt tctcttctac ttcccttttc    2640
ataaattagc tgtaatactc ctgttagcaa cttttaaaaa cagtaaaaaa ttgtctttct    2700
cggccgggcg cggtggctca cgcctgtaat cccagcactt tgggaggccg aggcgggtgg    2760
atcatgaggt caggagatcg agaccatcct ggctaacaag gtgaaacccc gtctctacta    2820
aaaatacaaa aaaaaaatta gccgggcacg gtggcgggcg cctgtagtcc cagctactcg    2880
ggaggctgag gcaggagaat ggcgtgaacc cgggaagcgg agcttgcagt gagccgagat    2940
tgcgccactg cagtccgcag tcccgcctgg gcgacagagc gagactccgt ctcaaaaaaa    3000
aaaaaaaaaa aaaaaaaaaa attgtctttc tcattatata ggtatcaaaa gtgttcagaa    3060
acaaatatac agcctttaag tggaaatttaga gctatctggt actattttta aaaaattcta    3120
accatcaaga aacaaaagtt caggattttc ttctcttatg gaacttttat ttgaaaggaa    3180
agtatagaaa agttggtctc actttccagt ggacaaattc accatatcgt cctgatctgt    3240
accatatgaa tgttaagaat atagattaag ttatctttttt ccttgattaa ggacaccagt    3300
caattatatg gatttcccag gactggtata tgtctgatag tcactggcat ggctgtatct    3360
gttgttaaat gtggagagac ttctgtattg ggtagtccat agctgctaat tggagcccca    3420
ggtaatccct gactgacctg gttcattccg ctgtacccccc ttgatctggc aactaaaggg    3480
ttaacagctg gaggcttctg ggatccagct tgagctggtg gttaagtaca ctgaacatca    3540
gccctggacc tctgcagtgc cacttattgt tcctaaaatt ctagattaag gcaaacccct    3600
tttggttgtc aagaacatag tgctgtctcc aaggaacagc ttagtcggtc ccaccagaag    3660
catctgttgg gagcaggttg ggcaccaacc cttgcaggac tttgggattt gggacaatgt    3720
agatttgtgt gagtgcacat taagtctcat tgcaaaatag aaaaaaaaaa gttaggaaaa    3780
aggagcaaga agttattctt ttaaagtaga gactgcctta ctcatcgtag cacctagcac    3840
ctggcgtaat gctggcatat ggtatgcaca taattaatat aaattgagcg aacgaatgca    3900
ggaatgggtg catgcctcct gcttcaccat caggatattc ttgttgggat aatggtaact    3960
cacatttata tagcagttta gactttacaa tgtggtgctt tgcaccttgt aaatttctaa    4020
tataattcca acatccttgg ttacttccag ttttccgtct cacatgtagt cctacacaag    4080 gttttttttcc aaaggagaat atgtagttaa ttggccaaga aattgcaagc tgggggaaaa    4140
attataaata ctgggaaata aaggattctt cataggggaac gaaacagggt ttgttaatga    4200
tttatgggaa ttatgtgaag ggccacatta tgcatcaaca ataccctcca gcctatattt    4260
caagcacatg cagtttttttg ccgcagtgct tctgctgcaa agacctaccc ccacttctct    4320
tagcctgtct gtccccactc cataccccccg accttttcatc cagctggcct gtgcttgcta    4380
aagctccctt tatcctttcc cagctccctt tccatgttgg agtaggttcc cccccttccat    4440 gctctcatag caccctgcaa ccttattagg ctgtaattat tacatagtta gattgatctc    4500
caactagatt gtcatctctt tggtggagag attacgttct tgtgtatctt cagtgcctga    4560
```

-continued

```
cacagaagtg tttctaaaag taacatctgc acacccctca aacagaatca caaggggcga   4620
ggccaagaaa tctgctctcc aagtgataac ttaaactttt taacatgctc ttcaggtgac   4680
acttaaactt gtttgaaaac ctctgtgtca taaaactaaa tattagctgg atgaatgtat   4740
ttgtatcttt ttctgtgttg gcctttgtga ggagaaatgc tgtctatgca ccaaatcaga   4800
gctgaaaaat tctagtgttt tgttaaaaaa aaaaaagaga gagagagagc tgggtttggt   4860
ggtgcatgcc tgtagtccca gctacttggg aagctaagcc aggaggactg cttgagcaca   4920
ggagttcaag tccagcctgg gcaacatggt aagaccccat tgctaataaa tgaataaatt   4980
tttctctcaa ggtgagagat actagtacta atactactac taataatgag atcactgtat   5040
gaattccttt ctgtttctac attaatccct ttctgtttct gggtgtgcat ttttgtgtgt   5100
aggcttatct gtcttgggcc tcttttgtca catattgctc atctgtgagc tgaggccctg   5160
actcactgag tattttgg gagcagaaga aggagacatt tctctccgaa aatgaactca   5220
acaggccacc ttcaggatgc ccccaatgcc acctcgctcc atgtgcctca ctcacaggaa   5280
ggaaacagca cctctctcca ggagggtctt caggatctca tccacacagc caccttggtg   5340
acctgtactt ttctactggc ggtcatcttc tgcctgggtt cctatggcaa cttcattgtc   5400
ttcttgtcct tcttcgatcc agccttcagg aaattcagaa ccaactttga tttcatgatc   5460
ctgaacctgt ccttctgtga cctcttcatt tgtggagtga cagcccccat gttcaccttt   5520
gtgttattct tcagctcagc cagtagtatc ccggatgctt tctgcttcac tttccatctc   5580
accagttcag gcttcatcat catgtctctg aagacagtgg cagtgatcgc cctgcaccgg   5640
ctccggatgg tgttggggaa acagcctaat cgcacggcct cctttccctg caccgtactc   5700
ctcaccctgc ttctctgggc caccagtttc accccttgcca ccttggctac cttgaaaacc   5760
agcaagtccc acctctgtct tcccatgtcc agtctgattg ctggaaaagg gaaagccatt   5820
ttgtctctct gtgtggtcga cttcaccttc tgtgttgctg tggtctctgt ctcttacatc   5880
atgattgctc agaccctgcg gaagaacgct caagtcagaa agtgcccccc tgtaatcaca   5940
gtcgatgctt ccagaccaca gccttttcatg ggggtccctg tgcagggagg tggagatccc   6000
atccagtgtg ccatgccggc tctgtatagg aaccagaatt acaacaaact gcagcacgtt   6060
cagacccgtg gatataccaa gagtcccaac caactggtca ccctgcagc aagccgactc   6120 cagctcgtat cagccatcaa cctctccact gccaaggatt ccaaagccgt ggtcacctgt   6180
gtgatcattg tgctgtcagt cctggtgtgc tgtcttccac tggggatttc cttggtacag   6240
gtggttctct ccagcaatgg gagcttcatt ctttaccagt ttgaattgtt tggatttact   6300
cttatatttt tcaagtcagg attaaaccct tttatatatt ctcggaacag tgcagggctg   6360
agaaggaaag tgctctggtg cctccaatac ataggcctgg gtttttctg ctgcaaacaa   6420 aagactcgac ttcgagccat gggaaaaggg aacctcgaag tcaacagaaa caaatcctcc   6480
catcatgaaa caaactctgc ctacatgtta tctccaaagc cacagaagaa atttgtggac   6540
caggcttgtg gcccaagtca ttcaaaagaa agtatggtga gtcccaagat ctctgctgga   6600
catcaacact gtggtcagag cagctcgacc cccatcaaca ctcggattga accttactac   6660
agcatctata acagcagccc ttcccaggag gagagcagcc catgtaactt acagccagta   6720
aactcttttg gatttgccaa ttcatatatt gccatgcatt atcacaccac taatgactta   6780
gtgcaggaat atgacagcac ttcagccaag cagattccag tccctccgt ttaaagtcat   6840 ggaggctata ggatcttatg taaacagttt ttgtttctga tagtaatgga ctttattcta   6900
acttgagatc agtggcggat caaaacctac aagattcaac tgaaaagttg gcagttatgg   6960
```

-continued

```
ttttctttca tctgatgtgt cagtatctgt tgatttgctt tgtagtttgt tgacatctta      7020
agatttgatg tgaaagtttt agattttta ccctgc                                7056

<210> SEQ ID NO 100
<211> LENGTH: 2054
<212> TYPE: RNA
<213> ORGANISM: homo sapien

<400> SEQUENCE: 100
gcgauggcga ugaugccucu aguccugcau cauccagagc ggcaggcgag cuggggguccg        60 gacugcgaga uggaggaggg gcgcgcugcg gcacccggca ggcuuaucug ucuugggccu       120
cuuuugucac auauugcuca ucugugagcu gaggcccuga cucacugagu auuuuugggg       180
agcagaagaa ggagacauuu cucuccgaaa augaacucaa caggccaccu ucaggaugcc       240
cccaaugcca ccucgcucca ugugccucac ucacaggaag gaaacagcac cucucuccag       300
gagggucuuc aggaucucau ccacacagcc accuuggga ccguacuuu ucuacuggcg         360 gucaucuucu gccuggguuc cuauggcaac uucauugucu ucuugccuu cuucgaucca        420 gccuucagga aauucagaac caacuuugau uucaugaucc ugaaccuguc cuucugugac        480
cucuucauuu guggagugac agcccccaug uucaccuuug uguuauucu cagcucagcc         540 aguaguaucc cggaugcuuu cugcuucacu uuccaucuca ccaguucagg cuucaucauc        600
augucucuga agacaguggc agugaucgcc cugcaccggc uccggauggu guuggggaaa       660
cagccuaauc gcacggccuc cuuucccugc accguacucc ucacccugcu ucucugggcc       720
accaguuuca cccuugccac cuuggcuacc uugaaaacca gcaaguccca ccucugucuu       780
cccaugucca gucugauugc uggaaaaggg aaagccauuu ugucucucug uguggucgac       840
uucaccuucu guguugcugu ggucucuguc ucuuacauca ugauugcuca gacccugcgg       900
aagaacgcuc aagucagaaa gugccccccu guaaucacag ucgaugcuuc cagaccacag       960
ccuuucaugg gggucccugu gcagggaggu ggagaucca uccagugugc caugccggcu       1020
cuguauagga accagaauua caacaaacug cagcacguuc agacccgugg auauaccaag      1080 aguccccaacc aacuggucac cccugcagca agccgacucc agcucguauc agccaucaac      1140
cucuccacug ccaaggauuc caaagccgug gucaccugug ugaucauugu gcugucaguc      1200 cugguggcu gucuuccacu gggggauuucc uugguacagg ugguucucuc cagcaauggg      1260
agcuucauuc uuuaccaguu ugaauuguuu ggauuuacuc uuauauuuuu caagucagga      1320
uuaaacccuu uuauauauuc ucggaacagu gcagggcuga gaaggaaagu gcucuggugc      1380
cuccaauaca uaggccuggg uuuuuucugc ugcaaacaaa agacucgacu ucgagccaug      1440
ggaaaaggga accucgaagu caacagaaac aaauccuccc aucaugaaac aaacucugcc      1500
uacauguuau cuccaaagcc acagaagaaa uuuguggacc aggcuugugg cccaagucau      1560
ucaaaagaaa guaggugag ucccaagauc ucugcuggac aucaacacug uggucagagc       1620
agcucgaccc ccaucaacac ucggauugaa ccuuacuaca gcaucuauaa cagcagcccu      1680
ucccaggagg agagcagccc auguaacuua cagccaguaa acucuuuugg auuugccaau      1740
ucauauauug ccaugcauua ucacaccacu aaugacuuug ugcaggaaua ugacagcacu      1800
ucagccaagc agauuccagu ccccuccguu uaaagucaug gaggcuauag gaucuuaugu      1860
aaacaguuuu uguuucugau aguaauggac uuuauucuaa cuugagauca guggcggauc      1920
aaaaccuaca agauucaacu gaaaaguugg caguuauggu uuucuuucau cugauguguc      1980
```

-continued

```
aguaucuguu gauuugcuuu guaguuuguu gacaucuuaa gauuugaugu gaaaguuuua    2040
gauuuuuuac ccug                                                    2054

<210> SEQ ID NO 101
<211> LENGTH: 1913
<212> TYPE: RNA
<213> ORGANISM: homo sapien

<400> SEQUENCE: 101
caggcuuacu gucuuggggcc ucuuuuguca cauauugcuc aucugugagc ugaggcccug    60
acucacugag uauuuuuggg gagcagaaga aggagacauu ucucuccgaa aaugaacuca    120
acaggccacc uucaggaugc ccccaaugcc accucgcucc augugccuca cucacaggaa    180
ggaaacagca ccucucucca ggagggucuca caggaucuca uccacacagc caccuuggug    240
accuguacuu uucuacuggc ggucaucuuc ugccuggguu ccuauggcaa cuucauuguc    300
uucuuguccu ucuucgaucc agccuucagg aaauucagaa ccaacuuuga uuucaugauc    360
cugaaccugu ccuucuguga ccucuucauu uguggaguga cagcccccau guucaccuuu    420
guguuauucu ucagcucagc caguaguauc ccggaugcuu ucugcuucac uuuccaucuc    480
accaguucag gcuucaucau caugucucug aagacagugg cagugaucgc ccugcaccgg    540
cuccggaugg uguugggaa acagccuaau cgcacggccu ccuuucccug caccguacuc    600
cucacccugc uucucugggc caccaguuuc accccugcca ccuuggcuac cuugaaaacc    660
agcaaguccc accucugucu ucccaugucc agucugauug cuggaaaagg gaaagccauu    720
uugucucucu guguggucga cuucacccuuc uguguugcug uggucucugu cucuuacauc    780
augauugcuc agacccugcg gaagaacgcu caagucagaa agugcccccc uguaaucaca    840
gucgaugcuu ccagaccaca gccuuucaug ggggucccug ugcagggagg uggagauccc    900
auccagugug ccaugccggc ucuguauagg aaccagaauu acgacaaacu gcagcacguu    960
cagacccgug gauauaccaa gagucccaac caacugguca ccccugcagc aagccgacuc    1020
cagcucguau cagccaucaa ccucuccacu gccaaggauu ccaaagccgu ggucaccugu    1080
gugaucauug ugcugucagu ccuggugugc ugucuuccac uggggauuuc cuugguacag    1140
gugguucucu ccagcaaugg gagcuucauu cuuuaccagu uugaauuguu uggauuuacu    1200
cuuauauuuu ucaagucagg auuaaaacccu uuuauauauu cucggaacag ugcagggcug    1260
agaaggaaag ugcucuggug ccuccaauac auaggccugg guuuuuucug cugcaaacaa    1320
aagacucgac uucgagccau gggaaaaggg aaccucgaag ucaacagaaa caaauccucc    1380
caucaugaaa caaacucugc cuacauguua ucuccaaagc cacagaagaa auuuguggac    1440
caggcuugug gcccaaguca uucaaaagaa aguaugggua gucccaagau cucugcggga    1500
caucaacacu guggucagag cagcucgacc cccaucaaca cucggauuga accuuacuac    1560
agcaucuaua acagcagccc uucccaggag gagagcagcc cauguaacuu acagccagua    1620
aacucuuuug gauuugccaa uucauauauu gccaugcauu aucacaccac uaaugacuua    1680
gugcaggaau augacagcac uucagccaag cagauuccag uccccuccgu uuaaaagucau    1740 ggaggcuaua ggaucuuaug uaaacaguuu uuguuucuga uaguaauggg cuuuauucua    1800
acuugagauc agugugcggau caaaaccuac aagauucaac ugaaaaguug gcaguuaugg    1860
uuuucuuuca ucugaugugu caguaucugu ugauuugcuu uguaguuugu uga    1913

<210> SEQ ID NO 102
<211> LENGTH: 1741
```

```
<212> TYPE: RNA
<213> ORGANISM: homo sapien

<400> SEQUENCE: 102
ggagcagaag aaggagacau uucucuccga aaaugaacuc aacaggccac cuucaggaug        60
cccccaaugc caccucgcuc caugugccuc acucacagga aggaaacagc accucucucc       120
aggagggucu ucaggaucuc auccacacag ccaccuuggu gaccuguacu uuucuacugg       180
cggucaucuu cugccugggu uccuauggca acuucauugu cuucuugucc uucuucgauc       240
cagccuucag gaaauucaga accaacuuug auuucaugau ccugaaccug uccuucugug       300
accucuucau uuguggagug acagccccca uguucaccuu uguguuauuc uucagcucag       360
ccaguaguau cccggaugcu uucugcuuca cuuuccaucu caccaguuca ggcuucauca       420
ucaugucucu gaagacagug gcagugaucg cccugcaccg gcuccggaug uguuggggga       480
aacagccuaa ucgcacggcc uccuuucccu gcaccguacu ccucacccug cuucucuggg       540
ccaccaguuu cacccuugcc accuuggcua ccuugaaaac cagcaagucc caccucuguc       600
uucccauguc cagucugauu gcuggaaaag ggaaagccau uuugucucuc ugugugggucg       660 acuucaccuu cuguguugcu guggucucug ucucuuacau caugauugcu cagacccugc       720
ggaagaacgc ucaagucaga aagugcccccc cguaaucac agucgaugcu uccagaccac       780
agccuuucau gggggucccu gugcaggag gucgagaucc cauccagugu gccaugccgg       840
cucuguauag gaaccagaau uacaacaaac ugcagcacgu ucagacccgu ggauauacca       900
agagucccaa ccaacugguc accccugcag caagccgacu ccagcucgua ucagccauca       960
accucuccac ugccaaggau uccaaagccg uggucaccug ugugaucauu gugcugucag      1020
uccuggugug cugucuucca cuggggauuu ccuugguaca ggugguucuc uccagcaaug      1080
ggagcuucau ucuuuaccag uuugaauugu uuggauuuac ucuuauauuu uucaagucag      1140
gauuaaaccc uuuuauauau ucucggaaca gugcagggcu gagaaggaaa gugcucuggu      1200
gccuccaaua cauaggccug gguuuuuucu gcugcaaaca aaagacucga cuucgagcca      1260
ugggaaaagg gaaccucgaa gucaacagaa acaaauccuc ccaucaugaa acaaacucug      1320
ccuacauguu aucuccaaag ccacagaaga aauuugugga ccaggcuugu ggcccaaguc      1380
auucaaaaga aaguauggug agucccaaga ucucugcugg acaucaacac uguggucaga      1440
gcagcucgac ccccaucaac acucggauug aaccuuacua cagcaucuau aacagcagcc      1500
cuucccagga ggagagcagc ccauguaacu uacagccagu aaacucuuuu ggauuugcca      1560
auucauauau ugccaugcau uaucacacca cuaaugacuu agugcaggaa uaugacagca      1620
cuucagccaa gcagauucca guccccuccg uuuaaagucaa uggaggcuau aggaucuuau      1680
guaaacaguu uuuguuucug auaguaaugg acuuuauucu aacuugagau agugccggau      1740
c                                                                      1741

<210> SEQ ID NO 103
<211> LENGTH: 1894
<212> TYPE: RNA
<213> ORGANISM: homo sapien

<400> SEQUENCE: 103
gugacugcgc cucugcgccc gcgucuugcc gcggcucccg ggaugcgcgg aggcgguggc        60
gauggcgaug augccucuag uccugcauca uccagagcgg caggcggagc uggggucogg       120 acugcgagau ggaggagggg cggcgcugcg gccacccggc aggcuuaucu gucuugggcc       180
```

-continued

| | | | | | |
|---|---|---|---|---|---|
| ucuuuuguca | cauauugcuc | aucugugagc | ugaggcccug | acucacugag | uauuuuuggg | 240 |
| gagcagaaga | aggagacauu | ucucuccgaa | aaugaacuca | acaggccacc | uucaggaugc | 300 |
| ccccaaugcc | accucgcucc | augugccuca | cucacaggaa | ggaaacagca | ccucucucca | 360 |
| ggagggucuu | caggaucuca | uccacacagc | caccuuggug | accuguacuu | uucuacuggc | 420 |
| ggucaucuuc | ugccuggguu | ccuauggcaa | cuucauuguc | uucuuguccu | ucuucgaucc | 480 |
| agccuucagg | aaauucagaa | ccaacuuuga | uuucaugauc | cugaaccugu | ccuucuguga | 540 |
| ccucuucauu | uguggaguga | cagcccccau | guucaccuuu | guguuauucu | ucagcucagc | 600 |
| caguaguauc | ccggaugcuu | ucugcuucac | uuuccaucuc | accaguucag | gcuucaucau | 660 |
| caugucucug | aagacagugg | cagugaucgc | ccugcaccgg | cuccggaugg | uguuggggaa | 720 |
| acagccuaau | cgcacggccu | ccuuucccug | caccguacuc | cucacccugc | uucucugggc | 780 |
| caccaguuuc | acccuugcca | ccuuggcuac | cuugaaaacc | agcaaguccc | accucugucu | 840 |
| ucccaugucc | agucugauug | cuggaaaagg | gaaagccauu | uugucucucu | guguggucga | 900 |
| cuucaccuuc | uguguugcug | uggucucugu | cucuuacauc | augauugcuc | agacccugcg | 960 |
| gaagaacgcu | caagucagaa | agugcccccc | uguaaucaca | gucgaugcuu | ccagaccaca | 1020 |
| gccuuucaug | gggguccccug | ugcagggagg | uggagaucc | auccagugug | ccaugccggc | 1080 |
| ucuguauagg | aaccagaauu | acaacaaacu | gcagcacguu | cagacccgug | gauauaccaa | 1140 |
| gagucccaac | caacugguca | ccccugcagc | aagccgacuc | cagcucguau | cagccaucaa | 1200 |
| ccucuccacu | gccaaggauu | ccaaagccgu | ggucaccugu | gugaucauug | ugcugucagu | 1260 |
| ccuggugugc | ugucuuccac | uggggauuuc | cuugguacag | gugguucucu | ccagcaaugg | 1320 |
| gagcuucauu | cuuuaccagu | uugaauuguu | uggauuuacu | cuuauauuuu | ucaagucagg | 1380 |
| auuaaacccu | uuuauauauu | cucggaacag | ugcagggcug | agaaggaaag | ugcucuggug | 1440 |
| ccuccaauac | auaggccugg | guuuuuucug | cugcaaacaa | aagacucgac | uucgagccau | 1500 |
| gggaaaaggg | aaccucgaag | ucaacagaaa | caaauccucc | caucaugaaa | caaacucugc | 1560 |
| cuacauguua | ucuccaaagc | cacagaagaa | auuuguggac | caggcuugug | gcccaaguca | 1620 |
| uucaaaagaa | aguaugguga | gucccaagau | cucugcugga | caucaacacu | guggucagag | 1680 |
| cagcucgacc | cccaucaaca | cucggauuga | accuuacuac | agcaucuaua | acagcagccc | 1740 |
| uucccaggag | gagagcagcc | cauguaacuu | acagccagua | aacucuuuug | gauuugccaa | 1800 |
| uucauauauu | gccaugcauu | aucacaccac | uaaugacuua | gugcaggaau | augacagcac | 1860 |
| uucagccaag | cagauuccag | uccccuccgu | uuaa | | | 1894 |

<210> SEQ ID NO 104
<211> LENGTH: 2054
<212> TYPE: DNA
<213> ORGANISM: homo sapien

<400> SEQUENCE: 104

| | | | | | |
|---|---|---|---|---|---|
| gcgatggcga | tgatgcctct | agtcctgcat | catccagagc | ggcaggcgag | ctggggtccg | 60 |
| gactgcgaga | tggaggaggg | gcgcgctgcg | gcacccggca | ggcttatctg | tcttgggcct | 120 |
| cttttgtcac | atattgctca | tctgtgagct | gaggccctga | ctcactgagt | atttttgggg | 180 |
| agcagaagaa | ggagacattt | ctctccgaaa | atgaactcaa | caggccacct | tcaggatgcc | 240 |
| cccaatgcca | cctcgctcca | tgtgcctcac | tcacaggaag | gaaacagcac | ctctctccag | 300 |
| gagggtcttc | aggatctcat | ccacacagcc | accttggtga | cctgtacttt | ctactggcg | 360 |
| gtcatcttct | gcctgggttc | ctatggcaac | ttcattgtct | tcttgtcctt | cttcgatcca | 420 |

-continued

```
gccttcagga aattcagaac caactttgat ttcatgatcc tgaacctgtc cttctgtgac     480
ctcttcattt gtggagtgac agcccccatg ttcacctttg tgttattctt cagctcagcc     540
agtagtatcc cggatgcttt ctgcttcact ttccatctca ccagttcagg cttcatcatc     600
atgtctctga agacagtggc agtgatcgcc ctgcaccggc tccggatggt gttggggaaa     660
cagcctaatc gcacggcctc ctttccctgc accgtactcc tcaccctgct tctctgggcc     720
accagtttca cccttgccac cttggctacc ttgaaaacca gcaagtccca cctctgtctt     780
cccatgtcca gtctgattgc tggaaaaggg aaagccattt tgtctctctg tgtggtcgac     840
ttcaccttct gtgttgctgt ggtctctgtc tcttacatca tgattgctca gaccctgcgg     900
aagaacgctc aagtcagaaa gtgccccccct gtaatcacag tcgatgcttc cagaccacag     960
cctttcatgg gggtccctgt gcagggaggt ggagatccca tccagtgtgc catgccggct    1020
ctgtatagga accagaatta caacaaactg cagcacgttc agacccgtgg atataccaag    1080
agtcccaacc aactggtcac ccctgcagca agccgactcc agctcgtatc agccatcaac    1140
ctctccactg ccaaggattc caaagccgtg gtcacctgtg tgatcattgt gctgtcagtc    1200
ctggtgtgct gtcttccact ggggatttcc ttggtacagg tggttctctc cagcaatggg    1260
agcttcattc tttaccagtt tgaattgttt ggatttactc ttatattttt caagtcagga    1320 ttaaacccctt ttatatattc tcggaacagt gcagggctga gaaggaaagt gctctggtgc    1380
ctccaataca taggcctggg ttttttctgc tgcaaacaaa agactcgact tcgagccatg    1440
ggaaaaggga acctcgaagt caacagaaac aaatcctccc atcatgaaac aaactctgcc    1500
tacatgttat ctccaaagcc acagaagaaa tttgtggacc aggcttgtgg cccaagtcat    1560
tcaaaagaaa gtatggtgag tcccaagatc tctgctggac atcaacactg tggtcagagc    1620
agctcgaccc ccatcaacac tcggattgaa ccttactaca gcatctataa cagcagccct    1680
tcccaggagg agagcagccc atgtaactta cagccagtaa actcttttgg atttgccaat    1740
tcatatattg ccatgcatta tcacaccact aatgacttag tgcaggaata tgacagcact    1800
tcagccaagc agattccagt cccctccgtt taaagtcatg gaggctatag gatcttatgt    1860
aaacagtttt tgtttctgat agtaatggac tttattctaa cttgagatca gtggcggatc    1920
aaaacctaca agattcaact gaaaagttgg cagttatggt tttctttcat ctgatgtgtc    1980
agtatctgtt gatttgcttt gtagtttgtt gacatcttaa gatttgatgt gaaagtttta    2040
gattttttac cctg                                                      2054
```

<210> SEQ ID NO 105
<211> LENGTH: 1913
<212> TYPE: DNA
<213> ORGANISM: homo sapien

<400> SEQUENCE: 105

```
caggcttact gtcttgggcc tcttttgtca catattgctc atctgtgagc tgaggccctg      60
actcactgag tattttttggg gagcagaaga aggagacatt tctctccgaa aatgaactca     120
acaggccacc ttcaggatgc ccccaatgcc acctcgctcc atgtgcctca ctcacaggaa     180
ggaaacagca cctctctcca ggagggtctt caggatctca tccacacagc caccttggtg     240
acctgtactt ttctactggc ggtcatcttc tgcctgggtt cctatggcaa cttcattgtc     300
ttcttgtcct tcttcgatcc agccttcagg aaattcagaa ccaactttga tttcatgatc     360
ctgaacctgt ccttctgtga cctcttcatt tgtggagtga cagcccccat gttcaccttt     420
```

-continued

```
gtgttattct tcagctcagc cagtagtatc ccggatgctt tctgcttcac tttccatctc      480
accagttcag gcttcatcat catgtctctg aagacagtgg cagtgatcgc cctgcaccgg      540
ctccggatgg tgttgggggaa acagcctaat cgcacggcct cctttccctg caccgtactc      600
ctcaccctgc ttctctgggc caccagtttc acccctgcca ccttggctac cttgaaaacc      660
agcaagtccc acctctgtct tcccatgtcc agtctgattg ctggaaaagg gaaagccatt      720
ttgtctctct gtgtggtcga cttcaccttc tgtgttgctg tggtctctgt ctcttacatc      780
atgattgctc agaccctgcg gaagaacgct caagtcagaa agtgccccc tgtaatcaca       840 gtcgatgctt ccagaccaca gcctttcatg ggggtccctg tgcagggagg tggagatccc      900
atccagtgtg ccatgccggc tctgtatagg aaccagaatt acgacaaact gcagcacgtt      960
cagacccgtg gatataccaa gagtcccaac caactggtca cccctgcagc aagccgactc     1020
cagctcgtat cagccatcaa cctctccact gccaaggatt ccaaagccgt ggtcacctgt     1080
gtgatcattg tgctgtcagt cctggtgtgc tgtcttccac tggggatttc cttggtacag     1140
gtggttctct ccagcaatgg gagcttcatt ctttaccagt ttgaattgtt tggatttact     1200 ctttatatttt tcaagtcagg attaaaccct tttatatatt ctcggaacag tgcagggctg     1260
agaaggaaag tgctctggtg cctccaatac ataggcctgg gttttttctg ctgcaaacaa     1320
aagactcgac ttcgagccat gggaaaaggg aacctcgaag tcaacagaaa caaatcctcc     1380
catcatgaaa caaactctgc ctacatgtta tctccaaagc cacagaagaa atttgtggac     1440
caggcttgtg gcccaagtca ttcaaaagaa agtatggtga gtcccaagat ctctgctgga     1500
catcaacact gtggtcagag cagctcgacc cccatcaaca ctcggattga accttactac     1560
agcatctata acagcagccc ttcccaggag gagagcagcc catgtaactt acagccagta     1620
aactcttttg gatttgccaa ttcatatatt gccatgcatt atcacaccac taatgactta     1680
gtgcaggaat atgacagcac ttcagccaag cagattccag tcccctccgt ttaaagtcat     1740
ggaggctata ggatcttatg taaacagttt ttgtttctga tagtaatggg ctttattcta     1800
acttgagatc agtggcggat caaaacctac aagattcaac tgaaaagttg gcagttatgg     1860
ttttctttca tctgatgtgt cagtatctgt tgatttgctt tgtagtttgt tga          1913
```

<210> SEQ ID NO 106
<211> LENGTH: 1741
<212> TYPE: DNA
<213> ORGANISM: homo sapien

<400> SEQUENCE: 106

```
ggagcagaag aaggagacat ttctctccga aaatgaactc aacaggccac cttcaggatg       60
cccccaatgc cacctcgctc catgtgcctc actcacagga aggaaacagc acctctctcc      120
aggagggtct tcaggatctc atccacacag ccaccttggt gacctgtact tttctactgg      180
cggtcatctt ctgcctgggt tcctatggca acttcattgt cttcttgtcc ttcttcgatc      240
cagccttcag gaaattcaga accaactttg atttcatgat cctgaacctg tccttctgtg      300
acctcttcat ttgtggagtg acagcccca tgttcacctt tgtgttattc ttcagctcag      360
ccagtagtat cccggatgct ttctgcttca ctttccatct caccagttca ggcttcatca      420
tcatgtctct gaagacagtg gcagtgatcg ccctgcaccg gctccggatg gtgttggggga      480 aacagcctaa tcgcacggcc tcctttccct gcaccgtact cctcaccctg cttctctggg      540
ccaccagttt caccccttgcc accttggcta ccttgaaaac cagcaagtcc cacctctgtc      600
ttcccatgtc cagtctgatt gctggaaaag ggaaagccat tttgtctctc tgtgtggtcg      660
```

-continued

```
acttcacctt ctgtgttgct gtggtctctg tctcttacat catgattgct cagaccctgc    720
ggaagaacgc tcaagtcaga aagtgccccc ctgtaatcac agtcgatgct tccagaccac    780
agcctttcat gggggtccct gtgcagggag gtggagatcc catccagtgt gccatgccgg    840
ctctgtatag gaaccagaat tacaacaaac tgcagcacgt tcagacccgt ggatatacca    900
agagtcccaa ccaactggtc acccctgcag caagccgact ccagctcgta tcagccatca    960
acctctccac tgccaaggat tccaaagccg tggtcacctg tgtgatcatt gtgctgtcag   1020
tcctggtgtg ctgtcttcca ctggggattt ccttggtaca ggtggttctc tccagcaatg   1080
ggagcttcat tctttaccag tttgaattgt ttggatttac tcttatattt ttcaagtcag   1140
gattaaaccc ttttatatat tctcggaaca gtgcagggct gagaaggaaa gtgctctggt   1200
gcctccaata cataggcctg ggttttttct gctgcaaaca aaagactcga cttcgagcca   1260
tgggaaaagg gaacctcgaa gtcaacagaa acaaatcctc ccatcatgaa acaaactctg   1320
cctacatgtt atctccaaag ccacagaaga aatttgtgga ccaggcttgt ggcccaagtc   1380
attcaaaaga aagtatggtg agtcccaaga tctctgctgg acatcaacac tgtggtcaga   1440
gcagctcgac ccccatcaac actcggattg aaccttacta cagcatctat aacagcagcc   1500
cttcccagga ggagagcagc ccatgtaact tacagccagt aaaactcttt ggatttgcca   1560
attcatatat tgccatgcat tatcacacca ctaatgactt agtgcaggaa tatgacagca   1620
cttcagccaa gcagattcca gtcccctccg tttaaagtca tggaggctat aggatcttat   1680
gtaaacagtt tttgtttctg atagtaatgg actttattct aacttgagat agtggcggat   1740
c                                                                   1741

<210> SEQ ID NO 107
<211> LENGTH: 1894
<212> TYPE: DNA
<213> ORGANISM: homo sapien

<400> SEQUENCE: 107
gtgactgcgc ctctgcgccc gcgtcttgcc gcggctcccg ggatgcgcgg aggcggtggc     60
gatggcgatg atgcctctag tcctgcatca tccagagcgg caggcggagc tggggtccgg    120
actgcgagat ggaggagggg cggcgctgcg gccacccggc aggcttatct gtcttgggcc    180
tcttttgtca catattgctc atctgtgagc tgaggccctg actcactgag tatttttggg    240
gagcagaaga aggagacatt tctctccgaa aatgaactca caggccacc ttcaggatgc     300 ccccaatgcc acctcgctcc atgtgcctca ctcacaggaa ggaaacagca cctctctcca    360
ggagggtctt caggatctca tccacacagc caccttggtg acctgtactt ttctactggc    420
ggtcatcttc tgcctgggtt cctatggcaa cttcattgtc ttcttgtcct tcttcgatcc    480
agccttcagg aaaattcagaa ccaactttga tttcatgatc ctgaacctgt ccttctgtga    540
cctcttcatt tgtggagtga cagcccccat gttcaccttt gtgttattct tcagctcagc    600
cagtagtatc ccggatgctt tctgcttcac tttccatctc accagttcag gcttcatcat    660
catgtctctg aagacagtgg cagtgatcgc cctgcaccgg ctccggatgg tgttggggaa    720
acagcctaat cgcacggcct cctttccctg caccgtactc ctcaccctgc ttctctgggc    780
caccagtttc accccttgcca ccttggctac cttgaaaacc agcaagtccc acctctgtct    840
tcccatgtcc agtctgattg ctggaaaagg gaaagccatt ttgtctctct gtgtggtcga    900
cttcaccttc tgtgttgctg tggtctctgt ctcttacatc atgattgctc agaccctgcg    960
```

```
gaagaacgct caagtcagaa agtgcccccc tgtaatcaca gtcgatgctt ccagaccaca    1020
gcctttcatg ggggtccctg tgcagggagg tggagatccc atccagtgtg ccatgccggc    1080
tctgtatagg aaccagaatt acaacaaact gcagcacgtt cagacccgtg gatataccaa    1140
gagtcccaac caactggtca cccctgcagc aagccgactc cagctcgtat cagccatcaa    1200
cctctccact gccaaggatt ccaaagccgt ggtcacctgt gtgatcattg tgctgtcagt    1260
cctggtgtgc tgtcttccac tggggatttc cttggtacag gtggttctct ccagcaatgg    1320
gagcttcatt ctttaccagt ttgaattgtt tggatttact cttatatttt tcaagtcagg    1380
attaaaccct tttatatatt ctcggaacag tgcagggctg agaaggaaag tgctctggtg    1440
cctccaatac ataggcctgg gttttttctg ctgcaaacaa aagactcgac ttcgagccat    1500
gggaaaaggg aacctcgaag tcaacagaaa caaatcctcc catcatgaaa caaactctgc    1560
ctacatgtta tctccaaagc cacagaagaa atttgtggac caggcttgtg gcccaagtca    1620
ttcaaaagaa agtatggtga gtcccaagat ctctgctgga catcaacact gtggtcagag    1680
cagctcgacc cccatcaaca ctcggattga accttactac agcatctata acagcagccc    1740
ttcccaggag gagagcagcc catgtaactt acagccagta aactcttttg gatttgccaa    1800
ttcatatatt gccatgcatt atcacaccac taatgactta gtgcaggaat atgacagcac    1860
ttcagccaag cagattccag tcccctccgt ttaa                                1894
```

```
<210> SEQ ID NO 108
<211> LENGTH: 540
<212> TYPE: PRT
<213> ORGANISM: homo sapien

<400> SEQUENCE: 108

Met Asn Ser Thr Gly His Leu Gln Asp Ala Pro Asn Ala Thr Ser Leu
1               5                   10                  15

His Val Pro His Ser Gln Glu Gly Asn Ser Thr Ser Leu Gln Glu Gly
                20                  25                  30

Leu Gln Asp Leu Ile His Thr Ala Thr Leu Val Thr Cys Thr Phe Leu
            35                  40                  45

Leu Ala Val Ile Phe Cys Leu Gly Ser Tyr Gly Asn Phe Ile Val Phe
        50                  55                  60

Leu Ser Phe Phe Asp Pro Ala Phe Arg Lys Phe Arg Thr Asn Phe Asp
65                  70                  75                  80

Phe Met Ile Leu Asn Leu Ser Phe Cys Asp Leu Phe Ile Cys Gly Val
                85                  90                  95

Thr Ala Pro Met Phe Thr Phe Val Leu Phe Phe Ser Ser Ala Ser Ser
                100                 105                 110

Ile Pro Asp Ala Phe Cys Phe Thr Phe His Leu Thr Ser Ser Gly Phe
            115                 120                 125

Ile Ile Met Ser Leu Lys Thr Val Ala Val Ile Ala Leu His Arg Leu
        130                 135                 140

Arg Met Val Leu Gly Lys Gln Pro Asn Arg Thr Ala Ser Phe Pro Cys
145                 150                 155                 160

Thr Val Leu Leu Thr Leu Leu Leu Trp Ala Thr Ser Phe Thr Leu Ala
                165                 170                 175

Thr Leu Ala Thr Leu Lys Thr Ser Lys Ser His Leu Cys Leu Pro Met
            180                 185                 190

Ser Ser Leu Ile Ala Gly Lys Gly Lys Ala Ile Leu Ser Leu Cys Val
        195                 200                 205
```

```
Val Asp Phe Thr Phe Cys Val Ala Val Val Ser Val Ser Tyr Ile Met
    210             215             220

Ile Ala Gln Thr Leu Arg Lys Asn Ala Gln Val Arg Lys Cys Pro Pro
225             230             235             240

Val Ile Thr Val Asp Ala Ser Arg Pro Gln Pro Phe Met Gly Val Pro
            245             250             255

Val Gln Gly Gly Gly Asp Pro Ile Gln Cys Ala Met Pro Ala Leu Tyr
            260             265             270

Arg Asn Gln Asn Tyr Asn Lys Leu Gln His Val Gln Thr Arg Gly Tyr
            275             280             285

Thr Lys Ser Pro Asn Gln Leu Val Thr Pro Ala Ala Ser Arg Leu Gln
    290             295             300

Leu Val Ser Ala Ile Asn Leu Ser Thr Ala Lys Asp Ser Lys Ala Val
305             310             315             320

Val Thr Cys Val Ile Ile Val Leu Ser Val Leu Val Cys Cys Leu Pro
            325             330             335

Leu Gly Ile Ser Leu Val Gln Val Val Leu Ser Ser Asn Gly Ser Phe
            340             345             350

Ile Leu Tyr Gln Phe Glu Leu Phe Gly Phe Thr Leu Ile Phe Phe Lys
            355             360             365

Ser Gly Leu Asn Pro Phe Ile Tyr Ser Arg Asn Ser Ala Gly Leu Arg
    370             375             380

Arg Lys Val Leu Trp Cys Leu Gln Tyr Ile Gly Leu Gly Phe Phe Cys
385             390             395             400

Cys Lys Gln Lys Thr Arg Leu Arg Ala Met Gly Lys Gly Asn Leu Glu
            405             410             415

Val Asn Arg Asn Lys Ser Ser His His Glu Thr Asn Ser Ala Tyr Met
            420             425             430

Leu Ser Pro Lys Pro Gln Lys Lys Phe Val Asp Gln Ala Cys Gly Pro
            435             440             445

Ser His Ser Lys Glu Ser Met Val Ser Pro Lys Ile Ser Ala Gly His
    450             455             460

Gln His Cys Gly Gln Ser Ser Ser Thr Pro Ile Asn Thr Arg Ile Glu
465             470             475             480

Pro Tyr Tyr Ser Ile Tyr Asn Ser Ser Pro Ser Gln Glu Glu Ser Ser
            485             490             495

Pro Cys Asn Leu Gln Pro Val Asn Ser Phe Gly Phe Ala Asn Ser Tyr
            500             505             510

Ile Ala Met His Tyr His Thr Thr Asn Asp Leu Val Gln Glu Tyr Asp
            515             520             525

Ser Thr Ser Ala Lys Gln Ile Pro Val Pro Ser Val
    530             535             540
```

```
<210> SEQ ID NO 109
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 109
aggcaucauc gccaucgcca                                                    20

<210> SEQ ID NO 110
<211> LENGTH: 20
```

-continued

```
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 110
agaggcauca ucgccaucgc                                               20

<210> SEQ ID NO 111
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 111
uagaggcauc aucgccaucg                                               20

<210> SEQ ID NO 112
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 112
cuagaggcau caucgccauc                                               20

<210> SEQ ID NO 113
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 113
acuagaggca ucaucgccau                                               20

<210> SEQ ID NO 114
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 114
gacuagaggc aucaucgcca                                               20

<210> SEQ ID NO 115
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 115
ggacuagagg caucaucgcc                                               20

<210> SEQ ID NO 116
<211> LENGTH: 20
<212> TYPE: RNA
```

-continued

```
<213> ORGANISM: artificial sequence
<220> FEATURE:
<223> OTHER INFORMATION: Synthetic sequence; antisense nucleic acid
      molecule

<400> SEQUENCE: 116
aggacuagag gcaucaucgc                                                   20

<210> SEQ ID NO 117
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 117
caggacuaga ggcaucaucg                                                   20

<210> SEQ ID NO 118
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 118
gcaggacuag aggcaucauc                                                   20

<210> SEQ ID NO 119
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 119
ugcaggacua gaggcaucau                                                   20

<210> SEQ ID NO 120
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 120
gaugaugcag gacuagaggc                                                   20

<210> SEQ ID NO 121
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 121
ggaugaugca ggacuagagg                                                   20

<210> SEQ ID NO 122
<211> LENGTH: 20
<212> TYPE: RNA
<213> ORGANISM: artificial sequence
```

```
<220> FEATURE:
<223> OTHER INFORMATION: Synthetic sequence; antisense nucleic acid
      molecule

<400> SEQUENCE: 122
uggaugaugc aggacuagag                                                 20

<210> SEQ ID NO 123
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 123
cuggaugaug caggacuaga                                                 20

<210> SEQ ID NO 124
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 124
ucuggaugau gcaggacuag                                                 20

<210> SEQ ID NO 125
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 125
cucuggauga ugcaggacua                                                 20

<210> SEQ ID NO 126
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 126
cgcucuggau gaugcaggac                                                 20

<210> SEQ ID NO 127
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 127
ugccgcucug gaugaugcag                                                 20

<210> SEQ ID NO 128
<211> LENGTH: 20
<212> TYPE: RNA
<213> ORGANISM: artificial sequence
<220> FEATURE:
```

-continued

```
<223> OTHER INFORMATION: Synthetic sequence; antisense nucleic acid
      molecule

<400> SEQUENCE: 128
cugccgcucu ggaugaugca                                               20

<210> SEQ ID NO 129
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 129
aagacagaua agccugccgg                                               20

<210> SEQ ID NO 130
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 130
caagacagau aagccugccg                                               20

<210> SEQ ID NO 131
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 131
ggcccaagac agauaagccu                                               20

<210> SEQ ID NO 132
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 132
gaggcccaag acagauaagc                                               20

<210> SEQ ID NO 133
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 133
ugacaaaaga ggcccaagac                                               20

<210> SEQ ID NO 134
<211> LENGTH: 20
<212> TYPE: RNA
<213> ORGANISM: artificial sequence
<220> FEATURE:
<223> OTHER INFORMATION: Synthetic sequence; antisense nucleic acid
```

-continued molecule

<400> SEQUENCE: 134
ugugacaaaa gaggcccaag                                                   20

<210> SEQ ID NO 135
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 135
augugacaaa agaggcccaa                                                   20

<210> SEQ ID NO 136
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 136
uaugugacaa aagaggccca                                                   20

<210> SEQ ID NO 137
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 137
gcaauaugug acaaaagagg                                                   20

<210> SEQ ID NO 138
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 138
acagaugagc aauaugugac                                                   20

<210> SEQ ID NO 139
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 139
uaggaaccca ggcagaagau                                                   20

<210> SEQ ID NO 140
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 140
ccauaggaac ccaggcagaa                                                   20

<210> SEQ ID NO 141
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 141
gccauaggaa cccaggcaga                                                   20

<210> SEQ ID NO 142
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 142
guugccauag gaacccaggc                                                   20

<210> SEQ ID NO 143
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 143
aguugccaua ggaacccagg                                                   20

<210> SEQ ID NO 144
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 144
gaaguugcca uaggaaccca                                                   20

<210> SEQ ID NO 145
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 145
ugaaguugcc auaggaaccc                                                   20

<210> SEQ ID NO 146
<211> LENGTH: 20
<212> TYPE: RNA
<213> ORGANISM: artificial sequence
<220> FEATURE:
<223> OTHER INFORMATION: Synthetic sequence; antisense nucleic acid
      molecule -continued

```
<400> SEQUENCE: 146
augaaguugc cauaggaacc                                                20

<210> SEQ ID NO 147
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 147
caaugaaguu gccauaggaa                                                20

<210> SEQ ID NO 148
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 148
acaaugaagu ugccauagga                                                20

<210> SEQ ID NO 149
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 149
gacaaugaag uugccauagg                                                20

<210> SEQ ID NO 150
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 150
agacaaugaa guugccauag                                                20

<210> SEQ ID NO 151
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 151
gaagacaaug aaguugccau                                                20

<210> SEQ ID NO 152
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 152
```

-continued gaucgaagaa ggacaagaag                                                        20

<210> SEQ ID NO 153
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 153
ggaucgaaga aggacaagaa                                                        20

<210> SEQ ID NO 154
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 154
uggaucgaag aaggacaaga                                                        20

<210> SEQ ID NO 155
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 155
cuggaucgaa gaaggacaag                                                        20

<210> SEQ ID NO 156
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 156
gcuggaucga agaaggacaa                                                        20

<210> SEQ ID NO 157
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 157
ggcuggaucg aagaaggaca                                                        20

<210> SEQ ID NO 158
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 158

-continued aggcuggauc gaagaaggac                                                    20

<210> SEQ ID NO 159
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 159
aaggcuggau cgaagaagga                                                    20

<210> SEQ ID NO 160
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 160
gaaggcugga ucgaagaagg                                                    20

<210> SEQ ID NO 161
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 161
ugaaggcugg aucgaagaag                                                    20

<210> SEQ ID NO 162
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 162
cugaaggcug gaucgaagaa                                                    20

<210> SEQ ID NO 163
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 163
ccugaaggcu ggaucgaaga                                                    20

<210> SEQ ID NO 164
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 164
uccugaaggc uggaucgaag                                                    20

```
<210> SEQ ID NO 165
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 165
uuccugaagg cuggaucgaa                                               20

<210> SEQ ID NO 166
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 166
uuuccugaag gcuggaucga                                               20

<210> SEQ ID NO 167
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 167
guugguucug aauuuccuga                                               20

<210> SEQ ID NO 168
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 168
acagaaggac agguucagga                                               20

<210> SEQ ID NO 169
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 169
cacagaagga cagguucagg                                               20

<210> SEQ ID NO 170
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 170
ucacagaagg acagguucag                                               20
```

-continued

```
<210> SEQ ID NO 171
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 171
gucacagaag gacagguuca                                                  20

<210> SEQ ID NO 172
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 172
gaggucacag aaggacaggu                                                  20

<210> SEQ ID NO 173
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 173
augaagaggu cacagaagga                                                  20

<210> SEQ ID NO 174
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 174
ucacuccaca aaugaagagg                                                  20

<210> SEQ ID NO 175
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 175
gucacuccac aaaugaagag                                                  20

<210> SEQ ID NO 176
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 176
gcugucacuc cacaaaugaa                                                  20
```

```
<210> SEQ ID NO 177
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 177
ggcugucacu ccacaaauga                                                        20

<210> SEQ ID NO 178
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 178
gggcugucac uccacaaaug                                                        20

<210> SEQ ID NO 179
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 179
uaacacaaag gugaacaugg                                                        20

<210> SEQ ID NO 180
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 180
gcugaagaau aacacaaagg                                                        20

<210> SEQ ID NO 181
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 181
uggcugagcu gaagaauaac                                                        20

<210> SEQ ID NO 182
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 182
guucuuccgc agggucugag                                                        20

<210> SEQ ID NO 183
```

-continued

```
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 183
cguucuuccg cagggucuga                                                  20

<210> SEQ ID NO 184
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 184
agcguucuuc cgcagggucu                                                  20

<210> SEQ ID NO 185
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 185
ugagcguucu uccgcagggu                                                  20

<210> SEQ ID NO 186
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 186
uugagcguuc uuccgcaggg                                                  20

<210> SEQ ID NO 187
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 187
cuugagcguu cuuccgcagg                                                  20

<210> SEQ ID NO 188
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 188
acuugagcgu ucuuccgcag                                                  20

<210> SEQ ID NO 189
<211> LENGTH: 20
```

-continued

```
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 189
gacuugagcg uucuuccgca                                                    20

<210> SEQ ID NO 190
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 190
ugacuugagc guucuuccgc                                                    20

<210> SEQ ID NO 191
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 191
cugacuugag cguucuuccg                                                    20

<210> SEQ ID NO 192
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 192
ucugacuuga gcguucuucc                                                    20

<210> SEQ ID NO 193
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 193
uucugacuug agcguucuuc                                                    20

<210> SEQ ID NO 194
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 194
uuucugacuu gagcguucuu                                                    20

<210> SEQ ID NO 195
<211> LENGTH: 20
<212> TYPE: RNA
```

-continued

```
<213> ORGANISM: artificial sequence
<220> FEATURE:
<223> OTHER INFORMATION: Synthetic sequence; antisense nucleic acid
      molecule

<400> SEQUENCE: 195
cuuucugacu ugagcguucu                                                   20

<210> SEQ ID NO 196
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 196
acuuucugac uugagcguuc                                                   20

<210> SEQ ID NO 197
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 197
cacuuucuga cuugagcguu                                                   20

<210> SEQ ID NO 198
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 198
gcacuuucug acuugagcgu                                                   20

<210> SEQ ID NO 199
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 199
ggcacuuucu gacuugagcg                                                   20

<210> SEQ ID NO 200
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 200
aagcaucgac ugugauuaca                                                   20

<210> SEQ ID NO 201
<211> LENGTH: 20
<212> TYPE: RNA
<213> ORGANISM: artificial sequence
```

-continued

```
<220> FEATURE:
<223> OTHER INFORMATION: Synthetic sequence; antisense nucleic acid
      molecule

<400> SEQUENCE: 201
gaagcaucga cugugauuac                                                        20

<210> SEQ ID NO 202
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 202
ggaagcaucg acugugauua                                                        20

<210> SEQ ID NO 203
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 203
uggaagcauc gacugugauu                                                        20

<210> SEQ ID NO 204
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 204
cuggaagcau cgacugugau                                                        20

<210> SEQ ID NO 205
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 205
ucuggaagca ucgacuguga                                                        20

<210> SEQ ID NO 206
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 206
gucuggaagc aucgacugug                                                        20

<210> SEQ ID NO 207
<211> LENGTH: 20
<212> TYPE: RNA
<213> ORGANISM: artificial sequence
<220> FEATURE:
```

-continued

<223> OTHER INFORMATION: Synthetic sequence; antisense nucleic acid
      molecule

<400> SEQUENCE: 207
ggucuggaag caucgacugu                                                     20

<210> SEQ ID NO 208
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 208
uggucuggaa gcaucgacug                                                     20

<210> SEQ ID NO 209
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 209
guggucugga agcaucgacu                                                     20

<210> SEQ ID NO 210
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 210
uguggucugg aagcaucgac                                                     20

<210> SEQ ID NO 211
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 211
gcuguggucu ggaagcaucg                                                     20

<210> SEQ ID NO 212
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 212
ggcugugguc uggaagcauc                                                     20

<210> SEQ ID NO 213
<211> LENGTH: 20
<212> TYPE: RNA
<213> ORGANISM: artificial sequence
<220> FEATURE:
<223> OTHER INFORMATION: Synthetic sequence; antisense nucleic acid -continued molecule

<400> SEQUENCE: 213
ccaugaaagg cuguggucug                                                    20

<210> SEQ ID NO 214
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 214
cccaugaaag gcuguggucu                                                    20

<210> SEQ ID NO 215
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 215
aucuccaccu cccugcacag                                                    20

<210> SEQ ID NO 216
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 216
gcacacugga ugggaucucc                                                    20

<210> SEQ ID NO 217
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 217
ggcacacugg augggaucuc                                                    20

<210> SEQ ID NO 218
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 218
ugguuccuau acagagccgg                                                    20

<210> SEQ ID NO 219
<211> LENGTH: 20
<212> TYPE: RNA
<213> ORGANISM: artificial sequence
<220> FEATURE:
<223> OTHER INFORMATION: Synthetic sequence; antisense nucleic acid
      molecule -continued

```
<400> SEQUENCE: 219
cugguuccua uacagagccg                                              20

<210> SEQ ID NO 220
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 220
ugggacucuu gguauaucca                                              20

<210> SEQ ID NO 221
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 221
uugggacucu ugguauaucc                                              20

<210> SEQ ID NO 222
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 222
guugggacuc uugguauauc                                              20

<210> SEQ ID NO 223
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 223
gguugggacu cuugguauau                                              20

<210> SEQ ID NO 224
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 224
ugguugggac ucuugguaua                                              20

<210> SEQ ID NO 225
<211> LENGTH: 20
<212> TYPE: RNA
<213> ORGANISM: artificial sequence
<220> FEATURE:
<223> OTHER INFORMATION: Synthetic sequence; antisense nucleic acid
      molecule
```

-continued

```
<400> SEQUENCE: 225
uugguuggga cucuugguau                                                  20

<210> SEQ ID NO 226
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 226
ucuguugacu ucgagguucc                                                  20

<210> SEQ ID NO 227
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 227
uucuguugac uucgagguuc                                                  20

<210> SEQ ID NO 228
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 228
uuucuguuga cuucgagguu                                                  20

<210> SEQ ID NO 229
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 229
guuucuguug acuucgaggu                                                  20

<210> SEQ ID NO 230
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 230
gaugggagga uuuguuucug                                                  20

<210> SEQ ID NO 231
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 231
```

-continued ugaugggagg auuuguuucu                                              20

<210> SEQ ID NO 232
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 232
caugauggga ggauuuguuu                                              20

<210> SEQ ID NO 233
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 233
cauguaggca gaguuuguuu                                              20

<210> SEQ ID NO 234
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 234
guggcuuugg agauaacaug                                              20

<210> SEQ ID NO 235
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 235
uguggcuuug gagauaacau                                              20

<210> SEQ ID NO 236
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 236
gggacucacc auacuuucuu                                              20

<210> SEQ ID NO 237
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 237

-continued guugaugucc agcagagauc                                                    20

<210> SEQ ID NO 238
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 238
uguugauguc cagcagagau                                                    20

<210> SEQ ID NO 239
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 239
aguguugaug uccagcagag                                                    20

<210> SEQ ID NO 240
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 240
caguguugau guccagcaga                                                    20

<210> SEQ ID NO 241
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 241
acaguguuga uguccagcag                                                    20

<210> SEQ ID NO 242
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 242
cacaguguug auguccagca                                                    20

<210> SEQ ID NO 243
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 243
gaccacagug uugaugucca                                                    20

```
<210> SEQ ID NO 244
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 244
ugaccacagu guugaugucc                                                    20

<210> SEQ ID NO 245
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 245
cugaccacag uguugauguc                                                    20

<210> SEQ ID NO 246
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 246
cucugaccac aguguugaug                                                    20

<210> SEQ ID NO 247
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 247
gcucugacca caguguugau                                                    20

<210> SEQ ID NO 248
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 248
ugcucugacc acaguguuga                                                    20

<210> SEQ ID NO 249
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 249
aagguucaau ccgaguguug                                                    20
```

```
<210> SEQ ID NO 250
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 250
gaguucauuu ucggagagaa                                                         20

<210> SEQ ID NO 251
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 251
ugaguucauu uucggagaga                                                         20

<210> SEQ ID NO 252
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 252
uugaguucau uuucggagag                                                         20

<210> SEQ ID NO 253
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 253
ccuguugagu ucauuuucgg                                                         20

<210> SEQ ID NO 254
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 254
gccuguugag uucauuuucg                                                         20

<210> SEQ ID NO 255
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 255
guggccuguu gaguucauuu                                                         20
```

-continued

```
<210> SEQ ID NO 256
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 256
gguggccugu ugaguucauu                                                  20

<210> SEQ ID NO 257
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 257
agguggccug uugaguucau                                                  20

<210> SEQ ID NO 258
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 258
aagguggccu guugaguuca                                                  20

<210> SEQ ID NO 259
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 259
gaagguggcc uguugaguuc                                                  20

<210> SEQ ID NO 260
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 260
cugaaggugg ccguugagu                                                   20

<210> SEQ ID NO 261
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 261
uccugaaggu ggccuguuga                                                  20

<210> SEQ ID NO 262
```

-continued

```
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 262
auccugaagg uggccuguug                                                    20

<210> SEQ ID NO 263
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 263
cauccugaag guggccuguu                                                    20

<210> SEQ ID NO 264
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 264
auggagcgag guggcauugg                                                    20

<210> SEQ ID NO 265
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 265
cauggagcga gguggcauug                                                    20

<210> SEQ ID NO 266
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 266
acauggagcg agguggcauu                                                    20

<210> SEQ ID NO 267
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 267
cacauggagc gagguggcau                                                    20

<210> SEQ ID NO 268
<211> LENGTH: 20
```

```
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 268
ugaggcacau ggagcgaggu                                                     20

<210> SEQ ID NO 269
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 269
gagugaggca cauggagcga                                                     20

<210> SEQ ID NO 270
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 270
ugagugaggc acauggagcg                                                     20

<210> SEQ ID NO 271
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 271
ccuuccugug agugaggcac                                                     20

<210> SEQ ID NO 272
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 272
uccuuccugu gagugaggca                                                     20

<210> SEQ ID NO 273
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 273
uuccuuccug ugagugaggc                                                     20

<210> SEQ ID NO 274
<211> LENGTH: 20
<212> TYPE: RNA
```

-continued

<213> ORGANISM: artificial sequence
<220> FEATURE:
<223> OTHER INFORMATION: Synthetic sequence; antisense nucleic acid
      molecule

<400> SEQUENCE: 274
ggugcuguuu ccuuccugug                                                20

<210> SEQ ID NO 275
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 275
gagagaggug cguuuccuu                                                 20

<210> SEQ ID NO 276
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 276
uggagagagg ugcuguuucc                                                20

<210> SEQ ID NO 277
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 277
ccuggagaga ggugcuguuu                                                20

<210> SEQ ID NO 278
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 278
ugaagacccu ccuggagaga                                                20

<210> SEQ ID NO 279
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 279
cugaagaccc uccuggagag                                                20

<210> SEQ ID NO 280
<211> LENGTH: 20
<212> TYPE: RNA
<213> ORGANISM: artificial sequence -continued

```
<220> FEATURE:
<223> OTHER INFORMATION: Synthetic sequence; antisense nucleic acid
      molecule

<400> SEQUENCE: 280
cuggcugagc ugaagaauaa                                                                  20

<210> SEQ ID NO 281
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 281
acuggcugag cugaagaaua                                                                  20

<210> SEQ ID NO 282
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 282
acuacuggcu gagcugaaga                                                                  20

<210> SEQ ID NO 283
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 283
uacuacuggc ugagcugaag                                                                  20

<210> SEQ ID NO 284
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 284
auacuacugg cugagcugaa                                                                  20

<210> SEQ ID NO 285
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 285
gauacuacug gcugagcuga                                                                  20

<210> SEQ ID NO 286
<211> LENGTH: 20
<212> TYPE: RNA
<213> ORGANISM: artificial sequence
<220> FEATURE:
```

-continued

<223> OTHER INFORMATION: Synthetic sequence; antisense nucleic acid
      molecule

<400> SEQUENCE: 286
ggauacuacu ggcugagcug                                                  20

<210> SEQ ID NO 287
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 287
gggauacuac uggcugagcu                                                  20

<210> SEQ ID NO 288
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 288
ccgggauacu acuggcugag                                                  20

<210> SEQ ID NO 289
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 289
uccgggauac uacuggcuga                                                  20

<210> SEQ ID NO 290
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 290
auccgggaua cuacuggcug                                                  20

<210> SEQ ID NO 291
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 291
ggugagaugg aaagugaagc                                                  20

<210> SEQ ID NO 292
<211> LENGTH: 20
<212> TYPE: RNA
<213> ORGANISM: artificial sequence
<220> FEATURE:
<223> OTHER INFORMATION: Synthetic sequence; antisense nucleic acid -continued

```
        molecule

<400> SEQUENCE: 292
acuggugaga uggaaaguga                                              20

<210> SEQ ID NO 293
<211> LENGTH: 20
<212> TYPE: RNA
<213> ORGANISM: artificial sequence
<220> FEATURE:
<223> OTHER INFORMATION: Synthetic sequence; antisense nucleic acid
        molecule

<400> SEQUENCE: 293
aacuggugag auggaaagug                                             20

<210> SEQ ID NO 294
<211> LENGTH: 20
<212> TYPE: RNA
<213> ORGANISM: artificial sequence
<220> FEATURE:
<223> OTHER INFORMATION: Synthetic sequence; antisense nucleic acid
        molecule

<400> SEQUENCE: 294
ccugaacugg ugagauggaa                                             20

<210> SEQ ID NO 295
<211> LENGTH: 20
<212> TYPE: RNA
<213> ORGANISM: artificial sequence
<220> FEATURE:
<223> OTHER INFORMATION: Synthetic sequence; antisense nucleic acid
        molecule

<400> SEQUENCE: 295
agccugaacu ggugagaugg                                             20

<210> SEQ ID NO 296
<211> LENGTH: 20
<212> TYPE: RNA
<213> ORGANISM: artificial sequence
<220> FEATURE:
<223> OTHER INFORMATION: Synthetic sequence; antisense nucleic acid
        molecule

<400> SEQUENCE: 296
gaagccugaa cuggugagau                                             20

<210> SEQ ID NO 297
<211> LENGTH: 20
<212> TYPE: RNA
<213> ORGANISM: artificial sequence
<220> FEATURE:
<223> OTHER INFORMATION: Synthetic sequence; antisense nucleic acid
        molecule

<400> SEQUENCE: 297
ugaagccuga acuggugaga                                             20

<210> SEQ ID NO 298
<211> LENGTH: 20
<212> TYPE: RNA
<213> ORGANISM: artificial sequence
<220> FEATURE:
<223> OTHER INFORMATION: Synthetic sequence; antisense nucleic acid
        molecule
```

-continued

<400> SEQUENCE: 298
ugaugaugaa gccugaacug                                                          20

<210> SEQ ID NO 299
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 299
caugaugaug aagccugaac                                                          20

<210> SEQ ID NO 300
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 300
acaugaugau gaagccugaa                                                          20

<210> SEQ ID NO 301
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 301
gacaugauga ugaagccuga                                                          20

<210> SEQ ID NO 302
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 302
gagacaugau gaugaagccu                                                          20

<210> SEQ ID NO 303
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 303
cacugccacu gucuucagag                                                          20

<210> SEQ ID NO 304
<211> LENGTH: 20
<212> TYPE: RNA
<213> ORGANISM: artificial sequence
<220> FEATURE:
<223> OTHER INFORMATION: Synthetic sequence; antisense nucleic acid
      molecule -continued

```
<400> SEQUENCE: 304
gcgaucacug ccacugucuu                                          20

<210> SEQ ID NO 305
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 305
agggcgauca cugccacugu                                          20

<210> SEQ ID NO 306
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 306
gugcgauuag gcuguuuccc                                          20

<210> SEQ ID NO 307
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 307
cgugcgauua ggcuguuucc                                          20

<210> SEQ ID NO 308
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 308
ccgugcgauu aggcuguuuc                                          20

<210> SEQ ID NO 309
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 309
gccgugcgau uaggcuguuu                                          20

<210> SEQ ID NO 310
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 310
```

-continued ggccgugcga uuaggcuguu                                          20

<210> SEQ ID NO 311
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 311
aggccgugcg auuaggcugu                                          20

<210> SEQ ID NO 312
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 312
aaggaggccg ugcgauuagg                                          20

<210> SEQ ID NO 313
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 313
aaaggaggcc gugcgauuag                                          20

<210> SEQ ID NO 314
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 314
gaaaggaggc cgugcgauua                                          20

<210> SEQ ID NO 315
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 315
ggaaaggagg ccgugcgauu                                          20

<210> SEQ ID NO 316
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 316

-continued agcaggguga ggaguacggu                                                     20

<210> SEQ ID NO 317
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 317
aagcagggug aggaguacgg                                                     20

<210> SEQ ID NO 318
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 318
cagagaagca gggugaggag                                                     20

<210> SEQ ID NO 319
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 319
agggugaaac ugguggccca                                                     20

<210> SEQ ID NO 320
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 320
aagggugaaa cugguggccc                                                     20

<210> SEQ ID NO 321
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 321
gcaaggguga aacugguggc                                                     20

<210> SEQ ID NO 322
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 322
uggcaagggu gaaacuggug                                                     20

<210> SEQ ID NO 323
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 323
uugguuggga cucuugguau                                             20

<210> SEQ ID NO 324
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 324
guugguuggg acucuuggua                                             20

<210> SEQ ID NO 325
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 325
caguugguug ggacucuugg                                             20

<210> SEQ ID NO 326
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 326
ugaccaguug guugggacuc                                             20

<210> SEQ ID NO 327
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 327
ggugaccagu ugguugggac                                             20

<210> SEQ ID NO 328
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 328
gggugaccag ugguugggga                                             20

<210> SEQ ID NO 329
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 329
uacgagcugg agucggcuug                                                        20

<210> SEQ ID NO 330
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 330
auacgagcug gagucggcuu                                                        20

<210> SEQ ID NO 331
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 331
gauacgagcu ggagucggcu                                                        20

<210> SEQ ID NO 332
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 332
ugauacgagc uggagucggc                                                        20

<210> SEQ ID NO 333
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 333
cugauacgag cuggagucgg                                                        20

<210> SEQ ID NO 334
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 334
gcugauacga gcuggagucg                                                        20

-continued

```
<210> SEQ ID NO 335
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 335
ggcugauacg agcuggaguc                                              20

<210> SEQ ID NO 336
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 336
uggcugauac gagcuggagu                                              20

<210> SEQ ID NO 337
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 337
auggcugaua cgagcuggag                                              20

<210> SEQ ID NO 338
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 338
gauggcugau acgagcugga                                              20

<210> SEQ ID NO 339
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 339
ugauggcuga uacgagcugg                                              20

<210> SEQ ID NO 340
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 340
uugauggcug auacgagcug                                              20

<210> SEQ ID NO 341
```

-continued

```
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 341
guugauggcu gauacgagcu                                                   20

<210> SEQ ID NO 342
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 342
gguugauggc ugauacgagc                                                   20

<210> SEQ ID NO 343
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 343
agguugaugg cugauacgag                                                   20

<210> SEQ ID NO 344
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 344
gagguugaug gcugauacga                                                   20

<210> SEQ ID NO 345
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 345
agagguugau ggcugauacg                                                   20

<210> SEQ ID NO 346
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 346
gagagguuga uggcugauac                                                   20

<210> SEQ ID NO 347
<211> LENGTH: 20
```

-continued

```
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 347
ggagagguug auggcugaua                                                   20

<210> SEQ ID NO 348
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 348
uggagagguu gauggcugau                                                   20

<210> SEQ ID NO 349
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 349
guggagaggu ugauggcuga                                                   20

<210> SEQ ID NO 350
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 350
uuggcagugg agagguugau                                                   20

<210> SEQ ID NO 351
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 351
ccuuggcagu ggagagguug                                                   20

<210> SEQ ID NO 352
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 352
cuuuggaauc cuuggcagug                                                   20

<210> SEQ ID NO 353
<211> LENGTH: 20
<212> TYPE: RNA
```

-continued

<213> ORGANISM: artificial sequence
<220> FEATURE:
<223> OTHER INFORMATION: Synthetic sequence; antisense nucleic acid
      molecule

<400> SEQUENCE: 353
ggacugacag cacaaugauc                                                      20

<210> SEQ ID NO 354
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 354
aggacugaca gcacaaugau                                                      20

<210> SEQ ID NO 355
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 355
caggacugac agcacaauga                                                      20

<210> SEQ ID NO 356
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 356
ccaggacuga cagcacaaug                                                      20

<210> SEQ ID NO 357
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 357
accaggacug acagcacaau                                                      20

<210> SEQ ID NO 358
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 358
caccaggacu gacagcacaa                                                      20

<210> SEQ ID NO 359
<211> LENGTH: 20
<212> TYPE: RNA
<213> ORGANISM: artificial sequence -continued

```
<220> FEATURE:
<223> OTHER INFORMATION: Synthetic sequence; antisense nucleic acid
      molecule

<400> SEQUENCE: 359
acaccaggac ugacagcaca                                                  20

<210> SEQ ID NO 360
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 360
cacaccagga cugacagcac                                                  20

<210> SEQ ID NO 361
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 361
gcacaccagg acugacagca                                                  20

<210> SEQ ID NO 362
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 362
ggaagacagc acaccaggac                                                  20

<210> SEQ ID NO 363
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 363
uggaagacag cacaccagga                                                  20

<210> SEQ ID NO 364
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 364
caccuguacc aaggaaaucc                                                  20

<210> SEQ ID NO 365
<211> LENGTH: 20
<212> TYPE: RNA
<213> ORGANISM: artificial sequence
<220> FEATURE:
```

-continued

```
<223> OTHER INFORMATION: Synthetic sequence; antisense nucleic acid
      molecule

<400> SEQUENCE: 365
agaaccaccu guaccaagga                                                20

<210> SEQ ID NO 366
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 366
uaagguucaa uccgaguguu                                                20

<210> SEQ ID NO 367
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 367
guaagguuca auccgagugu                                                20

<210> SEQ ID NO 368
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 368
aguaagguuc aauccgagug                                                20

<210> SEQ ID NO 369
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 369
uaguaagguu caauccgagu                                                20

<210> SEQ ID NO 370
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 370
guaguaaggu ucaauccgag                                                20

<210> SEQ ID NO 371
<211> LENGTH: 20
<212> TYPE: RNA
<213> ORGANISM: artificial sequence
<220> FEATURE:
<223> OTHER INFORMATION: Synthetic sequence; antisense nucleic acid
```

-continued molecule

<400> SEQUENCE: 371
uguaguaagg uucaauccga                                                                20

<210> SEQ ID NO 372
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 372
cuguaguaag guucaauccg                                                                20

<210> SEQ ID NO 373
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 373
gcuguaguaa gguucaaucc                                                                20

<210> SEQ ID NO 374
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 374
ugcuguagua agguucaauc                                                                20

<210> SEQ ID NO 375
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 375
gaugcuguag uaagguucaa                                                                20

<210> SEQ ID NO 376
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 376
agaugcugua guaagguuca                                                                20

<210> SEQ ID NO 377
<211> LENGTH: 20
<212> TYPE: RNA
<213> ORGANISM: artificial sequence
<220> FEATURE:
<223> OTHER INFORMATION: Synthetic sequence; antisense nucleic acid
      molecule -continued

<400> SEQUENCE: 377
uagaugcugu aguaagguuc                                              20

<210> SEQ ID NO 378
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 378
gcuguuauag augcuguagu                                              20

<210> SEQ ID NO 379
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 379
ugcuguuaua gaugcuguag                                              20

<210> SEQ ID NO 380
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 380
gcugcuguua uagaugcugu                                              20

<210> SEQ ID NO 381
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 381
ggcugcuguu auagaugcug                                              20

<210> SEQ ID NO 382
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 382
gggcugcugu uauagaugcu                                              20

<210> SEQ ID NO 383
<211> LENGTH: 20
<212> TYPE: RNA
<213> ORGANISM: artificial sequence
<220> FEATURE:
<223> OTHER INFORMATION: Synthetic sequence; antisense nucleic acid
      molecule -continued

```
<400> SEQUENCE: 383
aagggcugcu guuauagaug                                              20

<210> SEQ ID NO 384
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 384
ggaagggcug cguuauaga                                               20

<210> SEQ ID NO 385
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 385
uuacaugggc ugcucuccuc                                              20

<210> SEQ ID NO 386
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 386
guuacauggg cugcucuccu                                              20

<210> SEQ ID NO 387
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 387
aguuacaugg gcugcucucc                                              20

<210> SEQ ID NO 388
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 388
caaaagaguu uacuggcugu                                              20

<210> SEQ ID NO 389
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 389
```

-continued auccaaaaga guuuacuggc                                          20

<210> SEQ ID NO 390
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 390
cauauuccug cacuaaguca                                          20

<210> SEQ ID NO 391
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 391
auccugaaga cccuccugga                                          20

<210> SEQ ID NO 392
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 392
augagauccu gaagacccuc                                          20

<210> SEQ ID NO 393
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 393
gaugagaucc ugaagacccu                                          20

<210> SEQ ID NO 394
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 394
caggucacca agguggcugu                                          20

<210> SEQ ID NO 395
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 395

-continued acaggucacc aagguggcug                                                          20

<210> SEQ ID NO 396
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 396
guacagguca ccaagguggc                                                          20

<210> SEQ ID NO 397
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 397
aguacagguc accaaggugg                                                          20

<210> SEQ ID NO 398
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 398
aaguacaggu caccaaggug                                                          20

<210> SEQ ID NO 399
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 399
aaaguacagg ucaccaaggu                                                          20

<210> SEQ ID NO 400
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 400
aaaaguacag gucaccaagg                                                          20

<210> SEQ ID NO 401
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 401
gaaaaguaca ggucaccaag                                                          20

<210> SEQ ID NO 402
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 402
ccaguagaaa aguacagguc                                                  20

<210> SEQ ID NO 403
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 403
cgccaguaga aaaguacagg                                                  20

<210> SEQ ID NO 404
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 404
ccgccaguag aaaaguacag                                                  20

<210> SEQ ID NO 405
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 405
accgccagua gaaaaguaca                                                  20

<210> SEQ ID NO 406
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 406
gaccgccagu agaaaaguac                                                  20

<210> SEQ ID NO 407
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 407
ugaccgccag uagaaaagua                                                  20

<210> SEQ ID NO 408
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 408
augaccgcca guagaaaagu                                                        20

<210> SEQ ID NO 409
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 409
gaugaccgcc aguagaaaag                                                        20

<210> SEQ ID NO 410
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 410
agaugaccgc caguagaaaa                                                        20

<210> SEQ ID NO 411
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 411
aagaugaccg ccaguagaaa                                                        20

<210> SEQ ID NO 412
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 412
gaagaugacc gccaguagaa                                                        20

<210> SEQ ID NO 413
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 413
agaagaugac cgccaguaga                                                        20

-continued

```
<210> SEQ ID NO 414
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 414
cagaagauga ccgccaguag                                               20

<210> SEQ ID NO 415
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 415
gcagaagaug accgccagua                                               20

<210> SEQ ID NO 416
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 416
ggcagaagau gaccgccagu                                               20

<210> SEQ ID NO 417
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 417
aggcagaaga ugaccgccag                                               20

<210> SEQ ID NO 418
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 418
caggcagaag augaccgcca                                               20

<210> SEQ ID NO 419
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 419
acccaggcag aagaugaccg                                               20

<210> SEQ ID NO 420
```

-continued

```
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 420
aggaacccag gcagaagaug                                                           20

<210> SEQ ID NO 421
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 421
guggcaaggg ugaaacuggu                                                           20

<210> SEQ ID NO 422
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 422
gguggcaagg gugaaacugg                                                           20

<210> SEQ ID NO 423
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 423
agguggcaag ggugaaacug                                                           20

<210> SEQ ID NO 424
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 424
aagguggcaa gggugaaacu                                                           20

<210> SEQ ID NO 425
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 425
guuuucaagg uagccaaggu                                                           20

<210> SEQ ID NO 426
<211> LENGTH: 20
```

-continued

```
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 426
gguuuucaag guagccaagg                                                    20

<210> SEQ ID NO 427
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 427
ugguuuucaa gguagccaag                                                    20

<210> SEQ ID NO 428
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 428
cugguuuuca agguagccaa                                                    20

<210> SEQ ID NO 429
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 429
gugggacuug cugguuuuca                                                    20

<210> SEQ ID NO 430
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 430
cagagguggg acuugcuggu                                                    20

<210> SEQ ID NO 431
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 431
aagacagagg ugggacuugc                                                    20

<210> SEQ ID NO 432
<211> LENGTH: 20
<212> TYPE: RNA
```

<213> ORGANISM: artificial sequence
<220> FEATURE:
<223> OTHER INFORMATION: Synthetic sequence; antisense nucleic acid
      molecule

<400> SEQUENCE: 432
ggacauggga agacagaggu                                                    20

<210> SEQ ID NO 433
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 433
uggacauggg aagacagagg                                                    20

<210> SEQ ID NO 434
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 434
ucagacugga caugggaaga                                                    20

<210> SEQ ID NO 435
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 435
agcaaucaga cuggacaugg                                                    20

<210> SEQ ID NO 436
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 436
cagcaaucag acuggacaug                                                    20

<210> SEQ ID NO 437
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 437
ccuuuuccag caaucagacu                                                    20

<210> SEQ ID NO 438
<211> LENGTH: 20
<212> TYPE: RNA
<213> ORGANISM: artificial sequence -continued

```
<220> FEATURE:
<223> OTHER INFORMATION: Synthetic sequence; antisense nucleic acid
      molecule

<400> SEQUENCE: 438
ucccuuuucc agcaaucaga                                                   20

<210> SEQ ID NO 439
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 439
gcuuucccuu uuccagcaau                                                   20

<210> SEQ ID NO 440
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 440
aaauggcuuu cccuuuucca                                                   20

<210> SEQ ID NO 441
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 441
gacaaaaugg cuuucccuuu                                                   20

<210> SEQ ID NO 442
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 442
acauagagag acaaaauggc                                                   20

<210> SEQ ID NO 443
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 443
gaccacauag agagacaaaa                                                   20

<210> SEQ ID NO 444
<211> LENGTH: 20
<212> TYPE: RNA
<213> ORGANISM: artificial sequence
<220> FEATURE:
```

-continued

```
<223> OTHER INFORMATION: Synthetic sequence; antisense nucleic acid
      molecule

<400> SEQUENCE: 444
cgaccacaua gagagacaaa                                                    20

<210> SEQ ID NO 445
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 445
ucgaccacau agagagacaa                                                    20

<210> SEQ ID NO 446
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 446
caacacagaa ggugaagucg                                                    20

<210> SEQ ID NO 447
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 447
gcaacacaga aggugaaguc                                                    20

<210> SEQ ID NO 448
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 448
agaccacagc aacacagaag                                                    20

<210> SEQ ID NO 449
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 449
gagaccacag caacacagaa                                                    20

<210> SEQ ID NO 450
<211> LENGTH: 20
<212> TYPE: RNA
<213> ORGANISM: artificial sequence
<220> FEATURE:
<223> OTHER INFORMATION: Synthetic sequence; antisense nucleic acid
```

-continued

```
      molecule

<400> SEQUENCE: 450
agagaccaca gcaacacaga                                          20

<210> SEQ ID NO 451
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 451
cagagaccac agcaacacag                                          20

<210> SEQ ID NO 452
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 452
agagacagag accacagcaa                                          20

<210> SEQ ID NO 453
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 453
uaagagacag agaccacagc                                          20

<210> SEQ ID NO 454
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 454
guaagagaca gagaccacag                                          20

<210> SEQ ID NO 455
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 455
uguaagagac agagaccaca                                          20

<210> SEQ ID NO 456
<211> LENGTH: 20
<212> TYPE: RNA
<213> ORGANISM: artificial sequence
<220> FEATURE:
<223> OTHER INFORMATION: Synthetic sequence; antisense nucleic acid
      molecule
```

-continued

```
<400> SEQUENCE: 456
caugauguaa gagacagaga                                                20

<210> SEQ ID NO 457
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 457 cgcaggigucu gagcaaucau                                               20
```

```
cgcagggucu gagcaaucau                                               20

<210> SEQ ID NO 458
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 458
ccgcaggguc ugagcaauca                                               20

<210> SEQ ID NO 459
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 459
uccgcagggu cugagcaauc                                               20

<210> SEQ ID NO 460
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 460
uuccgcaggg ucugagcaau                                               20

<210> SEQ ID NO 461
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 461
cuuccgcagg gucugagcaa                                               20

<210> SEQ ID NO 462
<211> LENGTH: 20
<212> TYPE: RNA
<213> ORGANISM: artificial sequence
<220> FEATURE:
<223> OTHER INFORMATION: Synthetic sequence; antisense nucleic acid
      molecule
```

-continued

```
<400> SEQUENCE: 462
ucuuccgcag ggucugagca                                              20

<210> SEQ ID NO 463
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 463
uucuuccgca gggucugagc                                              20

<210> SEQ ID NO 464
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 464
ggagagaacc accuguacca                                              20

<210> SEQ ID NO 465
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 465
uggagagaac caccuguacc                                              20

<210> SEQ ID NO 466
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 466
cuggagagaa ccaccuguac                                              20

<210> SEQ ID NO 467
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 467
gcuggagaga accaccugua                                              20

<210> SEQ ID NO 468
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 468
```

-continued uugcuggaga gaaccaccug                                                20

<210> SEQ ID NO 469
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 469
auugcuggag agaaccaccu                                                20

<210> SEQ ID NO 470
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 470
ccauugcugg agagaaccac                                                20

<210> SEQ ID NO 471
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 471
ucccauugcu ggagagaacc                                                20

<210> SEQ ID NO 472
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 472
guaaagaaug aagcucccau                                                20

<210> SEQ ID NO 473
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 473
gguaaagaau gaagcuccca                                                20

<210> SEQ ID NO 474
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 474

-continued aggguuuaau ccugacuuga                                    20

<210> SEQ ID NO 475
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 475
aaggguuuaa uccugacuug                                    20

<210> SEQ ID NO 476
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 476
ugcacuguuc cgagaauaua                                    20

<210> SEQ ID NO 477
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 477
cugcacuguu ccgagaauau                                    20

<210> SEQ ID NO 478
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 478
ccugcacugu uccgagaaua                                    20

<210> SEQ ID NO 479
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 479
cccugcacug uuccgagaau                                    20

<210> SEQ ID NO 480
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 480
gcccugcacu guuccgagaa                                    20

-continued

```
<210> SEQ ID NO 481
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 481
agcccugcac uguuccgaga                                                  20

<210> SEQ ID NO 482
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 482
ucucagcccu gcacuguucc                                                  20

<210> SEQ ID NO 483
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 483
uucucagccc ugcacuguuc                                                  20

<210> SEQ ID NO 484
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 484
acuuuccuuc ucagcccugc                                                  20

<210> SEQ ID NO 485
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 485
gcaccagagc acuuuccuuc                                                  20

<210> SEQ ID NO 486
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 486
ggcaccagag cacuuuccuu                                                  20
```

<210> SEQ ID NO 487
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 487
aggcaccaga gcacuuuccu                                                            20

<210> SEQ ID NO 488
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 488
gaggcaccag agcacuuucc                                                            20

<210> SEQ ID NO 489
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 489
auuggaggca ccagagcacu                                                            20

<210> SEQ ID NO 490
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 490
cuauguauug gaggcaccag                                                            20

<210> SEQ ID NO 491
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 491
ccuauguauu ggaggcacca                                                            20

<210> SEQ ID NO 492
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 492
gucuuuuguu ugcagcagaa                                                            20

-continued

```
<210> SEQ ID NO 493
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 493
agucuuuugu uugcagcaga                                               20

<210> SEQ ID NO 494
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 494
ucgagucuuu uguuugcagc                                               20

<210> SEQ ID NO 495
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 495
gucgagucuu uuguuugcag                                               20

<210> SEQ ID NO 496
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 496
agucgagucu uuuguuugca                                               20

<210> SEQ ID NO 497
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 497
aagucgaguc uuuuguuugc                                               20

<210> SEQ ID NO 498
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 498
gaagucgagu cuuuuguuug                                               20

<210> SEQ ID NO 499
```

-continued

```
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 499
cgaagucgag ucuuuuguuu                                                    20

<210> SEQ ID NO 500
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 500
ucgaagucga gucuuuuguu                                                    20

<210> SEQ ID NO 501
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 501
ucgagguucc cuuuucccau                                                    20

<210> SEQ ID NO 502
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 502
uucgagguuc ccuuuuccca                                                    20

<210> SEQ ID NO 503
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 503
cuucgagguu cccuuuuccc                                                    20

<210> SEQ ID NO 504
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 504
acuucgaggu ucccuuuucc                                                    20

<210> SEQ ID NO 505
<211> LENGTH: 20
```

```
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 505
guugacuucg agguucccuu                                                  20

<210> SEQ ID NO 506
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 506
uguugacuuc gagguucccu                                                  20

<210> SEQ ID NO 507
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 507
gucauauucc ugcacuaagu                                                  20

<210> SEQ ID NO 508
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 508
ugucauauuc cugcacuaag                                                  20

<210> SEQ ID NO 509
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 509
cugucauauu ccugcacuaa                                                  20

<210> SEQ ID NO 510
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 510
gcugucauau uccugcacua                                                  20

<210> SEQ ID NO 511
<211> LENGTH: 20
<212> TYPE: RNA
```

```
<213> ORGANISM: artificial sequence
<220> FEATURE:
<223> OTHER INFORMATION: Synthetic sequence; antisense nucleic acid
      molecule

<400> SEQUENCE: 511
agugcuguca uauuccugca                                               20

<210> SEQ ID NO 512
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 512
aagugcuguc auauuccugc                                               20

<210> SEQ ID NO 513
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 513
ugaagugcug ucauauuccu                                               20

<210> SEQ ID NO 514
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 514
cugaagugcu gucauauucc                                               20

<210> SEQ ID NO 515
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 515
uggaaucugc uuggcugaag                                               20

<210> SEQ ID NO 516
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 516
acuggaaucu gcuuggcuga                                               20

<210> SEQ ID NO 517
<211> LENGTH: 20
<212> TYPE: RNA
<213> ORGANISM: artificial sequence
```

-continued

```
<220> FEATURE:
<223> OTHER INFORMATION: Synthetic sequence; antisense nucleic acid
      molecule

<400> SEQUENCE: 517
cgccacugau cucaaguuag                                               20

<210> SEQ ID NO 518
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 518
auccgccacu gaucucaagu                                               20

<210> SEQ ID NO 519
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 519
gguuuugauc cgccacugau                                               20

<210> SEQ ID NO 520
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 520
agguuuugau ccgccacuga                                               20

<210> SEQ ID NO 521
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 521
uagguuuuga uccgccacug                                               20

<210> SEQ ID NO 522
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 522
guagguuuug auccgccacu                                               20

<210> SEQ ID NO 523
<211> LENGTH: 20
<212> TYPE: RNA
<213> ORGANISM: artificial sequence
<220> FEATURE:
```

<223> OTHER INFORMATION: Synthetic sequence; antisense nucleic acid
      molecule

<400> SEQUENCE: 523
uguagguuuu gauccgccac                                                    20

<210> SEQ ID NO 524
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 524
uuguagguuu ugauccgcca                                                    20

<210> SEQ ID NO 525
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 525
cuuguagguu uugauccgcc                                                    20

<210> SEQ ID NO 526
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 526
ucuuguaggu uuugauccgc                                                    20

<210> SEQ ID NO 527
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 527
aucuuguagg uuuugauccg                                                    20

<210> SEQ ID NO 528
<211> LENGTH: 20
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 528
ccauaacugc caacuuuuca                                                    20

<210> SEQ ID NO 529
<211> LENGTH: 20
<212> TYPE: RNA
<213> ORGANISM: artificial sequence
<220> FEATURE:
<223> OTHER INFORMATION: Synthetic sequence; antisense nucleic acid

543

-continued

```
                    molecule

<400> SEQUENCE: 529
accauaacug ccaacuuuuc                                      20

<210> SEQ ID NO 530
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 530
cgguggcgau ggcgaugau                                      19

<210> SEQ ID NO 531
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 531
aucaucgcca ucgccaccg                                      19

<210> SEQ ID NO 532
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 532
gguggcgaug gcgaugaug                                      19

<210> SEQ ID NO 533
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 533
caucaucgcc aucgccacc                                      19

<210> SEQ ID NO 534
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 534
guggcgaugg cgaugaugc                                      19

<210> SEQ ID NO 535
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 535
```
gcaucaucgc caucgccac                                                                    19

<210> SEQ ID NO 536
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 536
uggcgauggc gaugaugcc                                                                    19

<210> SEQ ID NO 537
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 537
ggcaucaucg ccaucgcca                                                                    19

<210> SEQ ID NO 538
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 538
ggcgauggcg augaugccu                                                                    19

<210> SEQ ID NO 539
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 539
aggcaucauc gccaucgcc                                                                    19

<210> SEQ ID NO 540
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 540
cgaugaugcc ucuaguccu                                                                    19

<210> SEQ ID NO 541
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 541
aggacuagag gcaucaucg                                                                    19

<210> SEQ ID NO 542

-continued

```
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 542
gaugaugccu cuaguccug                                                        19

<210> SEQ ID NO 543
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 543
caggacuaga ggcaucauc                                                        19

<210> SEQ ID NO 544
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 544
augaugccuc uaguccugc                                                        19

<210> SEQ ID NO 545
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 545
gcaggacuag aggcaucau                                                        19

<210> SEQ ID NO 546
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 546
ugaugccucu aguccugca                                                        19

<210> SEQ ID NO 547
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 547
ugcaggacua gaggcauca                                                        19

<210> SEQ ID NO 548
<211> LENGTH: 19
<212> TYPE: RNA
<213> ORGANISM: artificial sequence
<220> FEATURE:
```

<223> OTHER INFORMATION: Synthetic sequence; sense nucleic acid molecule

<400> SEQUENCE: 548
gccucuaguc cugcaucau                                                                    19

<210> SEQ ID NO 549
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 549
augaugcagg acuagaggc                                                                    19

<210> SEQ ID NO 550
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 550
ccucuagucc ugcaucauc                                                                    19

<210> SEQ ID NO 551
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 551
gaugaugcag gacuagagg                                                                    19

<210> SEQ ID NO 552
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 552
cucuaguccu gcaucaucc                                                                    19

<210> SEQ ID NO 553
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 553
ggaugaugca ggacuagag                                                                    19

<210> SEQ ID NO 554
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 554
ucuaguccug caucaucca                                              19

<210> SEQ ID NO 555
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 555
uggaugaugc aggacuaga                                              19

<210> SEQ ID NO 556
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 556
cuaguccugc aucauccag                                              19

<210> SEQ ID NO 557
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 557
cuggaugaug caggacuag                                              19

<210> SEQ ID NO 558
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 558
uaguccugca ucauccaga                                              19

<210> SEQ ID NO 559
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 559
ucuggaugau gcaggacua                                              19

<210> SEQ ID NO 560
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 560
ccugcaucau ccagagcgg                                              19

<210> SEQ ID NO 561

```
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 561
ccgcucugga ugaugcagg                                                    19

<210> SEQ ID NO 562
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 562
cugcaucauc cagagcggc                                                    19

<210> SEQ ID NO 563
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 563
gccgcucugg augaugcag                                                    19

<210> SEQ ID NO 564
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 564
ugcaucaucc agagcggca                                                    19

<210> SEQ ID NO 565
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 565
ugccgcucug gaugaugca                                                    19

<210> SEQ ID NO 566
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 566
gcaucaucca gagcggcag                                                    19

<210> SEQ ID NO 567
<211> LENGTH: 19
<212> TYPE: RNA
<213> ORGANISM: artificial sequence
<220> FEATURE:
```

<223> OTHER INFORMATION: Synthetic sequence; antisense nucleic acid
      molecule

<400> SEQUENCE: 567
cugccgcucu ggaugaugc                                                   19

<210> SEQ ID NO 568
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 568
caucauccag agcggcagg                                                   19

<210> SEQ ID NO 569
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 569
ccugccgcuc uggaugaug                                                   19

<210> SEQ ID NO 570
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 570
aucauccaga gcggcaggc                                                   19

<210> SEQ ID NO 571
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 571
gccugccgcu cuggaugau                                                   19

<210> SEQ ID NO 572
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 572
ccggcaggcu uaucugucu                                                   19

<210> SEQ ID NO 573
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 573
agacagauaa gccugccgg                                          19

<210> SEQ ID NO 574
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 574
cggcaggcuu aucugucuu                                          19

<210> SEQ ID NO 575
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 575
aagacagaua agccugccg                                          19

<210> SEQ ID NO 576
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 576
ggcaggcuua ucugucuug                                          19

<210> SEQ ID NO 577
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 577
caagacagau aagccugcc                                          19

<210> SEQ ID NO 578
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 578
gcaggcuuau cugucuugg                                          19

<210> SEQ ID NO 579
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 579
ccaagacaga uaagccugc                                          19

```
<210> SEQ ID NO 580
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 580
aggcuuaucu gucuugggc                                                       19

<210> SEQ ID NO 581
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 581
gcccaagaca gauaagccu                                                       19

<210> SEQ ID NO 582
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 582
ggcuuaucug ucuugggcc                                                       19

<210> SEQ ID NO 583
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 583
ggcccaagac agauaagcc                                                       19

<210> SEQ ID NO 584
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 584
gcuuaucugu cuugggccu                                                       19

<210> SEQ ID NO 585
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 585
aggcccaaga cagauaagc                                                       19

<210> SEQ ID NO 586
<211> LENGTH: 19
<212> TYPE: RNA
<213> ORGANISM: artificial sequence
```

-continued

<220> FEATURE:
<223> OTHER INFORMATION: Synthetic sequence; sense nucleic acid molecule

<400> SEQUENCE: 586
cuuaucuguc uugggccuc                                                      19

<210> SEQ ID NO 587
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 587
gaggcccaag acagauaag                                                      19

<210> SEQ ID NO 588
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 588
uuaucugucu ugggccucu                                                      19

<210> SEQ ID NO 589
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 589
agaggcccaa gacagauaa                                                      19

<210> SEQ ID NO 590
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 590
gucuugggcc ucuuuuguc                                                      19

<210> SEQ ID NO 591
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 591
gacaaaagag gcccaagac                                                      19

<210> SEQ ID NO 592
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 592

-continued gggccucuuu ugucacaua                                                    19

<210> SEQ ID NO 593
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 593
uaugugacaa aagaggccc                                                    19

<210> SEQ ID NO 594
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 594
ggccucuuuu gucacauau                                                    19

<210> SEQ ID NO 595
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 595
auaugugaca aaagaggcc                                                    19

<210> SEQ ID NO 596
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 596
gccucuuuug ucacauauu                                                    19

<210> SEQ ID NO 597
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 597
aauaugugac aaaagaggc                                                    19

<210> SEQ ID NO 598
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 598
cuuuugucac auauugcuc                                                    19

-continued

```
<210> SEQ ID NO 599
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 599
gagcaauaug ugacaaaag                                                  19

<210> SEQ ID NO 600
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 600
uuuugucaca uauugcuca                                                  19

<210> SEQ ID NO 601
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 601
ugagcaauau gugacaaaa                                                  19

<210> SEQ ID NO 602
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 602
uuugucacau auugcucau                                                  19

<210> SEQ ID NO 603
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 603
augagcaaua ugugacaaa                                                  19

<210> SEQ ID NO 604
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 604
uugucacaua uugcucauc                                                  19

<210> SEQ ID NO 605
<211> LENGTH: 19
<212> TYPE: RNA
<213> ORGANISM: artificial sequence
```

```
<220> FEATURE:
<223> OTHER INFORMATION: Synthetic sequence; antisense nucleic acid
      molecule

<400> SEQUENCE: 605
gaugagcaau augugacaa                                                19

<210> SEQ ID NO 606
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 606
gucacauauu gcucaucug                                                19

<210> SEQ ID NO 607
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 607
cagaugagca auaugugac                                                19

<210> SEQ ID NO 608
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 608
ucacauauug cucaucugu                                                19

<210> SEQ ID NO 609
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 609
acagaugagc aauauguga                                                19

<210> SEQ ID NO 610
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 610
ucaucuguga gcugaggcc                                                19

<210> SEQ ID NO 611
<211> LENGTH: 19
<212> TYPE: RNA
<213> ORGANISM: artificial sequence
<220> FEATURE:
<223> OTHER INFORMATION: Synthetic sequence; antisense nucleic acid
      molecule
```

-continued

```
<400> SEQUENCE: 611
ggccucagcu cacagauga                                              19

<210> SEQ ID NO 612
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 612
caucugugag cugaggccc                                              19

<210> SEQ ID NO 613
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 613
gggccucagc ucacagaug                                              19

<210> SEQ ID NO 614
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 614
aucugugagc ugaggcccu                                              19

<210> SEQ ID NO 615
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 615
agggccucag cucacagau                                              19

<210> SEQ ID NO 616
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 616
cugugagcug aggcccuga                                              19

<210> SEQ ID NO 617
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 617
ucagggccuc agcucacag                                              19
```

<210> SEQ ID NO 618
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 618
gugagcugag gcccugacu                                                        19

<210> SEQ ID NO 619
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 619
agucagggcc ucagcucac                                                        19

<210> SEQ ID NO 620
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 620
gaggcccuga cucacugag                                                        19

<210> SEQ ID NO 621
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 621
cucagugagu cagggccuc                                                        19

<210> SEQ ID NO 622
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 622
ccaaugccac cucgcucca                                                        19

<210> SEQ ID NO 623
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 623
uggagcgagg uggcauugg                                                        19

<210> SEQ ID NO 624
<211> LENGTH: 19
<212> TYPE: RNA

-continued

```
<213> ORGANISM: artificial sequence
<220> FEATURE:
<223> OTHER INFORMATION: Synthetic sequence; sense nucleic acid molecule

<400> SEQUENCE: 624
caccucgcuc caugugccu                                                  19

<210> SEQ ID NO 625
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 625
aggcacaugg agcgaggug                                                  19

<210> SEQ ID NO 626
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 626
ucgcuccaug ugccucacu                                                  19

<210> SEQ ID NO 627
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 627
agugaggcac auggagcga                                                  19

<210> SEQ ID NO 628
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 628
cgcuccaugu gccucacuc                                                  19

<210> SEQ ID NO 629
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 629
gagugaggca cauggagcg                                                  19

<210> SEQ ID NO 630
<211> LENGTH: 19
<212> TYPE: RNA
<213> ORGANISM: artificial sequence
<220> FEATURE:
<223> OTHER INFORMATION: Synthetic sequence; sense nucleic acid molecule
```

-continued

```
<400> SEQUENCE: 630
gugccucacu cacaggaag                                                  19

<210> SEQ ID NO 631
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 631
cuuccuguga gugaggcac                                                  19

<210> SEQ ID NO 632
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 632
ugccucacuc acaggaagg                                                  19

<210> SEQ ID NO 633
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 633
ccuuccugug agugaggca                                                  19

<210> SEQ ID NO 634
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 634
gccucacuca caggaagga                                                  19

<210> SEQ ID NO 635
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 635
uccuuccugu gagugaggc                                                  19

<210> SEQ ID NO 636
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 636
ccucacucac aggaaggaa                                                  19
```

```
<210> SEQ ID NO 637
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 637
uuccuuccug ugagugagg                                                    19

<210> SEQ ID NO 638
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 638
ucucuccagg agggucuuc                                                    19

<210> SEQ ID NO 639
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 639
gaagacccuc cuggagaga                                                    19

<210> SEQ ID NO 640
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 640
aggagggucu ucaggaucu                                                    19

<210> SEQ ID NO 641
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 641
agauccugaa gacccuccu                                                    19

<210> SEQ ID NO 642
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 642
agggucuuca ggaucucau                                                    19

<210> SEQ ID NO 643
<211> LENGTH: 19
<212> TYPE: RNA
```

<213> ORGANISM: artificial sequence
<220> FEATURE:
<223> OTHER INFORMATION: Synthetic sequence; antisense nucleic acid
      molecule

<400> SEQUENCE: 643
augagauccu gaagacccu                                                    19

<210> SEQ ID NO 644
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 644
gggucuucag gaucucauc                                                    19

<210> SEQ ID NO 645
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 645
gaugagaucc ugaagaccc                                                    19

<210> SEQ ID NO 646
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 646
cacagccacc uuggugacc                                                    19

<210> SEQ ID NO 647
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 647
ggucaccaag guggcugug                                                    19

<210> SEQ ID NO 648
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 648
gccaccuugg ugaccugua                                                    19

<210> SEQ ID NO 649
<211> LENGTH: 19
<212> TYPE: RNA
<213> ORGANISM: artificial sequence
<220> FEATURE:
<223> OTHER INFORMATION: Synthetic sequence; antisense nucleic acid
      molecule -continued

```
<400> SEQUENCE: 649
uacaggucac caagguggc                                               19

<210> SEQ ID NO 650
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 650
ccaccuuggu gaccuguac                                               19

<210> SEQ ID NO 651
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 651
guacagguca ccaaggugg                                               19

<210> SEQ ID NO 652
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 652
caccuuggug accuguacu                                               19

<210> SEQ ID NO 653
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 653
aguacagguc accaaggug                                               19

<210> SEQ ID NO 654
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 654 accugguga ccuguacuu                                                19

<210> SEQ ID NO 655
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 655
aaguacaggu caccaaggu                                               19
```

-continued

```
<210> SEQ ID NO 656
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 656
ccuuggugac cuguacuuu                                                    19

<210> SEQ ID NO 657
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 657
aaaguacagg ucaccaagg                                                    19

<210> SEQ ID NO 658
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 658
cuuggugacc uguacuuuu                                                    19

<210> SEQ ID NO 659
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 659
aaaaguacag gucaccaag                                                    19

<210> SEQ ID NO 660
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 660
ggugaccugu acuuuucua                                                    19

<210> SEQ ID NO 661
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 661
uagaaaagua caggucacc                                                    19

<210> SEQ ID NO 662
<211> LENGTH: 19
```

-continued

```
<212> TYPE: RNA
<213> ORGANISM: artificial sequence
<220> FEATURE:
<223> OTHER INFORMATION: Synthetic sequence; sense nucleic acid molecule

<400> SEQUENCE: 662
gugaccugua cuuuucuac                                                      19

<210> SEQ ID NO 663
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 663
guagaaaagu acaggucac                                                      19

<210> SEQ ID NO 664
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 664 cguacuuuu cuacuggcg                                                       19

<210> SEQ ID NO 665
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 665
cgccaguaga aaaguacag                                                      19

<210> SEQ ID NO 666
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 666 uguacuuuc uacuggcgg                                                       19

<210> SEQ ID NO 667
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 667
ccgccaguag aaaaguaca                                                      19

<210> SEQ ID NO 668
<211> LENGTH: 19
<212> TYPE: RNA
<213> ORGANISM: artificial sequence
<220> FEATURE:
<223> OTHER INFORMATION: Synthetic sequence; sense nucleic acid molecule
```

```
<400> SEQUENCE: 668
guacuuuucu acuggcggu                                           19

<210> SEQ ID NO 669
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 669
accgccagua gaaaaguac                                           19

<210> SEQ ID NO 670
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 670
uacuuuucua cuggcgguc                                           19

<210> SEQ ID NO 671
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 671
gaccgccagu agaaaagua                                           19

<210> SEQ ID NO 672
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 672
acuuuucuac uggcgguca                                           19

<210> SEQ ID NO 673
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 673
ugaccgccag uagaaaagu                                           19

<210> SEQ ID NO 674
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 674
cuuuucuacu ggcggucau                                           19
```

-continued

```
<210> SEQ ID NO 675
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 675
augaccgcca guagaaaag                                                     19

<210> SEQ ID NO 676
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 676
uuuucuacug gcggucauc                                                     19

<210> SEQ ID NO 677
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 677
gaugaccgcc aguagaaaa                                                     19

<210> SEQ ID NO 678
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 678
uuucuacugg cggucaucu                                                     19

<210> SEQ ID NO 679
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 679
agaugaccgc caguagaaa                                                     19

<210> SEQ ID NO 680
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 680
uucuacuggc ggucaucuu                                                     19

<210> SEQ ID NO 681
<211> LENGTH: 19
```

-continued

<212> TYPE: RNA
<213> ORGANISM: artificial sequence
<220> FEATURE:
<223> OTHER INFORMATION: Synthetic sequence; antisense nucleic acid
      molecule

<400> SEQUENCE: 681
aagaugaccg ccaguagaa                                                    19

<210> SEQ ID NO 682
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 682
ucuacuggcg gucaucuuc                                                    19

<210> SEQ ID NO 683
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 683
gaagaugacc gccaguaga                                                    19

<210> SEQ ID NO 684
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 684
cuacuggcgg ucaucuucu                                                    19

<210> SEQ ID NO 685
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 685
agaagaugac cgccaguag                                                    19

<210> SEQ ID NO 686
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 686
uacuggcggu caucuucug                                                    19

<210> SEQ ID NO 687
<211> LENGTH: 19
<212> TYPE: RNA
<213> ORGANISM: artificial sequence
<220> FEATURE:
<223> OTHER INFORMATION: Synthetic sequence; antisense nucleic acid molecule

<400> SEQUENCE: 687
cagaagauga ccgccagua                                                          19

<210> SEQ ID NO 688
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 688
acuggcgguc aucuucugc                                                          19

<210> SEQ ID NO 689
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 689
gcagaagaug accgccagu                                                          19

<210> SEQ ID NO 690
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 690
cuggcgguca ucuucugcc                                                          19

<210> SEQ ID NO 691
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 691
ggcagaagau gaccgccag                                                          19

<210> SEQ ID NO 692
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 692
uggcggucau cuucugccu                                                          19

<210> SEQ ID NO 693
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 693

-continued aggcagaaga ugaccgcca                                             19

<210> SEQ ID NO 694
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 694
ggcggucauc uucugccug                                             19

<210> SEQ ID NO 695
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 695
caggcagaag augaccgcc                                             19

<210> SEQ ID NO 696
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 696
gcggucaucu ucugccugg                                             19

<210> SEQ ID NO 697
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 697
ccaggcagaa gaugaccgc                                             19

<210> SEQ ID NO 698
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 698
cggucaucuu cugccuggg                                             19

<210> SEQ ID NO 699
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 699
cccaggcaga agaugaccg                                             19

<210> SEQ ID NO 700

```
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 700
ggucaucuuc ugccugggu                                                              19

<210> SEQ ID NO 701
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 701
acccaggcag aagaugacc                                                             19

<210> SEQ ID NO 702
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 702
gucaucuucu gccuggguu                                                             19

<210> SEQ ID NO 703
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 703
aacccaggca gaagaugac                                                             19

<210> SEQ ID NO 704
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 704
ucaucuucug ccuggguuc                                                             19

<210> SEQ ID NO 705
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 705
gaacccaggc agaagauga                                                             19

<210> SEQ ID NO 706
<211> LENGTH: 19
<212> TYPE: RNA
<213> ORGANISM: artificial sequence
<220> FEATURE:
```

-continued

<223> OTHER INFORMATION: Synthetic sequence; sense nucleic acid molecule

<400> SEQUENCE: 706
caucuucugc cuggguucc                                                    19

<210> SEQ ID NO 707
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 707
ggaacccagg cagaagaug                                                    19

<210> SEQ ID NO 708
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 708
aucuucugcc uggguuccu                                                    19

<210> SEQ ID NO 709
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 709
aggaacccag gcagaagau                                                    19

<210> SEQ ID NO 710
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 710
cuucugccug gguuccuau                                                    19

<210> SEQ ID NO 711
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 711
auaggaaccc aggcagaag                                                    19

<210> SEQ ID NO 712
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 712
uucugccugg guuccuaug                                              19

<210> SEQ ID NO 713
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 713
cauaggaacc caggcagaa                                              19

<210> SEQ ID NO 714
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 714
ucugccuggg uuccuaugg                                              19

<210> SEQ ID NO 715
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 715
ccauaggaac ccaggcaga                                              19

<210> SEQ ID NO 716
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 716
cugccugggu uccuauggc                                              19

<210> SEQ ID NO 717
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 717
gccauaggaa cccaggcag                                              19

<210> SEQ ID NO 718
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 718
gccuggguuc cuauggcaa                                              19

<210> SEQ ID NO 719

-continued

```
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 719
uugccauagg aacccaggc                                                  19

<210> SEQ ID NO 720
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 720
ccuggguucc uauggcaac                                                  19

<210> SEQ ID NO 721
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 721
guugccauag gaacccagg                                                  19

<210> SEQ ID NO 722
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 722
guuccuaugg caacuucau                                                  19

<210> SEQ ID NO 723
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 723
augaaguugc cauaggaac                                                  19

<210> SEQ ID NO 724
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 724
uuccuauggc aacuucauu                                                  19

<210> SEQ ID NO 725
<211> LENGTH: 19
<212> TYPE: RNA
<213> ORGANISM: artificial sequence
<220> FEATURE:
```

-continued

<223> OTHER INFORMATION: Synthetic sequence; antisense nucleic acid
      molecule

<400> SEQUENCE: 725
aaugaaguug ccauaggaa                                                        19

<210> SEQ ID NO 726
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 726
uccuauggca acuucauug                                                        19

<210> SEQ ID NO 727
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 727
caaugaaguu gccauagga                                                        19

<210> SEQ ID NO 728
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 728
ccuauggcaa cuucauugu                                                        19

<210> SEQ ID NO 729
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 729
acaaugaagu ugccauagg                                                        19

<210> SEQ ID NO 730
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 730
cuauggcaac uucauuguc                                                        19

<210> SEQ ID NO 731
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 731

-continued

```
gacaaugaag uugccauag                                        19

<210> SEQ ID NO 732
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 732
uauggcaacu ucauugucu                                        19

<210> SEQ ID NO 733
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 733
agacaaugaa guugccaua                                        19

<210> SEQ ID NO 734
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 734
auggcaacuu cauugucuu                                        19

<210> SEQ ID NO 735
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 735
aagacaauga aguugccau                                        19

<210> SEQ ID NO 736
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 736
uggcaacuuc auugucuuc                                        19

<210> SEQ ID NO 737
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 737
gaagacaaug aaguugcca                                        19
```

```
<210> SEQ ID NO 738
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 738
ggcaacuuca uugucuucu                                                        19

<210> SEQ ID NO 739
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 739
agaagacaau gaaguugcc                                                        19

<210> SEQ ID NO 740
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 740
gcaacuucau ugucuucuu                                                        19

<210> SEQ ID NO 741
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 741
aagaagacaa ugaaguugc                                                        19

<210> SEQ ID NO 742
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 742
caacuucauu gucuucuug                                                        19

<210> SEQ ID NO 743
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 743
caagaagaca augaaguug                                                        19

<210> SEQ ID NO 744
<211> LENGTH: 19
<212> TYPE: RNA
<213> ORGANISM: artificial sequence
```

-continued

```
<220> FEATURE:
<223> OTHER INFORMATION: Synthetic sequence; sense nucleic acid molecule

<400> SEQUENCE: 744
cuucauuguc uucuugucc                                                    19

<210> SEQ ID NO 745
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 745
ggacaagaag acaaugaag                                                    19

<210> SEQ ID NO 746
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 746
uucauugucu ucuuguccu                                                    19

<210> SEQ ID NO 747
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 747
aggacaagaa gacaaugaa                                                    19

<210> SEQ ID NO 748
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 748
ucauugucuu cuuguccuu                                                    19

<210> SEQ ID NO 749
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 749
aaggacaaga agacaauga                                                    19

<210> SEQ ID NO 750
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 750
```

-continued

```
cauugucuuc uuguccuuc                                      19

<210> SEQ ID NO 751
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 751
gaaggacaag aagacaaug                                      19

<210> SEQ ID NO 752
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 752
ugucuucuug uccuucuuc                                      19

<210> SEQ ID NO 753
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 753
gaagaaggac aagaagaca                                      19

<210> SEQ ID NO 754
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 754
gucuucuugu ccuucuucg                                      19

<210> SEQ ID NO 755
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 755
cgaagaagga caagaagac                                      19

<210> SEQ ID NO 756
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 756
ucuucuuguc cuucuucga                                      19
```

-continued

```
<210> SEQ ID NO 757
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 757
ucgaagaagg acaagaaga                                                   19

<210> SEQ ID NO 758
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 758
cuucuugucc uucuucgau                                                   19

<210> SEQ ID NO 759
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 759
aucgaagaag gacaagaag                                                   19

<210> SEQ ID NO 760
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 760
uuguccuucu ucgauccag                                                   19

<210> SEQ ID NO 761
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 761
cuggaucgaa gaaggacaa                                                   19

<210> SEQ ID NO 762
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 762
uguccuucuu cgauccagc                                                   19

<210> SEQ ID NO 763
<211> LENGTH: 19
<212> TYPE: RNA
<213> ORGANISM: artificial sequence
```

```
<220> FEATURE:
<223> OTHER INFORMATION: Synthetic sequence; antisense nucleic acid
      molecule

<400> SEQUENCE: 763
gcuggaucga agaaggaca                                                          19

<210> SEQ ID NO 764
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 764
uucuucgauc cagccuuca                                                          19

<210> SEQ ID NO 765
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 765
ugaaggcugg aucgaagaa                                                          19

<210> SEQ ID NO 766
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 766
ucuucgaucc agccuucag                                                          19

<210> SEQ ID NO 767
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 767
cugaaggcug gaucgaaga                                                          19

<210> SEQ ID NO 768
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 768
cuucgaucca gccuucagg                                                          19

<210> SEQ ID NO 769
<211> LENGTH: 19
<212> TYPE: RNA
<213> ORGANISM: artificial sequence
<220> FEATURE:
<223> OTHER INFORMATION: Synthetic sequence; antisense nucleic acid
      molecule
```

-continued

<400> SEQUENCE: 769
ccugaaggcu ggaucgaag                                                          19

<210> SEQ ID NO 770
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 770
aacuuugauu ucaugaucc                                                          19

<210> SEQ ID NO 771
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 771
ggaucaugaa aucaaaguu                                                          19

<210> SEQ ID NO 772
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 772
acuuugauuu caugauccu                                                          19

<210> SEQ ID NO 773
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 773
aggaucauga aaucaaagu                                                          19

<210> SEQ ID NO 774
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 774
cuuugauuuc augauccug                                                          19

<210> SEQ ID NO 775
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 775
caggaucaug aaaucaaag                                                          19

```
<210> SEQ ID NO 776
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 776
uuugauuuca ugauccuga                                                            19

<210> SEQ ID NO 777
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 777
ucaggaucau gaaaucaaa                                                            19

<210> SEQ ID NO 778
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 778
uguccuucug ugaccucuu                                                            19

<210> SEQ ID NO 779
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 779
aagaggucac agaaggaca                                                            19

<210> SEQ ID NO 780
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 780
uucugugacc ucuucauuu                                                            19

<210> SEQ ID NO 781
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 781
aaaugaagag gucacagaa                                                            19

<210> SEQ ID NO 782
<211> LENGTH: 19
<212> TYPE: RNA
```

<213> ORGANISM: artificial sequence
<220> FEATURE:
<223> OTHER INFORMATION: Synthetic sequence; sense nucleic acid molecule

<400> SEQUENCE: 782
ucugugaccu cuucauuug                                                    19

<210> SEQ ID NO 783
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 783
caaaugaaga ggucacaga                                                    19

<210> SEQ ID NO 784
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 784
cugugaccuc uucauuugu                                                    19

<210> SEQ ID NO 785
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 785
acaaaugaag aggucacag                                                    19

<210> SEQ ID NO 786
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 786
ugugaccucu ucauuugug                                                    19

<210> SEQ ID NO 787
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 787
cacaaaugaa gaggucaca                                                    19

<210> SEQ ID NO 788
<211> LENGTH: 19
<212> TYPE: RNA
<213> ORGANISM: artificial sequence
<220> FEATURE:
<223> OTHER INFORMATION: Synthetic sequence; sense nucleic acid molecule -continued

```
<400> SEQUENCE: 788
ugaccucuuc auuugugga                                                       19

<210> SEQ ID NO 789
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 789
uccacaaaug aagagguca                                                       19

<210> SEQ ID NO 790
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 790
gaccucuuca uuuguggag                                                       19

<210> SEQ ID NO 791
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 791
cuccacaaau gaagagguc                                                       19

<210> SEQ ID NO 792
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 792
ucauuugugg agugacagc                                                       19

<210> SEQ ID NO 793
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 793
gcugucacuc cacaaauga                                                       19

<210> SEQ ID NO 794
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 794
cccauguuca ccuuugugu                                                       19
```

-continued

```
<210> SEQ ID NO 795
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 795
acacaaaggu gaacauggg                                                  19

<210> SEQ ID NO 796
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 796
ccauguucac cuuguguu                                                   19

<210> SEQ ID NO 797
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 797
aacacaaagg ugaacaugg                                                  19

<210> SEQ ID NO 798
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 798
cauguucacc uuguguua                                                   19

<210> SEQ ID NO 799
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 799
uaacacaaag gugaacaug                                                  19

<210> SEQ ID NO 800
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 800
auguucaccu uuguguuau                                                  19

<210> SEQ ID NO 801
<211> LENGTH: 19
<212> TYPE: RNA
```

-continued

```
<213> ORGANISM: artificial sequence
<220> FEATURE:
<223> OTHER INFORMATION: Synthetic sequence; antisense nucleic acid
      molecule

<400> SEQUENCE: 801
auaacacaaa ggugaacau                                                   19

<210> SEQ ID NO 802
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 802
uguucaccuu uguguuauu                                                   19

<210> SEQ ID NO 803
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 803
aauaacacaa aggugaaca                                                   19

<210> SEQ ID NO 804
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 804
guucaccuuu guguuauuc                                                   19

<210> SEQ ID NO 805
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 805
gaauaacaca aaggugaac                                                   19

<210> SEQ ID NO 806
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 806
caccuuugug uuauucuuc                                                   19

<210> SEQ ID NO 807
<211> LENGTH: 19
<212> TYPE: RNA
<213> ORGANISM: artificial sequence
<220> FEATURE:
<223> OTHER INFORMATION: Synthetic sequence; antisense nucleic acid
      molecule
```

-continued

```
<400> SEQUENCE: 807
gaagaauaac acaaaggug                                                        19

<210> SEQ ID NO 808
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 808
uuguguuauu cuucagcuc                                                        19

<210> SEQ ID NO 809
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 809
gagcugaaga auaacacaa                                                        19

<210> SEQ ID NO 810
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 810
uguguuauuc uucagcuca                                                        19

<210> SEQ ID NO 811
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 811
ugagcugaag aauaacaca                                                        19

<210> SEQ ID NO 812
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 812
guguuauucu ucagcucag                                                        19

<210> SEQ ID NO 813
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 813
cugagcugaa gaauaacac                                                        19
```

```
<210> SEQ ID NO 814
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 814
cuucagcuca gccaguagu                                                    19

<210> SEQ ID NO 815
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 815
acuacuggcu gagcugaag                                                    19

<210> SEQ ID NO 816
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 816
uucagcucag ccaguagua                                                    19

<210> SEQ ID NO 817
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 817
uacuacuggc ugagcugaa                                                    19

<210> SEQ ID NO 818
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 818
ucagcucagc caguaguau                                                    19

<210> SEQ ID NO 819
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 819
auacuacugg cugagcuga                                                    19

<210> SEQ ID NO 820
<211> LENGTH: 19
```

-continued

```
<212> TYPE: RNA
<213> ORGANISM: artificial sequence
<220> FEATURE:
<223> OTHER INFORMATION: Synthetic sequence; sense nucleic acid molecule

<400> SEQUENCE: 820
cagcucagcc aguaguauc                                                    19

<210> SEQ ID NO 821
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 821
gauacuacug gcugagcug                                                    19

<210> SEQ ID NO 822
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 822
agcucagcca guaguaucc                                                    19

<210> SEQ ID NO 823
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 823
ggauacuacu ggcugagcu                                                    19

<210> SEQ ID NO 824
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 824
gcucagccag uaguauccc                                                    19

<210> SEQ ID NO 825
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 825
gggauacuac uggcugagc                                                    19

<210> SEQ ID NO 826
<211> LENGTH: 19
<212> TYPE: RNA
<213> ORGANISM: artificial sequence
<220> FEATURE:
<223> OTHER INFORMATION: Synthetic sequence; sense nucleic acid molecule
```

-continued

```
<400> SEQUENCE: 826
cucagccagu aguaucccg                                              19

<210> SEQ ID NO 827
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 827
cgggauacua cuggcugag                                              19

<210> SEQ ID NO 828
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 828
ucagccagua guaucccgg                                              19

<210> SEQ ID NO 829
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 829
ccgggauacu acuggcuga                                              19

<210> SEQ ID NO 830
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 830
cagccaguag uaucccgga                                              19

<210> SEQ ID NO 831
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 831
uccgggauac uacuggcug                                              19

<210> SEQ ID NO 832
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 832
agccaguagu aucccggau                                              19
```

-continued

<210> SEQ ID NO 833
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 833
auccgggaua cuacuggcu                                                          19

<210> SEQ ID NO 834
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 834
ucugcuucac uuuccaucu                                                          19

<210> SEQ ID NO 835
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 835
agauggaaag ugaagcaga                                                          19

<210> SEQ ID NO 836
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 836
cuucacuuuc caucucacc                                                          19

<210> SEQ ID NO 837
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 837
ggugagaugg aaagugaag                                                          19

<210> SEQ ID NO 838
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 838
uucacuuucc aucucacca                                                          19

<210> SEQ ID NO 839
<211> LENGTH: 19

```
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 839
uggugagaug gaaagugaa                                                    19

<210> SEQ ID NO 840
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 840
ucacuuucca ucucaccag                                                    19

<210> SEQ ID NO 841
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 841
cuggugagau ggaaaguga                                                    19

<210> SEQ ID NO 842
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 842
cacuuuccau cucaccagu                                                    19

<210> SEQ ID NO 843
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 843
acuggugaga uggaaagug                                                    19

<210> SEQ ID NO 844
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 844
acuuuccauc ucaccaguu                                                    19

<210> SEQ ID NO 845
<211> LENGTH: 19
<212> TYPE: RNA
<213> ORGANISM: artificial sequence
<220> FEATURE:
<223> OTHER INFORMATION: Synthetic sequence; antisense nucleic acid
```

-continued

```
       molecule

<400> SEQUENCE: 845
aacuggugag auggaaagu                                                  19

<210> SEQ ID NO 846
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 846
cuuuccaucu caccaguuc                                                  19

<210> SEQ ID NO 847
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 847
gaacugguga gauggaaag                                                  19

<210> SEQ ID NO 848
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 848
ccaucucacc aguucaggc                                                  19

<210> SEQ ID NO 849
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 849
gccugaacug gugagaugg                                                  19

<210> SEQ ID NO 850
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 850
caucucacca guucaggcu                                                  19

<210> SEQ ID NO 851
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 851
```

-continued

```
agccugaacu ggugagaug                                              19

<210> SEQ ID NO 852
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 852
aucucaccag uucaggcuu                                              19

<210> SEQ ID NO 853
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 853
aagccugaac uggugagau                                              19

<210> SEQ ID NO 854
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 854
ucucaccagu ucaggcuuc                                              19

<210> SEQ ID NO 855
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 855
gaagccugaa cuggugaga                                              19

<210> SEQ ID NO 856
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 856
accaguucag gcuucauca                                              19

<210> SEQ ID NO 857
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 857
ugaugaagcc ugaacuggu                                              19

<210> SEQ ID NO 858
```

-continued

```
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 858
caguucaggc uucaucauc                                                        19

<210> SEQ ID NO 859
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 859
gaugaugaag ccugaacug                                                        19

<210> SEQ ID NO 860
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 860
aguucaggcu ucaucauca                                                        19

<210> SEQ ID NO 861
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 861
ugaugaugaa gccugaacu                                                        19

<210> SEQ ID NO 862
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 862
guucaggcuu caucaucau                                                        19

<210> SEQ ID NO 863
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 863
augaugauga agccugaac                                                        19

<210> SEQ ID NO 864
<211> LENGTH: 19
<212> TYPE: RNA
<213> ORGANISM: artificial sequence
<220> FEATURE:
```

-continued

```
<223> OTHER INFORMATION: Synthetic sequence; sense nucleic acid molecule

<400> SEQUENCE: 864
uucaggcuuc aucaucaug                                                    19

<210> SEQ ID NO 865
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 865
caugaugaug aagccugaa                                                    19

<210> SEQ ID NO 866
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 866
ucaggcuuca ucaucaugu                                                    19

<210> SEQ ID NO 867
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 867
acaugaugau gaagccuga                                                    19

<210> SEQ ID NO 868
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 868
caggcuucau caucauguc                                                    19

<210> SEQ ID NO 869
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 869
gacaugauga ugaagccug                                                    19

<210> SEQ ID NO 870
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 870
```
aggcuucauc aucaugucu                                          19

<210> SEQ ID NO 871
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 871
agacaugaug augaagccu                                                 19

<210> SEQ ID NO 872
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 872
ggcuucauca ucaugucuc                                                 19

<210> SEQ ID NO 873
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 873
gagacaugau gaugaagcc                                                 19

<210> SEQ ID NO 874
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 874
gcuucaucau caugucucu                                                 19

<210> SEQ ID NO 875
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 875
agagacauga ugaugaagc                                                 19

<210> SEQ ID NO 876
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 876
caucaucaug ucucugaag                                                 19

<210> SEQ ID NO 877

-continued

```
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 877
cuucagagac augaugaug                                                    19

<210> SEQ ID NO 878
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 878
cucugaagac aguggcagu                                                    19

<210> SEQ ID NO 879
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 879
acugccacug ucuucagag                                                    19

<210> SEQ ID NO 880
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 880
agacaguggc agugaucgc                                                    19

<210> SEQ ID NO 881
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 881
gcgaucacug ccacugucu                                                    19

<210> SEQ ID NO 882
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 882
gacaguggca gugaucgcc                                                    19

<210> SEQ ID NO 883
<211> LENGTH: 19
<212> TYPE: RNA
<213> ORGANISM: artificial sequence
<220> FEATURE:
```

<223> OTHER INFORMATION: Synthetic sequence; antisense nucleic acid
      molecule

<400> SEQUENCE: 883
ggcgaucacu gccacuguc                                                      19

<210> SEQ ID NO 884
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 884
acaguggcag ugaucgccc                                                      19

<210> SEQ ID NO 885
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 885
gggcgaucac ugccacugu                                                      19

<210> SEQ ID NO 886
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 886
caguggcagu gaucgcccu                                                      19

<210> SEQ ID NO 887
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 887
agggcgauca cugccacug                                                      19

<210> SEQ ID NO 888
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 888
aguggcagug aucgcccug                                                      19

<210> SEQ ID NO 889
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 889
cagggcgauc acugccacu                                    19

<210> SEQ ID NO 890
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 890
accggcuccg gaugguguu                                   19

<210> SEQ ID NO 891
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 891
aacaccaucc ggagccggu                                   19

<210> SEQ ID NO 892
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 892
acagccuaau cgcacggcc                                   19

<210> SEQ ID NO 893
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 893
ggccgugcga uuaggcugu                                   19

<210> SEQ ID NO 894
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 894
cagccuaauc gcacggccu                                   19

<210> SEQ ID NO 895
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 895
aggccgugcg auuaggcug                                   19

-continued

```
<210> SEQ ID NO 896
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 896
agccuaaucg cacggccuc                                                      19

<210> SEQ ID NO 897
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 897
gaggccgugc gauuaggcu                                                      19

<210> SEQ ID NO 898
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 898
gcaccguacu ccucacccu                                                      19

<210> SEQ ID NO 899
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 899
agggugagga guacggugc                                                      19

<210> SEQ ID NO 900
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 900
caccguacuc cucacccug                                                      19

<210> SEQ ID NO 901
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 901
cagggugagg aguacggug                                                      19

<210> SEQ ID NO 902
<211> LENGTH: 19
<212> TYPE: RNA
<213> ORGANISM: artificial sequence
```

-continued

---

```
<220> FEATURE:
<223> OTHER INFORMATION: Synthetic sequence; sense nucleic acid molecule

<400> SEQUENCE: 902
cuccucaccc ugcuucucu                                              19

<210> SEQ ID NO 903
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 903
agagaagcag ggugaggag                                             19

<210> SEQ ID NO 904
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 904
uccucacccu gcuucucug                                             19

<210> SEQ ID NO 905
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 905
cagagaagca gggugagga                                             19

<210> SEQ ID NO 906
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 906
ccucacccug cuucucugg                                             19

<210> SEQ ID NO 907
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 907
ccagagaagc agggugagg                                             19

<210> SEQ ID NO 908
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 908
```

-continued cugcuucucu gggccacca                                                                    19

<210> SEQ ID NO 909
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 909
ugguggccca gagaagcag                                                                    19

<210> SEQ ID NO 910
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 910
ugggccacca guuucaccc                                                                    19

<210> SEQ ID NO 911
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 911
gggugaaacu gguggccca                                                                    19

<210> SEQ ID NO 912
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 912
gggccaccag uuucacccu                                                                    19

<210> SEQ ID NO 913
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 913
agggugaaac ugguggccc                                                                    19

<210> SEQ ID NO 914
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 914
ggccaccagu uucacccuu                                                                    19

-continued

```
<210> SEQ ID NO 915
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 915
aagggugaaa cuggguggcc                                              19

<210> SEQ ID NO 916
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 916
gccaccaguu ucacccuug                                               19

<210> SEQ ID NO 917
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 917
caagggugaa acugguggc                                               19

<210> SEQ ID NO 918
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 918
caguuucacc cuugccacc                                               19

<210> SEQ ID NO 919
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 919
gguggcaagg gugaaacug                                               19

<210> SEQ ID NO 920
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 920
aguuucaccc uugccaccu                                               19

<210> SEQ ID NO 921
<211> LENGTH: 19
<212> TYPE: RNA
<213> ORGANISM: artificial sequence
```

-continued

```
<220> FEATURE:
<223> OTHER INFORMATION: Synthetic sequence; antisense nucleic acid
      molecule

<400> SEQUENCE: 921
agguggcaag ggugaaacu                                                  19

<210> SEQ ID NO 922
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 922
ccaccuuggc uaccuugaa                                                  19

<210> SEQ ID NO 923
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 923
uucaagguag ccaaggugg                                                  19

<210> SEQ ID NO 924
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 924
accagcaagu cccaccucu                                                  19

<210> SEQ ID NO 925
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 925
agagguggga cuugcuggu                                                  19

<210> SEQ ID NO 926
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 926
ccagcaaguc ccaccucug                                                  19

<210> SEQ ID NO 927
<211> LENGTH: 19
<212> TYPE: RNA
<213> ORGANISM: artificial sequence
<220> FEATURE:
<223> OTHER INFORMATION: Synthetic sequence; antisense nucleic acid
      molecule
```

-continued

```
<400> SEQUENCE: 927
cagagguggg acuugcugg                                                    19

<210> SEQ ID NO 928
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 928
cagcaagucc caccucugu                                                    19

<210> SEQ ID NO 929
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 929
acagaggugg gacuugcug                                                    19

<210> SEQ ID NO 930
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 930
agcaaguccc accucuguc                                                    19

<210> SEQ ID NO 931
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 931
gacagaggug ggacuugcu                                                    19

<210> SEQ ID NO 932
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 932
caagucccac cucugucuu                                                    19

<210> SEQ ID NO 933
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 933
aagacagagg ugggacuug                                                    19
```

```
<210> SEQ ID NO 934
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 934
caccucuguc uucccaugu                                                              19

<210> SEQ ID NO 935
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 935
acaugggaag acagaggug                                                             19

<210> SEQ ID NO 936
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 936
accucugucu ucccauguc                                                             19

<210> SEQ ID NO 937
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 937
gacaugggaa gacagaggu                                                             19

<210> SEQ ID NO 938
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 938
ccucugucuu cccaugucc                                                             19

<210> SEQ ID NO 939
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 939
ggacauggga agacagagg                                                             19

<210> SEQ ID NO 940
<211> LENGTH: 19
<212> TYPE: RNA
```

-continued

```
<213> ORGANISM: artificial sequence
<220> FEATURE:
<223> OTHER INFORMATION: Synthetic sequence; sense nucleic acid molecule

<400> SEQUENCE: 940
cucugucuuc ccaugucca                                                    19

<210> SEQ ID NO 941
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 941
uggacauggg aagacagag                                                    19

<210> SEQ ID NO 942
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 942
ccauguccag ucugauugc                                                    19

<210> SEQ ID NO 943
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 943
gcaaucagac uggacaugg                                                    19

<210> SEQ ID NO 944
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 944
cauguccagu cugauugcu                                                    19

<210> SEQ ID NO 945
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 945
agcaaucaga cuggacaug                                                    19

<210> SEQ ID NO 946
<211> LENGTH: 19
<212> TYPE: RNA
<213> ORGANISM: artificial sequence
<220> FEATURE:
<223> OTHER INFORMATION: Synthetic sequence; sense nucleic acid molecule
```

```
<400> SEQUENCE: 946
auguccaguc ugauugcug                                                      19

<210> SEQ ID NO 947
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 947
cagcaaucag acuggacau                                                      19

<210> SEQ ID NO 948
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 948
aaagccauuu ugucucucu                                                      19

<210> SEQ ID NO 949
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 949
agagagacaa aauggcuuu                                                      19

<210> SEQ ID NO 950
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 950
aagccauuuu gucucucua                                                      19

<210> SEQ ID NO 951
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 951
uagagagaca aaauggcuu                                                      19

<210> SEQ ID NO 952
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 952
agccauuuug ucucucuau                                                      19
```

<210> SEQ ID NO 953
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 953
auagagagac aaaauggcu                                                                          19

<210> SEQ ID NO 954
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 954
gccauuuugu cucucuaug                                                                          19

<210> SEQ ID NO 955
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 955
cauagagaga caaaauggc                                                                          19

<210> SEQ ID NO 956
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 956
ugucucucua uguggucga                                                                          19

<210> SEQ ID NO 957
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 957
ucgaccacau agagagaca                                                                          19

<210> SEQ ID NO 958
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 958
gucucucuau guggucgac                                                                          19

<210> SEQ ID NO 959
<211> LENGTH: 19
<212> TYPE: RNA

-continued

```
<213> ORGANISM: artificial sequence
<220> FEATURE:
<223> OTHER INFORMATION: Synthetic sequence; antisense nucleic acid
      molecule

<400> SEQUENCE: 959
gucgaccaca uagagagac                                                     19

<210> SEQ ID NO 960
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 960
ucucucuaug uggucgacu                                                     19

<210> SEQ ID NO 961
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 961
agucgaccac auagagaga                                                     19

<210> SEQ ID NO 962
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 962
cucucuaugu ggucgacuu                                                     19

<210> SEQ ID NO 963
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 963
aagucgacca cauagagag                                                     19

<210> SEQ ID NO 964
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 964
ucucuaugug gucgacuuc                                                     19

<210> SEQ ID NO 965
<211> LENGTH: 19
<212> TYPE: RNA
<213> ORGANISM: artificial sequence
<220> FEATURE:
<223> OTHER INFORMATION: Synthetic sequence; antisense nucleic acid
      molecule
```

-continued

```
<400> SEQUENCE: 965
gaagucgacc acauagaga                                                    19

<210> SEQ ID NO 966
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 966
cucuaugugg ucgacuuca                                                    19

<210> SEQ ID NO 967
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 967
ugaagucgac cacauagag                                                    19

<210> SEQ ID NO 968
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 968
ucuauguggu cgacuucac                                                    19

<210> SEQ ID NO 969
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 969
gugaagucga ccacauaga                                                    19

<210> SEQ ID NO 970
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 970
cuaugugguc gacuucacc                                                    19

<210> SEQ ID NO 971
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 971
ggugaagucg accacauag                                                    19
```

-continued

```
<210> SEQ ID NO 972
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 972
uauguggucg acuucaccu                                                    19

<210> SEQ ID NO 973
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 973
aggugaaguc gaccacaua                                                    19

<210> SEQ ID NO 974
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 974
ggucgacuuc accuucugu                                                    19

<210> SEQ ID NO 975
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 975
acagaaggug aagucgacc                                                    19

<210> SEQ ID NO 976
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 976
gucgacuuca ccuucugug                                                    19

<210> SEQ ID NO 977
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 977
cacagaaggu gaagucgac                                                    19

<210> SEQ ID NO 978
<211> LENGTH: 19
```

-continued

```
<212> TYPE: RNA
<213> ORGANISM: artificial sequence
<220> FEATURE:
<223> OTHER INFORMATION: Synthetic sequence; sense nucleic acid molecule

<400> SEQUENCE: 978
ucgacuucac cuucugugu                                                        19

<210> SEQ ID NO 979
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 979
acacagaagg ugaagucga                                                        19

<210> SEQ ID NO 980
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 980
cgacuucacc uucuguguu                                                        19

<210> SEQ ID NO 981
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 981
aacacagaag gugaagucg                                                        19

<210> SEQ ID NO 982
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 982
gacuucaccu ucuguguug                                                        19

<210> SEQ ID NO 983
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 983
caacacagaa ggugaaguc                                                        19

<210> SEQ ID NO 984
<211> LENGTH: 19
<212> TYPE: RNA
<213> ORGANISM: artificial sequence
<220> FEATURE:
<223> OTHER INFORMATION: Synthetic sequence; sense nucleic acid molecule
```

-continued

<400> SEQUENCE: 984
acuucaccuu cuguguugc                                                      19

<210> SEQ ID NO 985
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 985
gcaacacaga aggugaagu                                                      19

<210> SEQ ID NO 986
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 986
uucaccuucu guguugcug                                                      19

<210> SEQ ID NO 987
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 987
cagcaacaca gaaggugaa                                                      19

<210> SEQ ID NO 988
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 988
ucaccuucug uguugcugu                                                      19

<210> SEQ ID NO 989
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 989
acagcaacac agaagguga                                                      19

<210> SEQ ID NO 990
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 990
caccuucugu guugcugug                                                      19

<210> SEQ ID NO 991
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 991
cacagcaaca cagaaggug                                                                                                          19

<210> SEQ ID NO 992
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 992
accuucugug uugcugugg                                                                                                          19

<210> SEQ ID NO 993
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 993
ccacagcaac acagaaggu                                                                                                          19

<210> SEQ ID NO 994
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 994
ucuguguugc uguggucuc                                                                                                          19

<210> SEQ ID NO 995
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 995
gagaccacag caacacaga                                                                                                          19

<210> SEQ ID NO 996
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 996
cuguguugcu guggucucu                                                                                                          19

<210> SEQ ID NO 997
<211> LENGTH: 19

-continued

```
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 997
agagaccaca gcaacacag                                                 19

<210> SEQ ID NO 998
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 998
uguguugcug uggcucucug                                                19

<210> SEQ ID NO 999
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 999
cagagaccac agcaacaca                                                 19

<210> SEQ ID NO 1000
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1000
guguugcugu ggucucugu                                                 19

<210> SEQ ID NO 1001
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1001
acagagacca cagcaacac                                                 19

<210> SEQ ID NO 1002
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1002
uguugcugug gucucuguc                                                 19

<210> SEQ ID NO 1003
<211> LENGTH: 19
<212> TYPE: RNA
<213> ORGANISM: artificial sequence
<220> FEATURE:
<223> OTHER INFORMATION: Synthetic sequence; antisense nucleic acid
```

-continued

```
            molecule

<400> SEQUENCE: 1003
gacagagacc acagcaaca                                                    19

<210> SEQ ID NO 1004
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1004
uugcuguggu cucugucuc                                                    19

<210> SEQ ID NO 1005
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1005
gagacagaga ccacagcaa                                                    19

<210> SEQ ID NO 1006
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1006 ugcugguc ucugucucu                                                      19

<210> SEQ ID NO 1007
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1007
agagacagag accacagca                                                    19

<210> SEQ ID NO 1008
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1008
gcuguggucu cugucucuu                                                    19

<210> SEQ ID NO 1009
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1009
```
aagagacaga gaccacagc                                                            19

<210> SEQ ID NO 1010
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1010
cuguggucuc ugucucuua                                                            19

<210> SEQ ID NO 1011
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1011
uaagagacag agaccacag                                                            19

<210> SEQ ID NO 1012
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1012
uguggucucu gucucuuac                                                            19

<210> SEQ ID NO 1013
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1013
guaagagaca gagaccaca                                                            19

<210> SEQ ID NO 1014
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1014 guggcucug ucucuuaca                                                             19

<210> SEQ ID NO 1015
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1015
uguaagagac agagaccac                                                            19

<210> SEQ ID NO 1016

```
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1016
ucucugucuc uuacaucau                                                          19

<210> SEQ ID NO 1017
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1017
augauguaag agacagaga                                                          19

<210> SEQ ID NO 1018
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1018
cucugucucu uacaucaug                                                          19

<210> SEQ ID NO 1019
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1019
caugauguaa gagacagag                                                          19

<210> SEQ ID NO 1020
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1020
gucucuuaca ucaugauug                                                          19

<210> SEQ ID NO 1021
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1021
caaucaugau guaagagac                                                          19

<210> SEQ ID NO 1022
<211> LENGTH: 19
<212> TYPE: RNA
<213> ORGANISM: artificial sequence
<220> FEATURE:
```

-continued

```
<223> OTHER INFORMATION: Synthetic sequence; sense nucleic acid molecule

<400> SEQUENCE: 1022
ucucuuacau caugauugc                                                      19

<210> SEQ ID NO 1023
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1023
gcaaucauga uguaagaga                                                      19

<210> SEQ ID NO 1024
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1024
cucuuacauc augauugcu                                                      19

<210> SEQ ID NO 1025
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1025
agcaaucaug auguaagag                                                      19

<210> SEQ ID NO 1026
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1026
ucuuacauca ugauugcuc                                                      19

<210> SEQ ID NO 1027
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1027
gagcaaucau gauguaaga                                                      19

<210> SEQ ID NO 1028
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1028
```
cuuacaucau gauugcuca                                              19

<210> SEQ ID NO 1029
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1029
ugagcaauca ugauguaag                                             19

<210> SEQ ID NO 1030
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1030
uuacaucaug auugcucag                                             19

<210> SEQ ID NO 1031
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1031
cugagcaauc augauguaa                                             19

<210> SEQ ID NO 1032
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1032
uacaucauga uugcucaga                                             19

<210> SEQ ID NO 1033
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1033
ucugagcaau caugaugua                                             19

<210> SEQ ID NO 1034
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1034
acaucaugau ugcucagac                                             19

<210> SEQ ID NO 1035

-continued

```
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1035
gucugagcaa ucaugaugu                                                        19

<210> SEQ ID NO 1036
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1036
caucaugauu gcucagacc                                                        19

<210> SEQ ID NO 1037
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1037
ggucugagca aucaugaug                                                        19

<210> SEQ ID NO 1038
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1038
auugcucaga cccugcgga                                                        19

<210> SEQ ID NO 1039
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1039
uccgcagggu cugagcaau                                                        19

<210> SEQ ID NO 1040
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1040
uugcucagac ccugcggaa                                                        19

<210> SEQ ID NO 1041
<211> LENGTH: 19
<212> TYPE: RNA
<213> ORGANISM: artificial sequence
<220> FEATURE:
```

-continued

<223> OTHER INFORMATION: Synthetic sequence; antisense nucleic acid
      molecule

<400> SEQUENCE: 1041
uuccgcaggg ucugagcaa                                                    19

<210> SEQ ID NO 1042
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1042
ugcucagacc cugcggaag                                                    19

<210> SEQ ID NO 1043
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1043
cuuccgcagg gucugagca                                                    19

<210> SEQ ID NO 1044
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1044
gcucagaccc ugcggaaga                                                    19

<210> SEQ ID NO 1045
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1045
ucuuccgcag ggucugagc                                                    19

<210> SEQ ID NO 1046
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1046
cucagacccu gcggaagaa                                                    19

<210> SEQ ID NO 1047
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1047

```
uucuuccgca gggucugag                                         19

<210> SEQ ID NO 1048
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1048
uguaaucaca gucgaugcu                                         19

<210> SEQ ID NO 1049
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1049
agcaucgacu gugauuaca                                         19

<210> SEQ ID NO 1050
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1050
guaaucacag ucgaugcuu                                         19

<210> SEQ ID NO 1051
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1051
aagcaucgac ugugauuac                                         19

<210> SEQ ID NO 1052
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1052
uaaucacagu cgaugcuuc                                         19

<210> SEQ ID NO 1053
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1053
gaagcaucga cugugauua                                         19
```

-continued

```
<210> SEQ ID NO 1054
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1054
aaucacaguc gaugcuucc                                                      19

<210> SEQ ID NO 1055
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1055
ggaagcaucg acugugauu                                                      19

<210> SEQ ID NO 1056
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1056
aucacagucg augcuucca                                                      19

<210> SEQ ID NO 1057
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1057
uggaagcauc gacugugau                                                      19

<210> SEQ ID NO 1058
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1058
ucacagucga ugcuuccag                                                      19

<210> SEQ ID NO 1059
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1059
cuggaagcau cgacuguga                                                      19

<210> SEQ ID NO 1060
<211> LENGTH: 19
<212> TYPE: RNA
<213> ORGANISM: artificial sequence
```

<220> FEATURE:
<223> OTHER INFORMATION: Synthetic sequence; sense nucleic acid molecule

<400> SEQUENCE: 1060
cacagucgau gcuuccaga                                                          19

<210> SEQ ID NO 1061
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1061
ucuggaagca ucgacugug                                                          19

<210> SEQ ID NO 1062
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1062
acagucgaug cuuccagac                                                          19

<210> SEQ ID NO 1063
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1063
gucuggaagc aucgacugu                                                          19

<210> SEQ ID NO 1064
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1064
cagucgaugc uuccagacc                                                          19

<210> SEQ ID NO 1065
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1065
ggucuggaag caucgacug                                                          19

<210> SEQ ID NO 1066
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1066
agucgaugcu uccagacca                                              19

<210> SEQ ID NO 1067
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1067
uggucuggaa gcaucgacu                                             19

<210> SEQ ID NO 1068
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1068
gucgaugcuu ccagaccac                                             19

<210> SEQ ID NO 1069
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1069
guggucugga agcaucgac                                             19

<210> SEQ ID NO 1070
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1070
ucgaugcuuc cagaccaca                                             19

<210> SEQ ID NO 1071
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1071
uguggucugg aagcaucga                                             19

<210> SEQ ID NO 1072
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1072
agaccacagc cuuucaugg                                             19

-continued

```
<210> SEQ ID NO 1073
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1073
ccaugaaagg cuguggucu                                                     19

<210> SEQ ID NO 1074
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1074
gaccacagcc uuucauggg                                                     19

<210> SEQ ID NO 1075
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1075
cccaugaaag gcugugguc                                                     19

<210> SEQ ID NO 1076
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1076
agaucccauc cagugugcc                                                     19

<210> SEQ ID NO 1077
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1077
ggcacacugg augggaucu                                                     19

<210> SEQ ID NO 1078
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1078
gaucccaucc agugugcca                                                     19

<210> SEQ ID NO 1079
<211> LENGTH: 19
<212> TYPE: RNA
<213> ORGANISM: artificial sequence
```

```
<220> FEATURE:
<223> OTHER INFORMATION: Synthetic sequence; antisense nucleic acid
      molecule

<400> SEQUENCE: 1079
uggcacacug gaugggauc                                                    19

<210> SEQ ID NO 1080
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1080
ccauccagug ugccaugcc                                                    19

<210> SEQ ID NO 1081
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1081
ggcauggcac acuggaugg                                                    19

<210> SEQ ID NO 1082
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1082
cauccagugu gccaugccg                                                    19

<210> SEQ ID NO 1083
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1083
cggcauggca cacuggaug                                                    19

<210> SEQ ID NO 1084
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1084
auccagugug ccaugccgg                                                    19

<210> SEQ ID NO 1085
<211> LENGTH: 19
<212> TYPE: RNA
<213> ORGANISM: artificial sequence
<220> FEATURE:
<223> OTHER INFORMATION: Synthetic sequence; antisense nucleic acid
      molecule
```

-continued

<400> SEQUENCE: 1085
ccggcauggc acacuggau                                                          19

<210> SEQ ID NO 1086
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1086
aacugcagca cguucagac                                                          19

<210> SEQ ID NO 1087
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1087
gucugaacgu gcugcaguu                                                          19

<210> SEQ ID NO 1088
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1088
acugcagcac guucagacc                                                          19

<210> SEQ ID NO 1089
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1089
ggucugaacg ugcugcagu                                                          19

<210> SEQ ID NO 1090
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1090
uggauauacc aagaguccc                                                          19

<210> SEQ ID NO 1091
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1091
gggacucuug guauaucca                                                          19

-continued

<210> SEQ ID NO 1092
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1092
ggauauacca agaguccca                                           19

<210> SEQ ID NO 1093
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1093
ugggacucuu gguauaucc                                           19

<210> SEQ ID NO 1094
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1094
gauauaccaa gagucccaa                                           19

<210> SEQ ID NO 1095
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1095
uugggacucu ugguauauc                                           19

<210> SEQ ID NO 1096
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1096
auauaccaag agucccaac                                           19

<210> SEQ ID NO 1097
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1097
guugggacuc uugguauau                                           19

<210> SEQ ID NO 1098
<211> LENGTH: 19
<212> TYPE: RNA

-continued

```
<213> ORGANISM: artificial sequence
<220> FEATURE:
<223> OTHER INFORMATION: Synthetic sequence; sense nucleic acid molecule

<400> SEQUENCE: 1098
cagcaagccg acuccagcu                                                      19

<210> SEQ ID NO 1099
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1099
agcuggaguc ggcuugcug                                                      19

<210> SEQ ID NO 1100
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1100
agcaagccga cuccagcuc                                                      19

<210> SEQ ID NO 1101
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1101
gagcuggagu cggcuugcu                                                      19

<210> SEQ ID NO 1102
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1102
caagccgacu ccagcucgu                                                      19

<210> SEQ ID NO 1103
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1103
acgagcugga gucggcuug                                                      19

<210> SEQ ID NO 1104
<211> LENGTH: 19
<212> TYPE: RNA
<213> ORGANISM: artificial sequence
<220> FEATURE:
<223> OTHER INFORMATION: Synthetic sequence; sense nucleic acid molecule
```

```
<400> SEQUENCE: 1104
aagccgacuc cagcucgua                                                      19

<210> SEQ ID NO 1105
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1105
uacgagcugg agucggcuu                                                      19

<210> SEQ ID NO 1106
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1106
agccgacucc agcucguau                                                      19

<210> SEQ ID NO 1107
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1107
auacgagcug gagucggcu                                                      19

<210> SEQ ID NO 1108
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1108
gccgacucca gcucguauc                                                      19

<210> SEQ ID NO 1109
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1109
gauacgagcu ggagucggc                                                      19

<210> SEQ ID NO 1110
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1110
ccgacuccag cucguauca                                                      19
```

-continued

```
<210> SEQ ID NO 1111
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1111
ugauacgagc uggagucgg                                                     19

<210> SEQ ID NO 1112
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1112
cgacuccagc ucguaucag                                                     19

<210> SEQ ID NO 1113
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1113
cugauacgag cuggagucg                                                     19

<210> SEQ ID NO 1114
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1114
gacuccagcu cguaucagc                                                     19

<210> SEQ ID NO 1115
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1115
gcugauacga gcuggaguc                                                     19

<210> SEQ ID NO 1116
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1116
acuccagcuc guaucagcc                                                     19

<210> SEQ ID NO 1117
<211> LENGTH: 19
<212> TYPE: RNA
```

```
<213> ORGANISM: artificial sequence
<220> FEATURE:
<223> OTHER INFORMATION: Synthetic sequence; antisense nucleic acid
      molecule

<400> SEQUENCE: 1117
ggcugauacg agcuggagu                                              19

<210> SEQ ID NO 1118
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1118
agcucguauc agccaucaa                                              19

<210> SEQ ID NO 1119
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1119
uugauggcug auacgagcu                                              19

<210> SEQ ID NO 1120
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1120
gcucguauca gccaucaac                                              19

<210> SEQ ID NO 1121
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1121
guugauggcu gauacgagc                                              19

<210> SEQ ID NO 1122
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1122
agccaucaac cucuccacu                                              19

<210> SEQ ID NO 1123
<211> LENGTH: 19
<212> TYPE: RNA
<213> ORGANISM: artificial sequence
<220> FEATURE:
<223> OTHER INFORMATION: Synthetic sequence; antisense nucleic acid
      molecule
```

-continued

```
<400> SEQUENCE: 1123
aguggagagg uugauggcu                                              19

<210> SEQ ID NO 1124
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1124
cuccacugcc aaggauucc                                              19

<210> SEQ ID NO 1125
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1125
ggaauccuug gcaguggag                                              19

<210> SEQ ID NO 1126
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1126
cacugccaag gauuccaaa                                              19

<210> SEQ ID NO 1127
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1127
uuuggaaucc uuggcagug                                              19

<210> SEQ ID NO 1128
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1128
caccugugug aucauugug                                              19

<210> SEQ ID NO 1129
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1129
cacaaugauc acacaggug                                              19
```

```
<210> SEQ ID NO 1130
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1130
accuguguga ucauugugc                                                          19

<210> SEQ ID NO 1131
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1131
gcacaaugau cacacaggu                                                          19

<210> SEQ ID NO 1132
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1132
ccugugugau cauugugcu                                                          19

<210> SEQ ID NO 1133
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1133
agcacaauga ucacacagg                                                          19

<210> SEQ ID NO 1134
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1134
ugugaucauu gugcuguca                                                          19

<210> SEQ ID NO 1135
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1135
ugacagcaca augaucaca                                                          19

<210> SEQ ID NO 1136
<211> LENGTH: 19
```

-continued

<212> TYPE: RNA
<213> ORGANISM: artificial sequence
<220> FEATURE:
<223> OTHER INFORMATION: Synthetic sequence; sense nucleic acid molecule

<400> SEQUENCE: 1136
gugaucauug ugcugucag                                                    19

<210> SEQ ID NO 1137
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1137
cugacagcac aaugaucac                                                    19

<210> SEQ ID NO 1138
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1138
ugaucauugu gcugucagu                                                    19

<210> SEQ ID NO 1139
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1139
acugacagca caaugauca                                                    19

<210> SEQ ID NO 1140
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1140
gaucauugug cugucaguc                                                    19

<210> SEQ ID NO 1141
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1141
gacugacagc acaaugauc                                                    19

<210> SEQ ID NO 1142
<211> LENGTH: 19
<212> TYPE: RNA
<213> ORGANISM: artificial sequence
<220> FEATURE:
<223> OTHER INFORMATION: Synthetic sequence; sense nucleic acid molecule -continued

```
<400> SEQUENCE: 1142
aucauugugc ugucagucc                                                    19

<210> SEQ ID NO 1143
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1143
ggacugacag cacaaugau                                                    19

<210> SEQ ID NO 1144
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1144
ucauugugcu gucaguccu                                                    19

<210> SEQ ID NO 1145
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1145
aggacugaca gcacaauga                                                    19

<210> SEQ ID NO 1146
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1146
cauugugcug ucaguccug                                                    19

<210> SEQ ID NO 1147
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1147
caggacugac agcacaaug                                                    19

<210> SEQ ID NO 1148
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1148
gugcugucag uccuggugu                                                    19
```

-continued

```
<210> SEQ ID NO 1149
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1149
acaccaggac ugacagcac                                                   19

<210> SEQ ID NO 1150
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1150
ugcugucagu ccggugug                                                    19

<210> SEQ ID NO 1151
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1151
cacaccagga cugacagca                                                   19

<210> SEQ ID NO 1152
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1152
cugucagucc uggugugcu                                                   19

<210> SEQ ID NO 1153
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1153
agcacaccag gacugacag                                                   19

<210> SEQ ID NO 1154
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1154
caguccuggu gugcugucu                                                   19

<210> SEQ ID NO 1155
<211> LENGTH: 19
```

-continued

```
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1155
agacagcaca ccaggacug                                                      19

<210> SEQ ID NO 1156
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1156
aguccuggug ugcugucuu                                                      19

<210> SEQ ID NO 1157
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1157
aagacagcac accaggacu                                                      19

<210> SEQ ID NO 1158
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1158
guccuggugu gcugucuuc                                                      19

<210> SEQ ID NO 1159
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1159
gaagacagca caccaggac                                                      19

<210> SEQ ID NO 1160
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1160
uggugugcug ucuuccacu                                                      19

<210> SEQ ID NO 1161
<211> LENGTH: 19
<212> TYPE: RNA
<213> ORGANISM: artificial sequence
<220> FEATURE:
<223> OTHER INFORMATION: Synthetic sequence; antisense nucleic acid
```

-continued

```
        molecule

<400> SEQUENCE: 1161
aguggaagac agcacacca                                               19

<210> SEQ ID NO 1162
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1162
auuuccuugg uacaggugg                                               19

<210> SEQ ID NO 1163
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1163
ccaccuguac caaggaaau                                               19

<210> SEQ ID NO 1164
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1164
uuccuuggua caggugguu                                               19

<210> SEQ ID NO 1165
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1165
aaccaccugu accaaggaa                                               19

<210> SEQ ID NO 1166
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1166
uccuugguac aggugguuc                                               19

<210> SEQ ID NO 1167
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1167
```
gaaccaccug uaccaagga                           19

<210> SEQ ID NO 1168
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1168
ccuugguaca ggugguucu                           19

<210> SEQ ID NO 1169
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1169
agaaccaccu guaccaagg                           19

<210> SEQ ID NO 1170
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1170
acaggugguu cucuccagc                           19

<210> SEQ ID NO 1171
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1171
gcuggagaga accaccugu                           19

<210> SEQ ID NO 1172
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1172
caggugguuc ucuccagca                           19

<210> SEQ ID NO 1173
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1173
ugcuggagag aaccaccug                           19

<210> SEQ ID NO 1174

<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1174
aggugguucu cuccagcaa                                                  19

<210> SEQ ID NO 1175
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1175
uugcuggaga gaaccaccu                                                  19

<210> SEQ ID NO 1176
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1176
ggugguucuc uccagcaau                                                  19

<210> SEQ ID NO 1177
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1177
auugcuggag agaaccacc                                                  19

<210> SEQ ID NO 1178
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1178
gugguucucu ccagcaaug                                                  19

<210> SEQ ID NO 1179
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1179
cauugcugga gagaaccac                                                  19

<210> SEQ ID NO 1180
<211> LENGTH: 19
<212> TYPE: RNA
<213> ORGANISM: artificial sequence
<220> FEATURE:

<223> OTHER INFORMATION: Synthetic sequence; sense nucleic acid molecule

<400> SEQUENCE: 1180
ugguucucuc cagcaaugg                                                  19

<210> SEQ ID NO 1181
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1181
ccauugcugg agagaacca                                                  19

<210> SEQ ID NO 1182
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1182
gguucucucc agcaauggg                                                  19

<210> SEQ ID NO 1183
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1183
cccauugcug gagagaacc                                                  19

<210> SEQ ID NO 1184
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1184
guucucucca gcaauggga                                                  19

<210> SEQ ID NO 1185
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1185
ucccauugcu ggagagaac                                                  19

<210> SEQ ID NO 1186
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1186

-continued

```
gggagcuuca uucuuuacc                                               19

<210> SEQ ID NO 1187
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1187
gguaaagaau gaagcuccc                                               19

<210> SEQ ID NO 1188
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1188
ggagcuucau ucuuuacca                                               19

<210> SEQ ID NO 1189
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1189
ugguaaagaa ugaagcucc                                               19

<210> SEQ ID NO 1190
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1190
gcuucauucu uuaccaguu                                               19

<210> SEQ ID NO 1191
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1191
aacugguaaa gaaugaagc                                               19

<210> SEQ ID NO 1192
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1192
uucauucuuu accaguuug                                               19

<210> SEQ ID NO 1193
```

```
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1193
caaacuggua aagaaugaa                                                    19

<210> SEQ ID NO 1194
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1194
ucauucuuua ccaguuuga                                                    19

<210> SEQ ID NO 1195
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1195
ucaaacuggu aaagaauga                                                    19

<210> SEQ ID NO 1196
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1196
ucuuuaccag uuugaauug                                                    19

<210> SEQ ID NO 1197
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1197
caauucaaac ugguaaaga                                                    19

<210> SEQ ID NO 1198
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1198
cuuuaccagu ugaauugu                                                     19

<210> SEQ ID NO 1199
<211> LENGTH: 19
<212> TYPE: RNA
<213> ORGANISM: artificial sequence
<220> FEATURE:
```

-continued

```
<223> OTHER INFORMATION: Synthetic sequence; antisense nucleic acid
      molecule

<400> SEQUENCE: 1199
acaauucaaa cugguaaag                                               19

<210> SEQ ID NO 1200
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1200
gaauuguuug gauuuacuc                                               19

<210> SEQ ID NO 1201
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1201
gaguaaaucc aaacaauuc                                               19

<210> SEQ ID NO 1202
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1202
acccuuuuau auauucucg                                               19

<210> SEQ ID NO 1203
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1203
cgagaauaua uaaaagggu                                               19

<210> SEQ ID NO 1204
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1204
cccuuuuaua uauucucgg                                               19

<210> SEQ ID NO 1205
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1205
```
ccgagaauau auaaaaggg                                                        19

<210> SEQ ID NO 1206
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1206
ccuuuuauau auucucgga                                                        19

<210> SEQ ID NO 1207
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1207
uccgagaaua uauaaaagg                                                        19

<210> SEQ ID NO 1208
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1208
ugcucuggug ccuccaaua                                                        19

<210> SEQ ID NO 1209
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1209
uauuggaggc accagagca                                                        19

<210> SEQ ID NO 1210
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1210
gcucuggugc cuccaauac                                                        19

<210> SEQ ID NO 1211
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1211
guauuggagg caccagagc                                                        19

```
<210> SEQ ID NO 1212
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1212
cucuggugcc uccaauaca                                                          19

<210> SEQ ID NO 1213
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1213
uguauuggag gcaccagag                                                          19

<210> SEQ ID NO 1214
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1214
ucuggugccu ccaauacau                                                          19

<210> SEQ ID NO 1215
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1215
auguauugga ggcaccaga                                                          19

<210> SEQ ID NO 1216
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1216
cuggugccuc caauacaua                                                          19

<210> SEQ ID NO 1217
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1217
uauguauugg aggcaccag                                                          19

<210> SEQ ID NO 1218
<211> LENGTH: 19
<212> TYPE: RNA
<213> ORGANISM: artificial sequence
```

-continued

```
<220> FEATURE:
<223> OTHER INFORMATION: Synthetic sequence; sense nucleic acid molecule

<400> SEQUENCE: 1218
uggugccucc aauacauag                                                19

<210> SEQ ID NO 1219
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1219
cuauguauug gaggcacca                                                19

<210> SEQ ID NO 1220
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1220
ggugccucca auacauagg                                                19

<210> SEQ ID NO 1221
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1221
ccuauguauu ggaggcacc                                                19

<210> SEQ ID NO 1222
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1222
ccuccaauac auaggccug                                                19

<210> SEQ ID NO 1223
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1223
caggccuaug uauuggagg                                                19

<210> SEQ ID NO 1224
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1224
```

-continued cuccaauaca uaggccugg                                              19

<210> SEQ ID NO 1225
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1225
ccaggccuau guauuggag                                             19

<210> SEQ ID NO 1226
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1226
uccaauacau aggccuggg                                             19

<210> SEQ ID NO 1227
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1227
cccaggccua uguauugga                                             19

<210> SEQ ID NO 1228
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1228
ccaauacaua ggccugggu                                             19

<210> SEQ ID NO 1229
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1229
acccaggccu auguauugg                                             19

<210> SEQ ID NO 1230
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1230
caauacauag gccuggguu                                             19

```
<210> SEQ ID NO 1231
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1231
aacccaggcc uauguauug                                                    19

<210> SEQ ID NO 1232
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1232
aauacauagg ccuggguuu                                                    19

<210> SEQ ID NO 1233
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1233
aaacccaggc cuauguauu                                                    19

<210> SEQ ID NO 1234
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1234
auacauaggc cuggguuuu                                                    19

<210> SEQ ID NO 1235
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1235
aaaacccagg ccuauguau                                                    19

<210> SEQ ID NO 1236
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1236
ucgacuucga gccauggga                                                    19

<210> SEQ ID NO 1237
<211> LENGTH: 19
<212> TYPE: RNA
<213> ORGANISM: artificial sequence
```

-continued

```
<220> FEATURE:
<223> OTHER INFORMATION: Synthetic sequence; antisense nucleic acid
      molecule

<400> SEQUENCE: 1237
ucccauggcu cgaagucga                                                  19

<210> SEQ ID NO 1238
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1238
cgacuucgag ccaugggaa                                                  19

<210> SEQ ID NO 1239
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1239
uucccauggc ucgaagucg                                                  19

<210> SEQ ID NO 1240
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1240
aacucugccu acauguuau                                                  19

<210> SEQ ID NO 1241
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1241
auaacaugua ggcagaguu                                                  19

<210> SEQ ID NO 1242
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1242
acucugccua cauguuauc                                                  19

<210> SEQ ID NO 1243
<211> LENGTH: 19
<212> TYPE: RNA
<213> ORGANISM: artificial sequence
<220> FEATURE:
<223> OTHER INFORMATION: Synthetic sequence; antisense nucleic acid
      molecule
```

```
<400> SEQUENCE: 1243
gauaacaugu aggcagagu                                                    19

<210> SEQ ID NO 1244
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1244
ucugccuaca uguuaucuc                                                    19

<210> SEQ ID NO 1245
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1245
gagauaacau guaggcaga                                                    19

<210> SEQ ID NO 1246
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1246
cugccuacau guuaucucc                                                    19

<210> SEQ ID NO 1247
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1247
ggagauaaca uguaggcag                                                    19

<210> SEQ ID NO 1248
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1248
ugccuacaug uuaucucca                                                    19

<210> SEQ ID NO 1249
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1249
uggagauaac auguaggca                                                    19
```

<210> SEQ ID NO 1250
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1250
gccuacaugu uaucuccaa                                                             19

<210> SEQ ID NO 1251
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1251
uuggagauaa cauguaggc                                                             19

<210> SEQ ID NO 1252
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1252
ccuacauguu aucuccaaa                                                             19

<210> SEQ ID NO 1253
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1253
uuuggagaua acauguagg                                                             19

<210> SEQ ID NO 1254
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1254
cauguuaucu ccaaagcca                                                             19

<210> SEQ ID NO 1255
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1255
uggcuuugga gauaacaug                                                             19

<210> SEQ ID NO 1256
<211> LENGTH: 19
<212> TYPE: RNA

-continued

```
<213> ORGANISM: artificial sequence
<220> FEATURE:
<223> OTHER INFORMATION: Synthetic sequence; sense nucleic acid molecule

<400> SEQUENCE: 1256
auguuaucuc caaagccac                                                       19

<210> SEQ ID NO 1257
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1257
guggcuuugg agauaacau                                                       19

<210> SEQ ID NO 1258
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1258
aucuccaaag ccacagaag                                                       19

<210> SEQ ID NO 1259
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1259
cuucuguggc uuuggagau                                                       19

<210> SEQ ID NO 1260
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1260
cuccaaagcc acagaagaa                                                       19

<210> SEQ ID NO 1261
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1261
uucuucugug gcuuuggag                                                       19

<210> SEQ ID NO 1262
<211> LENGTH: 19
<212> TYPE: RNA
<213> ORGANISM: artificial sequence
<220> FEATURE:
<223> OTHER INFORMATION: Synthetic sequence; sense nucleic acid molecule
```

<400> SEQUENCE: 1262
aaauuugugg accaggcuu                                                                                  19

<210> SEQ ID NO 1263
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1263
aagccugguc cacaaauuu                                                                                  19

<210> SEQ ID NO 1264
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1264
auuuguggac caggcuugu                                                                                  19

<210> SEQ ID NO 1265
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1265
acaagccugg uccacaaau                                                                                  19

<210> SEQ ID NO 1266
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1266
uuguggacca ggcuugugg                                                                                  19

<210> SEQ ID NO 1267
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1267
ccacaagccu gguccacaa                                                                                  19

<210> SEQ ID NO 1268
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1268
uguggaccag gcuuguggc                                                                                  19

-continued

```
<210> SEQ ID NO 1269
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1269
gccacaagcc ugguccaca                                                  19

<210> SEQ ID NO 1270
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1270
gaccaggcuu guggcccaa                                                  19

<210> SEQ ID NO 1271
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1271
uugggccaca agccugguc                                                  19

<210> SEQ ID NO 1272
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1272
uuguggccca agucauuca                                                  19

<210> SEQ ID NO 1273
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1273
ugaaugacuu gggccacaa                                                  19

<210> SEQ ID NO 1274
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1274
uguggcccaa gucauucaa                                                  19

<210> SEQ ID NO 1275
<211> LENGTH: 19
<212> TYPE: RNA
```

-continued

```
<213> ORGANISM: artificial sequence
<220> FEATURE:
<223> OTHER INFORMATION: Synthetic sequence; antisense nucleic acid
      molecule

<400> SEQUENCE: 1275
uugaaugacu ugggccaca                                                 19

<210> SEQ ID NO 1276
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1276
guggcccaag ucauucaaa                                                 19

<210> SEQ ID NO 1277
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1277
uuugaaugac uugggccac                                                 19

<210> SEQ ID NO 1278
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1278
gcccaaguca uucaaaaga                                                 19

<210> SEQ ID NO 1279
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1279
ucuuuugaau gacuugggc                                                 19

<210> SEQ ID NO 1280
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1280
aaaguauggu gagucccaa                                                 19

<210> SEQ ID NO 1281
<211> LENGTH: 19
<212> TYPE: RNA
<213> ORGANISM: artificial sequence
<220> FEATURE:
<223> OTHER INFORMATION: Synthetic sequence; antisense nucleic acid
      molecule
```

-continued

<400> SEQUENCE: 1281
uugggacuca ccauacuuu                                              19

<210> SEQ ID NO 1282
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1282
aguaugguga gucccaaga                                             19

<210> SEQ ID NO 1283
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1283
ucuugggacu caccauacu                                             19

<210> SEQ ID NO 1284
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1284
guauggugag ucccaagau                                             19

<210> SEQ ID NO 1285
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1285
aucuugggac ucaccauac                                             19

<210> SEQ ID NO 1286
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1286
uauggugagu cccaagauc                                             19

<210> SEQ ID NO 1287
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1287
gaucuuggga cucaccaua                                             19

<210> SEQ ID NO 1288
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1288
ggugaguccc aagaucucu                                                                 19

<210> SEQ ID NO 1289
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1289
agagaucuug ggacucacc                                                                 19

<210> SEQ ID NO 1290
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1290
gugaguccca agaucucug                                                                 19

<210> SEQ ID NO 1291
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1291
cagagaucuu gggacucac                                                                 19

<210> SEQ ID NO 1292
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1292
aucucugcug gacaucaac                                                                 19

<210> SEQ ID NO 1293
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1293
guugaugucc agcagagau                                                                 19

<210> SEQ ID NO 1294
<211> LENGTH: 19

-continued

```
<212> TYPE: RNA
<213> ORGANISM: artificial sequence
<220> FEATURE:
<223> OTHER INFORMATION: Synthetic sequence; sense nucleic acid molecule

<400> SEQUENCE: 1294
uguggucaga gcagcucga                                                  19

<210> SEQ ID NO 1295
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1295
ucgagcugcu cugaccaca                                                  19

<210> SEQ ID NO 1296
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1296
guggucagag cagcucgac                                                  19

<210> SEQ ID NO 1297
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1297
gucgagcugc ucugaccac                                                  19

<210> SEQ ID NO 1298
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1298
aaccuuacua cagcaucua                                                  19

<210> SEQ ID NO 1299
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1299
uagaugcugu aguaagguu                                                  19

<210> SEQ ID NO 1300
<211> LENGTH: 19
<212> TYPE: RNA
<213> ORGANISM: artificial sequence
<220> FEATURE:
<223> OTHER INFORMATION: Synthetic sequence; sense nucleic acid molecule
```

-continued

```
<400> SEQUENCE: 1300
accuuacuac agcaucuau                                                    19

<210> SEQ ID NO 1301
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1301
auagaugcug uaguaaggu                                                    19

<210> SEQ ID NO 1302
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1302
ccuuacuaca gcaucuaua                                                    19

<210> SEQ ID NO 1303
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1303
uauagaugcu guaguaagg                                                    19

<210> SEQ ID NO 1304
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1304
cuuacuacag caucuauaa                                                    19

<210> SEQ ID NO 1305
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1305
uuauagaugc uguaguaag                                                    19

<210> SEQ ID NO 1306
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1306
gagcagccca uguaacuua                                                    19
```

```
<210> SEQ ID NO 1307
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1307
uaaguuacau gggcugcuc                                                19

<210> SEQ ID NO 1308
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1308
agcagcccau guaacuuac                                                19

<210> SEQ ID NO 1309
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1309
guaaguuaca ugggcugcu                                                19

<210> SEQ ID NO 1310
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1310
uggauuugcc aauucauau                                                19

<210> SEQ ID NO 1311
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1311
auaugaauug gcaaaucca                                                19

<210> SEQ ID NO 1312
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1312
ggauuugcca auucauaua                                                19

<210> SEQ ID NO 1313
<211> LENGTH: 19
```

```
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1313
uauaugaauu ggcaaaucc                                                      19

<210> SEQ ID NO 1314
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1314
auucauauau ugccaugca                                                      19

<210> SEQ ID NO 1315
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1315
ugcauggcaa uauaugaau                                                      19

<210> SEQ ID NO 1316
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1316
uucauauauu gccaugcau                                                      19

<210> SEQ ID NO 1317
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1317
augcauggca auauaugaa                                                      19

<210> SEQ ID NO 1318
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1318
ucauauauug ccaugcauu                                                      19

<210> SEQ ID NO 1319
<211> LENGTH: 19
<212> TYPE: RNA
<213> ORGANISM: artificial sequence
<220> FEATURE:
<223> OTHER INFORMATION: Synthetic sequence; antisense nucleic acid
```

-continued

```
       molecule

<400> SEQUENCE: 1319
aaugcauggc aauauauga                                           19

<210> SEQ ID NO 1320
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1320
auauugccau gcauuauca                                           19

<210> SEQ ID NO 1321
<211> LENGTH: 19
<212> TYPE: RNA
<213> ORGANISM: artificial sequence
<220> FEATURE:
<223> OTHER INFORMATION: Synthetic sequence; antisense nucleic acid
       molecule

<400> SEQUENCE: 1321
ugauaaugca uggcaauau                                           19

<210> SEQ ID NO 1322
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1322
uauugccaug cauuaucac                                           19

<210> SEQ ID NO 1323
<211> LENGTH: 19
<212> TYPE: RNA
<213> ORGANISM: artificial sequence
<220> FEATURE:
<223> OTHER INFORMATION: Synthetic sequence; antisense nucleic acid
       molecule

<400> SEQUENCE: 1323
gugauaaugc auggcaaua                                           19

<210> SEQ ID NO 1324
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1324
auugccaugc auuaucaca                                           19

<210> SEQ ID NO 1325
<211> LENGTH: 19
<212> TYPE: RNA
<213> ORGANISM: artificial sequence
<220> FEATURE:
<223> OTHER INFORMATION: Synthetic sequence; antisense nucleic acid
       molecule

<400> SEQUENCE: 1325
```

-continued

```
ugugauaaug cauggcaau                                          19

<210> SEQ ID NO 1326
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1326
uugccaugca uuaucacac                                          19

<210> SEQ ID NO 1327
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1327
gugugauaau gcauggcaa                                          19

<210> SEQ ID NO 1328
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1328
uuaucacacc acuaaugac                                          19

<210> SEQ ID NO 1329
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1329
gucauuagug gugugauaa                                          19

<210> SEQ ID NO 1330
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1330
uaucacacca cuaaugacu                                          19

<210> SEQ ID NO 1331
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1331
agucauuagu ggugugaua                                          19

<210> SEQ ID NO 1332
```

-continued

```
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1332
aucacaccac uaaugacuu                                                        19

<210> SEQ ID NO 1333
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1333
aagucauuag uggugugau                                                        19

<210> SEQ ID NO 1334
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1334
ucacaccacu aaugacuua                                                        19

<210> SEQ ID NO 1335
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1335
uaagucauua guggguga                                                         19

<210> SEQ ID NO 1336
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1336
uaaugacuua gugcaggaa                                                        19

<210> SEQ ID NO 1337
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1337
uuccugcacu aagucauua                                                        19

<210> SEQ ID NO 1338
<211> LENGTH: 19
<212> TYPE: RNA
<213> ORGANISM: artificial sequence
<220> FEATURE:
```

<223> OTHER INFORMATION: Synthetic sequence; sense nucleic acid molecule

<400> SEQUENCE: 1338
aaugacuuag ugcaggaau                                                    19

<210> SEQ ID NO 1339
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1339
auuccugcac uaagucauu                                                    19

<210> SEQ ID NO 1340
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1340
augacuuagu gcaggaaua                                                    19

<210> SEQ ID NO 1341
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1341
uauuccugca cuaagucau                                                    19

<210> SEQ ID NO 1342
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1342
ugacuuagug caggaauau                                                    19

<210> SEQ ID NO 1343
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1343
auauuccugc acuaaguca                                                    19

<210> SEQ ID NO 1344
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1344
gacuuagugc aggaauaug                                              19

<210> SEQ ID NO 1345
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1345
cauauuccug cacuaaguc                                              19

<210> SEQ ID NO 1346
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1346
acuuagugca ggaauauga                                              19

<210> SEQ ID NO 1347
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1347
ucauauuccu gcacuaagu                                              19

<210> SEQ ID NO 1348
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1348
cuuagugcag gaauaugac                                              19

<210> SEQ ID NO 1349
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1349
gucauauucc ugcacuaag                                              19

<210> SEQ ID NO 1350
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1350
uuagugcagg aauaugaca                                              19

<210> SEQ ID NO 1351

-continued

```
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1351
ugucauauuc cugcacuaa                                                        19

<210> SEQ ID NO 1352
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1352
uagugcagga auaugacag                                                        19

<210> SEQ ID NO 1353
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1353
cugucauauu ccugcacua                                                        19

<210> SEQ ID NO 1354
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1354
agugcaggaa uaugacagc                                                        19

<210> SEQ ID NO 1355
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1355
gcugucauau uccugcacu                                                        19

<210> SEQ ID NO 1356
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1356
gugcaggaau augacagca                                                        19

<210> SEQ ID NO 1357
<211> LENGTH: 19
<212> TYPE: RNA
<213> ORGANISM: artificial sequence
<220> FEATURE:
```

-continued

```
<223> OTHER INFORMATION: Synthetic sequence; antisense nucleic acid
      molecule

<400> SEQUENCE: 1357
ugcugucaua uuccugcac                                                  19

<210> SEQ ID NO 1358
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1358
ugcaggaaua ugacagcac                                                  19

<210> SEQ ID NO 1359
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1359
gugcugucau auuccugca                                                  19

<210> SEQ ID NO 1360
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1360
gaauaugaca gcacuucag                                                  19

<210> SEQ ID NO 1361
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1361
cugaagugcu gucauauuc                                                  19

<210> SEQ ID NO 1362
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1362
aauaugacag cacuucagc                                                  19

<210> SEQ ID NO 1363
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1363
```

-continued gcugaagugc ugucauauu                                                    19

<210> SEQ ID NO 1364
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1364
auaugacagc acuucagcc                                                    19

<210> SEQ ID NO 1365
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1365
ggcugaagug cugucauau                                                    19

<210> SEQ ID NO 1366
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1366
gacagcacuu cagccaagc                                                    19

<210> SEQ ID NO 1367
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1367
gcuuggcuga agugcuguc                                                    19

<210> SEQ ID NO 1368
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1368
acagcacuuc agccaagca                                                    19

<210> SEQ ID NO 1369
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1369
ugcuuggcug aagugcugu                                                    19

```
<210> SEQ ID NO 1370
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1370
cacuucagcc aagcagauu                                                   19

<210> SEQ ID NO 1371
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1371
aaucugcuug gcugaagug                                                   19

<210> SEQ ID NO 1372
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1372
acuucagcca agcagauuc                                                   19

<210> SEQ ID NO 1373
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1373
gaaucugcuu ggcugaagu                                                   19

<210> SEQ ID NO 1374
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1374
cuucagccaa gcagauucc                                                   19

<210> SEQ ID NO 1375
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1375
ggaaucugcu uggcugaag                                                   19

<210> SEQ ID NO 1376
<211> LENGTH: 19
<212> TYPE: RNA
<213> ORGANISM: artificial sequence
```

```
<220> FEATURE:
<223> OTHER INFORMATION: Synthetic sequence; sense nucleic acid molecule

<400> SEQUENCE: 1376
uucagccaag cagauucca                                              19

<210> SEQ ID NO 1377
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1377
uggaaucugc uuggcugaa                                              19

<210> SEQ ID NO 1378
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1378
ucagccaagc agauuccag                                              19

<210> SEQ ID NO 1379
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1379
cuggaaucug cuuggcuga                                              19

<210> SEQ ID NO 1380
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1380
cagccaagca gauuccagu                                              19

<210> SEQ ID NO 1381
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1381
acuggaaucu gcuuggcug                                              19

<210> SEQ ID NO 1382
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1382
```

-continued

```
ccaagcagau uccaguccc                                        19

<210> SEQ ID NO 1383
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1383
gggacuggaa ucugcuugg                                        19

<210> SEQ ID NO 1384
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1384
cccuccguuu aaagucaug                                        19

<210> SEQ ID NO 1385
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1385
caugacuuua aacggaggg                                        19

<210> SEQ ID NO 1386
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1386
ccuccguuua aagucaugg                                        19

<210> SEQ ID NO 1387
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1387
ccaugacuuu aaacggagg                                        19

<210> SEQ ID NO 1388
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1388
cuccguuuaa agucaugga                                        19
```

```
<210> SEQ ID NO 1389
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1389
uccaugacuu uaaacggag                                                    19

<210> SEQ ID NO 1390
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1390
guuuaaaguc auggaggcu                                                    19

<210> SEQ ID NO 1391
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1391
agccuccaug acuuuaaac                                                    19

<210> SEQ ID NO 1392
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1392
uuuaaaguca uggaggcua                                                    19

<210> SEQ ID NO 1393
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1393
uagccuccau gacuuuaaa                                                    19

<210> SEQ ID NO 1394
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1394
uuaaagucau ggaggcuau                                                    19

<210> SEQ ID NO 1395
<211> LENGTH: 19
<212> TYPE: RNA
<213> ORGANISM: artificial sequence
```

```
<220> FEATURE:
<223> OTHER INFORMATION: Synthetic sequence; antisense nucleic acid
      molecule

<400> SEQUENCE: 1395
auagccucca ugacuuuaa                                                    19

<210> SEQ ID NO 1396
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1396
uaaagucaug gaggcuaua                                                    19

<210> SEQ ID NO 1397
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1397
uauagccucc augacuuua                                                    19

<210> SEQ ID NO 1398
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1398
aaagucaugg aggcuauag                                                    19

<210> SEQ ID NO 1399
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1399
cuauagccuc caugacuuu                                                    19

<210> SEQ ID NO 1400
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1400
aagucaugga ggcuauagg                                                    19

<210> SEQ ID NO 1401
<211> LENGTH: 19
<212> TYPE: RNA
<213> ORGANISM: artificial sequence
<220> FEATURE:
<223> OTHER INFORMATION: Synthetic sequence; antisense nucleic acid
      molecule
```

-continued

```
<400> SEQUENCE: 1401
ccuauagccu ccaugacuu                                             19

<210> SEQ ID NO 1402
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1402
cauggaggcu auaggaucu                                             19

<210> SEQ ID NO 1403
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1403
agauccuaua gccuccaug                                             19

<210> SEQ ID NO 1404
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1404
auggaggcua uaggaucuu                                             19

<210> SEQ ID NO 1405
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1405
aagauccuau agccuccau                                             19

<210> SEQ ID NO 1406
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1406
uggaggcuau aggaucuua                                             19

<210> SEQ ID NO 1407
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1407
uaagauccua uagccucca                                             19
```

<210> SEQ ID NO 1408
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1408
ggaggcuaua ggaucuuau                                                19

<210> SEQ ID NO 1409
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1409
auaagauccu auagccucc                                               19

<210> SEQ ID NO 1410
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1410
gaggcuauag gaucuuaug                                                19

<210> SEQ ID NO 1411
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1411
cauaagaucc uauagccuc                                                19

<210> SEQ ID NO 1412
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1412
aggcuauagg aucuuaugu                                                19

<210> SEQ ID NO 1413
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1413
acauaagauc cuauagccu                                                19

<210> SEQ ID NO 1414
<211> LENGTH: 19
<212> TYPE: RNA

-continued

```
<213> ORGANISM: artificial sequence
<220> FEATURE:
<223> OTHER INFORMATION: Synthetic sequence; sense nucleic acid molecule

<400> SEQUENCE: 1414
ggcuauagga ucuuaugua                                                19

<210> SEQ ID NO 1415
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1415
uacauaagau ccuauagcc                                                19

<210> SEQ ID NO 1416
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1416
gcuauaggau cuuauguaa                                                19

<210> SEQ ID NO 1417
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1417
uuacauaaga uccuauagc                                                19

<210> SEQ ID NO 1418
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1418
uggacuuuau ucuaacuug                                                19

<210> SEQ ID NO 1419
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1419
caaguuagaa uaaagucca                                                19

<210> SEQ ID NO 1420
<211> LENGTH: 19
<212> TYPE: RNA
<213> ORGANISM: artificial sequence
<220> FEATURE:
<223> OTHER INFORMATION: Synthetic sequence; sense nucleic acid molecule
```

-continued

```
<400> SEQUENCE: 1420
aaaaguuggc aguuauggu                                             19

<210> SEQ ID NO 1421
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1421
accauaacug ccaacuuuu                                             19

<210> SEQ ID NO 1422
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1422
aaaguuggca guuaugguu                                            19

<210> SEQ ID NO 1423
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1423
aaccauaacu gccaacuuu                                             19

<210> SEQ ID NO 1424
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1424
aaguuggcag uuaugguuu                                            19

<210> SEQ ID NO 1425
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1425
aaaccauaac ugccaacuu                                            19

<210> SEQ ID NO 1426
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1426
aguuggcagu uaugguuu                                             19
```

-continued

```
<210> SEQ ID NO 1427
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1427
aaaaccauaa cugccaacu                                                         19

<210> SEQ ID NO 1428
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1428
guuggcaguu augguuuuc                                                         19

<210> SEQ ID NO 1429
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1429 gaaaccaua acugccaac                                                          19

<210> SEQ ID NO 1430
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1430
uuggcaguua ugguuuucu                                                         19

<210> SEQ ID NO 1431
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1431 agaaaccau aacugccaa                                                          19

<210> SEQ ID NO 1432
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1432
uaugguuuuc uuucaucug                                                         19

<210> SEQ ID NO 1433
<211> LENGTH: 19
<212> TYPE: RNA
```

-continued

```
<213> ORGANISM: artificial sequence
<220> FEATURE:
<223> OTHER INFORMATION: Synthetic sequence; antisense nucleic acid
      molecule

<400> SEQUENCE: 1433
cagaugaaag aaaaccaua                                              19

<210> SEQ ID NO 1434
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1434
ugguuuucuu ucaucugau                                              19

<210> SEQ ID NO 1435
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1435
aucagaugaa agaaaacca                                              19

<210> SEQ ID NO 1436
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1436
gguuuucuuu caucugaug                                              19

<210> SEQ ID NO 1437
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1437
caucagauga aagaaaacc                                              19

<210> SEQ ID NO 1438
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1438
uuucuuucau cugaugugu                                              19

<210> SEQ ID NO 1439
<211> LENGTH: 19
<212> TYPE: RNA
<213> ORGANISM: artificial sequence
<220> FEATURE:
<223> OTHER INFORMATION: Synthetic sequence; antisense nucleic acid
      molecule
```

<400> SEQUENCE: 1439
acacaucaga ugaaagaaa                                              19

<210> SEQ ID NO 1440
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1440
uucuuucauc gauguguc                                              19

<210> SEQ ID NO 1441
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1441
gacacaucag augaaagaa                                             19

<210> SEQ ID NO 1442
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1442
cuguugauuu gcuuuguag                                             19

<210> SEQ ID NO 1443
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1443
cuacaaagca aaucaacag                                             19

<210> SEQ ID NO 1444
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1444
uguugauuug cuuuguagu                                             19

<210> SEQ ID NO 1445
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1445
acuacaaagc aaaucaaca                                             19

<210> SEQ ID NO 1446
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1446
guugauuugc uuuguaguu                                                              19

<210> SEQ ID NO 1447
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1447
aacuacaaag caaaucaac                                                              19

<210> SEQ ID NO 1448
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1448
ugauuugcuu uguaguuug                                                              19

<210> SEQ ID NO 1449
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1449
caaacuacaa agcaaauca                                                              19

<210> SEQ ID NO 1450
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1450
cuuuguaguu uguugacau                                                              19

<210> SEQ ID NO 1451
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1451
augucaacaa acuacaaag                                                              19

<210> SEQ ID NO 1452
<211> LENGTH: 19

<212> TYPE: RNA
<213> ORGANISM: artificial sequence
<220> FEATURE:
<223> OTHER INFORMATION: Synthetic sequence; sense nucleic acid molecule

<400> SEQUENCE: 1452
guaguuuguu gacaucuua                                                                                          19

<210> SEQ ID NO 1453
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1453
uaagauguca acaaacuac                                                                                          19

<210> SEQ ID NO 1454
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1454
aguuuguuga caucuuaag                                                                                          19

<210> SEQ ID NO 1455
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1455
cuuaagaugu caacaaacu                                                                                          19

<210> SEQ ID NO 1456
<211> LENGTH: 19
<212> TYPE: RNA
<213> ORGANISM: artificial sequence
<220> FEATURE:
<223> OTHER INFORMATION: Synthetic sequence; sense nucleic acid molecule

<400> SEQUENCE: 1456
guuuguugac aucuuaaga                                                                                          19

<210> SEQ ID NO 1457
<211> LENGTH: 19
<212> TYPE: RNA
<213> ORGANISM: artificial sequence
<220> FEATURE:
<223> OTHER INFORMATION: Synthetic sequence; antisense nucleic acid
      molecule

<400> SEQUENCE: 1457
ucuuaagaug ucaacaaac                                                                                          19

<210> SEQ ID NO 1458
<211> LENGTH: 20
<212> TYPE: DNA
<213> ORGANISM: artificial sequence
<220> FEATURE:
<223> OTHER INFORMATION: Synthetic sequence; forward primer -continued

```
<400> SEQUENCE: 1458
gcttgtggcc caagtcattc                                                    20

<210> SEQ ID NO 1459
<211> LENGTH: 20
<212> TYPE: DNA
<213> ORGANISM: artificial sequence
<220> FEATURE:
<223> OTHER INFORMATION: Synthetic sequence; reverse primer

<400> SEQUENCE: 1459
gagtgttgat gggggtcgag                                                    20

<210> SEQ ID NO 1460
<211> LENGTH: 22
<212> TYPE: DNA
<213> ORGANISM: artificial sequence
<220> FEATURE:
<223> OTHER INFORMATION: Synthetic sequence; forward primer

<400> SEQUENCE: 1460
caccattggc aatgagcggt tc                                                 22

<210> SEQ ID NO 1461
<211> LENGTH: 22
<212> TYPE: DNA
<213> ORGANISM: artificial sequence
<220> FEATURE:
<223> OTHER INFORMATION: Synthetic sequence; reverse primer

<400> SEQUENCE: 1461
aggtctttgc ggatgtccac gt                                                 22
```

TREATMENT OF OBESITY WITH G-PROTEIN COUPLED RECEPTOR 75 (GPR75) INHIBITORS

REFERENCE TO SEQUENCE LISTING

This application includes a Sequence Listing submitted electronically as a text file named 18923804811SEQ, created on May 19, 2022, with a size of 533 kilobytes. The Sequence Listing is incorporated herein by reference.

FIELD

The present disclosure relates generally to the treatment of subjects having obesity with G-Protein Coupled Receptor 75 (GPR75) inhibitors, methods of identifying subjects having an increased risk of developing obesity, methods of detecting GPR75 variant nucleic acid molecules and variant polypeptides, and GPR75 variant nucleic acid molecules and GPR75 variant polypeptides.

BACKGROUND

Obesity and its cardio-metabolic complications, in particular type 2 diabetes and coronary artery disease, account for significant morbidity and mortality globally. There is a substantial unmet medical need for safe and effective weight loss approaches.

Lifestyle interventions on diet and physical activity are the first option for the management of obesity and overweight, but efficacy can be limited, and weight regain is common. Bariatric surgery can be highly effective for weight loss in severely obese or high-risk patients, but its use is limited by its invasive nature, cost, risk of perioperative adverse events including perioperative death. While a few drugs have demonstrated efficacy in weight-reduction, pharmacotherapy for the treatment of obesity is limited by the modest weight loss induced by most drugs, side effect profile of some agents, contraindications, low compliance, and barriers to treatment including underprescription.

GPR75 is a member of the G protein-coupled receptor family. GPRs are cell surface receptors that activate guanine-nucleotide binding proteins upon the binding of a ligand. GPR75 is activated by the chemokine CCL5/ RANTES. GPR75 is likely coupled to heterotrimeric Gq proteins, and stimulates inositol trisphosphate production and calcium mobilization upon activation. Together with CCL5/RANTES, GPR75 may play a role in neuron survival through activation of a downstream signaling pathway involving the PI3, Akt and MAP kinases. CCL5/RANTES may also regulate insulin secretion by pancreatic islet cells through activation of this receptor.

SUMMARY

The present disclosure provides methods of treating a subject having obesity, the method comprising administering a G-Protein Coupled Receptor 75 (GPR75) inhibitor to the subject. In some embodiments, the subject is GPR75 reference or is heterozygous for a GPR75 missense variant nucleic acid molecule encoding a predicted loss-of-function GPR75 polypeptide.

The present disclosure also provides methods of treating a subject having excessive weight, the method comprising administering a GPR75 inhibitor to the subject. In some embodiments, the subject is GPR75 reference or is heterozygous for a GPR75 missense variant nucleic acid molecule encoding a predicted loss-of-function GPR75 polypeptide.

The present disclosure also provides methods of treating a subject having elevated BMI, the method comprising administering a GPR75 inhibitor to the subject. In some embodiments, the subject is GPR75 reference or is heterozygous for a GPR75 missense variant nucleic acid molecule encoding a predicted loss-of-function GPR75 polypeptide.

The present disclosure also provides methods of treating a subject having elevated body fat mass, percentage, or volume, the method comprising administering a GPR75 inhibitor to the subject. In some embodiments, the subject is GPR75 reference or is heterozygous for a GPR75 missense variant nucleic acid molecule encoding a predicted loss-of-function GPR75 polypeptide.

The present disclosure also provides methods of treating a subject having excessive food intake, the method comprising administering a GPR75 inhibitor to the subject. In some embodiments, the subject is GPR75 reference or is heterozygous for a GPR75 missense variant nucleic acid molecule encoding a predicted loss-of-function GPR75 polypeptide.

The present disclosure also provides methods of treating a subject to prevent weight gain or to maintain weight loss, the method comprising administering a GPR75 inhibitor to the subject. In some embodiments, the subject is GPR75 reference or is heterozygous for a GPR75 missense variant nucleic acid molecule encoding a predicted loss-of-function GPR75 polypeptide.

The present disclosure also provides methods of treating a subject with a therapeutic agent that treats or inhibits obesity, wherein the subject is obese, the method comprising the steps of: determining whether the subject has a GPR75 missense variant nucleic acid molecule encoding a predicted loss-of-function GPR75 polypeptide by: obtaining or having obtained a biological sample from the subject; and performing or having performed a sequence analysis on the biological sample to determine if the subject has a genotype comprising the GPR75 missense variant nucleic acid molecule; and administering or continuing to administer the therapeutic agent that treats or inhibits obesity and/or a GPR75 inhibitor in a standard dosage amount to a subject that is GPR75 reference; and administering or continuing to administer the therapeutic agent that treats or inhibits obesity and/or a GPR75 inhibitor in an amount that is the same as or lower than a standard dosage amount to a subject that is heterozygous for a GPR75 missense variant nucleic acid molecule; wherein the presence of a genotype having the GPR75 missense variant nucleic acid molecule encoding a predicted loss-of-function GPR75 polypeptide indicates the subject has a reduced risk of developing obesity.

The present disclosure also provides methods of identifying a subject having an increased risk for developing obesity, wherein the method comprises: determining or having determined the presence or absence of a GPR75 missense variant nucleic acid molecule encoding a predicted loss-of-function GPR75 polypeptide in a biological sample obtained from the subject; wherein: when the subject is GPR75 reference, then the subject has an increased risk for developing obesity; and when the subject is heterozygous or homozygous for a GPR75 missense variant nucleic acid molecule, then the subject has a decreased risk for developing obesity.

The present disclosure also provides methods of detecting a human GPR75 variant nucleic acid molecule in a subject comprising assaying a sample obtained from the subject to determine whether a nucleic acid molecule in the sample is:

a genomic nucleic acid molecule comprising a nucleotide sequence: lacking a CCAGTAG heptanucleotide at positions corresponding to positions 5,540-5,546 according to SEQ ID NO:1, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:1, or the complement thereof; comprising an insertion of a thymine at a position corresponding to position 6,411 according to SEQ ID NO:6, or the complement thereof; or comprising a guanine at a position corresponding to position 5,831 according to SEQ ID NO:99, or the complement thereof; an mRNA molecule having a nucleotide sequence: lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; lacking a CCAGUAG heptanucleotide at positions corresponding to positions 600-606 according to SEQ ID NO:10, or the complement thereof; comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; lacking an AAAG tetranucleotide at positions corresponding to positions 980-983 according to SEQ ID NO:10, or the complement thereof; comprising an insertion of a uracil at a position corresponding to position 1,410 according to SEQ ID NO:15, or the complement thereof; comprising an insertion of a uracil at a position corresponding to position 1,311 according to SEQ ID NO:20, or the complement thereof; comprising an insertion of a uracil at a position corresponding to position 1,232 according to SEQ ID NO:25, or the complement thereof; comprising an insertion of a uracil at a position corresponding to position 1,471 according to SEQ ID NO:30, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof; or a cDNA molecule produced from an mRNA molecule, wherein the cDNA molecule has a nucleotide sequence: lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; lacking a CCAGTAG heptanucleotide at positions corresponding to positions 600-606 according to SEQ ID NO:34, or the complement thereof; comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; lacking an AAAG tetranucleotide at positions corresponding to positions 980-983 according to SEQ ID NO:34, or the complement thereof; comprising an insertion of a thymine at a position corresponding to position 1,410 according to SEQ ID NO:39, or the complement thereof; comprising an insertion of a thymine at a position corresponding to position 1,311 according to SEQ ID NO:44, or the complement thereof; comprising an insertion of a thymine at a position corresponding to position 1,232 according to SEQ ID NO:49, or the complement thereof; comprising an insertion of a thymine at a position corresponding to position 1,471 according to SEQ ID NO:54, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof.

The present disclosure also provides methods of detecting the presence of a human GPR75 Ala110fs, Ala116Thr, Tyr207Cys, Gln234Stop, Arg236fs, or Cys400fs variant polypeptide, comprising performing an assay on a sample obtained from a subject to determine whether a GPR75 protein in the sample comprises SEQ ID NO:56, SEQ ID NO:57, SEQ ID NO:58, SEQ ID NO:59, SEQ ID NO:60, or SEQ ID NO:108.

The present disclosure also provides isolated alteration-specific probes or alteration-specific primers comprising at least about 15 nucleotides, wherein the alteration-specific probe or alteration-specific primer comprises a nucleotide sequence which is complementary to a portion of a nucleotide sequence encoding a human GPR75 polypeptide, wherein the portion comprises a position corresponding to: positions 5,540-5,546 according to SEQ ID NO:2, or the complement thereof; positions 539-545 according to SEQ ID NO:11, or the complement thereof; positions 440-446 according to SEQ ID NO:16, or the complement thereof; positions 361-367 according to SEQ ID NO:21, or the complement thereof; positions 600-606 according to SEQ ID NO:26, or the complement thereof; positions 539-545 according to SEQ ID NO:35, or the complement thereof; positions 440-446 according to SEQ ID NO:40, or the complement thereof; positions 361-367 according to SEQ ID NO:45, or the complement thereof; or positions 600-606 according to SEQ ID NO:50, or the complement thereof; positions 5,920-5,923 according to SEQ ID NO:5, or the complement thereof; position 919-922 according to SEQ ID NO:14, or the complement thereof; positions 820-823 according to SEQ ID NO:19, or the complement thereof; positions 741-744 according to SEQ ID NO:24, or the complement thereof; position 980-983 according to SEQ ID NO:29, or the complement thereof; position 919-922 according to SEQ ID NO:38, or the complement thereof; positions 820-823 according to SEQ ID NO:43, or the complement thereof; positions 741-744 according to SEQ ID NO:48, or the complement thereof; or position 980-983 according to SEQ ID NO:53, or the complement thereof; or position 6,411 according to SEQ ID NO:6, or the complement thereof; position 1,410 according to SEQ ID NO:15, or the complement thereof; position 1,311 according to SEQ ID NO:20, or the complement thereof; position 1,232 according to SEQ ID NO:25, or the complement thereof; position 1,471 according to SEQ ID NO:30, or the complement thereof; position 1,410 according to SEQ ID NO:39, or the complement thereof; position 1,311 according to SEQ ID NO:44, or the complement thereof; position 1,232 according to SEQ ID NO:49, or the complement thereof; or position 1,471 according to SEQ ID NO:54, or the complement thereof; position 5,831 according to SEQ ID NO:61, or the complement thereof; position 830 according to SEQ ID NO:100, or the complement thereof; position 731 according to SEQ ID NO:101, or the complement thereof; position 652 according to SEQ ID NO:102, or the complement thereof; position 891 according to SEQ ID NO:103, or the complement thereof; position 830 according to SEQ ID NO:104, or the complement thereof; position 731 according to SEQ ID NO:105, or the complement thereof; position 652 according to SEQ ID NO:106, or the complement thereof; or position 891 according to SEQ ID NO:107, or the complement thereof.

The present disclosure also provides molecular complexes comprising an alteration-specific primer or an alteration-specific probe hybridized to a genomic nucleic acid molecule comprising a nucleotide sequence encoding a human GPR75 polypeptide, wherein the alteration-specific primer or the alteration-specific probe is hybridized to: nucleotides at positions corresponding to positions 5,539-5,540 according to SEQ ID NO:2, or the complement thereof; an adenine at a position corresponding to position 5,557 according to SEQ ID NO:3, or the complement thereof; a thymine at a position corresponding to position 5,911 according to SEQ ID NO:4, or the complement thereof; nucleotides at positions corresponding to positions 5,919-5,920 according to SEQ ID NO:5, or the complement thereof; a thymine at a position corresponding to position 6,411 according to SEQ ID NO:6, or the complement thereof; or a guanine at a position corresponding to position 5,831 according to SEQ ID NO:99, or the complement thereof.

The present disclosure also provides molecular complexes comprising an alteration-specific primer or an alteration-specific probe hybridized to an mRNA molecule comprising a nucleotide sequence encoding a human GPR75 polypeptide, wherein the alteration-specific primer or the alteration-specific probe is hybridized to: nucleotides at positions corresponding to positions 538-539 according to SEQ ID NO:11, or the complement thereof; nucleotides at positions corresponding to positions 439-440 according to SEQ ID NO:16, or the complement thereof; nucleotides at positions corresponding to positions 360-361 according to SEQ ID NO:21, or the complement thereof; nucleotides at positions corresponding to positions 599-600 according to SEQ ID NO:26, or the complement thereof; an adenine at a position corresponding to position 556 according to SEQ ID NO:12, or the complement thereof; an adenine at a position corresponding to position 457 according to SEQ ID NO:17, or the complement thereof; an adenine at a position corresponding to position 378 according to SEQ ID NO:22, or the complement thereof; an adenine at a position corresponding to position 617 according to SEQ ID NO:27, or the complement thereof; a uracil at a position corresponding to position 910 according to SEQ ID NO:13, or the complement thereof; a uracil at a position corresponding to position 811 according to SEQ ID NO:18, or the complement thereof; a uracil at a position corresponding to position 732 according to SEQ ID NO:23, or the complement thereof; a uracil at a position corresponding to position 971 according to SEQ ID NO:28, or the complement thereof; nucleotides at positions corresponding to positions 918-919 according to SEQ ID NO:14, or the complement thereof; nucleotides at positions corresponding to positions 819-820 according to SEQ ID NO:19, or the complement thereof; nucleotides at positions corresponding to positions 740-741 according to SEQ ID NO:24, or the complement thereof; nucleotides at positions corresponding to positions 979-980 according to SEQ ID NO:29, or the complement thereof; a uracil at a position corresponding to position 1,410 according to SEQ ID NO:15, or the complement thereof; a uracil at a position corresponding to position 1,311 according to SEQ ID NO:20, or the complement thereof; a uracil at a position corresponding to position 1,232 according to SEQ ID NO:25, or the complement thereof; a uracil at a position corresponding to position 1,471 according to SEQ ID NO:30, or the complement thereof; a guanine at a position corresponding to position 830 according to SEQ ID NO:100, or the complement thereof; a guanine at a position corresponding to position 731 according to SEQ ID NO:101, or the complement thereof; a guanine at a position corresponding to position 652 according to SEQ ID NO:102, or the complement thereof; or a guanine at a position corresponding to position 891 according to SEQ ID NO:103, or the complement thereof.

The present disclosure also provides molecular complexes comprising an alteration-specific primer or an alteration-specific probe hybridized to a cDNA molecule comprising a nucleotide sequence encoding a human GPR75 polypeptide, wherein the alteration-specific primer or the alteration-specific probe is hybridized to: nucleotides at positions corresponding to positions 538-539 according to SEQ ID NO:35, or the complement thereof; nucleotides at positions corresponding to positions 439-440 according to SEQ ID NO:40, or the complement thereof; nucleotides at positions corresponding to positions 360-361 according to SEQ ID NO:45, or the complement thereof; nucleotides at positions corresponding to positions 599-600 according to SEQ ID NO:50, or the complement thereof; an adenine at a position corresponding to position 556 according to SEQ ID NO:36, or the complement thereof; an adenine at a position corresponding to position 457 according to SEQ ID NO:41, or the complement thereof; an adenine at a position corresponding to position 378 according to SEQ ID NO:46, or the complement thereof; an adenine at a position corresponding to position 617 according to SEQ ID NO:51, or the complement thereof; a thymine at a position corresponding to position 910 according to SEQ ID NO:37, or the complement thereof; a thymine at a position corresponding to position 811 according to SEQ ID NO:42, or the complement thereof; a thymine at a position corresponding to position 732 according to SEQ ID NO:47, or the complement thereof; a thymine at a position corresponding to position 971 according to SEQ ID NO:52, or the complement thereof; nucleotides at positions corresponding to positions 918-919 according to SEQ ID NO:38, or the complement thereof; nucleotides at positions corresponding to positions 819-820 according to SEQ ID NO:43, or the complement thereof; nucleotides at positions corresponding to positions 740-741 according to SEQ ID NO:48, or the complement thereof; nucleotides at positions corresponding to positions 979-980 according to SEQ ID NO:53, or the complement thereof; a thymine at a position corresponding to position 1,410 according to SEQ ID NO:39, or the complement thereof; a thymine at a position corresponding to position 1,311 according to SEQ ID NO:44, or the complement thereof; a thymine at a position corresponding to position 1,232 according to SEQ ID NO:49, or the complement thereof; a thymine at a position corresponding to position 1,471 according to SEQ ID NO:54, or the complement thereof; a guanine at a position corresponding to position 830 according to SEQ ID NO:104, or the complement thereof; a guanine at a position corresponding to position 731 according to SEQ ID NO:105, or the complement thereof; a guanine at a position corresponding to position 652 according to SEQ ID NO:106, or the complement thereof; or a guanine at a position corresponding to position 891 according to SEQ ID NO:107, or the complement thereof.

The present disclosure also provides isolated nucleic acid molecules comprising a nucleotide sequence encoding a human GPR75 polypeptide, or the complement thereof, wherein the polypeptide comprises: a frameshift beginning at a position corresponding to position 110 according to SEQ ID NO:56, a frameshift beginning at a position corresponding to position 236 according to SEQ ID NO:59, or a frameshift beginning at a position corresponding to position 400 according to SEQ ID NO:60.

The present disclosure also provides isolated genomic nucleic acid molecules comprising a nucleotide sequence encoding a human GPR75 polypeptide, wherein the nucleotide sequence: lacks a CCAGTAG heptanucleotide at positions corresponding to positions 5,540-5,546 according to SEQ ID NO:1, or the complement thereof; lacks an AAAG tetranucleotide at positions corresponding to positions 5,920-5,923 according to SEQ ID NO:1, or the complement thereof; or comprises an insertion of a thymine at a position corresponding to position 6,411 according to SEQ ID NO:6, or the complement thereof.

The present disclosure also provides isolated mRNA molecules comprising a nucleotide sequence encoding a human GPR75 polypeptide, wherein the nucleotide sequence: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; or comprises an insertion of a uracil at a position corresponding to position 1,471 according to SEQ ID NO:30, or the complement thereof.

The present disclosure also provides isolated cDNA molecules comprising a nucleotide sequence encoding a human GPR75 polypeptide, wherein the nucleotide sequence: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; or comprises an insertion of a thymine at a position corresponding to position 1,471 according to SEQ ID NO:54, or the complement thereof.

The present disclosure also provides isolated human GPR75 polypeptides having an amino acid sequence at least about 90% identical to: SEQ ID NO:56, wherein the polypeptide lacks amino acids at positions corresponding to positions 110 to 540 according to SEQ ID NO:55; SEQ ID NO:59, wherein the polypeptide lacks amino acids at positions corresponding to positions 236 to 540 according to SEQ ID NO:55; or SEQ ID NO:60, wherein the polypeptide lacks amino acids at positions corresponding to positions 400 to 540 according to SEQ ID NO:55.

The present disclosure also provides therapeutic agents that treat or inhibit obesity for use in the treatment of obesity in a subject having: a genomic nucleic acid molecule having a nucleotide sequence encoding a human GPR75 polypeptide, wherein the nucleotide sequence: lacks a CCAGTAG heptanucleotide at positions corresponding to positions 5,540-5,546 according to SEQ ID NO:1, or the complement thereof; comprises an adenine at a position corresponding to position 5,557 according to SEQ ID NO:3, or the complement thereof; comprises a thymine at a position corresponding to position 5,911 according to SEQ ID NO:4, or the complement thereof; lacks an AAAG tetranucleotide at positions corresponding to positions 5,920-5,923 according to SEQ ID NO:1, or the complement thereof; comprises an insertion of a thymine at a position corresponding to position 6,411 according to SEQ ID NO:6, or the complement thereof; or comprises a guanine at a position corresponding to position 5,831 according to SEQ ID NO:99, or the complement thereof; an mRNA molecule having a nucleotide sequence encoding a human GPR75 polypeptide, wherein the nucleotide sequence: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; comprises an adenine at a position corresponding to position 556 according to SEQ ID NO:12, or the complement thereof; comprises an adenine at a position corresponding to position 457 according to SEQ ID NO:17, or the complement thereof; comprises an adenine at a position corresponding to position 378 according to SEQ ID NO:22, or the complement thereof; comprises an adenine at a position corresponding to position 617 according to SEQ ID NO:27, or the complement thereof; comprises a uracil at a position corresponding to position 910 according to SEQ ID NO:13, or the complement thereof; comprises a uracil at a position corresponding to position 811 according to SEQ ID NO:18, or the complement thereof; comprises a uracil at a position corresponding to position 732 according to SEQ ID NO:23, or the complement thereof; comprises a uracil at a position corresponding to position 971 according to SEQ ID NO:28, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; comprises an insertion of a uracil at a position corresponding to position 1,471 according to SEQ ID NO:30, or the complement thereof; comprises a guanine at a position corresponding to position 830 according to SEQ ID NO:100, or the complement thereof; comprises a guanine at a position corresponding to position 731 according to SEQ ID NO:101, or the complement thereof; comprises a guanine at a position corresponding to position 652 according to SEQ ID NO:102, or the complement thereof; or comprises a guanine at a position corresponding to position 891 according to SEQ ID NO:103, or the complement thereof; or a cDNA molecule having a nucleotide sequence encoding a human GPR75 polypeptide, wherein the nucleotide sequence: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; comprises an adenine at a position corresponding to position 556 according to SEQ ID NO:36, or the complement thereof; comprises an adenine at a position corresponding to position 457 according to SEQ ID NO:41, or the complement thereof; comprises an adenine at a position corresponding to position 378 according to SEQ ID NO:46, or the complement thereof; comprises an adenine at a position corresponding to position 617 according to SEQ ID NO:51, or the complement thereof; comprises a thymine at a position corresponding to position 910 according to SEQ ID NO:37, or the complement thereof; comprises a thymine at a position corresponding to position 811 according to SEQ ID NO:42, or the complement thereof; comprises a thymine at a position corresponding to position 732 according to SEQ ID NO:47, or the complement thereof; comprises a thymine at a position corresponding to position 971 according to SEQ ID NO:52, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; comprises an insertion of a thymine at a position corresponding to position 1,471 according to SEQ ID NO:54, or the complement thereof; comprises a guanine at a position corresponding to position 830 according to SEQ ID NO:104, or the complement thereof; comprises a guanine at a position corresponding to position 731 according to SEQ ID NO:105, or the complement thereof; comprises a guanine at a position corresponding to position 652 according to SEQ ID NO:106, or the complement thereof; or comprises a guanine at a position corresponding to position 891 according to SEQ ID NO:107, or the complement thereof.

The present disclosure also provides GPR75 inhibitors for use in the treatment of obesity in a subject having: a genomic nucleic acid molecule having a nucleotide sequence encoding a human GPR75 polypeptide, wherein the nucleotide sequence: lacks a CCAGTAG heptanucleotide at positions corresponding to positions 5,540-5,546 according to SEQ ID NO:1, or the complement thereof; comprises an adenine at a position corresponding to position 5,557 according to SEQ ID NO:3, or the complement thereof; comprises a thymine at a position corresponding to position 5,911 according to SEQ ID NO:4, or the complement thereof; lacks an AAAG tetranucleotide at positions corresponding to positions 5,920-5,923 according to SEQ ID NO:1, or the complement thereof; comprises an insertion of a thymine at a position corresponding to position 6,411 according to SEQ ID NO:6, or the complement thereof; or comprises a guanine at a position corresponding to position 5,831 according to SEQ ID NO:99, or the complement thereof; an mRNA molecule having a nucleotide sequence encoding a human GPR75 polypeptide, wherein the nucleotide sequence: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; comprises an adenine at a position corresponding to position 556 according to SEQ ID NO:12, or the complement thereof; comprises an adenine at a position corresponding to position 457 according to SEQ ID NO:17, or the complement thereof; comprises an adenine at a position corresponding to position 378 according to SEQ ID NO:22, or the complement thereof; comprises an adenine at a position corresponding to position 617 according to SEQ ID NO:27, or the complement thereof; comprises a uracil at a position corresponding to position 910 according to SEQ ID NO:13, or the complement thereof; comprises a uracil at a position corresponding to position 811 according to SEQ ID NO:18, or the complement thereof; comprises a uracil at a position corresponding to position 732 according to SEQ ID NO:23, or the complement thereof; comprises a uracil at a position corresponding to position 971 according to SEQ ID NO:28, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; comprises an insertion of a uracil at a position corresponding to position 1,471 according to SEQ ID NO:30, or the complement thereof; comprises a guanine at a position corresponding to position 830 according to SEQ ID NO:100, or the complement thereof; comprises a guanine at a position corresponding to position 731 according to SEQ ID NO:101, or the complement thereof; comprises a guanine at a position corresponding to position 652 according to SEQ ID NO:102, or the complement thereof; or comprises a guanine at a position corresponding to position 891 according to SEQ ID NO:103, or the complement thereof; or a cDNA molecule having a nucleotide sequence encoding a human GPR75 polypeptide, wherein the nucleotide sequence: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; comprises an adenine at a position corresponding to position 556 according to SEQ ID NO:36, or the complement thereof; comprises an adenine at a position corresponding to position 457 according to SEQ ID NO:41, or the complement thereof; comprises an adenine at a position corresponding to position 378 according to SEQ ID NO:46, or the complement thereof; comprises an adenine at a position corresponding to position 617 according to SEQ ID NO:51, or the complement thereof; comprises a thymine at a position corresponding to position 910 according to SEQ ID NO:37, or the complement thereof; comprises a thymine at a position corresponding to position 811 according to SEQ ID NO:42, or the complement thereof; comprises a thymine at a position corresponding to position 732 according to SEQ ID NO:47, or the complement thereof; comprises a thymine at a position corresponding to position 971 according to SEQ ID NO:52, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; comprises an insertion of a thymine at a position corresponding to position 1,471 according to SEQ ID NO:54, or the complement thereof; comprises a guanine at a position corresponding to position 830 according to SEQ ID NO:104, or the complement thereof; comprises a guanine at a position corresponding to position 731 according to SEQ ID NO:105, or the complement thereof; comprises a guanine at a position corresponding to position 652 according to SEQ ID NO:106, or the complement thereof; or comprises a guanine at a position corresponding to position 891 according to SEQ ID NO:107, or the complement thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying figures, which are incorporated in and constitute a part of this specification, illustrate several features of the present disclosure.

FIG. 1 shows baseline characteristics of individuals included in the exome-wide association study. Abbreviations: UKB, UK Biobank; GHS, Geisinger Health System; MCPS, Mexico City Prospective Study; SD, standard deviation; N, number of participants; WHO, World Health Organization; IQR, interquartile range; kg/m², kilograms per square meter; mg/dL, milligrams per deciliter; mmHg, millimeters of mercury.

FIG. 2 shows association results for GPR75 with body mass index in the UKB, GHS and MCPS cohorts. Abbreviations: CI, confidence intervals; SD, standard deviation; BMI, body mass index; AAF, alternative allele frequency; RR, reference-reference genotype; RA, reference-alternative heterozygous genotype; AA, alternative-alternative homozygous genotype; pLOF, predicted loss of function; UKB, UK Biobank; GHS, Geisinger Health System MyCode study; MCPS, Mexico City Prospective Study.

FIG. 3 shows association of GPR75 with body mass index in the exome-wide gene-burden analysis. The Table reports association statistics for the GPR75 gene for which the gene burden of rare pLOF variants was associated with body mass index at the exome-wide level of statistical significance ($p<3.6\times10^{-7}$). Analyses were performed in 645,626 participants from the UKB, GHS and MCPS studies. Genomic coordinates reflect chromosome and physical position in base pairs according to Genome Reference Consortium Human Build 38. Abbreviations: CI, confidence interval; SD, standard deviation; BMI, body mass index; AAF, alternative allele frequency; RR, reference-reference genotype; RA, reference-alternative heterozygous genotype; AA, alternative-alternative homozygous genotype; pLOF, predicted loss of function; Missense (1/5), missense variant predicted to be deleterious by at least 1 out of 5 in silico prediction algorithms; Missense (5/5), missense variant predicted to be deleterious by 5 out of 5 in silico prediction algorithms.

FIG. 5 shows association with body mass index of GPR75 pLOF variants within age and sex subgroups. Abbreviations: Confidence interval, CI; standard deviation, SD; body mass index, BMI; alternative allele frequency, AAF; P-value, p; reference-reference genotype, RR; reference-alternative genotype, RA; alternative-alternative genotype, AA; kilograms per square meter, kg/m²; predicted loss of function, pLOF.

FIG. 6 shows association with risk of obesity for GPR75 pLOF variants. Abbreviations: OR, odds ratio; CI, confidence intervals; P-value, p; AAF, alternative allele frequency; reference-reference genotype, RR; reference-alternative genotype, RA; alternative-alternative genotype, AA; pLOF, predicted loss of function. Results are from a meta-analysis of the UKB, GHS and MCPS studies.

FIG. 8 shows association of GPR75 pLOF variants with self-reported thinner than average comparative body size at age 10 in UKB. Abbreviations: predicted loss of function, pLOF; UK Biobank, UKB; alternative allele frequency, AAF; confidence interval, CI; odds ratio, OR; P-value, p; reference-reference genotype, RR; reference-alternative genotype, RA; alternative-alternative genotype, AA.

FIG. 10 shows association of pLOF genetic variants in GPR75 with cardio-metabolic phenotypes in the UKB, GHS and MCPS studies. Abbreviations: P-value, p; SD, standard deviations; CI, confidence intervals; pLOF, predicted loss of function; AAF, alternative allele frequency; RR, reference-reference genotype; RA, reference-alternative heterozygous genotype; AA, alternative-alternative homozygous genotype; Hemoglobin A1C, HbA1c; Aspartate transaminase, AST; Alanine transaminase, ALT; High-density lipoprotein cholesterol, HDL-C; Low-density lipoprotein cholesterol, LDL-C; milligrams per deciliter, mg/dL; millimetre of mercury, mmHg; units per liter, U/L.

FIG. 12 shows GPR75 predicted loss of function variants identified by exome-sequencing. The Table lists the predicted loss of function (pLOF) variants in the GPR75 gene found by exome sequencing which contributed to the gene burden analysis. Imputation INFO score values below 0.3 are typically considered to be of very low quality. Abbreviations: chromosome, position, reference, alternative, CPRA; alternative allele frequency, AAF; complementary DNA, cDNA; human genome variation society, HGVS.

FIG. 13 shows no association with BMI for the burden of rare nonsynonymous variants in ASB3 or GPR75-ASB3. Abbreviations: alternative allele frequency, AAF; confidence intervals, CI; standard deviation, SD; body mass index, BMI; kilograms per square meter, kg/m$^2$; P-value, p; reference-reference genotype, RR; reference-alternative genotype, RA; alternative-alternative genotype, AA; predicted loss of function, pLOF.

FIG. 14 shows association with BMI of the burden of pLOF variants in GPR75 after adjusting for ASB3, GPR75-ASB3 and common variants genotypes in the region. Abbreviations: Confidence interval, CI; standard deviation, SD; body mass index, BMI; kilograms per square meter, kg/m$^2$; P-value, p; alternative allele frequency, AAF; reference-reference genotype, RR; reference-alternative genotype, RA; alternative-alternative genotype, AA; predicted loss of function, pLOF. * standard covariates included all fine-mapped common variants from the GWAS analysis including rs59428052 near ASB3.

FIG. 15 shows common variants associated with BMI at the GPR75 locus. The Table reports a list of 26 common variants which were associated with BMI at the genome-wide threshold of statistical significance (p<5×10$^{-8}$) within 500 kb either side of GPR75 in Europeans. The variants are annotated to the nearest gene, and whether they are in LD (R^2>0.8) with an eQTL sentinel or nonsynonymous coding variant. At the GPR75 locus, no common variants were associated with BMI at genome-wide significance in admixed Americans. Abbreviations: chromosome, position, reference, alternative, CPRA; alternative allele frequency, AAF; posterior probability of causal association, PPA; linkage disequilibrium, LD; expression quantitative trait loci, eQTL.

FIG. 17 shows association of pLOF genetic variants in GPR75 with body mass index in sensitivity analyses. The Table reports leave-one-out analyses excluding one genetic variant at a time as well as an analysis excluding variants associated with lower BMI in individual-variant analyses (bottom row). Abbreviations: CI, confidence intervals; SD, standard deviation; BMI, body mass index; p, P-value; pLOF, predicted loss of function.

FIG. 18 shows predicted loss of function variants in GPR75 associated with BMI in individual variant analyses. This Table reports association statistics for GPR75 pLOF variants which were included in the gene burden analysis and were also individually associated with BMI at an inverse-variance weighted meta-analysis p<0.05. Abbreviations: AAF, alternative allele frequency; CI, confidence intervals; SD, standard deviation; BMI, body mass index; P-value, p; frame shift, fs; pLOF, predicted loss of function.

FIG. 19 shows in vitro expression studies of two predicted loss-of-function genetic variants in GPR75. Panel A shows results of quantitative reverse transcription polymerase chain reaction experiments which measured GPR75 mRNA levels. Expression of GPR75 was calculated relative to the beta-actin gene. Values represent the mean and standard deviation of 3 technical replicates representative of 1 of 3 biological replicate experiments performed for each condition. Panel B shows Western blotting analysis of GPR75 protein levels. GPR75 Ala110fs and Gln234* protein products correspond to the predicted molecular weight of 14 and 25 kDa, respectively. The results are representative of 3 biological replicates. Panel C shows immunofluorescence staining experiments describing the cellular localization of GPR75. The top images show intracellular staining achieved by membrane permeabilization, while the bottom images show plasma membrane localization (non-permeabilized cellular membrane). Panel D shows flow cytometry analysis of the cell surface expression of GPR75. Identified cell populations are presented in percent (%) of live HA-TAG GPR75 positive cells. Values represent the mean of 4 biological replicates per condition and their standard deviation. All experiments were performed in HEK293 cells that were transfected with green fluorescent protein control plasmids (Control), GPR75-wildtype (GPR75), GPR75-Ala110fs or GPR75-Gln234* plasmids. Abbreviations: SSC, side scatter; HA, hemagglutinin tag.

FIG. 20 shows association with BMI of N- vs C-terminal truncating genetic variants in GPR75. Abbreviations: CI, confidence intervals; SD, standard deviation; BMI, body mass index; p, p-value; AAF, alternative allele frequency; RR, reference-reference genotype; RA, reference-alternative heterozygous genotype; AA, alternative-alternative homozygous genotype; kg/m$^2$, kilograms per square meter.

FIG. 21 shows average body weights in GPR75 WT (designated with HIST and WT) and homozygote knockouts (designated with KO) male (top panel) and female (bottom panel) mice.

FIG. 24 shows weight-gain during high-fat diet and metabolic phenotype in mice with a genetic deletion of Gpr75. Panel A shows weekly body weight gain during a 14-weeks high-fat diet challenge; Panel B shows changes in fasting blood glucose before and after the high-fat diet challenge; Panel C shows results of a glucose tolerance test at the end of the 14-week high-fat diet challenge; Panel D shows plasma insulin at the end of the 14-week high-fat diet challenge. Each panel shows results in Gpr75$^{+/+}$ (WT), Gpr75$^{+/-}$ (HET), and Gpr75$^{-/-}$ (KO) mice. Number of mice included in each group and analysis are in parenthesis. Results are presented as mean±standard error. Abbreviations: ns, not statistically-significant; *p<0.05, p<0.01, *p<0.001, ****p<0.0001 by two-way ANOVA with Tukey's multiple comparisons test.

DESCRIPTION

Figure 4:
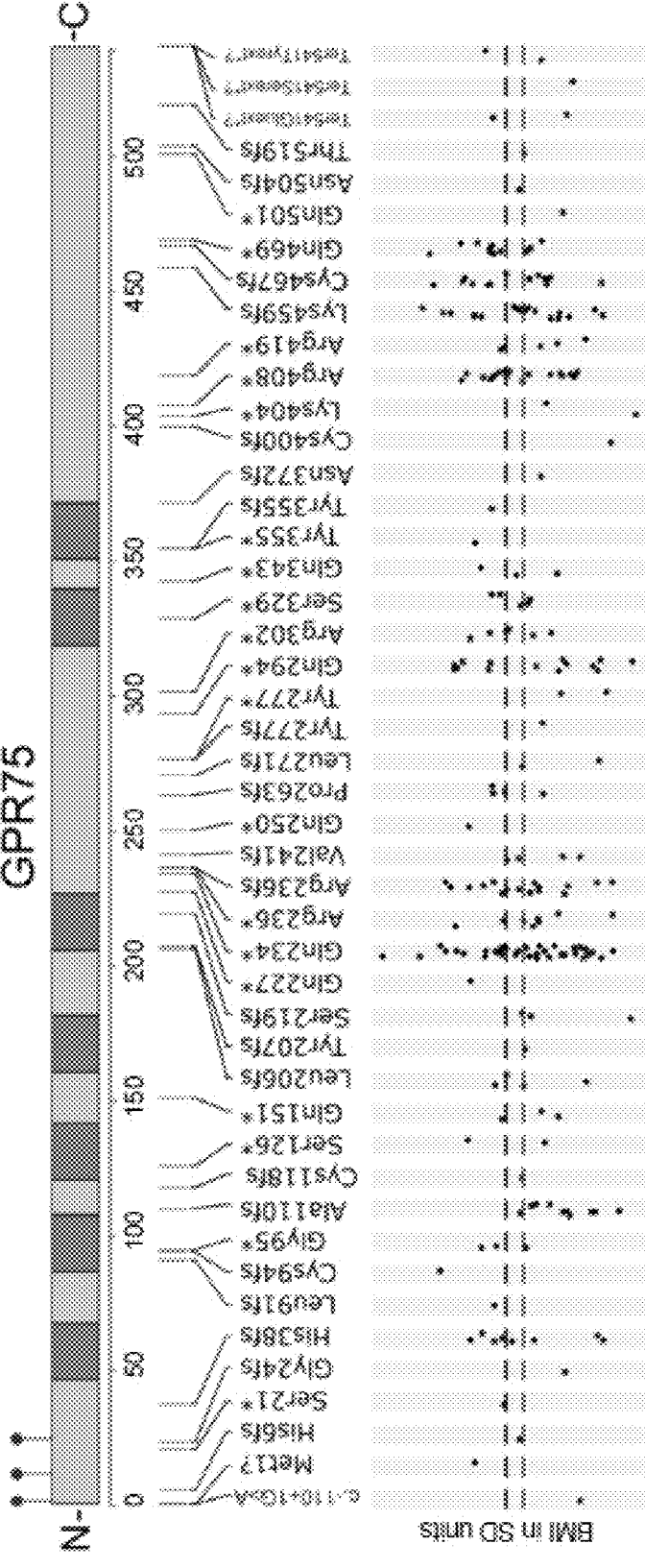
FIG. 4 shows protein-truncating variants in GPR75 associated with lower body mass index in humans. Panel A shows a linear model of the GPR75 protein and its domains (top; intra- and extra-cellular domains in yellow, transmembrane domains in orange), the distribution on the GPR75 protein of 46 predicted loss of function variants found by exome sequencing (middle) and the distribution of BMI in standardized units among heterozygous carriers of each variant (bottom). In the bottom sub-panel, horizontal blue bars show the mean BMI in non-carriers, while horizontal red bars show the overall covariates-adjusted mean BMI in carriers of any predicted loss-of-function genetic variant in GPR75. Panel B shows meta-analysis of the association with BMI of predicted loss-of-function variants in GPR75 in discovery and additional cohorts. Abbreviations: CI, confidence interval; RR, reference-reference genotype; RA, reference-alternative heterozygous genotype; AA, alternative-alternative homozygous genotype; DHS, Dallas Heart Study; SINAI, Mount Sinai BioMe cohort; DUKE, Duke Catheterization Genetics cohort; TAICHI, Taiwanese Chinese persons from the Taiwan Metabochip Consortium; PMBB, University of Pennsylvania Medicine BioBank; MALMO, Malmö Diet and Cancer Study; AFR, African ancestry; AMR; American ancestry; EAS, East Asian ancestry; EUR, European ancestry; SAS, South Asian ancestry. MCPS included individuals of Admixed American ancestry.
Figure 4:
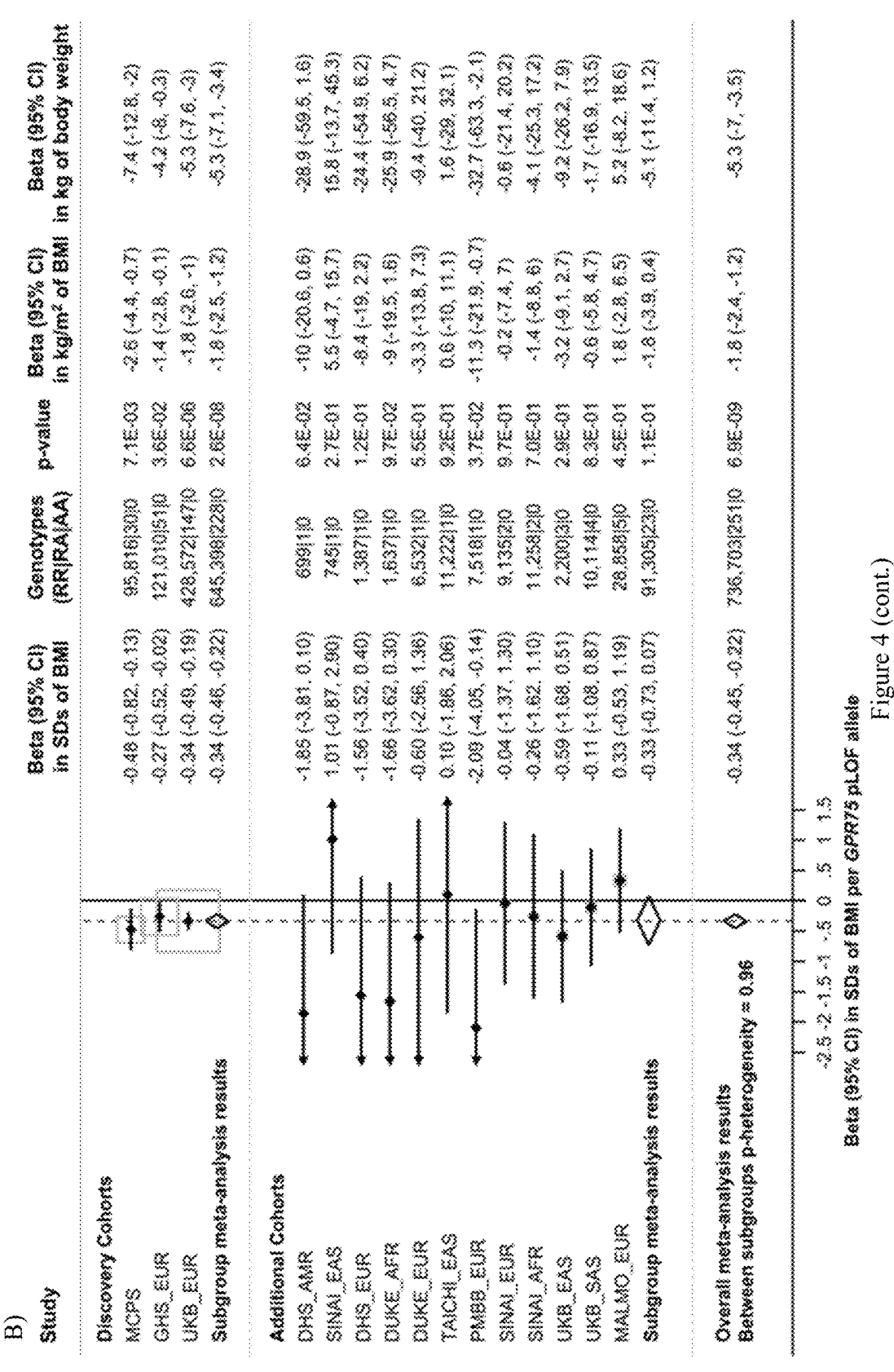

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or alternatively phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

Variants in the GPR75 gene associated with a decreased risk of developing obesity, excessive weight, elevated BMI, elevated body fat mass, percentage, or volume, and/or excessive food intake, in subjects has been identified in accordance with the present disclosure. For example, a genetic alteration that deletes the CCAGTAG heptanucleotide of positions 5,540-5,546 in the human GPR75 reference (see, SEQ ID NO:1), or changes the guanine nucleotide of position 5,557 in the human GPR75 reference (see, SEQ ID NO:1) to adenine, or the cytosine nucleotide of position 5,911 in the human GPR75 reference (see, SEQ ID NO:1) to thymine, or deletes the AAAG tetranucleotide at positions 5,920-5,923 in the human GPR75 reference (see, SEQ ID NO:1), or inserts the thymine nucleotide at position 6,411 in the human GPR75 reference (see, SEQ ID NO:1) has been observed to indicate that the human having such an alteration may have a decreased risk of developing obesity, excessive weight, elevated BMI, elevated body fat mass, percentage, or volume, and/or excessive food intake. It is believed that no variants of the GPR75 gene or protein have any known association with obesity, body weight, BMI, body fat mass, percentage, or volume, and/or body lean mass, percentage, or volume. Altogether, the genetic analyses described herein surprisingly indicate that the GPR75 gene and, in particular, variants in the GPR75 gene, associate with a decreased risk of developing obesity, associate with lower weight, lower BMI, lower body fat mass, percentage, or volume, and/or lower lean body mass, percentage, or volume. Therefore, subjects that are GPR75 reference that have an increased risk of developing obesity, excessive weight, elevated BMI, elevated body fat mass, percentage, or volume, and/or excessive food intake may be treated such that obesity is prevented, the symptoms thereof are reduced, and/or development of symptoms is repressed. Accordingly, the present disclosure provides methods of leveraging the identification of such variants in subjects to identify or stratify risk in such subjects of developing obesity, excessive weight, elevated BMI, elevated body fat mass, percentage, or volume, and/or excessive food intake, or to diagnose subjects as having an increased risk of developing obesity, excessive weight, elevated BMI, elevated body fat mass, percentage, or volume, and/or excessive food intake, such that subjects at risk or subjects with active disease may be treated accordingly. Additionally, the present disclosure provides isolated GPR75 variant genomic nucleic acid molecules, variant mRNA molecules, and variant cDNA molecules. Also provided herein are GPR75 loss-of-function variant nucleic acid molecules discovered to be associated with decreased risk of developing obesity, excessive weight, elevated BMI, elevated body fat mass, percentage, or volume, and/or excessive food intake.

Additional missense variants in the GPR75 gene that may be associated with a decreased risk of developing obesity, excessive weight, elevated BMI, elevated body fat mass, percentage, or volume, and/or excessive food intake comprise (according to GRCh38/hg38 (December 2013) human genome assembly) (and, hence, can be included in any of the embodiments described herein): a substitution of thymine with cytosine at the chromosome 2 position 53,854,656 resulting in replacement of glutamine with arginine at a position corresponding to position 34 according to SEQ ID NO:55; a substitution of guanine with alanine at the chromosome 2 position 53,854,330 resulting in replacement of arginine with tryptophan at a position corresponding to position 143 according to SEQ ID NO:55; a substitution of thymine with cytosine at the chromosome 2 position 53,854, 321 resulting in replacement of methionine with valine at a position corresponding to position 146 according to SEQ ID NO:55; a substitution of cytosine with guanine at the chromosome 2 position 53,854,191 resulting in replacement of cysteine with serine at a position corresponding to position 189 according to SEQ ID NO:55; a substitution of alanine with guanine at the chromosome 2 position 53,853,780 resulting in replacement of isoleucine with threonine at a position corresponding to position 326 according to SEQ ID NO:55; a substitution of thymine with adenine at the chromosome 2 position 53,853,634 resulting in replacement of isoleucine with leucine at a position corresponding to position 375 according to SEQ ID NO:55; and a substitution of cytosine with thymine at the chromosome 2 position 53,853, 181 resulting in replacement of glutamic acid with lysine at a position corresponding to position 526 according to SEQ ID NO:55.

Additional variants in the GPR75 gene may be associated with an increased risk of developing obesity, excessive weight, elevated BMI, elevated body fat mass, percentage, or volume, and/or excessive food intake, in subjects, and they may be considered gain-of-function (GOF) variants. Such GOF may include (according to GRCh38/hg38 (December 2013) human genome assembly): a substitution of adenine with thymine at the chromosome 2 position 53,854, 437 resulting in replacement of phenylalanine with tyrosine at position corresponding to position 107 according to SEQ ID NO:55; and a substitution of guanine with adenine at the chromosome 2 position 53,853,697 resulting in replacement of leucine with phenylalanine at position corresponding to position 354 according to SEQ ID NO:55. Thus, subjects having either variant may be treated with a GPR75 inhibitor. Such subjects can be assessed for the risk of developing obesity, excessive weight, elevated BMI, elevated body fat mass, percentage, or volume, and/or excessive food intake by detecting the presence of a GOF variant.

For purposes of the present disclosure, any particular human can be categorized as having one of three GPR75 genotypes: i) GPR75 reference; ii) heterozygous for a GPR75 missense variant nucleic acid molecule encoding a predicted loss-of-function GPR75 polypeptide; or iii) homozygous for a GPR75 missense variant nucleic acid molecule encoding a predicted loss-of-function GPR75 polypeptide. A human is GPR75 reference when the human does not have a copy of a GPR75 missense variant nucleic acid molecule. A human is heterozygous for a GPR75 missense variant nucleic acid molecule encoding a predicted loss-of-function GPR75 polypeptide when the human has a single copy of a GPR75 missense variant nucleic acid molecule encoding a predicted loss-of-function GPR75 polypeptide. As used herein, a GPR75 missense variant nucleic acid molecule is any GPR75 nucleic acid molecule (such as, a genomic nucleic acid molecule, an mRNA molecule, or a cDNA molecule) encoding a GPR75 polypeptide having a partial loss-of-function, a complete loss-of-function, a predicted partial loss-of-function, or a predicted complete loss-of-function. A human who has a GPR75 polypeptide having a partial loss-of-function (or predicted partial loss-of-function) is hypomorphic for GPR75. The GPR75 predicted loss-of-function variant nucleic acid molecule can be any nucleic acid molecule encoding GPR75 Ala110fs, Ala116Thr, Tyr207Cys, Gln234Stop, Arg236fs, or Cys400fs. The GPR75 missense variant nucleic acid molecule can also be any nucleic acid molecule encoding Lys404* and Ser219fs, or can be c.−110+1G>A. A human is homozygous for a GPR75 missense variant nucleic acid molecule encoding a predicted loss-of-function GPR75 polypeptide when the human has two copies of a GPR75 missense variant nucleic acid molecule.

For subjects that are genotyped or determined to be GPR75 reference, such subjects have an increased risk of developing obesity, excessive weight, elevated BMI, elevated body fat mass, percentage, or volume, and/or excessive food intake. For subjects that are genotyped or determined to be either GPR75 reference or heterozygous for a GPR75 missense variant nucleic acid molecule encoding a predicted loss-of-function GPR75 polypeptide, such subjects can be treated with a GPR75 inhibitor.

In any of the embodiments described herein, the GPR75 missense variant nucleic acid molecule can be any GPR75 nucleic acid molecule (such as, for example, genomic nucleic acid molecule, mRNA molecule, or cDNA molecule) encoding a GPR75 polypeptide having a partial loss-of-function, a complete loss-of-function, a predicted partial loss-of-function, or a predicted complete loss-of-function. For example, the GPR75 missense variant nucleic acid molecule can be any nucleic acid molecule encoding GPR75 Ala110fs, Ala116Thr, Tyr207Cys, Gln234Stop, Arg236fs, or Cys400fs. The GPR75 missense variant nucleic acid molecule can also be any nucleic acid molecule encoding Lys404* and Ser219fs, or can be c.−110+1G>A.

GPR75 missense variant nucleic acid molecules also include, but are not limited to, 2:53853134:T:G, 2:53853135:T:G, 2:53853136:A:C, 2:53853200:GGT:G, 2:53853245:GT:G, 2:53853256:G:A, 2:53853352:G:A, 2:53853354:CCA:C, 2:53853382:TG:T, 2:53853502:T:A, 2:53853535:G:A, 2:53853547:T:A, 2:53853560:G:GA, 2:53853641:GTT:G, 2:53853680:CAATTCAAACTGGT:C, 2:53853692:G:T, 2:53853730:G:A, 2:53853771:G:C, 2:53853853:G:A, 2:53853877:G:A, 2:53853926:G:T, 2:53853927:T:TA, 2:53853946:G:GT, 2:53853967:TGG:T, 2:53854009:G:A, 2:53854037:A:AG, 2:53854045:ACTTT: A, 2:53854051:T:A, 2:53854057:G:A, 2:53854078:G:A, 2:53854099:CAG:C, 2:53854135:CAT:C, 2:53854137: TAGAG:T, 2:53854306:G:A, 2:53854380:G:C, 2:53854409:A:AG, 2:53854421:ACTACTGG:A, 2:53854474:C:A, 2:53854476:C:CA, 2:53854485:AG:A, 2:53854644:TG:T, 2:53854685:TC:T, 2:53854695:G:T, 2:53854740:TG:T, 2:53854755:A:G, and 2:53859827:C:T (according to GRCh38/hg38 (December 2013) human genome assembly).

In any of the embodiments described herein, the GPR75 predicted loss-of-function polypeptide can be any GPR75 polypeptide having a partial loss-of-function, a complete loss-of-function, a predicted partial loss-of-function, or a predicted complete loss-of-function. In any of the embodiments described herein, the GPR75 predicted loss-of-function polypeptide can be any of the GPR75 polypeptides described herein including, for example, GPR75 Ala110fs, Ala116Thr, Tyr207Cys, Gln234Stop, Arg236fs, or Cys400fs. The GPR75 predicted loss-of-function polypeptide can also be Lys404* or Ser219fs.

In any of the embodiments described herein, the subject can be obese, or have excessive weight, elevated BMI, elevated body fat mass, percentage, or volume, and/or excessive food intake. In any of the embodiments described herein, the subject can be obese. In any of the embodiments described herein, the subject can have excessive weight. In any of the embodiments described herein, the subject can have elevated BMI. In any of the embodiments described herein, the subject can have elevated body fat mass, percentage, or volume. In any of the embodiments described herein, the subject can have excessive food intake.

Symptoms of obesity include, but are not limited to, excess body fat accumulation (particularly around the waist), breathlessness, increased sweating, snoring, inability to cope with sudden physical activity, feeling very tired every day, back and joint pains, skin problems (from moisture accumulating in the folds of skin).

The present disclosure provides methods of treating a subject having obesity, the methods comprising administering a GPR75 inhibitor to the subject. In some embodiments, the subject is GPR75 reference or is heterozygous for a GPR75 missense variant nucleic acid molecule encoding a predicted loss-of-function GPR75 polypeptide.

The present disclosure also provides methods of treating a subject having excessive weight, the methods comprising administering a GPR75 inhibitor to the subject. In some embodiments, the subject is GPR75 reference or is heterozygous for a GPR75 missense variant nucleic acid molecule encoding a predicted loss-of-function GPR75 polypeptide.

The present disclosure also provides methods of treating a subject having elevated BMI, the methods comprising administering a GPR75 inhibitor to the subject. In some embodiments, the subject is GPR75 reference or is heterozygous for a GPR75 missense variant nucleic acid molecule encoding a predicted loss-of-function GPR75 polypeptide.

The present disclosure also provides methods of treating a subject having elevated body fat mass, percentage, or volume, the methods comprising administering a GPR75 inhibitor to the subject. In some embodiments, the subject is GPR75 reference or is heterozygous for a GPR75 missense variant nucleic acid molecule encoding a predicted loss-of-function GPR75 polypeptide.

The present disclosure also provides methods of treating a subject having excessive food intake, the methods comprising administering a GPR75 inhibitor to the subject. In some embodiments, the subject is GPR75 reference or is heterozygous for a GPR75 missense variant nucleic acid molecule encoding a predicted loss-of-function GPR75 polypeptide.

The present disclosure also provides methods of treating a subject to prevent weight gain or to maintain weight loss, the method comprising administering a GPR75 inhibitor to the subject. In some embodiments, the subject is GPR75 reference or is heterozygous for a GPR75 missense variant nucleic acid molecule encoding a predicted loss-of-function GPR75 polypeptide.

In any of the embodiments described herein in which a subject is treated with a GPR75 inhibitor, the subject can be GPR75 reference (i.e., the subject does not have a copy of a GPR75 missense variant nucleic acid molecule encoding a predicted loss-of-function GPR75 polypeptide). In any of the embodiments described herein in which a subject is treated with a GPR75 inhibitor, the subject can be heterozygous for a GPR75 missense variant nucleic acid molecule encoding a predicted loss-of-function GPR75 polypeptide (i.e., the subject only has a single copy a reference GPR75 nucleic acid molecule). The subject's genotype need not be determined at the time of the administration of the GPR75 inhibitor.

In some embodiments, the GPR75 inhibitor comprises an inhibitory nucleic acid molecule. Examples of inhibitory nucleic acid molecules include, but are not limited to, antisense nucleic acid molecules, small interfering RNAs (siRNAs), and short hairpin RNAs (shRNAs). Such inhibitory nucleic acid molecules can be designed to target any region of a GPR75 nucleic acid molecule, such as an mRNA molecule. In some embodiments, the antisense RNA, siRNA, or shRNA hybridizes to a sequence within a GPR75 genomic nucleic acid molecule or mRNA molecule and decreases expression of the GPR75 polypeptide in a cell in the subject. In some embodiments, the GPR75 inhibitor comprises an antisense RNA that hybridizes to a GPR75 genomic nucleic acid molecule or mRNA molecule and decreases expression of the GPR75 polypeptide in a cell in the subject. In some embodiments, the antisense nucleic acid molecules comprise or consist of the nucleotide sequences set forth in SEQ ID NOs:109-529. In some embodiments, the GPR75 inhibitor comprises an siRNA that hybridizes to a GPR75 genomic nucleic acid molecule or mRNA molecule and decreases expression of the GPR75 polypeptide in a cell in the subject. In some embodiments, the siRNA molecules comprise or consist of the nucleotide sequences (sense and antisense strand pairs) set forth in SEQ ID NOs:530-1457 (i.e., SEQ ID NO:530 and SEQ ID NO:531, for example, form the sense and antisense strands, respectively, of an siRNA molecule; likewise with the sense and antisense strands of the remaining siRNA molecules set forth in SEQ ID NOs:530-1457). In some embodiments, the GPR75 inhibitor comprises an shRNA that hybridizes to a GPR75 genomic nucleic acid molecule or mRNA molecule and decreases expression of the GPR75 polypeptide in a cell in the subject. Suitable GPR75-specific siRNAs and shRNAs are disclosed in, for example, Garcia et al., Circ. Res., 2017, 120, 1776-1788.

The inhibitory nucleic acid molecules disclosed herein can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules disclosed herein can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH$_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:

Sense: mN*mN*/i2FN/mN/i2FN/mN/i2FN/mN/
    i2FN/mN/i2FN/mN/i2FN/mN/i2FN/mN/i2FN/
    *mN*/32FN/

Antisense: /52FN/*/i2FN/*mN/i2FN/mN/i2FN/mN/
    i2FN/mN/i2FN/mN/i2FN/mN/i2FN/mN/i2FN/
    mN/i2FN/mN*N*N wherein: "N" is the base; "2F" is a 2'-F modification; "m" is a 2'-O-methyl modification, "I" is an internal base; and "*" is a phosphorothioate backbone linkage.

The present disclosure also provides vectors comprising any one or more of the inhibitory nucleic acid molecules disclosed herein. In some embodiments, the vectors comprise any one or more of the inhibitory nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules disclosed herein. In some embodiments, the composition is a pharmaceutical composition. In some embodiments, the compositions comprise a carrier and/or excipient. Examples of carriers include, but are not limited to, poly (lactic acid) (PLA) microspheres, poly(D,L-lactic-cogly-colic-acid) (PLGA) microspheres, liposomes, micelles, inverse micelles, lipid cochleates, and lipid microtubules. A carrier may comprise a buffered salt solution such as PBS, HBSS, etc.

In some embodiments, the GPR75 inhibitor comprises a nuclease agent that induces one or more nicks or double-strand breaks at a recognition sequence(s) or a DNA-binding protein that binds to a recognition sequence within a GPR75 genomic nucleic acid molecule. The recognition sequence can be located within a coding region of the GPR75 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the GPR75 gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 bp for each ZFN, about 36 bp for a TALE protein or TALEN, and about 20 bp for a CRISPR/Cas guide RNA.

In some embodiments, CRISPR/Cas systems can be used to modify a GPR75 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of GPR75 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in a GPR75 genomic nucleic acid molecule or it can be a nickase that creates a single-strand break in a GPR75 genomic nucleic acid molecule. Additional examples of Cas proteins include, but are not limited to, Cas1, Cas1B, Cast, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of GPR75 genomic nucleic acid molecules can be generated by contacting a cell with a Cas protein and one or more gRNAs that hybridize to one or more gRNA recognition sequences within a target genomic locus in the GPR75 genomic nucleic acid molecule. For example, a gRNA recognition sequence can be located within a region of SEQ ID NO:1. The gRNA recognition sequence can also include or be proximate to a position corresponding to: position 5,540-5,546, 5,557, 5,911, 5,920-5,923, or 6,411 according to SEQ ID NO:1. For example, the gRNA recognition sequence can be located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to: position 5,540-5,546, 5,557, 5,911, 5,920-5,923, or 6,411 according to SEQ ID NO:1. The gRNA recognition sequence can include or be proximate to the start codon of a GPR75 genomic nucleic acid molecule or the stop codon of a GPR75 genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in a GPR75 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within a GPR75 genomic nucleic acid molecule. An exemplary gRNA is a gRNA effective to direct a Cas enzyme to bind to cleave a GPR75 genomic nucleic acid molecule, wherein the gRNA comprises a DNA-targeting segment that hybridizes to a gRNA recognition sequence within the GPR75 genomic nucleic acid molecule that includes or is proximate to a position corresponding to: position 5,540-5,546, 5,557, 5,911, 5,920-5,923, or 6,411 according to SEQ ID NO:1. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of a position corresponding to: position 5,540-5,546, 5,557, 5,911, 5,920-5,923, or 6,411 according to SEQ ID NO:1. Other exemplary gRNAs comprise a DNA-targeting segment that hybridizes to a gRNA recognition sequence present within a GPR75 genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human GPR75 reference gene are set forth in Table 1 as SEQ ID NOS:61-98.

TABLE 1

| Guide RNA Recognition Sequences Near GPR75 Variation(s) | | |
|---|---|---|
| Strand | gRNA Recognition Sequence | SEQ ID NO: |
| – | ACACCATCCGGAGCCGGTGCAGG | 61 |
| – | GAAAGCATCCGGGATACTACTGG | 62 |
| + | TGATCGCCCTGCACCGGCTCCGG | 63 |
| + | GCACCGGCTCCGGATGGTGTTGG | 64 |
| + | ACCGGCTCCGGATGGTGTTGGGG | 65 |
| + | CACCGGCTCCGGATGGTGTTGGG | 66 |
| – | GGAAAGGAGGCCGTGCGATTAGG | 67 |
| + | GGGGAAACAGCCTAATCGCACGG | 68 |
| – | CACCATCCGGAGCCGGTGCAGGG | 69 |
| + | TGGCAGTGATCGCCCTGCACCGG | 70 |
| – | CATGATGATGAAGCCTGAACTGG | 71 |
| + | CGCCCTGCACCGGCTCCGGATGG | 72 |
| – | TCCCCAACACCATCCGGAGCCGG | 73 |
| – | CTGTCACTCCACAAATGAAGAGG | 74 |
| – | GACTTGAGCGTTCTTCCGCAGGG | 75 |
| – | GCATCGACTGTGATTACAGGGGG | 76 |
| – | GCCGGCATGGCACACTGGATGGG | 77 |
| – | GAAGCATCGACTGTGATTACAGG | 78 |
| – | AGCATCGACTGTGATTACAGGGG | 79 |

TABLE 1-continued

Guide RNA Recognition Sequences Near GPR75
Variation(s)

| Strand | gRNA Recognition Sequence | SEQ ID NO: |
|--------|---------------------------|------------|
| − | TGACTTGAGCGTTCTTCCGCAGG | 80 |
| + | TCATGATTGCTCAGACCCTGCGG | 81 |
| − | CATCGACTGTGATTACAGGGGGG | 82 |
| − | AAGCATCGACTGTGATTACAGGG | 83 |
| + | TCCAGACCACAGCCTTTCATGGG | 84 |
| + | CCCATGTCCAGTCTGATTGCTGG | 85 |
| − | ACAGAGCCGGCATGGCACACTGG | 86 |
| + | CAGACCACAGCCTTTCATGGGGG | 87 |
| + | TTCATGGGGGTCCCTGTGCAGGG | 88 |
| + | AAGACTCGACTTCGAGCCATGGG | 89 |
| + | AAAGACTCGACTTCGAGCCATGG | 90 |
| + | CGACTTCGAGCCATGGGAAAAGG | 91 |
| + | TATATTCTCGGAACAGTGCAGGG | 92 |
| + | CTCTGGTGCCTCCAATACATAGG | 93 |
| + | ATATATTCTCGGAACAGTGCAGG | 94 |
| + | TGCCTCCAATACATAGGCCTGGG | 95 |
| − | AACCCAGGCCTATGTATTGGAGG | 96 |
| − | AAAAACCCAGGCCTATGTATTGG | 97 |
| − | TTCGAGGTTCCCTTTTCCCATGG | 98 |

The Cas protein and the gRNA form a complex, and the Cas protein cleaves the target GPR75 genomic nucleic acid molecule. The Cas protein can cleave the nucleic acid molecule at a site within or outside of the nucleic acid sequence present in the target GPR75 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the GPR75 genomic nucleic acid molecule to which a DNA-targeting segment of a gRNA will bind.

Such methods can result, for example, in a GPR75 genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the GPR75 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the GPR75 inhibitor comprises a small molecule. In some embodiments, the GPR75 inhibitor is an inhibitor of CCL5 (RANTES) including, but not limited to, [$^{44}$AANA$^{47}$]-RANTES and Met-CCL$_5$ (see, Braunersreuther et al., Arteriosclerosis, Thrombosis, and Vasc. Biol., 2008, 28, 1090-1096; Proudfoot et al., J. Biol. Chem., 1999, 274, 32478-32485; and Matsui et al., J. Neroimmunol., 2002, 128, 16-22). In some embodiments, the GPR75 inhibitor is an inhibitor of the interaction between GPR75 and 20-Hydroxyeicosatetraenoic acid (20-HETE), including, but not limited to, fatty acid analogs, terminal acetylenic fatty acids, terminal di-bromo fatty acids, sulfonated fatty acids, TS-011, Het0016, 5,14,20-HEDE, 5,14,20-HEDGE, 6,15,20-HEDE, 17-ODYA, DDMS, DDBB, 2,5,8,11,14,17-hexaoxanonadecan-19-yl-20-hydroxyeicosa 6(z), 15(z)-dienote (20-sola), and 6(z),15 (z)hyroxyeicosa-6,15-dienamido-diencoic acid (aaa) (see, Miyata et al., Br. J. Pharmacol., 2001, 133, 325-329; Miyata et al., J. Pharmacol. Exp. Ther., 2005, 314, 77-85; Pandey et al., J. Pharmacol. Exp. Ther., 2017, 363, 412-418; and Savas et al., J. Biol. Chem., 2016, 291, 16904-16919). In some embodiments, the GPR75 inhibitor is any of the antagonists described in PCT Publication WO 2017/156164. In some embodiments, the GPR75 inhibitor is an inhibitor of the interaction between GPR75 and 20-HETE is a blocking antibody.

In some embodiments, the methods of treatment further comprise detecting the absence of a GPR75 missense variant nucleic acid molecule encoding a predicted loss-of-function GPR75 polypeptide in a biological sample from the subject. As used throughout the present disclosure, a "GPR75 missense variant nucleic acid molecule" is any GPR75 nucleic acid molecule (such as, for example, genomic nucleic acid molecule, mRNA molecule, or cDNA molecule) encoding a GPR75 polypeptide having a partial loss-of-function, a complete loss-of-function, a predicted partial loss-of-function, or a predicted complete loss-of-function.

The present disclosure also provides methods of treating a subject with a therapeutic agent that treats or inhibits obesity, wherein the subject is obese. In some embodiments, the methods comprise determining whether the subject has a GPR75 missense variant nucleic acid molecule encoding a predicted loss-of-function GPR75 polypeptide by obtaining or having obtained a biological sample from the subject, and performing or having performed a sequence analysis on the biological sample to determine if the subject has a genotype comprising the GPR75 missense variant nucleic acid molecule. When the subject is GPR75 reference, the therapeutic agent that treats or inhibits obesity and/or a GPR75 inhibitor is administered or continued to be administered to the subject in a standard dosage amount. When the subject is heterozygous for a GPR75 missense variant nucleic acid molecule, the therapeutic agent that treats or inhibits obesity and/or a GPR75 inhibitor is administered or continued to be administered to the subject in an amount that is the same as or lower than a standard dosage amount. The presence of a genotype having the GPR75 missense variant nucleic acid molecule encoding a predicted loss-of-function GPR75 polypeptide indicates the subject has a reduced risk of developing obesity. In some embodiments, the subject is GPR75 reference. In some embodiments, the subject is heterozygous for a GPR75 missense variant nucleic acid molecule encoding a predicted loss-of-function GPR75 polypeptide.

For subjects that are genotyped or determined to be either GPR75 reference or heterozygous for a GPR75 missense variant nucleic acid molecule, such subjects can be treated with a GPR75 inhibitor, as described herein.

Detecting the presence or absence of a GPR75 missense variant nucleic acid molecule in a biological sample from a subject and/or determining whether a subject has a GPR75 missense variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when the subject is GPR75 reference, the subject is also administered a therapeutic agent that treats or inhibits obesity and/or a GPR75 inhibitor in a standard dosage amount. In some embodiments, when the subject is heterozygous for a GPR75 missense variant nucleic acid molecule, the subject is also administered a therapeutic agent that treats or inhibits obesity and/or a GPR75 inhibitor in a dosage amount that is the same as or lower than a standard dosage amount.

In some embodiments, the treatment methods further comprise detecting the absence of a GPR75 predicted loss-of-function polypeptide in a biological sample from the subject. In some embodiments, when the subject does not have a GPR75 predicted loss-of-function polypeptide, the subject is also administered a therapeutic agent that treats or inhibits obesity and/or a GPR75 inhibitor in a standard dosage amount. In some embodiments, when the subject has a GPR75 predicted loss-of-function polypeptide, the subject is also administered a therapeutic agent that treats or inhibits obesity and/or a GPR75 inhibitor in a dosage amount that is the same as or lower than a standard dosage amount.

The present disclosure also provides methods of treating a subject with a therapeutic agent that treats or inhibits obesity, wherein the subject is obese. In some embodiments, the method comprises determining whether the subject has a GPR75 predicted loss-of-function polypeptide by obtaining or having obtained a biological sample from the subject, and performing or having performed an assay on the biological sample to determine if the subject has a GPR75 predicted loss-of-function polypeptide. When the subject does not have a GPR75 predicted loss-of-function polypeptide, the therapeutic agent that treats or inhibits obesity and/or a GPR75 inhibitor is administered or continued to be administered to the subject in a standard dosage amount. When the subject has a GPR75 predicted loss-of-function polypeptide, the therapeutic agent that treats or inhibits obesity and/or a GPR75 inhibitor is administered or continued to be administered to the subject in an amount that is the same as or lower than a standard dosage amount. The presence of a GPR75 predicted loss-of-function polypeptide indicates the subject has a reduced risk of developing obesity. In some embodiments, the subject has a GPR75 predicted loss-of-function polypeptide. In some embodiments, the subject does not have a GPR75 predicted loss-of-function polypeptide.

Detecting the presence or absence of a GPR75 predicted loss-of-function polypeptide in a biological sample from a subject and/or determining whether a subject has a GPR75 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

Examples of therapeutic agents that treat or inhibit obesity and/or increased BMI include, but are not limited to, sibutramine, orlistat, phentermine, lorcaserin, naltrexone, liraglutide, diethylpropion, bupropion, metformin, pramlintide, topiramate, and zonisamide, or any combination thereof. Examples of therapeutic agents that treat or inhibit obesity and/or increased BMI also include, but are not limited to, sibutramine, orlistat, phentermine and topiramate, lorcaserin, bupropion and naltrexone, liraglutide, phentermine and diethylpropion, bupropion, metformin, pramlintide, topiramate, and zonisamide, or any combination thereof.

In some embodiments, the therapeutic agent that treats or inhibits obesity and/or increased BMI is a GLP1R agonist including, but not limited to, BYETTA® or BYDUREON® (exenatide), VICTOZA® or SAXENDA® (liraglutide), LYXUMIA® or ADLYXIN® (lixisenatide), TANZEUM® (albiglutide), TRULICITY® (dulaglutide), and OZEMPIC® (semaglutide), or any combination thereof. In some embodiments, the therapeutic agent that treats or inhibits obesity and/or increased BMI is BYETTA® (exenatide). In some embodiments, the therapeutic agent that treats or inhibits obesity and/or increased BMI is BYETTA® (exenatide). In some embodiments, the therapeutic agent that treats or inhibits obesity and/or increased BMI is VICTOZA® (liraglutide). In some embodiments, the therapeutic agent that treats or inhibits obesity and/or increased BMI is SAXENDA® (liraglutide). In some embodiments, the therapeutic agent that treats or inhibits obesity and/or increased BMI is LYXUMIA® (lixisenatide). In some embodiments, the therapeutic agent that treats or inhibits obesity and/or increased BMI is ADLYXIN® (lixisenatide). In some embodiments, the therapeutic agent that treats or inhibits obesity and/or increased BMI is TANZEUM® (albiglutide). In some embodiments, the therapeutic agent that treats or inhibits obesity and/or increased BMI is TRULICITY® (dulaglutide). In some embodiments, the therapeutic agent that treats or inhibits obesity and/or increased BMI is OZEMPIC® (semaglutide). In some embodiments, the therapeutic agent that treats or inhibits obesity and/or increased BMI is chosen from exenatide, liraglutide, lixisenatide, albiglutide, dulaglutide, and semaglutide, or any combination thereof. In some embodiments, the therapeutic agent that treats or inhibits obesity and/or increased BMI is exenatide. In some embodiments, the therapeutic agent that treats or inhibits obesity and/or increased BMI liraglutide. In some embodiments, the therapeutic agent that treats or inhibits obesity and/or increased BMI is lixisenatide. In some embodiments, the therapeutic agent that treats or inhibits obesity and/or increased BMI is albiglutide. In some embodiments, the therapeutic agent that treats or inhibits obesity and/or increased BMI is dulaglutide. In some embodiments, the therapeutic agent that treats or inhibits obesity and/or increased BMI is semaglutide.

In some embodiments, the therapeutic agent that treats or inhibits obesity and/or reduces BMI is a melanocortin 4 receptor (MC4R) agonist. In some embodiments, the MC4R agonist comprises a protein, a peptide, a nucleic acid molecule, or a small molecule. In some embodiments, the protein is a peptide analog of MC4R. In some embodiments, the peptide is setmelanotide. In some embodiments, the therapeutic agent that treats or inhibits obesity and/or reduces BMI is a combination of setmelanotide and one or more of sibutramine, orlistat, phentermine, lorcaserin, naltrexone, liraglutide, diethylpropion, bupropion, metformin, pramlintide, topiramate, and zonisamide. In some embodiments, the MC4R agonist is a peptide comprising the amino acid sequence His-Phe-Arg-Trp. In some embodiments, the small molecule is 1,2,3R,4-tetrahydroisoquinoline-3-carboxylic acid. In some embodiments, the MC4R agonist is ALB-127158(a).

In some embodiments, the dose of the therapeutic agents that treat or inhibit obesity and/or a GPR75 inhibitor can be reduced by about 10%, by about 20%, by about 30%, by about 40%, by about 50%, by about 60%, by about 70%, by about 80%, or by about 90% for subjects that are heterozygous for a GPR75 missense variant nucleic acid molecule (i.e., a lower than the standard dosage amount) compared to subjects that are GPR75 reference (who may receive a standard dosage amount). In some embodiments, the dose of the therapeutic agents that treat or inhibit obesity and/or a GPR75 inhibitor can be reduced by about 10%, by about 20%, by about 30%, by about 40%, or by about 50%. In addition, the dose of therapeutic agents that treat or inhibit obesity and/or a GPR75 inhibitor in subjects that are heterozygous for a GPR75 missense variant nucleic acid molecule can be administered less frequently compared to subjects that are GPR75 reference.

Administration of the therapeutic agents that treat or inhibit obesity and/or GPR75 inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit obesity and/or GPR75 inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

In some embodiments, the therapeutic agents that treat or inhibit obesity and/or GPR75 inhibitors (such as any of the inhibitory nucleic acid molecules disclosed herein) are administered intrathecally (i.e., introduction into the subarachnoid space of the spinal cord or into the spinal canal so that the therapeutic agent can reach the cerebrospinal fluid of a subject, or introduction into the anatomic space or potential space inside a sheath, including, by way of non-limiting examples, the arachnoid membrane of the brain or spinal cord). In some embodiments, intrathecal administration results in the therapeutic agent acting on, without limitation, the cortex, the cerebellum, the striatum, the cervical spine, the lumbar spine, or the thoracic spine. Therapeutic agents administered intrathecally may ultimately act on targets throughout the entire central nervous system. In some embodiments, the intrathecal administration is into the cisterna magna or by the lumbar area or region. In some embodiments, the intrathecal administration into the lumbar area or region results in delivery of the therapeutic agent to the distal spinal canal. Exemplary methods for intrathecal administration are described in, for example, Lazorthes et al., Advances in Drug Delivery Systems and Applications in Neurosurgery, 143-192. In some embodiments, the intrathecal administration is by injection, by bolus injection, by a catheter, or by a pump. In some embodiments, the intrathecal administration is by lumber puncture. In some embodiments, the pump is an osmotic pump. In some embodiments, the pump is implanted into subarachnoid space of the spinal canal, below the skin of the abdomen, or behind the chest wall. In some embodiments, the intrathecal administration is by an intrathecal delivery system for a therapeutic substance including a reservoir containing a volume of the therapeutic agent and a pump configured to deliver at least a portion of the therapeutic substance contained in the reservoir. In some embodiments, intrathecal administration is through intermittent or continuous access to an implanted intrathecal drug delivery device (IDDD). In some embodiments, the therapeutic substance is an inhibitory nucleic acid molecule. In some embodiments, the amount of the nucleic acid molecule administered intrathecally ranges from about 10 µg to about 2 mg, from about 50 µg to about 1500 µg, or from about 100 µg to about 1000 µg. In some embodiments, the therapeutic agent is disposed within a pharmaceutical composition. In some embodiments, the pharmaceutical composition does not comprise a preservative.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in obesity, a decrease/reduction in the severity of obesity (such as, for example, a reduction or inhibition of development or obesity), a decrease/reduction in symptoms and obesity-related effects, delaying the onset of symptoms and obesity-related effects, reducing the severity of symptoms of obesity-related effects, reducing the severity of an acute episode, reducing the number of symptoms and obesity-related effects, reducing the latency of symptoms and obesity-related effects, an amelioration of symptoms and obesity-related effects, reducing secondary symptoms, reducing secondary infections, preventing relapse to obesity, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of obesity development/progression (such as, for example, a complete or partial avoidance/inhibition or a delay), or an increased survival time of the affected host animal, following administration of a therapeutic protocol. Treatment of obesity encompasses the treatment of subjects already diagnosed as having any form of obesity at any clinical stage or manifestation, the delay of the onset or evolution or aggravation or deterioration of the symptoms or signs of obesity, and/or preventing and/or reducing the severity of obesity.

The present disclosure also provides methods of identifying a subject having an increased risk for developing obesity, excessive weight, elevated BMI, elevated body fat mass, percentage, or volume, and/or excessive food intake. In some embodiments, the method comprises determining or having determined in a biological sample obtained from the subject the presence or absence of a GPR75 missense variant nucleic acid molecule (such as a genomic nucleic acid molecule, mRNA molecule, and/or cDNA molecule) encoding a predicted loss-of-function GPR75 polypeptide. When the subject lacks a GPR75 missense variant nucleic acid molecule (i.e., the subject is genotypically categorized as a GPR75 reference), then the subject has an increased risk for developing obesity. When the subject has a GPR75 missense variant nucleic acid molecule (i.e., the subject is heterozygous or homozygous for a GPR75 missense variant nucleic acid molecule), then the subject has a decreased risk for developing obesity.

Having a single copy of a GPR75 missense variant nucleic acid molecule is more protective of a subject from developing obesity than having no copies of a GPR75 missense variant nucleic acid molecule. Without intending to be limited to any particular theory or mechanism of action, it is believed that a single copy of a GPR75 missense variant nucleic acid molecule (i.e., heterozygous for a GPR75 missense variant nucleic acid molecule) is protective of a subject from developing obesity, and it is also believed that having two copies of a GPR75 missense variant nucleic acid molecule (i.e., homozygous for a GPR75 missense variant nucleic acid molecule) may be more protective of a subject from developing obesity, relative to a subject with a single copy. Thus, in some embodiments, a single copy of a GPR75 missense variant nucleic acid molecule may not be completely protective, but instead, may be partially or incompletely protective of a subject from developing obesity. While not desiring to be bound by any particular theory, there may be additional factors or molecules involved in the development of obesity that are still present in a subject having a single copy of a GPR75 missense variant nucleic acid molecule, thus resulting in less than complete protection from the development of obesity.

Determining whether a subject has a GPR75 missense variant nucleic acid molecule in a biological sample from a subject and/or determining whether a subject has a GPR75 missense variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing obesity, the subject is further treated with a therapeutic agent that treats or inhibits obesity and/or a GPR75 inhibitor, as described herein. For example, when the subject is GPR75 reference, and therefore has an increased risk for developing obesity, the subject is administered a GPR75 inhibitor. In some embodiments, such a subject is also administered a therapeutic agent that treats or inhibits obesity. In some embodiments, when the subject is heterozygous for a GPR75 missense variant nucleic acid molecule, the subject is administered the therapeutic agent that treats or inhibits obesity and/or a GPR75 inhibitor in a dosage amount that is the same as or lower than a standard dosage amount. In some embodiments, the subject is GPR75 reference. In some embodiments, the subject is heterozygous for a GPR75 missense variant nucleic acid molecule.

The present disclosure also provides methods of detecting the presence or absence of a GPR75 missense genomic variant nucleic acid molecule in a biological sample from a subject, and/or a GPR75 missense variant mRNA molecule in a biological sample from a subject, and/or a GPR75 missense variant cDNA molecule produced from an mRNA molecule in a biological sample from a subject. It is understood that gene sequences within a population and mRNA molecules encoded by such genes can vary due to polymorphisms such as single-nucleotide polymorphisms. The sequences provided herein for the GPR75 variant genomic nucleic acid molecule, GPR75 variant mRNA molecule, and GPR75 variant cDNA molecule are only exemplary sequences. Other sequences for the GPR75 variant genomic nucleic acid molecule, variant mRNA molecule, and variant cDNA molecule are also possible.

The biological sample can be derived from any cell, tissue, or biological fluid from the subject. The biological sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any GPR75 variant nucleic acid molecule, preliminary processing designed to isolate or enrich the biological sample for the genomic DNA can be employed. A variety of techniques may be used for this purpose. When detecting the level of any GPR75 variant mRNA molecule, different techniques can be used enrich the biological sample with mRNA molecules. Various methods to detect the presence or level of an mRNA molecule or the presence of a particular variant genomic DNA locus can be used.

In some embodiments, detecting a human GPR75 missense variant nucleic acid molecule in a subject comprises assaying or genotyping a biological sample obtained from the subject to determine whether a GPR75 genomic nucleic acid molecule in the biological sample, and/or a GPR75 mRNA molecule in the biological sample, and/or a GPR75 cDNA molecule produced from an mRNA molecule in the biological sample, comprises one or more variations that cause a loss-of-function (partial or complete) or are predicted to cause a loss-of-function (partial or complete).

In some embodiments, the methods of detecting the presence or absence of a GPR75 missense variant nucleic acid molecule (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the nucleotide sequence: lacks a CCAGTAG heptanucleotide at positions corresponding to positions 5,540-5,546 according to SEQ ID NO:1 (for genomic nucleic acid molecules); lacks a CCAGUAG heptanucleotide at positions corresponding to positions 539-545 according to SEQ ID NO:7, lacks a CCAGUAG heptanucleotide at positions corresponding to positions 440-446 according to SEQ ID NO:8, lacks a CCAGUAG heptanucleotide at positions corresponding to positions 361-367 according to SEQ ID NO:9, or lacks a CCAGUAG heptanucleotide at positions corresponding to positions 600-606 according to SEQ ID NO:10 (for mRNA molecules); lacks a CCAGTAG heptanucleotide at positions corresponding to positions 539-545 according to SEQ ID NO:31, lacks a CCAGTAG heptanucleotide at positions corresponding to positions 440-446 according to SEQ ID NO:32, lacks a CCAGTAG heptanucleotide at positions corresponding to positions 361-367 according to SEQ ID NO:33, or lacks a CCAGTAG heptanucleotide at positions corresponding to positions 600-606 according to SEQ ID NO:34 (for cDNA molecules).

In some embodiments, the nucleotide sequence comprises: an adenine at a position corresponding to position 5,557 according to SEQ ID NO:3 (for genomic nucleic acid molecules); an adenine at a position corresponding to position 556 according to SEQ ID NO:12, an adenine at a position corresponding to position 457 according to SEQ ID NO:17, an adenine at a position corresponding to position 378 according to SEQ ID NO:22, or an adenine at a position corresponding to position 617 according to SEQ ID NO:27 (for mRNA molecules); an adenine at a position corresponding to position 556 according to SEQ ID NO:36, an adenine at a position corresponding to position 457 according to SEQ ID NO:41, an adenine at a position corresponding to position 378 according to SEQ ID NO:46, or an adenine at a position corresponding to position 617 according to SEQ ID NO:51 (for cDNA molecules).

In some embodiments, the nucleotide sequence comprises: a thymine at a position corresponding to position 5,911 according to SEQ ID NO:4 (for genomic nucleic acid molecules); a uracil at a position corresponding to position 910 according to SEQ ID NO:13, a uracil at a position corresponding to position 811 according to SEQ ID NO:18, a uracil at a position corresponding to position 732 according to SEQ ID NO:23, or a uracil at a position corresponding to position 971 according to SEQ ID NO:28 (for mRNA molecules); a thymine at a position corresponding to position 910 according to SEQ ID NO:37, a thymine at a position corresponding to position 811 according to SEQ ID NO:42, a thymine at a position corresponding to position 732 according to SEQ ID NO:47, or a thymine at a position corresponding to position 971 according to SEQ ID NO:52 (for cDNA molecules).

In some embodiments, the nucleotide sequence: lacks an AAAG tetranucleotide at positions corresponding to positions 5,920-5,923 according to SEQ ID NO:1 (for genomic nucleic acid molecules); lacks an AAAG tetranucleotide at positions corresponding to positions 919-922 according to SEQ ID NO:7, lacks an AAAG tetranucleotide at positions corresponding to positions 820-823 according to SEQ ID NO:8, lacks an AAAG tetranucleotide at positions corresponding to positions 741-744 according to SEQ ID NO:9, or lacks an AAAG tetranucleotide at positions corresponding to positions 980-983 according to SEQ ID NO:10 (for mRNA molecules); lacks an AAAG tetranucleotide at positions corresponding to positions 919-922 according to SEQ ID NO:31, lacks an AAAG tetranucleotide at positions corresponding to positions 820-823 according to SEQ ID NO:32, lacks an AAAG tetranucleotide at positions corresponding to positions 741-744 according to SEQ ID NO:33, or lacks an AAAG tetranucleotide at positions corresponding to positions 980-983 according to SEQ ID NO:34 (for cDNA molecules).

In some embodiments, the nucleotide sequence comprises: an insertion of a thymine at a position corresponding to position 6,411 according to SEQ ID NO:6 (for genomic nucleic acid molecules); an insertion of a uracil at a position corresponding to position 1,410 according to SEQ ID NO:15, an insertion of a uracil at a position corresponding to position 1,311 according to SEQ ID NO:20, an insertion of a uracil at a position corresponding to position 1,232 according to SEQ ID NO:25, or an insertion of a uracil at a position corresponding to position 1,471 according to SEQ ID NO:30 (for mRNA molecules); an insertion of a thymine at a position corresponding to position 1,410 according to SEQ ID NO:39, an insertion of a thymine at a position corresponding to position 1,311 according to SEQ ID NO:44, an insertion of a thymine at a position corresponding to position 1,232 according to SEQ ID NO:49, or an insertion of a thymine at a position corresponding to position 1,471 according to SEQ ID NO:54 (for cDNA molecules).

In some embodiments, the nucleotide sequence comprises: a guanine at a position corresponding to position 5,831 according to SEQ ID NO:99, or the complement thereof (for genomic nucleic acid molecules); a guanine at a position corresponding to position 830 according to SEQ ID NO:100, or the complement thereof; a guanine at a position corresponding to position 731 according to SEQ ID NO:101, or the complement thereof; a guanine at a position corresponding to position 652 according to SEQ ID NO:102, or the complement thereof; or a guanine at a position corresponding to position 891 according to SEQ ID NO:103, or the complement thereof (for mRNA molecules); a guanine at a position corresponding to position 830 according to SEQ ID NO:104, or the complement thereof; a guanine at a position corresponding to position 731 according to SEQ ID NO:105, or the complement thereof; a guanine at a position corresponding to position 652 according to SEQ ID NO:106, or the complement thereof; or a guanine at a position corresponding to position 891 according to SEQ ID NO:107, or the complement thereof (for cDNA molecules).

In some embodiments, the nucleotide sequence: lacks a CCAGTAG heptanucleotide at positions corresponding to positions 5,540-5,546 according to SEQ ID NO:1, or the complement thereof; comprises an adenine at a position corresponding to position 5,557 according to SEQ ID NO:3, or the complement thereof; comprises a thymine at a position corresponding to position 5,911 according to SEQ ID NO:4, or the complement thereof; lacks an AAAG tetranucleotide at positions corresponding to positions 5,920-5,923 according to SEQ ID NO:1, or the complement thereof; comprises an insertion of a thymine at a position corresponding to position 6,411 according to SEQ ID NO:6, or the complement thereof; or comprises a guanine at a position corresponding to position 5,831 according to SEQ ID NO:99, or the complement thereof.

In some embodiments, the nucleotide sequence: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; comprises an adenine at a position corresponding to position 556 according to SEQ ID NO:12, or the complement thereof; comprises an adenine at a position corresponding to position 457 according to SEQ ID NO:17, or the complement thereof; comprises an adenine at a position corresponding to position 378 according to SEQ ID NO:22, or the complement thereof; comprises an adenine at a position corresponding to position 617 according to SEQ ID NO:27, or the complement thereof; comprises a uracil at a position corresponding to position 910 according to SEQ ID NO:13, or the complement thereof; comprises a uracil at a position corresponding to position 811 according to SEQ ID NO:18, or the complement thereof; comprises a uracil at a position corresponding to position 732 according to SEQ ID NO:23, or the complement thereof; comprises a uracil at a position corresponding to position 971 according to SEQ ID NO:28, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; comprises an insertion of a uracil at a position corresponding to position 1,471 according to SEQ ID NO:30, or the complement thereof; comprises a guanine at a position corresponding to position 830 according to SEQ ID NO:100, or the complement thereof; comprises a guanine at a position corresponding to position 731 according to SEQ ID NO:101, or the complement thereof; comprises a guanine at a position corresponding to position 652 according to SEQ ID NO:102, or the complement thereof; or comprises a guanine at a position corresponding to position 891 according to SEQ ID NO:103, or the complement thereof.

In some embodiments, the nucleotide sequence: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; comprises an adenine at a position corresponding to position 556 according to SEQ ID NO:36, or the complement thereof; comprises an adenine at a position corresponding to position 457 according to SEQ ID NO:41, or the complement thereof; comprises an adenine at a position corresponding to position 378 according to SEQ ID NO:46, or the complement thereof; comprises an adenine at a position corresponding to position 617 according to SEQ ID NO:51, or the complement thereof; comprises a thymine at a position corresponding to position 910 according to SEQ ID NO:37, or the complement thereof; comprises a thymine at a position corresponding to position 811 according to SEQ ID NO:42, or the complement thereof; comprises a thymine at a position corresponding to position 732 according to SEQ ID NO:47, or the complement thereof; comprises a thymine at a position corresponding to position 971 according to SEQ ID NO:52, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; comprises an insertion of a thymine at a position corresponding to position 1,471 according to SEQ ID NO:54, or the complement thereof; comprises a guanine at a position corresponding to position 830 according to SEQ ID NO:104, or the complement thereof; comprises a guanine at a position corresponding to position 731 according to SEQ ID NO:105, or the complement thereof; comprises a guanine at a position corresponding to position 652 according to SEQ ID NO:106, or the complement thereof; or comprises a guanine at a position corresponding to position 891 according to SEQ ID NO:107, or the complement thereof.

In some embodiments, the biological sample comprises a cell or cell lysate. Such methods can further comprise, for example, obtaining a biological sample from the subject comprising a GPR75 genomic nucleic acid molecule or mRNA molecule, and if mRNA, optionally reverse transcribing the mRNA into cDNA. Such assays can comprise, for example determining the identity of these positions of the particular GPR75 nucleic acid molecule. In some embodiments, the method is an in vitro method.

In some embodiments, the determining step, detecting step, or sequence analysis comprises sequencing at least a portion of the nucleotide sequence of the GPR75 genomic nucleic acid molecule, the GPR75 mRNA molecule, or the GPR75 cDNA molecule in the biological sample, wherein the sequenced portion comprises one or more variations that cause a loss-of-function (partial or complete) or are predicted to cause a loss-of-function (partial or complete).

In some embodiments, the determining step, detecting step, or sequence analysis comprises sequencing at least a portion of: i) the nucleotide sequence of the GPR75 genomic nucleic acid molecule in the biological sample, wherein the sequenced portion comprises a position corresponding to positions 5,540-5,546 according to SEQ ID NO:2, or the complement thereof; ii) the nucleotide sequence of the GPR75 mRNA molecule in the biological sample, wherein the sequenced portion comprises a position corresponding to: positions 539-545 according to SEQ ID NO:11, or the complement thereof; positions 440-446 according to SEQ ID NO:16, or the complement thereof; positions 361-367 according to SEQ ID NO:21, or the complement thereof; or positions 600-606 according to SEQ ID NO:26, or the complement thereof; and/or iii) the nucleotide sequence of the GPR75 cDNA molecule produced from the mRNA in the biological sample, wherein the sequenced portion comprises a position corresponding to: positions 539-545 according to SEQ ID NO:35, or the complement thereof; positions 440-446 according to SEQ ID NO:40, or the complement thereof; positions 361-367 according to SEQ ID NO:45, or the complement thereof; or positions 600-606 according to SEQ ID NO:50, or the complement thereof. When the sequenced portion of the GPR75 nucleic acid molecule in the biological sample comprises: i) a deletion of a CCAGTAG heptanucleotide at positions corresponding to positions 5,540-5,546 according to SEQ ID NO:1; ii) a deletion of a CCAGUAG heptanucleotide at positions corresponding to positions 539-545 according to SEQ ID NO:7, a deletion of a CCAGUAG heptanucleotide at positions corresponding to positions 440-446 according to SEQ ID NO:8, a deletion of a CCAGUAG heptanucleotide at positions corresponding to positions 361-367 according to SEQ ID NO:9, or a deletion of a CCAGUAG heptanucleotide at positions corresponding to positions 600-606 according to SEQ ID NO:10; or iii) a deletion of a CCAGTAG heptanucleotide at positions corresponding to positions 539-545 according to SEQ ID NO:31, a deletion of a CCAGTAG heptanucleotide at positions corresponding to positions 440-446 according to SEQ ID NO:32, a deletion of a CCAGTAG heptanucleotide at positions corresponding to positions 361-367 according to SEQ ID NO:33, or a deletion of a CCAGTAG heptanucleotide at positions corresponding to positions 600-606 according to SEQ ID NO:34, then the GPR75 nucleic acid molecule in the biological sample is a GPR75 missense variant nucleic acid molecule.

In some embodiments, the determining step, detecting step, or sequence analysis comprises sequencing at least a portion of: i) the nucleotide sequence of the GPR75 genomic nucleic acid molecule in the biological sample, wherein the sequenced portion comprises a position corresponding to position 5,557 according to SEQ ID NO:3, or the complement thereof; ii) the nucleotide sequence of the GPR75 mRNA molecule in the biological sample, wherein the sequenced portion comprises a position corresponding to: position 556 according to SEQ ID NO:12, or the complement thereof; position 457 according to SEQ ID NO:17, or the complement thereof; position 378 according to SEQ ID NO:22, or the complement thereof; or position 617 according to SEQ ID NO:27, or the complement thereof; and/or iii) the nucleotide sequence of the GPR75 cDNA molecule produced from the mRNA in the biological sample, wherein the sequenced portion comprises a position corresponding to: position 556 according to SEQ ID NO:36, or the complement thereof; position 457 according to SEQ ID NO:41, or the complement thereof; position 378 according to SEQ ID NO:46, or the complement thereof; or position 617 according to SEQ ID NO:51, or the complement thereof. When the sequenced portion of the GPR75 nucleic acid molecule in the biological sample comprises: i) an adenine at a position corresponding to position 5,557 according to SEQ ID NO:3; ii) an adenine at a position corresponding to position 556 according to SEQ ID NO:12, an adenine at a position corresponding to position 457 according to SEQ ID NO:17, an adenine at a position corresponding to position 378 according to SEQ ID NO:22, or an adenine at a position corresponding to position 617 according to SEQ ID NO:27; or iii) an adenine at a position corresponding to position 556 according to SEQ ID NO:36, an adenine at a position corresponding to position 457 according to SEQ ID NO:41, an adenine at a position corresponding to position 378 according to SEQ ID NO:46, or an adenine at a position corresponding to position 617 according to SEQ ID NO:51, then the GPR75 nucleic acid molecule in the biological sample is a GPR75 missense variant nucleic acid molecule.

In some embodiments, the determining step, detecting step, or sequence analysis comprises sequencing at least a portion of: i) the nucleotide sequence of the GPR75 genomic nucleic acid molecule in the biological sample, wherein the sequenced portion comprises a position corresponding to position 5,911 according to SEQ ID NO:4, or the complement thereof; ii) the nucleotide sequence of the GPR75 mRNA molecule in the biological sample, wherein the sequenced portion comprises a position corresponding to: position 910 according to SEQ ID NO:13, or the complement thereof; position 811 according to SEQ ID NO:18, or the complement thereof; position 732 according to SEQ ID NO:23, or the complement thereof; or position 971 according to SEQ ID NO:28, or the complement thereof; and/or iii) the nucleotide sequence of the GPR75 cDNA molecule produced from the mRNA in the biological sample, wherein the sequenced portion comprises a position corresponding to: position 910 according to SEQ ID NO:37, or the complement thereof; position 811 according to SEQ ID NO:42, or the complement thereof; position 732 according to SEQ ID NO:47, or the complement thereof; or position 971 according to SEQ ID NO:52, or the complement thereof. When the sequenced portion of the GPR75 nucleic acid molecule in the biological sample comprises: i) a thymine at a position corresponding to position 5,911 according to SEQ ID NO:4; ii) a uracil at a position corresponding to position 910 according to SEQ ID NO:13, a uracil at a position corresponding to position 811 according to SEQ ID NO:18, a uracil at a position corresponding to position 732 according to SEQ ID NO:23, or a uracil at a position corresponding to position 971 according to SEQ ID NO:28; or iii) a thymine at a position corresponding to position 910 according to SEQ ID NO:37, a thymine at a position corresponding to position 811 according to SEQ ID NO:42, a thymine at a position corresponding to position 732 according to SEQ ID NO:47, or a thymine at a position corresponding to position 971 according to SEQ ID NO:52, then the GPR75 nucleic acid molecule in the biological sample is a GPR75 missense variant nucleic acid molecule.

In some embodiments, the determining step, detecting step, or sequence analysis comprises sequencing at least a portion of: i) the nucleotide sequence of the GPR75 genomic nucleic acid molecule in the biological sample, wherein the sequenced portion comprises a position corresponding to positions 5,920-5,923 according to SEQ ID NO:5, or the complement thereof; ii) the nucleotide sequence of the GPR75 mRNA molecule in the biological sample, wherein the sequenced portion comprises a position corresponding to: positions 919-922 according to SEQ ID NO:14, or the complement thereof; positions 820-823 according to SEQ ID NO:19, or the complement thereof; positions 741-744 according to SEQ ID NO:24, or the complement thereof; or positions 980-983 according to SEQ ID NO:29, or the complement thereof; and/or iii) the nucleotide sequence of the GPR75 cDNA molecule produced from the mRNA in the biological sample, wherein the sequenced portion comprises a position corresponding to: positions 919-922 according to SEQ ID NO:38, or the complement thereof; positions 820-823 according to SEQ ID NO:43, or the complement thereof; positions 741-744 according to SEQ ID NO:48, or the complement thereof; or positions 980-983 according to SEQ ID NO:53, or the complement thereof. When the sequenced portion of the GPR75 nucleic acid molecule in the biological sample comprises: i) a deletion of an AAAG tetranucleotide at positions corresponding to positions 5,920-5,923 according to SEQ ID NO:1; ii) a deletion of an AAAG tetranucleotide at positions corresponding to positions 919-922 according to SEQ ID NO:7, a deletion of an AAAG tetranucleotide at positions corresponding to positions 820-823 according to SEQ ID NO:8, a deletion of an AAAG tetranucleotide at positions corresponding to positions 741-744 according to SEQ ID NO:9, or a deletion of an AAAG tetranucleotide at positions corresponding to positions 980-983 according to SEQ ID NO:10; or iii) a deletion of an AAAG tetranucleotide at positions corresponding to positions 919-922 according to SEQ ID NO:31, a deletion of an AAAG tetranucleotide at positions corresponding to positions 820-823 according to SEQ ID NO:32, a deletion of an AAAG tetranucleotide at positions corresponding to positions 741-744 according to SEQ ID NO:33, or a deletion of an AAAG tetranucleotide at positions corresponding to positions 980-983 according to SEQ ID NO:34, then the GPR75 nucleic acid molecule in the biological sample is a GPR75 missense variant nucleic acid molecule.

In some embodiments, the determining step, detecting step, or sequence analysis comprises sequencing at least a portion of: i) the nucleotide sequence of the GPR75 genomic nucleic acid molecule in the biological sample, wherein the sequenced portion comprises a position corresponding to position 6,411 according to SEQ ID NO:6, or the complement thereof; ii) the nucleotide sequence of the GPR75 mRNA molecule in the biological sample, wherein the sequenced portion comprises a position corresponding to: position 1,410 according to SEQ ID NO:15, or the complement thereof; position 1,311 according to SEQ ID NO:20, or the complement thereof; position 1,232 according to SEQ ID NO:25, or the complement thereof; or position 1,471 according to SEQ ID NO:30 or the complement thereof; and/or iii) the nucleotide sequence of the GPR75 cDNA molecule produced from the mRNA in the biological sample, wherein the sequenced portion comprises a position corresponding to: position 1,410 according to SEQ ID NO:39, or the complement thereof; position 1,311 according to SEQ ID NO:44, or the complement thereof; position 1,232 according to SEQ ID NO:49, or the complement thereof; or position 1,471 according to SEQ ID NO:54, or the complement thereof. When the sequenced portion of the GPR75 nucleic acid molecule in the biological sample comprises: i) an insertion of a thymine at a position corresponding to position 6,411 according to SEQ ID NO:6; ii) an insertion of a uracil at a position corresponding to position 1,410 according to SEQ ID NO:15, an insertion of a uracil at a position corresponding to position 1,311 according to SEQ ID NO:20, an insertion of a uracil at a position corresponding to position 1,232 according to SEQ ID NO:25, or an insertion of a uracil at a position corresponding to position 1,471 according to SEQ ID NO:30; or iii) an insertion of a thymine at a position corresponding to position 1,410 according to SEQ ID NO:39, an insertion of a thymine at a position corresponding to position 1,311 according to SEQ ID NO:44, an insertion of a thymine at a position corresponding to position 1,232 according to SEQ ID NO:49, or an insertion of a thymine at a position corresponding to position 1,471 according to SEQ ID NO:54, then the GPR75 nucleic acid molecule in the biological sample is a GPR75 missense variant nucleic acid molecule.

In some embodiments, the determining step, detecting step, or sequence analysis comprises sequencing at least a portion of: i) the nucleotide sequence of the GPR75 genomic nucleic acid molecule in the biological sample, wherein the sequenced portion comprises a position corresponding to position 5,831 according to SEQ ID NO:99, or the complement thereof; ii) the nucleotide sequence of the GPR75 mRNA molecule in the biological sample, wherein the sequenced portion comprises a position corresponding to: position 830 according to SEQ ID NO:100, or the complement thereof; position 731 according to SEQ ID NO:101, or the complement thereof; position 652 according to SEQ ID NO:102, or the complement thereof; or position 891 according to SEQ ID NO:103, or the complement thereof; and/or iii) the nucleotide sequence of the GPR75 cDNA molecule produced from the mRNA in the biological sample, wherein the sequenced portion comprises a position corresponding to: position 830 according to SEQ ID NO:104, or the complement thereof; position 731 according to SEQ ID NO:105, or the complement thereof; position 652 according to SEQ ID NO:106, or the complement thereof; or position 891 according to SEQ ID NO:107, or the complement thereof. When the sequenced portion of the GPR75 nucleic acid molecule in the biological sample comprises: i) a guanine at a position corresponding to position 5,831 according to SEQ ID NO:99; ii) a guanine at a position corresponding to position 830 according to SEQ ID NO:100, a guanine at a position corresponding to position 731 according to SEQ ID NO:101, a guanine at a position corresponding to position 652 according to SEQ ID NO:102, or a guanine at a position corresponding to position 891 according to SEQ ID NO:103; or iii) a guanine at a position corresponding to position 830 according to SEQ ID NO:104, a guanine at a position corresponding to position 731 according to SEQ ID NO:105, a guanine at a position corresponding to position 652 according to SEQ ID NO:106, or a guanine at a position corresponding to position 891 according to SEQ ID NO:107, then the GPR75 nucleic acid molecule in the biological sample is a GPR75 missense variant nucleic acid molecule.

In some embodiments, the determining step, detecting step, or sequence analysis comprises sequencing at least a portion of the nucleotide sequence of the GPR75 genomic nucleic acid molecule in the biological sample, wherein the sequenced portion comprises a position corresponding to: positions 5,540-5,546 according to SEQ ID NO:2, or the complement thereof; position 5,557 according to SEQ ID NO:3, or the complement thereof; position 5,911 according to SEQ ID NO:4, or the complement thereof; positions 5,920-5,923 according to SEQ ID NO:5, or the complement thereof; position 6,411 according to SEQ ID NO:6, or the complement thereof; or position 5,831 according to SEQ ID NO:99, or the complement thereof. When the sequenced portion of the GPR75 nucleic acid molecule in the biological sample comprises: a deletion of a CCAGTAG heptanucleotide at positions corresponding to positions 5,540-5,546 according to SEQ ID NO:1, an adenine at a position corresponding to position 5,557 according to SEQ ID NO:3, a thymine at a position corresponding to position 5,911 according to SEQ ID NO:4, a deletion of an AAAG tetranucleotide at positions corresponding to positions 5,920-5,923 according to SEQ ID NO:1, an insertion of a thymine at a position corresponding to position 6,411 according to SEQ ID NO:6, or a guanine at a position corresponding to position 5,831 according to SEQ ID NO:99, then the GPR75 nucleic acid molecule in the biological sample is a GPR75 missense variant nucleic acid molecule.

In some embodiments, the determining step, detecting step, or sequence analysis comprises sequencing at least a portion of the nucleotide sequence of the GPR75 mRNA molecule in the biological sample, wherein the sequenced portion comprises a position corresponding to: positions 539-545 according to SEQ ID NO:11, or the complement thereof; positions 440-446 according to SEQ ID NO:16, or the complement thereof; positions 361-367 according to SEQ ID NO:21, or the complement thereof; positions 600-606 according to SEQ ID NO:26, or the complement thereof; position 556 according to SEQ ID NO:12, or the complement thereof; position 457 according to SEQ ID NO:17, or the complement thereof; position 378 according to SEQ ID NO:22, or the complement thereof; position 617 according to SEQ ID NO:27, or the complement thereof; position 910 according to SEQ ID NO:13, or the complement thereof; position 811 according to SEQ ID NO:18, or the complement thereof; position 732 according to SEQ ID NO:23, or the complement thereof; position 971 according to SEQ ID NO:28, or the complement thereof; positions 919-922 according to SEQ ID NO:14, or the complement thereof; positions 820-823 according to SEQ ID NO:19, or the complement thereof; positions 741-744 according to SEQ ID NO:24, or the complement thereof; positions 980-983 according to SEQ ID NO:29, or the complement thereof; position 1,410 according to SEQ ID NO:15, or the complement thereof; position 1,311 according to SEQ ID NO:20, or the complement thereof; position 1,232 according to SEQ ID NO:25, or the complement thereof; position 1,471 according to SEQ ID NO:30, or the complement thereof; position 830 according to SEQ ID NO:100, or the complement thereof; position 731 according to SEQ ID NO:101, or the complement thereof; position 652 according to SEQ ID NO:102, or the complement thereof; position 891 according to SEQ ID NO:103, or the complement thereof. When the sequenced portion of the GPR75 nucleic acid molecule in the biological sample: lacks a CCAGUAG heptanucleotide at positions corresponding to positions 539-545 according to SEQ ID NO:7; lacks a CCAGUAG heptanucleotide at positions corresponding to positions 440-446 according to SEQ ID NO:8; lacks a CCAGUAG heptanucleotide at positions corresponding to positions 361-367 according to SEQ ID NO:9; lacks a CCAGUAG heptanucleotide at positions corresponding to positions 600-606 according to SEQ ID NO:10; comprises an adenine at a position corresponding to position 556 according to SEQ ID NO:12; comprises an adenine at a position corresponding to position 457 according to SEQ ID NO:17; comprises an adenine at a position corresponding to position 378 according to SEQ ID NO:22; comprises an adenine at a position corresponding to position 617 according to SEQ ID NO:27; comprises a uracil at a position corresponding to position 910 according to SEQ ID NO:13; comprises a uracil at a position corresponding to position 811 according to SEQ ID NO:18; comprises a uracil at a position corresponding to position 732 according to SEQ ID NO:23; comprises a uracil at a position corresponding to position 971 according to SEQ ID NO:28; lacks an AAAG tetranucleotide at positions corresponding to positions 919-922 according to SEQ ID NO:7; lacks an AAAG tetranucleotide at positions corresponding to positions 820-823 according to SEQ ID NO:8; lacks an AAAG tetranucleotide at positions corresponding to positions 741-744 according to SEQ ID NO:9; lacks an AAAG tetranucleotide at positions corresponding to positions 980-983 according to SEQ ID NO:10; comprises an insertion of a uracil at a position corresponding to position 1,410 according to SEQ ID NO:15; comprises an insertion of a uracil at a position corresponding to position 1,311 according to SEQ ID NO:20; comprises an insertion of a uracil at a position corresponding to position 1,232 according to SEQ ID NO:25; comprises an insertion of a uracil at a position corresponding to position 1,471 according to SEQ ID NO:30; comprises a guanine at a position corresponding to position 830 according to SEQ ID NO:100; comprises a guanine at a position corresponding to position 731 according to SEQ ID NO:101; comprises a guanine at a position corresponding to position 652 according to SEQ ID NO:102; or comprises a guanine at a position corresponding to position 891 according to SEQ ID NO:103, then the GPR75 nucleic acid molecule in the biological sample is a GPR75 missense variant nucleic acid molecule. In some embodiments, the determining step, detecting step, or sequence analysis comprises sequencing at least a portion of the nucleotide sequence of the GPR75 cDNA molecule produced from the mRNA molecule in the biological sample, wherein the sequenced portion comprises a position corresponding to: positions 539-545 according to SEQ ID NO:35, or the complement thereof; positions 440-446 according to SEQ ID NO:40, or the complement thereof; positions 361-367 according to SEQ ID NO:45, or the complement thereof; positions 600-606 according to SEQ ID NO:50, or the complement thereof; position 556 according to SEQ ID NO:36, or the complement thereof; position 457 according to SEQ ID NO:41, or the complement thereof; position 378 according to SEQ ID NO:46, or the complement thereof; position 617 according to SEQ ID NO:51, or the complement thereof; position 910 according to SEQ ID NO:37, or the complement thereof; position 811 according to SEQ ID NO:42, or the complement thereof; position 732 according to SEQ ID NO:47, or the complement thereof; position 971 according to SEQ ID NO:52, or the complement thereof; positions 919-922 according to SEQ ID NO:38, or the complement thereof; positions 820-823 according to SEQ ID NO:43, or the complement thereof; positions 741-744 according to SEQ ID NO:48, or the complement thereof; positions 980-983 according to SEQ ID NO:53, or the complement thereof; position 1,410 according to SEQ ID NO:39, or the complement thereof; position 1,311 according to SEQ ID NO:44, or the complement thereof; position 1,232 according to SEQ ID NO:49, the complement thereof; position 1,471 according to SEQ ID NO:54, or the complement thereof; position 830 according to SEQ ID NO:104, or the complement thereof; position 731 according to SEQ ID NO:105, or the complement thereof; position 652 according to SEQ ID NO:106, or the complement thereof; or position 891 according to SEQ ID NO:107, or the complement thereof. When the sequenced portion of the GPR75 nucleic acid molecule in the biological sample: lacks a CCAGTAG heptanucleotide at positions corresponding to positions 539-545 according to SEQ ID NO:31; lacks a CCAGTAG heptanucleotide at positions corresponding to positions 440-446 according to SEQ ID NO:32; lacks a CCAGTAG heptanucleotide at positions corresponding to positions 361-367 according to SEQ ID NO:33; lacks a CCAGTAG heptanucleotide at positions corresponding to positions 600-606 according to SEQ ID NO:34; comprises an adenine at a position corresponding to position 556 according to SEQ ID NO:36; comprises an adenine at a position corresponding to position 457 according to SEQ ID NO:41; comprises an adenine at a position corresponding to position 378 according to SEQ ID NO:46; comprises an adenine at a position corresponding to position 617 according to SEQ ID NO:51; comprises a thymine at a position corresponding to position 910 according to SEQ ID NO:37; comprises a thymine at a position corresponding to position 811 according to SEQ ID NO:42; a comprises thymine at a position corresponding to position 732 according to SEQ ID NO:47; comprises a thymine at a position corresponding to position 971 according to SEQ ID NO:52; lacks an AAAG tetranucleotide at positions corresponding to positions 919-922 according to SEQ ID NO:31; lacks an AAAG tetranucleotide at positions corresponding to positions 820-823 according to SEQ ID NO:32; lacks an AAAG tetranucleotide at positions corresponding to positions 741-744 according to SEQ ID NO:33; lacks an AAAG tetranucleotide at positions corresponding to positions 980-983 according to SEQ ID NO:34; comprises an insertion of a thymine at a position corresponding to position 1,410 according to SEQ ID NO:39; comprises an insertion of a thymine at a position corresponding to position 1,311 according to SEQ ID NO:44; comprises an insertion of a thymine at a position corresponding to position 1,232 according to SEQ ID NO:49; comprises an insertion of a thymine at a position corresponding to position 1,471 according to SEQ ID NO:54; comprises a guanine at a position corresponding to position 830 according to SEQ ID NO:104; comprises a guanine at a position corresponding to position 731 according to SEQ ID NO:105; comprises a guanine at a position corresponding to position 652 according to SEQ ID NO:106; or comprises a guanine at a position corresponding to position 891 according to SEQ ID NO:107, then the GPR75 nucleic acid molecule in the biological sample is a GPR75 missense variant nucleic acid molecule.

In some embodiments, the determining step, detecting step, or sequence analysis comprises: a) contacting the biological sample with a primer hybridizing to a portion of the nucleotide sequence of the GPR75: i) genomic nucleic acid molecule that is proximate to a position corresponding to positions 5,540-5,546 according to SEQ ID NO:2; ii) mRNA molecule that is proximate to a position corresponding to: positions 539-545 according to SEQ ID NO:11, positions 440-446 according to SEQ ID NO:16, positions 361-367 according to SEQ ID NO:21, or positions 600-606 according to SEQ ID NO:26; and/or iii) cDNA molecule that is proximate to a position corresponding to: positions 539-545 according to SEQ ID NO:35, positions 440-446 according to SEQ ID NO:40, positions 361-367 according to SEQ ID NO:45, or positions 600-606 according to SEQ ID NO:50; b) extending the primer at least through the position of the nucleotide sequence of the GPR75: i) genomic nucleic acid molecule corresponding to positions 5,540-5,546 according to SEQ ID NO:2; ii) mRNA molecule corresponding to: positions 539-545 according to SEQ ID NO:11, positions 440-446 according to SEQ ID NO:16, positions 361-367 according to SEQ ID NO:21, or positions 600-606 according to SEQ ID NO:26; and/or iii) cDNA molecule corresponding to: positions 539-545 according to SEQ ID NO:35, positions 440-446 according to SEQ ID NO:40, positions 361-367 according to SEQ ID NO:45, or positions 600-606 according to SEQ ID NO:50; and c) determining whether the extension product of the primer comprises: i) a deletion of a CCAGTAG heptanucleotide at positions corresponding to positions 5,540-5,546 according to SEQ ID NO:1; ii) a deletion of a CCAGUAG heptanucleotide at positions corresponding to positions 539-545 according to SEQ ID NO:7, a deletion of a CCAGUAG heptanucleotide at positions corresponding to positions 440-446 according to SEQ ID NO:8, a deletion of a CCAGUAG heptanucleotide at positions corresponding to positions 361-367 according to SEQ ID NO:9, or a deletion of a CCAGUAG heptanucleotide at positions corresponding to positions 600-606 according to SEQ ID NO:10; or iii) a deletion of a CCAGTAG heptanucleotide at positions corresponding to positions 539-545 according to SEQ ID NO:31, a deletion of a CCAGTAG heptanucleotide at positions corresponding to positions 440-446 according to SEQ ID NO:32, a deletion of a CCAGTAG heptanucleotide at positions corresponding to positions 361-367 according to SEQ ID NO:33, or a deletion of a CCAGTAG heptanucleotide at positions corresponding to positions 600-606 according to SEQ ID NO:34.

In some embodiments, the determining step, detecting step, or sequence analysis comprises: a) contacting the biological sample with a primer hybridizing to a portion of the nucleotide sequence of the GPR75: i) genomic nucleic acid molecule that is proximate to a position corresponding to position 5,557 according to SEQ ID NO:3; ii) mRNA molecule that is proximate to a position corresponding to: position 556 according to SEQ ID NO:12, position 457 according to SEQ ID NO:17, position 378 according to SEQ ID NO:22, position 617 according to SEQ ID NO:27 and/or iii) cDNA molecule that is proximate to a position corresponding to: position 556 according to SEQ ID NO:36, position 457 according to SEQ ID NO:41, position 378 according to SEQ ID NO:46, or position 617 according to SEQ ID NO:51; b) extending the primer at least through the position of the nucleotide sequence of the GPR75: i) genomic nucleic acid molecule corresponding to position 5,557 according to SEQ ID NO:3; ii) mRNA molecule corresponding to: position 556 according to SEQ ID NO:12, position 457 according to SEQ ID NO:17, position 378 according to SEQ ID NO:22, or position 617 according to SEQ ID NO:27; and/or iii) cDNA molecule corresponding to: position 556 according to SEQ ID NO:36, position 457 according to SEQ ID NO:41, position 378 according to SEQ ID NO:46, or position 617 according to SEQ ID NO:51; and c) determining whether the extension product of the primer comprises: i) an adenine at a position corresponding to position 5,557 according to SEQ ID NO:3; ii) an adenine at a position corresponding to position 556 according to SEQ ID NO:12, an adenine at a position corresponding to position 457 according to SEQ ID NO:17, an adenine at a position corresponding to position 378 according to SEQ ID NO:22, or an adenine at a position corresponding to position 617 according to SEQ ID NO:27; or iii) an adenine at a position corresponding to position 556 according to SEQ ID NO:36, an adenine at a position corresponding to position 457 according to SEQ ID NO:41, an adenine at a position corresponding to position 378 according to SEQ ID NO:46, or an adenine at a position corresponding to position 617 according to SEQ ID NO:51.

In some embodiments, the determining step, detecting step, or sequence analysis comprises: a) contacting the biological sample with a primer hybridizing to a portion of the nucleotide sequence of the GPR75: i) genomic nucleic acid molecule that is proximate to a position corresponding to position 5,911 according to SEQ ID NO:4; ii) mRNA molecule that is proximate to a position corresponding to: position 910 according to SEQ ID NO:13, position 811 according to SEQ ID NO:18, position 732 according to SEQ ID NO:23, or position 971 according to SEQ ID NO:28; and/or iii) cDNA molecule that is proximate to a position corresponding to: position 910 according to SEQ ID NO:37, position 811 according to SEQ ID NO:42, position 732 according to SEQ ID NO:47, or position 971 according to SEQ ID NO:52; b) extending the primer at least through the position of the nucleotide sequence of the GPR75: i) genomic nucleic acid molecule corresponding to position 5,911 according to SEQ ID NO:4; ii) mRNA molecule corresponding to: position 910 according to SEQ ID NO:13, position 811 according to SEQ ID NO:18, position 732 according to SEQ ID NO:23, or position 971 according to SEQ ID NO:28; and/or iii) cDNA molecule corresponding to: position 910 according to SEQ ID NO:37, position 811 according to SEQ ID NO:42, position 732 according to SEQ ID NO:47, or position 971 according to SEQ ID NO:52; and c) determining whether the extension product of the primer comprises: i) a thymine at a position corresponding to position 5,911 according to SEQ ID NO:4; ii) a uracil at a position corresponding to position 910 according to SEQ ID NO:13, a uracil at a position corresponding to position 811 according to SEQ ID NO:18, a uracil at a position corresponding to position 732 according to SEQ ID NO:23, or a uracil at a position corresponding to position 971 according to SEQ ID NO:28; or iii) a thymine at a position corresponding to position 910 according to SEQ ID NO:37, a thymine at a position corresponding to position 811 according to SEQ ID NO:42, a thymine at a position corresponding to position 732 according to SEQ ID NO:47, or a thymine at a position corresponding to position 971 according to SEQ ID NO:52.

In some embodiments, the determining step, detecting step, or sequence analysis comprises: a) contacting the biological sample with a primer hybridizing to a portion of the nucleotide sequence of the GPR75: i) genomic nucleic acid molecule that is proximate to a position corresponding to positions 5,920-5,923 according to SEQ ID NO:5; ii) mRNA molecule that is proximate to a position corresponding to: positions 919-922 according to SEQ ID NO:14, positions 820-823 according to SEQ ID NO:19, positions 741-744 according to SEQ ID NO:24, or positions 980-983 according to SEQ ID NO:29; and/or iii) cDNA molecule that is proximate to a position corresponding to: positions 919-922 according to SEQ ID NO:38, positions 820-823 according to SEQ ID NO:43, positions 741-744 according to SEQ ID NO:48, or positions 980-983 according to SEQ ID NO:53; b) extending the primer at least through the position of the nucleotide sequence of the GPR75: i) genomic nucleic acid molecule corresponding to positions 5,920-5,923 according to SEQ ID NO:5; ii) mRNA molecule corresponding to: positions 919-922 according to SEQ ID NO:14, positions 820-823 according to SEQ ID NO:19, positions 741-744 according to SEQ ID NO:24, or positions 980-983 according to SEQ ID NO:29; and/or iii) cDNA molecule corresponding to: positions 919-922 according to SEQ ID NO:38, positions 820-823 according to SEQ ID NO:43, positions 741-744 according to SEQ ID NO:48, or positions 980-983 according to SEQ ID NO:53; and c) determining whether the extension product of the primer comprises: i) a deletion of an AAAG tetranucleotide at positions corresponding to positions 5,920-5,923 according to SEQ ID NO:1; ii) a deletion of an AAAG tetranucleotide at positions corresponding to positions 919-922 according to SEQ ID NO:7, a deletion of an AAAG tetranucleotide at positions corresponding to positions 820-823 according to SEQ ID NO:8, a deletion of an AAAG tetranucleotide at positions corresponding to positions 741-744 according to SEQ ID NO:9, or a deletion of an AAAG tetranucleotide at positions corresponding to positions 980-983 according to SEQ ID NO:10; or iii) a deletion of an AAAG tetranucleotide at positions corresponding to positions 919-922 according to SEQ ID NO:31, a deletion of an AAAG tetranucleotide at positions corresponding to positions 820-823 according to SEQ ID NO:32, a deletion of an AAAG tetranucleotide at positions corresponding to positions 741-744 according to SEQ ID NO:33, or a deletion of an AAAG tetranucleotide at positions corresponding to positions 980-983 according to SEQ ID NO:34.

In some embodiments, the determining step, detecting step, or sequence analysis comprises: a) contacting the biological sample with a primer hybridizing to a portion of the nucleotide sequence of the GPR75: i) genomic nucleic acid molecule that is proximate to a position corresponding to position 6,411 according to SEQ ID NO:6; ii) mRNA molecule that is proximate to a position corresponding to: position 1,410 according to SEQ ID NO:15, position 1,311 according to SEQ ID NO:20, position 1,232 according to SEQ ID NO:25, or position 1,471 according to SEQ ID NO:30; and/or iii) cDNA molecule that is proximate to a position corresponding to: position 1,410 according to SEQ ID NO:39, position 1,311 according to SEQ ID NO:44, position 1,232 according to SEQ ID NO:49, or position 1,471 according to SEQ ID NO:54; b) extending the primer at least through the position of the nucleotide sequence of the GPR75: i) genomic nucleic acid molecule corresponding to position 6,411 according to SEQ ID NO:6; ii) mRNA molecule corresponding to: position 1,410 according to SEQ ID NO:15, position 1,311 according to SEQ ID NO:20, position 1,232 according to SEQ ID NO:25, or position 1,471 according to SEQ ID NO:30; and/or iii) cDNA molecule corresponding to: position 1,410 according to SEQ ID NO:39, position 1,311 according to SEQ ID NO:44, position 1,232 according to SEQ ID NO:49, or position 1,471 according to SEQ ID NO:54; and c) determining whether the extension product of the primer comprises: i) an insertion of a thymine at a position corresponding to position 6,411 according to SEQ ID NO:6; ii) an insertion of a uracil at a position corresponding to position 1,410 according to SEQ ID NO:15, an insertion of a uracil at a position corresponding to position 1,311 according to SEQ ID NO:20, an insertion of a uracil at a position corresponding to position 1,232 according to SEQ ID NO:25, or an insertion of a uracil at a position corresponding to position 1,471 according to SEQ ID NO:30; or iii) an insertion of a thymine at a position corresponding to position 1,410 according to SEQ ID NO:39, an insertion of a thymine at a position corresponding to position 1,311 according to SEQ ID NO:44, an insertion of a thymine at a position corresponding to position 1,232 according to SEQ ID NO:49, or an insertion of a thymine at a position corresponding to position 1,471 according to SEQ ID NO:54.

In some embodiments, the determining step, detecting step, or sequence analysis comprises: a) contacting the biological sample with a primer hybridizing to a portion of the nucleotide sequence of the GPR75: i) genomic nucleic acid molecule that is proximate to a position corresponding to position 5,831 according to SEQ ID NO:99; ii) mRNA molecule that is proximate to a position corresponding to: position 830 according to SEQ ID NO:100; position 731 according to SEQ ID NO:101; position 652 according to SEQ ID NO:102; or position 891 according to SEQ ID NO:103; and/or iii) cDNA molecule that is proximate to a position corresponding to: position 830 according to SEQ ID NO:104; position 731 according to SEQ ID NO:105; position 652 according to SEQ ID NO:106; or position 891 according to SEQ ID NO:107; b) extending the primer at least through the position of the nucleotide sequence of the GPR75: i) genomic nucleic acid molecule that is proximate to a position corresponding to position 5,831 according to SEQ ID NO:99; ii) mRNA molecule that is proximate to a position corresponding to: position 830 according to SEQ ID NO:100; position 731 according to SEQ ID NO:101; position 652 according to SEQ ID NO:102; or position 891 according to SEQ ID NO:103; and/or iii) cDNA molecule that is proximate to a position corresponding to: position 830 according to SEQ ID NO:104; position 731 according to SEQ ID NO:105; position 652 according to SEQ ID NO:106; or position 891 according to SEQ ID NO:107; and c) determining whether the extension product of the primer comprises: i) a guanine at a position corresponding to position 5,831 according to SEQ ID NO:99, or the complement thereof; ii) a guanine at a position corresponding to position 830 according to SEQ ID NO:100, or the complement thereof; a guanine at a position corresponding to position 731 according to SEQ ID NO:101, or the complement thereof; a guanine at a position corresponding to position 652 according to SEQ ID NO:102, or the complement thereof; or a guanine at a position corresponding to position 891 according to SEQ ID NO:103, or the complement thereof; or iii) a guanine at a position corresponding to position 830 according to SEQ ID NO:104, or the complement thereof; a guanine at a position corresponding to position 731 according to SEQ ID NO:105, or the complement thereof; a guanine at a position corresponding to position 652 according to SEQ ID NO:106; or the complement thereof; or a guanine at a position corresponding to position 891 according to SEQ ID NO:107, or the complement thereof.

In some embodiments, the determining step, detecting step, or sequence analysis comprises: a) contacting the biological sample with a primer hybridizing to a portion of the nucleotide sequence of the GPR75 genomic nucleic acid molecule that is proximate to a position corresponding to: positions 5,540-5,546 according to SEQ ID NO:2, position 5,557 according to SEQ ID NO:3, position 5,911 according to SEQ ID NO:4, positions 5,920-5,923 according to SEQ ID NO:5, position 6,411 according to SEQ ID NO:6, or position 5,831 according to SEQ ID NO:99; b) extending the primer at least through the position of the nucleotide sequence of the GPR75 genomic nucleic acid molecule corresponding to: positions 5,540-5,546 according to SEQ ID NO:2, position 5,557 according to SEQ ID NO:3, position 5,911 according to SEQ ID NO:4, positions 5,920-5,923 according to SEQ ID NO:5, position 6,411 according to SEQ ID NO:6, or position 5,831 according to SEQ ID NO:99; and c) determining whether the extension product of the primer: lacks a CCAGTAG heptanucleotide at positions corresponding to positions 5,540-5,546 according to SEQ ID NO:1, comprises an adenine at a position corresponding to position 5,557 according to SEQ ID NO:3, comprises a thymine at a position corresponding to position 5,911 according to SEQ ID NO:4, lacks an AAAG tetranucleotide at positions corresponding to positions 5,920-5,923 according to SEQ ID NO:1, comprises an insertion of a thymine at a position corresponding to position 6,411 according to SEQ ID NO:6, or comprises a guanine at a position corresponding to position 5,831 according to SEQ ID NO:99, or the complement thereof.

In some embodiments, the determining step, detecting step, or sequence analysis comprises: a) contacting the biological sample with a primer hybridizing to a portion of the nucleotide sequence of the GPR75 mRNA molecule that is proximate to a position corresponding to: positions 539-545 according to SEQ ID NO:11, positions 440-446 according to SEQ ID NO:16, positions 361-367 according to SEQ ID NO:21, positions 600-606 according to SEQ ID NO:26, position 556 according to SEQ ID NO:12, position 457 according to SEQ ID NO:17, position 378 according to SEQ ID NO:22, position 617 according to SEQ ID NO:27, position 910 according to SEQ ID NO:13, position 811 according to SEQ ID NO:18, position 732 according to SEQ ID NO:23, position 971 according to SEQ ID NO:28, positions 919-922 according to SEQ ID NO:14, positions 820-823 according to SEQ ID NO:19, positions 741-744 according to SEQ ID NO:24, positions 980-983 according to SEQ ID NO:29, position 1,410 according to SEQ ID NO:15, position 1,311 according to SEQ ID NO:20, position 1,232 according to SEQ ID NO:25, position 1,471 according to SEQ ID NO:30; position 830 according to SEQ ID NO:100; position 731 according to SEQ ID NO:101; position 652 according to SEQ ID NO:102; or position 891 according to SEQ ID NO:103; b) extending the primer at least through the position of the nucleotide sequence of the GPR75 mRNA molecule corresponding to: positions 539-545 according to SEQ ID NO:11, positions 440-446 according to SEQ ID NO:16, positions 361-367 according to SEQ ID NO:21, positions 600-606 according to SEQ ID NO:26, position 556 according to SEQ ID NO:12, position 457 according to SEQ ID NO:17, position 378 according to SEQ ID NO:22, position 617 according to SEQ ID NO:27, position 910 according to SEQ ID NO:13, position 811 according to SEQ ID NO:18, position 732 according to SEQ ID NO:23, position 971 according to SEQ ID NO:28, positions 919-922 according to SEQ ID NO:14, positions 820-823 according to SEQ ID NO:19, positions 741-744 according to SEQ ID NO:24, positions 980-983 according to SEQ ID NO:29, position 1,410 according to SEQ ID NO:15, position 1,311 according to SEQ ID NO:20, position 1,232 according to SEQ ID NO:25, position 1,471 according to SEQ ID NO:30, position 830 according to SEQ ID NO:100, position 731 according to SEQ ID NO:101, position 652 according to SEQ ID NO:102, or position 891 according to SEQ ID NO:103; and c) determining whether the extension product of the primer: lacks a CCAGUAG heptanucleotide at positions corresponding to positions 539-545 according to SEQ ID NO:7, lacks a CCAGUAG heptanucleotide at positions corresponding to positions 440-446 according to SEQ ID NO:8, lacks a CCAGUAG heptanucleotide at positions corresponding to positions 361-367 according to SEQ ID NO:9, lacks a CCAGUAG heptanucleotide at positions corresponding to positions 600-606 according to SEQ ID NO:10, comprises an adenine at a position corresponding to position 556 according to SEQ ID NO:12, comprises an adenine at a position corresponding to position 457 according to SEQ ID NO:17, comprises an adenine at a position corresponding to position 378 according to SEQ ID NO:22, comprises an adenine at a position corresponding to position 617 according to SEQ ID NO:27, comprises a uracil at a position corresponding to position 910 according to SEQ ID NO:13, comprises a uracil at a position corresponding to position 811 according to SEQ ID NO:18, comprises a uracil at a position corresponding to position 732 according to SEQ ID NO:23, comprises a uracil at a position corresponding to position 971 according to SEQ ID NO:28, lacks an AAAG tetranucleotide at positions corresponding to positions 919-922 according to SEQ ID NO:7, lacks an AAAG tetranucleotide at positions corresponding to positions 820-823 according to SEQ ID NO:8, lacks an AAAG tetranucleotide at positions corresponding to positions 741-744 according to SEQ ID NO:9, lacks an AAAG tetranucleotide at positions corresponding to positions 980-983 according to SEQ ID NO:10, comprises an insertion of a uracil at a position corresponding to position 1,410 according to SEQ ID NO:15, comprises an insertion of a uracil at a position corresponding to position 1,311 according to SEQ ID NO:20, comprises an insertion of a uracil at a position corresponding to position 1,232 according to SEQ ID NO:25, comprises an insertion of a uracil at a position corresponding to position 1,471 according to SEQ ID NO:30, comprises a guanine at a position corresponding to position 830 according to SEQ ID NO:100, comprises a guanine at a position corresponding to position 731 according to SEQ ID NO:101, comprises a guanine at a position corresponding to position 652 according to SEQ ID NO:102, or comprises a guanine at a position corresponding to position 891 according to SEQ ID NO:103.

In some embodiments, the determining step, detecting step, or sequence analysis comprises: a) contacting the biological sample with a primer hybridizing to a portion of the nucleotide sequence of the GPR75 cDNA molecule that is proximate to a position corresponding to: positions 539-545 according to SEQ ID NO:35, positions 440-446 according to SEQ ID NO:40, positions 361-367 according to SEQ ID NO:45, positions 600-606 according to SEQ ID NO:50, position 556 according to SEQ ID NO:36, position 457 according to SEQ ID NO:41, position 378 according to SEQ ID NO:46, position 617 according to SEQ ID NO:51, position 910 according to SEQ ID NO:37, position 811 according to SEQ ID NO:42, position 732 according to SEQ ID NO:47, position 971 according to SEQ ID NO:52, positions 919-922 according to SEQ ID NO:38, positions 820-823 according to SEQ ID NO:43, positions 741-744 according to SEQ ID NO:48, positions 980-983 according to SEQ ID NO:53, position 1,410 according to SEQ ID NO:39, position 1,311 according to SEQ ID NO:44, position 1,232 according to SEQ ID NO:49, position 1,471 according to SEQ ID NO:54, position 830 according to SEQ ID NO:104, position 731 according to SEQ ID NO:105, position 652 according to SEQ ID NO:106, or position 891 according to SEQ ID NO:107; b) extending the primer at least through the position of the nucleotide sequence of the GPR75 cDNA molecule corresponding to: positions 539-545 according to SEQ ID NO:35, positions 440-446 according to SEQ ID NO:40, positions 361-367 according to SEQ ID NO:45, positions 600-606 according to SEQ ID NO:50, position 556 according to SEQ ID NO:36, position 457 according to SEQ ID NO:41, position 378 according to SEQ ID NO:46, position 617 according to SEQ ID NO:51, position 910 according to SEQ ID NO:37, position 811 according to SEQ ID NO:42, position 732 according to SEQ ID NO:47, position 971 according to SEQ ID NO:52, positions 919-922 according to SEQ ID NO:38, positions 820-823 according to SEQ ID NO:43, positions 741-744 according to SEQ ID NO:48, positions 980-983 according to SEQ ID NO:53, position 1,410 according to SEQ ID NO:39, position 1,311 according to SEQ ID NO:44, position 1,232 according to SEQ ID NO:49, position 1,471 according to SEQ ID NO:54, position 830 according to SEQ ID NO:104, position 731 according to SEQ ID NO:105, position 652 according to SEQ ID NO:106, or position 891 according to SEQ ID NO:107; and c) determining whether the extension product of the primer: lacks a CCAGTAG heptanucleotide at positions corresponding to positions 539-545 according to SEQ ID NO:31, lacks a CCAGTAG heptanucleotide at positions corresponding to positions 440-446 according to SEQ ID NO:32, lacks a CCAGTAG heptanucleotide at positions corresponding to positions 361-367 according to SEQ ID NO:33, lacks a CCAGTAG heptanucleotide at positions corresponding to positions 600-606 according to SEQ ID NO:34, comprises an adenine at a position corresponding to position 556 according to SEQ ID NO:36, comprises an adenine at a position corresponding to position 457 according to SEQ ID NO:41, comprises an adenine at a position corresponding to position 378 according to SEQ ID NO:46, comprises an adenine at a position corresponding to position 617 according to SEQ ID NO:51, comprises a thymine at a position corresponding to position 910 according to SEQ ID NO:37, comprises a thymine at a position corresponding to position 811 according to SEQ ID NO:42, comprises a thymine at a position corresponding to position 732 according to SEQ ID NO:47, comprises a thymine at a position corresponding to position 971 according to SEQ ID NO:52, lacks an AAAG tetranucleotide at positions corresponding to positions 919-922 according to SEQ ID NO:31, lacks an AAAG tetranucleotide at positions corresponding to positions 820-823 according to SEQ ID NO:32, lacks an AAAG tetranucleotide at positions corresponding to positions 741-744 according to SEQ ID NO:33, lacks an AAAG tetranucleotide at positions corresponding to positions 980-983 according to SEQ ID NO:34, comprises an insertion of a thymine at a position corresponding to position 1,410 according to SEQ ID NO:39, comprises an insertion of a thymine at a position corresponding to position 1,311 according to SEQ ID NO:44, comprises an insertion of a thymine at a position corresponding to position 1,232 according to SEQ ID NO:49, or comprises an insertion of a thymine at a position corresponding to position 1,471 according to SEQ ID NO:54, comprises a guanine at a position corresponding to position 830 according to SEQ ID NO:104, comprises a guanine at a position corresponding to position 731 according to SEQ ID NO:105, comprises a guanine at a position corresponding to position 652 according to SEQ ID NO:106, or comprises a guanine at a position corresponding to position 891 according to SEQ ID NO:107.

In some embodiments, the assay comprises sequencing the entire nucleic acid molecule. In some embodiments, only a GPR75 genomic nucleic acid molecule is analyzed. In some embodiments, only a GPR75 mRNA is analyzed. In some embodiments, only a GPR75 cDNA obtained from GPR75 mRNA is analyzed.

In some embodiments, the determining step, detecting step, or sequence analysis comprises: a) amplifying at least a portion of the nucleic acid molecule that encodes the human GPR75 polypeptide, wherein the amplified portion comprises: i) a deletion of a CCAGTAG heptanucleotide at positions corresponding to positions 5,540-5,546 according to SEQ ID NO:1, or the complement thereof; ii) a deletion of a CCAGUAG heptanucleotide at positions corresponding to positions 539-545 according to SEQ ID NO:7, or the complement thereof; a deletion of a CCAGUAG heptanucleotide at positions corresponding to positions 440-446 according to SEQ ID NO:8, or the complement thereof; a deletion of a CCAGUAG heptanucleotide at positions corresponding to positions 361-367 according to SEQ ID NO:9, or the complement thereof; or a deletion of a CCAGUAG heptanucleotide at positions corresponding to positions 600-606 according to SEQ ID NO:10, or the complement thereof; and/or iii) a deletion of a CCAGTAG heptanucleotide at positions corresponding to positions 539-545 according to SEQ ID NO:31, or the complement thereof; a deletion of a CCAGTAG heptanucleotide at positions corresponding to positions 440-446 according to SEQ ID NO:32, or the complement thereof; a deletion of a CCAGTAG heptanucleotide at positions corresponding to positions 361-367 according to SEQ ID NO:33, or the complement thereof; or a deletion of a CCAGTAG heptanucleotide at positions corresponding to positions 600-606 according to SEQ ID NO:34, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: i) lacking a CCAGTAG heptanucleotide at positions corresponding to positions 5,540-5,546 according to SEQ ID NO:1, or the complement thereof; ii) lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; or lacking a CCAGUAG heptanucleotide at positions corresponding to positions 600-606 according to SEQ ID NO:10, or the complement thereof; and/or iii) lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; or lacking a CCAGTAG heptanucleotide at positions corresponding to positions 600-606 according to SEQ ID NO:34, or the complement thereof; and d) detecting the detectable label.

In some embodiments, the determining step, detecting step, or sequence analysis comprises: a) amplifying at least a portion of the nucleic acid molecule that encodes the human GPR75 polypeptide, wherein the amplified portion comprises: i) an adenine at a position corresponding to position 5,557 according to SEQ ID NO:3, or the complement thereof; ii) an adenine at a position corresponding to position 556 according to SEQ ID NO:12, or the complement thereof; an adenine at a position corresponding to position 457 according to SEQ ID NO:17, or the complement thereof; an adenine at a position corresponding to position 378 according to SEQ ID NO:22, or the complement thereof; or an adenine at a position corresponding to position 617 according to SEQ ID NO:27, or the complement thereof; and/or iii) an adenine at a position corresponding to position 556 according to SEQ ID NO:36, or the complement thereof; an adenine at a position corresponding to position 457 according to SEQ ID NO:41, or the complement thereof; an adenine at a position corresponding to position 378 according to SEQ ID NO:46, or the complement thereof; or an adenine at a position corresponding to position 617 according to SEQ ID NO:51, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an adenine at a position corresponding to position 5,557 according to SEQ ID NO:3, or the complement thereof; ii) an adenine at a position corresponding to position 556 according to SEQ ID NO:12, or the complement thereof; an adenine at a position corresponding to position 457 according to SEQ ID NO:17, or the complement thereof; an adenine at a position corresponding to position 378 according to SEQ ID NO:22, or the complement thereof; or an adenine at a position corresponding to position 617 according to SEQ ID NO:27, or the complement thereof; and/or iii) an adenine at a position corresponding to position 556 according to SEQ ID NO:36, or the complement thereof; an adenine at a position corresponding to position 457 according to SEQ ID NO:41, or the complement thereof; an adenine at a position corresponding to position 378 according to SEQ ID NO:46, or the complement thereof; or an adenine at a position corresponding to position 617 according to SEQ ID NO:51, or the complement thereof; and d) detecting the detectable label.

In some embodiments, the determining step, detecting step, or sequence analysis comprises: a) amplifying at least a portion of the nucleic acid molecule that encodes the human GPR75 polypeptide, wherein the amplified portion comprises: i) a thymine at a position corresponding to position 5,911 according to SEQ ID NO:4, or the complement thereof; ii) a uracil at a position corresponding to position 910 according to SEQ ID NO:13, or the complement thereof; a uracil at a position corresponding to position 811 according to SEQ ID NO:18, or the complement thereof; a uracil at a position corresponding to position 732 according to SEQ ID NO:23, or the complement thereof; or a uracil at a position corresponding to position 971 according to SEQ ID NO:28, or the complement thereof; and/or iii) a thymine at a position corresponding to position 910 according to SEQ ID NO:37, or the complement thereof; a thymine at a position corresponding to position 811 according to SEQ ID NO:42, or the complement thereof; a thymine at a position corresponding to position 732 according to SEQ ID NO:47, or the complement thereof; or a thymine at a position corresponding to position 971 according to SEQ ID NO:52, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a thymine at a position corresponding to position 5,911 according to SEQ ID NO:4, or the complement thereof; ii) a uracil at a position corresponding to position 910 according to SEQ ID NO:13, or the complement thereof; a uracil at a position corresponding to position 811 according to SEQ ID NO:18, or the complement thereof; a uracil at a position corresponding to position 732 according to SEQ ID NO:23, or the complement thereof; or a uracil at a position corresponding to position 971 according to SEQ ID NO:28, or the complement thereof; and/or iii) a thymine at a position corresponding to position 910 according to SEQ ID NO:37, or the complement thereof; a thymine at a position corresponding to position 811 according to SEQ ID NO:42, or the complement thereof; a thymine at a position corresponding to position 732 according to SEQ ID NO:47, or the complement thereof; or a thymine at a position corresponding to position 971 according to SEQ ID NO:52, or the complement thereof; and d) detecting the detectable label.

In some embodiments, the determining step, detecting step, or sequence analysis comprises: a) amplifying at least a portion of the nucleic acid molecule that encodes the human GPR75 polypeptide, wherein the amplified portion comprises: i) a deletion of an AAAG tetranucleotide at positions corresponding to positions 5,920-5,923 according to SEQ ID NO:1, or the complement thereof; ii) a deletion of an AAAG tetranucleotide at positions corresponding to positions 919-922 according to SEQ ID NO:7, or the complement thereof; a deletion of an AAAG tetranucleotide at positions corresponding to positions 820-823 according to SEQ ID NO:8, or the complement thereof; a deletion of an AAAG tetranucleotide at positions corresponding to positions 741-744 according to SEQ ID NO:9, or the complement thereof; or a deletion of an AAAG tetranucleotide at positions corresponding to positions 980-983 according to SEQ ID NO:10, or the complement thereof; and/or iii) a deletion of an AAAG tetranucleotide at positions corresponding to positions 919-922 according to SEQ ID NO:31, or the complement thereof; a deletion of an AAAG tetranucleotide at positions corresponding to positions 820-823 according to SEQ ID NO:32, or the complement thereof; a deletion of an AAAG tetranucleotide at positions corresponding to positions 741-744 according to SEQ ID NO:33, or the complement thereof; or a deletion of an AAAG tetranucleotide at positions corresponding to positions 980-983 according to SEQ ID NO:34, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: i) lacking an AAAG tetranucleotide at positions corresponding to positions 5,920-5,923 according to SEQ ID NO:1, or the complement thereof; ii) lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; or lacking an AAAG tetranucleotide at positions corresponding to positions 980-983 according to SEQ ID NO:10, or the complement thereof; and/or iii) lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; or lacking an AAAG tetranucleotide at positions corresponding to positions 980-983 according to SEQ ID NO:34, or the complement thereof; and d) detecting the detectable label.

In some embodiments, the determining step, detecting step, or sequence analysis comprises: a) amplifying at least a portion of the nucleic acid molecule that encodes the human GPR75 polypeptide, wherein the amplified portion comprises: i) an insertion of a thymine at a position corresponding to position 6,411 according to SEQ ID NO:6, or the complement thereof; ii) an insertion of a uracil at a position corresponding to position 1,410 according to SEQ ID NO:15, or the complement thereof; an insertion of a uracil at a position corresponding to position 1,311 according to SEQ ID NO:20, or the complement thereof; an insertion of a uracil at a position corresponding to position 1,232 according to SEQ ID NO:25, or the complement thereof; or an insertion of a uracil at a position corresponding to position 1,471 according to SEQ ID NO:30, or the complement thereof; and/or iii) an insertion of a thymine at a position corresponding to position 1,410 according to SEQ ID NO:39, or the complement thereof; an insertion of a thymine at a position corresponding to position 1,311 according to SEQ ID NO:44, or the complement thereof; an insertion of a thymine at a position corresponding to position 1,232 according to SEQ ID NO:49, or the complement thereof; or an insertion of a thymine at a position corresponding to position 1,471 according to SEQ ID NO:54, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an insertion of a thymine at a position corresponding to position 6,411 according to SEQ ID NO:6, or the complement thereof; ii) an insertion of a uracil at a position corresponding to position 1,410 according to SEQ ID NO:15, or the complement thereof; an insertion of a uracil at a position corresponding to position 1,311 according to SEQ ID NO:20, or the complement thereof; an insertion of a uracil at a position corresponding to position 1,232 according to SEQ ID NO:25, or the complement thereof; or an insertion of a uracil at a position corresponding to position 1,471 according to SEQ ID NO:30, or the complement thereof; and/or iii) an insertion of a thymine at a position corresponding to position 1,410 according to SEQ ID NO:39, or the complement thereof; an insertion of a thymine at a position corresponding to position 1,311 according to SEQ ID NO:44, or the complement thereof; an insertion of a thymine at a position corresponding to position 1,232 according to SEQ ID NO:49, or the complement thereof; or an insertion of a thymine at a position corresponding to position 1,471 according to SEQ ID NO:54, or the complement thereof; and d) detecting the detectable label.

In some embodiments, the determining step, detecting step, or sequence analysis comprises: a) amplifying at least a portion of the nucleic acid molecule that encodes the human GPR75 polypeptide, wherein the amplified portion comprises: i) a guanine at a position corresponding to position 5,831 according to SEQ ID NO:99, or the complement thereof; ii) a guanine at a position corresponding to position 830 according to SEQ ID NO:100, or the complement thereof; a guanine at a position corresponding to position 731 according to SEQ ID NO:101, or the complement thereof; a guanine at a position corresponding to position 652 according to SEQ ID NO:102, or the complement thereof; or a guanine at a position corresponding to position 891 according to SEQ ID NO:103, or the complement thereof; and/or iii) a guanine at a position corresponding to position 830 according to SEQ ID NO:104, or the complement thereof; a guanine at a position corresponding to position 731 according to SEQ ID NO:105, or the complement thereof; a guanine at a position corresponding to position 652 according to SEQ ID NO:106, or the complement thereof; or a guanine at a position corresponding to position 891 according to SEQ ID NO:107, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a guanine at a position corresponding to position 5,831 according to SEQ ID NO:99, or the complement thereof; ii) a guanine at a position corresponding to position 830 according to SEQ ID NO:100, or the complement thereof; a guanine at a position corresponding to position 731 according to SEQ ID NO:101, or the complement thereof; a guanine at a position corresponding to position 652 according to SEQ ID NO:102, or the complement thereof; or a guanine at a position corresponding to position 891 according to SEQ ID NO:103, or the complement thereof; and/or iii) a guanine at a position corresponding to position 830 according to SEQ ID NO:104, or the complement thereof; a guanine at a position corresponding to position 731 according to SEQ ID NO:105, or the complement thereof; a guanine at a position corresponding to position 652 according to SEQ ID NO:106, or the complement thereof; or a guanine at a position corresponding to position 891 according to SEQ ID NO:107, or the complement thereof; and d) detecting the detectable label.

In some embodiments, the determining step, detecting step, or sequence analysis comprises: a) amplifying at least a portion of the nucleic acid molecule that encodes the human GPR75 polypeptide, wherein the amplified portion: lacks a CCAGTAG heptanucleotide at positions corresponding to positions 5,540-5,546 according to SEQ ID NO:1, or the complement thereof; comprises an adenine at a position corresponding to position 5,557 according to SEQ ID NO:3, or the complement thereof; comprises a thymine at a position corresponding to position 5,911 according to SEQ ID NO:4, or the complement thereof; lacks an AAAG tetranucleotide at positions corresponding to positions 5,920-5,923 according to SEQ ID NO:1, the complement thereof; comprises an insertion of a thymine at a position corresponding to position 6,411 according to SEQ ID NO:6, or the complement thereof; or comprises a guanine at a position corresponding to position 5,831 according to SEQ ID NO:99, or the complement thereof or; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGTAG heptanucleotide at positions corresponding to positions 5,540-5,546 according to SEQ ID NO:1, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:1, or the complement thereof; comprising an insertion of a thymine at a position corresponding to position 6,411 according to SEQ ID NO:6, or the complement thereof; or comprising a guanine at a position corresponding to position 5,831 according to SEQ ID NO:99, or the complement thereof; and d) detecting the detectable label.

In some embodiments, the determining step, detecting step, or sequence analysis comprises: a) amplifying at least a portion of the nucleic acid molecule that encodes the human GPR75 polypeptide, wherein the amplified portion: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; comprises an adenine at a position corresponding to position 556 according to SEQ ID NO:12, or the complement thereof; comprises an adenine at a position corresponding to position 457 according to SEQ ID NO:17, or the complement thereof; comprises an adenine at a position corresponding to position 378 according to SEQ ID NO:22, or the complement thereof; comprises an adenine at a position corresponding to position 617 according to SEQ ID NO:27, or the complement thereof; comprises a uracil at a position corresponding to position 910 according to SEQ ID NO:13, or the complement thereof; comprises a uracil at a position corresponding to position 811 according to SEQ ID NO:18, or the complement thereof; comprises a uracil at a position corresponding to position 732 according to SEQ ID NO:23, or the complement thereof; comprises a uracil at a position corresponding to position 971 according to SEQ ID NO:28, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; comprises an insertion of a uracil at a position corresponding to position 1,471 according to SEQ ID NO:30, or the complement thereof; comprises a guanine at a position corresponding to position 830 according to SEQ ID NO:100, or the complement thereof; comprises a guanine at a position corresponding to position 731 according to SEQ ID NO:101, or the complement thereof; comprises a guanine at a position corresponding to position 652 according to SEQ ID NO:102, or the complement thereof; or comprises a guanine at a position corresponding to position 891 according to SEQ ID NO:103, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; lacking a CCAGUAG heptanucleotide at positions corresponding to positions 600-606 according to SEQ ID NO:10, or the complement thereof; comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; lacking an AAAG tetranucleotide at positions corresponding to positions 980-983 according to SEQ ID NO:10, or the complement thereof; comprising an insertion of a uracil at a position corresponding to position 1,410 according to SEQ ID NO:15, or the complement thereof; comprising an insertion of a uracil at a position corresponding to position 1,311 according to SEQ ID NO:20, or the complement thereof; comprising an insertion of a uracil at a position corresponding to position 1,232 according to SEQ ID NO:25, or the complement thereof; comprising an insertion of a uracil at a position corresponding to position 1,471 according to SEQ ID NO:30, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof.

In some embodiments, the determining step, detecting step, or sequence analysis comprises: a) amplifying at least a portion of the nucleic acid molecule that encodes the human GPR75 polypeptide, wherein the amplified portion: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; comprises an adenine at a position corresponding to position 556 according to SEQ ID NO:36, or the complement thereof; comprises an adenine at a position corresponding to position 457 according to SEQ ID NO:41, or the complement thereof; comprises an adenine at a position corresponding to position 378 according to SEQ ID NO:46, or the complement thereof; comprises an adenine at a position corresponding to position 617 according to SEQ ID NO:51, or the complement thereof; comprises a thymine at a position corresponding to position 910 according to SEQ ID NO:37, or the complement thereof; comprises a thymine at a position corresponding to position 811 according to SEQ ID NO:42, or the complement thereof; comprises a thymine at a position corresponding to position 732 according to SEQ ID NO:47, or the complement thereof; comprises a thymine at a position corresponding to position 971 according to SEQ ID NO:52, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; comprises an insertion of a thymine at a position corresponding to position 1,471 according to SEQ ID NO:54, or the complement thereof; comprises a guanine at a position corresponding to position 830 according to SEQ ID NO:104, or the complement thereof; comprises a guanine at a position corresponding to position 731 according to SEQ ID NO:105, or the complement thereof;

comprises a guanine at a position corresponding to position 652 according to SEQ ID NO:106, or the complement thereof; or comprises a guanine at a position corresponding to position 891 according to SEQ ID NO:107, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; lacking a CCAGTAG heptanucleotide at positions corresponding to positions 600-606 according to SEQ ID NO:34, or the complement thereof; comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; lacking an AAAG tetranucleotide at positions corresponding to positions 980-983 according to SEQ ID NO:34, or the complement thereof; comprising an insertion of a thymine at a position corresponding to position 1,410 according to SEQ ID NO:39, or the complement thereof; comprising an insertion of a thymine at a position corresponding to position 1,311 according to SEQ ID NO:44, or the complement thereof; comprising an insertion of a thymine at a position corresponding to position 1,232 according to SEQ ID NO:49, or the complement thereof; comprising an insertion of a thymine at a position corresponding to position 1,471 according to SEQ ID NO:54, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: i) lacking a CCAGTAG heptanucleotide at positions corresponding to positions 5,540-5,546 according to SEQ ID NO:1, or the complement thereof; ii) lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; or lacking a CCAGUAG heptanucleotide at positions corresponding to positions 600-606 according to SEQ ID NO:10, or the complement thereof; and/or iii) lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; or lacking a CCAGTAG heptanucleotide at positions corresponding to positions 600-606 according to SEQ ID NO:34, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: i) an adenine at a position corresponding to position 5,557 according to SEQ ID NO:3, or the complement thereof; ii) an adenine at a position corresponding to position 556 according to SEQ ID NO:12, or the complement thereof; an adenine at a position corresponding to position 457 according to SEQ ID NO:17, or the complement thereof; an adenine at a position corresponding to position 378 according to SEQ ID NO:22, or the complement thereof; or an adenine at a position corresponding to position 617 according to SEQ ID NO:27, or the complement thereof; and/or iii) an adenine at a position corresponding to position 556 according to SEQ ID NO:36, or the complement thereof; an adenine at a position corresponding to position 457 according to SEQ ID NO:41, or the complement thereof; an adenine at a position corresponding to position 378 according to SEQ ID NO:46, or the complement thereof; or an adenine at a position corresponding to position 617 according to SEQ ID NO:51, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: i) a thymine at a position corresponding to position 5,911 according to SEQ ID NO:4, or the complement thereof; ii) a uracil at a position corresponding to position 910 according to SEQ ID NO:13, or the complement thereof; a uracil at a position corresponding to position 811 according to SEQ ID NO:18, or the complement thereof; a uracil at a position corresponding to position 732 according to SEQ ID NO:23, or the complement thereof; a or uracil at a position corresponding to position 971 according to SEQ ID NO:28, or the complement thereof; and/or iii) a thymine at a position corresponding to position 910 according to SEQ ID NO:37, or the complement thereof; a thymine at a position corresponding to position 811 according to SEQ ID NO:42, or the complement thereof; a thymine at a position corresponding to position 732 according to SEQ ID NO:47, or the complement thereof; or a thymine at a position corresponding to position 971 according to SEQ ID NO:52, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: i) lacking an AAAG tetranucleotide at positions corresponding to positions 5,920-5,923 according to SEQ ID NO:1, or the complement thereof; ii) lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; or lacking an AAAG tetranucleotide at positions corresponding to positions 980-983 according to SEQ ID NO:10, or the complement thereof; and/or iii) lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; or lacking an AAAG tetranucleotide at positions corresponding to positions 980-983 according to SEQ ID NO:34, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: i) an insertion of a thymine at a position corresponding to position 6,411 according to SEQ ID NO:6, or the complement thereof; ii) an insertion of a uracil at a position corresponding to position 1,410 according to SEQ ID NO:15, or the complement thereof; an insertion of a uracil at a position corresponding to position 1,311 according to SEQ ID NO:20, or the complement thereof; an insertion of a uracil at a position corresponding to position 1,232 according to SEQ ID NO:25, or the complement thereof; or an insertion of a uracil at a position corresponding to position 1,471 according to SEQ ID NO:30, or the complement thereof; and/or iii) an insertion of a thymine at a position corresponding to position 1,410 according to SEQ ID NO:39, or the complement thereof; an insertion of a thymine at a position corresponding to position 1,311 according to SEQ ID NO:44, or the complement thereof; an insertion of a thymine at a position corresponding to position 1,232 according to SEQ ID NO:49, or the complement thereof; or an insertion of a thymine at a position corresponding to position 1,471 according to SEQ ID NO:54, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: i) a guanine at a position corresponding to position 5,831 according to SEQ ID NO:99, or the complement thereof; ii) a guanine at a position corresponding to position 830 according to SEQ ID NO:100, or the complement thereof; a guanine at a position corresponding to position 731 according to SEQ ID NO:101, or the complement thereof; a guanine at a position corresponding to position 652 according to SEQ ID NO:102, or the complement thereof; or a guanine at a position corresponding to position 891 according to SEQ ID NO:103, or the complement thereof; and/or iii) a guanine at a position corresponding to position 830 according to SEQ ID NO:104, or the complement thereof; a guanine at a position corresponding to position 731 according to SEQ ID NO:105, or the complement thereof; a guanine at a position corresponding to position 652 according to SEQ ID NO:106, or the complement thereof; or a guanine at a position corresponding to position 891 according to SEQ ID NO:107, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGTAG heptanucleotide at positions corresponding to positions 5,540-5,546 according to SEQ ID NO:2, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:5, or the complement thereof; comprising an insertion of a thymine at a position corresponding to position 6,411 according to SEQ ID NO:6, or the complement thereof; or comprising a guanine at a position corresponding to position 5,831 according to SEQ ID NO:99, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; lacking a CCAGUAG heptanucleotide at positions corresponding to positions 600-606 according to SEQ ID NO:10, or the complement thereof; comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; lacking an AAAG tetranucleotide at positions corresponding to positions 980-983 according to SEQ ID NO:10, or the complement thereof; comprising an insertion of a uracil at a position corresponding to position 1,410 according to SEQ ID NO:15, or the complement thereof; comprising an insertion of a uracil at a position corresponding to position 1,311 according to SEQ ID NO:20, or the complement thereof; comprising an insertion of a uracil at a position corresponding to position 1,232 according to SEQ ID NO:25, or the complement thereof; comprising an insertion of a uracil at a position corresponding to position 1,471 according to SEQ ID NO:30, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; lacking a CCAGTAG heptanucleotide at positions corresponding to positions 600-606 according to SEQ ID NO:34, or the complement thereof; comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; lacking an AAAG tetranucleotide at positions corresponding to positions 980-983 according to SEQ ID NO:34, or the complement thereof; comprising an insertion of a thymine at a position corresponding to position 1,410 according to SEQ ID NO:39, or the complement thereof; comprising an insertion of a thymine at a position corresponding to position 1,311 according to SEQ ID NO:44, or the complement thereof; comprising an insertion of a thymine at a position corresponding to position 1,232 according to SEQ ID NO:49, or the complement thereof; comprising an insertion of a thymine at a position corresponding to position 1,471 according to SEQ ID NO:54, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof; and detecting the detectable label.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to a GPR75 variant genomic sequence, variant mRNA sequence, or variant cDNA sequence and not the corresponding GPR75 reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a GPR75 variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, to determine whether a GPR75 nucleic acid molecule (genomic nucleic acid molecule, mRNA molecule, or cDNA molecule), or complement thereof, within a biological sample comprises a nucleotide sequence lacking a CCAGTAG heptanucleotide at positions corresponding to positions 5,540-5,546 according to SEQ ID NO:1 (genomic nucleic acid molecule), a deletion of a CCAGUAG heptanucleotide at positions corresponding to positions 539-545 according to SEQ ID NO:7; a deletion of a CCAGUAG heptanucleotide at positions corresponding to positions 440-446 according to SEQ ID NO:8; a deletion of a CCAGUAG heptanucleotide at positions corresponding to positions 361-367 according to SEQ ID NO:9; or a deletion of a CCAGUAG heptanucleotide at positions corresponding to positions 600-606 according to SEQ ID NO:10 (for mRNA molecules); a deletion of a CCAGTAG heptanucleotide at positions corresponding to positions 539-545 according to SEQ ID NO:31; a deletion of a CCAGTAG heptanucleotide at positions corresponding to positions 440-446 according to SEQ ID NO:32; a deletion of a CCAGTAG heptanucleotide at positions corresponding to positions 361-367 according to SEQ ID NO:33; or a deletion of a CCAGTAG heptanucleotide at positions corresponding to positions 600-606 according to SEQ ID NO:34 (for cDNA molecules), the biological sample can be subjected to an amplification method using a primer pair that includes a first primer derived from the 5' flanking sequence adjacent to a deletion of a CCAGTAG heptanucleotide at positions corresponding to positions 5,540-5,546 according to SEQ ID NO:1, a deletion of a CCAGUAG heptanucleotide at positions corresponding to positions 539-545 according to SEQ ID NO:7, a deletion of a CCAGUAG heptanucleotide at positions corresponding to positions 440-446 according to SEQ ID NO:8, a deletion of a CCAGUAG heptanucleotide at positions corresponding to positions 361-367 according to SEQ ID NO:9, a deletion of a CCAGUAG heptanucleotide at positions corresponding to positions 600-606 according to SEQ ID NO:10, a deletion of a CCAGTAG heptanucleotide at positions corresponding to positions 539-545 according to SEQ ID NO:31, a deletion of a CCAGTAG heptanucleotide at positions corresponding to positions 440-446 according to SEQ ID NO:32, a deletion of a CCAGTAG heptanucleotide at positions corresponding to positions 361-367 according to SEQ ID NO:33, or a deletion of a CCAGTAG heptanucleotide at positions corresponding to positions 600-606 according to SEQ ID NO:34, and a second primer derived from the 3' flanking sequence adjacent to a deletion of a CCAGTAG heptanucleotide at positions corresponding to positions 5,540-5,546 according to SEQ ID NO:1, a deletion of a CCAGUAG heptanucleotide at positions corresponding to positions 539-545 according to SEQ ID NO:7, a deletion of a CCAGUAG heptanucleotide at positions corresponding to positions 440-446 according to SEQ ID NO:8, a deletion of a CCAGUAG heptanucleotide at positions corresponding to positions 361-367 according to SEQ ID NO:9, a deletion of a CCAGUAG heptanucleotide at positions corresponding to positions 600-606 according to SEQ ID NO:10, a deletion of a CCAGTAG heptanucleotide at positions corresponding to positions 539-545 according to SEQ ID NO:31, a deletion of a CCAGTAG heptanucleotide at positions corresponding to positions 440-446 according to SEQ ID NO:32, a deletion of a CCAGTAG heptanucleotide at positions corresponding to positions 361-367 according to SEQ ID NO:33, or a deletion of a CCAGTAG heptanucleotide at positions corresponding to positions 600-606 according to SEQ ID NO:34, to produce an amplicon that is indicative of the presence of a deletion of a CCAGTAG heptanucleotide at positions corresponding to positions 5,540-5,546 according to SEQ ID NO:1, a deletion of a CCAGUAG heptanucleotide at positions corresponding to positions 539-545 according to SEQ ID NO:7, a deletion of a CCAGUAG heptanucleotide at positions corresponding to positions 440-446 according to SEQ ID NO:8, a deletion of a CCAGUAG heptanucleotide at positions corresponding to positions 361-367 according to SEQ ID NO:9, a deletion of a CCAGUAG heptanucleotide at positions corresponding to positions 600-606 according to SEQ ID NO:10, a deletion of a CCAGTAG heptanucleotide at positions corresponding to positions 539-545 according to SEQ ID NO:31, a deletion of a CCAGTAG heptanucleotide at positions corresponding to positions 440-446 according to SEQ ID NO:32, a deletion of a CCAGTAG heptanucleotide at positions corresponding to positions 361-367 according to SEQ ID NO:33, or a deletion of a CCAGTAG heptanucleotide at positions corresponding to positions 600-606 according to SEQ ID NO:34. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions lacking a CCAGTAG heptanucleotide at positions corresponding to positions 5,540-5,546 according to SEQ ID NO:1, a deletion of a CCAGUAG heptanucleotide at positions corresponding to positions 539-545 according to SEQ ID NO:7, a deletion of a CCAGUAG heptanucleotide at positions corresponding to positions 440-446 according to SEQ ID NO:8, a deletion of a CCAGUAG heptanucleotide at positions corresponding to positions 361-367 according to SEQ ID NO:9, a deletion of a CCAGUAG heptanucleotide at positions corresponding to positions 600-606 according to SEQ ID NO:10, a deletion of a CCAGTAG heptanucleotide at positions corresponding to positions 539-545 according to SEQ ID NO:31, a deletion of a CCAGTAG heptanucleotide at positions corresponding to positions 440-446 according to SEQ ID NO:32, a deletion of a CCAGTAG heptanucleotide at positions corresponding to positions 361-367 according to SEQ ID NO:33, or a deletion of a CCAGTAG heptanucleotide at positions corresponding to positions 600-606 according to SEQ ID NO:34, and at least 1, 2, 3, 4, 5, 6, 7, 8, 9, 10, or more nucleotides on each side of positions lacking a CCAGTAG heptanucleotide at positions corresponding to positions 5,540-5,546 according to SEQ ID NO:1, a deletion of a CCAGUAG heptanucleotide at positions corresponding to positions 539-545 according to SEQ ID NO:7, a deletion of a CCAGUAG heptanucleotide at positions corresponding to positions 440-446 according to SEQ ID NO:8, a deletion of a CCAGUAG heptanucleotide at positions corresponding to positions 361-367 according to SEQ ID NO:9, a deletion of a CCAGUAG heptanucleotide at positions corresponding to positions 600-606 according to SEQ ID NO:10, a deletion of a CCAGTAG heptanucleotide at positions corresponding to positions 539-545 according to SEQ ID NO:31, a deletion of a CCAGTAG heptanucleotide at positions corresponding to positions 440-446 according to SEQ ID NO:32, a deletion of a CCAGTAG heptanucleotide at positions corresponding to positions 361-367 according to SEQ ID NO:33, or a deletion of a CCAGTAG heptanucleotide at positions corresponding to positions 600-606 according to SEQ ID NO:34.

In some embodiments, to determine whether a GPR75 nucleic acid molecule (genomic nucleic acid molecule, mRNA molecule, or cDNA molecule), or complement thereof, within a biological sample comprises a nucleotide sequence comprising an adenine at a position corresponding to position 5,557 according to SEQ ID NO:3 (genomic nucleic acid molecule), an adenine at a position corresponding to position 556 according to SEQ ID NO:12; an adenine at a position corresponding to position 457 according to SEQ ID NO:17; an adenine at a position corresponding to position 378 according to SEQ ID NO:22; or an adenine at a position corresponding to position 617 according to SEQ ID NO:27 (for mRNA molecules); an adenine at a position corresponding to position 556 according to SEQ ID NO:36; an adenine at a position corresponding to position 457 according to SEQ ID NO:41; an adenine at a position corresponding to position 378 according to SEQ ID NO:46; or an adenine at a position corresponding to position 617 according to SEQ ID NO:51 (for cDNA molecules), the biological sample can be subjected to an amplification method using a primer pair that includes a first primer derived from the 5' flanking sequence adjacent to an adenine at a position corresponding to position 5,557 according to SEQ ID NO:3, an adenine at a position corresponding to position 556 according to SEQ ID NO:12, an adenine at a position corresponding to position 457 according to SEQ ID NO:17, an adenine at a position corresponding to position 378 according to SEQ ID NO:22, an adenine at a position corresponding to position 617 according to SEQ ID NO:27, an adenine at a position corresponding to position 556 according to SEQ ID NO:36, an adenine at a position corresponding to position 457 according to SEQ ID NO:41, an adenine at a position corresponding to position 378 according to SEQ ID NO:46, or an adenine at a position corresponding to position 617 according to SEQ ID NO:51, and a second primer derived from the 3' flanking sequence adjacent to an adenine at a position corresponding to position 5,557 according to SEQ ID NO:3, an adenine at a position corresponding to position 556 according to SEQ ID NO:12, an adenine at a position corresponding to position 457 according to SEQ ID NO:17, an adenine at a position corresponding to position 378 according to SEQ ID NO:22, an adenine at a position corresponding to position 617 according to SEQ ID NO:27, an adenine at a position corresponding to position 556 according to SEQ ID NO:36, an adenine at a position corresponding to position 457 according to SEQ ID NO:41, an adenine at a position corresponding to position 378 according to SEQ ID NO:46, or an adenine at a position corresponding to position 617 according to SEQ ID NO:51 to produce an amplicon that is indicative of the presence of the SNP at positions encoding an adenine at a position corresponding to position 5,557 according to SEQ ID NO:3, an adenine at a position corresponding to position 556 according to SEQ ID NO:12, an adenine at a position corresponding to position 457 according to SEQ ID NO:17, an adenine at a position corresponding to position 378 according to SEQ ID NO:22, an adenine at a position corresponding to position 617 according to SEQ ID NO:27, an adenine at a position corresponding to position 556 according to SEQ ID NO:36, an adenine at a position corresponding to position 457 according to SEQ ID NO:41, an adenine at a position corresponding to position 378 according to SEQ ID NO:46, or an adenine at a position corresponding to position 617 according to SEQ ID NO:51. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 5,557 according to SEQ ID NO:3, an adenine at a position corresponding to position 556 according to SEQ ID NO:12, an adenine at a position corresponding to position 457 according to SEQ ID NO:17, an adenine at a position corresponding to position 378 according to SEQ ID NO:22, an adenine at a position corresponding to position 617 according to SEQ ID NO:27, an adenine at a position corresponding to position 556 according to SEQ ID NO:36, an adenine at a position corresponding to position 457 according to SEQ ID NO:41, an adenine at a position corresponding to position 378 according to SEQ ID NO:46, or an adenine at a position corresponding to position 617 according to SEQ ID NO:51, and at least 1, 2, 3, 4, 5, 6, 7, 8, 9, 10, or more nucleotides on each side of positions comprising an adenine at a position corresponding to position 5,557 according to SEQ ID NO:3, an adenine at a position corresponding to position 556 according to SEQ ID NO:12, an adenine at a position corresponding to position 457 according to SEQ ID NO:17, an adenine at a position corresponding to position 378 according to SEQ ID NO:22, an adenine at a position corresponding to position 617 according to SEQ ID NO:27, an adenine at a position corresponding to position 556 according to SEQ ID NO:36, an adenine at a position corresponding to position 457 according to SEQ ID NO:41, an adenine at a position corresponding to position 378 according to SEQ ID NO:46, or an adenine at a position corresponding to position 617 according to SEQ ID NO:51.

In some embodiments, to determine whether a GPR75 nucleic acid molecule (genomic nucleic acid molecule, mRNA molecule, or cDNA molecule), or complement thereof, within a biological sample comprises a nucleotide sequence comprising a thymine at a position corresponding to position 5,911 according to SEQ ID NO:4 (genomic nucleic acid molecule), a uracil at a position corresponding to position 910 according to SEQ ID NO:13; a uracil at a position corresponding to position 811 according to SEQ ID NO:18; a uracil at a position corresponding to position 732 according to SEQ ID NO:23; or a uracil at a position corresponding to position 971 according to SEQ ID NO:28 (for mRNA molecules); a thymine at a position corresponding to position 910 according to SEQ ID NO:37; a thymine at a position corresponding to position 811 according to SEQ ID NO:42; a thymine at a position corresponding to position 732 according to SEQ ID NO:47; or a thymine at a position corresponding to position 971 according to SEQ ID NO:52 (for cDNA molecules), the biological sample can be subjected to an amplification method using a primer pair that includes a first primer derived from the 5' flanking sequence adjacent to a thymine at a position corresponding to position 5,911 according to SEQ ID NO:4, a uracil at a position corresponding to position 910 according to SEQ ID NO:13, a uracil at a position corresponding to position 811 according to SEQ ID NO:18, a uracil at a position corresponding to position 732 according to SEQ ID NO:23, a uracil at a position corresponding to position 971 according to SEQ ID NO:28, a thymine at a position corresponding to position 910 according to SEQ ID NO:37, a thymine at a position corresponding to position 811 according to SEQ ID NO:42, a thymine at a position corresponding to position 732 according to SEQ ID NO:47, or a thymine at a position corresponding to position 971 according to SEQ ID NO:52, and a second primer derived from the 3' flanking sequence adjacent to a thymine at a position corresponding to position 5,911 according to SEQ ID NO:4, a uracil at a position corresponding to position 910 according to SEQ ID NO:13, a uracil at a position corresponding to position 811 according to SEQ ID NO:18, a uracil at a position corresponding to position 732 according to SEQ ID NO:23, a uracil at a position corresponding to position 971 according to SEQ ID NO:28, a thymine at a position corresponding to position 910 according to SEQ ID NO:37, a thymine at a position corresponding to position 811 according to SEQ ID NO:42, a thymine at a position corresponding to position 732 according to SEQ ID NO:47, or a thymine at a position corresponding to position 971 according to SEQ ID NO:52 to produce an amplicon that is indicative of the presence of the SNP at positions encoding a thymine at a position corresponding to position 5,911 according to SEQ ID NO:4, a uracil at a position corresponding to position 910 according to SEQ ID NO:13, a uracil at a position corresponding to position 811 according to SEQ ID NO:18, a uracil at a position corresponding to position 732 according to SEQ ID NO:23, a uracil at a position corresponding to position 971 according to SEQ ID NO:28, a thymine at a position corresponding to position 910 according to SEQ ID NO:37, a thymine at a position corresponding to position 811 according to SEQ ID NO:42, a thymine at a position corresponding to position 732 according to SEQ ID NO:47, or a thymine at a position corresponding to position 971 according to SEQ ID NO:52. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a thymine at a position corresponding to position 5,911 according to SEQ ID NO:4, a uracil at a position corresponding to position 910 according to SEQ ID NO:13, a uracil at a position corresponding to position 811 according to SEQ ID NO:18, a uracil at a position corresponding to position 732 according to SEQ ID NO:23, a uracil at a position corresponding to position 971 according to SEQ ID NO:28, a thymine at a position corresponding to position 910 according to SEQ ID NO:37, a thymine at a position corresponding to position 811 according to SEQ ID NO:42, a thymine at a position corresponding to position 732 according to SEQ ID NO:47, or a thymine at a position corresponding to position 971 according to SEQ ID NO:52, and at least 1, 2, 3, 4, 5, 6, 7, 8, 9, 10, or more nucleotides on each side of positions comprising a thymine at a position corresponding to position 5,911 according to SEQ ID NO:4, a uracil at a position corresponding to position 910 according to SEQ ID NO:13, a uracil at a position corresponding to position 811 according to SEQ ID NO:18, a uracil at a position corresponding to position 732 according to SEQ ID NO:23, a uracil at a position corresponding to position 971 according to SEQ ID NO:28, a thymine at a position corresponding to position 910 according to SEQ ID NO:37, a thymine at a position corresponding to position 811 according to SEQ ID NO:42, a thymine at a position corresponding to position 732 according to SEQ ID NO:47, or a thymine at a position corresponding to position 971 according to SEQ ID NO:52.

In some embodiments, to determine whether a GPR75 nucleic acid molecule (genomic nucleic acid molecule, mRNA molecule, or cDNA molecule), or complement thereof, within a biological sample comprises a nucleotide sequence lacking an AAAG tetranucleotide at positions corresponding to positions 5,920-5,923 according to SEQ ID NO:1 (genomic nucleic acid molecule), a deletion of an AAAG tetranucleotide at positions corresponding to positions 919-922 according to SEQ ID NO:7; a deletion of an AAAG tetranucleotide at positions corresponding to positions 820-823 according to SEQ ID NO:8; a deletion of an AAAG tetranucleotide at positions corresponding to positions 741-744 according to SEQ ID NO:9; or a deletion of an AAAG tetranucleotide at positions corresponding to positions 980-983 according to SEQ ID NO:10 (for mRNA molecules); a deletion of an AAAG tetranucleotide at positions corresponding to positions 919-922 according to SEQ ID NO:31; a deletion of an AAAG tetranucleotide at positions corresponding to positions 820-823 according to SEQ ID NO:32; a deletion of an AAAG tetranucleotide at positions corresponding to positions 741-744 according to SEQ ID NO:33; or a deletion of an AAAG tetranucleotide at positions corresponding to positions 980-983 according to SEQ ID NO:34 (for cDNA molecules), the biological sample can be subjected to an amplification method using a primer pair that includes a first primer derived from the 5' flanking sequence adjacent to a deletion of an AAAG tetranucleotide at positions corresponding to positions 5,920-5,923 according to SEQ ID NO:1, a deletion of an AAAG tetranucleotide at positions corresponding to positions 919-922 according to SEQ ID NO:7, a deletion of an AAAG tetranucleotide at positions corresponding to positions 820-823 according to SEQ ID NO:8, a deletion of an AAAG tetranucleotide at positions corresponding to positions 741-744 according to SEQ ID NO:9, a deletion of an AAAG tetranucleotide at positions corresponding to positions 980-983 according to SEQ ID NO:10, a deletion of an AAAG tetranucleotide at positions corresponding to positions 919-922 according to SEQ ID NO:31, a deletion of an AAAG tetranucleotide at positions corresponding to positions 820-823 according to SEQ ID NO:32, a deletion of an AAAG tetranucleotide at positions corresponding to positions 741-744 according to SEQ ID NO:33, or a deletion of an AAAG tetranucleotide at positions corresponding to positions 980-983 according to SEQ ID NO:34, and a second primer derived from the 3' flanking sequence adjacent to a deletion of an AAAG tetranucleotide at positions corresponding to positions 5,920-5,923 according to SEQ ID NO:1, a deletion of an AAAG tetranucleotide at positions corresponding to positions 919-922 according to SEQ ID NO:7, a deletion of an AAAG tetranucleotide at positions corresponding to positions 820-823 according to SEQ ID NO:8, a deletion of an AAAG tetranucleotide at positions corresponding to positions 741-744 according to SEQ ID NO:9, a deletion of an AAAG tetranucleotide at positions corresponding to positions 980-983 according to SEQ ID NO:10, a deletion of an AAAG tetranucleotide at positions corresponding to positions 919-922 according to SEQ ID NO:31, a deletion of an AAAG tetranucleotide at positions corresponding to positions 820-823 according to SEQ ID NO:32, a deletion of an AAAG tetranucleotide at positions corresponding to positions 741-744 according to SEQ ID NO:33, or a deletion of an AAAG tetranucleotide at positions corresponding to positions 980-983 according to SEQ ID NO:34 to produce an amplicon that is indicative of the presence of a deletion of an AAAG tetranucleotide at positions corresponding to positions 5,920-5,923 according to SEQ ID NO:1, a deletion of an AAAG tetranucleotide at positions corresponding to positions 919-922 according to SEQ ID NO:7, a deletion of an AAAG tetranucleotide at positions corresponding to positions 820-823 according to SEQ ID NO:8, a deletion of an AAAG tetranucleotide at positions corresponding to positions 741-744 according to SEQ ID NO:9, a deletion of an AAAG tetranucleotide at positions corresponding to positions 980-983 according to SEQ ID NO:10, a deletion of an AAAG tetranucleotide at positions corresponding to positions 919-922 according to SEQ ID NO:31, a deletion of an AAAG tetranucleotide at positions corresponding to positions 820-823 according to SEQ ID NO:32, a deletion of an AAAG tetranucleotide at positions corresponding to positions 741-744 according to SEQ ID NO:33, or a deletion of an AAAG tetranucleotide at positions corresponding to positions 980-983 according to SEQ ID NO:34. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions lacking an AAAG tetranucleotide at positions corresponding to positions 5,920-5,923 according to SEQ ID NO:1, a deletion of an AAAG tetranucleotide at positions corresponding to positions 919-922 according to SEQ ID NO:7, a deletion of an AAAG tetranucleotide at positions corresponding to positions 820-823 according to SEQ ID NO:8, a deletion of an AAAG tetranucleotide at positions corresponding to positions 741-744 according to SEQ ID NO:9, a deletion of an AAAG tetranucleotide at positions corresponding to positions 980-983 according to SEQ ID NO:10, a deletion of an AAAG tetranucleotide at positions corresponding to positions 919-922 according to SEQ ID NO:31, a deletion of an AAAG tetranucleotide at positions corresponding to positions 820-823 according to SEQ ID NO:32, a deletion of an AAAG tetranucleotide at positions corresponding to positions 741-744 according to SEQ ID NO:33, or a deletion of an AAAG tetranucleotide at positions corresponding to positions 980-983 according to SEQ ID NO:34, and at least 1, 2, 3, 4, 5, 6, 7, 8, 9, 10, or more nucleotides on each side of positions lacking an AAAG tetranucleotide at positions corresponding to positions 5,920-5,923 according to SEQ ID NO:1, a deletion of an AAAG tetranucleotide at positions corresponding to positions 919-922 according to SEQ ID NO:7, a deletion of an AAAG tetranucleotide at positions corresponding to positions 820-823 according to SEQ ID NO:8, a deletion of an AAAG tetranucleotide at positions corresponding to positions 741-744 according to SEQ ID NO:9, a deletion of an AAAG tetranucleotide at positions corresponding to positions 980-983 according to SEQ ID NO:10, a deletion of an AAAG tetranucleotide at positions corresponding to positions 919-922 according to SEQ ID NO:31, a deletion of an AAAG tetranucleotide at positions corresponding to positions 820-823 according to SEQ ID NO:32, a deletion of an AAAG tetranucleotide at positions corresponding to positions 741-744 according to SEQ ID NO:33, or a deletion of an AAAG tetranucleotide at positions corresponding to positions 980-983 according to SEQ ID NO:34.

In some embodiments, to determine whether a GPR75 nucleic acid molecule (genomic nucleic acid molecule, mRNA molecule, or cDNA molecule), or complement thereof, within a biological sample comprises a nucleotide sequence comprising an insertion of a thymine at a position corresponding to position 6,411 according to SEQ ID NO:6 (genomic nucleic acid molecule), an insertion of a uracil at a position corresponding to position 1,410 according to SEQ ID NO:15; an insertion of a uracil at a position corresponding to position 1,311 according to SEQ ID NO:20; an insertion of a uracil at a position corresponding to position 1,232 according to SEQ ID NO:25; or an insertion of a uracil at a position corresponding to position 1,471 according to SEQ ID NO:30 (for mRNA molecules); an insertion of a thymine at a position corresponding to position 1,410 according to SEQ ID NO:39; an insertion of a thymine at a position corresponding to position 1,311 according to SEQ ID NO:44; an insertion of a thymine at a position corresponding to position 1,232 according to SEQ ID NO:49; or an insertion of a thymine at a position corresponding to position 1,471 according to SEQ ID NO:54 (for cDNA molecules), the biological sample can be subjected to an amplification method using a primer pair that includes a first primer derived from the 5' flanking sequence adjacent to an insertion of a thymine at a position corresponding to position 6,411 according to SEQ ID NO:6, an insertion of a uracil at a position corresponding to position 1,410 according to SEQ ID NO:15, an insertion of a uracil at a position corresponding to position 1,311 according to SEQ ID NO:20, an insertion of a uracil at a position corresponding to position 1,232 according to SEQ ID NO:25, an insertion of a uracil at a position corresponding to position 1,471 according to SEQ ID NO:30, an insertion of a thymine at a position corresponding to position 1,410 according to SEQ ID NO:39, an insertion of a thymine at a position corresponding to position 1,311 according to SEQ ID NO:44, an insertion of a thymine at a position corresponding to position 1,232 according to SEQ ID NO:49, or an insertion of a thymine at a position corresponding to position 1,471 according to SEQ ID NO:54, and a second primer derived from the 3' flanking sequence adjacent to an insertion of a thymine at a position corresponding to position 6,411 according to SEQ ID NO:6, an insertion of a uracil at a position corresponding to position 1,410 according to SEQ ID NO:15, an insertion of a uracil at a position corresponding to position 1,311 according to SEQ ID NO:20, an insertion of a uracil at a position corresponding to position 1,232 according to SEQ ID NO:25, an insertion of a uracil at a position corresponding to position 1,471 according to SEQ ID NO:30, an insertion of a thymine at a position corresponding to position 1,410 according to SEQ ID NO:39, an insertion of a thymine at a position corresponding to position 1,311 according to SEQ ID NO:44, an insertion of a thymine at a position corresponding to position 1,232 according to SEQ ID NO:49, or an insertion of a thymine at a position corresponding to position 1,471 according to SEQ ID NO:54 to produce an amplicon that is indicative of the presence of an insertion of a thymine at a position corresponding to position 6,411 according to SEQ ID NO:6, an insertion of a uracil at a position corresponding to position 1,410 according to SEQ ID NO:15, an insertion of a uracil at a position corresponding to position 1,311 according to SEQ ID NO:20, an insertion of a uracil at a position corresponding to position 1,232 according to SEQ ID NO:25, an insertion of a uracil at a position corresponding to position 1,471 according to SEQ ID NO:30, an insertion of a thymine at a position corresponding to position 1,410 according to SEQ ID NO:39, an insertion of a thymine at a position corresponding to position 1,311 according to SEQ ID NO:44, an insertion of a thymine at a position corresponding to position 1,232 according to SEQ ID NO:49, or an insertion of a thymine at a position corresponding to position 1,471 according to SEQ ID NO:54. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an insertion of a thymine at a position corresponding to position 6,411 according to SEQ ID NO:6, an insertion of a uracil at a position corresponding to position 1,410 according to SEQ ID NO:15, an insertion of a uracil at a position corresponding to position 1,311 according to SEQ ID NO:20, an insertion of a uracil at a position corresponding to position 1,232 according to SEQ ID NO:25, an insertion of a uracil at a position corresponding to position 1,471 according to SEQ ID NO:30, an insertion of a thymine at a position corresponding to position 1,410 according to SEQ ID NO:39, an insertion of a thymine at a position corresponding to position 1,311 according to SEQ ID NO:44, an insertion of a thymine at a position corresponding to position 1,232 according to SEQ ID NO:49, or an insertion of a thymine at a position corresponding to position 1,471 according to SEQ ID NO:54, and at least 1, 2, 3, 4, 5, 6, 7, 8, 9, 10, or more nucleotides on each side of positions comprising an insertion of a thymine at a position corresponding to position 6,411 according to SEQ ID NO:6, an insertion of a uracil at a position corresponding to position 1,410 according to SEQ ID NO:15, an insertion of a uracil at a position corresponding to position 1,311 according to SEQ ID NO:20, an insertion of a uracil at a position corresponding to position 1,232 according to SEQ ID NO:25, an insertion of a uracil at a position corresponding to position 1,471 according to SEQ ID NO:30, an insertion of a thymine at a position corresponding to position 1,410 according to SEQ ID NO:39, an insertion of a thymine at a position corresponding to position 1,311 according to SEQ ID NO:44, an insertion of a thymine at a position corresponding to position 1,232 according to SEQ ID NO:49, or an insertion of a thymine at a position corresponding to position 1,471 according to SEQ ID NO:54.

In some embodiments, to determine whether a GPR75 nucleic acid molecule (genomic nucleic acid molecule, mRNA molecule, or cDNA molecule), or complement thereof, within a biological sample comprises a nucleotide sequence comprising a guanine at a position corresponding to position 5,831 according to SEQ ID NO:99 (genomic nucleic acid molecule), a guanine at a position corresponding to position 830 according to SEQ ID NO:100, a guanine at a position corresponding to position 731 according to SEQ ID NO:101, a guanine at a position corresponding to position 652 according to SEQ ID NO:102, or a guanine at a position corresponding to position 891 according to SEQ ID NO:103, (for mRNA molecules); a guanine at a position corresponding to position 830 according to SEQ ID NO:104, a guanine at a position corresponding to position 731 according to SEQ ID NO:105, a guanine at a position corresponding to position 652 according to SEQ ID NO:106, or a guanine at a position corresponding to position 891 according to SEQ ID NO:107 (for cDNA molecules), the biological sample can be subjected to an amplification method using a primer pair that includes a first primer derived from the 5' flanking sequence adjacent to guanine at a position corresponding to position 5,831 according to SEQ ID NO:99, a guanine at a position corresponding to position 830 according to SEQ ID NO:100, a guanine at a position corresponding to position 731 according to SEQ ID NO:101, a guanine at a position corresponding to position 652 according to SEQ ID NO:102, a guanine at a position corresponding to position 891 according to SEQ ID NO:103, a guanine at a position corresponding to position 830 according to SEQ ID NO:104, a guanine at a position corresponding to position 731 according to SEQ ID NO:105, a guanine at a position corresponding to position 652 according to SEQ ID NO:106, or a guanine at a position corresponding to position 891 according to SEQ ID NO:107, and a second primer derived from the 3' flanking sequence adjacent to guanine at a position corresponding to position 5,831 according to SEQ ID NO:99, a guanine at a position corresponding to position 830 according to SEQ ID NO:100, a guanine at a position corresponding to position 731 according to SEQ ID NO:101, a guanine at a position corresponding to position 652 according to SEQ ID NO:102, a guanine at a position corresponding to position 891 according to SEQ ID NO:103, a guanine at a position corresponding to position 830 according to SEQ ID NO:104, a guanine at a position corresponding to position 731 according to SEQ ID NO:105, a guanine at a position corresponding to position 652 according to SEQ ID NO:106, or a guanine at a position corresponding to position 891 according to SEQ ID NO:107, to produce an amplicon that is indicative of the presence of an insertion of guanine at a position corresponding to position 5,831 according to SEQ ID NO:99, a guanine at a position corresponding to position 830 according to SEQ ID NO:100, a guanine at a position corresponding to position 731 according to SEQ ID NO:101, a guanine at a position corresponding to position 652 according to SEQ ID NO:102, a guanine at a position corresponding to position 891 according to SEQ ID NO:103, a guanine at a position corresponding to position 830 according to SEQ ID NO:104, a guanine at a position corresponding to position 731 according to SEQ ID NO:105, a guanine at a position corresponding to position 652 according to SEQ ID NO:106, or a guanine at a position corresponding to position 891 according to SEQ ID NO:107. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an insertion of guanine at a position corresponding to position 5,831 according to SEQ ID NO:99, a guanine at a position corresponding to position 830 according to SEQ ID NO:100, a guanine at a position corresponding to position 731 according to SEQ ID NO:101, a guanine at a position corresponding to position 652 according to SEQ ID NO:102, a guanine at a position corresponding to position 891 according to SEQ ID NO:103, a guanine at a position corresponding to position 830 according to SEQ ID NO:104, a guanine at a position corresponding to position 731 according to SEQ ID NO:105, a guanine at a position corresponding to position 652 according to SEQ ID NO:106, or a guanine at a position corresponding to position 891 according to SEQ ID NO:107, and at least 1, 2, 3, 4, 5, 6, 7, 8, 9, 10, or more nucleotides on each side of positions comprising a guanine at a position corresponding to position 5,831 according to SEQ ID NO:99, a guanine at a position corresponding to position 830 according to SEQ ID NO:100, a guanine at a position corresponding to position 731 according to SEQ ID NO:101, a guanine at a position corresponding to position 652 according to SEQ ID NO:102, a guanine at a position corresponding to position 891 according to SEQ ID NO:103, a guanine at a position corresponding to position 830 according to SEQ ID NO:104, a guanine at a position corresponding to position 731 according to SEQ ID NO:105, a guanine at a position corresponding to position 652 according to SEQ ID NO:106, or a guanine at a position corresponding to position 891 according to SEQ ID NO:107.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a human GPR75 predicted loss-of-function polypeptide comprising performing an assay on a biological sample obtained from a subject to determine whether a GPR75 polypeptide in the subject contains one or more variations that causes the polypeptide to have a loss-of-function (partial or complete) or predicted loss-of-function (partial or complete). The GPR75 predicted loss-of-function polypeptide can be any of the GPR75 variant polypeptides described herein. In some embodiments, the methods detect the presence of GPR75 Ala110fs, Ala116Thr, Tyr207Cys, Gln234Stop, Arg236fs, or Cys400fs. In some embodiments, the methods detect the presence of Lys404*, Ser219fs, or c.–110+1G>A.

In some embodiments, the methods comprise performing an assay on a sample obtained from a subject to determine whether a GPR75 polypeptide in the sample comprises amino acids 110-130 according to SEQ ID NO:56. In some embodiments, the methods comprise performing an assay on a sample obtained from a subject to determine whether a GPR75 polypeptide in the sample comprises a threonine at a position corresponding to position 116 according to SEQ ID NO:57. In some embodiments, the methods comprise performing an assay on a sample obtained from a subject to determine whether a GPR75 polypeptide in the sample terminates at a position corresponding to position 233 according to SEQ ID NO:58. In some embodiments, the methods comprise performing an assay on a sample obtained from a subject to determine whether a GPR75 polypeptide in the sample comprises amino acids 236-239 according to SEQ ID NO:59. In some embodiments, the methods comprise performing an assay on a sample obtained from a subject to determine whether a GPR75 polypeptide in the sample comprises amino acids 400-425 according to SEQ ID NO:60. In some embodiments, the methods comprise performing an assay on a sample obtained from a subject to determine whether a GPR75 polypeptide in the sample comprises a cysteine at a position corresponding to position 207 according to SEQ ID NO:108.

In some embodiments, the detecting step comprises sequencing at least a portion of the polypeptide that comprises a position corresponding to any one or more of positions 110-130 according to SEQ ID NO:56 or SEQ ID NO:55. In some embodiments, the detecting step comprises sequencing at least a portion of the polypeptide that comprises a position corresponding to position 116 according to SEQ ID NO:57 or SEQ ID NO:55. In some embodiments, the detecting step comprises sequencing at least a portion of the polypeptide that comprises a position corresponding to any of positions 234-540 according to SEQ ID NO:55. In some embodiments, the detecting step comprises sequencing at least a portion of the polypeptide that comprises a position corresponding to any one or more of positions 236-239 according to SEQ ID NO:59 or SEQ ID NO:55. In some embodiments, the detecting step comprises sequencing at least a portion of the polypeptide that comprises a position corresponding to any one or more of positions 400-425 according to SEQ ID NO:60 or SEQ ID NO:55. In some embodiments, the detecting step comprises sequencing at least a portion of the polypeptide that comprises a position corresponding to position 207 according to SEQ ID NO:108.

In some embodiments, the detecting step comprises an immunoassay for detecting the presence of a polypeptide that comprises a position corresponding to any one or more of positions 110-130 according to SEQ ID NO:56 or SEQ ID NO:55. In some embodiments, the detecting step comprises an immunoassay for detecting the presence of a polypeptide that comprises a position corresponding to position 116 according to SEQ ID NO:57 or SEQ ID NO:55. In some embodiments, the detecting step comprises an immunoassay for detecting the presence of a polypeptide that comprises a position corresponding to any of positions 234-540 according to SEQ ID NO:55. In some embodiments, the detecting step comprises an immunoassay for detecting the presence of a polypeptide that comprises a position corresponding to any one or more of positions 236-239 according to SEQ ID NO:59 or SEQ ID NO:55. In some embodiments, the detecting step comprises an immunoassay for detecting the presence of a polypeptide that comprises a position corresponding to any one or more of positions 400-425 according to SEQ ID NO:60 or SEQ ID NO:55. In some embodiments, the detecting step comprises an immunoassay for detecting the presence of a polypeptide that comprises a position corresponding to position 207 according to SEQ ID NO:108 or SEQ ID NO:55.

In some embodiments, when the subject does not have a GPR75 predicted loss-of-function polypeptide, the subject has an increased risk for developing obesity or any of excessive weight, an elevated BMI, an elevated body fat mass, percentage, or volume, and/or excessive food intake. In some embodiments, when the subject has a GPR75 predicted loss-of-function polypeptide, the subject has a decreased risk for developing obesity or any of excessive weight, an elevated BMI, an elevated body fat mass, percentage, or volume, and/or excessive food intake.

The present disclosure also provides isolated nucleic acid molecules that hybridize to GPR75 variant genomic nucleic acid molecules, GPR75 variant mRNA molecules, and/or GPR75 variant cDNA molecules (such as any of the genomic variant nucleic acid molecules, mRNA variant molecules, and cDNA variant molecules disclosed herein). In some embodiments, the isolated nucleic acid molecules hybridize to a portion of the GPR75 nucleic acid molecule that includes a position corresponding to: positions 5,540-5,546 according to SEQ ID NO:2, positions 539-545 according to SEQ ID NO:11, positions 440-446 according to SEQ ID NO:16, positions 361-367 according to SEQ ID NO:21, positions 600-606 according to SEQ ID NO:26, positions 539-545 according to SEQ ID NO:35, positions 440-446 according to SEQ ID NO:40, positions 361-367 according to SEQ ID NO:45, or positions 600-606 according to SEQ ID NO:50.

In some embodiments, the isolated nucleic acid molecules hybridize to a portion of the GPR75 nucleic acid molecule that includes a position corresponding to: position 5,557 according to SEQ ID NO:3, position 556 according to SEQ ID NO:12, position 457 according to SEQ ID NO:17, position 378 according to SEQ ID NO:22, position 617 according to SEQ ID NO:27, position 556 according to SEQ ID NO:36, position 457 according to SEQ ID NO:41, position 378 according to SEQ ID NO:46, or position 617 according to SEQ ID NO:51.

In some embodiments, the isolated nucleic acid molecules hybridize to a portion of the GPR75 nucleic acid molecule that includes a position corresponding to: position 5,911 according to SEQ ID NO:4, position 910 according to SEQ ID NO:13, position 811 according to SEQ ID NO:18, position 732 according to SEQ ID NO:23, position 971 according to SEQ ID NO:28, position 910 according to SEQ ID NO:37, position 811 according to SEQ ID NO:42, position 732 according to SEQ ID NO:47, or position 971 according to SEQ ID NO:52.

In some embodiments, the isolated nucleic acid molecules hybridize to a portion of the GPR75 nucleic acid molecule that includes a position corresponding to: positions 5,920-5,923 according to SEQ ID NO:5, positions 919-922 according to SEQ ID NO:14, positions 820-823 according to SEQ ID NO:19, positions 741-744 according to SEQ ID NO:24, positions 980-983 according to SEQ ID NO:29, positions 919-922 according to SEQ ID NO:38, positions 820-823 according to SEQ ID NO:43, positions 741-744 according to SEQ ID NO:48, or positions 980-983 according to SEQ ID NO:53.

In some embodiments, the isolated nucleic acid molecules hybridize to a portion of the GPR75 nucleic acid molecule that includes a position corresponding to: position 6,411 according to SEQ ID NO:6, position 1,410 according to SEQ ID NO:15, position 1,311 according to SEQ ID NO:20, position 1,232 according to SEQ ID NO:25, position 1,471 according to SEQ ID NO:30, position 1,410 according to SEQ ID NO:39, position 1,311 according to SEQ ID NO:44, position 1,232 according to SEQ ID NO:49, or position 1,471 according to SEQ ID NO:54.

In some embodiments, the isolated nucleic acid molecules hybridize to a portion of the GPR75 nucleic acid molecule that includes a position corresponding to: position 5,831 according to SEQ ID NO:99, position 830 according to SEQ ID NO:100, position 731 according to SEQ ID NO:101, position 652 according to SEQ ID NO:102, position 891 according to SEQ ID NO:103, position 830 according to SEQ ID NO:104, position 731 according to SEQ ID NO:105, position 652 according to SEQ ID NO:106, or position 891 according to SEQ ID NO:107.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to GPR75 variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to GPR75 variant genomic nucleic acid molecules, GPR75 variant mRNA molecules, and/or GPR75 variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPR75 polypeptide, wherein the portion comprises a position corresponding to: positions 5,540-5,546 according to SEQ ID NO:2, or the complement thereof; positions 539-545 according to SEQ ID NO:11, or the complement thereof; positions 440-446 according to SEQ ID NO:16, or the complement thereof; positions 361-367 according to SEQ ID NO:21, or the complement thereof; positions 600-606 according to SEQ ID NO:26, or the complement thereof; positions 539-545 according to SEQ ID NO:35, or the complement thereof; positions 440-446 according to SEQ ID NO:40, or the complement thereof; positions 361-367 according to SEQ ID NO:45, or the complement thereof; or positions 600-606 according to SEQ ID NO:50, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPR75 polypeptide, wherein the portion comprises a position corresponding to: position 5,557 according to SEQ ID NO:3, or the complement thereof; position 556 according to SEQ ID NO:12, or the complement thereof; position 457 according to SEQ ID NO:17, or the complement thereof; position 378 according to SEQ ID NO:22, or the complement thereof; position 617 according to SEQ ID NO:27, or the complement thereof; position 556 according to SEQ ID NO:36, or the complement thereof; position 457 according to SEQ ID NO:41, or the complement thereof; position 378 according to SEQ ID NO:46, or the complement thereof; or position 617 according to SEQ ID NO:51, or the complement thereof. In some embodiments, the alteration-specific probe or alteration-specific primer comprises a nucleotide sequence which is complementary to a portion of a nucleotide sequence comprising positions corresponding to: positions 5,557-5,559 according to SEQ ID NO:3, or the complement thereof; positions 556-558 according to SEQ ID NO:12, or the complement thereof; positions 457-459 according to SEQ ID NO:17, or the complement thereof; positions 378-380 according to SEQ ID NO:22, or the complement thereof; positions 617-619 according to SEQ ID NO:27, or the complement thereof; positions 556-558 according to SEQ ID NO:36, or the complement thereof; positions 457-459 according to SEQ ID NO:41, or the complement thereof; positions 378-380 according to SEQ ID NO:46, or the complement thereof; or positions 617-619 according to SEQ ID NO:51, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPR75 polypeptide, wherein the portion comprises a position corresponding to: position 5,911 according to SEQ ID NO:4, or the complement thereof; position 910 according to SEQ ID NO:13, or the complement thereof; position 811 according to SEQ ID NO:18, or the complement thereof; position 732 according to SEQ ID NO:23, or the complement thereof; position 971 according to SEQ ID NO:28, or the complement thereof; position 910 according to SEQ ID NO:37, or the complement thereof; position 811 according to SEQ ID NO:42, or the complement thereof; position 732 according to SEQ ID NO:47, or the complement thereof; or position 971 according to SEQ ID NO:52, or the complement thereof. In some embodiments, the alteration-specific probe or alteration-specific primer comprises a nucleotide sequence which is complementary to a portion of a nucleotide sequence comprising positions corresponding to: positions 5,911-5,913 according to SEQ ID NO:4, or the complement thereof; positions 910-912 according to SEQ ID NO:13, or the complement thereof; positions 811-813 according to SEQ ID NO:18, or the complement thereof; positions 732-734 according to SEQ ID NO:23, or the complement thereof; positions 971-973 according to SEQ ID NO:28, or the complement thereof; positions 910-912 according to SEQ ID NO:37, or the complement thereof; positions 811-813 according to SEQ ID NO:42, or the complement thereof; positions 732-734 according to SEQ ID NO:47, or the complement thereof; or positions 971-973 according to SEQ ID NO:52, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPR75 polypeptide, wherein the portion comprises a position corresponding to: positions 5,920-5,923 according to SEQ ID NO:5, or the complement thereof; positions 919-922 according to SEQ ID NO:14, or the complement thereof; positions 820-823 according to SEQ ID NO:19, or the complement thereof; positions 741-744 according to SEQ ID NO:24, or the complement thereof; positions 980-983 according to SEQ ID NO:29, or the complement thereof; positions 919-922 according to SEQ ID NO:38, or the complement thereof; positions 820-823 according to SEQ ID NO:43, or the complement thereof; positions 741-744 according to SEQ ID NO:48, or the complement thereof; or positions 980-983 according to SEQ ID NO:53, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPR75 polypeptide, wherein the portion comprises a position corresponding to: position 6,411 according to SEQ ID NO:6, or the complement thereof; position 1,410 according to SEQ ID NO:15, or the complement thereof; position 1,311 according to SEQ ID NO:20, or the complement thereof; position 1,232 according to SEQ ID NO:25, or the complement thereof; position 1,471 according to SEQ ID NO:30, or the complement thereof; position 1,410 according to SEQ ID NO:39, or the complement thereof; position 1,311 according to SEQ ID NO:44, or the complement thereof; position 1,232 according to SEQ ID NO:49, or the complement thereof; or position 1,471 according to SEQ ID NO:54, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human GPR75 polypeptide, wherein the portion comprises a position corresponding to: position 5,831 according to SEQ ID NO:99, or the complement thereof; position 830 according to SEQ ID NO:100, or the complement thereof; position 731 according to SEQ ID NO:101, or the complement thereof; position 652 according to SEQ ID NO:102, or the complement thereof; position 891 according to SEQ ID NO:103, or the complement thereof; position 830 according to SEQ ID NO:104, or the complement thereof; position 731 according to SEQ ID NO:105, or the complement thereof; position 652 according to SEQ ID NO:106, or the complement thereof; or position 891 according to SEQ ID NO:107, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the GPR75 variant genomic nucleic acid molecules, GPR75 variant mRNA molecules, and/or GPR75 variant cDNA molecules disclosed herein. The primers described herein can be used to amplify GPR75 variant genomic nucleic acid molecules, GPR75 variant mRNA molecules, or GPR75 variant cDNA molecules, or a fragment thereof.

In the context of the disclosure "specifically hybridizes" means that the probe or primer (such as, for example, the alteration-specific probe or alteration-specific primer) does not hybridize to a nucleic acid sequence encoding a GPR75 reference genomic nucleic acid molecule, a GPR75 reference mRNA molecule, and/or a GPR75 reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The present disclosure also provides molecular complexes comprising or consisting of any of the G-protein coupled receptor 75 nucleic acid molecules (genomic nucleic acid molecules, mRNA molecules, or cDNA molecules), or complement thereof, described herein and any of the alteration-specific primers or alteration-specific probes described herein. In some embodiments, the GPR75 nucleic acid molecules (genomic nucleic acid molecules, mRNA molecules, or cDNA molecules), or complement thereof, in the molecular complexes are single-stranded. In some embodiments, the GPR75 nucleic acid molecule is any of the genomic nucleic acid molecules described herein. In some embodiments, the GPR75 nucleic acid molecule is any of the mRNA molecules described herein. In some embodiments, the GPR75 nucleic acid molecule is any of the cDNA molecules described herein. In some embodiments, the molecular complex comprises or consists of any of the GPR75 nucleic acid molecules (genomic nucleic acid molecules, mRNA molecules, or cDNA molecules), or complement thereof, described herein and any of the alteration-specific primers described herein. In some embodiments, the molecular complex comprises or consists of any of the GPR75 nucleic acid molecules (genomic nucleic acid molecules, mRNA molecules, or cDNA molecules), or complement thereof, described herein and any of the alteration-specific probes described herein.

In some embodiments, the molecular complex comprises or consists of an alteration-specific primer or an alteration-specific probe hybridized to a genomic nucleic acid molecule comprising a nucleotide sequence encoding a human GPR75 polypeptide, wherein the alteration-specific primer or the alteration-specific probe is hybridized to the genomic nucleic acid molecule: at nucleotides at positions corresponding to positions 5,539-5,540 according to SEQ ID NO:2, or the complement thereof; at an adenine at a position corresponding to position 5,557 according to SEQ ID NO:3, or the complement thereof; at thymine at a position corresponding to position 5,911 according to SEQ ID NO:4, or the complement thereof; at nucleotides at positions corresponding to positions 5,919-5,920 according to SEQ ID NO:5, or the complement thereof; at a thymine at a position corresponding to position 6,411 according to SEQ ID NO:6, or the complement thereof; or at a guanine at a position corresponding to position 5,831 according to SEQ ID NO:99, or the complement thereof.

In some embodiments, the molecular complex comprises or consists of an alteration-specific primer or an alteration-specific probe that is hybridized to a genomic nucleic acid molecule at: an ACT codon at positions corresponding to positions 5,557-5,559 according to SEQ ID NO:3, a TAA codon at positions corresponding to positions 5,911-5,913 according to SEQ ID NO:4, or a TGT codon at positions corresponding to positions 5,830-5,832 according to SEQ ID NO:99.

In some embodiments, the molecular complex comprises or consists of an alteration-specific primer or an alteration-specific probe hybridized to a genomic nucleic acid molecule that comprises SEQ ID NO:2, SEQ ID NO:3, SEQ ID NO:4, SEQ ID NO:5, SEQ ID NO:6, or SEQ ID NO:99.

In some embodiments, the molecular complex comprises or consists of an alteration-specific primer or an alteration-specific probe hybridized to an mRNA molecule comprising a nucleotide sequence encoding a human GPR75 polypeptide, wherein the alteration-specific primer or the alteration-specific probe is hybridized to the mRNA molecule: at nucleotides at positions corresponding to positions 538-539 according to SEQ ID NO:11, or the complement thereof; at nucleotides at positions corresponding to positions 439-440 according to SEQ ID NO:16, or the complement thereof; at nucleotides at positions corresponding to positions 360-361 according to SEQ ID NO:21, or the complement thereof; at nucleotides at positions corresponding to positions 599-600 according to SEQ ID NO:26, or the complement thereof; at an adenine at a position corresponding to position 556 according to SEQ ID NO:12, or the complement thereof; at an adenine at a position corresponding to position 457 according to SEQ ID NO:17, or the complement thereof; at an adenine at a position corresponding to position 378 according to SEQ ID NO:22, or the complement thereof; at an adenine at a position corresponding to position 617 according to SEQ ID NO:27, or the complement thereof; at a uracil at a position corresponding to position 910 according to SEQ ID NO:13, or the complement thereof; at a uracil at a position corresponding to position 811 according to SEQ ID NO:18, or the complement thereof; at a uracil at a position corresponding to position 732 according to SEQ ID NO:23, or the complement thereof; at a uracil at a position corresponding to position 971 according to SEQ ID NO:28, or the complement thereof; at nucleotides at positions corresponding to positions 918-919 according to SEQ ID NO:14, or the complement thereof; at nucleotides at positions corresponding to positions 819-820 according to SEQ ID NO:19, or the complement thereof; at nucleotides at positions corresponding to positions 740-741 according to SEQ ID NO:24, or the complement thereof; at nucleotides at positions corresponding to positions 979-980 according to SEQ ID NO:29, or the complement thereof; at a uracil at a position corresponding to position 1,410 according to SEQ ID NO:15, or the complement thereof; at a uracil at a position corresponding to position 1,311 according to SEQ ID NO:20, or the complement thereof; at a uracil at a position corresponding to position 1,232 according to SEQ ID NO:25, the complement thereof; at of a uracil at a position corresponding to position 1,471 according to SEQ ID NO:30, or the complement thereof; at a guanine at a position corresponding to position 830 according to SEQ ID NO:100, or the complement thereof; at a guanine at a position corresponding to position 731 according to SEQ ID NO:101, or the complement thereof; at a guanine at a position corresponding to position 652 according to SEQ ID NO:102, or the complement thereof; or at a guanine at a position corresponding to position 891 according to SEQ ID NO:103, or the complement thereof.

In some embodiments, the molecular complex comprises or consists of an alteration-specific primer or an alteration-specific probe that is hybridized to an mRNA molecule at: an ACU codon at positions corresponding to positions 556-558 according to SEQ ID NO:12, an ACU codon at positions corresponding to positions 457-459 according to SEQ ID NO:17, an ACU codon at positions corresponding to positions 378-380 according to SEQ ID NO:22, an ACU codon at positions corresponding to positions 617-619 according to SEQ ID NO:27; a UAA codon at positions corresponding to positions 910-912 according to SEQ ID NO:13, a UAA codon at positions corresponding to positions 811-813 according to SEQ ID NO:18, a UAA codon at positions corresponding to positions 732-734 according to SEQ ID NO:23, a UAA codon at positions corresponding to positions 971-973 according to SEQ ID NO:28, a UGU codon at positions corresponding to positions 829-831 according to SEQ ID NO:100, a UGU codon at positions corresponding to positions 730-732 according to SEQ ID NO:101, a UGU codon at positions corresponding to positions 651-653 according to SEQ ID NO:102, or a UGU codon at positions corresponding to positions 890-892 according to SEQ ID NO:103.

In some embodiments, the molecular complex comprises or consists of an alteration-specific primer or an alteration-specific probe hybridized to an mRNA molecule that comprises SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:100, SEQ ID NO:101, SEQ ID NO:102, or SEQ ID NO:103.

In some embodiments, the molecular complex comprises or consists of an alteration-specific primer or an alteration-specific probe hybridized to a cDNA molecule comprising a nucleotide sequence encoding a human GPR75 polypeptide, wherein the alteration-specific primer or the alteration-specific probe is hybridized to a cDNA molecule: at nucleotides at positions corresponding to positions 538-539 according to SEQ ID NO:35, or the complement thereof; at nucleotides at positions corresponding to positions 439-440 according to SEQ ID NO:40, or the complement thereof; at nucleotides at positions corresponding to positions 360-361 according to SEQ ID NO:45, or the complement thereof; at nucleotides at positions corresponding to positions 599-600 according to SEQ ID NO:50, or the complement thereof; at an adenine at a position corresponding to position 556 according to SEQ ID NO:36, or the complement thereof; at an adenine at a position corresponding to position 457 according to SEQ ID NO:41, or the complement thereof; at an adenine at a position corresponding to position 378 according to SEQ ID NO:46, or the complement thereof; at an adenine at a position corresponding to position 617 according to SEQ ID NO:51, or the complement thereof; at a thymine at a position corresponding to position 910 according to SEQ ID NO:37, or the complement thereof; at a thymine at a position corresponding to position 811 according to SEQ ID NO:42, or the complement thereof; at a thymine at a position corresponding to position 732 according to SEQ ID NO:47, or the complement thereof; at a thymine at a position corresponding to position 971 according to SEQ ID NO:52, or the complement thereof; at nucleotides at positions corresponding to positions 918-919 according to SEQ ID NO:38, or the complement thereof; at nucleotides at positions corresponding to positions 819-820 according to SEQ ID NO:43, or the complement thereof; at nucleotides at positions corresponding to positions 740-741 according to SEQ ID NO:48, or the complement thereof; at nucleotides at positions corresponding to positions 979-980 according to SEQ ID NO:53, or the complement thereof; at a thymine at a position corresponding to position 1,410 according to SEQ ID NO:39, or the complement thereof; at a thymine at a position corresponding to position 1,311 according to SEQ ID NO:44, or the complement thereof; at a thymine at a position corresponding to position 1,232 according to SEQ ID NO:49, or the complement thereof; at a thymine at a position corresponding to position 1,471 according to SEQ ID NO:54, or the complement thereof; at a guanine at a position corresponding to position 830 according to SEQ ID NO:104, or the complement thereof; at a guanine at a position corresponding to position 731 according to SEQ ID NO:105, or the complement thereof; at a guanine at a position corresponding to position 652 according to SEQ ID NO:106, or the complement thereof; or at a guanine at a position corresponding to position 891 according to SEQ ID NO:107, or the complement thereof.

In some embodiments, the molecular complex comprises or consists of an alteration-specific primer or an alteration-specific probe that is hybridized to a cDNA molecule at: an ACT codon at positions corresponding to positions 556-558 according to SEQ ID NO:36, an ACT codon at positions corresponding to positions 457-459 according to SEQ ID NO:41, an ACT codon at positions corresponding to positions 378-380 according to SEQ ID NO:46, an ACT codon at positions corresponding to positions 617-619 according to SEQ ID NO:51; a TAA codon at positions corresponding to positions 910-912 according to SEQ ID NO:37, a TAA codon at positions corresponding to positions 811-813 according to SEQ ID NO:42, a TAA codon at positions corresponding to positions 732-734 according to SEQ ID NO:47, a TAA codon at positions corresponding to positions 971-973 according to SEQ ID NO:52, a TGT codon at positions corresponding to positions 829-831 according to SEQ ID NO:104, a TGT codon at positions corresponding to positions 730-732 according to SEQ ID NO:105, a TGT codon at positions corresponding to positions 651-653 according to SEQ ID NO:106, or a TGT codon at positions corresponding to positions 890-892 according to SEQ ID NO:107.

In some embodiments, the molecular complex comprises or consists of an alteration-specific primer or an alteration-specific probe hybridized to a cDNA molecule that comprises SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54, SEQ ID NO:104, SEQ ID NO:105, SEQ ID NO:106, or SEQ ID NO:107.

In some embodiments, the molecular complex comprises an alteration-specific probe or an alteration-specific primer comprising a label. In some embodiments, the label is a fluorescent label, a radiolabel, or biotin. In some embodiments, the molecular complex further comprises a non-human polymerase.

The present disclosure also provides isolated nucleic acid molecules comprising a nucleotide sequence encoding a human GPR75 variant polypeptide. In some embodiments, the GPR75 variant polypeptide comprises a frameshift beginning at a position corresponding to position 110 according to SEQ ID NO:56, or the complement thereof. In some embodiments, the isolated nucleic acid molecule encodes a GPR75 variant polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:56, and comprises a frameshift beginning at a position corresponding to position 110 according to SEQ ID NO:56. In some embodiments, the isolated nucleic acid molecule encodes a GPR75 variant polypeptide having an amino acid sequence that has at least about 90% sequence identity to SEQ ID NO:56, and comprises a frameshift beginning at a position corresponding to position 110 according to SEQ ID NO:56. In some embodiments, the isolated nucleic acid molecule encodes a GPR75 variant polypeptide having an amino acid sequence that has at least about 92% sequence identity to SEQ ID NO:56, and comprises a frameshift beginning at a position corresponding to position 110 according to SEQ ID NO:56. In some embodiments, the isolated nucleic acid molecule encodes a GPR75 variant polypeptide having an amino acid sequence that has at least about 94% sequence identity to SEQ ID NO:56, and comprises a frameshift beginning at a position corresponding to position 110 according to SEQ ID NO:56. In some embodiments, the isolated nucleic acid molecule encodes a GPR75 variant polypeptide having an amino acid sequence that has at least about 96% sequence identity to SEQ ID NO:56, and comprises a frameshift beginning at a position corresponding to position 110 according to SEQ ID NO:56. In some embodiments, the isolated nucleic acid molecule encodes a GPR75 variant polypeptide having an amino acid sequence that has at least about 98% sequence identity to SEQ ID NO:56, and comprises a frameshift beginning at a position corresponding to position 110 according to SEQ ID NO:56. In some embodiments, the nucleic acid molecule encodes a GPR75 variant polypeptide comprising SEQ ID NO:56. In some embodiments, the nucleic acid molecule encodes a GPR75 variant polypeptide consisting of SEQ ID NO:56. Each of these nucleic acid molecules encodes a GPR75 polypeptide that lacks amino acids at positions corresponding to positions 110-540 according to SEQ ID NO:55. In some embodiments, each of these nucleic acid molecules encodes a GPR75 polypeptide that comprises amino acids at positions corresponding to positions 110-130 according to SEQ ID NO:56.

In some embodiments, the GPR75 variant polypeptide comprises a threonine at a position corresponding to position 116 according to SEQ ID NO:57, or the complement thereof. In some embodiments, the isolated nucleic acid molecule encodes a GPR75 variant polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:57, and comprises a threonine at a position corresponding to position 116 according to SEQ ID NO:57. In some embodiments, the isolated nucleic acid molecule encodes a GPR75 variant polypeptide having an amino acid sequence that has at least about 90% sequence identity to SEQ ID NO:57, and comprises a threonine at a position corresponding to position 116 according to SEQ ID NO:57. In some embodiments, the isolated nucleic acid molecule encodes a GPR75 variant polypeptide having an amino acid sequence that has at least about 92% sequence identity to SEQ ID NO:57, and comprises a threonine at a position corresponding to position 116 according to SEQ ID NO:57. In some embodiments, the isolated nucleic acid molecule encodes a GPR75 variant polypeptide having an amino acid sequence that has at least about 94% sequence identity to SEQ ID NO:57, and comprises a threonine at a position corresponding to position 116 according to SEQ ID NO:57. In some embodiments, the isolated nucleic acid molecule encodes a GPR75 variant polypeptide having an amino acid sequence that has at least about 96% sequence identity to SEQ ID NO:57, and comprises a threonine at a position corresponding to position 116 according to SEQ ID NO:57. In some embodiments, the isolated nucleic acid molecule encodes a GPR75 variant polypeptide having an amino acid sequence that has at least about 98% sequence identity to SEQ ID NO:57, and comprises a threonine at a position corresponding to position 116 according to SEQ ID NO:57. In some embodiments, the nucleic acid molecule encodes a GPR75 variant polypeptide comprising SEQ ID NO:57. In some embodiments, the nucleic acid molecule encodes a GPR75 variant polypeptide consisting of SEQ ID NO:57.

In some embodiments, the GPR75 variant polypeptide terminates at a position corresponding to position 233 according to SEQ ID NO:58, or the complement thereof. In some embodiments, the isolated nucleic acid molecule encodes a GPR75 variant polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:58, and terminates at a position corresponding to position 233 according to SEQ ID NO:58. In some embodiments, the isolated nucleic acid molecule encodes a GPR75 variant polypeptide having an amino acid sequence that has at least about 90% sequence identity to SEQ ID NO:58, and terminates at a position corresponding to position 233 according to SEQ ID NO:58. In some embodiments, the isolated nucleic acid molecule encodes a GPR75 variant polypeptide having an amino acid sequence that has at least about 92% sequence identity to SEQ ID NO:58, and terminates at a position corresponding to position 233 according to SEQ ID NO:58. In some embodiments, the isolated nucleic acid molecule encodes a GPR75 variant polypeptide having an amino acid sequence that has at least about 94% sequence identity to SEQ ID NO:58, and terminates at a position corresponding to position 233 according to SEQ ID NO:58. In some embodiments, the isolated nucleic acid molecule encodes a GPR75 variant polypeptide having an amino acid sequence that has at least about 96% sequence identity to SEQ ID NO:58, and terminates at a position corresponding to position 233 according to SEQ ID NO:58. In some embodiments, the isolated nucleic acid molecule encodes a GPR75 variant polypeptide having an amino acid sequence that has at least about 98% sequence identity to SEQ ID NO:58, and terminates at a position corresponding to position 233 according to SEQ ID NO:58. In some embodiments, the nucleic acid molecule encodes a GPR75 variant polypeptide comprising SEQ ID NO:58. In some embodiments, the nucleic acid molecule encodes a GPR75 variant polypeptide consisting of SEQ ID NO:58.

In some embodiments, the GPR75 variant polypeptide comprises a frameshift beginning at a position corresponding to position 236 according to SEQ ID NO:59, or the complement thereof. In some embodiments, the isolated nucleic acid molecule encodes a GPR75 variant polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:59, and comprises a frameshift beginning at a position corresponding to position 236 according to SEQ ID NO:59. In some embodiments, the isolated nucleic acid molecule encodes a GPR75 variant polypeptide having an amino acid sequence that has at least about 90% sequence identity to SEQ ID NO:59, and comprises a frameshift beginning at a position corresponding to position 236 according to SEQ ID NO:59. In some embodiments, the isolated nucleic acid molecule encodes a GPR75 variant polypeptide having an amino acid sequence that has at least about 92% sequence identity to SEQ ID NO:59, and comprises a frameshift beginning at a position corresponding to position 236 according to SEQ ID NO:59. In some embodiments, the isolated nucleic acid molecule encodes a GPR75 variant polypeptide having an amino acid sequence that has at least about 94% sequence identity to SEQ ID NO:59, and comprises a frameshift beginning at a position corresponding to position 236 according to SEQ ID NO:59. In some embodiments, the isolated nucleic acid molecule encodes a GPR75 variant polypeptide having an amino acid sequence that has at least about 96% sequence identity to SEQ ID NO:59, and comprises a frameshift beginning at a position corresponding to position 236 according to SEQ ID NO:59. In some embodiments, the isolated nucleic acid molecule encodes a GPR75 variant polypeptide having an amino acid sequence that has at least about 98% sequence identity to SEQ ID NO:59, and comprises a frameshift beginning at a position corresponding to position 236 according to SEQ ID NO:59. In some embodiments, the nucleic acid molecule encodes a GPR75 variant polypeptide comprising SEQ ID NO:59. In some embodiments, the nucleic acid molecule encodes a GPR75 variant polypeptide consisting of SEQ ID NO:59. Each of these nucleic acid molecules encodes a GPR75 polypeptide that lacks amino acids at positions corresponding to positions 236-540 according to SEQ ID NO:55. In some embodiments, each of these nucleic acid molecules encodes a GPR75 polypeptide that comprises amino acids at positions corresponding to positions 236-239 according to SEQ ID NO:59.

In some embodiments, the GPR75 variant polypeptide comprises a frameshift beginning at a position corresponding to position 400 according to SEQ ID NO:60, or the complement thereof. In some embodiments, the isolated nucleic acid molecule encodes a GPR75 variant polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:60, and comprises a frameshift beginning at a position corresponding to position 400 according to SEQ ID NO:60. In some embodiments, the isolated nucleic acid molecule encodes a GPR75 variant polypeptide having an amino acid sequence that has at least about 90% sequence identity to SEQ ID NO:60, and comprises a frameshift beginning at a position corresponding to position 400 according to SEQ ID NO:60. In some embodiments, the isolated nucleic acid molecule encodes a GPR75 variant polypeptide having an amino acid sequence that has at least about 92% sequence identity to SEQ ID NO:60, and comprises a frameshift beginning at a position corresponding to position 400 according to SEQ ID NO:60. In some embodiments, the isolated nucleic acid molecule encodes a GPR75 variant polypeptide having an amino acid sequence that has at least about 94% sequence identity to SEQ ID NO:60, and comprises a frameshift beginning at a position corresponding to position 400 according to SEQ ID NO:60. In some embodiments, the isolated nucleic acid molecule encodes a GPR75 variant polypeptide having an amino acid sequence that has at least about 96% sequence identity to SEQ ID NO:60, and comprises a frameshift beginning at a position corresponding to position 400 according to SEQ ID NO:60. In some embodiments, the isolated nucleic acid molecule encodes a GPR75 variant polypeptide having an amino acid sequence that has at least about 98% sequence identity to SEQ ID NO:60, and comprises a frameshift beginning at a position corresponding to position 400 according to SEQ ID NO:60. In some embodiments, the nucleic acid molecule encodes a GPR75 variant polypeptide comprising SEQ ID NO:60. In some embodiments, the nucleic acid molecule encodes a GPR75 variant polypeptide consisting of SEQ ID NO:60. Each of these nucleic acid molecules encodes a GPR75 polypeptide that lacks amino acids at positions corresponding to positions 400-540 according to SEQ ID NO:55. In some embodiments, each of these nucleic acid molecules encodes a GPR75 polypeptide that comprises amino acids at positions corresponding to positions 400-425 according to SEQ ID NO:60.

In some embodiments, the GPR75 variant polypeptide comprises a cysteine at a position corresponding to position 207 according to SEQ ID NO:108, or the complement thereof. In some embodiments, the isolated nucleic acid molecule encodes a GPR75 variant polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:108, and comprises a cysteine at a position corresponding to position 207 according to SEQ ID NO:108. In some embodiments, the isolated nucleic acid molecule encodes a GPR75 variant polypeptide having an amino acid sequence that has at least about 90% sequence identity to SEQ ID NO:108, and comprises a cysteine at a position corresponding to position 207 according to SEQ ID NO:108. In some embodiments, the isolated nucleic acid molecule encodes a GPR75 variant polypeptide having an amino acid sequence that has at least about 92% sequence identity to SEQ ID NO:108, and comprises a cysteine at a position corresponding to position 207 according to SEQ ID NO:108. In some embodiments, the isolated nucleic acid molecule encodes a GPR75 variant polypeptide having an amino acid sequence that has at least about 94% sequence identity to SEQ ID NO:108, and comprises a cysteine at a position corresponding to position 207 according to SEQ ID NO:108. In some embodiments, the isolated nucleic acid molecule encodes a GPR75 variant polypeptide having an amino acid sequence that has at least about 96% sequence identity to SEQ ID NO:108, and comprises a cysteine at a position corresponding to position 207 according to SEQ ID NO:108. In some embodiments, the isolated nucleic acid molecule encodes a GPR75 variant polypeptide having an amino acid sequence that has at least about 98% sequence identity to SEQ ID NO:108, and comprises a cysteine at a position corresponding to position 207 according to SEQ ID NO:108. In some embodiments, the nucleic acid molecule encodes a GPR75 variant polypeptide comprising SEQ ID NO:108. In some embodiments, the nucleic acid molecule encodes a GPR75 variant polypeptide consisting of SEQ ID NO:108.

The nucleotide sequence of a GPR75 reference genomic nucleic acid molecule is set forth in SEQ ID NO:1. See, also, ENSG00000119737.6, hg38 chr2:53,852,912-53,859,967. Referring to SEQ ID NO:1, positions 5,540-5,546 are a CCAGTAG heptanucleotide. Referring to SEQ ID NO:1, position 5,557 is a guanine. Referring to SEQ ID NO:1, position 5,911 is a cytosine. Referring to SEQ ID NO:1, positions 5,920-5,923 are an AAAG tetranucleotide. Referring to SEQ ID NO:1, position 6,411 is a cytosine. Referring to SEQ ID NO:1, position 5,831 is an adenine.

A variant genomic nucleic acid molecule of GPR75 exists, wherein the CCAGTAG heptanucleotide at positions 5,540-5,546 (referring to SEQ ID NO:1) is deleted. The nucleotide sequence of this GPR75 variant genomic nucleic acid molecule is set forth in SEQ ID NO:2.

Another variant genomic nucleic acid molecule of GPR75 exists, wherein the guanine at position 5,557 (referring to SEQ ID NO:1) is replaced with adenine. The nucleotide sequence of this GPR75 variant genomic nucleic acid molecule is set forth in SEQ ID NO:3.

Another variant genomic nucleic acid molecule of GPR75 exists, wherein the cytosine at position 5,911 (referring to SEQ ID NO:1) is replaced with thymine. The nucleotide sequence of this GPR75 variant genomic nucleic acid molecule is set forth in SEQ ID NO:4.

Another variant genomic nucleic acid molecule of GPR75 exists, wherein the AAAG tetranucleotide at positions 5,920-5,923 (referring to SEQ ID NO:1) is deleted. The nucleotide sequence of this GPR75 variant genomic nucleic acid molecule is set forth in SEQ ID NO:5.

Another variant genomic nucleic acid molecule of GPR75 exists, a thymine is inserted at position 6,411 (referring to SEQ ID NO:1). The nucleotide sequence of this GPR75 variant genomic nucleic acid molecule is set forth in SEQ ID NO:6.

Another variant genomic nucleic acid molecule of GPR75 exists, wherein the adenine at position 5,831 (referring to SEQ ID NO:1) is replaced with guanine. The nucleotide sequence of this GPR75 variant genomic nucleic acid molecule is set forth in SEQ ID NO:99.

Another variant genomic nucleic acid molecule of GPR75 exists, wherein the thymine at position 53,853,547 on chromosome 2 (according to GRCh38/hg38 (December 2013) human genome assembly) is replaced with adenine, resulting in Lys404*. Referring to SEQ ID NO:1, the variation is AAG to TAG (at the codon at positions 6,421-6,423 on the coding strand). Each of the methods described herein in regard to any of the variants described herein can be carried out with this additional variant (i.e., genomic, mRNA, and cDNA molecules) as well.

Another variant genomic nucleic acid molecule of GPR75 exists, wherein the CAG beginning at position 53,854,099 on chromosome 2 (according to GRCh38/hg38 (December 2013) human genome assembly) is replaced with cytosine, resulting in Ser219fs. Referring to SEQ ID NO:1, the variation is GTC (at positions 5,869-5,871 on the coding strand) to G. Each of the methods described herein in regard to any of the variants described herein can be carried out with this additional variant (i.e., genomic, mRNA, and cDNA molecules) as well.

Another variant genomic nucleic acid molecule of GPR75 exists, wherein the cytosine at position 53,859,827 on chromosome 2 (according to GRCh38/hg38 (December 2013) human genome assembly) is replaced with thymine (with a cDNA designated c.−110+1G>A), which is a splice donor site variation 110 bases upstream of the start codon. Referring to SEQ ID NO:1, the variation is G (at position 141 on the coding strand) to A. Each of the methods described herein in regard to any of the variants described herein can be carried out with this additional variant (i.e., genomic, mRNA, and cDNA molecules) as well.

The present disclosure also provides isolated genomic nucleic acid molecules comprising or consisting of a nucleotide sequence encoding a human GPR75 polypeptide. In some embodiments, the nucleotide sequence of the genomic nucleic acid molecule lacks a CCAGTAG heptanucleotide at positions corresponding to positions 5,540-5,546 according to SEQ ID NO:1, or the complement thereof. An example is set forth in SEQ ID NO:2.

In some embodiments, the nucleotide sequence of the genomic nucleic acid molecule lacks an AAAG tetranucleotide at positions corresponding to positions 5,920-5,923 according to SEQ ID NO:1, or the complement thereof. An example is set forth in SEQ ID NO:5.

In some embodiments, the nucleotide sequence of the genomic nucleic acid molecule comprises an insertion of a thymine at a position corresponding to position 6,411 according to SEQ ID NO:1, or the complement thereof. An example is set forth in SEQ ID NO:6.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and lacks a CCAGTAG heptanucleotide at positions corresponding to positions 5,540-5,546 according to SEQ ID NO:1, or the complement thereof. In some embodiments, the isolated genomic nucleic acid molecules comprise or consist of a nucleotide sequence that has at least about 90% sequence identity to SEQ ID NO:2, and lacks a CCAGTAG heptanucleotide at positions corresponding to positions 5,540-5,546 according to SEQ ID NO:1, or the complement thereof. In some embodiments, the isolated genomic nucleic acid molecules comprise or consist of a nucleotide sequence that has at least about 92% sequence identity to SEQ ID NO:2, and lacks a CCAGTAG heptanucleotide at positions corresponding to positions 5,540-5,546 according to SEQ ID NO:1, or the complement thereof. In some embodiments, the isolated genomic nucleic acid molecules comprise or consist of a nucleotide sequence that has at least about 94% sequence identity to SEQ ID NO:2, and lacks a CCAGTAG heptanucleotide at positions corresponding to positions 5,540-5,546 according to SEQ ID NO:1, or the complement thereof. In some embodiments, the isolated genomic nucleic acid molecules comprise or consist of a nucleotide sequence that has at least about 96% sequence identity to SEQ ID NO:2, and lacks a CCAGTAG heptanucleotide at positions corresponding to positions 5,540-5,546 according to SEQ ID NO:1, or the complement thereof. In some embodiments, the isolated genomic nucleic acid molecules comprise or consist of a nucleotide sequence that has at least about 98% sequence identity to SEQ ID NO:2, and lacks a CCAGTAG heptanucleotide at positions corresponding to positions 5,540-5,546 according to SEQ ID NO:1, or the complement thereof.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:5, and lacks an AAAG tetranucleotide at positions corresponding to positions 5,920-5,923 according to SEQ ID NO:1, or the complement thereof. In some embodiments, the isolated genomic nucleic acid molecules comprise or consist of a nucleotide sequence that has at least about 90% sequence identity to SEQ ID NO:5, and lacks an AAAG tetranucleotide at positions corresponding to positions 5,920-5,923 according to SEQ ID NO:1, or the complement thereof. In some embodiments, the isolated genomic nucleic acid molecules comprise or consist of a nucleotide sequence that has at least about 92% sequence identity to SEQ ID NO:5, and lacks an AAAG tetranucleotide at positions corresponding to positions 5,920-5,923 according to SEQ ID NO:1, or the complement thereof. In some embodiments, the isolated genomic nucleic acid molecules comprise or consist of a nucleotide sequence that has at least about 94% sequence identity to SEQ ID NO:5, and lacks an AAAG tetranucleotide at positions corresponding to positions 5,920-5,923 according to SEQ ID NO:1, or the complement thereof. In some embodiments, the isolated genomic nucleic acid molecules comprise or consist of a nucleotide sequence that has at least about 96% sequence identity to SEQ ID NO:5, and lacks an AAAG tetranucleotide at positions corresponding to positions 5,920-5,923 according to SEQ ID NO:1, or the complement thereof. In some embodiments, the isolated genomic nucleic acid molecules comprise or consist of a nucleotide sequence that has at least about 98% sequence identity to SEQ ID NO:5, and lacks an AAAG tetranucleotide at positions corresponding to positions 5,920-5,923 according to SEQ ID NO:1, or the complement thereof.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6, and comprises an insertion of a thymine at a position corresponding to position 6,411 according to SEQ ID NO:6, or the complement thereof. In some embodiments, the isolated genomic nucleic acid molecules comprise or consist of a nucleotide sequence that has at least about 90% sequence identity to SEQ ID NO:6, and comprises an insertion of a thymine at a position corresponding to position 6,411 according to SEQ ID NO:6, or the complement thereof. In some embodiments, the isolated genomic nucleic acid molecules comprise or consist of a nucleotide sequence that has at least about 92% sequence identity to SEQ ID NO:6, and comprises an insertion of a thymine at a position corresponding to position 6,411 according to SEQ ID NO:6, or the complement thereof. In some embodiments, the isolated genomic nucleic acid molecules comprise or consist of a nucleotide sequence that has at least about 94% sequence identity to SEQ ID NO:6, and comprises an insertion of a thymine at a position corresponding to position 6,411 according to SEQ ID NO:6, or the complement thereof. In some embodiments, the isolated genomic nucleic acid molecules comprise or consist of a nucleotide sequence that has at least about 96% sequence identity to SEQ ID NO:6, and comprises an insertion of a thymine at a position corresponding to position 6,411 according to SEQ ID NO:6, or the complement thereof. In some embodiments, the isolated genomic nucleic acid molecules comprise or consist of a nucleotide sequence that has at least about 98% sequence identity to SEQ ID NO:6, and comprises an insertion of a thymine at a position corresponding to position 6,411 according to SEQ ID NO:6, or the complement thereof.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:99, and comprises a guanine at a position corresponding to position 5,831 according to SEQ ID NO:99, or the complement thereof. In some embodiments, the isolated genomic nucleic acid molecules comprise or consist of a nucleotide sequence that has at least about 90% sequence identity to SEQ ID NO:99, and comprises a guanine at a position corresponding to position 5,831 according to SEQ ID NO:99, or the complement thereof. In some embodiments, the isolated genomic nucleic acid molecules comprise or consist of a nucleotide sequence that has at least about 92% sequence identity to SEQ ID NO:99, and comprises a guanine at a position corresponding to position 5,831 according to SEQ ID NO:99, or the complement thereof. In some embodiments, the isolated genomic nucleic acid molecules comprise or consist of a nucleotide sequence that has at least about 94% sequence identity to SEQ ID NO:99, and comprises a guanine at a position corresponding to position 5,831 according to SEQ ID NO:99, or the complement thereof. In some embodiments, the isolated genomic nucleic acid molecules comprise or consist of a nucleotide sequence that has at least about 96% sequence identity to SEQ ID NO:99, and comprises a guanine at a position corresponding to position 5,831 according to SEQ ID NO:99, or the complement thereof. In some embodiments, the isolated genomic nucleic acid molecules comprise or consist of a nucleotide sequence that has at least about 98% sequence identity to SEQ ID NO:99, and comprises a guanine at a position corresponding to position 5,831 according to SEQ ID NO:99, or the complement thereof.

Herein, if reference is made to percent sequence identity, the higher percentages of sequence identity are preferred over the lower ones.

In some embodiments, the isolated genomic nucleic acid molecules comprise SEQ ID NO:2. In some embodiments, the isolated genomic nucleic acid molecules consist of SEQ ID NO:2. In some embodiments, the isolated genomic nucleic acid molecules comprise SEQ ID NO:3. In some embodiments, the isolated genomic nucleic acid molecules consist of SEQ ID NO:3. In some embodiments, the isolated genomic nucleic acid molecules comprise SEQ ID NO:4. In some embodiments, the isolated genomic nucleic acid molecules consist of SEQ ID NO:4. In some embodiments, the isolated genomic nucleic acid molecules comprise SEQ ID NO:5. In some embodiments, the isolated genomic nucleic acid molecules consist of SEQ ID NO:5. In some embodiments, the isolated genomic nucleic acid molecules comprise SEQ ID NO:6. In some embodiments, the isolated genomic nucleic acid molecules consist of SEQ ID NO:6. In some embodiments, the isolated genomic nucleic acid molecules comprise SEQ ID NO:99. In some embodiments, the isolated genomic nucleic acid molecules consist of SEQ ID NO:99.

In some embodiments, the isolated genomic nucleic acid molecules comprise less than the entire genomic DNA sequence. In some embodiments, the isolated genomic nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, or at least about 10000 contiguous nucleotides of any of the GPR75 genomic nucleic acid molecules disclosed herein. In some embodiments, the isolated genomic nucleic acid molecules comprise or consist of at least about 1000 to at least about 2000 contiguous nucleotides of any of the GPR75 genomic nucleic acid molecules disclosed herein. In some embodiments, these isolated genomic nucleic acid molecules lack a CCAGTAG heptanucleotide at positions corresponding to positions 5,540-5,546 according to SEQ ID NO:1. In some embodiments, these isolated genomic nucleic acid molecules lack an AAAG tetranucleotide at positions corresponding to positions 5,920-5,923 according to SEQ ID NO:1. In some embodiments, these isolated genomic nucleic acid molecules comprise the insertion of thymine at a position corresponding to position 6,411 according to SEQ ID NO:6.

The nucleotide sequence of a GPR75 reference mRNA molecule is set forth in SEQ ID NO:7. Referring to SEQ ID NO:7, positions 539-545 are a CCAGUAG heptanucleotide. Referring to SEQ ID NO:7, position 566 is a guanine. Referring to SEQ ID NO:7, position 910 is a cytosine. Referring to SEQ ID NO:7, positions 919-922 are an AAAG tetranucleotide. Referring to SEQ ID NO:7, position 1,410 is a cytosine. Referring to SEQ ID NO:7, position 830 is an adenine.

The nucleotide sequence of another GPR75 reference mRNA molecule is set forth in SEQ ID NO:8. Referring to SEQ ID NO:8, positions 440-446 are a CCAGUAG heptanucleotide. Referring to SEQ ID NO:8, position 457 is a guanine. Referring to SEQ ID NO:8, position 811 is a cytosine. Referring to SEQ ID NO:8, positions 820-823 are an AAAG tetranucleotide. Referring to SEQ ID NO:8, position 1,311 is a cytosine. Referring to SEQ ID NO:8, position 731 is an adenine.

The nucleotide sequence of another GPR75 reference mRNA molecule is set forth in SEQ ID NO:9. Referring to SEQ ID NO:9, positions 361-367 are a CCAGUAG heptanucleotide. Referring to SEQ ID NO:9, position 378 is a guanine. Referring to SEQ ID NO:9, position 732 is a cytosine. Referring to SEQ ID NO:9, positions 741-744 are an AAAG tetranucleotide. Referring to SEQ ID NO:9, position 1,232 is a cytosine. Referring to SEQ ID NO:9, position 652 is an adenine.

The nucleotide sequence of another GPR75 reference mRNA molecule is set forth in SEQ ID NO:10. Referring to SEQ ID NO:10, positions 600-606 are a CCAGUAG heptanucleotide. Referring to SEQ ID NO:10, position 617 is a guanine. Referring to SEQ ID NO:10, position 971 is a cytosine. Referring to SEQ ID NO:10, positions 980-983 are an AAAG tetranucleotide. Referring to SEQ ID NO:10, position 1,471 is a cytosine. Referring to SEQ ID NO:10, position 891 is an adenine.

A variant mRNA molecule of GPR75 exists, wherein the CCAGUAG heptanucleotide at positions 539-545 (referring to SEQ ID NO:7) is deleted. The nucleotide sequence of this GPR75 variant mRNA molecule is set forth in SEQ ID NO:11.

Another variant mRNA molecule of GPR75 exists, wherein the CCAGUAG heptanucleotide at positions 440-446 (referring to SEQ ID NO:8) is deleted. The nucleotide sequence of this GPR75 variant mRNA molecule is set forth in SEQ ID NO:16.

Another variant mRNA molecule of GPR75 exists, wherein the CCAGUAG heptanucleotide at positions 361-367 (referring to SEQ ID NO:9) is deleted. The nucleotide sequence of this GPR75 variant mRNA molecule is set forth in SEQ ID NO:21.

Another variant mRNA molecule of GPR75 exists, wherein the CCAGUAG heptanucleotide at positions 600-606 (referring to SEQ ID NO:10) is deleted. The nucleotide sequence of this GPR75 variant mRNA molecule is set forth in SEQ ID NO:26.

A variant mRNA molecule of GPR75 exists, wherein the guanine at position 556 (referring to SEQ ID NO:7) is replaced with adenine. The nucleotide sequence of this GPR75 variant mRNA molecule is set forth in SEQ ID NO:12.

Another variant mRNA molecule of GPR75 exists, wherein the guanine at position 457 (referring to SEQ ID NO:8) is replaced with adenine. The nucleotide sequence of this GPR75 variant mRNA molecule is set forth in SEQ ID NO:17.

Another variant mRNA molecule of GPR75 exists, wherein the guanine at position 378 (referring to SEQ ID NO:9) is replaced with adenine. The nucleotide sequence of this GPR75 variant mRNA molecule is set forth in SEQ ID NO:22.

Another variant mRNA molecule of GPR75 exists, wherein the guanine at position 617 (referring to SEQ ID NO:10) is replaced with adenine. The nucleotide sequence of this GPR75 variant mRNA molecule is set forth in SEQ ID NO:27.

A variant mRNA molecule of GPR75 exists, wherein the cytosine at position 910 (referring to SEQ ID NO:7) is replaced with uracil. The nucleotide sequence of this GPR75 variant mRNA molecule is set forth in SEQ ID NO:13.

Another variant mRNA molecule of GPR75 exists, wherein the cytosine at position 811 (referring to SEQ ID NO:8) is replaced with uracil. The nucleotide sequence of this GPR75 variant mRNA molecule is set forth in SEQ ID NO:18.

Another variant mRNA molecule of GPR75 exists, wherein the cytosine at position 732 (referring to SEQ ID NO:9) is replaced with uracil. The nucleotide sequence of this GPR75 variant mRNA molecule is set forth in SEQ ID NO:23.

Another variant mRNA molecule of GPR75 exists, wherein the cytosine at position 971 (referring to SEQ ID NO:10) is replaced with uracil. The nucleotide sequence of this GPR75 variant mRNA molecule is set forth in SEQ ID NO:28.

A variant mRNA molecule of GPR75 exists, wherein the AAAG tetranucleotide at positions 919-922 (referring to SEQ ID NO:7) is deleted. The nucleotide sequence of this GPR75 variant mRNA molecule is set forth in SEQ ID NO:14.

Another variant mRNA molecule of GPR75 exists, wherein the AAAG tetranucleotide at positions 820-823 (referring to SEQ ID NO:8) is deleted. The nucleotide sequence of this GPR75 variant mRNA molecule is set forth in SEQ ID NO:19.

Another variant mRNA molecule of GPR75 exists, wherein the AAAG tetranucleotide at positions 741-744 (referring to SEQ ID NO:9) is deleted. The nucleotide sequence of this GPR75 variant mRNA molecule is set forth in SEQ ID NO:24.

Another variant mRNA molecule of GPR75 exists, wherein AAAG tetranucleotide at positions 980-983 (referring to SEQ ID NO:10) is replaced with deleted. The nucleotide sequence of this GPR75 variant mRNA molecule is set forth in SEQ ID NO:29.

A variant mRNA molecule of GPR75 exists, wherein a uracil is inserted at position 1,410 (referring to SEQ ID NO:7). The nucleotide sequence of this GPR75 variant mRNA molecule is set forth in SEQ ID NO:15.

Another variant mRNA molecule of GPR75 exists, wherein a uracil is inserted at position 1,311 (referring to SEQ ID NO:8). The nucleotide sequence of this GPR75 variant mRNA molecule is set forth in SEQ ID NO:20.

Another variant mRNA molecule of GPR75 exists, wherein a uracil is inserted at position 1,232 (referring to SEQ ID NO:9). The nucleotide sequence of this GPR75 variant mRNA molecule is set forth in SEQ ID NO:25.

Another variant mRNA molecule of GPR75 exists, wherein a uracil is inserted at position 1,471 (referring to SEQ ID NO:10). The nucleotide sequence of this GPR75 variant mRNA molecule is set forth in SEQ ID NO:30.

A variant mRNA molecule of GPR75 exists, wherein the adenine at position 830 (referring to SEQ ID NO:7) is replaced with guanine. The nucleotide sequence of this GPR75 variant mRNA molecule is set forth in SEQ ID NO:100.

Another variant mRNA molecule of GPR75 exists, wherein the adenine at position 731 (referring to SEQ ID NO:8) is replaced with guanine. The nucleotide sequence of this GPR75 variant mRNA molecule is set forth in SEQ ID NO:101.

Another variant mRNA molecule of GPR75 exists, wherein the adenine at position 652 (referring to SEQ ID NO:9) is replaced with guanine. The nucleotide sequence of this GPR75 variant mRNA molecule is set forth in SEQ ID NO:102.

Another variant mRNA molecule of GPR75 exists, wherein the adenine at position 891 (referring to SEQ ID NO:10) is replaced with guanine. The nucleotide sequence of this GPR75 variant mRNA molecule is set forth in SEQ ID NO:103.

The present disclosure also provides isolated mRNA molecules comprising or consisting of a nucleotide sequence encoding a human GPR75 polypeptide, wherein the nucleotide sequence lacks a CCAGUAG heptanucleotide at positions corresponding to positions 539-545 according to SEQ ID NO:7, or the complement thereof. An example is set forth in SEQ ID NO:11.

The present disclosure also provides isolated mRNA molecules comprising or consisting of a nucleotide sequence encoding a human GPR75 polypeptide, wherein the nucleotide sequence lacks a CCAGUAG heptanucleotide at positions corresponding to positions 440-446 according to SEQ ID NO:8, or the complement thereof. An example is set forth in SEQ ID NO:16.

The present disclosure also provides isolated mRNA molecules comprising or consisting of a nucleotide sequence encoding a human GPR75 polypeptide, wherein the nucleotide sequence lacks a CCAGUAG heptanucleotide at positions corresponding to positions 361-367 according to SEQ ID NO:9, or the complement thereof. An example is set forth in SEQ ID NO:21.

The present disclosure also provides isolated mRNA molecules comprising or consisting of a nucleotide sequence encoding a human GPR75 polypeptide, wherein the nucleotide sequence lacks a CCAGUAG heptanucleotide at positions corresponding to positions 600-606 according to SEQ ID NO:10, or the complement thereof. An example is set forth in SEQ ID NO:26.

The present disclosure also provides isolated mRNA molecules comprising or consisting of a nucleotide sequence encoding a human GPR75 polypeptide, wherein the nucleotide sequence lacks an AAAG tetranucleotide at positions corresponding to positions 919-922 according to SEQ ID NO:7, or the complement thereof. An example is set forth in SEQ ID NO:14.

The present disclosure also provides isolated mRNA molecules comprising or consisting of a nucleotide sequence encoding a human GPR75 polypeptide, wherein the nucleotide sequence lacks an AAAG tetranucleotide at positions corresponding to positions 820-823 according to SEQ ID NO:8, or the complement thereof. An example is set forth in SEQ ID NO:19.

The present disclosure also provides isolated mRNA molecules comprising or consisting of a nucleotide sequence encoding a human GPR75 polypeptide, wherein the nucleotide sequence lacks an AAAG tetranucleotide at positions corresponding to positions 741-744 according to SEQ ID NO:9, or the complement thereof. An example is set forth in SEQ ID NO:24.

The present disclosure also provides isolated mRNA molecules comprising or consisting of a nucleotide sequence encoding a human GPR75 polypeptide, wherein the nucleotide sequence lacks an AAAG tetranucleotide at positions corresponding to positions 980-983 according to SEQ ID NO:10, or the complement thereof. An example is set forth in SEQ ID NO:29.

The present disclosure also provides isolated mRNA molecules comprising or consisting of a nucleotide sequence encoding a human GPR75 polypeptide, wherein the nucleotide sequence comprises an insertion of a uracil at a position corresponding to position 1,410 according to SEQ ID NO:15, or the complement thereof.

The present disclosure also provides isolated mRNA molecules comprising or consisting of a nucleotide sequence encoding a human GPR75 polypeptide, wherein the nucleotide sequence comprises an insertion of a uracil at a position corresponding to position 1,311 according to SEQ ID NO:20, or the complement thereof.

The present disclosure also provides isolated mRNA molecules comprising or consisting of a nucleotide sequence encoding a human GPR75 polypeptide, wherein the nucleotide sequence comprises an insertion of a uracil at a position corresponding to position 1,232 according to SEQ ID NO:25, or the complement thereof.

The present disclosure also provides isolated mRNA molecules comprising or consisting of a nucleotide sequence encoding a human GPR75 polypeptide, wherein the nucleotide sequence comprises an insertion of a uracil at a position corresponding to position 1,471 according to SEQ ID NO:30, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:11, and lacks a CCAGUAG heptanucleotide at positions corresponding to positions 539-545 according to SEQ ID NO:7, or the complement thereof. In some embodiments, the isolated mRNA molecules comprise or consist of a nucleotide sequence that has at least about 90% sequence identity to SEQ ID NO:11, and lacks a CCAGUAG heptanucleotide at positions corresponding to positions 539-545 according to SEQ ID NO:7, or the complement thereof. In some embodiments, the isolated mRNA molecules comprise or consist of a nucleotide sequence that has at least about 92% sequence identity to SEQ ID NO:11, and lacks a CCAGUAG heptanucleotide at positions corresponding to positions 539-545 according to SEQ ID NO:7, or the complement thereof. In some embodiments, the isolated mRNA molecules comprise or consist of a nucleotide sequence that has at least about 94% sequence identity to SEQ ID NO:11, and lacks a CCAGUAG heptanucleotide at positions corresponding to positions 539-545 according to SEQ ID NO:7, or the complement thereof. In some embodiments, the isolated mRNA molecules comprise or consist of a nucleotide sequence that has at least about 96% sequence identity to SEQ ID NO:11, and lacks a CCAGUAG heptanucleotide at positions corresponding to positions 539-545 according to SEQ ID NO:7, or the complement thereof. In some embodiments, the isolated mRNA molecules comprise or consist of a nucleotide sequence that has at least about 98% sequence identity to SEQ ID NO:11, and lacks a CCAGUAG heptanucleotide at positions corresponding to positions 539-545 according to SEQ ID NO:7, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:16, and lacks a CCAGUAG heptanucleotide at positions corresponding to positions 440-446 according to SEQ ID NO:8, or the complement thereof. In some embodiments, the isolated mRNA molecules comprise or consist of a nucleotide sequence that has at least about 90% sequence identity to SEQ ID NO:16, and lacks a CCAGUAG heptanucleotide at positions corresponding to positions 440-446 according to SEQ ID NO:8, or the complement thereof. In some embodiments, the isolated mRNA molecules comprise or consist of a nucleotide sequence that has at least about 92% sequence identity to SEQ ID NO:16, and lacks a CCAGUAG heptanucleotide at positions corresponding to positions 440-446 according to SEQ ID NO:8, or the complement thereof. In some embodiments, the isolated mRNA molecules comprise or consist of a nucleotide sequence that has at least about 94% sequence identity to SEQ ID NO:16, and lacks a CCAGUAG heptanucleotide at positions corresponding to positions 440-446 according to SEQ ID NO:8, or the complement thereof. In some embodiments, the isolated mRNA molecules comprise or consist of a nucleotide sequence that has at least about 96% sequence identity to SEQ ID NO:16, and lacks a CCAGUAG heptanucleotide at positions corresponding to positions 440-446 according to SEQ ID NO:8, or the complement thereof. In some embodiments, the isolated mRNA molecules comprise or consist of a nucleotide sequence that has at least about 98% sequence identity to SEQ ID NO:16, and lacks a CCAGUAG heptanucleotide at positions corresponding to positions 440-446 according to SEQ ID NO:7, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:21, and lacks a CCAGUAG heptanucleotide at positions corresponding to positions 361-367 according to SEQ ID NO:9, or the complement thereof. In some embodiments, the isolated mRNA molecules comprise or consist of a nucleotide sequence that has at least about 90% sequence identity to SEQ ID NO:21, and lacks a CCAGUAG heptanucleotide at positions corresponding to positions 361-367 according to SEQ ID NO:9, or the complement thereof. In some embodiments, the isolated mRNA molecules comprise or consist of a nucleotide sequence that has at least about 92% sequence identity to SEQ ID NO:21, and lacks a CCAGUAG heptanucleotide at positions corresponding to positions 361-367 according to SEQ ID NO:9, or the complement thereof. In some embodiments, the isolated mRNA molecules comprise or consist of a nucleotide sequence that has at least about 94% sequence identity to SEQ ID NO:21, and lacks a CCAGUAG heptanucleotide at positions corresponding to positions 361-367 according to SEQ ID NO:9, or the complement thereof. In some embodiments, the isolated mRNA molecules comprise or consist of a nucleotide sequence that has at least about 96% sequence identity to SEQ ID NO:21, and lacks a CCAGUAG heptanucleotide at positions corresponding to positions 361-367 according to SEQ ID NO:9, or the complement thereof. In some embodiments, the isolated mRNA molecules comprise or consist of a nucleotide sequence that has at least about 98% sequence identity to SEQ ID NO:21, and lacks a CCAGUAG heptanucleotide at positions corresponding to positions 361-367 according to SEQ ID NO:9, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:26, and lacks a CCAGUAG heptanucleotide at positions corresponding to positions 600-606 according to SEQ ID NO:10, or the complement thereof. In some embodiments, the isolated mRNA molecules comprise or consist of a nucleotide sequence that has at least about 90% sequence identity to SEQ ID NO:26, and lacks a CCAGUAG heptanucleotide at positions corresponding to positions 600-606 according to SEQ ID NO:10, or the complement thereof. In some embodiments, the isolated mRNA molecules comprise or consist of a nucleotide sequence that has at least about 92% sequence identity to SEQ ID NO:26, and lacks a CCAGUAG heptanucleotide at positions corresponding to positions 600-606 according to SEQ ID NO:10, or the complement thereof. In some embodiments, the isolated mRNA molecules comprise or consist of a nucleotide sequence that has at least about 94% sequence identity to SEQ ID NO:26, and lacks a CCAGUAG heptanucleotide at positions corresponding to positions 600-606 according to SEQ ID NO:10, or the complement thereof. In some embodiments, the isolated mRNA molecules comprise or consist of a nucleotide sequence that has at least about 96% sequence identity to SEQ ID NO:26, and lacks a CCAGUAG heptanucleotide at positions corresponding to positions 600-606 according to SEQ ID NO:10, or the complement thereof. In some embodiments, the isolated mRNA molecules comprise or consist of a nucleotide sequence that has at least about 98% sequence identity to SEQ ID NO:26, and lacks a CCAGUAG heptanucleotide at positions corresponding to positions 600-606 according to SEQ ID NO:10, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:14, and lacks an AAAG tetranucleotide at positions corresponding to positions 919-922 according to SEQ ID NO:7, or the complement thereof. In some embodiments, the isolated mRNA molecules comprise or consist of a nucleotide sequence that has at least about 90% sequence identity to SEQ ID NO:14, and lacks an AAAG tetranucleotide at positions corresponding to positions 919-922 according to SEQ ID NO:7, or the complement thereof. In some embodiments, the isolated mRNA molecules comprise or consist of a nucleotide sequence that has at least about 92% sequence identity to SEQ ID NO:14, and lacks an AAAG tetranucleotide at positions corresponding to positions 919-922 according to SEQ ID NO:7, or the complement thereof. In some embodiments, the isolated mRNA molecules comprise or consist of a nucleotide sequence that has at least about 94% sequence identity to SEQ ID NO:14, and lacks an AAAG tetranucleotide at positions corresponding to positions 919-922 according to SEQ ID NO:7, or the complement thereof. In some embodiments, the isolated mRNA molecules comprise or consist of a nucleotide sequence that has at least about 96% sequence identity to SEQ ID NO:14, and lacks an AAAG tetranucleotide at positions corresponding to positions 919-922 according to SEQ ID NO:7, or the complement thereof. In some embodiments, the isolated mRNA molecules comprise or consist of a nucleotide sequence that has at least about 98% sequence identity to SEQ ID NO:14, and lacks an AAAG tetranucleotide at positions corresponding to positions 919-922 according to SEQ ID NO:7, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:19, and lacks an AAAG tetranucleotide at positions corresponding to positions 820-823 according to SEQ ID NO:8, or the complement thereof. In some embodiments, the isolated mRNA molecules comprise or consist of a nucleotide sequence that has at least about 90% sequence identity to SEQ ID NO:19, and lacks an AAAG tetranucleotide at positions corresponding to positions 820-823 according to SEQ ID NO:8, or the complement thereof. In some embodiments, the isolated mRNA molecules comprise or consist of a nucleotide sequence that has at least about 92% sequence identity to SEQ ID NO:19, and lacks an AAAG tetranucleotide at positions corresponding to positions 820-823 according to SEQ ID NO:8, or the complement thereof. In some embodiments, the isolated mRNA molecules comprise or consist of a nucleotide sequence that has at least about 94% sequence identity to SEQ ID NO:19, and lacks an AAAG tetranucleotide at positions corresponding to positions 820-823 according to SEQ ID NO:8, or the complement thereof. In some embodiments, the isolated mRNA molecules comprise or consist of a nucleotide sequence that has at least about 96% sequence identity to SEQ ID NO:19, and lacks an AAAG tetranucleotide at positions corresponding to positions 820-823 according to SEQ ID NO:8, or the complement thereof. In some embodiments, the isolated mRNA molecules comprise or consist of a nucleotide sequence that has at least about 98% sequence identity to SEQ ID NO:19, and lacks an AAAG tetranucleotide at positions corresponding to positions 820-823 according to SEQ ID NO:8, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:24, and lacks an AAAG tetranucleotide at positions corresponding to positions 741-744 according to SEQ ID NO:9, or the complement thereof. In some embodiments, the isolated mRNA molecules comprise or consist of a nucleotide sequence that has at least about 90% sequence identity to SEQ ID NO:24, and lacks an AAAG tetranucleotide at positions corresponding to positions 741-744 according to SEQ ID NO:9, or the complement thereof. In some embodiments, the isolated mRNA molecules comprise or consist of a nucleotide sequence that has at least about 92% sequence identity to SEQ ID NO:24, and lacks an AAAG tetranucleotide at positions corresponding to positions 741-744 according to SEQ ID NO:9, or the complement thereof. In some embodiments, the isolated mRNA molecules comprise or consist of a nucleotide sequence that has at least about 94% sequence identity to SEQ ID NO:24, and lacks an AAAG tetranucleotide at positions corresponding to positions 741-744 according to SEQ ID NO:9, or the complement thereof. In some embodiments, the isolated mRNA molecules comprise or consist of a nucleotide sequence that has at least about 96% sequence identity to SEQ ID NO:24, and lacks an AAAG tetranucleotide at positions corresponding to positions 741-744 according to SEQ ID NO:9, or the complement thereof. In some embodiments, the isolated mRNA molecules comprise or consist of a nucleotide sequence that has at least about 98% sequence identity to SEQ ID NO:24, and lacks an AAAG tetranucleotide at positions corresponding to positions 741-744 according to SEQ ID NO:9, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:29, and lacks an AAAG tetranucleotide at positions corresponding to positions 980-983 according to SEQ ID NO:10, or the complement thereof. In some embodiments, the isolated mRNA molecules comprise or consist of a nucleotide sequence that has at least about 90% sequence identity to SEQ ID NO:29, and lacks an AAAG tetranucleotide at positions corresponding to positions 980-983 according to SEQ ID NO:10, or the complement thereof. In some embodiments, the isolated mRNA molecules comprise or consist of a nucleotide sequence that has at least about 92% sequence identity to SEQ ID NO:29, and lacks an AAAG tetranucleotide at positions corresponding to positions 980-983 according to SEQ ID NO:10, or the complement thereof. In some embodiments, the isolated mRNA molecules comprise or consist of a nucleotide sequence that has at least about 94% sequence identity to SEQ ID NO:29, and lacks an AAAG tetranucleotide at positions corresponding to positions 980-983 according to SEQ ID NO:10, or the complement thereof. In some embodiments, the isolated mRNA molecules comprise or consist of a nucleotide sequence that has at least about 96% sequence identity to SEQ ID NO:29, and lacks an AAAG tetranucleotide at positions corresponding to positions 980-983 according to SEQ ID NO:10, or the complement thereof. In some embodiments, the isolated mRNA molecules comprise or consist of a nucleotide sequence that has at least about 98% sequence identity to SEQ ID NO:29, and lacks an AAAG tetranucleotide at positions corresponding to positions 980-983 according to SEQ ID NO:10, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:15, and comprises an insertion of a uracil at a position corresponding to position 1,410 according to SEQ ID NO:15, or the complement thereof. In some embodiments, the isolated mRNA molecules comprise or consist of a nucleotide sequence that has at least about 90% sequence identity to SEQ ID NO:15, and comprises an insertion of a uracil at a position corresponding to position 1,410 according to SEQ ID NO:15, or the complement thereof. In some embodiments, the isolated mRNA molecules comprise or consist of a nucleotide sequence that has at least about 92% sequence identity to SEQ ID NO:15, and comprises an insertion of a uracil at a position corresponding to position 1,410 according to SEQ ID NO:15, or the complement thereof. In some embodiments, the isolated mRNA molecules comprise or consist of a nucleotide sequence that has at least about 94% sequence identity to SEQ ID NO:15, and comprises an insertion of a uracil at a position corresponding to position 1,410 according to SEQ ID NO:15, or the complement thereof. In some embodiments, the isolated mRNA molecules comprise or consist of a nucleotide sequence that has at least about 96% sequence identity to SEQ ID NO:15, and comprises an insertion of a uracil at a position corresponding to position 1,410 according to SEQ ID NO:15, or the complement thereof. In some embodiments, the isolated mRNA molecules comprise or consist of a nucleotide sequence that has at least about 98% sequence identity to SEQ ID NO:15, and comprises an insertion of a uracil at a position corresponding to position 1,410 according to SEQ ID NO:15, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:20, and comprises an insertion of a uracil at a position corresponding to position 1,311 according to SEQ ID NO:20, or the complement thereof. In some embodiments, the isolated mRNA molecules comprise or consist of a nucleotide sequence that has at least about 90% sequence identity to SEQ ID NO:20, and comprises an insertion of a uracil at a position corresponding to position 1,311 according to SEQ ID NO:20, or the complement thereof. In some embodiments, the isolated mRNA molecules comprise or consist of a nucleotide sequence that has at least about 92% sequence identity to SEQ ID NO:20, and comprises an insertion of a uracil at a position corresponding to position 1,311 according to SEQ ID NO:20, or the complement thereof. In some embodiments, the isolated mRNA molecules comprise or consist of a nucleotide sequence that has at least about 94% sequence identity to SEQ ID NO:20, and comprises an insertion of a uracil at a position corresponding to position 1,311 according to SEQ ID NO:20, or the complement thereof. In some embodiments, the isolated mRNA molecules comprise or consist of a nucleotide sequence that has at least about 96% sequence identity to SEQ ID NO:20, and comprises an insertion of a uracil at a position corresponding to position 1,311 according to SEQ ID NO:20, or the complement thereof. In some embodiments, the isolated mRNA molecules comprise or consist of a nucleotide sequence that has at least about 98% sequence identity to SEQ ID NO:20, and comprises an insertion of a uracil at a position corresponding to position 1,311 according to SEQ ID NO:20, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:25, and comprises an insertion of a uracil at a position corresponding to position 1,232 according to SEQ ID NO:25, or the complement thereof. In some embodiments, the isolated mRNA molecules comprise or consist of a nucleotide sequence that has at least about 90% sequence identity to SEQ ID NO:25, and comprises an insertion of a uracil at a position corresponding to position 1,232 according to SEQ ID NO:25, or the complement thereof. In some embodiments, the isolated mRNA molecules comprise or consist of a nucleotide sequence that has at least about 92% sequence identity to SEQ ID NO:25, and comprises an insertion of a uracil at a position corresponding to position 1,232 according to SEQ ID NO:25, or the complement thereof. In some embodiments, the isolated mRNA molecules comprise or consist of a nucleotide sequence that has at least about 94% sequence identity to SEQ ID NO:25, and comprises an insertion of a uracil at a position corresponding to position 1,232 according to SEQ ID NO:25, or the complement thereof. In some embodiments, the isolated mRNA molecules comprise or consist of a nucleotide sequence that has at least about 96% sequence identity to SEQ ID NO:25, and comprises an insertion of a uracil at a position corresponding to position 1,232 according to SEQ ID NO:25, or the complement thereof. In some embodiments, the isolated mRNA molecules comprise or consist of a nucleotide sequence that has at least about 98% sequence identity to SEQ ID NO:25, and comprises an insertion of a uracil at a position corresponding to position 1,232 according to SEQ ID NO:25, or the complement thereof.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:30, and comprises an insertion of a uracil at a position corresponding to position 1,471 according to SEQ ID NO:30, or the complement thereof. In some embodiments, the isolated mRNA molecules comprise or consist of a nucleotide sequence that has at least about 90% sequence identity to SEQ ID NO:30, and comprises an insertion of a uracil at a position corresponding to position 1,471 according to SEQ ID NO:30, or the complement thereof. In some embodiments, the isolated mRNA molecules comprise or consist of a nucleotide sequence that has at least about 92% sequence identity to SEQ ID NO:30, and comprises an insertion of a uracil at a position corresponding to position 1,471 according to SEQ ID NO:30, or the complement thereof. In some embodiments, the isolated mRNA molecules comprise or consist of a nucleotide sequence that has at least about 94% sequence identity to SEQ ID NO:30, and comprises an insertion of a uracil at a position corresponding to position 1,471 according to SEQ ID NO:30, or the complement thereof. In some embodiments, the isolated mRNA molecules comprise or consist of a nucleotide sequence that has at least about 96% sequence identity to SEQ ID NO:30, and comprises an insertion of a uracil at a position corresponding to position 1,471 according to SEQ ID NO:30, or the complement thereof. In some embodiments, the isolated mRNA molecules comprise or consist of a nucleotide sequence that has at least about 98% sequence identity to SEQ ID NO:30, and comprises an insertion of a uracil at a position corresponding to position 1,471 according to SEQ ID NO:30, or the complement thereof.

Herein, if reference is made to percent sequence identity, the higher percentages of sequence identity are preferred over the lower ones.

In some embodiments, the isolated mRNA molecules comprise SEQ ID NO:11. In some embodiments, the isolated mRNA molecules consist of SEQ ID NO:11. In some embodiments, the isolated mRNA molecules comprise SEQ ID NO:16. In some embodiments, the isolated mRNA molecules consist of SEQ ID NO:16. In some embodiments, the isolated mRNA molecules comprise SEQ ID NO:21. In some embodiments, the isolated mRNA molecules consist of SEQ ID NO:21. In some embodiments, the isolated mRNA molecules comprise SEQ ID NO:26. In some embodiments, the isolated mRNA molecules consist of SEQ ID NO:26

In some embodiments, the isolated mRNA molecules comprise SEQ ID NO:14. In some embodiments, the isolated mRNA molecules consist of SEQ ID NO:14. In some embodiments, the isolated mRNA molecules comprise SEQ ID NO:19. In some embodiments, the isolated mRNA molecules consist of SEQ ID NO:19. In some embodiments, the isolated mRNA molecules comprise SEQ ID NO:24. In some embodiments, the isolated mRNA molecules consist of SEQ ID NO:24. In some embodiments, the isolated mRNA molecules comprise SEQ ID NO:29. In some embodiments, the isolated mRNA molecules consist of SEQ ID NO:29.

In some embodiments, the isolated mRNA molecules comprise SEQ ID NO:15. In some embodiments, the isolated mRNA molecules consist of SEQ ID NO:15. In some embodiments, the isolated mRNA molecules comprise SEQ ID NO:20. In some embodiments, the isolated mRNA molecules consist of SEQ ID NO:20. In some embodiments, the isolated mRNA molecules comprise SEQ ID NO:25. In some embodiments, the isolated mRNA molecules consist of SEQ ID NO:25. In some embodiments, the isolated mRNA molecules comprise SEQ ID NO:30. In some embodiments, the isolated mRNA molecules consist of SEQ ID NO:30.

The nucleotide sequence of a GPR75 reference cDNA molecule is set forth in SEQ ID NO:31. Referring to SEQ ID NO:31, positions 539-545 are a CCAGTAG heptanucleotide. Referring to SEQ ID NO:31, position 556 is a guanine. Referring to SEQ ID NO:31, position 910 is a cytosine. Referring to SEQ ID NO:31, positions 919-922 are an AAAG tetranucleotide. Referring to SEQ ID NO:31, position 1,410 is a cytosine. Referring to SEQ ID NO:31, position 830 is an adenine.

The nucleotide sequence of another GPR75 reference cDNA molecule is set forth in SEQ ID NO:32. Referring to SEQ ID NO:32, positions 440-446 are a CCAGTAG heptanucleotide. Referring to SEQ ID NO:32, position 457 is a guanine. Referring to SEQ ID NO:32, position 811 is a cytosine. Referring to SEQ ID NO:32, positions 820-823 are an AAAG tetranucleotide. Referring to SEQ ID NO:32, position 1,311 is a cytosine. Referring to SEQ ID NO:32, position 731 is an adenine.

The nucleotide sequence of another GPR75 reference cDNA molecule is set forth in SEQ ID NO:33. Referring to SEQ ID NO:33, positions 361-367 are a CCAGTAG heptanucleotide. Referring to SEQ ID NO:33, position 378 is a guanine. Referring to SEQ ID NO:33, position 732 is a cytosine. Referring to SEQ ID NO:33, positions 741-744 are an AAAG tetranucleotide. Referring to SEQ ID NO:33, position 1,232 is a cytosine. Referring to SEQ ID NO:33, position 652 is an adenine.

The nucleotide sequence of another GPR75 reference cDNA molecule is set forth in SEQ ID NO:34. Referring to SEQ ID NO:34, positions 600-606 are a CCAGTAG heptanucleotide. Referring to SEQ ID NO:34, position 617 is a guanine. Referring to SEQ ID NO:34, position 971 is a cytosine. Referring to SEQ ID NO:34, positions 980-983 are an AAAG tetranucleotide. Referring to SEQ ID NO:34, position 1,471 is a cytosine. Referring to SEQ ID NO:34, position 891 is an adenine.

A variant cDNA molecule of GPR75 exists, wherein the CCAGTAG heptanucleotide at positions 539-545 (referring to SEQ ID NO:31) is deleted. The nucleotide sequence of this GPR75 variant cDNA molecule is set forth in SEQ ID NO:35.

Another variant cDNA molecule of GPR75 exists, wherein the CCAGTAG heptanucleotide at positions 440-446 (referring to SEQ ID NO:32) is deleted. The nucleotide sequence of this GPR75 variant cDNA molecule is set forth in SEQ ID NO:40.

Another variant cDNA molecule of GPR75 exists, wherein the CCAGTAG heptanucleotide at positions 361-367 (referring to SEQ ID NO:33) is deleted. The nucleotide sequence of this GPR75 variant cDNA molecule is set forth in SEQ ID NO:45.

Another variant cDNA molecule of GPR75 exists, wherein the CCAGTAG heptanucleotide at positions 600-606 (referring to SEQ ID NO:34) is deleted. The nucleotide sequence of this GPR75 variant cDNA molecule is set forth in SEQ ID NO:50.

A variant cDNA molecule of GPR75 exists, wherein the guanine at position 556 (referring to SEQ ID NO:31) is replaced with adenine. The nucleotide sequence of this GPR75 variant cDNA molecule is set forth in SEQ ID NO:36.

Another variant cDNA molecule of GPR75 exists, wherein the guanine at position 457 (referring to SEQ ID NO:32) is replaced with adenine. The nucleotide sequence of this GPR75 variant cDNA molecule is set forth in SEQ ID NO:41.

Another variant cDNA molecule of GPR75 exists, wherein the guanine at position 378 (referring to SEQ ID NO:33) is replaced with adenine. The nucleotide sequence of this GPR75 variant cDNA molecule is set forth in SEQ ID NO:46.

Another variant cDNA molecule of GPR75 exists, wherein the guanine at position 617 (referring to SEQ ID NO:34) is replaced with adenine. The nucleotide sequence of this GPR75 variant cDNA molecule is set forth in SEQ ID NO:51.

A variant cDNA molecule of GPR75 exists, wherein the cytosine at position 910 (referring to SEQ ID NO:31) is replaced with thymine. The nucleotide sequence of this GPR75 variant cDNA molecule is set forth in SEQ ID NO:37.

Another variant cDNA molecule of GPR75 exists, wherein the cytosine at position 811 (referring to SEQ ID NO:32) is replaced with thymine. The nucleotide sequence of this GPR75 variant cDNA molecule is set forth in SEQ ID NO:42.

Another variant cDNA molecule of GPR75 exists, wherein the cytosine at position 732 (referring to SEQ ID NO:33) is replaced with thymine. The nucleotide sequence of this GPR75 variant cDNA molecule is set forth in SEQ ID NO:47.

Another variant cDNA molecule of GPR75 exists, wherein the cytosine at position 971 (referring to SEQ ID NO:34) is replaced with thymine. The nucleotide sequence of this GPR75 variant cDNA molecule is set forth in SEQ ID NO:52.

A variant cDNA molecule of GPR75 exists, wherein the AGCC tetranucleotide at positions 919-922 (referring to SEQ ID NO:31) is deleted. The nucleotide sequence of this GPR75 variant cDNA molecule is set forth in SEQ ID NO:38.

Another variant cDNA molecule of GPR75 exists, wherein the AGCC tetranucleotide at positions 820-823 (referring to SEQ ID NO:32) is deleted. The nucleotide sequence of this GPR75 variant cDNA molecule is set forth in SEQ ID NO:43.

Another variant cDNA molecule of GPR75 exists, wherein the AGCC tetranucleotide at positions 741-744 (referring to SEQ ID NO:33) is deleted. The nucleotide sequence of this GPR75 variant cDNA molecule is set forth in SEQ ID NO:48.

Another variant cDNA molecule of GPR75 exists, wherein the AGCC tetranucleotide at positions 980-983 (referring to SEQ ID NO:34) is replaced with deleted. The nucleotide sequence of this GPR75 variant cDNA molecule is set forth in SEQ ID NO:53.

A variant cDNA molecule of GPR75 exists, wherein a thymine is inserted at position 1,410. The nucleotide sequence of this GPR75 variant cDNA molecule is set forth in SEQ ID NO:39.

Another variant cDNA molecule of GPR75 exists, wherein a thymine is inserted at position 1,311. The nucleotide sequence of this GPR75 variant cDNA molecule is set forth in SEQ ID NO:44.

Another variant cDNA molecule of GPR75 exists, wherein a thymine is inserted at position 1,232. The nucleotide sequence of this GPR75 variant cDNA molecule is set forth in SEQ ID NO:49.

Another variant cDNA molecule of GPR75 exists, wherein a thymine is inserted at position 1,471. The nucleotide sequence of this GPR75 variant cDNA molecule is set forth in SEQ ID NO:54.

A variant cDNA molecule of GPR75 exists, wherein the adenine at position 830 (referring to SEQ ID NO:31) is replaced with guanine. The nucleotide sequence of this GPR75 variant cDNA molecule is set forth in SEQ ID NO:104.

Another variant cDNA molecule of GPR75 exists, wherein the adenine at position 731 (referring to SEQ ID NO:32) is replaced with guanine. The nucleotide sequence of this GPR75 variant cDNA molecule is set forth in SEQ ID NO:105.

Another variant cDNA molecule of GPR75 exists, wherein the adenine at position 652 (referring to SEQ ID NO:33) is replaced with guanine. The nucleotide sequence of this GPR75 variant cDNA molecule is set forth in SEQ ID NO:106.

Another variant cDNA molecule of GPR75 exists, wherein the adenine at position 891 (referring to SEQ ID NO:34) is replaced with guanine. The nucleotide sequence of this GPR75 variant cDNA molecule is set forth in SEQ ID NO:107.

The present disclosure also provides isolated cDNA molecules comprising or consisting of a nucleotide sequence encoding a human GPR75 polypeptide, wherein the nucleotide sequence lacks a CCAGTAG heptanucleotide at positions corresponding to positions 539-545 according to SEQ ID NO:31, or the complement thereof. An example is set forth in SEQ ID NO:35.

The present disclosure also provides isolated cDNA molecules comprising or consisting of a nucleotide sequence encoding a human GPR75 polypeptide, wherein the nucleotide sequence lacks a CCAGTAG heptanucleotide at positions corresponding to positions 440-446 according to SEQ ID NO:32, or the complement thereof. An example is set forth in SE ID NO:40.

The present disclosure also provides isolated cDNA molecules comprising or consisting of a nucleotide sequence encoding a human GPR75 polypeptide, wherein the nucleotide sequence lacks a CCAGTAG heptanucleotide at positions corresponding to positions 361-367 according to SEQ ID NO:43, or the complement thereof. An example is set forth in SE ID NO:45.

The present disclosure also provides isolated cDNA molecules comprising or consisting of a nucleotide sequence encoding a human GPR75 polypeptide, wherein the nucleotide sequence lacks a CCAGTAG heptanucleotide at positions corresponding to positions 600-606 according to SEQ ID NO:34, or the complement thereof. An example is set forth in SE ID NO:50.

The present disclosure also provides isolated cDNA molecules comprising or consisting of a nucleotide sequence encoding a human GPR75 polypeptide, wherein the nucleotide sequence lacks an AAAG tetranucleotide at positions corresponding to positions 919-922 according to SEQ ID NO:31, or the complement thereof. An example is set forth in SE ID NO:38.

The present disclosure also provides isolated cDNA molecules comprising or consisting of a nucleotide sequence encoding a human GPR75 polypeptide, wherein the nucleotide sequence lacks an AAAG tetranucleotide at positions corresponding to positions 820-823 according to SEQ ID NO:32, or the complement thereof. An example is set forth in SE ID NO:43.

The present disclosure also provides isolated cDNA molecules comprising or consisting of a nucleotide sequence encoding a human GPR75 polypeptide, wherein the nucleotide sequence lacks an AAAG tetranucleotide at positions corresponding to positions 741-744 according to SEQ ID NO:33, or the complement thereof. An example is set forth in SE ID NO:48.

The present disclosure also provides isolated cDNA molecules comprising or consisting of a nucleotide sequence encoding a human GPR75 polypeptide, wherein the nucleotide sequence lacks an AAAG tetranucleotide at positions corresponding to positions 980-983 according to SEQ ID NO:34, or the complement thereof. An example is set forth in SE ID NO:53.

The present disclosure also provides isolated cDNA molecules comprising or consisting of a nucleotide sequence encoding a human GPR75 polypeptide, wherein the nucleotide sequence comprises an insertion of a thymine at a position corresponding to position 1,410 according to SEQ ID NO:39, or the complement thereof.

The present disclosure also provides isolated cDNA molecules comprising or consisting of a nucleotide sequence encoding a human GPR75 polypeptide, wherein the nucleotide sequence comprises an insertion of a thymine at a position corresponding to position 1,311 according to SEQ ID NO:44, or the complement thereof.

The present disclosure also provides isolated cDNA molecules comprising or consisting of a nucleotide sequence encoding a human GPR75 polypeptide, wherein the nucleotide sequence comprises an insertion of a thymine at a position corresponding to position 1,232 according to SEQ ID NO:49, or the complement thereof.

The present disclosure also provides isolated cDNA molecules comprising or consisting of a nucleotide sequence encoding a human GPR75 polypeptide, wherein the nucleotide sequence comprises or an insertion of a thymine at a position corresponding to position 1,471 according to SEQ ID NO:54, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:35, and lacks a CCAGTAG heptanucleotide at positions corresponding to positions 539-545 according to SEQ ID NO:31, or the complement thereof. In some embodiments, the isolated cDNA molecules comprise or consist of a nucleotide sequence that has at least about 90% sequence identity to SEQ ID NO:35, and lacks a CCAGTAG heptanucleotide at positions corresponding to positions 539-545 according to SEQ ID NO:31, or the complement thereof. In some embodiments, the isolated cDNA molecules comprise or consist of a nucleotide sequence that has at least about 92% sequence identity to SEQ ID NO:35, and lacks a CCAGTAG heptanucleotide at positions corresponding to positions 539-545 according to SEQ ID NO:31, or the complement thereof. In some embodiments, the isolated cDNA molecules comprise or consist of a nucleotide sequence that has at least about 94% sequence identity to SEQ ID NO:35, and lacks a CCAGTAG heptanucleotide at positions corresponding to positions 539-545 according to SEQ ID NO:31, or the complement thereof. In some embodiments, the isolated cDNA molecules comprise or consist of a nucleotide sequence that has at least about 96% sequence identity to SEQ ID NO:35, and lacks a CCAGTAG heptanucleotide at positions corresponding to positions 539-545 according to SEQ ID NO:31, or the complement thereof. In some embodiments, the isolated cDNA molecules comprise or consist of a nucleotide sequence that has at least about 98% sequence identity to SEQ ID NO:35, and lacks a CCAGTAG heptanucleotide at positions corresponding to positions 539-545 according to SEQ ID NO:31, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:40, and lacks a CCAGTAG heptanucleotide at positions corresponding to positions 440-446 according to SEQ ID NO:32, or the complement thereof. In some embodiments, the isolated cDNA molecules comprise or consist of a nucleotide sequence that has at least about 90% sequence identity to SEQ ID NO:40, and lacks a CCAGTAG heptanucleotide at positions corresponding to positions 440-446 according to SEQ ID NO:32, or the complement thereof. In some embodiments, the isolated cDNA molecules comprise or consist of a nucleotide sequence that has at least about 92% sequence identity to SEQ ID NO:40, and lacks a CCAGTAG heptanucleotide at positions corresponding to positions 440-446 according to SEQ ID NO:32, or the complement thereof. In some embodiments, the isolated cDNA molecules comprise or consist of a nucleotide sequence that has at least about 94% sequence identity to SEQ ID NO:40, and lacks a CCAGTAG heptanucleotide at positions corresponding to positions 440-446 according to SEQ ID NO:32, or the complement thereof. In some embodiments, the isolated cDNA molecules comprise or consist of a nucleotide sequence that has at least about 96% sequence identity to SEQ ID NO:40, and lacks a CCAGTAG heptanucleotide at positions corresponding to positions 440-446 according to SEQ ID NO:32, or the complement thereof. In some embodiments, the isolated cDNA molecules comprise or consist of a nucleotide sequence that has at least about 98% sequence identity to SEQ ID NO:40, and lacks a CCAGTAG heptanucleotide at positions corresponding to positions 440-446 according to SEQ ID NO:32, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:45, and lacks a CCAGTAG heptanucleotide at positions corresponding to positions 361-367 according to SEQ ID NO:33, or the complement thereof. In some embodiments, the isolated cDNA molecules comprise or consist of a nucleotide sequence that has at least about 90% sequence identity to SEQ ID NO:45, and lacks a CCAGTAG heptanucleotide at positions corresponding to positions 361-367 according to SEQ ID NO:33, or the complement thereof. In some embodiments, the isolated cDNA molecules comprise or consist of a nucleotide sequence that has at least about 92% sequence identity to SEQ ID NO:45, and lacks a CCAGTAG heptanucleotide at positions corresponding to positions 361-367 according to SEQ ID NO:33, or the complement thereof. In some embodiments, the isolated cDNA molecules comprise or consist of a nucleotide sequence that has at least about 94% sequence identity to SEQ ID NO:45, and lacks a CCAGTAG heptanucleotide at positions corresponding to positions 361-367 according to SEQ ID NO:33, or the complement thereof. In some embodiments, the isolated cDNA molecules comprise or consist of a nucleotide sequence that has at least about 96% sequence identity to SEQ ID NO:45, and lacks a CCAGTAG heptanucleotide at positions corresponding to positions 361-367 according to SEQ ID NO:33, or the complement thereof. In some embodiments, the isolated cDNA molecules comprise or consist of a nucleotide sequence that has at least about 98% sequence identity to SEQ ID NO:45, and lacks a CCAGTAG heptanucleotide at positions corresponding to positions 361-367 according to SEQ ID NO:33, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:50, and lacks a CCAGTAG heptanucleotide at positions corresponding to positions 600-606 according to SEQ ID NO:34, or the complement thereof. In some embodiments, the isolated cDNA molecules comprise or consist of a nucleotide sequence that has at least about 90% sequence identity to SEQ ID NO:50, and lacks a CCAGTAG heptanucleotide at positions corresponding to positions 600-606 according to SEQ ID NO:34, or the complement thereof. In some embodiments, the isolated cDNA molecules comprise or consist of a nucleotide sequence that has at least about 92% sequence identity to SEQ ID NO:50, and lacks a CCAGTAG heptanucleotide at positions corresponding to positions 600-606 according to SEQ ID NO:34, or the complement thereof. In some embodiments, the isolated cDNA molecules comprise or consist of a nucleotide sequence that has at least about 94% sequence identity to SEQ ID NO:50, and lacks a CCAGTAG heptanucleotide at positions corresponding to positions 600-606 according to SEQ ID NO:34, or the complement thereof. In some embodiments, the isolated cDNA molecules comprise or consist of a nucleotide sequence that has at least about 96% sequence identity to SEQ ID NO:50, and lacks a CCAGTAG heptanucleotide at positions corresponding to positions 600-606 according to SEQ ID NO:34, or the complement thereof. In some embodiments, the isolated cDNA molecules comprise or consist of a nucleotide sequence that has at least about 98% sequence identity to SEQ ID NO:50, and lacks a CCAGTAG heptanucleotide at positions corresponding to positions 600-606 according to SEQ ID NO:34, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:38, and lacks an AAAG tetranucleotide at positions corresponding to positions 919-922 according to SEQ ID NO:31, or the complement thereof. In some embodiments, the isolated cDNA molecules comprise or consist of a nucleotide sequence that has at least about 90% sequence identity to SEQ ID NO:38, and lacks an AAAG tetranucleotide at positions corresponding to positions 919-922 according to SEQ ID NO:31, or the complement thereof. In some embodiments, the isolated cDNA molecules comprise or consist of a nucleotide sequence that has at least about 92% sequence identity to SEQ ID NO:38, and lacks an AAAG tetranucleotide at positions corresponding to positions 919-922 according to SEQ ID NO:31, or the complement thereof. In some embodiments, the isolated cDNA molecules comprise or consist of a nucleotide sequence that has at least about 94% sequence identity to SEQ ID NO:38, and lacks an AAAG tetranucleotide at positions corresponding to positions 919-922 according to SEQ ID NO:31, or the complement thereof. In some embodiments, the isolated cDNA molecules comprise or consist of a nucleotide sequence that has at least about 96% sequence identity to SEQ ID NO:38, and lacks an AAAG tetranucleotide at positions corresponding to positions 919-922 according to SEQ ID NO:31, or the complement thereof. In some embodiments, the isolated cDNA molecules comprise or consist of a nucleotide sequence that has at least about 98% sequence identity to SEQ ID NO:38, and lacks an AAAG tetranucleotide at positions corresponding to positions 919-922 according to SEQ ID NO:31, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:43, and lacks an AAAG tetranucleotide at positions corresponding to positions 820-823 according to SEQ ID NO:32, or the complement thereof. In some embodiments, the isolated cDNA molecules comprise or consist of a nucleotide sequence that has at least about 90% sequence identity to SEQ ID NO:43, and lacks an AAAG tetranucleotide at positions corresponding to positions 820-823 according to SEQ ID NO:32, or the complement thereof. In some embodiments, the isolated cDNA molecules comprise or consist of a nucleotide sequence that has at least about 92% sequence identity to SEQ ID NO:43, and lacks an AAAG tetranucleotide at positions corresponding to positions 820-823 according to SEQ ID NO:32, or the complement thereof. In some embodiments, the isolated cDNA molecules comprise or consist of a nucleotide sequence that has at least about 94% sequence identity to SEQ ID NO:43, and lacks an AAAG tetranucleotide at positions corresponding to positions 820-823 according to SEQ ID NO:32, or the complement thereof. In some embodiments, the isolated cDNA molecules comprise or consist of a nucleotide sequence that has at least about 96% sequence identity to SEQ ID NO:43, and lacks an AAAG tetranucleotide at positions corresponding to positions 820-823 according to SEQ ID NO:32, or the complement thereof. In some embodiments, the isolated cDNA molecules comprise or consist of a nucleotide sequence that has at least about 98% sequence identity to SEQ ID NO:43, and lacks an AAAG tetranucleotide at positions corresponding to positions 820-823 according to SEQ ID NO:32, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:48, and lacks an AAAG tetranucleotide at positions corresponding to positions 741-744 according to SEQ ID NO:33, or the complement thereof. In some embodiments, the isolated cDNA molecules comprise or consist of a nucleotide sequence that has at least about 90% sequence identity to SEQ ID NO:48, and lacks an AAAG tetranucleotide at positions corresponding to positions 741-744 according to SEQ ID NO:33, or the complement thereof. In some embodiments, the isolated cDNA molecules comprise or consist of a nucleotide sequence that has at least about 92% sequence identity to SEQ ID NO:48, and lacks an AAAG tetranucleotide at positions corresponding to positions 741-744 according to SEQ ID NO:33, or the complement thereof. In some embodiments, the isolated cDNA molecules comprise or consist of a nucleotide sequence that has at least about 94% sequence identity to SEQ ID NO:48, and lacks an AAAG tetranucleotide at positions corresponding to positions 741-744 according to SEQ ID NO:33, or the complement thereof. In some embodiments, the isolated cDNA molecules comprise or consist of a nucleotide sequence that has at least about 96% sequence identity to SEQ ID NO:48, and lacks an AAAG tetranucleotide at positions corresponding to positions 741-744 according to SEQ ID NO:33, or the complement thereof. In some embodiments, the isolated cDNA molecules comprise or consist of a nucleotide sequence that has at least about 98% sequence identity to SEQ ID NO:48, and lacks an AAAG tetranucleotide at positions corresponding to positions 741-744 according to SEQ ID NO:33, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:53, and lacks an AAAG tetranucleotide at positions corresponding to positions 980-983 according to SEQ ID NO:34, or the complement thereof. In some embodiments, the isolated cDNA molecules comprise or consist of a nucleotide sequence that has at least about 90% sequence identity to SEQ ID NO:53, and lacks an AAAG tetranucleotide at positions corresponding to positions 980-983 according to SEQ ID NO:34, or the complement thereof. In some embodiments, the isolated cDNA molecules comprise or consist of a nucleotide sequence that has at least about 92% sequence identity to SEQ ID NO:53, and lacks an AAAG tetranucleotide at positions corresponding to positions 980-983 according to SEQ ID NO:34, or the complement thereof. In some embodiments, the isolated cDNA molecules comprise or consist of a nucleotide sequence that has at least about 94% sequence identity to SEQ ID NO:53, and lacks an AAAG tetranucleotide at positions corresponding to positions 980-983 according to SEQ ID NO:34, or the complement thereof. In some embodiments, the isolated cDNA molecules comprise or consist of a nucleotide sequence that has at least about 96% sequence identity to SEQ ID NO:53, and lacks an AAAG tetranucleotide at positions corresponding to positions 980-983 according to SEQ ID NO:34, or the complement thereof. In some embodiments, the isolated cDNA molecules comprise or consist of a nucleotide sequence that has at least about 98% sequence identity to SEQ ID NO:53, and lacks an AAAG tetranucleotide at positions corresponding to positions 980-983 according to SEQ ID NO:34, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:39, and comprises an insertion of a thymine at a position corresponding to position 1,410 according to SEQ ID NO:39, or the complement thereof. In some embodiments, the isolated cDNA molecules comprise or consist of a nucleotide sequence that has at least about 90% sequence identity to SEQ ID NO:39, and comprises an insertion of a thymine at a position corresponding to position 1,410 according to SEQ ID NO:39, or the complement thereof. In some embodiments, the isolated cDNA molecules comprise or consist of a nucleotide sequence that has at least about 92% sequence identity to SEQ ID NO:39, and comprises an insertion of a thymine at a position corresponding to position 1,410 according to SEQ ID NO:39, or the complement thereof. In some embodiments, the isolated cDNA molecules comprise or consist of a nucleotide sequence that has at least about 94% sequence identity to SEQ ID NO:39, and comprises an insertion of a thymine at a position corresponding to position 1,410 according to SEQ ID NO:39, or the complement thereof. In some embodiments, the isolated cDNA molecules comprise or consist of a nucleotide sequence that has at least about 96% sequence identity to SEQ ID NO:39, and comprises an insertion of a thymine at a position corresponding to position 1,410 according to SEQ ID NO:39, or the complement thereof. In some embodiments, the isolated cDNA molecules comprise or consist of a nucleotide sequence that has at least about 98% sequence identity to SEQ ID NO:39, and comprises an insertion of a thymine at a position corresponding to position 1,410 according to SEQ ID NO:39, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:44, and comprises an insertion of a thymine at a position corresponding to position 1,311 according to SEQ ID NO:44, or the complement thereof. In some embodiments, the isolated cDNA molecules comprise or consist of a nucleotide sequence that has at least about 90% sequence identity to SEQ ID NO:44, and comprises an insertion of a thymine at a position corresponding to position 1,311 according to SEQ ID NO:44, or the complement thereof. In some embodiments, the isolated cDNA molecules comprise or consist of a nucleotide sequence that has at least about 92% sequence identity to SEQ ID NO:44, and comprises an insertion of a thymine at a position corresponding to position 1,311 according to SEQ ID NO:44, or the complement thereof. In some embodiments, the isolated cDNA molecules comprise or consist of a nucleotide sequence that has at least about 94% sequence identity to SEQ ID NO:44, and comprises an insertion of a thymine at a position corresponding to position 1,311 according to SEQ ID NO:44, or the complement thereof. In some embodiments, the isolated cDNA molecules comprise or consist of a nucleotide sequence that has at least about 96% sequence identity to SEQ ID NO:44, and comprises an insertion of a thymine at a position corresponding to position 1,311 according to SEQ ID NO:44, or the complement thereof. In some embodiments, the isolated cDNA molecules comprise or consist of a nucleotide sequence that has at least about 98% sequence identity to SEQ ID NO:44, and comprises an insertion of a thymine at a position corresponding to position 1,311 according to SEQ ID NO:44, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:49, and comprises an insertion of a thymine at a position corresponding to position 1,232 according to SEQ ID NO:49, or the complement thereof. In some embodiments, the isolated cDNA molecules comprise or consist of a nucleotide sequence that has at least about 90% sequence identity to SEQ ID NO:49, and comprises an insertion of a thymine at a position corresponding to position 1,232 according to SEQ ID NO:49, or the complement thereof. In some embodiments, the isolated cDNA molecules comprise or consist of a nucleotide sequence that has at least about 92% sequence identity to SEQ ID NO:49, and comprises an insertion of a thymine at a position corresponding to position 1,232 according to SEQ ID NO:49, or the complement thereof. In some embodiments, the isolated cDNA molecules comprise or consist of a nucleotide sequence that has at least about 94% sequence identity to SEQ ID NO:49, and comprises an insertion of a thymine at a position corresponding to position 1,232 according to SEQ ID NO:49, or the complement thereof. In some embodiments, the isolated cDNA molecules comprise or consist of a nucleotide sequence that has at least about 96% sequence identity to SEQ ID NO:49, and comprises an insertion of a thymine at a position corresponding to position 1,232 according to SEQ ID NO:49, or the complement thereof. In some embodiments, the isolated cDNA molecules comprise or consist of a nucleotide sequence that has at least about 98% sequence identity to SEQ ID NO:49, and comprises an insertion of a thymine at a position corresponding to position 1,232 according to SEQ ID NO:49, or the complement thereof.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:54, and comprises or an insertion of a thymine at a position corresponding to position 1,471 according to SEQ ID NO:54, or the complement thereof. In some embodiments, the isolated cDNA molecules comprise or consist of a nucleotide sequence that has at least about 90% sequence identity to SEQ ID NO:54, and comprises or an insertion of a thymine at a position corresponding to position 1,471 according to SEQ ID NO:54, or the complement thereof. In some embodiments, the isolated cDNA molecules comprise or consist of a nucleotide sequence that has at least about 92% sequence identity to SEQ ID NO:54, and comprises or an insertion of a thymine at a position corresponding to position 1,471 according to SEQ ID NO:54, or the complement thereof. In some embodiments, the isolated cDNA molecules comprise or consist of a nucleotide sequence that has at least about 94% sequence identity to SEQ ID NO:54, and comprises or an insertion of a thymine at a position corresponding to position 1,471 according to SEQ ID NO:54, or the complement thereof. In some embodiments, the isolated cDNA molecules comprise or consist of a nucleotide sequence that has at least about 96% sequence identity to SEQ ID NO:54, and comprises or an insertion of a thymine at a position corresponding to position 1,471 according to SEQ ID NO:54, or the complement thereof. In some embodiments, the isolated cDNA molecules comprise or consist of a nucleotide sequence that has at least about 98% sequence identity to SEQ ID NO:54, and comprises or an insertion of a thymine at a position corresponding to position 1,471 according to SEQ ID NO:54, or the complement thereof.

Herein, if reference is made to percent sequence identity, the higher percentages of sequence identity are preferred over the lower ones.

In some embodiments, the isolated cDNA molecules comprise SEQ ID NO:35. In some embodiments, the isolated cDNA molecules consist of SEQ ID NO:35. In some embodiments, the isolated cDNA molecules comprise SEQ ID NO:40. In some embodiments, the isolated cDNA molecules consist of SEQ ID NO:40. In some embodiments, the isolated cDNA molecules comprise SEQ ID NO:45. In some embodiments, the isolated cDNA molecules consist of SEQ ID NO:45. In some embodiments, the isolated cDNA molecules comprise SEQ ID NO:50. In some embodiments, the isolated cDNA molecules consist of SEQ ID NO:50.

In some embodiments, the isolated cDNA molecules comprise SEQ ID NO:38. In some embodiments, the isolated cDNA molecules consist of SEQ ID NO:38. In some embodiments, the isolated cDNA molecules comprise SEQ ID NO:43. In some embodiments, the isolated cDNA molecules consist of SEQ ID NO:43. In some embodiments, the isolated cDNA molecules comprise SEQ ID NO:48. In some embodiments, the isolated cDNA molecules consist of SEQ ID NO:48. In some embodiments, the isolated cDNA molecules comprise SEQ ID NO:53. In some embodiments, the isolated cDNA molecules consist of SEQ ID NO:53.

In some embodiments, the isolated cDNA molecules comprise SEQ ID NO:39. In some embodiments, the isolated cDNA molecules consist of SEQ ID NO:39. In some embodiments, the isolated cDNA molecules comprise SEQ ID NO:44. In some embodiments, the isolated cDNA molecules consist of SEQ ID NO:44. In some embodiments, the isolated cDNA molecules comprise SEQ ID NO:49. In some embodiments, the isolated cDNA molecules consist of SEQ ID NO:49. In some embodiments, the isolated cDNA molecules comprise SEQ ID NO:54. In some embodiments, the isolated cDNA molecules consist of SEQ ID NO:54.

In some embodiments, the isolated mRNA molecules or cDNA molecules comprise less than the entire mRNA or cDNA sequence. In some embodiments, the isolated mRNA molecules or cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, or at least about 2000 contiguous nucleotides of any of the GPR75 mRNA molecules or cDNA molecules disclosed herein. In some embodiments, the isolated mRNA molecules or cDNA molecules comprise or consist of at least about 400 to at least about 500 contiguous nucleotides of any of the GPR75 mRNA molecules or cDNA molecules disclosed herein. In some embodiments, the isolated cDNA molecules comprise or consist of at least about 1000 to at least about 2000 contiguous nucleotides of any of the GPR75 mRNA molecules or cDNA molecules disclosed herein.

In some embodiments, these isolated mRNA molecules comprise a UAUCCCG heptanucleotide at the position corresponding to positions 539-545 according to SEQ ID NO:11, a UAUCCCG heptanucleotide at the position corresponding to positions 440-446 according to SEQ ID NO:16, a UAUCCCG heptanucleotide at the position corresponding to positions 361-367 according to SEQ ID NO:21, or a UAUCCCG heptanucleotide at the position corresponding to positions 600-606 according to SEQ ID NO:26. In some embodiments, these isolated mRNA molecules comprise an adenine at the position corresponding to position 556 according to SEQ ID NO:12, an adenine at the position corresponding to position 457 according to SEQ ID NO:17, an adenine at the position corresponding to position 378 according to SEQ ID NO:22, or an adenine at the position corresponding to position 617 according to SEQ ID NO:27. In some embodiments, these isolated mRNA molecules comprise a uracil at the position corresponding to position 910 according to SEQ ID NO:13, a uracil at the position corresponding to position 811 according to SEQ ID NO:18, a uracil at the position corresponding to position 732 according to SEQ ID NO:23, or a uracil at the position corresponding to position 971 according to SEQ ID NO:28. In some embodiments, these isolated mRNA molecules comprise an AGCC tetranucleotide at the position corresponding to positions 919-922 according to SEQ ID NO:14, an AGCC tetranucleotide at the position corresponding to positions 820-823 according to SEQ ID NO:19, an AGCC tetranucleotide at the position corresponding to positions 741-744 according to SEQ ID NO:24, or an AGCC tetranucleotide at the position corresponding to positions 980-983 according to SEQ ID NO:29. In some embodiments, these isolated mRNA molecules comprise an insertion of a uracil at the position corresponding to position 1,410 according to SEQ ID NO:15, an insertion of a uracil at the position corresponding to position 1,311 according to SEQ ID NO:20, an insertion of a uracil at the position corresponding to position 1,232 according to SEQ ID NO:25, or an insertion of a uracil at the position corresponding to position 1,471 according to SEQ ID NO:30. In some embodiments, these isolated mRNA molecules comprise a guanine at the position corresponding to position 830 according to SEQ ID NO:100, a guanine at the position corresponding to position 731 according to SEQ ID NO:101, a guanine at the position corresponding to position 652 according to SEQ ID NO:102, or a guanine at the position corresponding to position 891 according to SEQ ID NO:103.

In some embodiments, these isolated cDNA molecules comprise a TATCCCG heptanucleotide at the position corresponding to positions 539-545 according to SEQ ID NO:35, a TATCCCG heptanucleotide at the position corresponding to positions 440-446 according to SEQ ID NO:40, a TATCCCG heptanucleotide at the position corresponding to positions 361-367 according to SEQ ID NO:45, or a TATCCCG heptanucleotide at the position corresponding to positions 600-606 according to SEQ ID NO:50. In some embodiments, these isolated cDNA molecules comprise an adenine at the position corresponding to position 556 according to SEQ ID NO:36, an adenine at the position corresponding to position 457 according to SEQ ID NO:41, an adenine at the position corresponding to position 378 according to SEQ ID NO:46, or an adenine at the position corresponding to position 617 according to SEQ ID NO:51. In some embodiments, these isolated cDNA molecules comprise a thymine at the position corresponding to position 910 according to SEQ ID NO:37, a thymine at the position corresponding to position 811 according to SEQ ID NO:42, a thymine at the position corresponding to position 732 according to SEQ ID NO:47, or a thymine at the position corresponding to position 971 according to SEQ ID NO:52.

In some embodiments, these isolated cDNA molecules comprise an AGCC tetranucleotide at the position corresponding to positions 919-922 according to SEQ ID NO:38, an AGCC tetranucleotide at the position corresponding to positions 820-823 according to SEQ ID NO:43, an AGCC tetranucleotide at the position corresponding to positions 741-744 according to SEQ ID NO:48, or an AGCC tetranucleotide at the position corresponding to positions 980-983 according to SEQ ID NO:53. In some embodiments, these isolated cDNA molecules comprise an insertion of a thymine at the position corresponding to position 1,410 according to SEQ ID NO:39, an insertion of a thymine at the position corresponding to position 1,311 according to SEQ ID NO:44, an insertion of a thymine at the position corresponding to position 1,232 according to SEQ ID NO:49, or an insertion of a thymine at the position corresponding to position 1,471 according to SEQ ID NO:54. In some embodiments, these isolated cDNA molecules comprise a guanine at the position corresponding to position 830 according to SEQ ID NO:104, a guanine at the position corresponding to position 731 according to SEQ ID NO:105, a guanine at the position corresponding to position 652 according to SEQ ID NO:106, or a guanine at the position corresponding to position 891 according to SEQ ID NO:107.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

The present disclosure also provides fragments of any of the isolated genomic nucleic acid molecules, mRNA molecules, or cDNA molecules disclosed herein. In some embodiments, the fragments comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 contiguous residues of any of the nucleic acid molecules disclosed herein, or any complement thereof. In some embodiments, the fragments comprise or consist of at least about 20, at least about 25, at least about 30, or at least about 35 contiguous residues of any of the nucleic acid molecules disclosed herein, or any complement thereof. In this regard, the longer fragments are preferred over the shorter ones. Such fragments may be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $-O[(CH_2)_nO]_mCH_3$, $-O(CH_2)_nOCH_3$, $-O(CH_2)_nNH_2$, $-O(CH_2)_nCH_3$, $-O(CH_2)_n-ONH_2$, and $-O(CH_2)_nON[(CH_2)_nCH_3)]_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

Desired regulatory sequences for mammalian host cell expression can include, for example, viral elements that direct high levels of polypeptide expression in mammalian cells, such as promoters and/or enhancers derived from retroviral LTRs, cytomegalovirus (CMV) (such as, for example, CMV promoter/enhancer), Simian Virus 40 (SV40) (such as, for example, SV40 promoter/enhancer), adenovirus, (such as, for example, the adenovirus major late promoter (AdMLP)), polyoma and strong mammalian promoters such as native immunoglobulin and actin promoters. Methods of expressing polypeptides in bacterial cells or fungal cells (such as, for example, yeast cells) are also well known. A promoter can be, for example, a constitutively active promoter, a conditional promoter, an inducible promoter, a temporally restricted promoter (such as, for example, a developmentally regulated promoter), or a spatially restricted promoter (such as, for example, a cell-specific or tissue-specific promoter).

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the isolated nucleic acid molecules, genomic nucleic acid molecules, mRNA molecules, and/or cDNA molecules disclosed herein. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1, SEQ ID NO:7, or SEQ ID NO:31). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding a human GPR75 polypeptide, wherein the nucleotide sequence lacks a CCAGTAG heptanucleotide at positions corresponding to positions 5,540-5,546 according to SEQ ID NO:1 means that if the nucleotide sequence of the GPR75 genomic nucleic acid molecule is aligned to the sequence of SEQ ID NO:1, the GPR75 sequence has a deletion of a CCAGTAG heptanucleotide residue at the position that corresponds to positions 5,540-5,546 of SEQ ID NO:1. The same applies for mRNA molecules comprising a nucleotide sequence encoding a human GPR75 polypeptide, wherein the nucleotide sequence lacks a CCAGUAG heptanucleotide at positions corresponding to positions 539-545 according to SEQ ID NO:7, and cDNA molecules comprising a nucleotide sequence encoding a human GPR75 polypeptide, wherein the nucleotide sequence lacks a CCAGTAG heptanucleotide at positions corresponding to positions 539-545 according to SEQ ID NO:31. In other words, these phrases refer to a nucleic acid molecule encoding a GPR75 polypeptide, wherein the genomic nucleic acid molecule has a nucleotide sequence that lacks a CCAGTAG heptanucleotide according to SEQ ID NO:1 and, thus, comprises nucleotides that are homologous to the TATCCCG nucleotides at positions 5,540-5,546 of SEQ ID NO:2 (or wherein the mRNA molecule has a nucleotide sequence that lacks a CCAGUAG heptanucleotide according to SEQ ID NO:7 and, thus, comprises nucleotides that are homologous to the UAUCCCG heptanucleotide residue at positions 539-545 of SEQ ID NO:11, or wherein the cDNA molecule has a nucleotide sequence that lacks a CCAGTAG heptanucleotide according to SEQ ID NO:31 and, thus, comprises residues that are homologous to the TATCCCG residues at positions 539-545 of SEQ ID NO:35). Herein, such a sequence is also referred to as "GPR75 sequence with the Ala110fs alteration" or "GPR75 sequence with the Ala110fs variation" referring to genomic nucleic acid molecules. The same can be carried out for all other molecules disclosed herein.

As described herein, a position within a GPR75 genomic nucleic acid molecule that corresponds to positions 5,540-5,546 according to SEQ ID NO:2, for example, can be identified by performing a sequence alignment between the nucleotide sequence of a particular GPR75 nucleic acid molecule and the nucleotide sequence of SEQ ID NO:2. A variety of computational algorithms exist that can be used for performing a sequence alignment to identify a nucleotide position that corresponds to, for example, positions 5,540-5,546 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The amino acid sequence of a GPR75 reference polypeptide is set forth in SEQ ID NO:55. Referring to SEQ ID NO:55, the GPR75 reference polypeptide is 540 amino acids in length. Referring to SEQ ID NO:55, position 110 is alanine. Referring to SEQ ID NO:55, position 116 is alanine. Referring to SEQ ID NO:55, position 207 is tyrosine. Referring to SEQ ID NO:55, position 234 is glutamine. Referring to SEQ ID NO:55, position 236 is arginine. Referring to SEQ ID NO:55, position 400 is cysteine.

A GPR75 variant polypeptide exists (SEQ ID NO:56; Ala110fs), wherein the alanine at position 110 (referring to SEQ ID NO:55) is altered due to a frameshift mutation in the underlying mRNA molecule, resulting in a truncated 130 amino acid polypeptide. Referring to SEQ ID NO:56, the nucleotides at positions 110-130 are different than the corresponding nucleotides at the same positions of SEQ ID NO:55.

Another GPR75 variant polypeptide exists (SEQ ID NO:57; Ala116Thr), wherein the alanine at position 116 (referring to SEQ ID NO:55) is replaced with a threonine, resulting in a 540 amino acid polypeptide.

Another GPR75 variant polypeptide exists (SEQ ID NO:58; Gln234Stop), wherein the glutamine at position 234 (referring to SEQ ID NO:55) is altered due to a mutation in the underlying mRNA molecule introducing a Stop codon at amino acid position 234, resulting in a truncated 233 amino acid polypeptide.

Another GPR75 variant polypeptide exists (SEQ ID NO:59; Arg236fs), wherein the arginine at position 236 (referring to SEQ ID NO:55) is altered due to a frameshift mutation in the underlying mRNA molecule, resulting in a truncated 239 amino acid polypeptide. Referring to SEQ ID NO:59, the nucleotides at positions 236-239 are different than the corresponding nucleotides at the same positions of SEQ ID NO:55.

Another GPR75 variant polypeptide exists (SEQ ID NO:60; Cys400fs), wherein the cysteine at position 400 (referring to SEQ ID NO:55) is altered due to a frameshift mutation in the underlying mRNA molecule, resulting in a truncated 425 amino acid polypeptide. Referring to SEQ ID NO:60, the nucleotides at positions 400-425 are different than the corresponding nucleotides at the same positions of SEQ ID NO:55.

Another GPR75 variant polypeptide exists (SEQ ID NO:108; Tyr207Cys), wherein the tyrosine at position 207 (referring to SEQ ID NO:55) is replaced with a cysteine, resulting in a 540 amino acid polypeptide.

The present disclosure also provides isolated human GPR75 polypeptides having an amino acid sequence at least about 90%, at least about 91%, at least about 92%, at least about 93%, at least about 94%, at least about 95%, at least about 96%, at least about 97%, at least about 98%, or at least about 99% identical to SEQ ID NO:56, and comprising nucleotides at positions corresponding to positions 110-130 according to SEQ ID NO:56. In some embodiments, the isolated human GPR75 polypeptides have an amino acid sequence at least about 90% identical to SEQ ID NO:56, and comprising nucleotides at positions corresponding to positions 110-130 according to SEQ ID NO:56. In some embodiments, the isolated human GPR75 polypeptides have an amino acid sequence at least about 92% identical to SEQ ID NO:56, and comprising nucleotides at positions corresponding to positions 110-130 according to SEQ ID NO:56. In some embodiments, the isolated human GPR75 polypeptides have an amino acid sequence at least about 94% identical to SEQ ID NO:56, and comprising nucleotides at positions corresponding to positions 110-130 according to SEQ ID NO:56. In some embodiments, the isolated human GPR75 polypeptides have an amino acid sequence at least about 96% identical to SEQ ID NO:56, and comprising nucleotides at positions corresponding to positions 110-130 according to SEQ ID NO:56. In some embodiments, the isolated human GPR75 polypeptides have an amino acid sequence at least about 98% identical to SEQ ID NO:56, and comprising nucleotides at positions corresponding to positions 110-130 according to SEQ ID NO:56. In some embodiments, these GPR75 polypeptides lack amino acids at positions corresponding to positions 110-540 according to SEQ ID NO:55.

The present disclosure also provides isolated human GPR75 polypeptides having an amino acid sequence at least about 90%, at least about 91%, at least about 92%, at least about 93%, at least about 94%, at least about 95%, at least about 96%, at least about 97%, at least about 98%, or at least about 99% identical to SEQ ID NO:59, and comprising nucleotides at positions corresponding to positions 236-239 according to SEQ ID NO:59. In some embodiments, the isolated human GPR75 polypeptides have an amino acid sequence at least about 90% identical to SEQ ID NO:59, and comprising nucleotides at positions corresponding to positions 236-239 according to SEQ ID NO:59. In some embodiments, the isolated human GPR75 polypeptides have an amino acid sequence at least about 92% identical to SEQ ID NO:59, and comprising nucleotides at positions corresponding to positions 236-239 according to SEQ ID NO:59. In some embodiments, the isolated human GPR75 polypeptides have an amino acid sequence at least about 94% identical to SEQ ID NO:59, and comprising nucleotides at positions corresponding to positions 236-239 according to SEQ ID NO:59. In some embodiments, the isolated human GPR75 polypeptides have an amino acid sequence at least about 96% identical to SEQ ID NO:59, and comprising nucleotides at positions corresponding to positions 236-239 according to SEQ ID NO:59. In some embodiments, the isolated human GPR75 polypeptides have an amino acid sequence at least about 98% identical to SEQ ID NO:59, and comprising nucleotides at positions corresponding to positions 236-239 according to SEQ ID NO:59. In some embodiments, these GPR75 polypeptides lack amino acids at positions corresponding to positions 236-540 according to SEQ ID NO:55.

The present disclosure also provides isolated human GPR75 polypeptides having an amino acid sequence at least about 90%, at least about 91%, at least about 92%, at least about 93%, at least about 94%, at least about 95%, at least about 96%, at least about 97%, at least about 98%, or at least about 99% identical to SEQ ID NO:60, and comprising nucleotides at positions corresponding to positions 400-425 according to SEQ ID NO:60. In some embodiments, the isolated human GPR75 polypeptides have an amino acid sequence at least about 90% identical to SEQ ID NO:60, and comprising nucleotides at positions corresponding to positions 400-425 according to SEQ ID NO:60. In some embodiments, the isolated human GPR75 polypeptides have an amino acid sequence at least about 92% identical to SEQ ID NO:60, and comprising nucleotides at positions corresponding to positions 400-425 according to SEQ ID NO:60. In some embodiments, the isolated human GPR75 polypeptides have an amino acid sequence at least about 94% identical to SEQ ID NO:60, and comprising nucleotides at positions corresponding to positions 400-425 according to SEQ ID NO:60. In some embodiments, the isolated human GPR75 polypeptides have an amino acid sequence at least about 96% identical to SEQ ID NO:60, and comprising nucleotides at positions corresponding to positions 400-425 according to SEQ ID NO:60. In some embodiments, the isolated human GPR75 polypeptides have an amino acid sequence at least about 98% identical to SEQ ID NO:60, and comprising nucleotides at positions corresponding to positions 400-425 according to SEQ ID NO:60. In some embodiments, these GPR75 polypeptides lack amino acids at positions corresponding to positions 400-540 according to SEQ ID NO:55.

In some embodiments, the amino acid sequence of the isolated human GPR75 polypeptide comprises or consists of SEQ ID NO:56. In some embodiments, the amino acid sequence of the isolated human GPR75 polypeptide comprises SEQ ID NO:56. In some embodiments, the amino acid sequence of the isolated human GPR75 polypeptide consists of SEQ ID NO:56.

In some embodiments, the amino acid sequence of the isolated human GPR75 polypeptide comprises or consists of SEQ ID NO:59. In some embodiments, the amino acid sequence of the isolated human GPR75 polypeptide comprises SEQ ID NO:59. In some embodiments, the amino acid sequence of the isolated human GPR75 polypeptide consists of SEQ ID NO:59.

In some embodiments, the amino acid sequence of the isolated human GPR75 polypeptide comprises or consists of SEQ ID NO:60. In some embodiments, the amino acid sequence of the isolated human GPR75 polypeptide comprises SEQ ID NO:60. In some embodiments, the amino acid sequence of the isolated human GPR75 polypeptide consists of SEQ ID NO:60.

In some embodiments, the isolated polypeptides comprise or consist of an amino acid sequence at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, at least about 350, at least about 400, at least about 450, at least about 500, at least about 550, or at least about 600 contiguous amino acids of any of the GPR75 polypeptides disclosed herein. In some embodiments, the isolated polypeptides comprise or consist of an amino acid sequence at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, at least about 350, at least about 400, at least about 450, at least about 500, at least about 550, or at least about 600 contiguous amino acids of any of the GPR75 polypeptides disclosed herein.

The isolated polypeptides disclosed herein can comprise an amino acid sequence of a naturally occurring GPR75 polypeptide, or can comprise a non-naturally occurring sequence. In some embodiments, the naturally occurring sequence can differ from the non-naturally occurring sequence due to conservative amino acid substitutions. For example, the sequence can be identical with the exception of conservative amino acid substitutions.

In some embodiments, the isolated polypeptides comprise non-natural or modified amino acids or peptide analogs. For example, there are numerous D-amino acids or amino acids which have a different functional substituent than the naturally occurring amino acids.

The present disclosure also provides nucleic acid molecules encoding any of the polypeptides disclosed herein. This includes all degenerate sequences related to a specific polypeptide sequence (i.e., all nucleic acids having a sequence that encodes one particular polypeptide sequence as well as all nucleic acids, including degenerate nucleic acids, encoding the disclosed variants and derivatives of the protein sequences). Thus, while each particular nucleic acid sequence may not be written out herein, each and every sequence is in fact disclosed and described herein through the disclosed polypeptide sequences.

The present disclosure also provides compositions comprising any one or more of the nucleic acid molecules and/or any one or more of the polypeptides disclosed herein. In some embodiments, the compositions comprise a carrier. Examples of carriers include, but are not limited to, poly (lactic acid) (PLA) microspheres, poly(D,L-lactic-coglycolic-acid) (PLGA) microspheres, liposomes, micelles, inverse micelles, lipid cochleates, and lipid microtubules.

The present disclosure also provides methods of producing any of the GPR75 polypeptides or fragments thereof disclosed herein. Such GPR75 polypeptides or fragments thereof can be produced by any suitable method.

The present disclosure also provides cells comprising any one or more of the nucleic acid molecules and/or any one or more of the polypeptides disclosed herein. The cells can be in vitro, ex vivo, or in vivo. Nucleic acid molecules can be linked to a promoter and other regulatory sequences so they are expressed to produce an encoded protein.

In some embodiments, the cell is a totipotent cell or a pluripotent cell such as, for example, an embryonic stem (ES) cell such as a rodent ES cell, a mouse ES cell, or a rat ES cell. In some embodiments, the cell is a primary somatic cell, or a cell that is not a primary somatic cell. The cell can be from any source. For example, the cell can be a eukaryotic cell, an animal cell, a plant cell, or a fungal (such as, for example, yeast) cell. Such cells can be fish cells or bird cells, or such cells can be mammalian cells, such as human cells, non-human mammalian cells, rodent cells, mouse cells or rat cells. Mammals include, but are not limited to, humans, non-human primates, monkeys, apes, cats dogs, horses, bulls, deer, bison, sheep, rodents (such as, for example, mice, rats, hamsters, guinea pigs), livestock (such as, for example, bovine species such as cows, steer, etc.; ovine species such as sheep, goats, etc.; and porcine species such as pigs and boars). The term "non-human animal" excludes humans.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or inhibit obesity for use in the treatment of obesity (or for use in the preparation of a medicament for treating obesity) in a subject, wherein the subject has any of the genomic nucleic acid molecules, mRNA molecules, and/or cDNA molecules encoding a human GPR75 polypeptide described herein. The therapeutic agents that treat or inhibit obesity can be any of the therapeutic agents that treat or inhibit obesity described herein.

In some embodiments, the subject comprises: i) a genomic nucleic acid molecule having a nucleotide sequence encoding a human GPR75 polypeptide, wherein the nucleotide sequence lacks a CCAGTAG heptanucleotide at positions corresponding to positions 5,540-5,546 according to SEQ ID NO:1, or the complement thereof; ii) an mRNA molecule having a nucleotide sequence encoding a human GPR75 polypeptide, wherein the nucleotide sequence: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; or lacks a CCAGUAG heptanucleotide at positions corresponding to positions 600-606 according to SEQ ID NO:10, or the complement thereof; or iii) a cDNA molecule having a nucleotide sequence encoding a human GPR75 polypeptide, wherein the nucleotide sequence: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; or lacks a CCAGTAG heptanucleotide at positions corresponding to positions 600-606 according to SEQ ID NO:34, or the complement thereof.

In some embodiments, the subject comprises: a genomic nucleic acid molecule having a nucleotide sequence encoding a human GPR75 polypeptide, wherein the nucleotide sequence lacks a CCAGTAG heptanucleotide at a position corresponding to positions 5,540-5,546 according to SEQ ID NO:1, or the complement thereof; an mRNA molecule having a nucleotide sequence encoding a human GPR75 polypeptide, wherein the nucleotide sequence lacks a CCAGUAG heptanucleotide at positions corresponding to positions 539-545 according to SEQ ID NO:7, or the complement thereof; a cDNA molecule having a nucleotide sequence encoding a human GPR75 polypeptide, wherein the nucleotide sequence lacks a CCAGTAG heptanucleotide at positions corresponding to positions 539-545 according to SEQ ID NO:31, or the complement thereof.

In some embodiments, the subject comprises: i) a genomic nucleic acid molecule having a nucleotide sequence encoding a human GPR75 polypeptide, wherein the nucleotide sequence comprises an adenine at a position corresponding to position 5,557 according to SEQ ID NO:3, or the complement thereof; ii) an mRNA molecule having a nucleotide sequence encoding a human GPR75 polypeptide, wherein the nucleotide sequence comprises: an adenine at a position corresponding to position 556 according to SEQ ID NO:12, or the complement thereof; an adenine at a position corresponding to position 457 according to SEQ ID NO:17, or the complement thereof; an adenine at a position corresponding to position 378 according to SEQ ID NO:22, or the complement thereof; or an adenine at a position corresponding to position 617 according to SEQ ID NO:27, or the complement thereof; or iii) a cDNA molecule having a nucleotide sequence encoding a human GPR75 polypeptide, wherein the nucleotide sequence comprises: an adenine at a position corresponding to position 556 according to SEQ ID NO:36, or the complement thereof; an adenine at a position corresponding to position 457 according to SEQ ID NO:41, or the complement thereof; an adenine at a position corresponding to position 378 according to SEQ ID NO:46, or the complement thereof; an adenine at a position corresponding to position 617 according to SEQ ID NO:51, or the complement thereof.

In some embodiments, the subject comprises: a genomic nucleic acid molecule having a nucleotide sequence encoding a human GPR75 polypeptide, wherein the nucleotide sequence comprises an adenine at a position corresponding to position 5,557 according to SEQ ID NO:3, or the complement thereof; an mRNA molecule having a nucleotide sequence encoding a human GPR75 polypeptide, wherein the nucleotide sequence comprises an adenine at a position corresponding to position 556 according to SEQ ID NO:12, or the complement thereof; a cDNA molecule having a nucleotide sequence encoding a human GPR75 polypeptide, wherein the nucleotide sequence comprises an adenine at a position corresponding to position 556 according to SEQ ID NO:36, or the complement thereof.

In some embodiments, the subject comprises: i) a genomic nucleic acid molecule having a nucleotide sequence encoding a human GPR75 polypeptide, wherein the nucleotide sequence comprises a thymine at a position corresponding to position 5,911 according to SEQ ID NO:4, or the complement thereof; ii) an mRNA molecule having a nucleotide sequence encoding a human GPR75 polypeptide, wherein the nucleotide sequence comprises: a uracil at a position corresponding to position 910 according to SEQ ID NO:13, or the complement thereof; a uracil at a position corresponding to position 811 according to SEQ ID NO:18, or the complement thereof; a uracil at a position corresponding to position 732 according to SEQ ID NO:23, or the complement thereof; or a uracil at a position corresponding to position 971 according to SEQ ID NO:28, or the complement thereof; or iii) a cDNA molecule having a nucleotide sequence encoding a human GPR75 polypeptide, wherein the nucleotide sequence comprises: a thymine at a position corresponding to position 910 according to SEQ ID NO:37, or the complement thereof; a thymine at a position corresponding to position 811 according to SEQ ID NO:42, or the complement thereof; a thymine at a position corresponding to position 732 according to SEQ ID NO:47, or the complement thereof; or a thymine at a position corresponding to position 971 according to SEQ ID NO:52, or the complement thereof.

In some embodiments, the subject comprises: a genomic nucleic acid molecule having a nucleotide sequence encoding a human GPR75 polypeptide, wherein the nucleotide sequence comprises a thymine at a position corresponding to position 5,991 according to SEQ ID NO:4, or the complement thereof; an mRNA molecule having a nucleotide sequence encoding a human GPR75 polypeptide, wherein the nucleotide sequence comprises a uracil at a position corresponding to position 910 according to SEQ ID NO:13, or the complement thereof; a cDNA molecule having a nucleotide sequence encoding a human GPR75 polypeptide, wherein the nucleotide sequence comprises a thymine at a position corresponding to position 910 according to SEQ ID NO:37, or the complement thereof; or a GPR75 polypeptide that comprises a stop codon at a position corresponding to position 234 according to SEQ ID NO:58.

In some embodiments, the subject comprises: i) a genomic nucleic acid molecule having a nucleotide sequence encoding a human GPR75 polypeptide, wherein the nucleotide sequence lacks an AAAG tetranucleotide at positions corresponding to positions 5,920-5,923 according to SEQ ID NO:1, or the complement thereof; ii) an mRNA molecule having a nucleotide sequence encoding a human GPR75 polypeptide, wherein the nucleotide sequence: lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; or lacks an AAAG tetranucleotide at positions corresponding to positions 980-983 according to SEQ ID NO:10, or the complement thereof; or iii) a cDNA molecule having a nucleotide sequence encoding a human GPR75 polypeptide, wherein the nucleotide sequence: lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; or lacks an AAAG tetranucleotide at positions corresponding to positions 980-983 according to SEQ ID NO:34, or the complement thereof.

In some embodiments, the subject comprises: a genomic nucleic acid molecule having a nucleotide sequence encoding a human GPR75 polypeptide, wherein the nucleotide sequence lacks an AAAG heptanucleotide at a position corresponding to positions 5,920-5,923 according to SEQ ID NO:1, or the complement thereof; an mRNA molecule having a nucleotide sequence encoding a human GPR75 polypeptide, wherein the nucleotide sequence lacks an AAAG tetranucleotide at positions corresponding to positions 919-922 according to SEQ ID NO:7, or the complement thereof; or a cDNA molecule having a nucleotide sequence encoding a human GPR75 polypeptide, wherein the nucleotide sequence lacks an AAAG tetranucleotide at positions corresponding to positions 919-922 according to SEQ ID NO:31, or the complement thereof.

In some embodiments, the subject comprises: i) a genomic nucleic acid molecule having a nucleotide sequence encoding a human GPR75 polypeptide, wherein the nucleotide sequence comprises an insertion of a thymine at a position corresponding to position 6,411 according to SEQ ID NO:6, or the complement thereof; ii) an mRNA molecule having a nucleotide sequence encoding a human GPR75 polypeptide, wherein the nucleotide sequence comprises: an insertion of a uracil at a position corresponding to position 1,410 according to SEQ ID NO:15, or the complement thereof; an insertion of a uracil at a position corresponding to position 1,311 according to SEQ ID NO:20, or the complement thereof; an insertion of a uracil at a position corresponding to position 1,232 according to SEQ ID NO:25, or the complement thereof; or an insertion of a uracil at a position corresponding to position 1,471 according to SEQ ID NO:30, or the complement thereof; or iii) a cDNA molecule having a nucleotide sequence encoding a human GPR75 polypeptide, wherein the nucleotide sequence comprises: an insertion of a thymine at a position corresponding to position 1,410 according to SEQ ID NO:39, or the complement thereof; an insertion of a thymine at a position corresponding to position 1,311 according to SEQ ID NO:44, or the complement thereof; an insertion of a thymine at a position corresponding to position 1,232 according to SEQ ID NO:49, or the complement thereof; or an insertion of a thymine at a position corresponding to position 1,471 according to SEQ ID NO:54, or the complement thereof.

In some embodiments, the subject comprises: a genomic nucleic acid molecule having a nucleotide sequence encoding a human GPR75 polypeptide, wherein the nucleotide sequence comprises an insertion of thymine at a position corresponding to position 6,411 according to SEQ ID NO:6, or the complement thereof; an mRNA molecule having a nucleotide sequence encoding a human GPR75 polypeptide, wherein the nucleotide sequence comprises an insertion of a uracil at a position corresponding to position 1,410 according to SEQ ID NO:15, or the complement thereof; or a cDNA molecule having a nucleotide sequence encoding a human GPR75 polypeptide, wherein the nucleotide sequence comprises an insertion of a thymine at a position corresponding to position 1,410 according to SEQ ID NO:39, or the complement thereof.

In some embodiments, the subject comprises: i) a genomic nucleic acid molecule having a nucleotide sequence encoding a human GPR75 polypeptide, wherein the nucleotide sequence comprises a guanine at a position corresponding to position 5,831 according to SEQ ID NO:99, or the complement thereof; ii) an mRNA molecule having a nucleotide sequence encoding a human GPR75 polypeptide, wherein the nucleotide sequence comprises: a guanine at a position corresponding to position 830 according to SEQ ID NO:100, or the complement thereof; a guanine at a position corresponding to position 731 according to SEQ ID NO:101, or the complement thereof; a guanine at a position corresponding to position 652 according to SEQ ID NO:102, or the complement thereof; or a guanine at a position corresponding to position 891 according to SEQ ID NO:103, or the complement thereof; or iii) a cDNA molecule having a nucleotide sequence encoding a human GPR75 polypeptide, wherein the nucleotide sequence comprises: a guanine at a position corresponding to position 830 according to SEQ ID NO:104, or the complement thereof; a guanine at a position corresponding to position 731 according to SEQ ID NO:105, or the complement thereof; a guanine at a position corresponding to position 652 according to SEQ ID NO:106, or the complement thereof; or a guanine at a position corresponding to position 891 according to SEQ ID NO:107, or the complement thereof.

In some embodiments, the subject comprises: a genomic nucleic acid molecule having a nucleotide sequence encoding a human GPR75 polypeptide, wherein the nucleotide sequence comprises a guanine at a position corresponding to position 5,831 according to SEQ ID NO:99, or the complement thereof; an mRNA molecule having a nucleotide sequence encoding a human GPR75 polypeptide, wherein the nucleotide sequence comprises a guanine at a position corresponding to position 830 according to SEQ ID NO:100, or the complement thereof; a cDNA molecule having a nucleotide sequence encoding a human GPR75 polypeptide, wherein the nucleotide sequence comprises a guanine at a position corresponding to position 830 according to SEQ ID NO:104, or the complement thereof; or a GPR75 polypeptide that comprises a cysteine at a position corresponding to position 207 according to SEQ ID NO:108.

The present disclosure also provides GPR75 inhibitors for use in the treatment of obesity (or for use in the preparation of a medicament for treating obesity) in a subject, wherein the subject has any of the genomic nucleic acid molecules, mRNA molecules, and/or cDNA molecules encoding a human GPR75 polypeptide described herein. The GPR75 inhibitors can be any of the GPR75 inhibitors described herein.

In some embodiments, the subject comprises: i) a genomic nucleic acid molecule having a nucleotide sequence encoding a human GPR75 polypeptide, wherein the nucleotide sequence lacks a CCAGTAG heptanucleotide at positions corresponding to positions 5,540-5,546 according to SEQ ID NO:1, or the complement thereof; ii) an mRNA molecule having a nucleotide sequence encoding a human GPR75 polypeptide, wherein the nucleotide sequence: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; or lacks a CCAGUAG heptanucleotide at positions corresponding to positions 600-606 according to SEQ ID NO:10, or the complement thereof; or iii) a cDNA molecule having a nucleotide sequence encoding a human GPR75 polypeptide, wherein the nucleotide sequence: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; or lacks a CCAGTAG heptanucleotide at positions corresponding to positions 600-606 according to SEQ ID NO:34, or the complement thereof.

In some embodiments, the subject comprises: a genomic nucleic acid molecule having a nucleotide sequence encoding a human GPR75 polypeptide, wherein the nucleotide sequence lacks a CCAGTAG heptanucleotide at a position corresponding to positions 5,540-5,546 according to SEQ ID NO:1, or the complement thereof; an mRNA molecule having a nucleotide sequence encoding a human GPR75 polypeptide, wherein the nucleotide sequence lacks a CCAGUAG heptanucleotide at positions corresponding to positions 539-545 according to SEQ ID NO:7, or the complement thereof; a cDNA molecule having a nucleotide sequence encoding a human GPR75 polypeptide, wherein the nucleotide sequence lacks a CCAGTAG heptanucleotide at positions corresponding to positions 539-545 according to SEQ ID NO:31, or the complement thereof.

In some embodiments, the subject comprises: i) a genomic nucleic acid molecule having a nucleotide sequence encoding a human GPR75 polypeptide, wherein the nucleotide sequence comprises an adenine at a position corresponding to position 5,557 according to SEQ ID NO:3, or the complement thereof; ii) an mRNA molecule having a nucleotide sequence encoding a human GPR75 polypeptide, wherein the nucleotide sequence comprises: an adenine at a position corresponding to position 556 according to SEQ ID NO:12, or the complement thereof; an adenine at a position corresponding to position 457 according to SEQ ID NO:17, or the complement thereof; an adenine at a position corresponding to position 378 according to SEQ ID NO:22, or the complement thereof; or an adenine at a position corresponding to position 617 according to SEQ ID NO:27, or the complement thereof; or iii) a cDNA molecule having a nucleotide sequence encoding a human GPR75 polypeptide, wherein the nucleotide sequence comprises: an adenine at a position corresponding to position 556 according to SEQ ID NO:36, or the complement thereof; an adenine at a position corresponding to position 457 according to SEQ ID NO:41, or the complement thereof; an adenine at a position corresponding to position 378 according to SEQ ID NO:46, or the complement thereof; an adenine at a position corresponding to position 617 according to SEQ ID NO:51, or the complement thereof.

In some embodiments, the subject comprises: a genomic nucleic acid molecule having a nucleotide sequence encoding a human GPR75 polypeptide, wherein the nucleotide sequence comprises an adenine at a position corresponding to position 5,557 according to SEQ ID NO:3, or the complement thereof; an mRNA molecule having a nucleotide sequence encoding a human GPR75 polypeptide, wherein the nucleotide sequence comprises an adenine at a position corresponding to position 556 according to SEQ ID NO:12, or the complement thereof; a cDNA molecule having a nucleotide sequence encoding a human GPR75 polypeptide, wherein the nucleotide sequence comprises an adenine at a position corresponding to position 556 according to SEQ ID NO:36, or the complement thereof.

In some embodiments, the subject comprises: i) a genomic nucleic acid molecule having a nucleotide sequence encoding a human GPR75 polypeptide, wherein the nucleotide sequence comprises a thymine at a position corresponding to position 5,911 according to SEQ ID NO:4, or the complement thereof; ii) an mRNA molecule having a nucleotide sequence encoding a human GPR75 polypeptide, wherein the nucleotide sequence comprises: a uracil at a position corresponding to position 910 according to SEQ ID NO:13, or the complement thereof; a uracil at a position corresponding to position 811 according to SEQ ID NO:18, or the complement thereof; a uracil at a position corresponding to position 732 according to SEQ ID NO:23, or the complement thereof; or a uracil at a position corresponding to position 971 according to SEQ ID NO:28, or the complement thereof; or iii) a cDNA molecule having a nucleotide sequence encoding a human GPR75 polypeptide, wherein the nucleotide sequence comprises: a thymine at a position corresponding to position 910 according to SEQ ID NO:37, or the complement thereof; a thymine at a position corresponding to position 811 according to SEQ ID NO:42, or the complement thereof; a thymine at a position corresponding to position 732 according to SEQ ID NO:47, or the complement thereof; or a thymine at a position corresponding to position 971 according to SEQ ID NO:52, or the complement thereof.

In some embodiments, the subject comprises: a genomic nucleic acid molecule having a nucleotide sequence encoding a human GPR75 polypeptide, wherein the nucleotide sequence comprises a thymine at a position corresponding to position 5,991 according to SEQ ID NO:4, or the complement thereof; an mRNA molecule having a nucleotide sequence encoding a human GPR75 polypeptide, wherein the nucleotide sequence comprises a uracil at a position corresponding to position 910 according to SEQ ID NO:13, or the complement thereof; a cDNA molecule having a nucleotide sequence encoding a human GPR75 polypeptide, wherein the nucleotide sequence comprises a thymine at a position corresponding to position 910 according to SEQ ID NO:37, or the complement thereof; or a GPR75 polypeptide that comprises a stop codon at a position corresponding to position 234 according to SEQ ID NO:58.

In some embodiments, the subject comprises: i) a genomic nucleic acid molecule having a nucleotide sequence encoding a human GPR75 polypeptide, wherein the nucleotide sequence lacks an AAAG tetranucleotide at positions corresponding to positions 5,920-5,923 according to SEQ ID NO:1, or the complement thereof; ii) an mRNA molecule having a nucleotide sequence encoding a human GPR75 polypeptide, wherein the nucleotide sequence: lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; or lacks an AAAG tetranucleotide at positions corresponding to positions 980-983 according to SEQ ID NO:10, or the complement thereof; or iii) a cDNA molecule having a nucleotide sequence encoding a human GPR75 polypeptide, wherein the nucleotide sequence: lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; or lacks an AAAG tetranucleotide at positions corresponding to positions 980-983 according to SEQ ID NO:34, or the complement thereof.

In some embodiments, the subject comprises: a genomic nucleic acid molecule having a nucleotide sequence encoding a human GPR75 polypeptide, wherein the nucleotide sequence lacks an AAAG heptanucleotide at a position corresponding to positions 5,920-5,923 according to SEQ ID NO:1, or the complement thereof; an mRNA molecule having a nucleotide sequence encoding a human GPR75 polypeptide, wherein the nucleotide sequence lacks an AAAG tetranucleotide at positions corresponding to positions 919-922 according to SEQ ID NO:7, or the complement thereof; or a cDNA molecule having a nucleotide sequence encoding a human GPR75 polypeptide, wherein the nucleotide sequence lacks an AAAG tetranucleotide at positions corresponding to positions 919-922 according to SEQ ID NO:31, or the complement thereof.

In some embodiments, the subject comprises: i) a genomic nucleic acid molecule having a nucleotide sequence encoding a human GPR75 polypeptide, wherein the nucleotide sequence comprises an insertion of a thymine at a position corresponding to position 6,411 according to SEQ ID NO:6, or the complement thereof; ii) an mRNA molecule having a nucleotide sequence encoding a human GPR75 polypeptide, wherein the nucleotide sequence comprises: an insertion of a uracil at a position corresponding to position 1,410 according to SEQ ID NO:15, or the complement thereof; an insertion of a uracil at a position corresponding to position 1,311 according to SEQ ID NO:20, or the complement thereof; an insertion of a uracil at a position corresponding to position 1,232 according to SEQ ID NO:25, or the complement thereof; or an insertion of a uracil at a position corresponding to position 1,471 according to SEQ ID NO:30, or the complement thereof; or iii) a cDNA molecule having a nucleotide sequence encoding a human GPR75 polypeptide, wherein the nucleotide sequence comprises: an insertion of a thymine at a position corresponding to position 1,410 according to SEQ ID NO:39, or the complement thereof; an insertion of a thymine at a position corresponding to position 1,311 according to SEQ ID NO:44, or the complement thereof; an insertion of a thymine at a position corresponding to position 1,232 according to SEQ ID NO:49, or the complement thereof; or an insertion of a thymine at a position corresponding to position 1,471 according to SEQ ID NO:54, or the complement thereof.

In some embodiments, the subject comprises: a genomic nucleic acid molecule having a nucleotide sequence encoding a human GPR75 polypeptide, wherein the nucleotide sequence comprises an insertion of thymine at a position corresponding to position 6,411 according to SEQ ID NO:6, or the complement thereof; an mRNA molecule having a nucleotide sequence encoding a human GPR75 polypeptide, wherein the nucleotide sequence comprises an insertion of a uracil at a position corresponding to position 1,410 according to SEQ ID NO:15, or the complement thereof; or a cDNA molecule having a nucleotide sequence encoding a human GPR75 polypeptide, wherein the nucleotide sequence comprises an insertion of a thymine at a position corresponding to position 1,410 according to SEQ ID NO:39, or the complement thereof.

In some embodiments, the subject comprises: i) a genomic nucleic acid molecule having a nucleotide sequence encoding a human GPR75 polypeptide, wherein the nucleotide sequence comprises a guanine at a position corresponding to position 5,831 according to SEQ ID NO:99, or the complement thereof; ii) an mRNA molecule having a nucleotide sequence encoding a human GPR75 polypeptide, wherein the nucleotide sequence comprises: a guanine at a position corresponding to position 830 according to SEQ ID NO:100, or the complement thereof; a guanine at a position corresponding to position 731 according to SEQ ID NO:101, or the complement thereof; a guanine at a position corresponding to position 652 according to SEQ ID NO:102, or the complement thereof; or a guanine at a position corresponding to position 891 according to SEQ ID NO:103, or the complement thereof; or iii) a cDNA molecule having a nucleotide sequence encoding a human GPR75 polypeptide, wherein the nucleotide sequence comprises: a guanine at a position corresponding to position 830 according to SEQ ID NO:100, or the complement thereof; a guanine at a position corresponding to position 731 according to SEQ ID NO:101, or the complement thereof; a guanine at a position corresponding to position 652 according to SEQ ID NO:102, or the complement thereof; or a guanine at a position corresponding to position 891 according to SEQ ID NO:103, or the complement thereof.

In some embodiments, the subject comprises: a genomic nucleic acid molecule having a nucleotide sequence encoding a human GPR75 polypeptide, wherein the nucleotide sequence comprises a guanine at a position corresponding to position 5,831 according to SEQ ID NO:99, or the complement thereof; an mRNA molecule having a nucleotide sequence encoding a human GPR75 polypeptide, wherein the nucleotide sequence comprises a guanine at a position corresponding to position 830 according to SEQ ID NO:100, or the complement thereof; a cDNA molecule having a nucleotide sequence encoding a human GPR75 polypeptide, wherein the nucleotide sequence comprises a guanine at a position corresponding to position 830 according to SEQ ID NO:104, or the complement thereof; or a GPR75 polypeptide that comprises a cysteine at a position corresponding to position 207 according to SEQ ID NO:108.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following representative embodiments are presented:

Embodiment 1. A method of treating a subject having obesity, the method comprising administering a G-Protein Coupled Receptor 75 (GPR75) inhibitor to the subject.

Embodiment 2. A method of treating a subject having excessive weight, the method comprising administering a GPR75 inhibitor to the subject.

Embodiment 3. A method of treating a subject having elevated BMI, the method comprising administering a GPR75 inhibitor to the subject.

Embodiment 4. A method of treating a subject having elevated body fat mass, percentage, or volume, the method comprising administering a GPR75 inhibitor to the subject.

Embodiment 5. A method of treating a subject having excessive food intake, or to prevent weight gain, or to maintain weight loss, the method comprising administering a GPR75 inhibitor to the subject.

Embodiment 6. The method according to any one of embodiments 1 to 5, wherein the GPR75 inhibitor comprises an antisense nucleic acid molecule, a small interfering RNA (siRNA), or a short hairpin RNA (shRNA) that hybridizes to a GPR75 mRNA.

Embodiment 7. The method according to any one of embodiments 1 to 5, wherein the GPR75 inhibitor comprises a Cas protein and guide RNA (gRNA) that hybridizes to a gRNA recognition sequence within a GPR75 genomic nucleic acid molecule.

Embodiment 8. The method according to embodiment 7, wherein the Cas protein is Cas9 or Cpf1.

Embodiment 9. The method according to embodiment 7 or embodiment 8, wherein the gRNA recognition sequence includes or is proximate to a position corresponding to: position 5,540-5,546 according to SEQ ID NO:1, position 5,557 according to SEQ ID NO:1, position 5,911 according to SEQ ID NO:1, positions 5,920-5,923 according to SEQ ID NO:1, position 6,411 according to SEQ ID NO:1, or position 5,831 according to SEQ ID NO:1.

Embodiment 10. The method according to embodiment 7 or embodiment 8, wherein the gRNA recognition sequence is located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to: position 5,540-5,546 according to SEQ ID NO:1, position 5,557 according to SEQ ID NO:1, position 5,911 according to SEQ ID NO:1, positions 5,920-5,923 according to SEQ ID NO:1, position 6,411 according to SEQ ID NO:1, or position 5,831 according to SEQ ID NO:1.

Embodiment 11. The method according to embodiment 7 or embodiment 8, wherein a Protospacer Adjacent Motif (PAM) sequence is about 2 to about 6 nucleotides downstream of the gRNA recognition sequence.

Embodiment 12. The method according to any one of embodiments 7 to 11, wherein the gRNA comprises from about 17 to about 23 nucleotides.

Embodiment 13. The method according to any one of embodiments 7 to 11, wherein the gRNA recognition sequence comprises a nucleotide sequence according to any one of SEQ ID NOs:61-98.

Embodiment 14. The method according to any one of embodiments 1 to 13, further comprising detecting the absence of a GPR75 missense variant nucleic acid molecule encoding a predicted loss-of-function GPR75 polypeptide in a biological sample from the subject.

Embodiment 15. The method according to embodiment 14, further comprising administering a therapeutic agent that treats or inhibits obesity in a standard dosage amount to a subject that is GPR75 reference.

Embodiment 16. The method according to embodiment 14, further comprising administering a therapeutic agent that treats or inhibits obesity in a dosage amount that is the same as or lower than a standard dosage amount to a subject that is heterozygous for a GPR75 missense variant nucleic acid molecule.

Embodiment 17. The method according to any one of embodiments 14 to 16, wherein the GPR75 missense variant nucleic acid molecule is a nucleic acid molecule encoding Ala110fs, Ala116Thr, Tyr207Cys, Gln234Stop, Arg236fs, or Cys400fs.

Embodiment 18. The method according to embodiment 17, wherein the GPR75 missense variant nucleic acid molecule is:

a genomic nucleic acid molecule having a nucleotide sequence: lacking a CCAGTAG heptanucleotide at positions corresponding to positions 5,540-5,546 according to SEQ ID NO:1; comprising an adenine at a position corresponding to position 5,557 according to SEQ ID NO:3; comprising a thymine at a position corresponding to position 5,911 according to SEQ ID NO:4; lacking an AAAG tetranucleotide at positions corresponding to positions 5,920-5,923 according to SEQ ID NO:1; comprising an insertion of a thymine at a position corresponding to position 6,411 according to SEQ ID NO:6; or comprising a guanine at a position corresponding to position 5,831 according to SEQ ID NO:99;

an mRNA molecule having a nucleotide sequence: lacking a CCAGUAG heptanucleotide at positions corresponding to positions 539-545 according to SEQ ID NO:7, lacking a CCAGUAG heptanucleotide at positions corresponding to positions 440-446 according to SEQ ID NO:8, lacking a CCAGUAG heptanucleotide at positions corresponding to positions 361-367 according to SEQ ID NO:9, lacking a CCAGUAG heptanucleotide at positions corresponding to positions 600-606 according to SEQ ID NO:10; comprising an adenine at a position corresponding to position 556 according to SEQ ID NO:12, comprising an adenine at a position corresponding to position 457 according to SEQ ID NO:17, comprising an adenine at a position corresponding to position 378 according to SEQ ID NO:22, comprising an adenine at a position corresponding to position 617 according to SEQ ID NO:27; comprising a uracil at a position corresponding to position 910 according to SEQ ID NO:13, comprising a uracil at a position corresponding to position 811 according to SEQ ID NO:18, comprising a uracil at a position corresponding to position 732 according to SEQ ID NO:23, comprising a uracil at a position corresponding to position 971 according to SEQ ID NO:28; lacking an AAAG tetranucleotide at positions corresponding to positions 919-922 according to SEQ ID NO:7, lacking an AAAG tetranucleotide at positions corresponding to positions 820-823 according to SEQ ID NO:8, lacking an AAAG tetranucleotide at positions corresponding to positions 741-744 according to SEQ ID NO:9, lacking an AAAG tetranucle-otide at positions corresponding to positions 980-983 according to SEQ ID NO:10; comprising an insertion of a uracil at a position corresponding to position 1,410 according to SEQ ID NO:15, comprising an insertion of a uracil at a position corresponding to position 1,311 according to SEQ ID NO:20, comprising an insertion of a uracil at a position corresponding to position 1,232 according to SEQ ID NO:25, comprising an insertion of a uracil at a position corresponding to position 1,471 according to SEQ ID NO:30, comprising a guanine at a position corresponding to position 830 according to SEQ ID NO:100, comprising a guanine at a position corresponding to position 731 according to SEQ ID NO:101, comprising a guanine at a position corresponding to position 652 according to SEQ ID NO:102, or comprising a guanine at a position corresponding to position 891 according to SEQ ID NO:103; or a cDNA molecule produced from an mRNA molecule, wherein the cDNA molecule has a nucleotide sequence: lacking a CCAGTAG heptanucleotide at positions corresponding to positions 539-545 according to SEQ ID NO:31, lacking a CCAGTAG heptanucleotide at positions corresponding to positions 440-446 according to SEQ ID NO:32, lacking a CCAGTAG heptanucleotide at positions corresponding to positions 361-367 according to SEQ ID NO:33, lacking a CCAGTAG heptanucleotide at positions corresponding to positions 600-606 according to SEQ ID NO:34; comprising an adenine at a position corresponding to position 556 according to SEQ ID NO:36, comprising an adenine at a position corresponding to position 457 according to SEQ ID NO:41, comprising an adenine at a position corresponding to position 378 according to SEQ ID NO:46, comprising an adenine at a position corresponding to position 617 according to SEQ ID NO:51; comprising a thymine at a position corresponding to position 910 according to SEQ ID NO:37, comprising a thymine at a position corresponding to position 811 according to SEQ ID NO:42, comprising a thymine at a position corresponding to position 732 according to SEQ ID NO:47, comprising a thymine at a position corresponding to position 971 according to SEQ ID NO:52; lacking an AAAG tetranucleotide at positions corresponding to positions 919-922 according to SEQ ID NO:31, lacking an AAAG tetranucleotide at positions corresponding to positions 820-823 according to SEQ ID NO:32, lacking an AAAG tetranucleotide at positions corresponding to positions 741-744 according to SEQ ID NO:33, lacking an AAAG tetranucleotide at positions corresponding to positions 980-983 according to SEQ ID NO:34; comprising an insertion of a thymine at a position corresponding to position 1,410 according to SEQ ID NO:39, comprising an insertion of a thymine at a position corresponding to position 1,311 according to SEQ ID NO:44, comprising an insertion of a thymine at a position corresponding to position 1,232 according to SEQ ID NO:49, comprising an insertion of a thymine at a position corresponding to position 1,471 according to SEQ ID NO:54, comprising a guanine at a position corresponding to position 830 according to SEQ ID NO:104, comprising a guanine at a position corresponding to position 731 according to SEQ ID NO:105, comprising a guanine at a position corresponding to position 652 according to SEQ ID NO:106, or comprising a guanine at a position corresponding to position 891 according to SEQ ID NO:107.

Embodiment 19. The method according to any one of embodiments 14 to 18, wherein the detecting step is carried out in vitro.

Embodiment 20. The method according to any one of embodiments 14 to 19, wherein the detecting step comprises sequencing at least a portion of the nucleotide sequence of the GPR75 genomic nucleic acid molecule in the biological sample, wherein the sequenced portion comprises a position corresponding to: positions 5,540-5,546 according to SEQ ID NO:2 or SEQ ID NO:1, or the complement thereof; position 5,557 according to SEQ ID NO:3, or the complement thereof; position 5,911 according to SEQ ID NO:4, or the complement thereof; positions 5,920-5,923 according to SEQ ID NO:5 or SEQ ID NO:1, or the complement thereof; position 6,411 according to SEQ ID NO:6, or the complement thereof; or position 5,831 according to SEQ ID NO:99, or the complement thereof;

wherein when the sequenced portion of the GPR75 genomic nucleic acid molecule in the biological sample: lacks a CCAGTAG heptanucleotide at positions corresponding to positions 5,540-5,546 according to SEQ ID NO:1; comprises an adenine at a position corresponding to position 5,557 according to SEQ ID NO:3; comprises a thymine at a position corresponding to position 5,911 according to SEQ ID NO:4; lacks an AAAG tetranucleotide at positions corresponding to positions 5,920-5,923 according to SEQ ID NO:1; comprises an insertion of a thymine at a position corresponding to position 6,411 according to SEQ ID NO:6; or comprises a guanine at a position corresponding to position 5,831 according to SEQ ID NO:99, or the complement thereof; then the GPR75 genomic nucleic acid molecule in the biological sample is a GPR75 missense variant nucleic acid molecule.

Embodiment 21. The method according to any one of embodiments 14 to 19, wherein the detecting step comprises sequencing at least a portion of the nucleotide sequence of the GPR75 mRNA molecule in the biological sample, wherein the sequenced portion comprises a position corresponding to: positions 539-545 according to SEQ ID NO:11, or the complement thereof; positions 440-446 according to SEQ ID NO:16, or the complement thereof; positions 361-367 according to SEQ ID NO:21, or the complement thereof; positions 600-606 according to SEQ ID NO:26, or the complement thereof; position 556 according to SEQ ID NO:12, or the complement thereof; position 457 according to SEQ ID NO:17, or the complement thereof; position 378 according to SEQ ID NO:22, or the complement thereof; position 617 according to SEQ ID NO:27, or the complement thereof; position 910 according to SEQ ID NO:13, or the complement thereof; position 811 according to SEQ ID NO:18, or the complement thereof; position 732 according to SEQ ID NO:23, or the complement thereof; position 971 according to SEQ ID NO:28, or the complement thereof; positions 919-922 according to SEQ ID NO:14, or the complement thereof; positions 820-823 according to SEQ ID NO:19, or the complement thereof; positions 741-744 according to SEQ ID NO:24, or the complement thereof; positions 980-983 according to SEQ ID NO:29, or the complement thereof; position 1,410 according to SEQ ID NO:15, or the complement thereof; position 1,311 according to SEQ ID NO:20, or the complement thereof; position 1,232 according to SEQ ID NO:25, or the complement thereof; position 1,471 according to SEQ ID NO:30, or the complement thereof; position 830 according to SEQ ID NO:100, or the complement thereof; position 731 according to SEQ ID NO:101, or the complement thereof; position 652 according to SEQ ID NO:102, or the complement thereof; position 891 according to SEQ ID NO:103, or the complement thereof;

wherein when the sequenced portion of the GPR75 mRNA molecule in the biological sample: lacks a CCAGUAG heptanucleotide at positions corresponding to positions 539-545 according to SEQ ID NO:7; lacks a CCAGUAG heptanucleotide at positions corresponding to positions 440-446 according to SEQ ID NO:8; lacks a CCAGUAG heptanucleotide at positions corresponding to positions 361-367 according to SEQ ID NO:9; lacks a CCAGUAG heptanucleotide at positions corresponding to positions 600-606 according to SEQ ID NO:10; comprises an adenine at a position corresponding to position 556 according to SEQ ID NO:12; comprises an adenine at a position corresponding to position 457 according to SEQ ID NO:17; comprises an adenine at a position corresponding to position 378 according to SEQ ID NO:22; comprises an adenine at a position corresponding to position 617 according to SEQ ID NO:27; comprises a uracil at a position corresponding to position 910 according to SEQ ID NO:13; comprises a uracil at a position corresponding to position 811 according to SEQ ID NO:18; comprises a uracil at a position corresponding to position 732 according to SEQ ID NO:23; comprises a uracil at a position corresponding to position 971 according to SEQ ID NO:28; lacks an AAAG tetranucleotide at positions corresponding to positions 919-922 according to SEQ ID NO:7; lacks an AAAG tetranucleotide at positions corresponding to positions 820-823 according to SEQ ID NO:8; lacks an AAAG tetranucleotide at positions corresponding to positions 741-744 according to SEQ ID NO:9; lacks an AAAG tetranucleotide at positions corresponding to positions 980-983 according to SEQ ID NO:10; comprises an insertion of a uracil at a position corresponding to position 1,410 according to SEQ ID NO:15; comprises an insertion of a uracil at a position corresponding to position 1,311 according to SEQ ID NO:20; comprises an insertion of a uracil at a position corresponding to position 1,232 according to SEQ ID NO:25; comprises an insertion of a uracil at a position corresponding to position 1,471 according to SEQ ID NO:30; comprises a guanine at a position corresponding to position 830 according to SEQ ID NO:100; comprises a guanine at a position corresponding to position 731 according to SEQ ID NO:101; comprises a guanine at a position corresponding to position 652 according to SEQ ID NO:102; or comprises a guanine at a position corresponding to position 891 according to SEQ ID NO:103, then the GPR75 mRNA molecule in the biological sample is a GPR75 missense variant mRNA molecule.

Embodiment 22. The method according to any one of embodiments 14 to 19, wherein the detecting step comprises sequencing at least a portion of the nucleotide sequence of the GPR75 cDNA molecule produced from an mRNA molecule in the biological sample, wherein the sequenced portion comprises a position corresponding to: positions 539-545 according to SEQ ID NO:35, or the complement thereof; positions 440-446 according to SEQ ID NO:40, or the complement thereof; positions 361-367 according to SEQ ID NO:45, or the complement thereof; positions 600-606 according to SEQ ID NO:50, or the complement thereof; position 556 according to SEQ ID NO:36, or the complement thereof; position 457 according to SEQ ID NO:41, or the complement thereof; position 378 according to SEQ ID NO:46, or the complement thereof; position 617 according to SEQ ID NO:51, or the complement thereof; position 910 according to SEQ ID NO:37, or the complement thereof; position 811 according to SEQ ID NO:42, or the complement thereof; position 732 according to SEQ ID NO:47, or the complement thereof; position 971 according to SEQ ID NO:52, or the complement thereof; positions 919-922 according to SEQ ID NO:38, or the complement thereof; positions 820-823 according to SEQ ID NO:43, or the complement thereof; positions 741-744 according to SEQ ID NO:48, or the complement thereof; positions 980-983 according to SEQ ID NO:53, or the complement thereof; position 1,410 according to SEQ ID NO:39, or the complement thereof; position 1,311 according to SEQ ID NO:44, or the complement thereof; position 1,232 according to SEQ ID NO:49, or the complement thereof; position 1,471 according to SEQ ID NO:54, or the complement thereof; position 830 according to SEQ ID NO:104, or the complement thereof; position 731 according to SEQ ID NO:105, or the complement thereof; position 652 according to SEQ ID NO:106, or the complement thereof; or position 891 according to SEQ ID NO:107, or the complement thereof;

wherein when the sequenced portion of the GPR75 cDNA molecule in the biological sample: lacks a CCAGTAG heptanucleotide at positions corresponding to positions 539-545 according to SEQ ID NO:31; lacks a CCAGTAG heptanucleotide at positions corresponding to positions 440-446 according to SEQ ID NO:32; lacks a CCAGTAG heptanucleotide at positions corresponding to positions 361-367 according to SEQ ID NO:33; lacks a CCAGTAG heptanucleotide at positions corresponding to positions 600-606 according to SEQ ID NO:34; comprises an adenine at a position corresponding to position 556 according to SEQ ID NO:36; comprises an adenine at a position corresponding to position 457 according to SEQ ID NO:41; comprises an adenine at a position corresponding to position 378 according to SEQ ID NO:46; comprises an adenine at a position corresponding to position 617 according to SEQ ID NO:51; comprises a thymine at a position corresponding to position 910 according to SEQ ID NO:37; comprises a thymine at a position corresponding to position 811 according to SEQ ID NO:42; comprises a thymine at a position corresponding to position 732 according to SEQ ID NO:47; comprises a thymine at a position corresponding to position 971 according to SEQ ID NO:52; lacks an AAAG tetranucleotide at positions corresponding to positions 919-922 according to SEQ ID NO:31; lacks an AAAG tetranucleotide at positions corresponding to positions 820-823 according to SEQ ID NO:32; lacks an AAAG tetranucleotide at positions corresponding to positions 741-744 according to SEQ ID NO:33; lacks an AAAG tetranucleotide at positions corresponding to positions 980-983 according to SEQ ID NO:34; comprises an insertion of a thymine at a position corresponding to position 1,410 according to SEQ ID NO:39; comprises an insertion of a thymine at a position corresponding to position 1,311 according to SEQ ID NO:44; comprises an insertion of a thymine at a position corresponding to position 1,232 according to SEQ ID NO:49; comprises an insertion of a thymine at a position corresponding to position 1,471 according to SEQ ID NO:54; comprises a guanine at a position corresponding to position 830 according to SEQ ID NO:104; comprises a guanine at a position corresponding to position 731 according to SEQ ID NO:105; comprises a guanine at a position corresponding to position 652 according to SEQ ID NO:106; or comprises a guanine at a position corresponding to position 891 according to SEQ ID NO:107, then the GPR75 cDNA molecule in the biological sample is a GPR75 missense variant cDNA molecule.

Embodiment 23. The method according to any one of embodiments 14 to 19, wherein the detecting step comprises:

a) contacting the biological sample with a primer hybridizing to a portion of the nucleotide sequence of the GPR75 genomic nucleic acid molecule that is proximate to a position corresponding to: positions 5,540-5,546 according to SEQ ID NO:2, position 5,557 according to SEQ ID NO:3, position 5,911 according to SEQ ID NO:4, positions 5,920-5,923 according to SEQ ID NO:5, position 6,411 according to SEQ ID NO:6, or position 5,831 according to SEQ ID NO:99;

b) extending the primer at least through the position of the nucleotide sequence of the GPR75 genomic nucleic acid molecule corresponding to: positions 5,540-5,546 according to SEQ ID NO:2, position 5,557 according to SEQ ID NO:3, position 5,911 according to SEQ ID NO:4, positions 5,920-5,923 according to SEQ ID NO:5, position 6,411 according to SEQ ID NO:6, or position 5,831 according to SEQ ID NO:99; and c) determining whether the extension product of the primer: lacks a CCAGTAG heptanucleotide at positions corresponding to positions 5,540-5,546 according to SEQ ID NO:1, comprises an adenine at a position corresponding to position 5,557 according to SEQ ID NO:3, comprises a thymine at a position corresponding to position 5,911 according to SEQ ID NO:4, lacks an AAAG tetranucleotide at positions corresponding to positions 5,920-5,923 according to SEQ ID NO:1, comprises an insertion of thymine at a position corresponding to position 6,411 according to SEQ ID NO:6, or comprises a guanine at a position corresponding to position 5,831 according to SEQ ID NO:99.

Embodiment 24. The method according to any one of embodiments 14 to 19, wherein the detecting step comprises:

a) contacting the biological sample with a primer hybridizing to a portion of the nucleotide sequence of the GPR75 mRNA molecule that is proximate to a position corresponding to: positions 539-545 according to SEQ ID NO:11, positions 440-446 according to SEQ ID NO:16, positions 361-367 according to SEQ ID NO:21, positions 600-606 according to SEQ ID NO:26, position 556 according to SEQ ID NO:12, position 457 according to SEQ ID NO:17, position 378 according to SEQ ID NO:22, position 617 according to SEQ ID NO:27, position 910 according to SEQ ID NO:13, position 811 according to SEQ ID NO:18, position 732 according to SEQ ID NO:23, position 971 according to SEQ ID NO:28, positions 919-922 according to SEQ ID NO:14, positions 820-823 according to SEQ ID NO:19, positions 741-744 according to SEQ ID NO:24, positions 980-983 according to SEQ ID NO:29, position 1,410 according to SEQ ID NO:15, position 1,311 according to SEQ ID NO:20, position 1,232 according to SEQ ID NO:25, position 1,471 according to SEQ ID NO:30, position 830 according to SEQ ID NO:100, position 731 according to SEQ ID NO:101, position 652 according to SEQ ID NO:102, or position 891 according to SEQ ID NO:103;

b) extending the primer at least through the position of the nucleotide sequence of the GPR75 mRNA molecule corresponding to: positions 539-545 according to SEQ ID NO:11, positions 440-446 according to SEQ ID NO:16, positions 361-367 according to SEQ ID NO:21, positions 600-606 according to SEQ ID NO:26, position 556 according to SEQ ID NO:12, position 457 according to SEQ ID NO:17, position 378 according to SEQ ID NO:22, position 617 according to SEQ ID NO:27, position 910 according to SEQ ID NO:13, position 811 according to SEQ ID NO:18, position 732 according to SEQ ID NO:23, position 971 according to SEQ ID NO:28, positions 919-922 according to SEQ ID NO:14, positions 820-823 according to SEQ ID NO:19, positions 741-744 according to SEQ ID NO:24, positions 980-983 according to SEQ ID NO:29, position 1,410 according to SEQ ID NO:15, position 1,311 according to SEQ ID NO:20, position 1,232 according to SEQ ID NO:25, position 1,471 according to SEQ ID NO:30, position 830 according to SEQ ID NO:100, position 731 according to SEQ ID NO:101, position 652 according to SEQ ID NO:102, or position 891 according to SEQ ID NO:103; and c) determining whether the extension product of the primer: lacks a CCAGUAG heptanucleotide at positions corresponding to positions 539-545 according to SEQ ID NO:7, lacks a CCAGUAG heptanucleotide at positions corresponding to positions 440-446 according to SEQ ID NO:8, lacks a CCAGUAG heptanucleotide at positions corresponding to positions 361-367 according to SEQ ID NO:9, lacks a CCAGUAG heptanucleotide at positions corresponding to positions 600-606 according to SEQ ID NO:10, comprises an adenine at a position corresponding to position 556 according to SEQ ID NO:12, comprises an adenine at a position corresponding to position 457 according to SEQ ID NO:17, comprises an adenine at a position corresponding to position 378 according to SEQ ID NO:22, comprises an adenine at a position corresponding to position 617 according to SEQ ID NO:27, comprises a uracil at a position corresponding to position 910 according to SEQ ID NO:13, comprises a uracil at a position corresponding to position 811 according to SEQ ID NO:18, comprises a uracil at a position corresponding to position 732 according to SEQ ID NO:23, comprises a uracil at a position corresponding to position 971 according to SEQ ID NO:28, lacks an AAAG tetranucleotide at positions corresponding to positions 919-922 according to SEQ ID NO:7, lacks an AAAG tetranucleotide at positions corresponding to positions 820-823 according to SEQ ID NO:8, lacks an AAAG tetranucleotide at positions corresponding to positions 741-744 according to SEQ ID NO:9, lacks an AAAG tetranucleotide at positions corresponding to positions 980-983 according to SEQ ID NO:10, comprises an insertion of a uracil at a position corresponding to position 1,410 according to SEQ ID NO:15, comprises an insertion of a uracil at a position corresponding to position 1,311 according to SEQ ID NO:20, comprises an insertion of a uracil at a position corresponding to position 1,232 according to SEQ ID NO:25, comprises an insertion of a uracil at a position corresponding to position 1,471 according to SEQ ID NO:30, comprises a guanine at a position corresponding to position 830 according to SEQ ID NO:100, comprises a guanine at a position corresponding to position 731 according to SEQ ID NO:101, comprises a guanine at a position corresponding to position 652 according to SEQ ID NO:102, or comprises a guanine at a position corresponding to position 891 according to SEQ ID NO:103.

Embodiment 25. The method according to any one of embodiments 14 to 19, wherein the detecting step comprises:

a) contacting the biological sample with a primer hybridizing to a portion of the nucleotide sequence of the GPR75 cDNA molecule that is proximate to a position corresponding to: positions 539-545 according to SEQ ID NO:35, positions 440-446 according to SEQ ID NO:40, positions 361-367 according to SEQ ID NO:45, positions 600-606 according to SEQ ID NO:50, position 556 according to SEQ ID NO:36, position 457 according to SEQ ID NO:41, position 378 according to SEQ ID NO:46, position 617 according to SEQ ID NO:51, position 910 according to SEQ ID NO:37, position 811 according to SEQ ID NO:42, position 732 according to SEQ ID NO:47, position 971 according to SEQ ID NO:52, positions 919-922 according to SEQ ID NO:38, positions 820-823 according to SEQ ID NO:43, positions 741-744 according to SEQ ID NO:48, positions 980-983 according to SEQ ID NO:53, position 1,410 according to SEQ ID NO:39, position 1,311 according to SEQ ID NO:44, position 1,232 according to SEQ ID NO:49, position 1,471 according to SEQ ID NO:54, position 830 according to SEQ ID NO:104, position 731 according to SEQ ID NO:105, position 652 according to SEQ ID NO:106, or position 891 according to SEQ ID NO:107;

b) extending the primer at least through the position of the nucleotide sequence of the GPR75 cDNA molecule corresponding to: positions 539-545 according to SEQ ID NO:35, positions 440-446 according to SEQ ID NO:40, positions 361-367 according to SEQ ID NO:45, positions 600-606 according to SEQ ID NO:50, position 556 according to SEQ ID NO:36, position 457 according to SEQ ID NO:41, position 378 according to SEQ ID NO:46, position 617 according to SEQ ID NO:51, position 910 according to SEQ ID NO:37, position 811 according to SEQ ID NO:42, position 732 according to SEQ ID NO:47, position 971 according to SEQ ID NO:52, positions 919-922 according to SEQ ID NO:38, positions 820-823 according to SEQ ID NO:43, positions 741-744 according to SEQ ID NO:48, positions 980-983 according to SEQ ID NO:53, position 1,410 according to SEQ ID NO:39, position 1,311 according to SEQ ID NO:44, position 1,232 according to SEQ ID NO:49, position 1,471 according to SEQ ID NO:54, position 830 according to SEQ ID NO:104, position 731 according to SEQ ID NO:105, position 652 according to SEQ ID NO:106, or position 891 according to SEQ ID NO:107; and c) determining whether the extension product of the primer: lacks a CCAGTAG heptanucleotide at positions corresponding to positions 539-545 according to SEQ ID NO:31, lacks a CCAGTAG heptanucleotide at positions corresponding to positions 440-446 according to SEQ ID NO:32, lacks a CCAGTAG heptanucleotide at positions corresponding to positions 361-367 according to SEQ ID NO:33, lacks a CCAGTAG heptanucleotide at positions corresponding to positions 600-606 according to SEQ ID NO:34, comprises an adenine at a position corresponding to position 556 according to SEQ ID NO:36, comprises an adenine at a position corresponding to position 457 according to SEQ ID NO:41, comprises an adenine at a position corresponding to position 378 according to SEQ ID NO:46, comprises an adenine at a position corresponding to position 617 according to SEQ ID NO:51, comprises a thymine at a position corresponding to position 910 according to SEQ ID NO:37, comprises a thymine at a position corresponding to position 811 according to SEQ ID NO:42, comprises a thymine at a position corresponding to position 732 according to SEQ ID NO:47, comprises a thymine at a position corresponding to position 971 according to SEQ ID NO:52, lacks an AAAG tetranucleotide at positions corresponding to positions 919-922 according to SEQ ID NO:31, lacks an AAAG tetranucleotide at positions corresponding to positions 820-823 according to SEQ ID NO:32, lacks an AAAG tetranucleotide at positions corresponding to positions 741-744 according to SEQ ID NO:33, lacks an AAAG tetranucleotide at positions corresponding to positions 980-983 according to SEQ ID NO:34, comprises an insertion of a thymine at a position corresponding to position 1,410 according to SEQ ID NO:39, comprises an insertion of a thymine at a position corresponding to position 1,311 according to SEQ ID NO:44, comprises an insertion of a thymine at a position corresponding to position 1,232 according to SEQ ID NO:49, comprises an insertion of a thymine at a position corresponding to position 1,471 according to SEQ ID NO:54, comprises a guanine at a position corresponding to position 830 according to SEQ ID NO:104, comprises a guanine at a position corresponding to position 731 according to SEQ ID NO:105, comprises a guanine at a position corresponding to position 652 according to SEQ ID NO:106, or comprises a guanine at a position corresponding to position 891 according to SEQ ID NO:107.

Embodiment 26. The method according to any one of embodiments 20 to 25, wherein the detecting step comprises sequencing the entire nucleic acid molecule.

Embodiment 27. The method according to any one of embodiments 14 to 19, wherein the detecting step comprises:

a) amplifying at least a portion of the nucleic acid molecule that encodes the human GPR75 polypeptide, wherein the portion: lacks a CCAGTAG heptanucleotide at positions corresponding to positions 5,540-5,546 according to SEQ ID NO:1, or the complement thereof; comprises an adenine at a position corresponding to position 5,557 according to SEQ ID NO:3, or the complement thereof; comprises a thymine at a position corresponding to position 5,911 according to SEQ ID NO:4, or the complement thereof; lacks an AAAG tetranucleotide at positions corresponding to positions 5,920-5,923 according to SEQ ID NO:1, or the complement thereof; comprises an insertion of a thymine at a position corresponding to position 6,411 according to SEQ ID NO:6, or the complement thereof; or comprises a guanine at a position corresponding to position 5,831 according to SEQ ID NO:99, or the complement thereof b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGTAG heptanucleotide at positions corresponding to positions 5,540-5,546 according to SEQ ID NO:1, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:1, or the complement thereof; comprising an insertion of a thymine at a position corresponding to position 6,411 according to SEQ ID NO:6, or the complement thereof, or comprises a guanine at a position corresponding to position 5,831 according to SEQ ID NO:99, or the complement thereof; and d) detecting the detectable label.

Embodiment 28. The method according to any one of embodiments 14 to 19, wherein the detecting step comprises:

a) amplifying at least a portion of the nucleic acid molecule that encodes the human GPR75 polypeptide, wherein the portion: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; comprises an adenine at a position corresponding to position 556 according to SEQ ID NO:12, or the complement thereof; comprises an adenine at a position corresponding to position 457 according to SEQ ID NO:17, or the complement thereof; comprises an adenine at a position corresponding to position 378 according to SEQ ID NO:22, or the complement thereof; comprises an adenine at a position corresponding to position 617 according to SEQ ID NO:27, or the complement thereof; comprises a uracil at a position corresponding to position 910 according to SEQ ID NO:13, or the complement thereof; comprises a uracil at a position corresponding to position 811 according to SEQ ID NO:18, or the complement thereof; comprises a uracil at a position corresponding to position 732 according to SEQ ID NO:23, or the complement thereof; comprises a uracil at a position corresponding to position 971 according to SEQ ID NO:28, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; comprises an insertion of a uracil at a position corresponding to position 1,471 according to SEQ ID NO:30, or the complement thereof; comprises a guanine at a position corresponding to position 830 according to SEQ ID NO:100, or the complement thereof; comprises a guanine at a position corresponding to position 731 according to SEQ ID NO:101, or the complement thereof; comprises a guanine at a position corresponding to position 652 according to SEQ ID NO:102, or the complement thereof; or comprises a guanine at a position corresponding to position 891 according to SEQ ID NO:103, or the complement thereof;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; lacking a CCAGUAG heptanucleotide at positions corresponding to positions 600-606 according to SEQ ID NO:10, or the complement thereof; comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; lacking an AAAG tetranucleotide at positions corresponding to positions 980-983 according to SEQ ID NO:10, or the complement thereof; comprising an insertion of a uracil at a position corresponding to position 1,410 according to SEQ ID NO:15, or the complement thereof; comprising an insertion of a uracil at a position corresponding to position 1,311 according to SEQ ID NO:20, or the complement thereof; comprising an insertion of a uracil at a position corresponding to position 1,232 according to SEQ ID NO:25, or the complement thereof; comprising an insertion of a uracil at a position corresponding to position 1,471 according to SEQ ID NO:30, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof; and d) detecting the detectable label.

Embodiment 29. The method according to any one of embodiments 14 to 19, wherein the detecting step comprises:

a) amplifying at least a portion of the nucleic acid molecule that encodes the human GPR75 polypeptide, wherein the portion: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; comprises an adenine at a position corresponding to position 556 according to SEQ ID NO:36, or the complement thereof; comprises an adenine at a position corresponding to position 457 according to SEQ ID NO:41, or the complement thereof; comprises an adenine at a position corresponding to position 378 according to SEQ ID NO:46, or the complement thereof; comprises an adenine at a position corresponding to position 617 according to SEQ ID NO:51, or the complement thereof; comprises a thymine at a position corresponding to position 910 according to SEQ ID NO:37, or the complement thereof; comprises a thymine at a position corresponding to position 811 according to SEQ ID NO:42, or the complement thereof; comprises a thymine at a position corresponding to position 732 according to SEQ ID NO:47, or the complement thereof; comprises a thymine at a position corresponding to position 971 according to SEQ ID NO:52, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; comprises an insertion of a thymine at a position corresponding to position 1,471 according to SEQ ID NO:54, or the complement thereof; comprises a guanine at a position corresponding to position 830 according to SEQ ID NO:104, or the complement thereof; comprises a guanine at a position corresponding to position 731 according to SEQ ID NO:105, or the complement thereof; comprises a guanine at a position corresponding to position 652 according to SEQ ID NO:106, or the complement thereof; or comprises a guanine at a position corresponding to position 891 according to SEQ ID NO:107, or the complement thereof;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; lacking a CCAGTAG heptanucleotide at positions corresponding to positions 600-606 according to SEQ ID NO:34, or the complement thereof; comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; lacking an AAAG tetranucleotide at positions corresponding to positions 980-983 according to SEQ ID NO:34, or the complement thereof; comprising an insertion of a thymine at a position corresponding to position 1,410 according to SEQ ID NO:39, or the complement thereof; comprising an insertion of a thymine at a position corresponding to position 1,311 according to SEQ ID NO:44, or the complement thereof; comprising an insertion of a thymine at a position corresponding to position 1,232 according to SEQ ID NO:49, or the complement thereof; comprising an insertion of a thymine at a position corresponding to position 1,471 according to SEQ ID NO:54, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof; and d) detecting the detectable label.

Embodiment 30. The method according to embodiment 29, wherein the nucleic acid molecule in the sample is mRNA and the mRNA is reverse-transcribed into cDNA prior to the amplifying step.

Embodiment 31. The method according to any one of embodiments 14 to 19, wherein the detecting step comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGTAG heptanucleotide at positions corresponding to positions 5,540-5,546 according to SEQ ID NO:1, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:1, or the complement thereof; comprising an insertion of a thymine at a position corresponding to position 6,411 according to SEQ ID NO:6, or the complement thereof or comprising a guanine at a position corresponding to position 5,831 according to SEQ ID NO:99, or the complement thereof; and detecting the detectable label.

Embodiment 32. The method according to any one of embodiments 14 to 19, wherein the detecting step comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; lacking a CCAGUAG heptanucleotide at positions corresponding to positions 600-606 according to SEQ ID NO:10, or the complement thereof; comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; lacking an AAAG tetranucleotide at positions corresponding to positions 980-983 according to SEQ ID NO:10, or the complement thereof; comprising an insertion of a uracil at a position corresponding to position 1,410 according to SEQ ID NO:15, or the complement thereof; comprising an insertion of a uracil at a position corresponding to position 1,311 according to SEQ ID NO:20, or the complement thereof; comprising an insertion of a uracil at a position corresponding to position 1,232 according to SEQ ID NO:25, or the complement thereof; comprising an insertion of a uracil at a position corresponding to position 1,471 according to SEQ ID NO:30, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof; and detecting the detectable label.

Embodiment 33. The method according to any one of embodiments 14 to 19, wherein the detecting step comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; lacking a CCAGTAG heptanucleotide at positions corresponding to positions 600-606 according to SEQ ID NO:34, or the complement thereof; comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; lacking an AAAG tetranucleotide at positions corresponding to positions 980-983 according to SEQ ID NO:34, or the complement thereof; comprising an insertion of a thymine at a position corresponding to position 1,410 according to SEQ ID NO:39, or the complement thereof; comprising an insertion of a thymine at a position corresponding to position 1,311 according to SEQ ID NO:44, or the complement thereof; comprising an insertion of a thymine at a position corresponding to position 1,232 according to SEQ ID NO:49, or the complement thereof; or comprising an insertion of a thymine at a position corresponding to position 1,471 according to SEQ ID NO:54, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof; and detecting the detectable label.

Embodiment 34. A method of treating a subject with a therapeutic agent that treats or inhibits obesity, wherein the subject is obese, the method comprising the steps of:

determining whether the subject has a G-Protein Coupled Receptor 75 (GPR75) missense variant nucleic acid molecule encoding a predicted loss-of-function GPR75 polypeptide by:

obtaining or having obtained a biological sample from the subject; and performing or having performed a sequence analysis on the biological sample to determine if the subject has a genotype comprising the GPR75 missense variant nucleic acid molecule; and administering or continuing to administer the therapeutic agent that treats or inhibits obesity and/or a GPR75 inhibitor in a standard dosage amount to a subject that is GPR75 reference; and administering or continuing to administer the therapeutic agent that treats or inhibits obesity and/or a GPR75 inhibitor in an amount that is the same as or lower than a standard dosage amount to a subject that is heterozygous for a GPR75 missense variant nucleic acid molecule;

wherein the presence of a genotype having the GPR75 missense variant nucleic acid molecule encoding a predicted loss-of-function GPR75 polypeptide indicates the subject has a reduced risk of developing obesity.

Embodiment 35. The method according to embodiment 34, wherein the subject is GPR75 reference, and the subject is administered or continued to be administered the therapeutic agent that treats or inhibits obesity and/or a GPR75 inhibitor in a standard dosage amount.

Embodiment 36. The method according to embodiment 34, wherein the subject is heterozygous for a GPR75 missense variant nucleic acid molecule, and the subject is administered or continued to be administered the therapeutic agent that treats or inhibits obesity and/or a GPR75 inhibitor in an amount that is the same as or lower than a standard dosage amount.

Embodiment 37. The method according to any one of embodiments 34 to 36, wherein the GPR75 missense variant nucleic acid molecule is a nucleic acid molecule encoding Ala110fs, Ala116Thr, Tyr207Cys, Gln234Stop, Arg236fs, or Cys400fs.

Embodiment 38. The method according to embodiment 37, wherein the GPR75 missense variant nucleic acid molecule is:

a genomic nucleic acid molecule having a nucleotide sequence: lacking a CCAGTAG heptanucleotide at positions corresponding to positions 5,540-5,546 according to SEQ ID NO:1, comprising an adenine at a position corresponding to position 5,557 according to SEQ ID NO:3, comprising a thymine at a position corresponding to position 5,911 according to SEQ ID NO:4, lacking an AAAG tetranucleotide at positions corresponding to positions 5,920-5,923 according to SEQ ID NO:1, comprising an insertion of a thymine at a position corresponding to position 6,411 according to SEQ ID NO:6, or comprising a guanine at a position corresponding to position 5,831 according to SEQ ID NO:99;

an mRNA molecule having a nucleotide sequence: lacking a CCAGUAG heptanucleotide at positions corresponding to positions 539-545 according to SEQ ID NO:7, lacking a CCAGUAG heptanucleotide at positions corresponding to positions 440-446 according to SEQ ID NO:8, lacking a CCAGUAG heptanucleotide at positions corresponding to positions 361-367 according to SEQ ID NO:9, lacking a CCAGUAG heptanucleotide at positions corresponding to positions 600-606 according to SEQ ID NO:10; comprising an adenine at a position corresponding to position 556 according to SEQ ID NO:12, comprising an adenine at a position corresponding to position 457 according to SEQ ID NO:17, comprising an adenine at a position corresponding to position 378 according to SEQ ID NO:22, comprising an adenine at a position corresponding to position 617 according to SEQ ID NO:27; comprising a uracil at a position corresponding to position 910 according to SEQ ID NO:13, comprising a uracil at a position corresponding to position 811 according to SEQ ID NO:18, comprising a uracil at a position corresponding to position 732 according to SEQ ID NO:23, comprising a uracil at a position corresponding to position 971 according to SEQ ID NO:28; lacking an AAAG tetranucleotide at positions corresponding to positions 919-922 according to SEQ ID NO:7, lacking an AAAG tetranucleotide at positions corresponding to positions 820-823 according to SEQ ID NO:8, lacking an AAAG tetranucleotide at positions corresponding to positions 741-744 according to SEQ ID NO:9, lacking an AAAG tetranucleotide at positions corresponding to positions 980-983 according to SEQ ID NO:10; comprising an insertion of a uracil at a position corresponding to position 1,410 according to SEQ ID NO:15, comprising an insertion of a uracil at a position corresponding to position 1,311 according to SEQ ID NO:20, comprising an insertion of a uracil at a position corresponding to position 1,232 according to SEQ ID NO:25, or comprising an insertion of a uracil at a position corresponding to position 1,471 according to SEQ ID NO:30, comprising a guanine at a position corresponding to position 830 according to SEQ ID NO:100, comprising a guanine at a position corresponding to position 731 according to SEQ ID NO:101, comprising a guanine at a position corresponding to position 652 according to SEQ ID NO:102, or comprising a guanine at a position corresponding to position 891 according to SEQ ID NO:103; or a cDNA molecule produced from an mRNA molecule, wherein the cDNA molecule has a nucleotide sequence: lacking a CCAGTAG heptanucleotide at positions corresponding to positions 539-545 according to SEQ ID NO:31, lacking a CCAGTAG heptanucleotide at positions corresponding to positions 440-446 according to SEQ ID NO:32, lacking a CCAGTAG heptanucleotide at positions corresponding to positions 361-367 according to SEQ ID NO:33, lacking a CCAGTAG heptanucleotide at positions corresponding to positions 600-606 according to SEQ ID NO:34; comprising an adenine at a position corresponding to position 556 according to SEQ ID NO:36, comprising an adenine at a position corresponding to position 457 according to SEQ ID NO:41, comprising an adenine at a position corresponding to position 378 according to SEQ ID NO:46, comprising an adenine at a position corresponding to position 617 according to SEQ ID NO:51; comprising a thymine at a position corresponding to position 910 according to SEQ ID NO:37, comprising a thymine at a position corresponding to position 811 according to SEQ ID NO:42, comprising a thymine at a position corresponding to position 732 according to SEQ ID NO:47, comprising a thymine at a position corresponding to position 971 according to SEQ ID NO:52; lacking an AAAG tetranucleotide at positions corresponding to positions 919-922 according to SEQ ID NO:31, lacking an AAAG tetranucleotide at positions corresponding to positions 820-823 according to SEQ ID NO:32, lacking an AAAG tetranucleotide at positions corresponding to positions 741-744 according to SEQ ID NO:33, lacking an AAAG tetranucleotide at positions corresponding to positions 980-983 according to SEQ ID NO:34; comprising an insertion of a thymine at a position corresponding to position 1,410 according to SEQ ID NO:39, comprising an insertion of a thymine at a position corresponding to position 1,311 according to SEQ ID NO:44, comprising an insertion of a thymine at a position corresponding to position 1,232 according to SEQ ID NO:49, comprising an insertion of a thymine at a position corresponding to position 1,471 according to SEQ ID NO:54, comprising a guanine at a position corresponding to position 830 according to SEQ ID NO:104, comprising a guanine at a position corresponding to position 731 according to SEQ ID NO:105, comprising a guanine at a position corresponding to position 652 according to SEQ ID NO:106, or comprising a guanine at a position corresponding to position 891 according to SEQ ID NO:107.

Embodiment 39. The method according to any one of embodiments 34 to 38, wherein the sequence analysis comprises sequencing at least a portion of the nucleotide sequence of the GPR75 genomic nucleic acid molecule in the biological sample, wherein the sequenced portion comprises a position corresponding to: positions 5,540-5,546 according to SEQ ID NO:2, or the complement thereof; position 5,557 according to SEQ ID NO:3, or the complement thereof; position 5,911 according to SEQ ID NO:4, or the complement thereof; positions 5,920-5,923 according to SEQ ID NO:5, or the complement thereof; position 6,411 according to SEQ ID NO:6, or the complement thereof; or position 5,831 according to SEQ ID NO:99, or the complement thereof;

wherein when the sequenced portion of the GPR75 genomic nucleic acid molecule in the biological sample: lacks a CCAGTAG heptanucleotide at positions corresponding to positions 5,540-5,546 according to SEQ ID NO:1, comprises an adenine at a position corresponding to position 5,557 according to SEQ ID NO:3, comprises a thymine at a position corresponding to position 5,911 according to SEQ ID NO:4, lacks an AAAG tetranucleotide at positions corresponding to positions 5,920-5,923 according to SEQ ID NO:1, comprises an insertion of a thymine at a position corresponding to position 6,411 according to SEQ ID NO:6, or comprises a guanine at a position corresponding to position 5,831 according to SEQ ID NO:99, then the GPR75 genomic nucleic acid molecule in the biological sample is a GPR75 missense variant genomic nucleic acid molecule.

Embodiment 40. The method according to any one of embodiments 34 to 38, wherein the sequence analysis comprises sequencing at least a portion of the nucleotide sequence of the GPR75 mRNA molecule in the biological sample, wherein the sequenced portion comprises a position corresponding to: positions 539-545 according to SEQ ID NO:11, or the complement thereof; positions 440-446 according to SEQ ID NO:16, or the complement thereof; positions 361-367 according to SEQ ID NO:21, or the complement thereof; positions 600-606 according to SEQ ID NO:26, or the complement thereof; position 556 according to SEQ ID NO:12, or the complement thereof; position 457 according to SEQ ID NO:17, or the complement thereof; position 378 according to SEQ ID NO:22, or the complement thereof; position 617 according to SEQ ID NO:27, or the complement thereof; position 910 according to SEQ ID NO:13, or the complement thereof; position 811 according to SEQ ID NO:18, or the complement thereof; position 732 according to SEQ ID NO:23, or the complement thereof; position 971 according to SEQ ID NO:28, or the complement thereof; positions 919-922 according to SEQ ID NO:14, or the complement thereof; positions 820-823 according to SEQ ID NO:19, or the complement thereof; positions 741-744 according to SEQ ID NO:24, or the complement thereof; positions 980-983 according to SEQ ID NO:29, or the complement thereof; position 1,410 according to SEQ ID NO:15, or the complement thereof; position 1,311 according to SEQ ID NO:20, the complement thereof; position 1,232 according to SEQ ID NO:25, or the complement thereof; or position 1,471 according to SEQ ID NO:30, or the complement thereof; position 830 according to SEQ ID NO:100, or the complement thereof; position 731 according to SEQ ID NO:101, or the complement thereof; position 652 according to SEQ ID NO:102, or the complement thereof; or position 891 according to SEQ ID NO:103, or the complement thereof;

wherein when the sequenced portion of the GPR75 mRNA molecule in the biological sample: lacks a CCAGUAG heptanucleotide at positions corresponding to positions 539-545 according to SEQ ID NO:7; lacks a CCAGUAG heptanucleotide at positions corresponding to positions 440-446 according to SEQ ID NO:8; lacks a CCAGUAG heptanucleotide at positions corresponding to positions 361-367 according to SEQ ID NO:9; lacks a CCAGUAG heptanucleotide at positions corresponding to positions 600-606 according to SEQ ID NO:10; comprises an adenine at a position corresponding to position 556 according to SEQ ID NO:12; comprises an adenine at a position corresponding to position 457 according to SEQ ID NO:17; comprises an adenine at a position corresponding to position 378 according to SEQ ID NO:22; comprises an adenine at a position corresponding to position 617 according to SEQ ID NO:27; comprises a uracil at a position corresponding to position 910 according to SEQ ID NO:13; comprises a uracil at a position corresponding to position 811 according to SEQ ID NO:18; comprises a uracil at a position corresponding to position 732 according to SEQ ID NO:23; comprises a uracil at a position corresponding to position 971 according to SEQ ID NO:28; lacks an AAAG tetranucleotide at positions corresponding to positions 919-922 according to SEQ ID NO:7; lacks an AAAG tetranucleotide at positions corresponding to positions 820-823 according to SEQ ID NO:8; lacks an AAAG tetranucleotide at positions corresponding to positions 741-744 according to SEQ ID NO:9; lacks an AAAG tetranucleotide at positions corresponding to positions 980-983 according to SEQ ID NO:10; comprises an insertion of a uracil at a position corresponding to position 1,410 according to SEQ ID NO:15; comprises an insertion of a uracil at a position corresponding to position 1,311 according to SEQ ID NO:20; comprises an insertion of a uracil at a position corresponding to position 1,232 according to SEQ ID NO:25; comprises an insertion of a uracil at a position corresponding to position 1,471 according to SEQ ID NO:30; comprises a guanine at a position corresponding to position 830 according to SEQ ID NO:100; comprises a guanine at a position corresponding to position 731 according to SEQ ID NO:101; comprises a guanine at a position corresponding to position 652 according to SEQ ID NO:102; or comprises a guanine at a position corresponding to position 891 according to SEQ ID NO:103, then the GPR75 mRNA molecule in the biological sample is a GPR75 missense variant mRNA molecule.

Embodiment 41. The method according to any one of embodiments 34 to 38, wherein the sequence analysis comprises sequencing at least a portion of the nucleotide sequence of the GPR75 cDNA molecule in the biological sample, wherein the sequenced portion comprises a position corresponding to: positions 539-545 according to SEQ ID NO:35, or the complement thereof; positions 440-446 according to SEQ ID NO:40, or the complement thereof; positions 361-367 according to SEQ ID NO:45, or the complement thereof; positions 600-606 according to SEQ ID NO:50, or the complement thereof; position 556 according to SEQ ID NO:36, or the complement thereof; position 457 according to SEQ ID NO:41, or the complement thereof; position 378 according to SEQ ID NO:46, or the complement thereof; position 617 according to SEQ ID NO:51, or the complement thereof; position 910 according to SEQ ID NO:37, or the complement thereof; position 811 according to SEQ ID NO:42, or the complement thereof; position 732 according to SEQ ID NO:47, or the complement thereof; position 971 according to SEQ ID NO:52, or the complement thereof; positions 919-922 according to SEQ ID NO:38, or the complement thereof; positions 820-

823 according to SEQ ID NO:43, or the complement thereof; positions 741-744 according to SEQ ID NO:48, or the complement thereof; positions 980-983 according to SEQ ID NO:53, or the complement thereof; position 1,410 according to SEQ ID NO:39, or the complement thereof; position 1,311 according to SEQ ID NO:44, or the complement thereof; position 1,232 according to SEQ ID NO:49, or the complement thereof; position 1,471 according to SEQ ID NO:54, or the complement thereof; position 830 according to SEQ ID NO:104, or the complement thereof; position 731 according to SEQ ID NO:105, or the complement thereof; position 652 according to SEQ ID NO:106, or the complement thereof; or position 891 according to SEQ ID NO:107, or the complement thereof;

wherein when the sequenced portion of the GPR75 cDNA molecule in the biological sample: lacks a CCAGTAG heptanucleotide at positions corresponding to positions 539-545 according to SEQ ID NO:31; lacks a CCAGTAG heptanucleotide at positions corresponding to positions 440-446 according to SEQ ID NO:32; lacks a CCAGTAG heptanucleotide at positions corresponding to positions 361-367 according to SEQ ID NO:33; lacks a CCAGTAG heptanucleotide at positions corresponding to positions 600-606 according to SEQ ID NO:34; comprises an adenine at a position corresponding to position 556 according to SEQ ID NO:36; comprises an adenine at a position corresponding to position 457 according to SEQ ID NO:41; comprises an adenine at a position corresponding to position 378 according to SEQ ID NO:46; comprises an adenine at a position corresponding to position 617 according to SEQ ID NO:51; comprises a thymine at a position corresponding to position 910 according to SEQ ID NO:37; comprises a thymine at a position corresponding to position 811 according to SEQ ID NO:42; comprises a thymine at a position corresponding to position 732 according to SEQ ID NO:47; comprises a thymine at a position corresponding to position 971 according to SEQ ID NO:52; lacks an AAAG tetranucleotide at positions corresponding to positions 919-922 according to SEQ ID NO:31; lacks an AAAG tetranucleotide at positions corresponding to positions 820-823 according to SEQ ID NO:32; lacks an AAAG tetranucleotide at positions corresponding to positions 741-744 according to SEQ ID NO:33; lacks an AAAG tetranucleotide at positions corresponding to positions 980-983 according to SEQ ID NO:34; comprises an insertion of a thymine at a position corresponding to position 1,410 according to SEQ ID NO:39; comprises an insertion of a thymine at a position corresponding to position 1,311 according to SEQ ID NO:44; comprises an insertion of a thymine at a position corresponding to position 1,232 according to SEQ ID NO:49; or comprises an insertion of a thymine at a position corresponding to position 1,471 according to SEQ ID NO:54; comprises a guanine at a position corresponding to position 830 according to SEQ ID NO:104; comprises a guanine at a position corresponding to position 731 according to SEQ ID NO:105; comprises a guanine at a position corresponding to position 652 according to SEQ ID NO:106; or comprises a guanine at a position corresponding to position 891 according to SEQ ID NO:107, then the GPR75 cDNA molecule in the biological sample is a GPR75 missense variant cDNA molecule.

Embodiment 42. The method according to any one of embodiments 34 to 38, wherein the sequence analysis comprises:

a) contacting the biological sample with a primer hybridizing to a portion of the nucleotide sequence of the GPR75 genomic nucleic acid molecule that is proximate to a position corresponding to: positions 5,540-5,546 according to SEQ ID NO:2, position 5,557 according to SEQ ID NO:3, position 5,911 according to SEQ ID NO:4, positions 5,920-5,923 according to SEQ ID NO:5, position 6,411 according to SEQ ID NO:6, or position 5,831 according to SEQ ID NO:99;

b) extending the primer at least through the position of the nucleotide sequence of the GPR75 genomic nucleic acid molecule corresponding to: positions 5,540-5,546 according to SEQ ID NO:2, position 5,557 according to SEQ ID NO:3, position 5,911 according to SEQ ID NO:4, positions 5,920-5,923 according to SEQ ID NO:5, position 6,411 according to SEQ ID NO:6, position 6,411 according to SEQ ID NO:6, or position 5,831 according to SEQ ID NO:99; and c) determining whether the extension product of the primer: lacks a CCAGTAG heptanucleotide at positions corresponding to positions 5,540-5,546 according to SEQ ID NO:1, comprises an adenine at a position corresponding to position 5,557 according to SEQ ID NO:3, comprises a thymine at a position corresponding to position 5,911 according to SEQ ID NO:4, lacks an AAAG tetranucleotide at positions corresponding to positions 5,920-5,923 according to SEQ ID NO:1, comprises an insertion of a thymine at a position corresponding to position 6,411 according to SEQ ID NO:6, or comprises a guanine at a position corresponding to position 5,831 according to SEQ ID NO:99.

Embodiment 43. The method according to any one of embodiments 34 to 38, wherein the sequence analysis comprises:

a) contacting the biological sample with a primer hybridizing to a portion of the nucleotide sequence of the GPR75 mRNA molecule that is proximate to a position corresponding to: positions 539-545 according to SEQ ID NO:11, positions 440-446 according to SEQ ID NO:16, positions 361-367 according to SEQ ID NO:21, positions 600-606 according to SEQ ID NO:26, position 556 according to SEQ ID NO:12, position 457 according to SEQ ID NO:17, position 378 according to SEQ ID NO:22, position 617 according to SEQ ID NO:27, position 910 according to SEQ ID NO:13, position 811 according to SEQ ID NO:18, position 732 according to SEQ ID NO:23, position 971 according to SEQ ID NO:28, positions 919-922 according to SEQ ID NO:14, positions 820-823 according to SEQ ID NO:19, positions 741-744 according to SEQ ID NO:24, positions 980-983 according to SEQ ID NO:29, position 1,410 according to SEQ ID NO:15, position 1,311 according to SEQ ID NO:20, position 1,232 according to SEQ ID NO:25, position 1,471 according to SEQ ID NO:30, position 830 according to SEQ ID NO:100, position 731 according to SEQ ID NO:101, position 652 according to SEQ ID NO:102, or position 891 according to SEQ ID NO:103;

b) extending the primer at least through the position of the nucleotide sequence of the GPR75 mRNA molecule corresponding to: positions 539-545 according to SEQ ID NO:11, positions 440-446 according to SEQ ID NO:16, positions 361-367 according to SEQ ID NO:21, positions 600-606 according to SEQ ID NO:26, position 556 according to SEQ ID NO:12, position 457 according to SEQ ID NO:17, position 378 according to SEQ ID NO:22, position 617 according to SEQ ID NO:27, position 910 according to SEQ ID NO:13, position 811 according to SEQ ID NO:18, position 732 according to SEQ ID NO:23, position 971 according to SEQ ID NO:28, positions 919-922 according to SEQ ID NO:14, positions 820-823 according to SEQ ID NO:19, positions 741-744 according to SEQ ID NO:24, positions 980-983 according to SEQ ID NO:29, position 1,410 according to SEQ ID NO:15, position 1,311 according to SEQ ID NO:20, position 1,232 according to SEQ ID NO:25, position 1,471 according to SEQ ID NO:30, position 830 according to SEQ ID NO:100, position 731 according to SEQ ID NO:101, position 652 according to SEQ ID NO:102, or position 891 according to SEQ ID NO:103; and c) determining whether the extension product of the primer: lacks a CCAGUAG heptanucleotide at positions corresponding to positions 539-545 according to SEQ ID NO:7, lacks a CCAGUAG heptanucleotide at positions corresponding to positions 440-446 according to SEQ ID NO:8, lacks a CCAGUAG heptanucleotide at positions corresponding to positions 361-367 according to SEQ ID NO:9, lacks a CCAGUAG heptanucleotide at positions corresponding to positions 600-606 according to SEQ ID NO:10, comprises an adenine at a position corresponding to position 556 according to SEQ ID NO:12, comprises an adenine at a position corresponding to position 457 according to SEQ ID NO:17, comprises an adenine at a position corresponding to position 378 according to SEQ ID NO:22, comprises an adenine at a position corresponding to position 617 according to SEQ ID NO:27, comprises a uracil at a position corresponding to position 910 according to SEQ ID NO:13, comprises a uracil at a position corresponding to position 811 according to SEQ ID NO:18, comprises a uracil at a position corresponding to position 732 according to SEQ ID NO:23, comprises a uracil at a position corresponding to position 971 according to SEQ ID NO:28, lacks an AAAG tetranucleotide at positions corresponding to positions 919-922 according to SEQ ID NO:7, lacks an AAAG tetranucleotide at positions corresponding to positions 820-823 according to SEQ ID NO:8, lacks an AAAG tetranucleotide at positions corresponding to positions 741-744 according to SEQ ID NO:9, lacks an AAAG tetranucleotide at positions corresponding to positions 980-983 according to SEQ ID NO:10, comprises an insertion of a uracil at a position corresponding to position 1,410 according to SEQ ID NO:15, comprises an insertion of a uracil at a position corresponding to position 1,311 according to SEQ ID NO:20, comprises an insertion of a uracil at a position corresponding to position 1,232 according to SEQ ID NO:25, comprises an insertion of a uracil at a position corresponding to position 1,471 according to SEQ ID NO:30, comprises a guanine at a position corresponding to position 830 according to SEQ ID NO:100, comprises a guanine at a position corresponding to position 731 according to SEQ ID NO:101, comprises a guanine at a position corresponding to position 652 according to SEQ ID NO:102, or comprises a guanine at a position corresponding to position 891 according to SEQ ID NO:103.

Embodiment 44. The method according to any one of embodiments 34 to 38, wherein the sequence analysis comprises:

a) contacting the biological sample with a primer hybridizing to a portion of the nucleotide sequence of the GPR75 cDNA molecule that is proximate to a position corresponding to: positions 539-545 according to SEQ ID NO:35, positions 440-446 according to SEQ ID NO:40, positions 361-367 according to SEQ ID NO:45, positions 600-606 according to SEQ ID NO:50, position 556 according to SEQ ID NO:36, position 457 according to SEQ ID NO:41, position 378 according to SEQ ID NO:46, position 617 according to SEQ ID NO:51, position 910 according to SEQ ID NO:37, position 811 according to SEQ ID NO:42, position 732 according to SEQ ID NO:47, position 971 according to SEQ ID NO:52, positions 919-922 according to SEQ ID NO:38, positions 820-823 according to SEQ ID NO:43, positions 741-744 according to SEQ ID NO:48, positions 980-983 according to SEQ ID NO:53, position 1,410 according to SEQ ID NO:39, position 1,311 according to SEQ ID NO:44, position 1,232 according to SEQ ID NO:49, position 1,471 according to SEQ ID NO:54, position 830 according to SEQ ID NO:104, position 731 according to SEQ ID NO:105, position 652 according to SEQ ID NO:106, or position 891 according to SEQ ID NO:107;

b) extending the primer at least through the position of the nucleotide sequence of the GPR75 cDNA molecule corresponding to: positions 539-545 according to SEQ ID NO:35, positions 440-446 according to SEQ ID NO:40, positions 361-367 according to SEQ ID NO:45, positions 600-606 according to SEQ ID NO:50, position 556 according to SEQ ID NO:36, position 457 according to SEQ ID NO:41, position 378 according to SEQ ID NO:46, position 617 according to SEQ ID NO:51, position 910 according to SEQ ID NO:37, position 811 according to SEQ ID NO:42, position 732 according to SEQ ID NO:47, position 971 according to SEQ ID NO:52, positions 919-922 according to SEQ ID NO:38, positions 820-823 according to SEQ ID NO:43, positions 741-744 according to SEQ ID NO:48, positions 980-983 according to SEQ ID NO:53, position 1,410 according to SEQ ID NO:39, position 1,311 according to SEQ ID NO:44, position 1,232 according to SEQ ID NO:49, position 1,471 according to SEQ ID NO:54, position 830 according to SEQ ID NO:104, position 731 according to SEQ ID NO:105, position 652 according to SEQ ID NO:106, or position 891 according to SEQ ID NO:107; and c) determining whether the extension product of the primer: lacks a CCAGTAG heptanucleotide at positions corresponding to positions 539-545 according to SEQ ID NO:31, lacks a CCAGTAG heptanucleotide at positions corresponding to positions 440-446 according to SEQ ID NO:32, lacks a CCAGTAG heptanucleotide at positions corresponding to positions 361-367 according to SEQ ID NO:33, lacks a CCAGTAG heptanucleotide at positions corresponding to positions 600-606 according to SEQ ID NO:34, comprises an adenine at a position corresponding to position 556 according to SEQ ID NO:36, comprises an adenine at a position corresponding to position 457 according to SEQ ID NO:41, comprises an adenine at a position corresponding to position 378 according to SEQ ID NO:46, comprises an adenine at a position corresponding to position 617 according to SEQ ID NO:51, comprises a thymine at a position corresponding to position 910 according to SEQ ID NO:37, comprises a thymine at a position corresponding to position 811 according to SEQ ID NO:42, comprises a thymine at a position corresponding to position 732 according to SEQ ID NO:47, comprises a thymine at a position corresponding to position 971 according to SEQ ID NO:52, lacks an AAAG tetranucleotide at positions corresponding to positions 919-922 according to SEQ ID NO:31, lacks an AAAG tetranucleotide at positions corresponding to positions 820-823 according to SEQ ID NO:32, lacks an AAAG tetranucleotide at positions corresponding to positions 741-744 according to SEQ ID NO:33, lacks an AAAG tetranucleotide at positions corresponding to positions 980-983 according to SEQ ID NO:34, comprises an insertion of a thymine at a position corresponding to position 1,410 according to SEQ ID NO:39, comprises an insertion of a thymine at a position corresponding to position 1,311 according to SEQ ID NO:44, comprises an insertion of a thymine at a position corresponding to position 1,232 according to SEQ ID NO:49, comprises an insertion of a thymine at a position corresponding to position 1,471 according to SEQ ID NO:54, comprises a guanine at a position corresponding to position 830 according to SEQ ID NO:104, comprises a guanine at a position corresponding to position 731 according to SEQ ID NO:105, comprises a guanine at a position corresponding to position 652 according to SEQ ID NO:106, or comprises a guanine at a position corresponding to position 891 according to SEQ ID NO:107.

Embodiment 45. The method according to any one of embodiments 39 to 44, wherein the sequence analysis comprises sequencing the entire nucleic acid molecule.

Embodiment 46. The method according to any one of embodiments 34 to 38, wherein the sequence analysis comprises:

a) amplifying at least a portion of the nucleic acid molecule that encodes the human GPR75 polypeptide, wherein the portion: lacks a CCAGTAG heptanucleotide at positions corresponding to positions 5,540-5,546 according to SEQ ID NO:1, or the complement thereof; comprises an adenine at a position corresponding to position 5,557 according to SEQ ID NO:3, or the complement thereof; comprises a thymine at a position corresponding to position 5,911 according to SEQ ID NO:4, or the complement thereof; lacks an AAAG tetranucleotide at positions corresponding to positions 5,920-5,923 according to SEQ ID NO:1, or the complement thereof; comprises an insertion of a thymine at a position corresponding to position 6,411 according to SEQ ID NO:6, or the complement thereof; or comprises a guanine at a position corresponding to position 5,831 according to SEQ ID NO:99;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGTAG heptanucleotide at positions corresponding to positions 5,540-5,546 according to SEQ ID NO:1, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:1, or the complement thereof; comprising an insertion of a thymine at a position corresponding to position 6,411 according to SEQ ID NO:6, or the complement thereof; or comprising a guanine at a position corresponding to position 5,831 according to SEQ ID NO:99; and d) detecting the detectable label.

Embodiment 47. The method according to any one of embodiments 34 to 38, wherein the sequence analysis comprises:

a) amplifying at least a portion of the nucleic acid molecule that encodes the human GPR75 polypeptide, wherein the portion: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; comprises an adenine at a position corresponding to position 556 according to SEQ ID NO:12, or the complement thereof; comprises an adenine at a position corresponding to position 457 according to SEQ ID NO:17, or the complement thereof; comprises an adenine at a position corresponding to position 378 according to SEQ ID NO:22, or the complement thereof; comprises an adenine at a position corresponding to position 617 according to SEQ ID NO:27, or the complement thereof; comprises a uracil at a position corresponding to position 910 according to SEQ ID NO:13, or the complement thereof; comprises a uracil at a position corresponding to position 811 according to SEQ ID NO:18, or the complement thereof; comprises a uracil at a position corresponding to position 732 according to SEQ ID NO:23, or the complement thereof; comprises a uracil at a position corresponding to position 971 according to SEQ ID NO:28, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; comprises an insertion of a uracil at a position corresponding to position 1,471 according to SEQ ID NO:30, or the complement thereof; comprises a guanine at a position corresponding to position 830 according to SEQ ID NO:100; comprises a guanine at a position corresponding to position 731 according to SEQ ID NO:101; comprises a guanine at a position corresponding to position 652 according to SEQ ID NO:102; or comprises a guanine at a position corresponding to position 891 according to SEQ ID NO:103, or the complement thereof;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; lacking a CCAGUAG heptanucleotide at positions corresponding to positions 600-606 according to SEQ ID NO:10, or the complement thereof; comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; lacking an AAAG tetranucleotide at positions corresponding to positions 980-983 according to SEQ ID NO:10, or the complement thereof; comprising an insertion of a uracil at a position corresponding to position 1,410 according to SEQ ID NO:15, or the complement thereof; comprising an insertion of a uracil at a position corresponding to position 1,311 according to SEQ ID NO:20, or the complement thereof; comprising an insertion of a uracil at a position corresponding to position 1,232 according to SEQ ID NO:25, or the complement thereof; comprising an insertion of a uracil at a position corresponding to position 1,471 according to SEQ ID NO:30, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof; and d) detecting the detectable label.

Embodiment 48. The method according to any one of embodiments 34 to 38, wherein the sequence analysis comprises:

a) amplifying at least a portion of the nucleic acid molecule that encodes the human GPR75 polypeptide, wherein the portion: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; comprises an adenine at a position corresponding to position 556 according to SEQ ID NO:36, or the complement thereof; comprises an adenine at a position corresponding to position 457 according to SEQ ID NO:41, or the complement thereof; comprises an adenine at a position corresponding to position 378 according to SEQ ID NO:46, or the complement thereof; comprises an adenine at a position corresponding to position 617 according to SEQ ID NO:51, or the complement thereof; comprises a thymine at a position corresponding to position 910 according to SEQ ID NO:37, or the complement thereof; comprises a thymine at a position corresponding to position 811 according to SEQ ID NO:42, or the complement thereof; comprises a thymine at a position corresponding to position 732 according to SEQ ID NO:47, or the complement thereof; comprises a thymine at a position corresponding to position 971 according to SEQ ID NO:52, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; comprises an insertion of a thymine at a position corresponding to position 1,471 according to SEQ ID NO:54, or the complement thereof; comprises a guanine at a position corresponding to position 830 according to SEQ ID NO:104, or the complement thereof; comprises a guanine at a position corresponding to position 731 according to SEQ ID NO:105, or the complement thereof; comprises a guanine at a position corresponding to position 652 according to SEQ ID NO:106, or the complement thereof; or comprises a guanine at a position corresponding to position 891 according to SEQ ID NO:107, or the complement thereof;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; lacking a CCAGTAG heptanucleotide at positions corresponding to positions 600-606 according to SEQ ID NO:34, or the complement thereof; comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; lacking an AAAG tetranucleotide at positions corresponding to positions 980-983 according to SEQ ID NO:34, or the complement thereof; comprising an insertion of a thymine at a position corresponding to position 1,410 according to SEQ ID NO:39, or the complement thereof; comprising an insertion of a thymine at a position corresponding to position 1,311 according to SEQ ID NO:44, or the complement thereof; comprising an insertion of a thymine at a position corresponding to position 1,232 according to SEQ ID NO:49, or the complement thereof; comprising an insertion of a thymine at a position corresponding to position 1,471 according to SEQ ID NO:54, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof; and d) detecting the detectable label.

Embodiment 49. The method according to embodiment 48, wherein the nucleic acid molecule in the sample is mRNA and the mRNA is reverse-transcribed into cDNA prior to the amplifying step.

Embodiment 50. The method according to any one of embodiments 34 to 38, wherein the sequence analysis comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGTAG heptanucleotide at positions corresponding to positions 5,540-5,546 according to SEQ ID NO:1, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:1, or the complement thereof; comprising an insertion of a thymine at a position corresponding to position 6,411 according to SEQ ID NO:6, or the complement thereof; or comprising a guanine at a position corresponding to position 5,831 according to SEQ ID NO:99, or the complement thereof; and detecting the detectable label.

Embodiment 51. The method according to any one of embodiments 34 to 38, wherein the sequence analysis comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; lacking a CCAGUAG heptanucleotide at positions corresponding to positions 600-606 according to SEQ ID NO:10, or the complement thereof; comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; lacking an AAAG tetranucleotide at positions corresponding to positions 980-983 according to SEQ ID NO:10, or the complement thereof; comprising an insertion of a uracil at a position corresponding to position 1,410 according to SEQ ID NO:15, or the complement thereof; comprising an insertion of a uracil at a position corresponding to position 1,311 according to SEQ ID NO:20, or the complement thereof; comprising an insertion of a uracil at a position corresponding to position 1,232 according to SEQ ID NO:25, or the complement thereof; comprising an insertion of a uracil at a position corresponding to position 1,471 according to SEQ ID NO:30, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof; and detecting the detectable label.

Embodiment 52. The method according to any one of embodiments 34 to 38, wherein the sequence analysis comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; lacking a CCAGTAG heptanucleotide at positions corresponding to positions 600-606 according to SEQ ID NO:34, or the complement thereof; comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; lacking an AAAG tetranucleotide at positions corresponding to positions 980-983 according to SEQ ID NO:34, or the complement thereof; comprising an insertion of a thymine at a position corresponding to position 1,410 according to SEQ ID NO:39, or the complement thereof; comprising an insertion of a thymine at a position corresponding to position 1,311 according to SEQ ID NO:44, or the complement thereof; comprising an insertion of a thymine at a position corresponding to position 1,232 according to SEQ ID NO:49, or the complement thereof; comprising an insertion of a thymine at a position corresponding to position 1,471 according to SEQ ID NO:54, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof; and detecting the detectable label.

Embodiment 53. The method according to any one of embodiments 34 to 52, wherein the nucleic acid molecule is present within a cell obtained from the subject.

Embodiment 54. The method according to any one of embodiments 34 to 53, wherein the GPR75 inhibitor comprises an antisense nucleic acid molecule, a small interfering RNA (siRNA), or a short hairpin RNA (shRNA) that hybridizes to a GPR75 mRNA.

Embodiment 55. The method according to any one of embodiments 34 to 53, wherein the GPR75 inhibitor comprises a Cas protein and guide RNA (gRNA) that hybridizes to a gRNA recognition sequence within a GPR75 genomic nucleic acid molecule.

Embodiment 56. The method according to embodiment 55, wherein the Cas protein is Cas9 or Cpf1.

Embodiment 57. The method according to embodiment 55 or embodiment 56, wherein the gRNA recognition sequence includes or is proximate to a position corresponding to: position 5,540-5,546 according to SEQ ID NO:1, position 5,557 according to SEQ ID NO:1, position 5,911 according to SEQ ID NO:1, positions 5,920-5,923 according to SEQ ID NO:1, position 6,411 according to SEQ ID NO:1 or position 5,831 according to SEQ ID NO:1.

Embodiment 58. The method according to embodiment 55 or embodiment 56, wherein the gRNA recognition sequence is located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to: position 5,540-5,546 according to SEQ ID NO:1, position 5,557 according to SEQ ID NO:1, position 5,911 according to SEQ ID NO:1, positions 5,920-5,923 according to SEQ ID NO:1, position 6,411 according to SEQ ID NO:1, or position 5,831 according to SEQ ID NO:1.

Embodiment 59. The method according to embodiment 55 or embodiment 56, wherein a Protospacer Adjacent Motif (PAM) sequence is about 2 to 6 nucleotides downstream of the gRNA recognition sequence.

Embodiment 60. The method according to any one of embodiments 55 to 59, wherein the gRNA comprises from about 17 to about 23 nucleotides.

Embodiment 61. The method according to any one of embodiments 55 to 60, wherein the gRNA recognition sequence comprises a nucleotide sequence according to any one of SEQ ID NOS:61-98.

Embodiment 62. A method of identifying a subject having an increased risk for developing obesity, wherein the method comprises:

determining or having determined the presence or absence of a G-Protein Coupled Receptor 75 (GPR75) missense variant nucleic acid molecule encoding a predicted loss-of-function GPR75 polypeptide in a biological sample obtained from the subject;

wherein:

when the subject is GPR75 reference, then the subject has an increased risk for developing obesity; and when the subject is heterozygous for a GPR75 missense variant nucleic acid molecule or homozygous for a GPR75 missense variant nucleic acid molecule, then the subject has a decreased risk for developing obesity.

Embodiment 63. The method according to embodiment 62, wherein the GPR75 missense variant nucleic acid molecule is a nucleic acid molecule encoding Ala110fs, Ala116Thr, Tyr207Cys, Gln234Stop, Arg236fs, or Cys400fs.

Embodiment 64. The method according to embodiment 63, wherein the GPR75 missense variant nucleic acid molecule is:

a genomic nucleic acid molecule having a nucleotide sequence: lacking a CCAGTAG heptanucleotide at positions corresponding to positions 5,540-5,546 according to SEQ ID NO:1, comprising an adenine at a position corresponding to position 5,557 according to SEQ ID NO:3, comprising a thymine at a position corresponding to position 5,911 according to SEQ ID NO:4, lacking an AAAG tetranucleotide at positions corresponding to positions 5,920-5,923 according to SEQ ID NO:1, comprising an insertion of a thymine at a position corresponding to position 6,411 according to SEQ ID NO:6, or comprising a guanine at a position corresponding to position 5,831 according to SEQ ID NO:99;

an mRNA molecule having a nucleotide sequence: lacking a CCAGUAG heptanucleotide at positions corresponding to positions 539-545 according to SEQ ID NO:7, lacking a CCAGUAG heptanucleotide at positions corresponding to positions 440-446 according to SEQ ID NO:8, lacking a CCAGUAG heptanucleotide at positions corresponding to positions 361-367 according to SEQ ID NO:9, lacking a CCAGUAG heptanucleotide at positions corresponding to positions 600-

606 according to SEQ ID NO:10; comprising an adenine at a position corresponding to position 556 according to SEQ ID NO:12, comprising an adenine at a position corresponding to position 457 according to SEQ ID NO:17, comprising an adenine at a position corresponding to position 378 according to SEQ ID NO:22, comprising an adenine at a position corresponding to position 617 according to SEQ ID NO:27; comprising a uracil at a position corresponding to position 910 according to SEQ ID NO:13, comprising a uracil at a position corresponding to position 811 according to SEQ ID NO:18, comprising a uracil at a position corresponding to position 732 according to SEQ ID NO:23, comprising a uracil at a position corresponding to position 971 according to SEQ ID NO:28; lacking an AAAG tetranucleotide at positions corresponding to positions 919-922 according to SEQ ID NO:7, lacking an AAAG tetranucleotide at positions corresponding to positions 820-823 according to SEQ ID NO:8, lacking an AAAG tetranucleotide at positions corresponding to positions 741-744 according to SEQ ID NO:9, lacking an AAAG tetranucleotide at positions corresponding to positions 980-983 according to SEQ ID NO:10; comprising an insertion of a uracil at a position corresponding to position 1,410 according to SEQ ID NO:15, comprising an insertion of a uracil at a position corresponding to position 1,311 according to SEQ ID NO:20, comprising an insertion of a uracil at a position corresponding to position 1,232 according to SEQ ID NO:25, comprising an insertion of a uracil at a position corresponding to position 1,471 according to SEQ ID NO:30, comprising a guanine at a position corresponding to position 830 according to SEQ ID NO:100, comprising a guanine at a position corresponding to position 731 according to SEQ ID NO:101, comprising a guanine at a position corresponding to position 652 according to SEQ ID NO:102, or comprising a guanine at a position corresponding to position 891 according to SEQ ID NO:103; or a cDNA molecule produced from an mRNA molecule, wherein the cDNA molecule has a nucleotide sequence: lacking a CCAGTAG heptanucleotide at positions corresponding to positions 539-545 according to SEQ ID NO:31, lacking a CCAGTAG heptanucleotide at positions corresponding to positions 440-446 according to SEQ ID NO:32, lacking a CCAGTAG heptanucleotide at positions corresponding to positions 361-367 according to SEQ ID NO:33, lacking a CCAGTAG heptanucleotide at positions corresponding to positions 600-606 according to SEQ ID NO:34; comprising an adenine at a position corresponding to position 556 according to SEQ ID NO:36, comprising an adenine at a position corresponding to position 457 according to SEQ ID NO:41, comprising an adenine at a position corresponding to position 378 according to SEQ ID NO:46, comprising an adenine at a position corresponding to position 617 according to SEQ ID NO:51; comprising a thymine at a position corresponding to position 910 according to SEQ ID NO:37, comprising a thymine at a position corresponding to position 811 according to SEQ ID NO:42, comprising a thymine at a position corresponding to position 732 according to SEQ ID NO:47, comprising a thymine at a position corresponding to position 971 according to SEQ ID NO:52; lacking an AAAG tetranucleotide at positions corresponding to positions 919-922 according to SEQ ID NO:31, lacking an AAAG tetranucleotide at positions corresponding to positions 820-823 according to SEQ ID NO:32, lacking an AAAG tetranucleotide at positions corresponding to positions 741-744 according to SEQ ID NO:33, lacking an AAAG tetranucleotide at positions corresponding to positions 980-983 according to SEQ ID NO:34; comprising an insertion of a thymine at a position corresponding to position 1,410 according to SEQ ID NO:39, comprising an insertion of a thymine at a position corresponding to position 1,311 according to SEQ ID NO:44, comprising an insertion of a thymine at a position corresponding to position 1,232 according to SEQ ID NO:49, comprising an insertion of a thymine at a position corresponding to position 1,471 according to SEQ ID NO:54, comprising a guanine at a position corresponding to position 830 according to SEQ ID NO:104, comprising a guanine at a position corresponding to position 731 according to SEQ ID NO:105, comprising a guanine at a position corresponding to position 652 according to SEQ ID NO:106, or comprising a guanine at a position corresponding to position 891 according to SEQ ID NO:107.

Embodiment 65. The method according to any one of embodiments 62 to 64, wherein the determining step is carried out in vitro.

Embodiment 66. The method according to any one of embodiments 62 to 64, wherein the determining step comprises sequencing at least a portion of the nucleotide sequence of the GPR75 genomic nucleic acid molecule in the biological sample, wherein the sequenced portion comprises a position corresponding to: positions 5,540-5,546 according to SEQ ID NO:2, or the complement thereof; position 5,557 according to SEQ ID NO:3, or the complement thereof; position 5,911 according to SEQ ID NO:4, or the complement thereof; positions 5,920-5,923 according to SEQ ID NO:5, or the complement thereof; position 6,411 according to SEQ ID NO:6, or the complement thereof; or position 5,831 according to SEQ ID NO:99, or the complement thereof;

wherein when the sequenced portion of the GPR75 genomic nucleic acid molecule in the biological sample: lacks a CCAGTAG heptanucleotide at positions corresponding to positions 5,540-5,546 according to SEQ ID NO:1, comprises an adenine at a position corresponding to position 5,557 according to SEQ ID NO:3, comprises a thymine at a position corresponding to position 5,911 according to SEQ ID NO:4, lacks an AAAG tetranucleotide at positions corresponding to positions 5,920-5,923 according to SEQ ID NO:1, comprises an insertion of a thymine at a position corresponding to position 6,411 according to SEQ ID NO:6, or comprises a guanine at a position corresponding to position 5,831 according to SEQ ID NO:99, then the GPR75 genomic nucleic acid molecule in the biological sample is a GPR75 missense variant genomic nucleic acid molecule.

Embodiment 67. The method according to any one of embodiments 62 to 66, wherein the determining step comprises sequencing at least a portion of the nucleotide sequence of the GPR75 mRNA molecule in the biological sample, wherein the sequenced portion comprises a position corresponding to: positions 539-545 according to SEQ ID NO:11, or the complement thereof; positions 440-446 according to SEQ ID NO:16, or the complement thereof; positions 361-367 according to SEQ ID NO:21, or the complement thereof; positions 600-606 according to SEQ ID NO:26, or the complement thereof; position 556 according to SEQ ID NO:12, or the complement thereof; position 457 according to SEQ ID NO:17, or the complement thereof; position 378 according to SEQ ID NO:22, or the complement thereof; position 617 according to SEQ ID NO:27, or the complement thereof; position 910 according to SEQ ID NO:13, or the complement thereof; position 811 according to SEQ ID NO:18, or the complement thereof; position 732 according to SEQ ID NO:23, or the complement thereof; position 971 according to SEQ ID NO:28, or the complement thereof; positions 919-922 according to SEQ ID NO:14, or the complement thereof; positions 820-823 according to SEQ ID NO:19, or the complement thereof; positions 741-744 according to SEQ ID NO:24, or the complement thereof; positions 980-983 according to SEQ ID NO:29, or the complement thereof; position 1,410 according to SEQ ID NO:15, or the complement thereof; position 1,311 according to SEQ ID NO:20, or the complement thereof; position 1,232 according to SEQ ID NO:25, or the complement thereof; position 1,471 according to SEQ ID NO:30, or the complement thereof; position 830 according to SEQ ID NO:100, or the complement thereof; position 731 according to SEQ ID NO:101, or the complement thereof; position 652 according to SEQ ID NO:102, or the complement thereof; or position 891 according to SEQ ID NO:103, or the complement thereof;

wherein when the sequenced portion of the GPR75 mRNA molecule in the biological sample: lacks a CCAGUAG heptanucleotide at positions corresponding to positions 539-545 according to SEQ ID NO:7; lacks a CCAGUAG heptanucleotide at positions corresponding to positions 440-446 according to SEQ ID NO:8; lacks a CCAGUAG heptanucleotide at positions corresponding to positions 361-367 according to SEQ ID NO:9; lacks a CCAGUAG heptanucleotide at positions corresponding to positions 600-606 according to SEQ ID NO:10; comprises an adenine at a position corresponding to position 556 according to SEQ ID NO:12; comprises an adenine at a position corresponding to position 457 according to SEQ ID NO:17; comprises an adenine at a position corresponding to position 378 according to SEQ ID NO:22; comprises an adenine at a position corresponding to position 617 according to SEQ ID NO:27; comprises a uracil at a position corresponding to position 910 according to SEQ ID NO:13; comprises a uracil at a position corresponding to position 811 according to SEQ ID NO:18; comprises a uracil at a position corresponding to position 732 according to SEQ ID NO:23; comprises a uracil at a position corresponding to position 971 according to SEQ ID NO:28; lacks an AAAG tetranucleotide at positions corresponding to positions 919-922 according to SEQ ID NO:7; lacks an AAAG tetranucleotide at positions corresponding to positions 820-823 according to SEQ ID NO:8; lacks an AAAG tetranucleotide at positions corresponding to positions 741-744 according to SEQ ID NO:9; lacks an AAAG tetranucleotide at positions corresponding to positions 980-983 according to SEQ ID NO:10; comprises an insertion of a uracil at a position corresponding to position 1,410 according to SEQ ID NO:15; comprises an insertion of a uracil at a position corresponding to position 1,311 according to SEQ ID NO:20; comprises an insertion of a uracil at a position corresponding to position 1,232 according to SEQ ID NO:25; comprises an insertion of a uracil at a position corresponding to position 1,471 according to SEQ ID NO:30; comprises a guanine at a position corresponding to position 830 according to SEQ ID NO:100; comprises a guanine at a position corresponding to position 731 according to SEQ ID NO:101; comprises a guanine at a position corresponding to position 652 according to SEQ ID NO:102; or comprises a guanine at a position corresponding to position 891 according to SEQ ID NO:103; then the GPR75 mRNA molecule in the biological sample is a GPR75 missense variant genomic nucleic acid molecule.

Embodiment 68. The method according to any one of embodiments 62 to 66, wherein the determining step comprises sequencing at least a portion of the nucleotide sequence of the GPR75 cDNA molecule in the biological sample, wherein the sequenced portion comprises a position corresponding to: positions 539-545 according to SEQ ID NO:35, or the complement thereof; positions 440-446 according to SEQ ID NO:40, or the complement thereof; positions 361-367 according to SEQ ID NO:45, or the complement thereof; positions 600-606 according to SEQ ID NO:50, or the complement thereof; position 556 according to SEQ ID NO:36, or the complement thereof; position 457 according to SEQ ID NO:41, or the complement thereof; position 378 according to SEQ ID NO:46, or the complement thereof; position 617 according to SEQ ID NO:51, or the complement thereof; position 910 according to SEQ ID NO:37, or the complement thereof; position 811 according to SEQ ID NO:42, or the complement thereof; position 732 according to SEQ ID NO:47, or the complement thereof; position 971 according to SEQ ID NO:52, or the complement thereof; positions 919-922 according to SEQ ID NO:38, or the complement thereof; positions 820-823 according to SEQ ID NO:43, or the complement thereof; positions 741-744 according to SEQ ID NO:48, or the complement thereof; positions 980-983 according to SEQ ID NO:53, or the complement thereof; position 1,410 according to SEQ ID NO:39, or the complement thereof; position 1,311 according to SEQ ID NO:44, or the complement thereof; position 1,232 according to SEQ ID NO:49, or the complement thereof; position 1,471 according to SEQ ID NO:54, or the complement thereof; position 830 according to SEQ ID NO:104, or the complement thereof; position 731 according to SEQ ID NO:105, or the complement thereof; position 652 according to SEQ ID NO:106, or the complement thereof; or position 891 according to SEQ ID NO:107, or the complement thereof;

wherein when the sequenced portion of the GPR75 cDNA molecule in the biological sample: lacks a CCAGTAG heptanucleotide at positions corresponding to positions 539-545 according to SEQ ID NO:31; lacks a CCAGTAG heptanucleotide at positions corresponding to positions 440-446 according to SEQ ID NO:32; lacks a CCAGTAG heptanucleotide at positions corresponding to positions 361-367 according to SEQ ID NO:33; lacks a CCAGTAG heptanucleotide at positions corresponding to positions 600-606 according to SEQ ID NO:34; comprises an adenine at a position corresponding to position 556 according to SEQ ID NO:36; comprises an adenine at a position corresponding to position 457 according to SEQ ID NO:41; comprises an adenine at a position corresponding to position 378 according to SEQ ID NO:46; comprises an adenine at a position corresponding to position 617 according to SEQ ID NO:51; comprises a thymine at a position corresponding to position 910 according to SEQ ID NO:37; comprises a thymine at a position corresponding to position 811 according to SEQ ID NO:42; comprises a thymine at a position corresponding to position 732 according to SEQ ID NO:47; comprises a thymine at a position corresponding to position 971 according to SEQ ID NO:52; lacks an AAAG tetranucleotide at positions corresponding to positions 919-922 according to SEQ ID NO:31; lacks an AAAG tetranucleotide at positions corresponding to positions 820-823 according to SEQ ID NO:32; lacks an AAAG tetranucleotide at positions corresponding to positions 741-744 according to SEQ ID NO:33; lacks an AAAG tetranucleotide at positions corresponding to positions 980-983 according to SEQ ID NO:34; comprises an insertion of a thymine at a position corresponding to position 1,410 according to SEQ ID NO:39; comprises an insertion of a thymine at a position corresponding to position 1,311 according to SEQ ID NO:44; comprises an insertion of a thymine at a position corresponding to position 1,232 according to SEQ ID NO:49; comprises an insertion of a thymine at a position corresponding to position 1,471 according to SEQ ID NO:54; comprises a guanine at a position corresponding to position 830 according to SEQ ID NO:104; comprises a guanine at a position corresponding to position 731 according to SEQ ID NO:105; comprises a guanine at a position corresponding to position 652 according to SEQ ID NO:106; or comprises a guanine at a position corresponding to position 891 according to SEQ ID NO:107; then the GPR75 cDNA molecule in the biological sample is a GPR75 missense variant cDNA molecule.

Embodiment 69. The method according to any one of embodiments 62 to 66, wherein the determining step comprises:

a) contacting the biological sample with a primer hybridizing to a portion of the nucleotide sequence of the GPR75 genomic nucleic acid molecule that is proximate to a position corresponding to: positions 5,540-5,546 according to SEQ ID NO:2, position 5,557 according to SEQ ID NO:3, position 5,911 according to SEQ ID NO:4, positions 5,920-5,923 according to SEQ ID NO:5, position 6,411 according to SEQ ID NO:6, or position corresponding to position 5,831 according to SEQ ID NO:99;

b) extending the primer at least through the position of the nucleotide sequence of the GPR75 genomic nucleic acid molecule corresponding to: positions 5,540-5,546 according to SEQ ID NO:2, position 5,557 according to SEQ ID NO:3, position 5,911 according to SEQ ID NO:4, positions 5,920-5,923 according to SEQ ID NO:5, position 6,411 according to SEQ ID NO:6, or position corresponding to position 5,831 according to SEQ ID NO:99; and c) determining whether the extension product of the primer: lacks a CCAGTAG heptanucleotide at positions corresponding to positions 5,540-5,546 according to SEQ ID NO:1, comprises an adenine at a position corresponding to position 5,557 according to SEQ ID NO:3, comprises a thymine at a position corresponding to position 5,911 according to SEQ ID NO:4, lacks an AAAG tetranucleotide at positions corresponding to positions 5,920-5,923 according to SEQ ID NO:1, comprises an insertion of a thymine at a position corresponding to position 6,411 according to SEQ ID NO:6, or comprises a guanine at a position corresponding to position 5,831 according to SEQ ID NO:99.

Embodiment 70. The method according to any one of embodiments 62 to 66, wherein the determining step comprises:

a) contacting the biological sample with a primer hybridizing to a portion of the nucleotide sequence of the GPR75 mRNA molecule that is proximate to a position corresponding to: positions 539-545 according to SEQ ID NO:11, positions 440-446 according to SEQ ID NO:16, positions 361-367 according to SEQ ID NO:21, positions 600-606 according to SEQ ID NO:26, position 556 according to SEQ ID NO:12, position 457 according to SEQ ID NO:17, position 378 according to SEQ ID NO:22, position 617 according to SEQ ID NO:27, position 910 according to SEQ ID NO:13, position 811 according to SEQ ID NO:18, position 732 according to SEQ ID NO:23, position 971 according to SEQ ID NO:28, positions 919-922 according to SEQ ID NO:14, positions 820-823 according to SEQ ID NO:19, positions 741-744 according to SEQ ID NO:24, positions 980-983 according to SEQ ID NO:29, position 1,410 according to SEQ ID NO:15, position 1,311 according to SEQ ID NO:20, position 1,232 according to SEQ ID NO:25, position 1,471 according to SEQ ID NO:30, position 830 according to SEQ ID NO:100, position 731 according to SEQ ID NO:101, position 652 according to SEQ ID NO:102, or position 891 according to SEQ ID NO:103;

b) extending the primer at least through the position of the nucleotide sequence of the GPR75 mRNA molecule corresponding to: positions 539-545 according to SEQ ID NO:11, positions 440-446 according to SEQ ID NO:16, positions 361-367 according to SEQ ID NO:21, positions 600-606 according to SEQ ID NO:26, position 556 according to SEQ ID NO:12, position 457 according to SEQ ID NO:17, position 378 according to SEQ ID NO:22, position 617 according to SEQ ID NO:27, position 910 according to SEQ ID NO:13, position 811 according to SEQ ID NO:18, position 732 according to SEQ ID NO:23, position 971 according to SEQ ID NO:28, positions 919-922 according to SEQ ID NO:14, positions 820-823 according to SEQ ID NO:19, positions 741-744 according to SEQ ID NO:24, positions 980-983 according to SEQ ID NO:29, position 1,410 according to SEQ ID NO:15, position 1,311 according to SEQ ID NO:20, position 1,232 according to SEQ ID NO:25, position 1,471 according to SEQ ID NO:30, position 830 according to SEQ ID NO:100, position 731 according to SEQ ID NO:101, position 652 according to SEQ ID NO:102, or position 891 according to SEQ ID NO:103; and c) determining whether the extension product of the primer: lacks a CCAGUAG heptanucleotide at positions corresponding to positions 539-545 according to SEQ ID NO:7, lacks a CCAGUAG heptanucleotide at positions corresponding to positions 440-446 according to SEQ ID NO:8, lacks a CCAGUAG heptanucleotide at positions corresponding to positions 361-367 according to SEQ ID NO:9, lacks a CCAGUAG heptanucleotide at positions corresponding to positions 600-606 according to SEQ ID NO:10, comprises an adenine at a position corresponding to position 556 according to SEQ ID NO:12, comprises an adenine at a position corresponding to position 457 according to SEQ ID NO:17, comprises an adenine at a position corresponding to position 378 according to SEQ ID NO:22, comprises an adenine at a position corresponding to position 617 according to SEQ ID NO:27, comprises a uracil at a position corresponding to position 910 according to SEQ ID NO:13, comprises a uracil at a position corresponding to position 811 according to SEQ ID NO:18, comprises a uracil at a position corresponding to position 732 according to SEQ ID NO:23, comprises a uracil at a position corresponding to position 971 according to SEQ ID NO:28, lacks an AAAG tetranucleotide at positions corresponding to positions 919-922 according to SEQ ID NO:7, lacks an AAAG tetranucleotide at positions corresponding to positions 820-823 according to SEQ ID NO:8, lacks an AAAG tetranucleotide at positions corresponding to positions 741-744 according to SEQ ID NO:9, lacks an AAAG tetranucleotide at positions corresponding to positions 980-983 according to SEQ ID NO:10, comprises an insertion of a uracil at a position corresponding to position 1,410 according to SEQ ID NO:15, comprises an insertion of a uracil at a position corresponding to position 1,311 according to SEQ ID NO:20, comprises an insertion of a uracil at a position corresponding to position 1,232 according to SEQ ID NO:25, comprises an insertion of a uracil at a position corresponding to position 1,471 according to SEQ ID NO:30, comprises a guanine at a position corresponding to position 830 according to SEQ ID NO:100, comprises a guanine at a position corresponding to position 731 according to SEQ ID NO:101, comprises a guanine at a position corresponding to position 652 according to SEQ ID NO:102, or comprises a guanine at a position corresponding to position 891 according to SEQ ID NO:103.

Embodiment 71. The method according to any one of embodiments 62 to 66, wherein the determining step comprises:

a) contacting the biological sample with a primer hybridizing to a portion of the nucleotide sequence of the GPR75 cDNA molecule that is proximate to a position corresponding to: positions 539-545 according to SEQ ID NO:35, positions 440-446 according to SEQ ID NO:40, positions 361-367 according to SEQ ID NO:45, positions 600-606 according to SEQ ID NO:50, position 556 according to SEQ ID NO:36, position 457 according to SEQ ID NO:41, position 378 according to SEQ ID NO:46, position 617 according to SEQ ID NO:51, position 910 according to SEQ ID NO:37, position 811 according to SEQ ID NO:42, position 732 according to SEQ ID NO:47, position 971 according to SEQ ID NO:52, positions 919-922 according to SEQ ID NO:38, positions 820-823 according to SEQ ID NO:43, positions 741-744 according to SEQ ID NO:48, positions 980-983 according to SEQ ID NO:53, position 1,410 according to SEQ ID NO:39, position 1,311 according to SEQ ID NO:44, position 1,232 according to SEQ ID NO:49, position 1,471 according to SEQ ID NO:54, position 830 according to SEQ ID NO:104, position 731 according to SEQ ID NO:105, position 652 according to SEQ ID NO:106, or position 891 according to SEQ ID NO:107;

b) extending the primer at least through the position of the nucleotide sequence of the GPR75 cDNA molecule corresponding to: positions 539-545 according to SEQ ID NO:35, positions 440-446 according to SEQ ID NO:40, positions 361-367 according to SEQ ID NO:45, positions 600-606 according to SEQ ID NO:50, position 556 according to SEQ ID NO:36, position 457 according to SEQ ID NO:41, position 378 according to SEQ ID NO:46, position 617 according to SEQ ID NO:51, position 910 according to SEQ ID NO:37, position 811 according to SEQ ID NO:42, position 732 according to SEQ ID NO:47, position 971 according to SEQ ID NO:52, positions 919-922 according to SEQ ID NO:38, positions 820-823 according to SEQ ID NO:43, positions 741-744 according to SEQ ID NO:48, positions 980-983 according to SEQ ID NO:53, position 1,410 according to SEQ ID NO:39, position 1,311 according to SEQ ID NO:44, position 1,232 according to SEQ ID NO:49, position 1,471 according to SEQ ID NO:54, position 830 according to SEQ ID NO:104, position 731 according to SEQ ID NO:105, position 652 according to SEQ ID NO:106, or position 891 according to SEQ ID NO:107, and c) determining whether the extension product of the primer: lacks a CCAGTAG heptanucleotide at positions corresponding to positions 539-545 according to SEQ ID NO:31, lacks a CCAGTAG heptanucleotide at positions corresponding to positions 440-446 according to SEQ ID NO:32, lacks a CCAGTAG heptanucleotide at positions corresponding to positions 361-367 according to SEQ ID NO:33, lacks a CCAGTAG heptanucleotide at positions corresponding to positions 600-606 according to SEQ ID NO:34, comprises an adenine at a position corresponding to position 556 according to SEQ ID NO:36, comprises an adenine at a position corresponding to position 457 according to SEQ ID NO:41, comprises an adenine at a position corresponding to position 378 according to SEQ ID NO:46, comprises an adenine at a position corresponding to position 617 according to SEQ ID NO:51, comprises a thymine at a position corresponding to position 910 according to SEQ ID NO:37, comprises a thymine at a position corresponding to position 811 according to SEQ ID NO:42, comprises a thymine at a position corresponding to position 732 according to SEQ ID NO:47, comprises a thymine at a position corresponding to position 971 according to SEQ ID NO:52, lacks an AAAG tetranucleotide at positions corresponding to positions 919-922 according to SEQ ID NO:31, lacks an AAAG tetranucleotide at positions corresponding to positions 820-823 according to SEQ ID NO:32, lacks an AAAG tetranucleotide at positions corresponding to positions 741-744 according to SEQ ID NO:33, lacks an AAAG tetranucleotide at positions corresponding to positions 980-983 according to SEQ ID NO:34, comprises an insertion of a thymine at a position corresponding to position 1,410 according to SEQ ID NO:39, comprises an insertion of a thymine at a position corresponding to position 1,311 according to SEQ ID NO:44, comprises an insertion of a thymine at a position corresponding to position 1,232 according to SEQ ID NO:49, comprises an insertion of a thymine at a position corresponding to position 1,471 according to SEQ ID NO:54, comprises a guanine at a position corresponding to position 830 according to SEQ ID NO:104, comprises a guanine at a position corresponding to position 731 according to SEQ ID NO:105, comprises a guanine at a position corresponding to position 652 according to SEQ ID NO:106, or comprises a guanine at a position corresponding to position 891 according to SEQ ID NO:107.

Embodiment 72. The method according to any one of embodiments 67 to 71, wherein the determining step comprises sequencing the entire nucleic acid molecule.

Embodiment 73. The method according to any one of embodiments 62 to 66, wherein the determining step comprises:

a) amplifying at least a portion of the nucleic acid molecule that encodes the human GPR75 polypeptide, wherein the portion: lacks a CCAGTAG heptanucleotide at positions corresponding to positions 5,540-5,546 according to SEQ ID NO:1, or the complement thereof; comprises an adenine at a position corresponding to position 5,557 according to SEQ ID NO:3, or the complement thereof; comprises a thymine at a position corresponding to position 5,911 according to SEQ ID NO:4, or the complement thereof; lacks an AAAG tetranucleotide at positions corresponding to positions 5,920-5,923 according to SEQ ID NO:1, or the complement thereof; comprises an insertion of a thymine at a position corresponding to position 6,411 according to SEQ ID NO:6, or the complement thereof; or comprises a guanine at a position corresponding to position 5,831 according to SEQ ID NO:99, or the complement thereof;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGTAG heptanucleotide at positions corresponding to positions 5,540-5,546 according to SEQ ID NO:1, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:1, or the complement thereof; comprising an insertion of a thymine at a position corresponding to position 6,411 according to SEQ ID NO:6, or the complement thereof; or comprising a guanine at a position corresponding to position 5,831 according to SEQ ID NO:99, or the complement thereof; and d) detecting the detectable label.

Embodiment 74. The method according to any one of embodiments 62 to 66, wherein the determining step comprises:

a) amplifying at least a portion of the nucleic acid molecule that encodes the human GPR75 polypeptide, wherein the portion: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; comprises an adenine at a position corresponding to position 556 according to SEQ ID NO:12, or the complement thereof; comprises an adenine at a position corresponding to position 457 according to SEQ ID NO:17, or the complement thereof; comprises an adenine at a position corresponding to position 378 according to SEQ ID NO:22, or the complement thereof; comprises an adenine at a position corresponding to position 617 according to SEQ ID NO:27, or the complement thereof; comprises a uracil at a position corresponding to position 910 according to SEQ ID NO:13, or the complement thereof; comprises a uracil at a position corresponding to position 811 according to SEQ ID NO:18, or the complement thereof; comprises a uracil at a position corresponding to position 732 according to SEQ ID NO:23, or the complement thereof; comprises a uracil at a position corresponding to position 971 according to SEQ ID NO:28, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; comprises an insertion of a uracil at a position corresponding to position 1,471 according to SEQ ID NO:30, or the complement thereof; comprises a guanine at a position corresponding to position 830 according to SEQ ID NO:100, or the complement thereof; comprises a guanine at a position corresponding to position 731 according to SEQ ID NO:101, or the complement thereof; comprises a guanine at a position corresponding to position 652 according to SEQ ID NO:102, or the complement thereof; or comprises a guanine at a position corresponding to position 891 according to SEQ ID NO:103, or the complement thereof;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; lacking a CCAGUAG heptanucleotide at positions corresponding to positions 600-606 according to SEQ ID NO:10, or the complement thereof; comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; lacking an AAAG tetranucleotide at positions corresponding to positions 980-983 according to SEQ ID NO:10, or the complement thereof; comprising an insertion of a uracil at a position corresponding to position 1,410 according to SEQ ID NO:15, or the complement thereof; comprising an insertion of a uracil at a position corresponding to position 1,311 according to SEQ ID NO:20, or the complement thereof; comprising an insertion of a uracil at a position corresponding to position 1,232 according to SEQ ID NO:25, or the complement thereof; comprising an insertion of a uracil at a position corresponding to position 1,471 according to SEQ ID NO:30, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof; and d) detecting the detectable label.

Embodiment 75. The method according to any one of embodiments 62 to 66, wherein the determining step comprises:

a) amplifying at least a portion of the nucleic acid molecule that encodes the human GPR75 polypeptide, wherein the portion: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; comprises an adenine at a position corresponding to position 556 according to SEQ ID NO:36, or the complement thereof; comprises an adenine at a position corresponding to position 457 according to SEQ ID NO:41, or the complement thereof; comprises an adenine at a position corresponding to position 378 according to SEQ ID NO:46, or the complement thereof; comprises an adenine at a position corresponding to position 617 according to SEQ ID NO:51, or the complement thereof; comprises a thymine at a position corresponding to position 910 according to SEQ ID NO:37, or the complement thereof; comprises a thymine at a position corresponding to position 811 according to SEQ ID NO:42, or the complement thereof; comprises a thymine at a position corresponding to position 732 according to SEQ ID NO:47, or the complement thereof; comprises a thymine at a position corresponding to position 971 according to SEQ ID NO:52, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; comprises an insertion of a thymine at a position corresponding to position 1,471 according to SEQ ID NO:54, or the complement thereof; comprises a guanine at a position corresponding to position 830 according to SEQ ID NO:104, or the complement thereof; comprises a guanine at a position corresponding to position 731 according to SEQ ID NO:105, or the complement thereof; comprises a guanine at a position corresponding to position 652 according to SEQ ID NO:106, or the complement thereof; or comprises a guanine at a position corresponding to position 891 according to SEQ ID NO:107, or the complement thereof;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; lacking a CCAGTAG heptanucleotide at positions corresponding to positions 600-606 according to SEQ ID NO:34, or the complement thereof; comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; lacking an AAAG tetranucleotide at positions corresponding to positions 980-983 according to SEQ ID NO:34, or the complement thereof; comprising an insertion of a thymine at a position corresponding to position 1,410 according to SEQ ID NO:39, or the complement thereof; comprising an insertion of a thymine at a position corresponding to position 1,311 according to SEQ ID NO:44, or the complement thereof; comprising an insertion of a thymine at a position corresponding to position 1,232 according to SEQ ID NO:49, or the complement thereof; comprising an insertion of a thymine at a position corresponding to position 1,471 according to SEQ ID NO:54, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof; and d) detecting the detectable label.

Embodiment 76. The method according to embodiment 75, wherein the nucleic acid molecule in the sample is mRNA and the mRNA is reverse-transcribed into cDNA prior to the amplifying step.

Embodiment 77. The method according to any one of embodiments 62 to 66, wherein the detecting step comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGTAG heptanucleotide at positions corresponding to positions 5,540-5,546 according to SEQ ID NO:1, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:1, or the complement thereof; comprising an insertion of a thymine at a position corresponding to position 6,411 according to SEQ ID NO:6, or the complement thereof; or comprising a guanine at a position corresponding to position 5,831 according to SEQ ID NO:99, or the complement thereof; and detecting the detectable label.

Embodiment 78. The method according to any one of embodiments 62 to 66, wherein the detecting step comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; lacking a CCAGUAG heptanucleotide at positions corresponding to positions 600-606 according to SEQ ID NO:10, or the complement thereof; comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; lacking an AAAG tetranucleotide at positions corresponding to positions 980-983 according to SEQ ID NO:10, or the complement thereof; comprising an insertion of a uracil at a position corresponding to position 1,410 according to SEQ ID NO:15, or the complement thereof; comprising an insertion of a uracil at a position corresponding to position 1,311 according to SEQ ID NO:20, or the complement thereof; comprising an insertion of a uracil at a position corresponding to position 1,232 according to SEQ ID NO:25, or the complement thereof; or comprising an insertion of a uracil at a position corresponding to position 1,471 according to SEQ ID NO:30, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof; and detecting the detectable label.

Embodiment 79. The method according to any one of embodiments 62 to 66, wherein the detecting step comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; lacking a CCAGTAG heptanucleotide at positions corresponding to positions 600-606 according to SEQ ID NO:34, or the complement thereof; comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; lacking an AAAG tetranucleotide at positions corresponding to positions 980-983 according to SEQ ID NO:34, or the complement thereof; comprising an insertion of a thymine at a position corresponding to position 1,410 according to SEQ ID NO:39, or the complement thereof; comprising an insertion of a thymine at a position corresponding to position 1,311 according to SEQ ID NO:44, or the complement thereof; comprising an insertion of a thymine at a position corresponding to position 1,232 according to SEQ ID NO:49, or the complement thereof; comprising an insertion of a thymine at a position corresponding to position 1,471 according to SEQ ID NO:54, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof; and detecting the detectable label.

Embodiment 80. The method according to any one of embodiments 62 to 79, wherein the subject is GPR75 reference, and the subject is administered a therapeutic agent that treats or inhibits obesity and/or a GPR75 inhibitor in a standard dosage amount.

Embodiment 81. The method according to any one of embodiments 62 to 79, wherein the subject is heterozygous for a GPR75 missense variant nucleic acid molecule, and the subject is administered a therapeutic agent that treats or inhibits obesity and/or a GPR75 inhibitor in an amount that is the same as or lower than a standard dosage amount.

Embodiment 82. A method of detecting a human G-Protein Coupled Receptor 75 (GPR75) variant nucleic acid molecule in a subject comprising assaying a sample obtained from the subject to determine whether a nucleic acid molecule in the sample is:

a genomic nucleic acid molecule comprising a nucleotide sequence: lacking a CCAGTAG heptanucleotide at positions corresponding to positions 5,540-5,546 according to SEQ ID NO:1, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:1, or the complement thereof; comprising an insertion of a thymine at a position corresponding to position 6,411 according to SEQ ID NO:6, or the complement thereof; or comprising a guanine at a position corresponding to position 5,831 according to SEQ ID NO:99, or the complement thereof;

an mRNA molecule having a nucleotide sequence: lacking a CCAGUAG heptanucleotide at positions corresponding to positions 539-545 according to SEQ ID NO:7 or the complement thereof, lacking a CCAGUAG heptanucleotide at positions corresponding to positions 440-446 according to SEQ ID NO:8 or the complement thereof, lacking a CCAGUAG heptanucleotide at positions corresponding to positions 361-367 according to SEQ ID NO:9 or the complement thereof, lacking a CCAGUAG heptanucleotide at positions corresponding to positions 600-606 according to SEQ ID NO:10 or the complement thereof; comprising an adenine at a position corresponding to position 556 according to SEQ ID NO:12 or the complement thereof, comprising an adenine at a position corresponding to position 457 according to SEQ ID NO:17 or the complement thereof, comprising an adenine at a position corresponding to position 378 according to SEQ ID NO:22 or the complement thereof, comprising an adenine at a position corresponding to position 617 according to SEQ ID NO:27 or the complement thereof; comprising a uracil at a position corresponding to position 910 according to SEQ ID NO:13 or the complement thereof, comprising a uracil at a position corresponding to position 811 according to SEQ ID NO:18 or the complement thereof, comprising a uracil at a position corresponding to position 732 according to SEQ ID NO:23 or the complement thereof, comprising a uracil at a position corresponding to position 971 according to SEQ ID NO:28 or the complement thereof; lacking an AAAG tetranucleotide at positions corresponding to positions 919-922 according to SEQ ID NO:7 or the complement thereof, lacking an AAAG tetranucleotide at positions corresponding to positions 820-823 according to SEQ ID NO:8 or the complement thereof, lacking an AAAG tetranucleotide at positions corresponding to positions 741-744 according to SEQ ID NO:9 or the complement thereof, lacking an AAAG tetranucleotide at positions corresponding to positions 980-983 according to SEQ ID NO:10 or the complement thereof; comprising an insertion of a uracil at a position corresponding to position 1,410 according to SEQ ID NO:15 or the complement thereof, comprising an insertion of a uracil at a position corresponding to position 1,311 according to SEQ ID NO:20 or the complement thereof, comprising an insertion of a uracil at a position corresponding to position 1,232 according to SEQ ID NO:25 or the complement thereof, comprising an insertion of a uracil at a position corresponding to position 1,471 according to SEQ ID NO:30 or the complement thereof, comprising a guanine at a position corresponding to position 830 according to SEQ ID NO:100, or the complement thereof, comprising a guanine at a position corresponding to position 731 according to SEQ ID NO:101, or the complement thereof, comprising a guanine at a position corresponding to position 652 according to SEQ ID NO:102, or the complement thereof, or comprising a guanine at a position corresponding to position 891 according to SEQ ID NO:103, or the complement thereof; or a cDNA molecule produced from an mRNA molecule, wherein the cDNA molecule has a nucleotide sequence: lacking a CCAGTAG heptanucleotide at positions corresponding to positions 539-545 according to SEQ ID NO:31 or the complement thereof, lacking a CCAGTAG heptanucleotide at positions corresponding to positions 440-446 according to SEQ ID NO:32 or the complement thereof, lacking a CCAGTAG heptanucleotide at positions corresponding to positions 361-367 according to SEQ ID NO:33 or the complement thereof, lacking a CCAGTAG heptanucleotide at positions corresponding to positions 600-606 according to SEQ ID NO:34 or the complement thereof; comprising an adenine at a position corresponding to position 556 according to SEQ ID NO:36 or the complement thereof, comprising an adenine at a position corresponding to position 457 according to SEQ ID NO:41 or the complement thereof, comprising an adenine at a position corresponding to position 378 according to SEQ ID NO:46 or the complement thereof, comprising an adenine at a position corresponding to position 617 according to SEQ ID NO:51 or the complement thereof; comprising a thymine at a position corresponding to position 910 according to SEQ ID NO:37 or the complement thereof, comprising a thymine at a position corresponding to position 811 according to SEQ ID NO:42 or the complement thereof, comprising a thymine at a position corresponding to position 732 according to SEQ ID NO:47 or the complement thereof, comprising a thymine at a position corresponding to position 971 according to SEQ ID NO:52 or the complement thereof; lacking an AAAG tetranucleotide at positions corresponding to positions 919-922 according to SEQ ID NO:31 or the complement thereof, lacking an AAAG tetranucleotide at positions corresponding to positions 820-823 according to SEQ ID NO:32 or the complement thereof, lacking an AAAG tetranucleotide at positions corresponding to positions 741-744 according to SEQ ID NO:33 or the complement thereof, lacking an AAAG tetranucleotide at positions corresponding to positions 980-983 according to SEQ ID NO:34 or the complement thereof; comprising an insertion of a thymine at a position corresponding to position 1,410 according to SEQ ID NO:39 or the complement thereof, comprising an insertion of a thymine at a position corresponding to position 1,311 according to SEQ ID NO:44 or the complement thereof, comprising an insertion of a thymine at a position corresponding to position 1,232 according to SEQ ID NO:49 or the complement thereof, comprising an insertion of a thymine at a position corresponding to position 1,471 according to SEQ ID NO:54 or the complement thereof, comprising a guanine at a position corresponding to position 830 according to SEQ ID NO:104 or the complement thereof, comprising a guanine at a position corresponding to position 731 according to SEQ ID NO:105 or the complement thereof, comprising a guanine at a position corresponding to position 652 according to SEQ ID NO:106 or the complement thereof, or comprising a guanine at a position corresponding to position 891 according to SEQ ID NO:107, or the complement thereof.

Embodiment 83. The method according to embodiment 82, wherein the method is an in vitro method.

Embodiment 84. The method according to embodiment 82 or embodiment 83, wherein the assay comprises sequencing at least a portion of the nucleic acid molecule, wherein the sequenced portion: lacks a CCAGTAG heptanucleotide at positions corresponding to positions 5,540-5,546 according to SEQ ID NO:1, or the complement thereof; comprises an adenine at a position corresponding to position 5,557 according to SEQ ID NO:3, or the complement thereof; comprises a thymine at a position corresponding to position 5,911 according to SEQ ID NO:4, or the complement thereof; lacks an AAAG tetranucleotide at positions corresponding to positions 5,920-5,923 according to SEQ ID NO:1, or the complement thereof; comprises an insertion of a thymine at a position corresponding to position 6,411 according to SEQ ID NO:6, or the complement thereof; or comprises a guanine at a position corresponding to position 5,831 according to SEQ ID NO:99, or the complement thereof.

Embodiment 85. The method according to embodiment 82 or embodiment 83, wherein the assay comprises sequencing at least a portion of the nucleic acid molecule, wherein the sequenced portion: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; comprises an adenine at a position corresponding to position 556 according to SEQ ID NO:12, or the complement thereof; comprises an adenine at a position corresponding to position 457 according to SEQ ID NO:17, or the complement thereof; comprises an adenine at a position corresponding to position 378 according to SEQ ID NO:22, or the complement thereof; comprises an adenine at a position corresponding to position 617 according to SEQ ID NO:27, or the complement thereof; comprises a uracil at a position corresponding to position 910 according to SEQ ID NO:13, or the complement thereof; comprises a uracil at a position corresponding to position 811 according to SEQ ID NO:18, or the complement thereof; comprises a uracil at a position corresponding to position 732 according to SEQ ID NO:23, or the complement thereof; comprises a uracil at a position corresponding to position 971 according to SEQ ID NO:28, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; comprises an insertion of a uracil at a position corresponding to position 1,471 according to SEQ ID NO:30, or the complement thereof; comprises a guanine at a position corresponding to position 830 according to SEQ ID NO:100, or the complement thereof; comprises a guanine at a position corresponding to position 731 according to SEQ ID NO:101, or the complement thereof; comprises a guanine at a position corresponding to position 652 according to SEQ ID NO:102, or the complement thereof; or comprises a guanine at a position corresponding to position 891 according to SEQ ID NO:103, or the complement thereof.

Embodiment 86. The method according to embodiment 82 or embodiment 83, wherein the assay comprises sequencing at least a portion of the nucleic acid molecule, wherein the sequenced portion: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; comprises an adenine at a position corresponding to position 556 according to SEQ ID NO:36, or the complement thereof; comprises an adenine at a position corresponding to position 457 according to SEQ ID NO:41, or the complement thereof; comprises an adenine at a position corresponding to position 378 according to SEQ ID NO:46, or the complement thereof; comprises an adenine at a position corresponding to position 617 according to SEQ ID NO:51, or the complement thereof; comprises a thymine at a position corresponding to position 910 according to SEQ ID NO:37, or the complement thereof; comprises a thymine at a position corresponding to position 811 according to SEQ ID NO:42, or the complement thereof; comprises a thymine at a position corresponding to position 732 according to SEQ ID NO:47, or the complement thereof; comprises a thymine at a position corresponding to position 971 according to SEQ ID NO:52, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, the complement thereof; comprises an insertion of a thymine at a position corresponding to position 1,471 according to SEQ ID NO:54, or the complement thereof; comprises a guanine at a position corresponding to position 830 according to SEQ ID NO:104, or the complement thereof; comprises a guanine at a position corresponding to position 731 according to SEQ ID NO:105, or the complement thereof; comprises a guanine at a position corresponding to position 652 according to SEQ ID NO:106, or the complement thereof; or comprises a guanine at a position corresponding to position 891 according to SEQ ID NO:107, or the complement thereof.

Embodiment 87. The method according to embodiment 82 or embodiment 83, wherein the assay comprises:

a) contacting the sample with a primer hybridizing to a portion of the nucleotide sequence of the GPR75 genomic nucleic acid molecule that is proximate to a position corresponding to: positions 5,540-5,546 according to SEQ ID NO:2, position 5,557 according to SEQ ID NO:3, position 5,911 according to SEQ ID NO:4, positions 5,920-5,923 according to SEQ ID NO:5, position 6,411 according to SEQ ID NO:6, or position 5,831 according to SEQ ID NO:99;

b) extending the primer at least through the position of the nucleotide sequence of the GPR75 genomic nucleic acid molecule corresponding to: positions 5,540-5,546 according to SEQ ID NO:2, position 5,557 according to SEQ ID NO:3, position 5,911 according to SEQ ID NO:4, positions 5,920-5,923 according to SEQ ID NO:5, position 6,411 according to SEQ ID NO:6, or position 5,831 according to SEQ ID NO:99; and c) determining whether the extension product of the primer: lacks a CCAGTAG heptanucleotide at positions corresponding to positions 5,540-5,546 according to SEQ ID NO:1, comprises an adenine at a position corresponding to position 5,557 according to SEQ ID NO:3, comprises a thymine at a position corresponding to position 5,911 according to SEQ ID NO:4, lacks an AAAG tetranucleotide at positions corresponding to positions 5,920-5,923 according to SEQ ID NO:1, comprises an insertion of a thymine at a position corresponding to position 6,411 according to SEQ ID NO:6, or comprises guanine at a position corresponding to position 5,831 according to SEQ ID NO:99.

Embodiment 88. The method according to embodiment 82 or embodiment 83, wherein the assay comprises:

a) contacting the sample with a primer hybridizing to a portion of the nucleotide sequence of the GPR75 mRNA molecule that is proximate to a position corresponding to: positions 539-545 according to SEQ ID NO:11, positions 440-446 according to SEQ ID NO:16, positions 361-367 according to SEQ ID NO:21, positions 600-606 according to SEQ ID NO:26, position 556 according to SEQ ID NO:12, position 457 according to SEQ ID NO:17, position 378 according to SEQ ID NO:22, position 617 according to SEQ ID NO:27, position 910 according to SEQ ID NO:13, position 811 according to SEQ ID NO:18, position 732 according to SEQ ID NO:23, position 971 according to SEQ ID NO:28, positions 919-922 according to SEQ ID NO:14, positions 820-823 according to SEQ ID NO:19, positions 741-744 according to SEQ ID NO:24, positions 980-983 according to SEQ ID NO:29, position 1,410 according to SEQ ID NO:15, position 1,311 according to SEQ ID NO:20, position 1,232 according to SEQ ID NO:25, position 1,471 according to SEQ ID NO:30, position 830 according to SEQ ID NO:100, position 731 according to SEQ ID NO:101, position 652 according to SEQ ID NO:102, or position 891 according to SEQ ID NO:103;

b) extending the primer at least through the position of the nucleotide sequence of the GPR75 mRNA molecule corresponding to: positions 539-545 according to SEQ ID NO:11, positions 440-446 according to SEQ ID NO:16, positions 361-367 according to SEQ ID NO:21, positions 600-606 according to SEQ ID NO:26, position 556 according to SEQ ID NO:12, position 457 according to SEQ ID NO:17, position 378 according to SEQ ID NO:22, position 617 according to SEQ ID NO:27, position 910 according to SEQ ID NO:13, position 811 according to SEQ ID NO:18, position 732 according to SEQ ID NO:23, position 971 according to SEQ ID NO:28, positions 919-922 according to SEQ ID NO:14, positions 820-823 according to SEQ ID NO:19, positions 741-744 according to SEQ ID NO:24, positions 980-983 according to SEQ ID NO:29, position 1,410 according to SEQ ID NO:15, position 1,311 according to SEQ ID NO:20, position 1,232 according to SEQ ID NO:25, position 1,471 according to SEQ ID NO:30, position 830 according to SEQ ID NO:100, position 731 according to SEQ ID NO:101, position 652 according to SEQ ID NO:102, or position 891 according to SEQ ID NO:103; and c) determining whether the extension product of the primer: lacks a CCAGUAG heptanucleotide at positions corresponding to positions 539-545 according to SEQ ID NO:7, lacks a CCAGUAG heptanucleotide at positions corresponding to positions 440-446 according to SEQ ID NO:8, lacks a CCAGUAG heptanucleotide at positions corresponding to positions 361-367 according to SEQ ID NO:9, lacks a CCAGUAG heptanucleotide at positions corresponding to positions 600-606 according to SEQ ID NO:10, comprises an adenine at a position corresponding to position 556 according to SEQ ID NO:12, comprises an adenine at a position corresponding to position 457 according to SEQ ID NO:17, comprises an adenine at a position corresponding to position 378 according to SEQ ID NO:22, comprises an adenine at a position corresponding to position 617 according to SEQ ID NO:27, comprises a uracil at a position corresponding to position 910 according to SEQ ID NO:13, comprises a uracil at a position corresponding to position 811 according to SEQ ID NO:18, comprises a uracil at a position corresponding to position 732 according to SEQ ID NO:23, comprises a uracil at a position corresponding to position 971 according to SEQ ID NO:28, lacks an AAAG tetranucleotide at positions corresponding to positions 919-922 according to SEQ ID NO:7, lacks an AAAG tetranucleotide at positions corresponding to positions 820-823 according to SEQ ID NO:8, lacks an AAAG tetranucleotide at positions corresponding to positions 741-744 according to SEQ ID NO:9, lacks an AAAG tetranucleotide at positions corresponding to positions 980-983 according to SEQ ID NO:10, comprises an insertion of a uracil at a position corresponding to position 1,410 according to SEQ ID NO:15, comprises an insertion of a uracil at a position corresponding to position 1,311 according to SEQ ID NO:20, comprises an insertion of a uracil at a position corresponding to position 1,232 according to SEQ ID NO:25, comprises an insertion of a uracil at a position corresponding to position 1,471 according to SEQ ID NO:30, comprises a guanine at a position corresponding to position 830 according to SEQ ID NO:100, comprises a guanine at a position corresponding to position 731 according to SEQ ID NO:101, comprises a guanine at a position corresponding to position 652 according to SEQ ID NO:102, or comprises a guanine at a position corresponding to position 891 according to SEQ ID NO:103.

Embodiment 89. The method according to embodiment 82 or embodiment 83, wherein the assay comprises:

a) contacting the sample with a primer hybridizing to a portion of the nucleotide sequence of the GPR75 cDNA molecule that is proximate to a position corresponding to: positions 539-545 according to SEQ ID NO:35, positions 440-446 according to SEQ ID NO:40, positions 361-367 according to SEQ ID NO:45, positions 600-606 according to SEQ ID NO:50, position 556 according to SEQ ID NO:36, position 457 according to SEQ ID NO:41, position 378 according to SEQ ID NO:46, position 617 according to SEQ ID NO:51, position 910 according to SEQ ID NO:37, position 811 according to SEQ ID NO:42, position 732 according to SEQ ID NO:47, position 971 according to SEQ ID NO:52, positions 919-922 according to SEQ ID NO:38, positions 820-823 according to SEQ ID NO:43, positions 741-744 according to SEQ ID NO:48, positions 980-983 according to SEQ ID NO:53, position 1,410 according to SEQ ID NO:39, position 1,311 according to SEQ ID NO:44, position 1,232 according to SEQ ID NO:49, position 1,471 according to SEQ ID NO:54, position 830 according to SEQ ID NO:104, position 731 according to SEQ ID NO:105, position 652 according to SEQ ID NO:106, or position 891 according to SEQ ID NO:107;

b) extending the primer at least through the position of the nucleotide sequence of the GPR75 cDNA molecule corresponding to: positions 539-545 according to SEQ ID NO:35, positions 440-446 according to SEQ ID NO:40, positions 361-367 according to SEQ ID NO:45, positions 600-606 according to SEQ ID NO:50, position 556 according to SEQ ID NO:36, position 457 according to SEQ ID NO:41, position 378 according to SEQ ID NO:46, position 617 according to SEQ ID NO:51, position 910 according to SEQ ID NO:37, position 811 according to SEQ ID NO:42, position 732 according to SEQ ID NO:47, position 971 according to SEQ ID NO:52, positions 919-922 according to SEQ ID NO:38, positions 820-823 according to SEQ ID NO:43, positions 741-744 according to SEQ ID NO:48, positions 980-983 according to SEQ ID NO:53, position 1,410 according to SEQ ID NO:39, position 1,311 according to SEQ ID NO:44, position 1,232 according to SEQ ID NO:49, or position 1,471 according to SEQ ID NO:54, position 830 according to SEQ ID NO:104, position 731 according to SEQ ID NO:105, position 652 according to SEQ ID NO:106, or position 891 according to SEQ ID NO:107; and c) determining whether the extension product of the primer: lacks a CCAGTAG heptanucleotide at positions corresponding to positions 539-545 according to SEQ ID NO:31, lacks a CCAGTAG heptanucleotide at positions corresponding to positions 440-446 according to SEQ ID NO:32, lacks a CCAGTAG heptanucleotide at positions corresponding to positions 361-367 according to SEQ ID NO:33, lacks a CCAGTAG heptanucleotide at positions corresponding to positions 600-606 according to SEQ ID NO:34, comprises an adenine at a position corresponding to position 556 according to SEQ ID NO:36, comprises an adenine at a position corresponding to position 457 according to SEQ ID NO:41, comprises an adenine at a position corresponding to position 378 according to SEQ ID NO:46, comprises an adenine at a position corresponding to position 617 according to SEQ ID NO:51, comprises a thymine at a position corresponding to position 910 according to SEQ ID NO:37, comprises a thymine at a position corresponding to position 811 according to SEQ ID NO:42, comprises a thymine at a position corresponding to position 732 according to SEQ ID NO:47, comprises a thymine at a position corresponding to position 971 according to SEQ ID NO:52, lacks an AAAG tetranucleotide at positions corresponding to positions 919-922 according to SEQ ID NO:31, lacks an AAAG tetranucleotide at positions corresponding to positions 820-823 according to SEQ ID NO:32, lacks an AAAG tetranucleotide at positions corresponding to positions 741-744 according to SEQ ID NO:33, lacks an AAAG tetranucleotide at positions corresponding to positions 980-983 according to SEQ ID NO:34, comprises an insertion of a thymine at a position corresponding to position 1,410 according to SEQ ID NO:39, comprises an insertion of a thymine at a position corresponding to position 1,311 according to SEQ ID NO:44, comprises an insertion of a thymine at a position corresponding to position 1,232 according to SEQ ID NO:49, comprises an insertion of a thymine at a position corresponding to position 1,471 according to SEQ ID NO:54, comprises a guanine at a position corresponding to position 830 according to SEQ ID NO:104, comprises a guanine at a position corresponding to position 731 according to SEQ ID NO:105, comprises a guanine at a position corresponding to position 652 according to SEQ ID NO:106, or comprises a guanine at a position corresponding to position 891 according to SEQ ID NO:107.

Embodiment 90. The method according to any one of embodiments 84 to 89, wherein the assay comprises sequencing the entire nucleic acid molecule.

Embodiment 91. The method according to embodiment 82 or embodiment 83, wherein the assay comprises:

a) amplifying at least a portion of the nucleic acid molecule that encodes the human GPR75 polypeptide, wherein the portion: lacks a CCAGTAG heptanucleotide at positions corresponding to positions 5,540-5,546 according to SEQ ID NO:1, or the complement thereof; comprises an adenine at a position corresponding to position 5,557 according to SEQ ID NO:3, or the complement thereof; comprises a thymine at a position corresponding to position 5,911 according to SEQ ID NO:4, or the complement thereof; lacks an AAAG tetranucleotide at positions corresponding to positions 5,920-5,923 according to SEQ ID NO:1, or the complement thereof; comprises an insertion of a thymine at a position corresponding to position 6,411 according to SEQ ID NO:6, or the complement thereof; or position 5,831 according to SEQ ID NO:99, or the complement thereof;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGTAG heptanucleotide at positions corresponding to positions 5,540-5,546 according to SEQ ID NO:1, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:1, or the complement thereof; comprising an insertion of a thymine at a position corresponding to position 6,411 according to SEQ ID NO:6, or the complement thereof; or comprising a guanine at a position corresponding to position 5,831 according to SEQ ID NO:99, or the complement thereof; and d) detecting the detectable label.

Embodiment 92. The method according to embodiment 82 or embodiment 83, wherein the assay comprises:

a) amplifying at least a portion of the nucleic acid molecule that encodes the human GPR75 polypeptide, wherein the portion: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; comprises an adenine at a position corresponding to position 556 according to SEQ ID NO:12, or the complement thereof; comprises an adenine at a position corresponding to position 457 according to SEQ ID NO:17, or the complement thereof; comprises an adenine at a position corresponding to position 378 according to SEQ ID NO:22, or the complement thereof; comprises an adenine at a position corresponding to position 617 according to SEQ ID NO:27, or the complement thereof; comprises a uracil at a position corresponding to position 910 according to SEQ ID NO:13, or the complement thereof; comprises a uracil at a position corresponding to position 811 according to SEQ ID NO:18, or the complement thereof; comprises a uracil at a position corresponding to position 732 according to SEQ ID NO:23, or the complement thereof; comprises a uracil at a position corresponding to position 971 according to SEQ ID NO:28, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; comprises an insertion of a uracil at a position corresponding to position 1,471 according to SEQ ID NO:30, or the complement thereof; comprises a guanine at a position corresponding to position 830 according to SEQ ID NO:100, or the complement thereof; comprises a guanine at a position corresponding to position 731 according to SEQ ID NO:101, or the complement thereof; comprises a guanine at a position corresponding to position 652 according to SEQ ID NO:102, or the complement thereof; or comprises a guanine at a position corresponding to position 891 according to SEQ ID NO:103, or the complement thereof;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; lacking a CCAGUAG heptanucleotide at positions corresponding to positions 600-606 according to SEQ ID NO:10, or the complement thereof; comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; lacking an AAAG tetranucleotide at positions corresponding to positions 980-983 according to SEQ ID NO:10, or the complement thereof; comprising an insertion of a uracil at a position corresponding to position 1,410 according to SEQ ID NO:15, or the complement thereof; comprising an insertion of a uracil at a position corresponding to position 1,311 according to SEQ ID NO:20, or the complement thereof; comprising an insertion of a uracil at a position corresponding to position 1,232 according to SEQ ID NO:25, or the complement thereof; comprising an insertion of a uracil at a position corresponding to position 1,471 according to SEQ ID NO:30, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof; and d) detecting the detectable label.

Embodiment 93. The method according to embodiment 82 or embodiment 83, wherein the assay comprises:

a) amplifying at least a portion of the nucleic acid molecule that encodes the human GPR75 polypeptide, wherein the portion: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; comprises an adenine at a position corresponding to position 556 according to SEQ ID NO:36, or the complement thereof; comprises an adenine at a position corresponding to position 457 according to SEQ ID NO:41, or the complement thereof; comprises an adenine at a position corresponding to position 378 according to SEQ ID NO:46, or the complement thereof; comprises an adenine at a position corresponding to position 617 according to SEQ ID NO:51, or the complement thereof; comprises a thymine at a position corresponding to position 910 according to SEQ ID NO:37, or the complement thereof; comprises a thymine at a position corresponding to position 811 according to SEQ ID NO:42, or the complement thereof; comprises a thymine at a position corresponding to position 732 according to SEQ ID NO:47, or the complement thereof; comprises a thymine at a position corresponding to position 971 according to SEQ ID NO:52, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; comprises an insertion of a thymine at a position corresponding to position 1,471 according to SEQ ID NO:54, or the complement thereof; comprises a guanine at a position corresponding to position 830 according to SEQ ID NO:104, or the complement thereof; comprises a guanine at a position corresponding to position 731 according to SEQ ID NO:105, or the complement thereof; comprises a guanine at a position corresponding to position 652 according to SEQ ID NO:106, or the complement thereof; or comprises a guanine at a position corresponding to position 891 according to SEQ ID NO:107, or the complement thereof;

b) labeling the amplified nucleic acid molecule with a detectable label;

c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule: lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; lacking a CCAGTAG heptanucleotide at positions corresponding to positions 600-606 according to SEQ ID NO:34, or the complement thereof; comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; lacking an AAAG tetranucleotide at positions corresponding to positions 980-983 according to SEQ ID NO:34, or the complement thereof; comprising an insertion of a thymine at a position corresponding to position 1,410 according to SEQ ID NO:39, or the complement thereof; comprising an insertion of a thymine at a position corresponding to position 1,311 according to SEQ ID NO:44, or the complement thereof; comprising an insertion of a thymine at a position corresponding to position 1,232 according to SEQ ID NO:49, or the complement thereof; comprising an insertion of a thymine at a position corresponding to position 1,471 according to SEQ ID NO:54, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof; and d) detecting the detectable label.

Embodiment 94. The method according to embodiment 93, wherein the nucleic acid molecule in the sample is mRNA and the mRNA is reverse-transcribed into cDNA prior to the amplifying step.

Embodiment 95. The method according to embodiment 82 or embodiment 83, wherein the assay comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGTAG heptanucleotide at positions corresponding to positions 5,540-5,546 according to SEQ ID NO:1, or the complement thereof; comprising an adenine at a position corresponding to position 5,557 according to SEQ ID NO:3, or the complement thereof; comprising a thymine at a position corresponding to position 5,911 according to SEQ ID NO:4, or the complement thereof; lacking an AAAG tetranucleotide at positions corresponding to positions 5,920-5,923 according to SEQ ID NO:1, or the complement thereof; comprising an insertion of a thymine at a position corresponding to position 6,411 according to SEQ ID NO:6, or the complement thereof; or comprising a guanine at a position corresponding to position 5,831 according to SEQ ID NO:99, or the complement thereof; and detecting the detectable label.

Embodiment 96. The method according to embodiment 82 or embodiment 83, wherein the assay comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGUAG heptanucleotide at positions corresponding to positions 539-545 according to SEQ ID NO:7, or the complement thereof; lacking a CCAGUAG heptanucleotide at positions corresponding to positions 440-446 according to SEQ ID NO:8, or the complement thereof; lacking a CCAGUAG heptanucleotide at positions corresponding to positions 361-367 according to SEQ ID NO:9, or the complement thereof; lacking a CCAGUAG heptanucleotide at positions corresponding to positions 600-606 according to SEQ ID NO:10, or the complement thereof; comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; lacking an AAAG tetranucleotide at positions corresponding to positions 919-922 according to SEQ ID NO:7, or the complement thereof; lacking an AAAG tetranucleotide at positions corresponding to positions 820-823 according to SEQ ID NO:8, or the complement thereof; lacking an AAAG tetranucleotide at positions corresponding to positions 741-744 according to SEQ ID NO:9, or the complement thereof; lacking an AAAG tetranucleotide at positions corresponding to positions 980-983 according to SEQ ID NO:10, or the complement thereof; comprising an insertion of a uracil at a position corresponding to position 1,410 according to SEQ ID NO:15, or the complement thereof; comprising an insertion of a uracil at a position corresponding to position 1,311 according to SEQ ID NO:20, or the complement thereof; comprising an insertion of a uracil at a position corresponding to position 1,232 according to SEQ ID NO:25, or the complement thereof; comprising an insertion of a uracil at a position corresponding to position 1,471 according to SEQ ID NO:30, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof; and detecting the detectable label.

Embodiment 97. The method according to embodiment 82 or embodiment 83, wherein the assay comprises:

contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule: lacking a CCAGTAG heptanucleotide at positions corresponding to positions 539-545 according to SEQ ID NO:31, or the complement thereof; lacking a CCAGTAG heptanucleotide at positions corresponding to positions 440-446 according to SEQ ID NO:32, or the complement thereof; lacking a CCAGTAG heptanucleotide at positions corresponding to positions 361-367 according to SEQ ID NO:33, or the complement thereof; lacking a CCAGTAG heptanucleotide at positions corresponding to positions 600-606 according to SEQ ID NO:34, or the complement thereof; comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; lacking an AAAG tetranucleotide at positions corresponding to positions 919-922 according to SEQ ID NO:31, or the complement thereof; lacking an AAAG tetranucleotide at positions corresponding to positions 820-823 according to SEQ ID NO:32, or the complement thereof; lacking an AAAG tetranucleotide at positions corresponding to positions 741-744 according to SEQ ID NO:33, or the complement thereof; lacking an AAAG tetranucleotide at positions corresponding to positions 980-983 according to SEQ ID NO:34, or the complement thereof; comprising an insertion of a thymine at a position corresponding to position 1,410 according to SEQ ID NO:39, or the complement thereof; comprising an insertion of a thymine at a position corresponding to position 1,311 according to SEQ ID NO:44, or the complement thereof; comprising an insertion of a thymine at a position corresponding to position 1,232 according to SEQ ID NO:49, or the complement thereof; comprising an insertion of a thymine at a position corresponding to position 1,471 according to SEQ ID NO:54, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof; and detecting the detectable label.

Embodiment 98. The method according to any one of embodiments 82 to 97, wherein the nucleic acid molecule is present within a cell obtained from the subject.

Embodiment 99. A method of detecting the presence of a human G-Protein Coupled Receptor 75 (GPR75) Ala110fs, Ala116Thr, Tyr207Cys, Gln234Stop, Arg236fs, or Cys400fs variant polypeptide, comprising performing an assay on a sample obtained from a subject to determine whether a GPR75 protein in the sample comprises SEQ ID NO:56, SEQ ID NO:57, SEQ ID NO:58, SEQ ID NO:59, SEQ ID NO:60, or SEQ ID NO:108.

Embodiment 100. The method according to embodiment 99, wherein the assay comprises sequencing the polypeptide.

Embodiment 101. The method according to embodiment 99, wherein the assay is an immunoassay.

Embodiment 102. An isolated alteration-specific probe or alteration-specific primer comprising at least about 15 nucleotides, wherein the alteration-specific probe or alteration-specific primer comprises a nucleotide sequence which is complementary to a portion of a nucleotide sequence encoding a human G-Protein Coupled Receptor 75 (GPR75) polypeptide, wherein the portion comprises a position corresponding to: positions 5,540-5,546 according to SEQ ID NO:2, or the complement thereof;

positions 539-545 according to SEQ ID NO:11, or the complement thereof; positions 440-446 according to SEQ ID NO:16, or the complement thereof; positions 361-367 according to SEQ ID NO:21, or the complement thereof; positions 600-606 according to SEQ ID NO:26, or the complement thereof; positions 539-545 according to SEQ ID NO:35, or the complement thereof; positions 440-446 according to SEQ ID NO:40, or the complement thereof; positions 361-367 according to SEQ ID NO:45, or the complement thereof; or positions 600-606 according to SEQ ID NO:50, or the complement thereof;

positions 5,920-5,923 according to SEQ ID NO:5, or the complement thereof; position 919-922 according to SEQ ID NO:14, or the complement thereof; positions 820-823 according to SEQ ID NO:19, or the complement thereof; positions 741-744 according to SEQ ID NO:24, or the complement thereof; position 980-983 according to SEQ ID NO:29, or the complement thereof; position 919-922 according to SEQ ID NO:38, or the complement thereof; positions 820-823 according to SEQ ID NO:43, or the complement thereof; positions 741-744 according to SEQ ID NO:48, or the complement thereof; or position 980-983 according to SEQ ID NO:53, or the complement thereof; or position 6,411 according to SEQ ID NO:6, or the complement thereof; position 1,410 according to SEQ ID NO:15, or the complement thereof; position 1,311 according to SEQ ID NO:20, or the complement thereof; position 1,232 according to SEQ ID NO:25, or the complement thereof; position 1,471 according to SEQ ID NO:30, or the complement thereof; position 1,410 according to SEQ ID NO:39, or the complement thereof; position 1,311 according to SEQ ID NO:44, or the complement thereof; position 1,232 according to SEQ ID NO:49, or the complement thereof; or position 1,471 according to SEQ ID NO:54, or the complement thereof.

Embodiment 103. The alteration-specific probe or alteration-specific primer according to embodiment 102, comprising a nucleotide sequence which is complementary to a portion of a nucleotide sequence comprising a position corresponding to: positions 5,540-5,546 according to SEQ ID NO:2, or the complement thereof; positions 5,920-5,923 according to SEQ ID NO:5, or the complement thereof; or position 6,411 according to SEQ ID NO:6, or the complement thereof.

Embodiment 104. The alteration-specific probe or alteration-specific primer according to embodiment 102, comprising a nucleotide sequence which is complementary to a portion of a nucleotide sequence comprising a position corresponding to: positions 539-545 according to SEQ ID NO:11, or the complement thereof; positions 440-446 according to SEQ ID NO:16, or the complement thereof; positions 361-367 according to SEQ ID NO:21, or the complement thereof; positions 600-606 according to SEQ ID NO:26, or the complement thereof; position 919-922 according to SEQ ID NO:14, or the complement thereof; positions 820-823 according to SEQ ID NO:19, or the complement thereof; positions 741-744 according to SEQ ID NO:24, or the complement thereof; position 980-983 according to SEQ ID NO:29, or the complement thereof; position 1,410 according to SEQ ID NO:15, or the complement thereof; position 1,311 according to SEQ ID NO:20, or the complement thereof; position 1,232 according to SEQ ID NO:25, or the complement thereof; or position 1,471 according to SEQ ID NO:30, or the complement thereof.

Embodiment 105. The alteration-specific probe or alteration-specific primer according to embodiment 102, comprising a nucleotide sequence which is complementary to a portion of a nucleotide sequence comprising a position corresponding to: positions 539-545 according to SEQ ID NO:35, or the complement thereof; positions 440-446 according to SEQ ID NO:40, or the complement thereof; positions 361-367 according to SEQ ID NO:45, or the complement thereof; positions 600-606 according to SEQ ID NO:50, or the complement thereof; position 919-922 according to SEQ ID NO:38, or the complement thereof; positions 820-823 according to SEQ ID NO:43, or the complement thereof; positions 741-744 according to SEQ ID NO:48, or the complement thereof; position 980-983 according to SEQ ID NO:53, or the complement thereof; position 1,410 according to SEQ ID NO:39, or the complement thereof; position 1,311 according to SEQ ID NO:44, or the complement thereof; position 1,232 according to SEQ ID NO:49, or the complement thereof; or position 1,471 according to SEQ ID NO:54, or the complement thereof.

Embodiment 106. The alteration-specific probe or alteration-specific primer according to any one of embodiments 102 to 105, wherein the alteration-specific probe or alteration-specific primer comprises DNA.

Embodiment 107. The alteration-specific probe or alteration-specific primer according to any one of embodiments 102 to 105, wherein the alteration-specific probe or alteration-specific primer comprises RNA.

Embodiment 108. The alteration-specific probe or alteration-specific primer according to any one of embodiments 102 to 107, wherein the alteration-specific probe or alteration-specific primer comprises a label.

Embodiment 109. The alteration-specific probe or alteration-specific primer according to embodiment 108, wherein the label is a fluorescent label, a radiolabel, or biotin.

Embodiment 110. A support comprising a substrate to which an alteration-specific probe or alteration-specific primer according to any one of embodiments 102 to 109 is attached.

Embodiment 111. The support according to embodiment 110, wherein the support is a microarray.

Embodiment 112. A molecular complex comprising an alteration-specific primer or an alteration-specific probe hybridized to a genomic nucleic acid molecule comprising a nucleotide sequence encoding a human G-Protein Coupled Receptor 75 (GPR75) polypeptide, wherein the alteration-specific primer or the alteration-specific probe is hybridized to the genomic nucleic acid molecule: at nucleotides at positions corresponding to positions 5,539-5,540 according to SEQ ID NO:2, or the complement thereof; at an adenine at a position corresponding to position 5,557 according to SEQ ID NO:3, or the complement thereof; at a thymine at a position corresponding to position 5,911 according to SEQ ID NO:4, or the complement thereof; at nucleotides at positions corresponding to positions 5,919-5,920 according to SEQ ID NO:5, or the complement thereof; at a thymine at a position corresponding to position 6,411 according to SEQ ID NO:6, or the complement thereof; or at a guanine at a position corresponding to position 5,831 according to SEQ ID NO:99, or the complement thereof.

Embodiment 113. The molecular complex according to embodiment 112, wherein the genomic nucleic acid molecule comprises SEQ ID NO:2, SEQ ID NO:3, SEQ ID NO:4, SEQ ID NO:5, SEQ ID NO:6, or SEQ ID NO:99.

Embodiment 114. A molecular complex comprising an alteration-specific primer or an alteration-specific probe hybridized to an mRNA molecule comprising a nucleotide sequence encoding a human G-Protein Coupled Receptor 75 (GPR75) polypeptide, wherein the alteration-specific primer or the alteration-specific probe is hybridized to the mRNA molecule: at nucleotides at positions corresponding to positions 538-539 according to SEQ ID NO:11, or the complement thereof; at nucleotides at positions corresponding to positions 439-440 according to SEQ ID NO:16, or the complement thereof; at nucleotides at positions corresponding to positions 360-361 according to SEQ ID NO:21, or the complement thereof; at nucleotides at positions corresponding to positions 599-600 according to SEQ ID NO:26, or the complement thereof; at an adenine at a position corresponding to position 556 according to SEQ ID NO:12, or the complement thereof; at an adenine at a position corresponding to position 457 according to SEQ ID NO:17, or the complement thereof; at an adenine at a position corresponding to position 378 according to SEQ ID NO:22, or the complement thereof; at an adenine at a position corresponding to position 617 according to SEQ ID NO:27, or the complement thereof; at a uracil at a position corresponding to position 910 according to SEQ ID NO:13, or the complement thereof; at a uracil at a position corresponding to position 811 according to SEQ ID NO:18, or the complement thereof; at a uracil at a position corresponding to position 732 according to SEQ ID NO:23, or the complement thereof; at a uracil at a position corresponding to position 971 according to SEQ ID NO:28, or the complement thereof; at nucleotides at positions corresponding to positions 918-919 according to SEQ ID NO:14, or the complement thereof; at nucleotides at positions corresponding to positions 819-820 according to SEQ ID NO:19, or the complement thereof; at nucleotides at positions corresponding to positions 740-741 according to SEQ ID NO:24, or the complement thereof; at nucleotides at positions corresponding to positions 979-980 according to SEQ ID NO:29, or the complement thereof; at a uracil at a position corresponding to position 1,410 according to SEQ ID NO:15, or the complement thereof; at a uracil at a position corresponding to position 1,311 according to SEQ ID NO:20, or the complement thereof; at a uracil at a position corresponding to position 1,232 according to SEQ ID NO:25, or the complement thereof; at a uracil at a position corresponding to position 1,471 according to SEQ ID NO:30, or the complement thereof; at a guanine at a position corresponding to position 830 according to SEQ ID NO:100, or the complement thereof; at a guanine at a position corresponding to position 731 according to SEQ ID NO:101, or the complement thereof; at a guanine at a position corresponding to position 652 according to SEQ ID NO:102, or the complement thereof; or at a guanine at a position corresponding to position 891 according to SEQ ID NO:103, or the complement thereof.

Embodiment 115. The molecular complex according to embodiment 114, wherein the mRNA molecule comprises SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:100, SEQ ID NO:101, SEQ ID NO:102, or SEQ ID NO:103.

Embodiment 116. A molecular complex comprising an alteration-specific primer or an alteration-specific probe hybridized to a cDNA molecule comprising a nucleotide sequence encoding a human G-Protein Coupled Receptor 75 (GPR75) polypeptide, wherein the alteration-specific primer or the alteration-specific probe is hybridized to: nucleotides at positions corresponding to positions 538-539 according to SEQ ID NO:35, or the complement thereof; nucleotides at positions corresponding to positions 439-440 according to SEQ ID NO:40, or the complement thereof; nucleotides at positions corresponding to positions 360-361 according to SEQ ID NO:45, or the complement thereof; nucleotides at positions corresponding to positions 599-600 according to SEQ ID NO:50, or the complement thereof; comprising an adenine at a position corresponding to position 556 according to SEQ ID NO:36, or the complement thereof; an adenine at a position corresponding to position 457 according to SEQ ID NO:41, or the complement thereof; an adenine at a position corresponding to position 378 according to SEQ ID NO:46, or the complement thereof; an adenine at a position corresponding to position 617 according to SEQ ID NO:51, or the complement thereof; a thymine at a position corresponding to position 910 according to SEQ ID NO:37, or the complement thereof; a thymine at a position corresponding to position 811 according to SEQ ID NO:42, or the complement thereof; a thymine at a position corresponding to position 732 according to SEQ ID NO:47, or the complement thereof; a thymine at a position corresponding to position 971 according to SEQ ID NO:52, or the complement thereof; nucleotides at positions corresponding to positions 918-919 according to SEQ ID NO:38, or the complement thereof; nucleotides at positions corresponding to positions 819-820 according to SEQ ID NO:43, or the complement thereof; nucleotides at positions corresponding to positions 740-741 according to SEQ ID NO:48, or the complement thereof; nucleotides at positions corresponding to positions 979-980 according to SEQ ID NO:53, or the complement thereof; a thymine at a position corresponding to position 1,410 according to SEQ ID NO:39, or the complement thereof; a thymine at a position corresponding to position 1,311 according to SEQ ID NO:44, or the complement thereof; a thymine at a position corresponding to position 1,232 according to SEQ ID NO:49, or the complement thereof; a thymine at a position corresponding to position 1,471 according to SEQ ID NO:54, or the complement thereof; a guanine at a position corresponding to position 830 according to SEQ ID NO:104, or the complement thereof; a guanine at a position corresponding to position 731 according to SEQ ID NO:105, or the complement thereof; a guanine at a position corresponding to position 652 according to SEQ ID NO:106, or the complement thereof; or a guanine at a position corresponding to position 891 according to SEQ ID NO:107, or the complement thereof.

Embodiment 117. The molecular complex according to embodiment 116, wherein the cDNA molecule comprises SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, or SEQ ID NO:54, SEQ ID NO:104, SEQ ID NO:105, SEQ ID NO:106, or SEQ ID NO:107.

Embodiment 118. The molecular complex according to any one of embodiments 112 to 117, wherein the alteration-specific probe or alteration-specific primer comprises a label.

Embodiment 119. The molecular complex according to embodiment 118, wherein the label is a fluorescent label, a radiolabel, or biotin.

Embodiment 120. The molecular complex according to any one of embodiments 112 to 119, further comprising a non-human polymerase.

Embodiment 121. An isolated nucleic acid molecule comprising a nucleotide sequence encoding a human G-Protein Coupled Receptor 75 (GPR75) polypeptide, or the complement thereof, wherein the polypeptide comprises: a frameshift beginning at a position corresponding to position 110 according to SEQ ID NO:56, a frameshift beginning at a position corresponding to position 236 according to SEQ ID NO:59, or a frameshift beginning at a position corresponding to position 400 according to SEQ ID NO:60.

Embodiment 122. The isolated nucleic acid molecule, or the complement thereof, according to embodiment 121, wherein the nucleic acid molecule encodes a GPR75 polypeptide having an amino acid sequence at least about 90% identical to: SEQ ID NO:56, wherein the polypeptide comprises a frameshift beginning at a position corresponding to position 110 according to SEQ ID NO:56; SEQ ID NO:59, wherein the polypeptide comprises a frameshift beginning at a position corresponding to position 236 according to SEQ ID NO:59; or SEQ ID NO:60, wherein the polypeptide comprises a frameshift beginning at a position corresponding to position 400 according to SEQ ID NO:60.

Embodiment 123. The nucleic acid molecule, or complement thereof, according to embodiment 121, wherein the polypeptide comprises SEQ ID NO:56, SEQ ID NO:59, or SEQ ID NO:60.

Embodiment 124. A vector comprising the isolated nucleic acid molecule, or the complement thereof, according to any one of embodiments 121 to 123.

Embodiment 125. The vector according to embodiment 124, wherein the vector is a plasmid.

Embodiment 126. The vector according to embodiment 124, wherein the vector is a virus.

Embodiment 127. A host cell comprising the isolated nucleic acid molecule, or the complement thereof, according to any one of embodiments 121 to 123.

Embodiment 128. A host cell comprising the vector according to any one of embodiments 124 to 126.

Embodiment 129. The host cell according to embodiment 127 or embodiment 128, wherein the nucleotide sequence is operably linked to a promoter active in the host cell.

Embodiment 130. The host cell according to embodiment 129, wherein the promoter is an exogenous promoter.

Embodiment 131. The host cell according to embodiment 129 or embodiment 130, wherein the promoter is an inducible promoter.

Embodiment 132. The host cell according to any one of embodiments 127 to 131, wherein the host cell is a bacterial cell, a yeast cell, an insect cell, or a mammalian cell.

Embodiment 133. A composition comprising the isolated nucleic acid molecule, or the complement thereof, according to any one of embodiments 121 to 123 and a carrier.

Embodiment 134. A composition comprising the vector according to any one of embodiments 124 to 126 and a carrier.

Embodiment 135. An isolated genomic nucleic acid molecule comprising a nucleotide sequence encoding a human G-Protein Coupled Receptor 75 (GPR75) polypeptide, wherein the nucleotide sequence: lacks a CCAGTAG heptanucleotide at positions corresponding to positions 5,540-5,546 according to SEQ ID NO:1, or the complement thereof; a lacks an AAAG tetranucleotide at positions corresponding to positions 5,920-5,923 according to SEQ ID NO:1, or the complement thereof; or comprises an insertion of a thymine at a position corresponding to position 6,411 according to SEQ ID NO:6, or the complement thereof.

Embodiment 136. The isolated genomic nucleic acid molecule, or the complement thereof, according to embodiment 135, wherein the nucleotide sequence has at least 90% sequence identity to: SEQ ID NO:2, and lacks a CCAGTAG heptanucleotide at positions corresponding to positions 5,540-5,546 according to SEQ ID NO:1; SEQ ID NO:5, and lacks an AAAG tetranucleotide at positions corresponding to positions 5,920-5,923 according to SEQ ID NO:1; or SEQ ID NO:6, and comprises an insertion of a thymine at a position corresponding to position 6,411 according to SEQ ID NO:6.

Embodiment 137. The isolated genomic nucleic acid molecule, or the complement thereof, according to embodiment 136, wherein the nucleic acid molecule comprises SEQ ID NO:2, SEQ ID NO:5, or SEQ ID NO:6.

Embodiment 138. A vector comprising the isolated genomic nucleic acid molecule, or the complement thereof, according to any one of embodiments 135 to 137.

Embodiment 139. The vector according to embodiment 138, wherein the vector is a plasmid.

Embodiment 140. The vector according to embodiment 138, wherein the vector is a virus.

Embodiment 141. A host cell comprising the isolated genomic nucleic acid molecule, or the complement thereof, according to any one of embodiments 135 to 137.

Embodiment 142. A host cell comprising the vector according to any one of embodiments 138 to 140.

Embodiment 143. The host cell according to embodiment 141 or embodiment 142, wherein the nucleotide sequence is operably linked to a promoter active in the host cell.

Embodiment 144. The host cell according to embodiment 143, wherein the promoter is an exogenous promoter.

Embodiment 145. The host cell according to embodiment 143 or embodiment 144, wherein the promoter is an inducible promoter.

Embodiment 146. The host cell according to any one of embodiments 141 to 145, wherein the host cell is a bacterial cell, a yeast cell, an insect cell, or a mammalian cell.

Embodiment 147. A composition comprising the isolated genomic nucleic acid molecule, or the complement thereof, according to any one of embodiments 135 to 137 and a carrier.

Embodiment 148. A composition comprising the vector according to any one of embodiments 138 to 140 and a carrier.

Embodiment 149. An isolated mRNA molecule comprising a nucleotide sequence encoding a human G-Protein Coupled Receptor 75 (GPR75) polypeptide, wherein the nucleotide sequence: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; or comprises an insertion of a uracil at a position corresponding to position 1,471 according to SEQ ID NO:30, or the complement thereof.

Embodiment 150. The isolated mRNA molecule, or the complement thereof, according to embodiment 149, wherein the nucleotide sequence has at least 90% sequence identity to: SEQ ID NO:11, and lacks a CCAGUAG heptanucleotide at positions corresponding to positions 539-545 according to SEQ ID NO:7; SEQ ID NO:16, and lacks a CCAGUAG heptanucleotide at positions corresponding to positions 440-446 according to SEQ ID NO:8; SEQ ID NO:21, and lacks a CCAGUAG heptanucleotide at positions corresponding to positions 361-367 according to SEQ ID NO:9; SEQ ID NO:26, and lacks a CCAGUAG heptanucleotide at positions corresponding to positions 600-606 according to SEQ ID NO:10; SEQ ID NO:14, and lacks an AAAG tetranucleotide at positions corresponding to positions 919-922 according to SEQ ID NO:7; SEQ ID NO:19, and lacks an AAAG tetranucleotide at positions corresponding to positions 820-823 according to SEQ ID NO:8; SEQ ID NO:24, and lacks an AAAG tetranucleotide at positions corresponding to positions 741-744 according to SEQ ID NO:9; SEQ ID NO:29, and lacks an AAAG tetranucleotide at positions corresponding to positions 980-983 according to SEQ ID NO:10; SEQ ID NO:15, and comprises an insertion of a uracil at a position corresponding to position 1,410 according to SEQ ID NO:15; SEQ ID NO:20, and comprises an insertion of a uracil at a position corresponding to position 1,311 according to SEQ ID NO:20; SEQ ID NO:25, and comprises an insertion of a uracil at a position corresponding to position 1,232 according to SEQ ID NO:25; or SEQ ID NO:30, and comprises an insertion of a uracil at a position corresponding to position 1,471 according to SEQ ID NO:30.

Embodiment 151. The isolated mRNA molecule, or the complement thereof, according to embodiment 149, wherein the nucleic acid molecule comprises SEQ ID NO:11, SEQ ID NO:14, SEQ ID NO:15, SEQ ID NO:16, SEQ ID NO:19, SEQ ID NO:20, SEQ ID NO:21, SEQ ID NO:24, SEQ ID NO:25, SEQ ID NO:26, SEQ ID NO:29, or SEQ ID NO:30.

Embodiment 152. A vector comprising the isolated mRNA molecule, or the complement thereof, according to any one of embodiments 149 to 151.

Embodiment 153. The vector according to embodiment 152, wherein the vector is a plasmid.

Embodiment 154. The vector according to embodiment 152, wherein the vector is a virus.

Embodiment 155. A host cell comprising the isolated mRNA molecule, or the complement thereof, according to any one of embodiments 149 to 151.

Embodiment 156. A host cell comprising the vector according to any one of embodiments 152 to 154.

Embodiment 157. The host cell according to embodiment 155 or embodiment 156, wherein the nucleotide sequence is operably linked to a promoter active in the host cell.

Embodiment 158. The host cell according to embodiment 157, wherein the promoter is an exogenous promoter.

Embodiment 159. The host cell according to embodiment 157 or embodiment 158, wherein the promoter is an inducible promoter.

Embodiment 160. The host cell according to any one of embodiments 155 to 159, wherein the host cell is a bacterial cell, a yeast cell, an insect cell, or a mammalian cell.

Embodiment 161. A composition comprising the isolated mRNA molecule, or the complement thereof, according to any one of embodiments 149 to 151 and a carrier.

Embodiment 162. A composition comprising the vector according to any one of embodiments 152 to 154 and a carrier.

Embodiment 163. An isolated cDNA molecule comprising a nucleotide sequence encoding a human G-Protein Coupled Receptor 75 (GPR75) polypeptide, wherein the nucleotide sequence: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; or comprises an insertion of a thymine at a position corresponding to position 1,471 according to SEQ ID NO:54, or the complement thereof.

Embodiment 164. The isolated cDNA molecule, or the complement thereof, according to embodiment 163, wherein the nucleotide sequence has at least 90% sequence identity to: SEQ ID NO:35, and lacks a CCAGTAG heptanucleotide at positions corresponding to positions 539-545 according to SEQ ID NO:31; SEQ ID NO:40, and lacks a CCAGTAG heptanucleotide at positions corresponding to positions 440-446 according to SEQ ID NO:32; SEQ ID NO:45, and lacks a CCAGTAG heptanucleotide at positions corresponding to positions 361-367 according to SEQ ID NO:33; SEQ ID NO:50, and lacks a CCAGTAG heptanucleotide at positions corresponding to positions 600-606 according to SEQ ID NO:34; SEQ ID NO:38, and lacks an AAAG tetranucleotide at positions corresponding to positions 919-922 according to SEQ ID NO:31; SEQ ID NO:43, and lacks an AAAG tetranucleotide at positions corresponding to positions 820-823 according to SEQ ID NO:32; SEQ ID NO:48, and lacks an AAAG tetranucleotide at positions corresponding to positions 741-744 according to SEQ ID NO:33; SEQ ID NO:53, and lacks an AAAG tetranucleotide at positions corresponding to positions 980-983 according to SEQ ID NO:34; SEQ ID NO:39, and comprises an insertion of a thymine at a position corresponding to position 1,410 according to SEQ ID NO:39; SEQ ID NO:44, and comprises an insertion of a thymine at a position corresponding to position 1,311 according to SEQ ID NO:44; SEQ ID NO:49, and comprises an insertion of a thymine at a position corresponding to position 1,232 according to SEQ ID NO:49; or SEQ ID NO:54, and comprises or an insertion of a thymine at a position corresponding to position 1,471 according to SEQ ID NO:54.

Embodiment 165. The isolated cDNA molecule, or the complement thereof, according to embodiment 163, wherein the nucleic acid molecule comprises SEQ ID NO:35, SEQ ID NO:38, SEQ ID NO:39, SEQ ID NO:40, SEQ ID NO:43, SEQ ID NO:44, SEQ ID NO:45, SEQ ID NO:48, SEQ ID NO:49, SEQ ID NO:50, SEQ ID NO:53, or SEQ ID NO:54.

Embodiment 166. A vector comprising the cDNA molecule, or the complement thereof, according to any one of embodiments 163 to 165.

Embodiment 167. The vector according to embodiment 166, wherein the vector is a plasmid.

Embodiment 168. The vector according to embodiment 166, wherein the vector is a virus.

Embodiment 169. A host cell comprising the cDNA molecule, or the complement thereof, according to any one of embodiments 163 to 165.

Embodiment 170. A host cell comprising the vector according to any one of embodiments 166 to 168.

Embodiment 171. The host cell according to embodiment 169 or embodiment 170, wherein the nucleotide sequence is operably linked to a promoter active in the host cell.

Embodiment 172. The host cell according to embodiment 171, wherein the promoter is an exogenous promoter.

Embodiment 173. The host cell according to embodiment 171 or embodiment 172, wherein the promoter is an inducible promoter.

Embodiment 174. The host cell according to any one of embodiments 169 to 173, wherein the host cell is a bacterial cell, a yeast cell, an insect cell, or a mammalian cell.

Embodiment 175. A composition comprising the cDNA molecule, or the complement thereof, according to any one of embodiments 163 to 165 and a carrier.

Embodiment 176. A composition comprising the vector according to any one of embodiments 166 to 168 and a carrier.

Embodiment 177. An isolated human G-Protein Coupled Receptor 75 (GPR75) polypeptide having an amino acid sequence at least about 90% identical to: SEQ ID NO:56, wherein the polypeptide lacks amino acids at positions corresponding to positions 110 to 540 according to SEQ ID NO:55; SEQ ID NO:59, wherein the polypeptide lacks amino acids at positions corresponding to positions 236 to 540 according to SEQ ID NO:55; or SEQ ID NO:60, wherein the polypeptide lacks amino acids at positions corresponding to positions 400 to 540 according to SEQ ID NO:55.

Embodiment 178. The polypeptide according to embodiment 177, wherein the polypeptide comprises SEQ ID NO:56, SEQ ID NO:59, or SEQ ID NO:60.

Embodiment 179. The polypeptide according to embodiment 177 or embodiment 178, wherein the polypeptide is fused to a heterologous molecule.

Embodiment 180. The polypeptide according to embodiment 179, wherein the heterologous molecule comprises an immunoglobulin Fc domain, a peptide purification tag, a fluorescent protein, or a transduction domain.

Embodiment 181. The polypeptide according to any one of embodiments 177 to 180, wherein the polypeptide is linked to a label.

Embodiment 182. The polypeptide according to embodiment 181, wherein the label is a fluorescent label or a radiolabel.

Embodiment 183. The polypeptide according to embodiment 181, wherein the label comprises polyethylene glycol, polysialic acid, or glycolic acid.

Embodiment 184. A composition comprising the polypeptide according to any one of embodiments 177 to 183 and a carrier or excipient.

Embodiment 185. A host cell expressing the polypeptide according to any one of embodiments 177 to 183.

Embodiment 186. A method of producing the polypeptide according to any one of embodiments 177 to 183, comprising culturing a host cell comprising a nucleic acid molecule encoding the polypeptide, whereby the host cell expresses the polypeptide, and recovering the expressed polypeptide.

Embodiment 187. The method according to embodiment 186, wherein the nucleic acid molecule is under control of a heterologous promoter.

Embodiment 188. The method according to embodiment 186 or embodiment 187, wherein the nucleic acid molecule is under control of an inducible promoter.

Embodiment 189. An isolated nucleic acid molecule comprising a nucleotide sequence encoding a human G-Protein Coupled Receptor 75 (GPR75) polypeptide, or the complement thereof, wherein the polypeptide: comprises a threonine at a position corresponding to position 116 according to SEQ ID NO:57, terminates at a position corresponding to position 233 according to SEQ ID NO:58, or comprises a cysteine at a position corresponding to position 207 according to SEQ ID NO:99.

Embodiment 190. The isolated nucleic acid molecule, or the complement thereof, according to embodiment 189, wherein the nucleic acid molecule encodes a GPR75 polypeptide having an amino acid sequence at least about 90% identical to: SEQ ID NO:57, wherein the polypeptide comprises a threonine at a position corresponding to position 116 according to SEQ ID NO:57; SEQ ID NO:58, wherein the polypeptide terminates at a position corresponding to position 233 according to SEQ ID NO:58; or SEQ ID NO:99, wherein the polypeptide comprises a cysteine at a position corresponding to position 207 according to SEQ ID NO:99.

Embodiment 191. The nucleic acid molecule, or complement thereof, according to embodiment 189, wherein the polypeptide comprises SEQ ID NO:57, SEQ ID NO:58, or SEQ ID NO:99.

Embodiment 192. A vector comprising the isolated nucleic acid molecule, or the complement thereof, according to any one of embodiments 189 to 191.

Embodiment 193. The vector according to embodiment 192, wherein the vector is a plasmid.

Embodiment 194. The vector according to embodiment 192, wherein the vector is a virus.

Embodiment 195. A host cell comprising the isolated nucleic acid molecule, or the complement thereof, according to any one of embodiments 189 to 191.

Embodiment 196. A host cell comprising the vector according to any one of embodiments 192 to 194.

Embodiment 197. The host cell according to embodiment 195 or embodiment 196, wherein the nucleotide sequence is operably linked to a promoter active in the host cell.

Embodiment 198. The host cell according to embodiment 197, wherein the promoter is an exogenous promoter.

Embodiment 199. The host cell according to embodiment 197 or embodiment 198, wherein the promoter is an inducible promoter.

Embodiment 200. The host cell according to any one of embodiments 195 to 199, wherein the host cell is a bacterial cell, a yeast cell, an insect cell, or a mammalian cell.

Embodiment 201. A composition comprising the isolated nucleic acid molecule, or the complement thereof, according to any one of embodiments 189 to 191 and a carrier.

Embodiment 202. A composition comprising the vector according to any one of embodiments 192 to 194 and a carrier.

Embodiment 203. An isolated mRNA molecule comprising a nucleotide sequence encoding a human G-Protein Coupled Receptor 75 (GPR75) polypeptide, wherein the nucleotide sequence comprises: comprising an adenine at a position corresponding to position 556 according to SEQ ID NO:12, or the complement thereof; comprising an adenine at a position corresponding to position 457 according to SEQ ID NO:17, or the complement thereof; comprising an adenine at a position corresponding to position 378 according to SEQ ID NO:22, or the complement thereof; comprising an adenine at a position corresponding to position 617 according to SEQ ID NO:27, or the complement thereof; comprising a uracil at a position corresponding to position 910 according to SEQ ID NO:13, or the complement thereof; comprising a uracil at a position corresponding to position 811 according to SEQ ID NO:18, or the complement thereof; comprising a uracil at a position corresponding to position 732 according to SEQ ID NO:23, or the complement thereof; comprising a uracil at a position corresponding to position 971 according to SEQ ID NO:28, or the complement thereof; comprising a guanine at a position corresponding to position 830 according to SEQ ID NO:100, or the complement thereof; comprising a guanine at a position corresponding to position 731 according to SEQ ID NO:101, or the complement thereof; comprising a guanine at a position corresponding to position 652 according to SEQ ID NO:102, or the complement thereof; or comprising a guanine at a position corresponding to position 891 according to SEQ ID NO:103, or the complement thereof.

Embodiment 204. The isolated mRNA molecule, or the complement thereof, according to embodiment 203, wherein the nucleotide sequence has at least 90% sequence identity to: SEQ ID NO:12 and comprises an adenine at a position corresponding to position 556 according to SEQ ID NO:12, or the complement thereof; SEQ ID NO:17 and comprises an adenine at a position corresponding to position 457 according to SEQ ID NO:17, or the complement thereof; SEQ ID NO:22 and comprises an adenine at a position corresponding to position 378 according to SEQ ID NO:22, or the complement thereof; SEQ ID NO:27 and comprises an adenine at a position corresponding to position 617 according to SEQ ID NO:27, or the complement thereof; SEQ ID NO:13 and comprises a uracil at a position corresponding to position 910 according to SEQ ID NO:13, or the complement thereof; SEQ ID NO:18 and comprises a uracil at a position corresponding to position 811 according to SEQ ID NO:18, or the complement thereof; SEQ ID NO:23 and comprises a uracil at a position corresponding to position 732 according to SEQ ID NO:23, or the complement thereof; SEQ ID NO:28 and comprises a uracil at a position corresponding to position 971 according to SEQ ID NO:28, or the complement thereof; SEQ ID NO:100 and comprises a guanine at a position corresponding to position 830 according to SEQ ID NO:100, or the complement thereof; SEQ ID NO:101 and comprises a guanine at a position corresponding to position 731 according to SEQ ID NO:101, or the complement thereof; SEQ ID NO:102 and comprises a guanine at a position corresponding to position 652 according to SEQ ID NO:102, or the complement thereof; or SEQ ID NO:103 and comprises a guanine at a position corresponding to position 891 according to SEQ ID NO:103, or the complement thereof.

Embodiment 205. The isolated mRNA molecule, or the complement thereof, according to embodiment 203, wherein the nucleic acid molecule comprises SEQ ID NO:12, SEQ ID NO:17, SEQ ID NO:22, SEQ ID NO:27, SEQ ID NO:13, SEQ ID NO:18, SEQ ID NO:23, SEQ ID NO:28, SEQ ID NO:100, SEQ ID NO:101, SEQ ID NO:102, or SEQ ID NO:103.

Embodiment 206. A vector comprising the isolated mRNA molecule, or the complement thereof, according to any one of embodiments 203 to 205.

Embodiment 207. The vector according to embodiment 206, wherein the vector is a plasmid.

Embodiment 208. The vector according to embodiment 206, wherein the vector is a virus.

Embodiment 209. A host cell comprising the isolated mRNA molecule, or the complement thereof, according to any one of embodiments 203 to 205.

Embodiment 210. A host cell comprising the vector according to any one of embodiments 206 to 208.

Embodiment 211. The host cell according to embodiment 209 or embodiment 210, wherein the nucleotide sequence is operably linked to a promoter active in the host cell.

Embodiment 212. The host cell according to embodiment 211, wherein the promoter is an exogenous promoter.

Embodiment 213. The host cell according to embodiment 211 or embodiment 212, wherein the promoter is an inducible promoter.

Embodiment 214. The host cell according to any one of embodiments 209 to 213, wherein the host cell is a bacterial cell, a yeast cell, an insect cell, or a mammalian cell.

Embodiment 215. A composition comprising the isolated mRNA molecule, or the complement thereof, according to any one of embodiments 203 to 205 and a carrier.

Embodiment 216. A composition comprising the vector according to any one of embodiments 206 to 208 and a carrier.

Embodiment 217. An isolated cDNA molecule comprising a nucleotide sequence encoding a human G-Protein Coupled Receptor 75 (GPR75) polypeptide, wherein the nucleotide sequence comprises: comprising an adenine at a position corresponding to position 556 according to SEQ ID NO:36, or the complement thereof; comprising an adenine at a position corresponding to position 457 according to SEQ ID NO:41, or the complement thereof; comprising an adenine at a position corresponding to position 378 according to SEQ ID NO:46, or the complement thereof; comprising an adenine at a position corresponding to position 617 according to SEQ ID NO:51, or the complement thereof; comprising a thymine at a position corresponding to position 910 according to SEQ ID NO:37, or the complement thereof; comprising a thymine at a position corresponding to position 811 according to SEQ ID NO:42, or the complement thereof; comprising a thymine at a position corresponding to position 732 according to SEQ ID NO:47, or the complement thereof; comprising a thymine at a position corresponding to position 971 according to SEQ ID NO:52, or the complement thereof; comprising a guanine at a position corresponding to position 830 according to SEQ ID NO:104, or the complement thereof; comprising a guanine at a position corresponding to position 731 according to SEQ ID NO:105, or the complement thereof; comprising a guanine at a position corresponding to position 652 according to SEQ ID NO:106, or the complement thereof; or comprising a guanine at a position corresponding to position 891 according to SEQ ID NO:107, or the complement thereof.

Embodiment 218. The isolated cDNA molecule, or the complement thereof, according to embodiment 217, wherein the nucleotide sequence has at least 90% sequence identity to: SEQ ID NO:36 and comprises an adenine at a position corresponding to position 556 according to SEQ ID NO:36, or the complement thereof; SEQ ID NO:41 and comprises an adenine at a position corresponding to position 457 according to SEQ ID NO:41, or the complement thereof; SEQ ID NO:46 and comprises an adenine at a position corresponding to position 378 according to SEQ ID NO:46, or the complement thereof; SEQ ID NO:51 and comprises an adenine at a position corresponding to position 617 according to SEQ ID NO:51, or the complement thereof; SEQ ID NO:37 and comprises a thymine at a position corresponding to position 910 according to SEQ ID NO:37, or the complement thereof; SEQ ID NO:42 and comprises a thymine at a position corresponding to position 811 according to SEQ ID NO:42, or the complement thereof; SEQ ID NO:47 and comprises a thymine at a position corresponding to position 732 according to SEQ ID NO:47, or the complement thereof; SEQ ID NO:52 and comprises a thymine at a position corresponding to position 971 according to SEQ ID NO:52, or the complement thereof; SEQ ID NO:104 and comprises a guanine at a position corresponding to position 830 according to SEQ ID NO:104, or the complement thereof; SEQ ID NO:105 and comprises a guanine at a position corresponding to position 731 according to SEQ ID NO:105, or the complement thereof; SEQ ID NO:106 and comprises a guanine at a position corresponding to position 652 according to SEQ ID NO:106, or the complement thereof; or SEQ ID NO:107 and comprises a guanine at a position corresponding to position 891 according to SEQ ID NO:107, or the complement thereof.

Embodiment 219. The isolated cDNA molecule, or the complement thereof, according to embodiment 217, wherein the nucleic acid molecule comprises SEQ ID NO:36, SEQ ID NO:41, SEQ ID NO:46, SEQ ID NO:51, SEQ ID NO:37, SEQ ID NO:42, SEQ ID NO:47, SEQ ID NO:52, SEQ ID NO:104, SEQ ID NO:105, SEQ ID NO:106, or SEQ ID NO:107.

Embodiment 220. A vector comprising the isolated cDNA molecule, or the complement thereof, according to any one of embodiments 217 to 219.

Embodiment 221. The vector according to embodiment 220, wherein the vector is a plasmid.

Embodiment 222. The vector according to embodiment 220, wherein the vector is a virus.

Embodiment 223. A host cell comprising the isolated cDNA molecule, or the complement thereof, according to any one of embodiments 217 to 219.

Embodiment 224. A host cell comprising the vector according to any one of embodiments 220 to 222.

Embodiment 225. The host cell according to embodiment 223 or embodiment 224, wherein the nucleotide sequence is operably linked to a promoter active in the host cell.

Embodiment 226. The host cell according to embodiment 225, wherein the promoter is an exogenous promoter.

Embodiment 227. The host cell according to embodiment 225 or embodiment 226, wherein the promoter is an inducible promoter.

Embodiment 228. The host cell according to any one of embodiments 223 to 227, wherein the host cell is a bacterial cell, a yeast cell, an insect cell, or a mammalian cell.

Embodiment 229. A composition comprising the isolated cDNA molecule, or the complement thereof, according to any one of embodiments 217 to 219 and a carrier.

Embodiment 230. A composition comprising the vector according to any one of embodiments 220 to 222 and a carrier.

Embodiment 231. An isolated genomic nucleic acid molecule comprising a nucleotide sequence encoding a human G-Protein Coupled Receptor 75 (GPR75) polypeptide, wherein the nucleotide sequence comprises: an adenine at a position corresponding to position 5,557 according to SEQ ID NO:3, or the complement thereof; a thymine at a position corresponding to position 5,911 according to SEQ ID NO:4, or the complement thereof; or a guanine at a position corresponding to position 5,831 according to SEQ ID NO:99, or the complement thereof.

Embodiment 232. The isolated genomic nucleic acid molecule, or the complement thereof, according to embodiment 231, wherein the nucleotide sequence has at least 90% sequence identity to: SEQ ID NO:3, and comprises an adenine at a position corresponding to position 5,557 according to SEQ ID NO:3; SEQ ID NO:4, and comprises a thymine at a position corresponding to position 5,911 according to SEQ ID NO:4; or SEQ ID NO:99, and comprises a guanine at a position corresponding to position 5,831 according to SEQ ID NO:99.

Embodiment 233. The isolated genomic nucleic acid molecule, or the complement thereof, according to embodiment 231, wherein the nucleic acid molecule comprises SEQ ID NO:3, SEQ ID NO:4, or SEQ ID NO:99.

Embodiment 234. A vector comprising the isolated genomic nucleic acid molecule, or the complement thereof, according to any one of embodiments 231 to 233.

Embodiment 235. The vector according to embodiment 234, wherein the vector is a plasmid.

Embodiment 236. The vector according to embodiment 234, wherein the vector is a virus.

Embodiment 237. A host cell comprising the isolated genomic nucleic acid molecule, or the complement thereof, according to any one of embodiments 231 to 233.

Embodiment 238. A host cell comprising the vector according to any one of embodiments 234 to 236.

Embodiment 239. The host cell according to embodiment 237 or embodiment 238, wherein the nucleotide sequence is operably linked to a promoter active in the host cell.

Embodiment 240. The host cell according to embodiment 239, wherein the promoter is an exogenous promoter.

Embodiment 241. The host cell according to embodiment 239 or embodiment 240, wherein the promoter is an inducible promoter.

Embodiment 242. The host cell according to any one of embodiments 237 to 241, wherein the host cell is a bacterial cell, a yeast cell, an insect cell, or a mammalian cell.

Embodiment 243. A composition comprising the isolated genomic nucleic acid molecule, or the complement thereof, according to any one of embodiments 231 to 233 and a carrier.

Embodiment 244. A composition comprising the vector according to any one of embodiments 234 to 236 and a carrier.

Embodiment 245. An isolated human G-Protein Coupled Receptor 75 (GPR75) polypeptide having an amino acid sequence at least about 90% identical to: SEQ ID NO:57, wherein the polypeptide comprises a threonine at a position corresponding to position 116 according to SEQ ID NO:57; SEQ ID NO:58, wherein the polypeptide terminates at a position corresponding to position 233 according to SEQ ID NO:58; or SEQ ID NO:99, wherein the polypeptide comprises a cysteine at a position corresponding to position 207 according to SEQ ID NO:99.

Embodiment 246. The polypeptide according to embodiment 245, wherein the polypeptide comprises SEQ ID NO:57, SEQ ID NO:58, or SEQ ID NO:99.

Embodiment 247. The polypeptide according to embodiment 245 or embodiment 246, wherein the polypeptide is fused to a heterologous molecule.

Embodiment 248. The polypeptide according to embodiment 247, wherein the heterologous molecule comprises an immunoglobulin Fc domain, a peptide purification tag, a fluorescent protein, or a transduction domain.

Embodiment 249. The polypeptide according to any one of embodiments 245 to 248, wherein the polypeptide is linked to a label.

Embodiment 250. The polypeptide according to embodiment 249, wherein the label is a fluorescent label or a radiolabel.

Embodiment 251. The polypeptide according to embodiment 249, wherein the label comprises polyethylene glycol, polysialic acid, or glycolic acid.

Embodiment 252. A composition comprising the polypeptide according to any one of embodiments 245 to 251 and a carrier or excipient.

Embodiment 253. A host cell expressing the polypeptide according to any one of embodiments 245 to 251.

Embodiment 254. A method of producing the polypeptide according to any one of embodiments 245 to 251, comprising culturing a host cell comprising a nucleic acid molecule encoding the polypeptide, whereby the host cell expresses the polypeptide, and recovering the expressed polypeptide.

Embodiment 255. The method according to embodiment 254, wherein the nucleic acid molecule is under control of a heterologous promoter.

Embodiment 256. The method according to embodiment 254 or embodiment 255, wherein the nucleic acid molecule is under control of an inducible promoter.

Embodiment 257. A therapeutic agent that treats or inhibits obesity for use in the treatment of obesity in a subject having:

a genomic nucleic acid molecule having a nucleotide sequence encoding a human G-Protein Coupled Receptor 75 (GPR75) polypeptide, wherein the nucleotide sequence: lacks a CCAGTAG heptanucleotide at positions corresponding to positions 5,540-5,546 according to SEQ ID NO:1, or the complement thereof; comprises an adenine at a position corresponding to position 5,557 according to SEQ ID NO:3, or the complement thereof; comprises a thymine at a position corresponding to position 5,911 according to SEQ ID NO:4, or the complement thereof; lacks an AAAG tetranucleotide at positions corresponding to positions 5,920-5,923 according to SEQ ID NO:1, or the complement thereof; comprises an insertion of a thymine at a position corresponding to position 6,411 according to SEQ ID NO:6, or the complement thereof; or comprises a guanine at a position corresponding to position 5,831 according to SEQ ID NO:99, or the complement thereof;

an mRNA molecule having a nucleotide sequence encoding a human GPR75 polypeptide, wherein the nucleotide sequence: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; comprises an adenine at a position corresponding to position 556 according to SEQ ID NO:12, or the complement thereof; comprises an adenine at a position corresponding to position 457 according to SEQ ID NO:17, or the complement thereof; comprises an adenine at a position corresponding to position 378 according to SEQ ID NO:22, or the complement thereof; comprises an adenine at a position corresponding to position 617 according to SEQ ID NO:27, or the complement thereof; comprises a uracil at a position corresponding to position 910 according to SEQ ID NO:13, or the complement thereof; comprises a uracil at a position corresponding to position 811 according to SEQ ID NO:18, or the complement thereof; comprises a uracil at a position corresponding to position 732 according to SEQ ID NO:23, or the complement thereof; comprises a uracil at a position corresponding to position 971 according to SEQ ID NO:28, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; comprises an insertion of a uracil at a position corresponding to position 1,471 according to SEQ ID NO:30, or the complement thereof; comprises a guanine at a position corresponding to position 830 according to SEQ ID NO:100, or the complement thereof; comprises a guanine at a position corresponding to position 731 according to SEQ ID NO:101, or the complement thereof; comprises a guanine at a position corresponding to position 652 according to SEQ ID NO:102, or the complement thereof; or comprises a guanine at a position corresponding to position 891 according to SEQ ID NO:103, or the complement thereof; or a cDNA molecule having a nucleotide sequence encoding a human GPR75 polypeptide, wherein the nucleotide sequence: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; comprises an adenine at a position corresponding to position 556 according to SEQ ID NO:36, or the complement thereof; comprises an adenine at a position corresponding to position 457 according to SEQ ID NO:41, or the complement thereof; comprises an adenine at a position corresponding to position 378 according to SEQ ID NO:46, or the complement thereof; comprises an adenine at a position corresponding to position 617 according to SEQ ID NO:51, or the complement thereof; comprises a thymine at a position corresponding to position 910 according to SEQ ID NO:37, or the complement thereof; comprises a thymine at a position corresponding to position 811 according to SEQ ID NO:42, or the complement thereof; comprises a thymine at a position corresponding to position 732 according to SEQ ID NO:47, or the complement thereof; comprises a thymine at a position corresponding to position 971 according to SEQ ID NO:52, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; comprises an insertion of a thymine at a position corresponding to position 1,471 according to SEQ ID NO:54, or the complement thereof; comprises a guanine at a position corresponding to position 830 according to SEQ ID NO:104, or the complement thereof; comprises a guanine at a position corresponding to position 731 according to SEQ ID NO:105, or the complement thereof; comprises a guanine at a position corresponding to position 652 according to SEQ ID NO:106, or the complement thereof; or comprises a guanine at a position corresponding to position 891 according to SEQ ID NO:107, or the complement thereof.

Embodiment 258. A G-Protein Coupled Receptor 75 (GPR75) inhibitor for use in the treatment of obesity in a subject having:

a genomic nucleic acid molecule having a nucleotide sequence encoding a human G-Protein Coupled Receptor 75 (GPR75) polypeptide, wherein the nucleotide sequence: lacks a CCAGTAG heptanucleotide at positions corresponding to positions 5,540-5,546 according to SEQ ID NO:1, or the complement thereof; comprises an adenine at a position corresponding to position 5,557 according to SEQ ID NO:3, or the complement thereof; comprises a thymine at a position corresponding to position 5,911 according to SEQ ID NO:4, or the complement thereof; lacks an AAAG tetranucleotide at positions corresponding to positions 5,920-5,923 according to SEQ ID NO:1, or the complement thereof; comprises an insertion of a thymine at a position corresponding to position 6,411 according to SEQ ID NO:6, or the complement thereof; or comprises a guanine at a position corresponding to position 5,831 according to SEQ ID NO:99, or the complement thereof;

an mRNA molecule having a nucleotide sequence encoding a human GPR75 polypeptide, wherein the nucleotide sequence: lacks a CCAGUAG heptanucleotide at positions corresponding to positions 539-545 according to SEQ ID NO:7, or the complement thereof; lacks a CCAGUAG heptanucleotide at positions corresponding to positions 440-446 according to SEQ ID NO:8, or the complement thereof; lacks a CCAGUAG heptanucleotide at positions corresponding to positions 361-367 according to SEQ ID NO:9, or the complement thereof; lacks a CCAGUAG heptanucleotide at positions corresponding to positions 600-606 according to SEQ ID NO:10, or the complement thereof; comprises an adenine at a position corresponding to position 556 according to SEQ ID NO:12, or the complement thereof; comprises an adenine at a position corresponding to position 457 according to SEQ ID NO:17, or the complement thereof; comprises an adenine at a position corresponding to position 378 according to SEQ ID NO:22, or the complement thereof; comprises an adenine at a position corresponding to position 617 according to SEQ ID NO:27, or the complement thereof; comprises a uracil at a position corresponding to position 910 according to SEQ ID NO:13, or the complement thereof; comprises a uracil at a position corresponding to position 811 according to SEQ ID NO:18, or the complement thereof; comprises a uracil at a position corresponding to position 732 according to SEQ ID NO:23, or the complement thereof; comprises a uracil at a position corresponding to position 971 according to SEQ ID NO:28, or the complement thereof; lacks an AAAG tetranucleotide at positions corresponding to positions 919-922 according to SEQ ID NO:7, or the complement thereof; lacks an AAAG tetranucleotide at positions corresponding to positions 820-823 according to SEQ ID NO:8, or the complement thereof; lacks an AAAG tetranucleotide at positions corresponding to positions 741-744 according to SEQ ID NO:9, or the complement thereof; lacks an AAAG tetranucleotide at positions corresponding to positions 980-983 according to SEQ ID NO:10, or the complement thereof; comprises an insertion of a uracil at a position corresponding to position 1,410 according to SEQ ID NO:15, or the complement thereof; comprises an insertion of a uracil at a position corresponding to position 1,311 according to SEQ ID NO:20, or the complement thereof; comprises an insertion of a uracil at a position corresponding to position 1,232 according to SEQ ID NO:25, or the complement thereof; comprises an insertion of a uracil at a position corresponding to position 1,471 according to SEQ ID NO:30, or the complement thereof; comprises a guanine at a position corresponding to position 830 according to SEQ ID NO:100, or the complement thereof; comprises a guanine at a position corresponding to position 731 according to SEQ ID NO:101, or the complement thereof; comprises a guanine at a position corresponding to position 652 according to SEQ ID NO:102, or the complement thereof; or comprises a guanine at a position corresponding to position 891 according to SEQ ID NO:103, or the complement thereof; or a cDNA molecule having a nucleotide sequence encoding a human GPR75 polypeptide, wherein the nucleotide sequence: lacks a CCAGTAG heptanucleotide at positions corresponding to positions 539-545 according to SEQ ID NO:31, or the complement thereof; lacks a CCAGTAG heptanucleotide at positions corresponding to positions 440-446 according to SEQ ID NO:32, or the complement thereof; lacks a CCAGTAG heptanucleotide at positions corresponding to positions 361-367 according to SEQ ID NO:33, or the complement thereof; lacks a CCAGTAG heptanucleotide at positions corresponding to positions 600-606 according to SEQ ID NO:34, or the complement thereof; comprises an adenine at a position corresponding to position 556 according to SEQ ID NO:36, or the complement thereof; comprises an adenine at a position corresponding to position 457 according to SEQ ID NO:41, or the complement thereof; comprises an adenine at a position corresponding to position 378 according to SEQ ID NO:46, or the complement thereof; comprises an adenine at a position corresponding to position 617 according to SEQ ID NO:51, or the complement thereof; comprises a thymine at a position corresponding to position 910 according to SEQ ID NO:37, or the complement thereof; comprises a thymine at a position corresponding to position 811 according to SEQ ID NO:42, or the complement thereof; comprises a thymine at a position corresponding to position 732 according to SEQ ID NO:47, or the complement thereof; comprises a thymine at a position corresponding to position 971 according to SEQ ID NO:52, or the complement thereof; lacks an AAAG tetranucleotide at positions corresponding to positions 919-922 according to SEQ ID NO:31, or the complement thereof; lacks an AAAG tetranucleotide at positions corresponding to positions 820-823 according to SEQ ID NO:32, or the complement thereof; lacks an AAAG tetranucleotide at positions corresponding to positions 741-744 according to SEQ ID NO:33, or the complement thereof; lacks an AAAG tetranucleotide at positions corresponding to positions 980-983 according to SEQ ID NO:34, or the complement thereof; comprises an insertion of a thymine at a position corresponding to position 1,410 according to SEQ ID NO:39, or the complement thereof; comprises an insertion of a thymine at a position corresponding to position 1,311 according to SEQ ID NO:44, or the complement thereof; comprises an insertion of a thymine at a position corresponding to position 1,232 according to SEQ ID NO:49, or the complement thereof; comprises an insertion of a thymine at a position corresponding to position 1,471 according to SEQ ID NO:54, or the complement thereof; comprises a guanine at a position corresponding to position 830 according to SEQ ID NO:104, or the complement thereof; comprises a guanine at a position corresponding to position 731 according to SEQ ID NO:105, or the complement thereof; comprises a guanine at a position corresponding to position 652 according to SEQ ID NO:106, or the complement thereof; or comprises a guanine at a position corresponding to position 891 according to SEQ ID NO:107, or the complement thereof.

Embodiment 259. The GPR75 inhibitor according to embodiment 258, which is an antisense nucleic acid molecule, a small interfering RNA (siRNA), or a short hairpin RNA (shRNA) that hybridizes to a GPR75 mRNA.

Embodiment 260. The GPR75 inhibitor according to embodiment 258, which comprises a Cas protein and guide RNA (gRNA) that hybridizes to a gRNA recognition sequence within a GPR75 genomic nucleic acid molecule.

Embodiment 261. The GPR75 inhibitor according to embodiment 260, wherein the Cas protein is Cas9 or Cpf1.

Embodiment 262. The GPR75 inhibitor according to embodiment 260 or embodiment 261, wherein the gRNA recognition sequence includes or is proximate to: position 5,540-5,546 according to SEQ ID NO:1, position 5,557 according to SEQ ID NO:1, position 5,911 according to SEQ ID NO:1, positions 5,920-5,923 according to SEQ ID NO:1, position 6,411 according to SEQ ID NO:1, or position 5,831 according to SEQ ID NO:1.

Embodiment 263. The GPR75 inhibitor according to embodiment 260 or embodiment 261, wherein the gRNA recognition sequence is located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to: position 5,540-5,546 according to SEQ ID NO:1, position 5,557 according to SEQ ID NO:1, position 5,911 according to SEQ ID NO:1, positions 5,920-5,923 according to SEQ ID NO:1, position 6,411 according to SEQ ID NO:1, or position 5,831 according to SEQ ID NO:1.

Embodiment 264. The GPR75 inhibitor according to embodiment 260 or embodiment 261, wherein a Protospacer Adjacent Motif (PAM) sequence is about 2 to about 6 nucleotides downstream of the gRNA recognition sequence.

Embodiment 265. The GPR75 inhibitor according to any one of embodiments 260 to 264, wherein the gRNA comprises from about 17 to about 23 nucleotides.

Embodiment 266. The GPR75 inhibitor according to any one of embodiments 260 to 265, wherein the gRNA recognition sequence comprises a nucleotide sequence according to any one of SEQ ID NOS:61-98.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: Materials and Methods

Participating Cohorts

Discovery genetic association studies were performed in the United Kingdom (UK) Biobank (UKB) cohort (Sudlow et al., PLoS Med 12, 2015, e1001779), in the MyCode Community Health Initiative cohort from the Geisinger Health System (GHS) (Carey et al., Genet. Med., 2016, 18, 906-913) and in the Mexico City Prospective Study (MCPS) (Tapia-Conyer et al., Int. J. Epidemiol., 2006, 35, 243-249). The UKB is a population-based cohort study of people aged between 40 and 69 years recruited through 22 testing centers in the UK between 2006-2010. A total of 428,719 European ancestry participants with available whole-exome sequencing and clinical phenotype data were included (FIG. 1). UK Biobank has approval from the North West Multi-centre Research Ethics Committee (MREC; 11/NW/0382), which covers the UK. The GHS MyCode study is a health system-based cohort of patients from Central and Eastern Pennsylvania (USA) recruited in 2007-2019. A total of 121,061 European ancestry participants with available whole-exome sequencing and clinical phenotype data were included (FIG. 1). The GHS MyCode study was approved by the Geisinger Institutional Review Board (2006-0258). The MCPS is a cohort study of people aged 35 years recruited from two contiguous urban districts in Mexico City in 1998-2004. The study design and clinical characteristics of participants in MCPS have been described in detail in previous publications (Tapia-Conyer et al., Int. J. Epidemiol., 2006, 35, 243-249; and Alegre-Diaz et al., N. Engl. J. Med., 2016, 375, 1961-1971). A total of 95,846 individuals of Admixed American ancestry with available whole-exome sequencing and clinical phenotype data were included (FIG. 1). The MCPS study was approved by the Mexican Ministry of Health, the Mexican National Council for Science and Technology, and the University of Oxford.

The association with BMI of GPR75 predicted loss-of-function (pLOF) variants was further estimated in an additional 91,328 exomes not included in the discovery set. These included participants of non-European ancestries from the UK Biobank (UKB, N=12,321) (Sudlow et al., PLoS Med 12, 2015, e1001779), and participants in the Mount Sinai BioMe cohort (SINAI, N=21,143), the University of Pennsylvania Medicine BioBank (PMBB; N=7,519), the Duke Catheterization Genetics (CATHGEN) cohort (DUKE; N=8,171) (Kraus et al., J. Cardiovasc. Transl. Res., 2015, 8, 449-457), the Taiwanese Chinese from Taiwan Metabochip consortium (TAICHI; N=11,223) (Assimes et al., PLoS One 11, 2016, e0138014), the Dallas Heart Study (DHS; N=2,088) (Victor et al., Am. J. Cardiol., 2004, 93, 1473-1480) and the Malmö Diet and Cancer Study (MALMO; N=28,863) (Berglund et al., J. Intern. Med., 1993, 233, 45-51). All studies were approved by relevant ethics committees and participants provided informed consent for participation in these studies.

Phenotype Definitions

Body mass index was calculated as weight in kilograms divided by the square of height in meters on the basis of anthropometric measurements taken at one of the study visits. BMI measured at the baseline visit was the outcome variable in UKB and MCPS, while median BMI from clinical encounters present in the GHS database was the outcome variable for GHS consistent with previous studies (Dewey et al., Science, 2016, 354). BMI categories were defined on the basis of the World Health Organization classification (WHO, Obesity and overweight, 2020). BMI values were transformed by the inverse standard normal function, applied within each ancestry group and separately in men and women. Body weight differences were calculated for a person 170 cm tall. Overall and regional body lean and fat masses, percentages and body-surface normalized indices were measured by bioelectrical impedance in the UKB cohort. At the baseline visit, UKB also collected self-reported information on comparative body size at age 10 by asking the multiple choice question: "When you were 10 years old, compared to average would you describe yourself as: thinner, plumper, about average, do not know, prefer not to answer?".

Genotype Data

High coverage whole exome sequencing was performed as previously described in detail (Dewey et al., Science, 2016, 354; and Van Hout et al., Nature, 2020, 586, 749-756) and as summarized below. NimbleGen probes (VCRome; for part of the GHS cohort) or a modified version of the xGen design available from Integrated DNA Technologies (IDT; for the rest of GHS and other cohorts) were used for target sequence capture of the exome. A unique 6 base pair (bp) barcode (VCRome) or 10 bp barcode (IDT) was added to each DNA fragment during library preparation to facilitate multiplexed exome capture and sequencing. Equal amounts of sample were pooled prior to exome capture. Sequencing was performed using 75 bp paired-end reads on Illumina v4 HiSeq 2500 (for part of the GHS cohort) or NovaSeq (for the rest of GHS and other cohorts) instruments. Sequencing had a coverage depth (i.e., number of sequence-reads covering each nucleotide in the target areas of the genome) sufficient to provide greater than 20× coverage over 85% of targeted bases in 96% of VCRome samples and 20× coverage over 90% of targeted bases in 99% of IDT samples. Data processing steps included sample de-multiplexing using Illumina software, alignment to the GRCh38 Human Genome reference sequence including generation of binary alignment and mapping files (BAM), processing of BAM files (e.g., marking of duplicate reads and other read mapping evaluations). Variant calling and annotation were based on the GRCh38 Human Genome reference sequence and Ensembl v85 gene definitions using the snpEff software. The snpEff predictions that involve protein-coding transcripts with an annotated start and stop were then combined into a single functional impact prediction by selecting the most deleterious functional effect class for each gene. The hierarchy (from most to least deleterious) for these annotations was frameshift, stop-gain, stop-loss, splice acceptor, splice donor, stop-lost, in-frame indel, missense, other annotations. Predicted LOF genetic variants included: a) insertions or deletions resulting in a frameshift, b) insertions, deletions or single nucleotide variants resulting in the introduction of a premature stop codon or in the loss of the transcription start site or stop site, and c) variants in donor or acceptor splice sites. Missense variants were classified for likely functional impact according to the number of in silico prediction algorithms that predicted deleteriousness using SIFT (Kumar et al., Nat. Protoc., 2009, 4, 1073-1081), Polyphen2_HDIV and Polyphen2_HVAR (Adzhubei et al., Nat. Methods, 2010, 7, 248-249), LRT (Chun et al., Genome Res., 2009, 19, 1553-1561) and MutationTaster (Schwarz et al., Nat. Methods, 2010, 7, 575-576). For each gene, the alternative allele frequency (AAF) and functional annotation of each variant determined inclusion into these 7 gene burden exposures: 1) pLOF variants with AAF<1%; 2) pLOF or missense variants predicted deleterious by 5/5 algorithms with AAF<1%; 3) pLOF or missense variants predicted deleterious by 5/5 algorithms with AAF<0.1%; 4) pLOF or missense variants predicted deleterious by at least 1/5 algorithms with AAF<1%; 5) pLOF or missense variants predicted deleterious by at least 1/5 algorithms with AAF<0.1%; 6) pLOF or any missense with AAF<1%; and 7) pLOF or any missense variants with AAF<0.1%.

SNP array genotyping was performed in the UKB as previously described (Bycroft et al., Nature, 2018, 562, 203-209). In GHS, genotyping was performed using the Human Omni Express Exome array (OMNI) and the Global Screening array (GSA). In MCPS, genotyping was performed using the GSA array.

In Vitro Studies of GPR75 Variants

In vitro validation studies were performed for two GPR75 pLOF genetic variants (Ala110fs and Gln234*) that were: a) individually associated with lower BMI (p<0.05), and b) had at least 10 heterozygous carriers. Briefly, pcDNA 3.1 plasmids encoding for N-terminally HA-tagged wild-type, Ala110fs and Gln234* GPR75 were transiently transfected using Fugene 6 (Promega) in HEK293 cells. HEK293 and HEK293T cell lines were purchased from ATCC and maintained in the Regeneron Tissue Culture Core. Their identity was confirmed by STR profiling. In vitro assays included mRNA and protein analysis by Taqman and Western Blotting, and protein localization by fluorescence-activated cell sorting and immunofluorescence.

Cell culture, plasmids and cell transfection: HEK293 cells were maintained in Dulbecco's modified Eagle's medium supplemented with 10% fetal bovine serum, and antibiotics (50 units/mL penicillin and 50 µg/mL streptomycin; Thermo Fisher Scientific). pcDNA 3.1 plasmids encoding for N-terminus HA-tagged GPR75 wild-type, Ala110fs and Gln234* were synthesized by GenScript (USA). Cells at approximately 60-70% confluence were transiently transfected with plasmid containing cDNA encoding HA-tagged GPR75 wild-type, Ala110fs and Gln234* and green fluorescent protein control plasmid using FuGENE 6 (Promega) according to the manufacturer's protocol (Promega Literature: #TM350), at a ratio of 1 µg DNA:5 µl FuGENE transfection reagent. After 48 hours, cells were washed with 1×DPBS (Thermo Fisher Scientific) and collected for downstream analysis.

Western blotting: Transfected HEK293 were collected in RIPA buffer for cell lysis and 5-10 µg of protein was loaded per sample. The following primary antibodies were used: HA (mouse monoclonal, Sigma cat. Cat #H3663) and GAPDH 14C10 (Rabbit mAb, Cell Signaling Cat #2118). The appropriate LI-COR secondary IRDye antibodies (anti-rabbit (926-32211) and anti-mouse (926-32210)) were used to detect and quantify immunoblots using a LI-COR Odyssey Infrared Imaging System (LI-COR, Lincoln, Nebr.).

Flow cytometry: Cells were washed once with 1×DPBS (Cat #14190144). Cell Dissociation Buffer (Cat #13150016) was added and cells were incubated at 37° C. for 3 minutes. Cells were re-suspended in culture media and centrifuged at 200×g for 5 minutes. Cells were washed twice with DPBS, re-suspended in DPBS, aliquoted and stained with Live/Dead Blue Fixable Viability Dye (Thermo Fisher Scientific) at room temperature for 15 minutes with no light. Cells were washed twice with DPBS—all washes centrifuged at 400×g for 5 minutes and all staining in the dark. Cells were treated with human Fc Block (BD Biosciences) in MACS buffer (Miltenyi Biotec) for 15 minutes at 4° C. and stained with alexa fluor anti-HA.11 epitope tag antibody (Cat #682404) at 1:100 dilution in MACS buffer for 30 minutes at 4° C. Cells were washed with MACS buffer and fixed with CytoFix (BD Biosciences) for 15 minutes at 4° C. Cells were washed twice with MACS buffer, filtered and FACS was performed on a CytoFLEX (Beckman Coulter). Data was analyzed using FlowJo 10.6.2 (Becton Dickinson & Company).

Immunofluorescence assays: For immunofluorescence assays, cells were seeded onto open 8-well u-Slides (chamber slide) with a glass bottom (Ibidi, cat #80827) at a density of 14,000 cells/well. At 48 hours post-transfection, cells were fixed in ice-cold 4% PFA for 10 minutes at RT and washed 3× with ice-cold 1×DPBS (all subsequent wash steps were carried out 3 times ice-cold 1×DPBS for 5 minutes per wash). Cells that were not permeabilized were blocked for 1 hour using 10% normal donkey serum (NDS) (Jackson Immunoresearch Laboratories, #017-000-121), while permeabilized cells were blocked in 10% NDS with 0.1% TRITON X-100™ (2-[4-(2,4,4-trimethylpentan-2-yl) phenoxy]ethanol); these were subsequently used as staining buffers for non-permeabilized and permeabilized cells, respectively. Cells were incubated with 1:500 (non-permeabilized) or 1:3000 (permeabilized) anti-HA antibody (Sigma, Cat #H3663) for 1 hour at RT, washed and then incubated for 1 hour with 1:1000 alexa fluor 594-conjugated anti-mouse secondary antibody (Thermo Fisher Scientific, Cat #A-21203). Wells were then washed, and slides were mounted with ProLong® Gold Antifade Reagent with DAPI (Cell Signaling, #8961). Slides were imaged using Zeiss confocal LSM880.

Quantitative real-time polymerase chain reaction: RNA was extracted from transfected HEK293 using TRIzol reagent and following the manufacturer's instructions (Thermo Fisher Scientific). Genomic DNA was removed using MagMAX™Turbo™DNase Buffer and TURBO DNase (Ambion by Life Technologies). mRNA (up to 2 µg) was reverse-transcribed into cDNA using SuperScript® VILO™ Master Mix (ThermoFisher Scientific). GPR75 cDNA was amplified with the PowerUp SYBR Green Master Mix (Thermo Fisher Scientific) using the QuantStudio 6 Flex Real-Time PCR System (Thermo Fisher Scientific). ACTINB housekeeping gene was used as the internal control gene to normalize cDNA input differences. Expression of GPR75 was calculated relative to ACTINB housekeeping gene.

Primer Sequences were as Follows:

GPR75-forward: 5'-GCTTGTGGCCCAAGTCATTC-3' (SEQ ID NO:1458)

GPR75-reverse: 5'-GAGTGTTGATGGGGGTCGAG-3' (SEQ ID NO:1459)

ACTINB-forward: 5'-CACCATTGGCAAT-GAGCGGTTC-3' (SEQ ID NO:1460)

ACT/NB-reverse: 5'-AGGTCTTTGCGGATGTC-CACGT-3' (SEQ ID NO:1461)

Mouse Models

The genetically engineered Gpr75$^{-/-}$ mouse strain was created using Regeneron's VelociGene® technology (Valenzuela et al., Nat. Biotechnol., 2003, 21, 652-659; and Poueymirou et al., Nat. Biotechnol., 2007, 25, 91-99). Briefly, C57Bl/6NTac embryonic stem cells were targeted for ablation of the entire Gpr75 locus, beginning immediately after the endogenous ATG and ending at the Gpr75 stop codon. Ablation was achieved using a modified bacterial artificial chromosome (BAC) targeting construct such that BAC Gpr75 sequence was replaced with a self-deleting, floxed lacZ reporter cassette containing a neomycin resistance gene under the control of the human UBC (ubiquitin) promoter. The deletion was engineered such that the lacZ reporter was inserted in frame immediately after the endogenous ATG. This construct was electroporated into C57Bl/6NTac embryonic stem cells. Following selection with neomycin, correctly targeted clones were identified by TaqMan analysis and microinjected into 8-cell Swiss Webster embryos (Charles River Laboratories), resulting in FO VelociMouse® fully derived from the injected modified embryonic stem cells (Poueymirou et al., Nat. Biotechnol., 2007, 25, 91-99).

Heterozygous Gpr75$^{-/+}$ mice were bred to generate age-matched wild type Gpr75$^{+/+}$, heterozygous Gpr75$^{-}$/+ and knock-out Gpr75$^{-/-}$ littermates that were used for experimentation. Male and female mice were housed in static cages (4/cage) with free access to food and water and fed either control chow diet or a high-fat diet (HFD; Envigo, #TD.03584, Huntingdon, UK) for 14 weeks. The control diet consisted of the following components in amounts represented by percent kilocalories (kcal): 13.4% fat, 58.0% carbohydrate, and 28.7% protein. HFD consisted of the following components in percent kilocalories: 58.4% fat, 26.6% carbohydrate, and 15.0% protein.

Fasting blood glucose was measured after overnight fasting before and at the end of the diet-feeding period. An intra-peritoneal glucose tolerance test was performed at the end of the experiment. Followed by an overnight fasting period, glucose (2 g/kg) was administered to each mouse by intra-peritoneal injection. The tip of the tail of each mouse was scratched to draw blood. Blood samples were collected at 0, 30, 60, 90, and 120 minutes, and glucose was measured using Contour blood glucose monitoring system (Bayer, Whippany, N.J.). After these measurements, blood was collected in capillary tubes and used for insulin measurements. Blood was centrifuged at 2,000 rpm for 15 minutes to separate the plasma. Ultra-Sensitive Mouse Insulin ELISA kit (Crystal Chem. #90080, Elk Grove Village,IL.) was used to quantify plasma insulin levels as per manufacturer's instructions. Plasma levels of leptin and adiponectin were measured by ELISA according to the manufacturer's instructions (Abcam, Cambridge, Mass.; #ab100718 and #ab108785 for leptin and adiponectin, respectively).

Statistics: The Graph Pad Prism version 9 software was used for statistical analysis. Significance of difference in mean values was determined using repeated measures two-way ANOVA followed by Tukey's post hoc multiple comparison test. A p-value<0.05 was considered to be significant.

Additional high-fat and chow diet experiments were conducted in separate cohorts of mice to further characterize body composition and response in a diet induced obesity model.

Statistical Analysis

Overview: The association with BMI of genetic variants or their gene burden was estimated by fitting mixed-effects regression models using BOLT-LMM v2.3.4 (Loh et al., Nat. Genet., 2018, 50, 906-908) or REGENIE v1.0 (Mbatchou et al., Nat. Genet., 2021). These approaches account for relatedness and population structure by estimating a polygenic score using genotypes from across the genome. Then, the association of genetic variants or their burden is estimated conditional upon that polygenic score along with other covariates. To ensure that rare coding variant or gene-burden associations were statistically independent of BMI-associated common genetic variants, exome association analyses were further adjusted for sentinel common variants (AAF1%) identified by fine-mapping genome-wide associations of common alleles with BMI as described below. Results across cohorts were pooled using inverse-variance weighted meta-analysis.

Association with BMI of the burden of rare nonsynonymous variants identified by exome-sequencing: In the primary analysis of this study, the association with BMI of the burden of rare nonsynonymous variants in each gene was estimated by fitting mixed-effects regression models adjusted for a polygenic score that approximates a genomic kinship matrix using BOLT-LMM v2.3.4 (Loh et al., Nat. Genet., 2018, 50, 906-908) or REGENIE v1.0 (Mbatchou et al., Nat. Genet., 2021). Analyses were further adjusted for age, age$^2$, sex, an age-by-sex interaction term, experimental batch-related covariates, and genetic principal components. Ensuring that rare variants associations are independent of nearby trait-associated common alleles is essential for the correct causal variant and gene attribution in studies focused on exome variation (Mahajan et al., Nat. Genet., 2018, 50, 559-571). To ensure that burden associations were statistically independent of BMI-associated common genetic variants, the exome-wide association analyses were adjusted for common variants identified by fine-mapping genome-wide associations of common alleles with BMI (see, GWAS of common variants and fine-mapping). In line with previous similar studies (Do et al., Nature, 2015, 518, 102-106; and Flannick et al., Nature, 2019, 570, 71-76), the exome-wide level of statistical significance for the gene burden analysis was defined as p<3.6×10$^{-07}$, a Bonferroni correction for 20,000 genes and seven variant selection models.

Rare nonsynonymous single variant analysis: In a secondary analysis, the association with BMI of individual rare nonsynonymous variants (minor allele frequency <1% and minor allele count >25) identified by exome sequencing was estimated. The same analytical approach was used as with the gene burden analysis, including adjustment for BMI-associated common variants identified by fine-mapping. This step is preferred to confirm the conditionally-independent nature of the association of these rare variants (Mahajan et al., Nat. Genet., 2018, 50, 559-571). In this analysis, a statistical threshold was used for association of p<5×10$^{-08}$, a Bonferroni correction for ⁻1,000,000 rare nonsynonymous variants tested in this analysis which is also the conventional threshold for genome-wide significance used in GWAS (C. Wellcome Trust Case Control, Nature, 2007, 447, 661-678).

GWAS of common variants and fine-mapping: BMI-associated common variants were identified by performing a genome-wide association study including over 12 million common-to-low-frequency genetic variants imputed using the Haplotype Reference Consortium panel (McCarthy et al., Nat. Genet., 2016, 48, 1279-1283) or the TOPMed Imputation Server (see, world wide web at "imputation.biodatacatalyst.nhlbi.nih.gov/#!pages/home; v1.5.7). In the GHS study, imputation was performed separately in samples genotyped with the Illumina Human Omni Express Exome array (OMNI set) and the Global Screening array (GSA set).

Dosage data from imputed variants were then merged across the two GHS sets, to obtain a combined dataset for association analysis. Genome-wide association analyses were performed in the GHS, UKB and MCPS cohorts separately by fitting mixed-effects linear regression models using BOLT-LMM v2.3.4 (Loh et al., Nat. Genet., 2018, 50, 906-908) or REGENIE v1.0 (Mbatchou et al., Nat. Genet., 2021). Results from the UKB and GHS analyses were then combined by inverse variance-weighted meta-analysis to obtain a genome-wide meta-analysis in the European subset of the discovery cohorts. To identify conditionally-independent genetic association signals driven by common variants, fine-mapping at genomic regions harboring genetic variants associated with BMI at the genome-wide significance threshold of p<5×10⁻⁰⁸ using the FINEMAP software was performed (Benner et al., Bioinformatics, 2016, 32, 1493-1501). Linkage disequilibrium was estimated using genetic data from the exact set of individuals included in the genome-wide association analyses. Fine-mapping was performed separately in the meta-analysis of the European ancestry GHS and UKB cohorts and in the Admixed American ancestry analysis in the MCPS cohort. Fine-mapping identifies independent common variant signals and assigns a posterior probability of causal association (PPA) for variants assigned to a given independent signal. For each locus that was fine-mapped, the 95% credible variant set, i.e., the minimal set of variants that capture the 95% posterior probability of causal association, were identified. The sentinel variant was also defined as the variant with the highest posterior probability of causal association at each given independent signal.

Generation of a genome wide-polygenic score for BMI in the UKB study: A polygenic score capturing predisposition to higher BMI due to over 2.5 million common variants was generated using the LDpred software (Vilhjalmsson et al., Am. J. Hum. Genet., 2015, 97, 576-592) with a rho parameter value of 1, from the results of a previous large genome-wide association study in an independent dataset (Adzhubei et al., Nat. Methods, 2010, 7, 248-249).

Phenome-wide analysis for GPR75 predicted loss-of-function variants: A phenome-wide analysis of the association of pLOF variants in GPR75 with hundreds of continuous traits or disease outcomes in the GHS and UKB studies was performed. To increase power, inverse-variance weighted meta-analysis was performed using the METAL software (Willer et al., Bioinformatics, 2010, 26, 2190-2191) to combine association results across GHS and UKB for disease outcomes available in both studies. To minimize the risk of false positive associations due to the small number of variant carriers, outcomes with 25 individuals carrying GPR75 pLOF genetic variants, determined based on individuals with a non-missing phenotype for continuous traits, or based on affected individuals for binary disease outcomes were excluded. After these exclusions, results were available for 2,173 outcomes. To control for the number of statistical tests performed, associations were considered statistically significant if the association p-value met a Bonferroni correction for 2,173 tests, that is p<2.3× 10⁻⁵ (corresponding to a p-value threshold of 0.05 divided by 2,173 statistical tests).

Continuous traits and disease outcomes were defined as described below. In the UKB study, for continuous traits, the values of biomarker, imaging variables or other continuous traits measured during one of the UKB visits or their averages within a given study visit or across study visits were used as outcomes. For binary disease outcomes, case status definition required one or more of the following criteria to apply: a) self-reported disease status or use of medication at digital questionnaire or interview with a trained nurse, or b) EHR of inpatient encounters from the UK National Health Service Hospital Episode Statistics database coded using the ICD-10 coding system. For each binary outcome, controls were individuals without any of the criteria for case definition. In the GHS study, for binary disease outcomes, case status definition required one or more of the following criteria to apply: 1) a problem-list entry of the ICD-10 diagnosis code, 2) an inpatient hospitalization-discharge ICD-10 diagnosis code, or 3) an encounter ICD-10 diagnosis code entered for 2 separate outpatient visits on separate calendar days. Controls were individuals without any of the criteria for case definition. Individuals were excluded if they had the relevant ICD-10 code associated with only one outpatient encounter. For continuous traits, data cleaning was performed by removing non-physiological lab values, invalid or contaminated specimens, and those that were over 5× upper limit of normal. Then the minimum, median, and maximum laboratory result values over the duration of follow-up were derived for each patient and used as outcomes.

Example 2: Loss-of-Function in GPR75 is Associated with Lower BMI, Lower Body Fat and Protection Against Obesity High-coverage whole exome sequencing was performed in 645,626 individuals (Example 1), including 428,719 European ancestry individuals from the United Kingdom Biobank cohort (UKB; FIG. 1), 121,061 European ancestry individuals from the MyCode Community Health Initiative cohort from the USA-based Geisinger Health System (GHS; FIG. 1) and 95,846 Admixed American ancestry individuals from the Mexico City Prospective Study (MCPS; FIG. 1).

In an exome-wide meta-analysis across these three cohorts, the burden of rare pLOF variants in the GPR75 gene was associated with lower BMI at the exome-wide level of statistical significance (inverse-variance weighted (IVW) meta-analysis p<3.6×10⁻⁰⁷, a Bonferroni correction for 20,000 genes and seven variant selection models (Example 1)).

Predicted loss-of-function variants in GPR75 were observed in ˜4 out of every 10,000 sequenced people, with similar frequency across populations (FIG. 2), and carrier status was associated with 0.34 standard deviations lower BMI, corresponding to 1.8 kg/m² lower BMI or approximately 5.3 kg or 12 lbs lower body weight (FIG. 3 and FIG. 4A).

Figure 7:
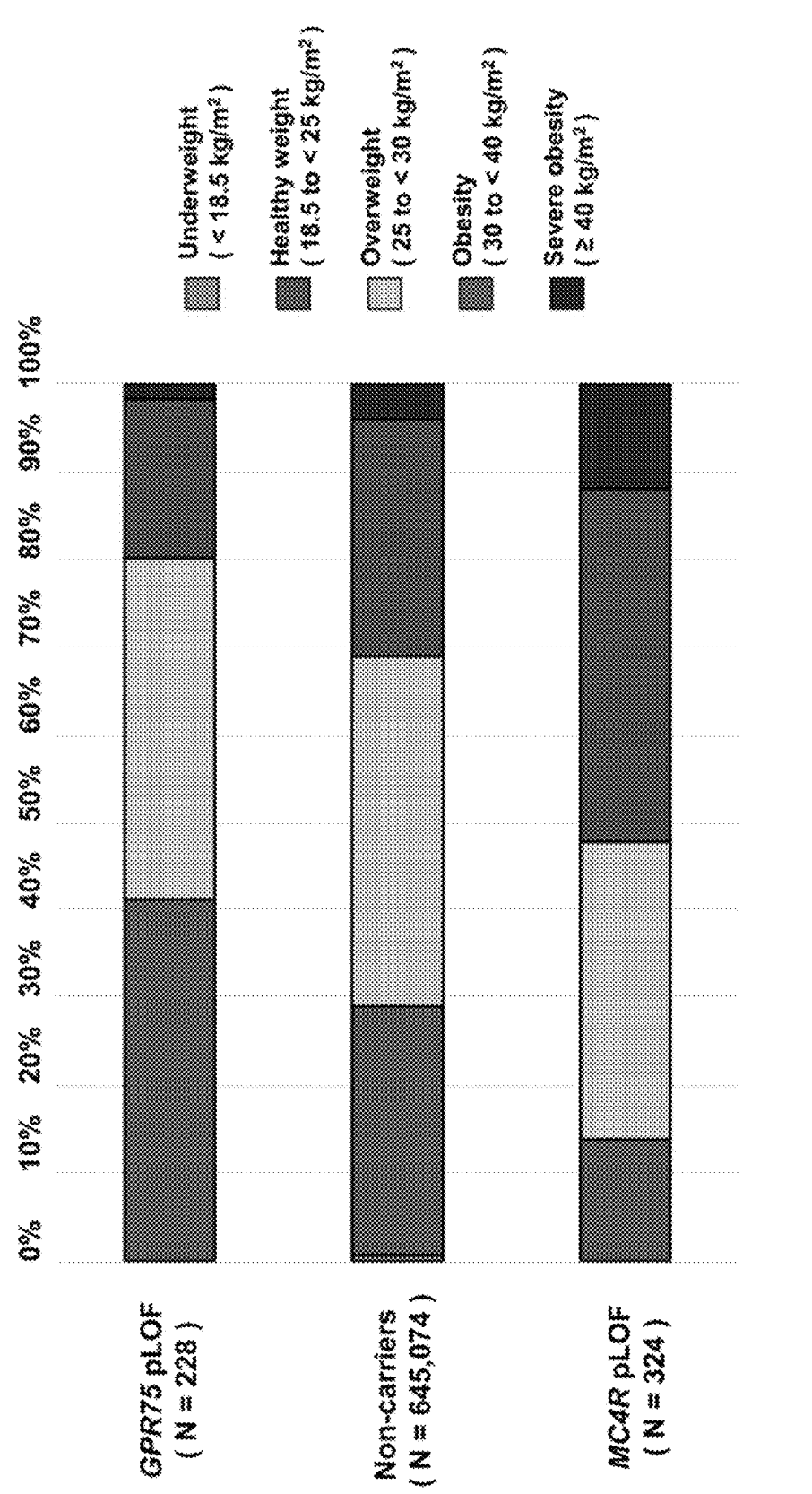
FIG. 7 shows distribution in body mass index categories for carriers and non-carriers of predicted loss-of-function variants in GPR75 or MC4R. Distribution of heterozygous carriers of predicted loss of function genetic variants in GPR75 (top), non-carriers (middle) and heterozygous carriers of predicted loss of function genetic variants in MC4R (bottom) in body mass index categories according to the World Health Organization's classification in the UKB, GHS and MCPS cohorts.

The association with lower BMI was directionally consistent and statistically significant in each of the constituent cohorts of the discovery meta-analysis (FIG. 2), as well as within age and sex subgroups (FIG. 5). The association of GPR75 pLOF variants with lower BMI was further corroborated in a combined analysis including an additional 91,328 individuals not included in the discovery set (per-allele beta in standard deviation (SD) units of BMI in the meta-analysis of discovery and additional cohorts, −0.34, 95% confidence interval (CI), −0.45, −0.22, p=6.9×10⁻⁰⁹; FIG. 4B). This strong association with lower BMI was accompanied by a corresponding association with protection against obesity. Heterozygous carriers of GPR75 pLOF variants had 54% lower odds of obesity compared to non-carriers in a meta-analysis of the UKB, GHS and MCPS cohorts (FIG. 6; per-allele odds ratio, 0.46, 95% confidence interval, 0.31, 0.67, p=6.9×10⁵) and their distribution across BMI categories was dramatically shifted towards lower BMI categories (FIG. 7). In UKB, GPR75 pLOF carriers were more likely to self-report a thinner than average comparative body size at age 10 compared to non-carriers (FIG. 8).

Figure 9:
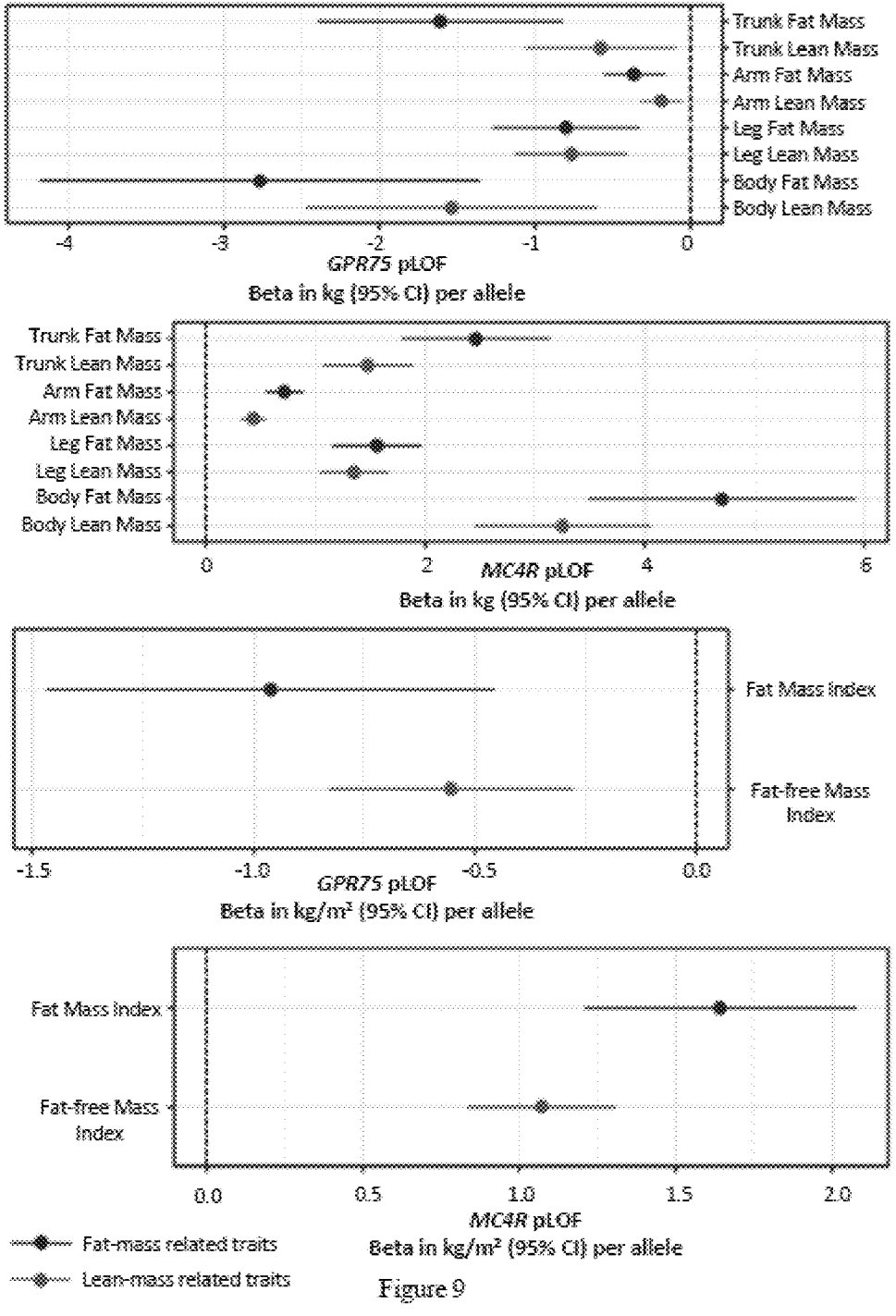
FIG. 9 shows association of pLOF variants in GPR75 and MC4R with body fat and lean mass indices estimated by bioelectrical impedance. Association analyses were performed in 423,418 participants of the UK Biobank study who underwent whole exome sequencing and bioelectrical impedance measurements. Abbreviations: pLOF, predicted loss of function; kg, kilograms; CI, confidence interval.

Body composition analysis with bioimpedance in UKB showed that the association with lower BMI was driven by an association with lower overall body fat mass and lower body fat percentage (FIG. 9). In an agnostic phenome-wide analysis of GPR75 pLOF variants (Example 1), statistically-significant associations with common diagnoses or measured continuous traits after correction for the number of statistical tests performed (2,173 phenotypes tested; Bonferroni-corrected p-value threshold, $p < 2.3 \times 10^5$), reflecting the rarity of these variants and the stringent multiple test correction, was not observed.

A detailed analysis of metabolic traits revealed a nominally-significant association (IVW meta-analysis $p < 0.05$) with higher high-density lipoprotein cholesterol, which is consistent with a favorable metabolic profile (FIG. 10). Carriers of pLOF in GPR75 had lower odds of type 2 diabetes compared to non-carriers (63,492 cases and 549, 961 controls; per-allele odds ratio, 0.92; 95% confidence interval, 0.59, 1.45; p=0.73; FIG. 10), but the difference was not statistically significant. Exome sequencing association statistics was interrogated from up to 20,791 type 2 diabetes cases and 24,440 controls included in the T2D Knowledge Portal (world wide web at "t2d.hugeamp.org/"; Accessed Jan. 8, 2021), and similarly observed numerically lower odds of type 2 diabetes in carriers of GPR75 pLOF variants (odds ratio for type 2 diabetes, 0.52, 95% CI, 0.14 to 1.97; p=0.30; alternative allele frequency, 0.03%). Due to the rarity of pLOF variants in GPR75 and given the genetic relationship between BMI and type 2 diabetes, it is estimated that millions of people would need to be sequenced to detect an association at $p < 0.05$ (FIG. 10). An analysis for HbA1c, a continuous biomarker of glycemic levels, led to similar results (FIG. 10).

Figure 11:
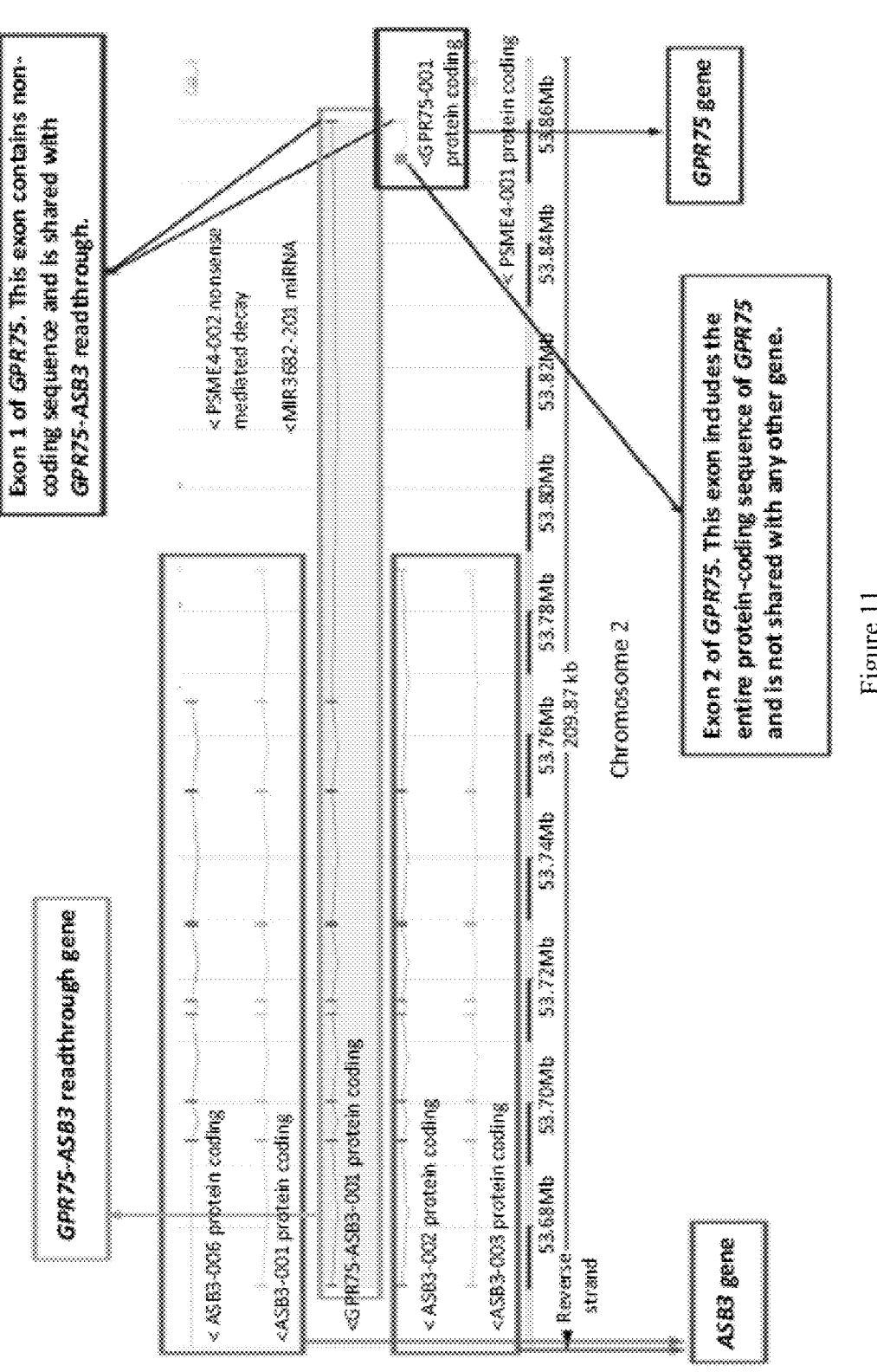
FIG. 11 shows GPR75, ASB3 and GPR75-ASB3 genes. The figure shows the gene model and chromosomal locations for the GPR75, GPR75-ASB3 and ASB3 genes. GPR75 shares exon 1, containing non-coding sequence, with the GPR75-ASB3 readthrough gene. Exon 2 of GPR75, containing its entire coding sequence, is exclusive to the GPR75 gene and is not shared with any other gene. ASB3 and GPR75-ASB3 share several exons with each other but not with GPR75. The underlying representation is from Ensembl region plot (Version 85).

Example 3: The Association with Lower Adiposity for Rare Protein-Truncating Variants can be Confidently Attributed to the GPR75 Gene The genomic context of the BMI association for pLOF variants in GPR75 was examined. The first and smallest exon of GPR75, containing untranslated sequence, is included in both GPR75 and in a putative GPR75-ASB3 readthrough gene with the nearby Ankyrin Repeat and SOCS Box Containing 3 (ASB3; FIG. 11). The second and final GPR75 exon (containing the entire translated region of GPR75) is not shared with any other gene or transcript (FIG. 11). A number of analyses was conducted to ensure that the association of pLOF variants could be firmly attributed to the GPR75 gene. First, 45 of the 46 pLOF variants in GPR75 that contributed to the association with lower BMI were located in exon 2 (FIG. 12), which is exclusive to the GPR75 gene (FIG. 11). Accordingly, the burden genotypes for pLOF variants in GPR75 had no linkage disequilibrium (LD; $R^2 < 0.0001$) with the burden genotype for pLOF variants affecting the GPR75-ASB3 readthrough gene or the ASB3 gene. Second, the association with BMI of the burden of rare coding variants in ASB3 or in the GPR75-ASB3 readthrough gene in the large exome sequencing meta-analysis was estimated. There was no association with BMI for the burden of rare nonsynonymous variants in ASB3 or GPR75-ASB3 across multiple statistical models with different variant annotation and allele frequency inclusion criteria (FIG. 13), including a lack of association for pLOF variants in either ASB3 or GPR75-ASB3 (FIG. 13). Finally, the association with BMI for the burden of rare pLOF variants in GPR75 conditional upon ASB3 and GPR75-ASB3 genotypes was estimated. The association of GPR75 pLOF variants with lower BMI was unaffected by adjusting for ASB3 and GPR75-ASB3 genotypes (FIG. 14). Therefore, the association with lower BMI for rare pLOF variants in GPR75 can be confidently attributed to the GPR75 gene.

Figure 16:
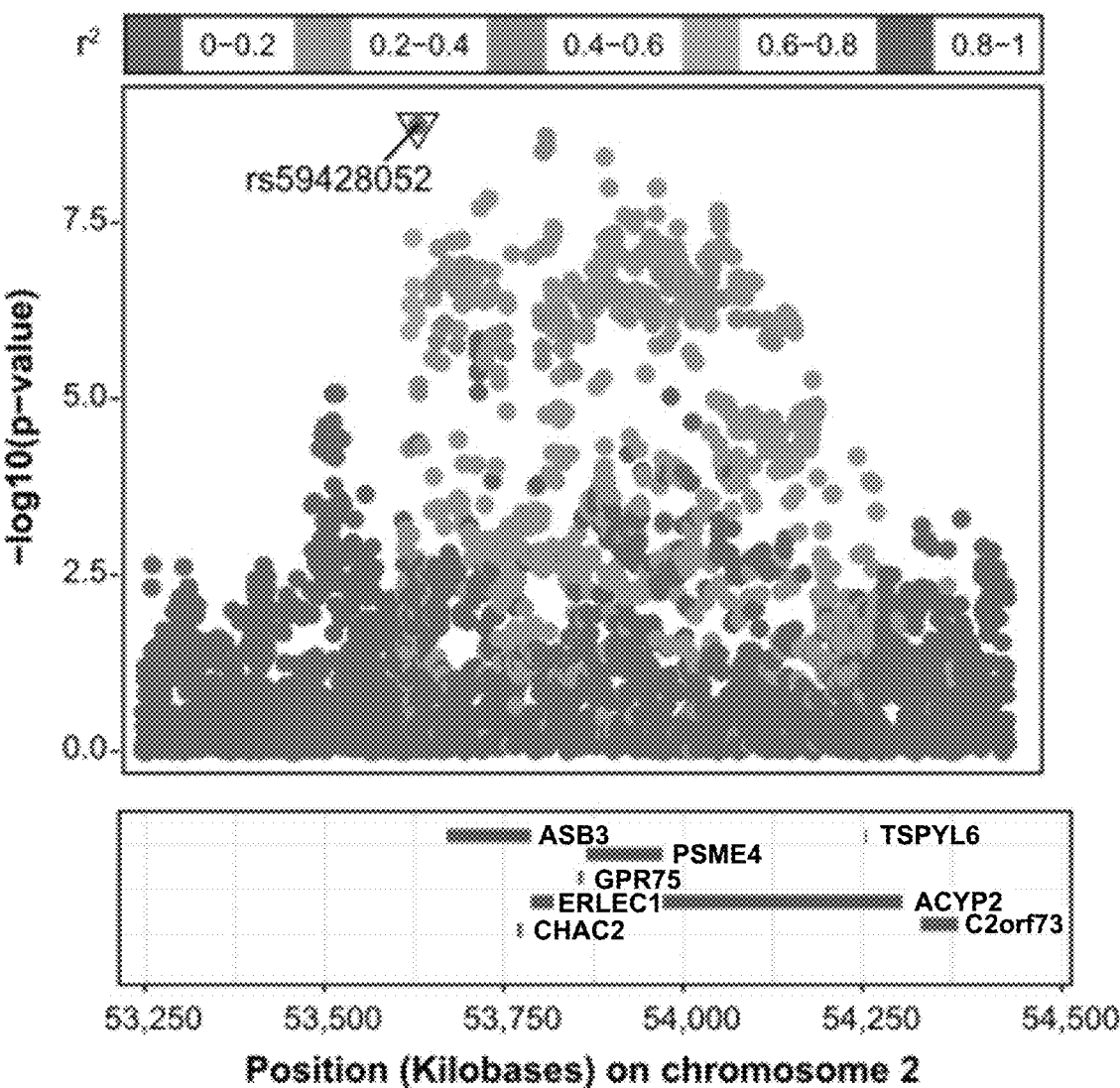
FIG. 16 shows associations with BMI for common variants at the GPR75 locus. Results from GWAS analyses of common imputed variants in European ancestry individuals from UKB and GHS are shown in the left panel and those from GWAS analyses in admixed Americans from the MCPS cohort in the right panel. The sentinel variant in the GWAS of European individuals (rs59428052) is highlighted in the left panel. There were no genome-wide significant associations in Admixed Americans (p<5×10$^{-8}$).
Figure 16:
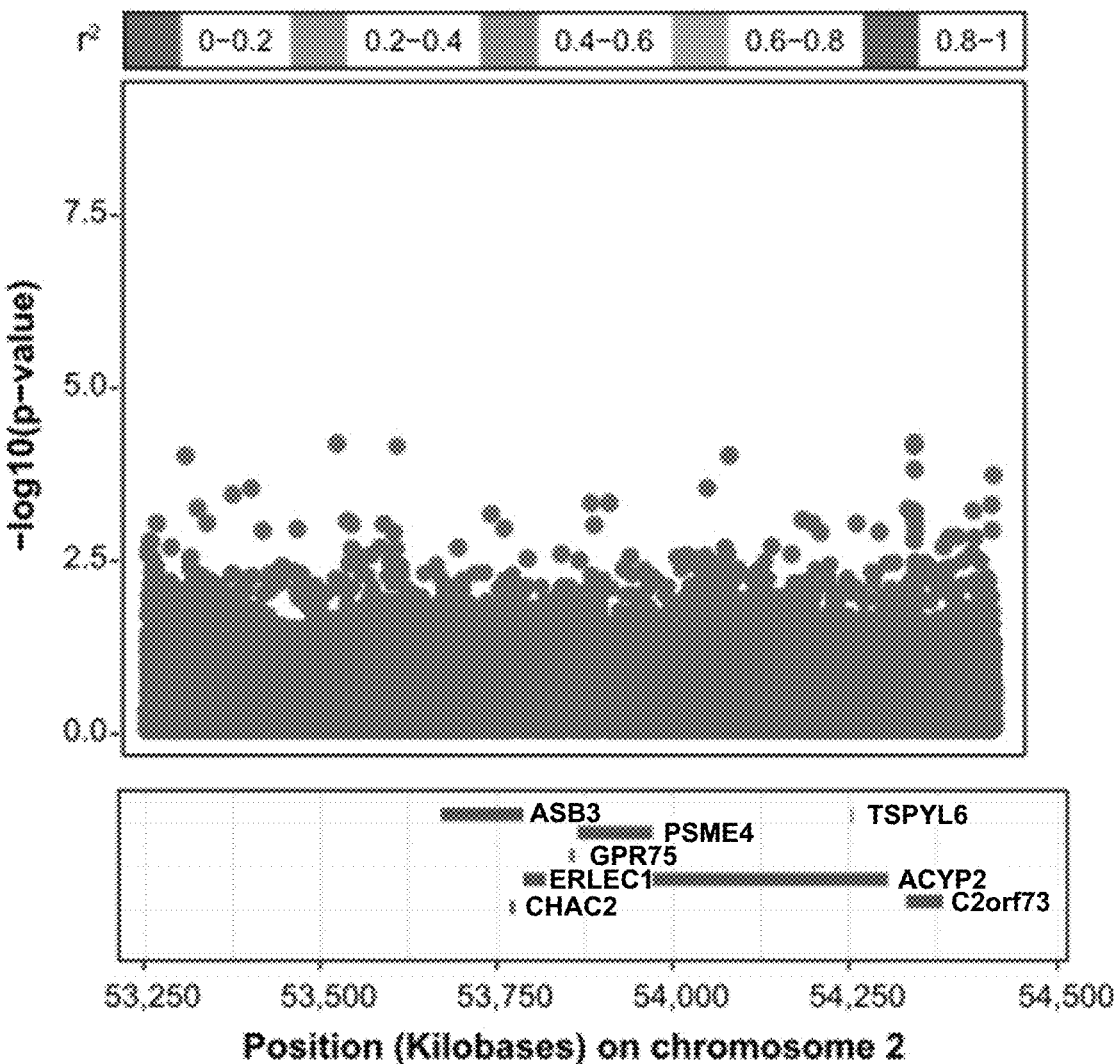

It was also explored whether there were common variant associations in the locus. In the 1 Mb window surrounding GPR75 (500 kb either side of the gene), there were 26 common variants associated with BMI at the genome-wide level of statistical significance (IVW meta-analysis, $p < 5 \times 10^{-08}$) in the GWAS of imputed common variants in Europeans (FIG. 15 and FIG. 16), while there were no genome-wide significant associations in admixed Americans (FIG. 16). These 26 variants all fine-mapped to a signal led by rs59428052 (G-allele frequency, 14.7%; posterior probability of causal association, 30.4%; per-allele beta in SD units of BMI, −0.015; 95% confidence interval, −0.020 to −0.010; $p = 1.3 \times 10^{-09}$), which is an intergenic variant nearest to ASB3 and approximately 200 kb downstream of GPR75. The rs59428052 variant did not co-localize with any eQTL signal nor were any of the additional 25 variants at the locus in LD ($R^2 > 0.8$) with any sentinel eQTLs in GTEx v8 (FIG. 14). Two of the 26 variants were in LD with a missense variant in ASB3 and GPR75-ASB3 (rs36020289), which does not affect the GPR75 transcript (FIG. 14).

A formal conditional analysis was performed adjusting for the 26 common variants associated with BMI in the region and identified that the association with lower BMI for pLOF variants in GPR75 remains unchanged (FIG. 14). Therefore, the association with lower BMI for rare pLOF variants in GPR75 is independent of any of the 26 common variants associated with BMI at the locus in Europeans.

In summary, the human genetic analysis at the locus indicates that: a) rare pLOF variants in GPR75 are associated with lower BMI with a large effect association, b) the pLOF association is attributed to GPR75 and not to other nearby transcripts, cc) the signal is independent of BMI-associated common variants in the region, and d) the small-effect intergenic common variant signal found in that region by GWAS fine-mapping in Europeans has no apparent link with GPR75.

Example 4: Loss-of-Function Variants in GPR75 Associated with Lower Body Adiposity Results in Intracellular Retention of a Truncated GPR75 Receptor The association with lower BMI for pLOF variants in GPR75 was due to multiple independent rare pLOF variants predicted to truncate GPR75 at different locations (FIG. 4A and FIG. 12). Due to their rarity, none of the 46 rare pLOF variants found by exome sequencing in the analysis were well ascertained by array-genotyping or imputation (FIG. 12). Leave-one-out analyses showed that the burden signal was robust to the exclusion of one pLOF variant at a time (FIG. 17). Out of 46 rare pLOF variants in GPR75, five were individually associated with lower BMI at a nominal level of statistical significance (IVW meta-analysis $p < 0.05$; Ala110fs; Ser219fs; Gln234*; Cys400fs, Lys404*; FIG. 18), while none was associated with higher BMI. When excluding all 5 of these variant sites from analysis, the remaining set of pLOF variants was still associated with lower BMI (FIG. 17).

The two most frequent (minor allele count 1.0) amongst the pLOF variants individually associated with BMI expressed in vitro showed that they result in cellular retention of a truncated receptor likely leading to a complete loss of function (FIG. 19).

It is predicted that that the loss of a functional copy (i.e., haploinsufficiency) or production of a truncated protein that disrupts receptor multimers (i.e., dominant negative effects) may explain the association of GPR75 truncation with lower BMI. It is hypothesized that in the case of haploinsufficiency the earlier N-terminal truncation of GPR75 would result in greater phenotypic impact than a C-terminal truncation within the last intracellular domain. Genetic variants resulting in truncation of GPR75 before the final intracellular domain were associated with $-2.1$ kg/m$^2$ lower BMI (IVW meta-analysis p=$4.1 \times 10^{-07}$) as compared with $-1.4$ kg/m$^2$ lower BMI (IVW meta-analysis p=0.012) for variants resulting in truncation within the final domain (FIG. 20). This difference was even more pronounced for truncations within the last 100 amino-acids of the final C-terminal domain (FIG. 20).

Figure 22:
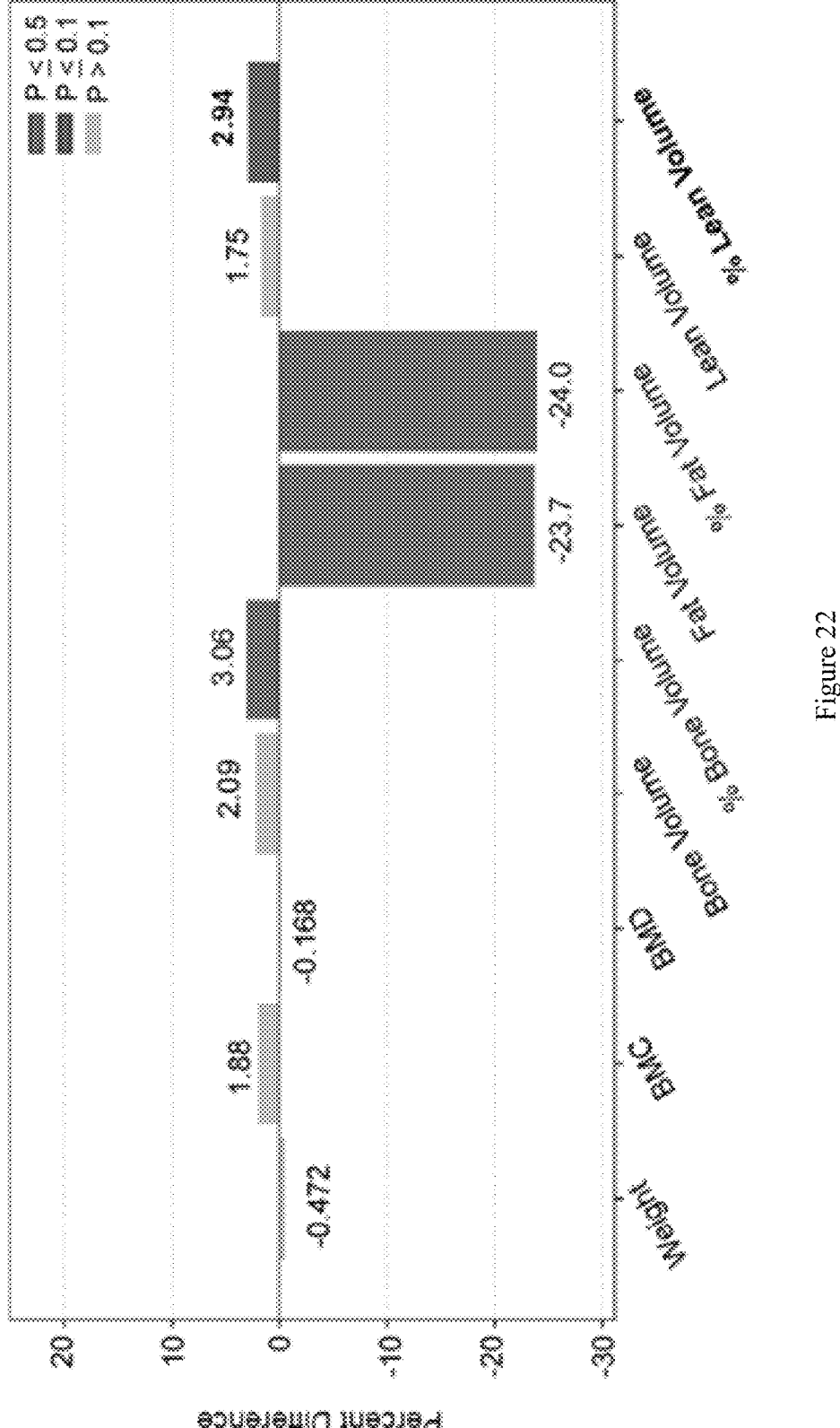
FIG. 22 shows percentage difference of body composition of male homozygote knockouts (designated with KO) compared to wild type. BMC, bone mineral content; BMD, bone mineral density; P, p-value.
Figure 23:
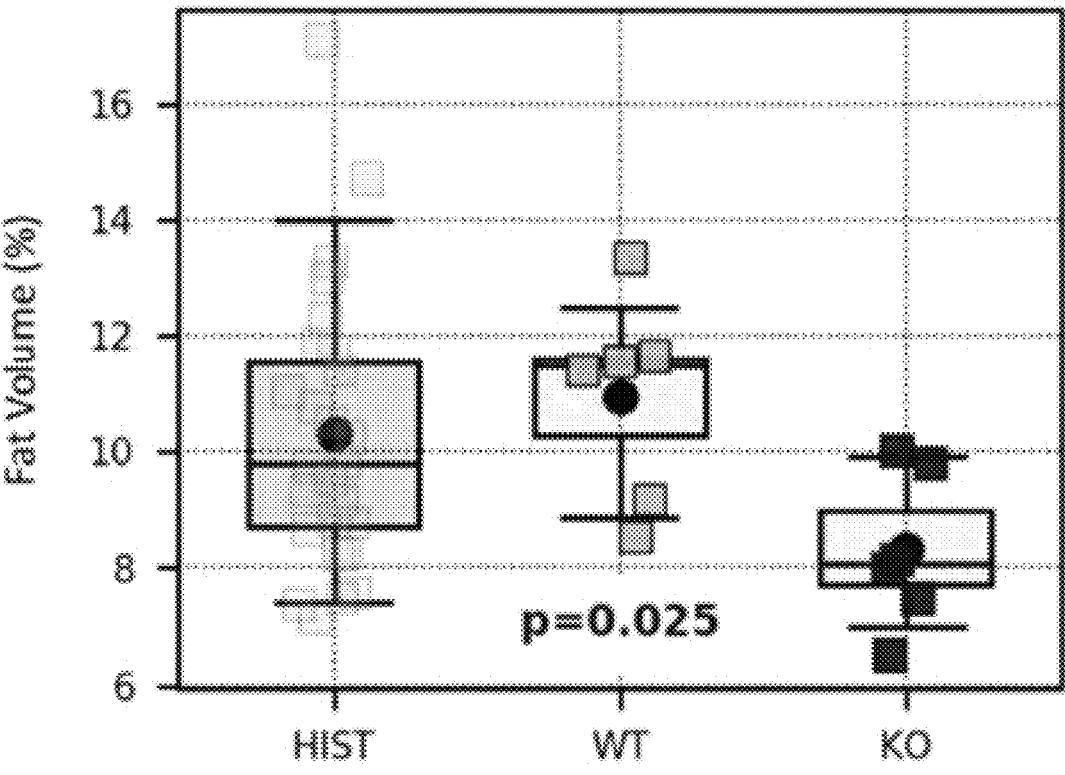
FIG. 23 shows average fat volume and percent fat volume of GPR75 WT (HIST and WT) and homozygote knockouts (designated with KO) male mice.
Figure 23:
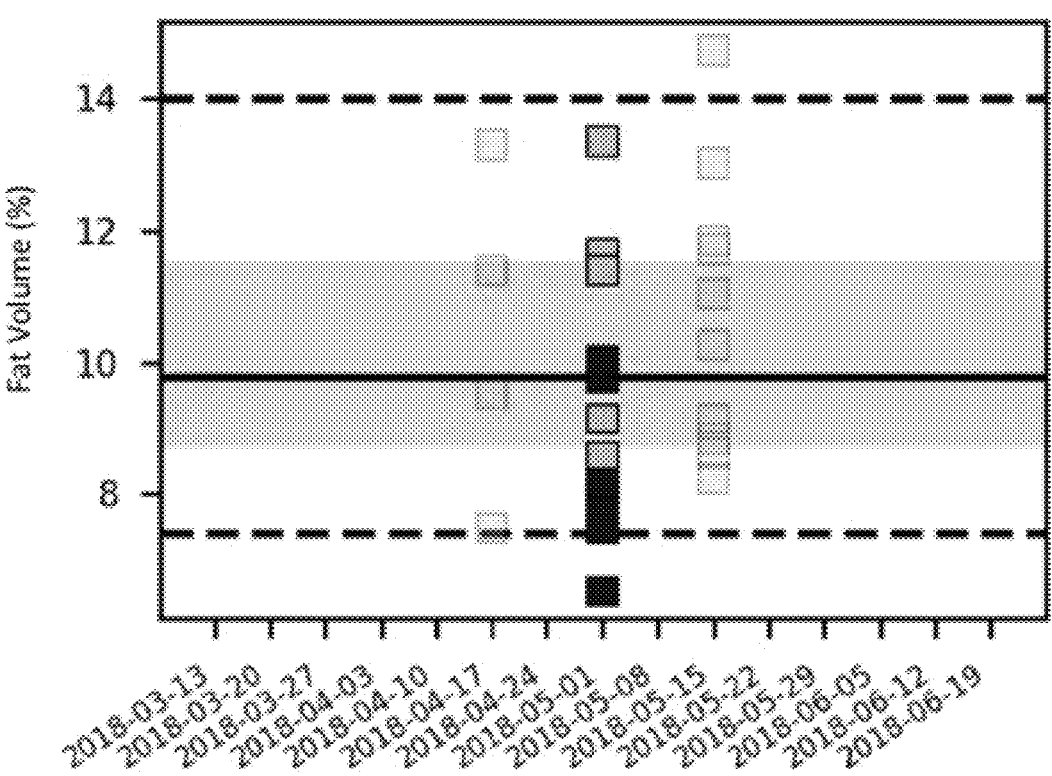

Example 5: Gpr75 Deletion in High-Fat Diet Induced Obesity and its Glycemic Consequences in Mice GPR75-KO male mice displayed 7% lower body weight compared to wild-type (FIG. 21). In contrast, no significant difference was observed in female mice (FIG. 21). A more detailed body composition analysis of GPR75-KO mice is summarized in FIG. 22. Gpr75 KO mice had 24% lower fat volume and percent fat compared to wild-type (FIG. 22 and FIG. 23), a statistically significant difference.

Figure 25:
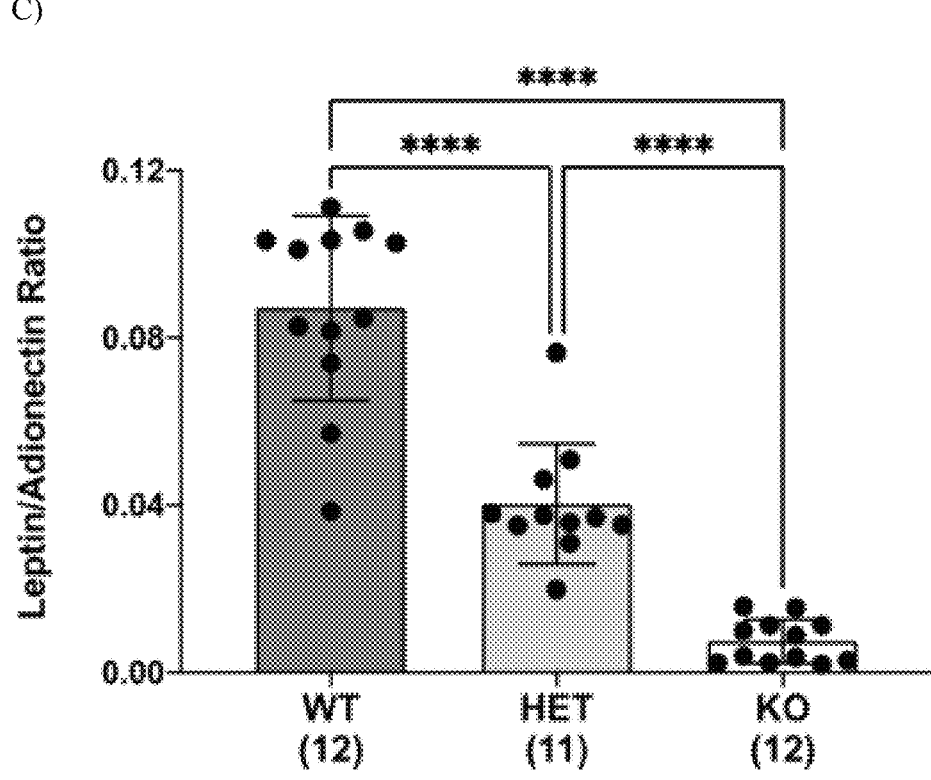
FIG. 25 shows plasma leptin, adiponectin and leptin-adiponectin ratio in mouse experiments. Panel A shows plasma leptin levels in Gpr75$^{+/+}$ (WT), Gpr75$^{+/-}$ (HET), and Gpr75$^{-/-}$ (KO) mice after the high-fat diet challenge expressed as fold difference compared to wild-type (set as 1). Absolute levels (mean±standard deviation) for wild-type mice were 208±42 pg/mL. Panel B shows plasma adiponectin levels in Gpr75$^{+/+}$ (WT), Gpr75$^{+/-}$ (HET), and Gpr75$^{-/-}$ (KO) mice after the high-fat diet challenge expressed as fold difference compared to wild-type (set as 1). Absolute levels (mean±standard deviation) for wild-type mice were 3,911±1,656 ng/mL. Panel C shows ratio of leptin to adiponectin in Gpr75$^{+/+}$ (WT), Gpr75$^{+/-}$ (HET), and Gpr75$^{-/-}$ (KO) expressed in ratio units. Number of mice included in each group and analysis are in parenthesis in the x-axis labels. Results are presented as mean±standard deviation. ns, not statistically-significant; *p<0.05, p<0.01, *p<0.001, ****p<0.0001 by two-way ANOVA with Tukey's multiple comparisons test.

In a mouse model of high-fat diet (HFD) induced obesity, experimental deletion of Gpr75 protected against weight gain and its associated abnormalities in glucose and insulin metabolism (FIG. 24). When placed on HFD for 14 weeks, Gpr75$^{+/+}$ mice approximately doubled their weight. Body weight changed from an average (standard deviation) of 20.9 (2.1) to 43.3 (6.5) grams (body weight change, +22.4 grams). In contrast, mice with a genetic deletion of Gpr75 gained less weight in an allele-dose dependent fashion (body weight change +16.9 grams, difference in weight-change with wild-type $-5.5$ grams or $-25\%$ for Gpr75$^{+/-}$ mice; body weight change +12.6 grams, difference in weight-change with wild-type $-9.8$ grams or $-44\%$ for the Gpr75$^{-/-}$ mice; FIG. 24A). Increases in fasting blood glucose seen with HFD in Gpr75$^{+/+}$ mice were reduced in an allele-dose dependent manner in Gpr75$^{-/+}$ and Gpr75$^{-/-}$ mice (FIG. 24B). Mice with a genetic deletion in Gpr75 were also resistant to HFD-induced impairments in glucose tolerance and insulin sensitivity (FIG. 24C and FIG. 24D). At the end of 14 weeks of HFD, plasma leptin levels were lower in Gpr75$^{-/-}$ and Gpr75$^{+/-}$ mice compared to wild-type mice (FIG. 25A), whereas adiponectin levels were higher resulting in a 2- and 10-fold lower leptin to adiponectin ratio in Gpr75$^{+/-}$ and Gpr75$^{-/-}$ mice compared to wild-type (FIG. 25B and FIG. 25C).

Further analyses in a distinct set of experiments studied the effects of genetic deficiency of Gpr75 on body composition and blood glucose levels in addition to body weight in Gpr75+/+, Gpr75+/− and Gpr75−/− mice maintained on a chow diet or following a switch to a 60% high fat diet starting on week 0 for 9 weeks. Body weight was examined weekly. Blood glucose levels were measured at weeks −1, 4 and 8. Fat mass, lean mass and bone mass were quantified by micro-computed tomography (mCT) on weeks 0, 5 and 9.

Figure 26:
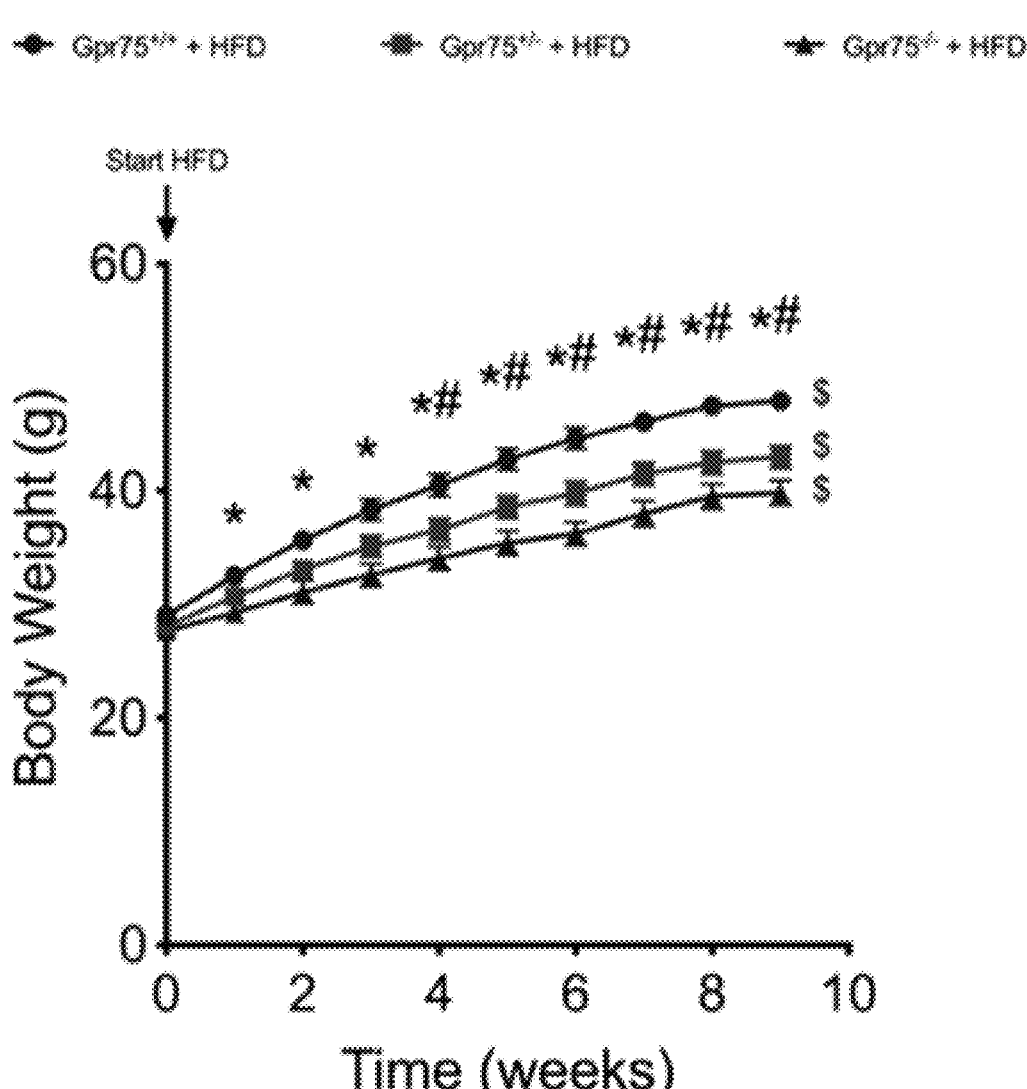
FIG. 26 shows body weight, fat mass, lean mass, bone mass, and blood glucose levels measured in high-fat diet mouse experiments. Body weight (Panel A), fat mass (Panel B, top), lean mass (Panel B, middle), bone mass (Panel B, bottom) and blood glucose levels (Panel C) for Gpr75$^{+/+}$, Gpr75$^{+/-}$ and Gpr75$^{-/-}$ mice (black circles, red squares and blue triangles, respectively) maintained on chow diet (week 0 or −1) and during 9 weeks of high fat diet feeding (HFD). *, P<0.05 for Gpr75$^{-/-}$ vs Gpr75$^{+/+}$ mice. #, P<0.05 for Gpr75$^{+/-}$ vs Gpr75$^{+/+}$ mice. $, P<0.05 for the last high fat diet data point vs the first data point obtained on chow diet prior to high fat diet feeding, for the respective genotype.
Figure 26:
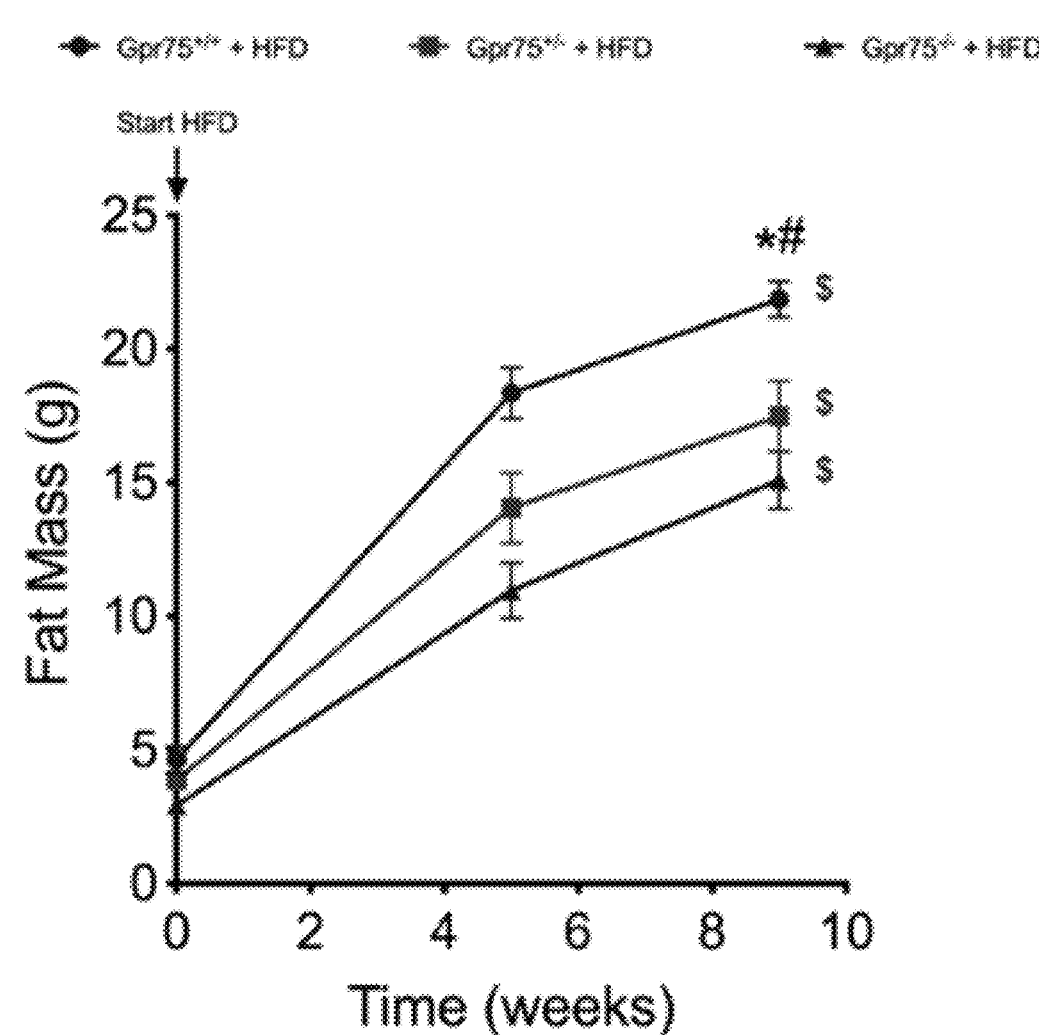
Figure 26:
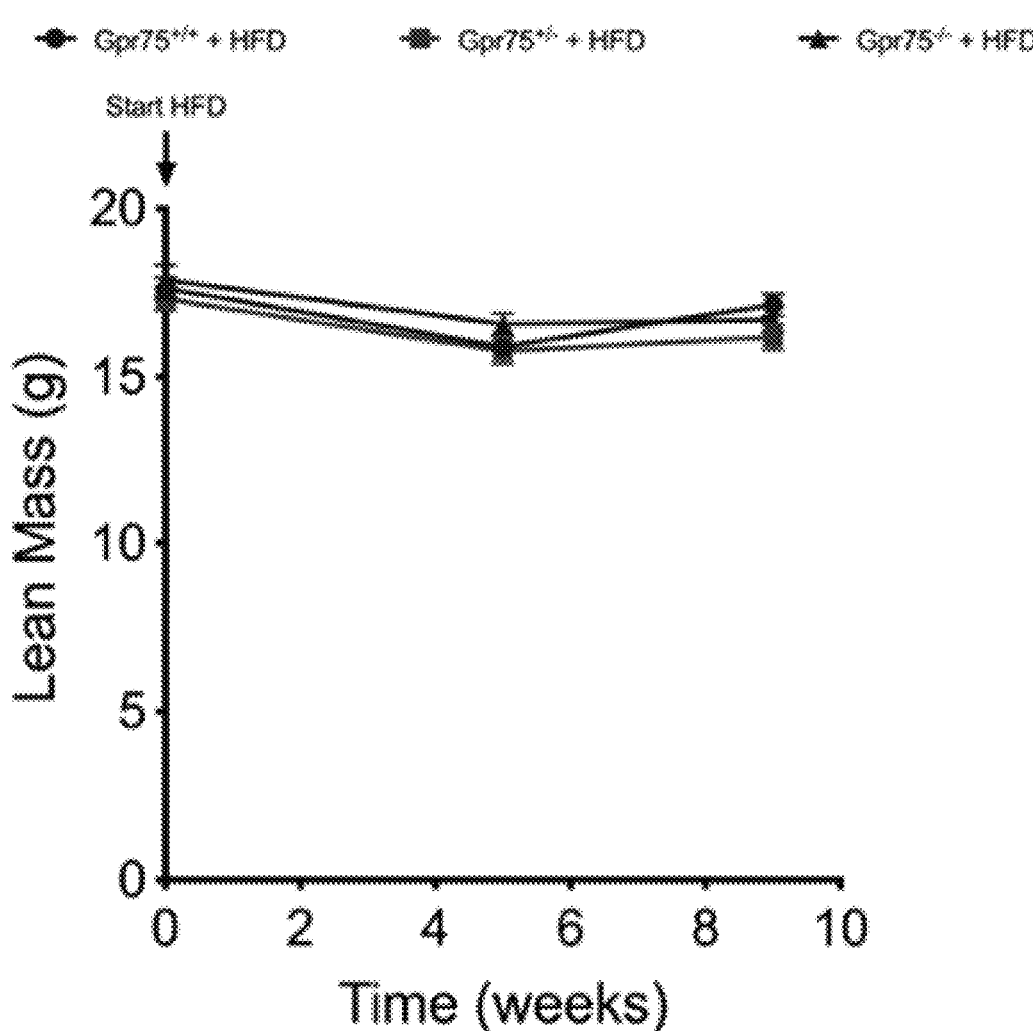
Figure 26:
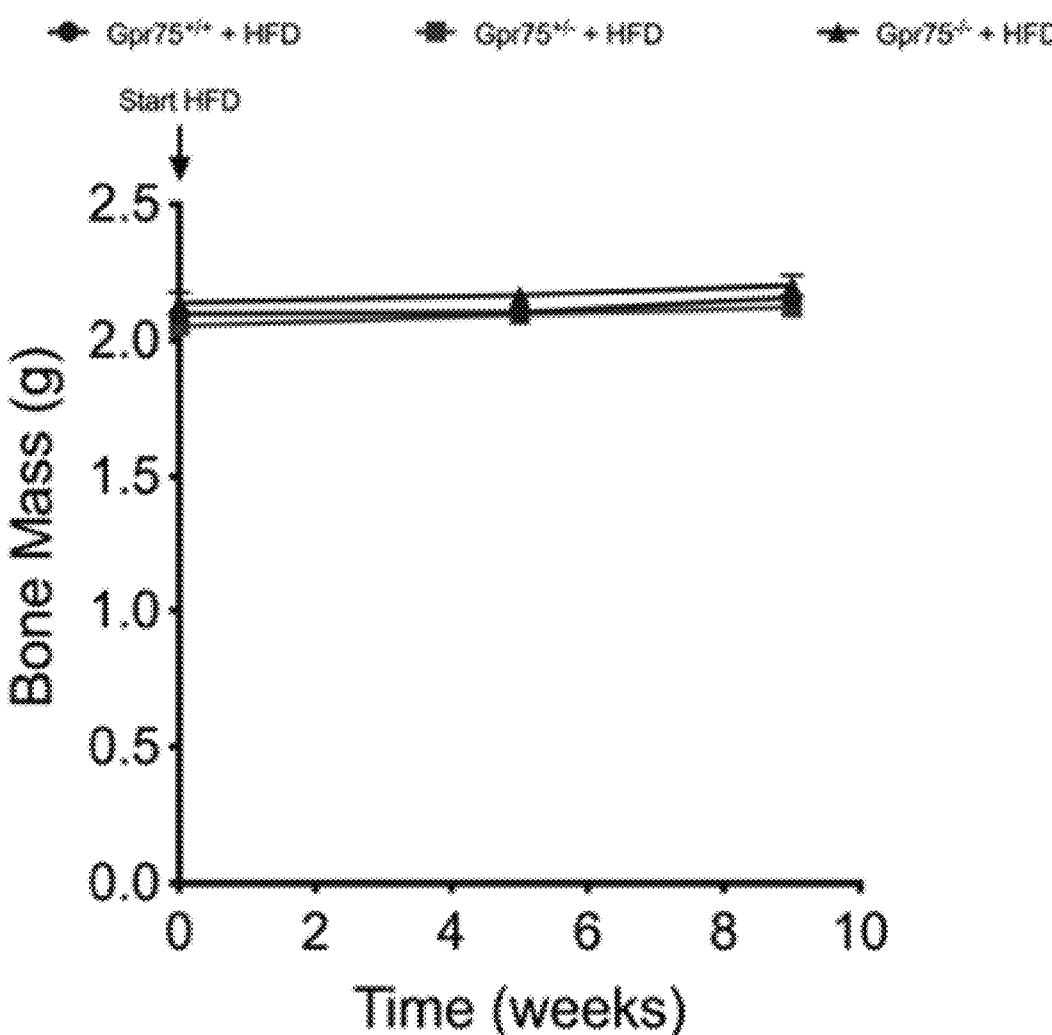
Figure 26:
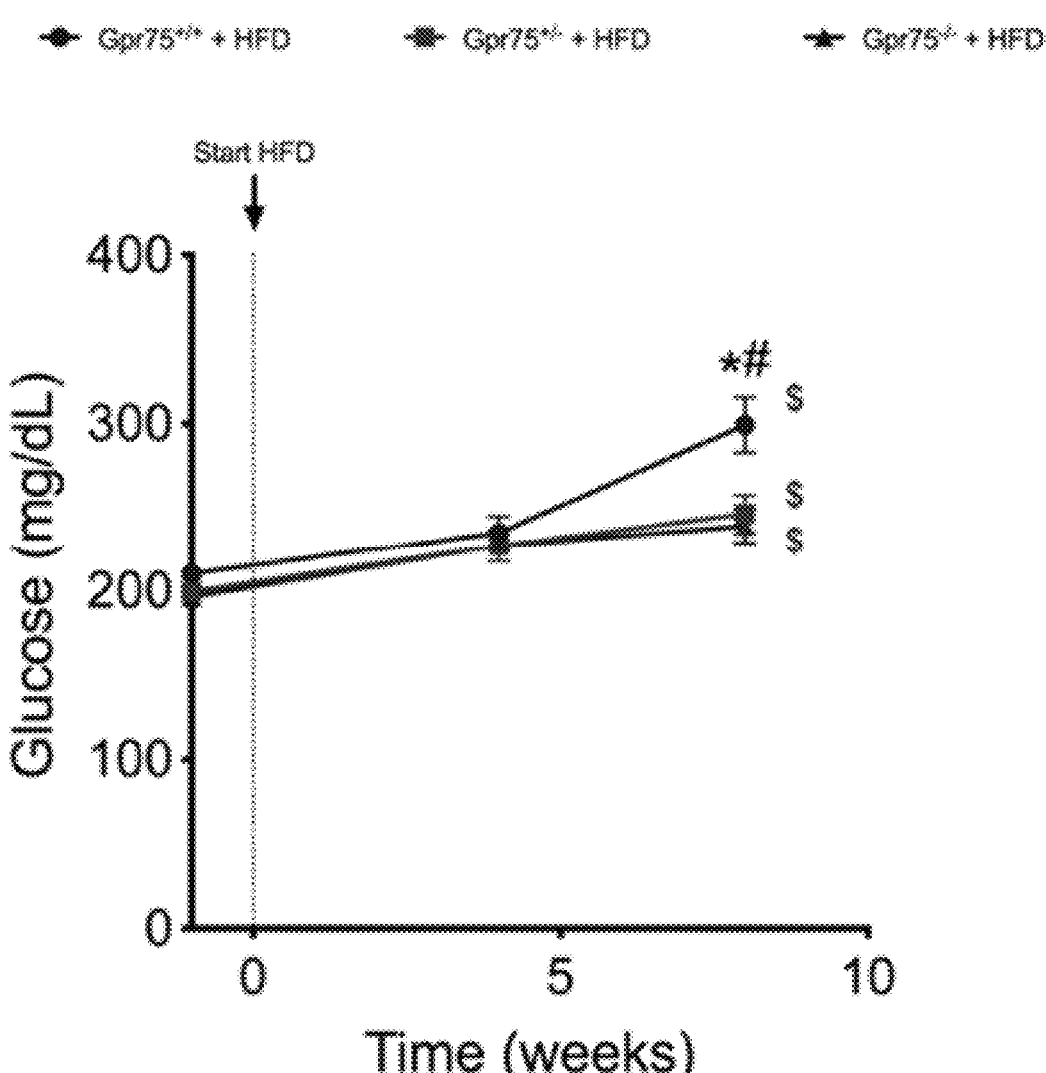

Prior to a switch from chow diet to high fat diet feeding, 10- to 15-week-old male Gpr75$^{+/+}$, Gpr75$^{+/-}$ and Gpr75$^{-/-}$ mice did not exhibit differences in body weight (week 0, FIG. 26, Panel A), lean mass (week 0, FIG. 26, Panel B), bone mass (week 0, FIG. 26, Panel B) or blood glucose levels (week −1, FIG. 26, Panel C). However, Gpr75$^{-/-}$ mice exhibited a significant reduction in fat mass when compared to Gpr75$^{+/+}$ and Gpr75$^{+/-}$ mice (FIG. 26, Panel B). After 9 weeks of high fat diet feeding Gpr75$^{+/+}$, Gpr75$^{+/-}$ and Gpr75$^{-/-}$ mice gained body weight relative to their body weight at week 0 (FIG. 26, Panel A). Following the switch to high fat diet feeding, the body weight of Gpr75$^{-/-}$ mice was significantly lower than Gpr75$^{+/+}$ mice starting at 1 week of high fat diet feeding thru to 9 weeks of high fat diet feeding (FIG. 26, Panel A). In addition, the body weight of Gpr75$^{+}$ mice was significantly lower than Gpr75$^{+/+}$ mice starting at 4 weeks of high fat diet feeding thru to 9 weeks mice (FIG. 26, Panel A). In summary, Gpr75$^{+/-}$ and Gpr75$^{-/-}$ mice show reduced body weight gain with high fat diet feeding.

Assessment of body composition by mCT, revealed that after 9 weeks of high fat diet feeding Gpr75$^{+/+}$, Gpr75$^{+/-}$ and Gpr75$^{-/-}$ mice gained fat mass relative to week 0. At 5 and 9 weeks post-high fat diet feeding, Gpr75$^{-/-}$ and Gpr75$^{+/-}$ mice exhibited less fat mass relative to Gpr75$^{+/+}$ mice (FIG. 26, Panel B). Lean mass and bone mass (FIG. 26, Panel B) were not significantly different amongst Gpr75$^{+/+}$, Gpr75$^{+/-}$ and Gpr75$^{-/-}$ mice after 5 and 9 weeks of high fat diet feeding. In summary, Gpr75$^{-/-}$ and Gpr75$^{+/-}$ mice show a reduction in fat mass gain with high fat feeding.

After 8 weeks of high fat diet feeding Gpr75$^{+/+}$, Gpr75$^{+/-}$ and Gpr75$^{-/-}$ mice showed significant increases in blood glucose levels relative to their blood glucose levels with chow diet feeding at week −1 (FIG. 26, Panel C). After 4 weeks of high fat diet feeding no differences in blood glucose levels were observed between Gpr75$^{+/+}$, Gpr75$^{+/-}$ and Gpr75$^{-/-}$ mice (FIG. 26, Panel C). However, after 8 weeks of high fat diet feeding, Gpr75$^{-/-}$ and Gpr75$^{+/-}$ mice exhibited significantly lower blood glucose levels than Gpr75$^{+/+}$ mice (FIG. 26, Panel C). These data suggest that Gpr75$^{+/-}$ and Gpr75$^{-/-}$ mice show protection from hyperglycemia associated with high fat diet feeding.

Figure 27:
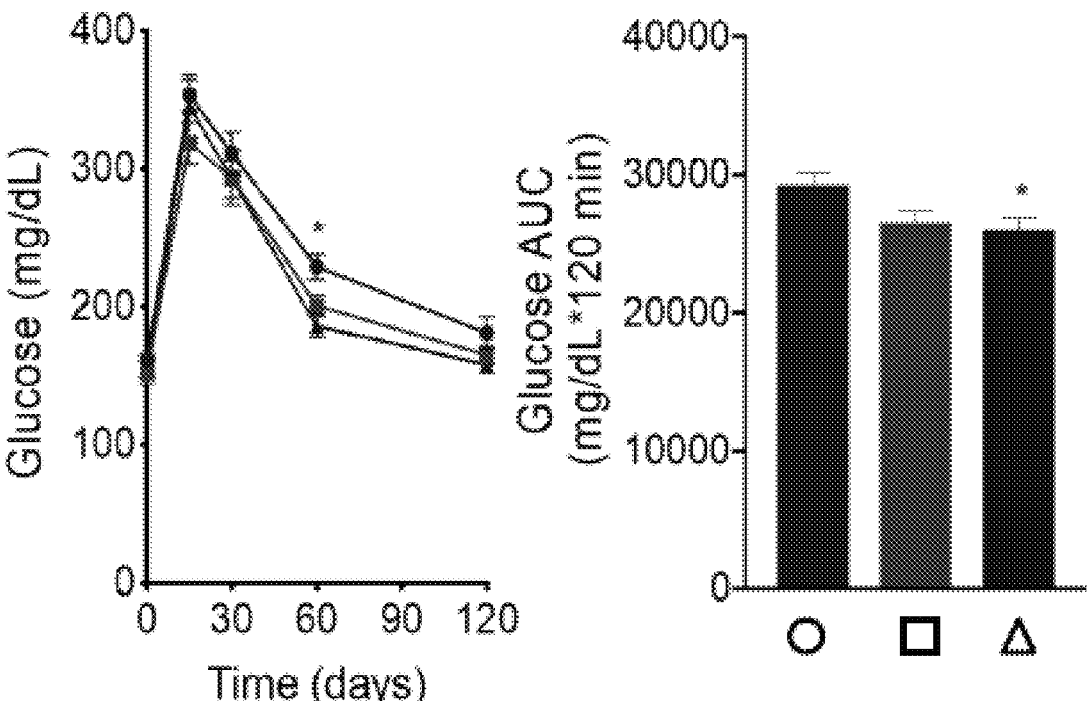
FIG. 27 shows chow-fed female Gpr75 knockout mice are not insulin resistant and exhibit improved glucose tolerance.

Example 6: Chow-Fed Female Gpr75 Knockout Mice are not Insulin Resistant and Exhibit Improved Glucose Tolerance An oral glucose tolerance test was performed on 13-week old female Gpr75$^{+/+}$, Gpr75$^{+/-}$ and Gpr75$^{-/-}$ mice. Animals were fasted at 7 a.m. for 4 hours, and then were given a 2 g/kg dose of dextrose (Hospira, Inc, NDC 0409-6658-02)) via oral gavage at 11 a.m. Glucose measurements were taken using an AlphaTRAK2 glucose meter (Zoetis, Cat #71676-01) and test strips (Zoetis, Cat #71681-01) at 0, 15, 30, 60, and 120 minutes post dextrose administration. Results are shown in FIG. 27.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating an obese subject, the method comprising administering a G-Protein Coupled Receptor 75 (GPR75) inhibitor to the obese subject, wherein the obese subject has been determined to not be heterozygous or homozygous for a GPR75 missense variant nucleic acid molecule encoding a predicted loss-of-function GPR75, polypeptide;

wherein the GPR75 inhibitor comprises a inhibitory nucleic acid molecule.

2. The method according to claim 1, wherein the GPR75 inhibitory nucleic acid molecule comprises an antisense nucleic acid molecule that hybridizes to a GPR75 mRNA.

3. The method according to claim 1, wherein the GPR75 inhibitory nucleic acid molecule comprises a small interfering RNA (siRNA) that hybridizes to a GPR75 mRNA.

4. The method according to claim 1, wherein the GPR75 inhibitory nucleic acid molecule comprises a short hairpin RNA (shRNA) that hybridizes to a GPR75 mRNA.

5. The method according to claim 2, wherein the obese subject is also administered liraglutide.

6. The method according to claim 3, wherein the obese subject is also administered liraglutide.

7. The method according to claim 4, wherein the obese subject is also administered liraglutide.

8. The method according to claim 2, wherein the obese subject is also administered exenatide.

9. The method according to claim 3, wherein the obese subject is also administered exenatide.

10. The method according to claim 4, wherein the obese subject is also administered exenatide.

11. The method according to claim 2, wherein the obese subject is also administered lixisenatide.

12. The method according to claim 3, wherein the obese subject is further administered lixisenatide.

13. The method according to claim 4, wherein the obese subject is further administered lixisenatide.

14. The method according to claim 2, wherein the obese subject is also administered albiglutide.

15. The method according to claim 3, wherein the obese subject is also administered albiglutide.

16. The method according to claim 4, wherein the obese subject is also administered albiglutide.

17. The method according to claim 2, wherein the obese subject is also administered dulaglutide.

18. The method according to claim 3, wherein the obese subject is also administered dulaglutide.

19. The method according to claim 4, wherein the obese subject is also administered dulaglutide.

20. The method according to claim 2, wherein the obese subject is also administered semaglutide.

21. The method according to claim 3, wherein the obese subject is also administered semaglutide.

22. The method according to claim 4, wherein the obese subject is also administered semaglutide.

23. The method according to claim 1, wherein the obese subject is a human.

*    *    *    *    *